US008664220B2

(12) United States Patent
Clark et al.

(10) Patent No.: US 8,664,220 B2
(45) Date of Patent: Mar. 4, 2014

(54) POLYCYCLIC COMPOUNDS AS LYSOPHOSPHATIDIC ACID RECEPTOR ANTAGONISTS

(75) Inventors: Ryan Clark, San Diego, CA (US);
Brian Andrew Stearns, Encinitas, CA (US); Jill Melissa Scott, Poway, CA (US); Heather Renee Coate, San Diego, CA (US); Lucy Zhao, San Diego, CA (US); Thomas J. Seiders, San Diego, CA (US); Deborah Volkots, New York, NY (US); Jeannie Arruda, San Diego, CA (US); Nicholas Simon Stock, San Diego, CA (US); Yen Pham Truong, San Diego, CA (US); David Nathan Zalatan, Palo Alto, CA (US)

(73) Assignee: Amira Pharmaceuticals, Inc., Princeton, NJ (US)

( * ) Notice: Subject to any disclaimer, the term of this patent is extended or adjusted under 35 U.S.C. 154(b) by 0 days.

(21) Appl. No.: 13/499,052

(22) PCT Filed: Sep. 29, 2010

(86) PCT No.: PCT/US2010/050787
§ 371 (c)(1),
(2), (4) Date: Nov. 16, 2012

(87) PCT Pub. No.: WO2011/041462
PCT Pub. Date: Apr. 7, 2011

(65) Prior Publication Data
US 2013/0072490 A1 Mar. 21, 2013

Related U.S. Application Data

(60) Provisional application No. 61/247,877, filed on Oct. 1, 2009.

(51) Int. Cl.
*A61K 31/42* (2006.01)
*C07D 261/14* (2006.01)

(52) U.S. Cl.
USPC .................. 514/236.8; 514/380; 514/254.04; 548/245; 548/247; 546/272.1; 544/367

(58) Field of Classification Search
USPC .......... 514/236.8, 380, 254.04; 548/245, 247; 544/367; 546/272.1
See application file for complete search history.

(56) References Cited

U.S. PATENT DOCUMENTS

| | | | |
|---|---|---|---|
| 6,762,200 B2 | 7/2004 | Takagi et al. |
| 6,964,975 B2 | 11/2005 | Ueno et al. |
| 7,094,797 B2 | 8/2006 | Horie et al. |
| 7,115,642 B2 | 10/2006 | Singh et al. |
| 7,135,469 B2 | 11/2006 | Pinto |
| 7,153,880 B2 | 12/2006 | Singh et al. |
| 7,217,704 B2 | 5/2007 | Miller et al. |
| 7,229,987 B2 | 6/2007 | Ammenn et al. |
| 7,285,680 B2 | 10/2007 | Habashita et al. |
| 7,288,558 B2 | 10/2007 | Nakade et al. |
| 7,300,917 B2 | 11/2007 | Nakade et al. |
| 7,402,605 B2 | 7/2008 | Tani et al. |
| 7,517,996 B2 | 4/2009 | Yamamoto et al. |
| 7,820,682 B2 | 10/2010 | Terakado et al. |
| 7,875,745 B2 | 1/2011 | Tanaka et al. |
| 8,048,902 B2 | 11/2011 | Hutchinson et al. |
| 8,058,300 B2 | 11/2011 | Hutchinson et al. |
| 8,124,645 B2 | 2/2012 | Terakado et al. |
| 8,217,066 B2 * | 7/2012 | Seiders et al. ................. 514/380 |
| 2004/0014662 A1 | 1/2004 | Lindquist et al. |
| 2004/0167132 A1 | 8/2004 | Shankar et al. |
| 2004/0171037 A1 | 9/2004 | Li et al. |
| 2004/0171582 A1 | 9/2004 | Nakade et al. |
| 2004/0192739 A1 | 9/2004 | Solow-Cordero et al. |
| 2004/0204383 A1 | 10/2004 | Tigyi et al. |
| 2005/0065194 A1 | 3/2005 | Shankar et al. |
| 2005/0101518 A1 | 5/2005 | Solow-Cordero et al. |
| 2005/0113283 A1 | 5/2005 | Solow-Cordero et al. |
| 2005/0261298 A1 | 11/2005 | Solow-Cordero et al. |
| 2008/0051372 A1 | 2/2008 | Chun |
| 2008/0064731 A1 | 3/2008 | Nakade et al. |
| 2008/0234230 A1 | 9/2008 | Nakade et al. |
| 2010/0034814 A1 | 2/2010 | Sabbadini et al. |
| 2011/0082164 A1 | 4/2011 | Clark et al. |
| 2011/0082182 A1 | 4/2011 | Buckman et al. |

FOREIGN PATENT DOCUMENTS

| | | |
|---|---|---|
| EP | 0 702 012 | 3/1996 |
| EP | 1 258 484 | 11/2002 |
| EP | 1 340 749 | 9/2003 |
| EP | 1 550 461 | 7/2005 |
| GB | 2466121 | 6/2010 |
| GB | 2470833 | 12/2010 |

(Continued)

OTHER PUBLICATIONS

Anliker, B. et al., "Cell surface receptors in lysophospholipid signaling", Seminars in Cell & Developmental Biology, vol. 15, pp. 457-465 (2004).

Bissantz, C., "Development and Application of New Methods for the Virtual Screening of Chemical Databases", Dissertation ETH No. 14771, Swiss Federal Institute of Technology, Zurich, pp. 1-268 (2002).

Byrn, S. et al., "Pharmaceutical Solids: A Strategic Approach to Regulatory Considerations", Pharmaceutical Research, vol. 12, No. 7, pp. 945-954 (1995).

(Continued)

*Primary Examiner* — Rei-tsang Shiao
(74) *Attorney, Agent, or Firm* — Maureen S. Gibbons

(57) ABSTRACT

Described herein are compounds that are antagonists of lysophosphatidic receptor(s). Also described are pharmaceutical compositions and medicaments that include the compounds described herein, as well as methods of using such antagonists, alone and in combination with other compounds, for treating LPA-dependent or LPA-mediated conditions or diseases.

4 Claims, No Drawings

(56) References Cited

FOREIGN PATENT DOCUMENTS

| | | |
|---|---|---|
| JP | 11-240873 | 9/1999 |
| JP | 2003-261545 | 9/2003 |
| JP | 2006-096712 | 4/2006 |
| WO | WO 98/28282 | 7/1998 |
| WO | WO 00/59902 | 10/2000 |
| WO | WO 01/60819 | 8/2001 |
| WO | WO 02/00651 | 1/2002 |
| WO | WO 02/085290 | 10/2002 |
| WO | WO 03/062392 | 7/2003 |
| WO | WO 03/097047 | 11/2003 |
| WO | WO 2004/031118 | 4/2004 |
| WO | WO 2005/012269 | 2/2005 |
| WO | WO 2005/066138 | 7/2005 |
| WO | WO 2005/123671 | 12/2005 |
| WO | WO 2006/131336 | 12/2006 |
| WO | WO 2007/007588 | 1/2007 |
| WO | WO 2007/024922 | 3/2007 |
| WO | WO 2007/096647 | 8/2007 |
| WO | WO 2007/139946 | 12/2007 |
| WO | WO 2008/014286 | 1/2008 |
| WO | WO 2008/024979 | 2/2008 |
| WO | WO 2008/112201 | 9/2008 |
| WO | WO 2009/011850 | 1/2009 |
| WO | WO 2009/135590 | 11/2009 |
| WO | WO 2010/068775 | 6/2010 |
| WO | WO 2010/077882 | 7/2010 |
| WO | WO 2010/077883 | 7/2010 |
| WO | WO 2010/141761 | 12/2010 |
| WO | WO 2010/141768 | 12/2010 |
| WO | WO 2011/017350 | 2/2011 |
| WO | WO 2011/041461 | 4/2011 |
| WO | WO 2011/041462 | 4/2011 |
| WO | WO 2011/041694 | 4/2011 |
| WO | WO 2011/041729 | 4/2011 |

OTHER PUBLICATIONS

Castelino, F.V. et al., "Amelioration of Dermal Fibrosis by Genetic Deletion or Pharmacologic Antagonism of Lysophosphatidic Acid Receptor 1 in a Mouse Model of Scleroderma", Arthritis & Rheumatism, vol. 63, No. 5, pp. 1405-1415 (2011).
Castelino, F.V. et al., "Genetic deletion or pharmacologic antagonism of $LPA_1$ ameliorates dermal fibrosis in a mouse model of systemic sclerosis", 11th International Workshop on Scleroderma Research, Boston, Massachusetts, Aug. 1-4, 2010, Abstracts, p. S-57 (2010).
Choi, J.W. et al., "Biological roles of lysophospholipid receptors revealed by genetic null mice: An update", Biochimica et Biophysica Acta, vol. 1781, pp. 531-539 (2008).
Chun, J., "Lysophospholipids in the nervous system", Prostaglandins & Other Lipid Mediators, vol. 77, pp. 46-51 (2005).
Chun, J. et al., "Lysophospholipid Receptors as Potential Drug Targets in Tissue Transplantation and Autoimmune Diseases", Current Pharmaceutical Design, vol. 12, No. 2, pp. 161-171 (2006).
Evans, J.F. et al., "Seeing the future of bioactive lipid drug targets", Nature Chemical Biology, vol. 6, pp. 476-479 (2010).
Fukushima, N. et al., "The LPA receptors", Prostaglandins & Other Lipid Mediators, vol. 64, pp. 21-32 (2001).
Gardell, S.E. et al., "Emerging medicinal roles for lysophospholipid signaling", Trends in Molecular Medicine, vol. 12, No. 2, pp. 65-75 (2006).
Golub, T.R. et al., "Molecular Classification of Cancer: Class Discovery and Class Prediction by Gene Expression Monitoring", Science, vol. 286, pp. 531-537 (1999).
Ishii, I. et al., "Lysophospholipid Receptors: Signaling and Biology", Annu. Rev. Biochem., vol. 73, pp. 321-354 (2004).
Kainuma, M. et al., "Design, synthesis, and evaluation of non-steroidal farnesoid X receptor (FXR) antagonist", Bioorganic & Medicinal Chemistry, vol. 15, pp. 2587-2600 (2007).
Lala, P.K. et al., "Role of nitric oxide in tumor progression: Lessons from experimental tumors", Cancer and Metastasis Reviews, vol. 17, pp. 91-106 (1998).
Ley, K. et al., "From lung injury to fibrosis", Nature Medicine, vol. 14, No. 1, pp. 20-21 (2008).
Mills, G.B. et al., "The Emerging Role of Lysophosphatidic Acid in Cancer", Nature Reviews: Cancer, vol. 3, pp. 582-591 (2003).
Murph, M.M. et al., "Sharpening the edges of understanding the structure/function of the LPA1 receptor: Expression in cancer and mechanisms of regulation", Biochimica et Biophysica Acta, vol. 1781, pp. 547-557 (2008).
Ohta, H. et al., "Ki16425, a Subtype-Selective Antagonist for EDG-Family Lysophosphatidic Acid Receptors", Molecular Pharmacology, vol. 64, No. 4, pp. 994-1005 (2003).
Parrill, A.L. et al., "Sphingosine 1-phosphate and lysophosphatidic acid receptors: agonist and antagonist binding and progress toward development of receptor-specific ligands", Seminars in Cell & Developmental Biology, vol. 15, pp. 467-476 (2004).
Pradère, J.-P. et al., "$LPA_1$ Receptor Activation Promotes Renal Interstitial Fibrosis", J. Am. Soc. Nephroi., vol. 18, pp. 3110-3118 (2007).
Pradère, J.-P. et al., "Lysophosphatidic acid and renal fibrosis", Biochimica et Biophysica Acta, vol. 1781, pp. 582-587 (2008).
Prestwich, G.D. et al., "New metabolically stabilized analogues of lysophosphatidic acid: agonists, antagonists and enzyme inhibitors", Biochemical Society Transactions, vol. 33, No. 6, pp. 1357-1361 (2005).
Sardar, V.M. et al., "Molecular basis for lysophosphatidic acid receptor antagonist selectivity", Biochimica et Biophysica Acta, vol. 1582, pp. 309-317 (2002).
Scott, I., "Lysophosphatidic acid is an important mediator of fibroblast recruitment in IPF", Thorax, vol. 63, No. 7, p. 654 (2008).
Swaney, J.S. et al., "A novel, orally active $LPA_1$ receptor antagonist inhibits lung fibrosis in the mouse bleomycin model", British Journal of Pharmacology, vol. 160, pp. 1699-1713 (2010).
Swaney, J.S. et al., "Pharmacokinetic and Pharmacodynamic Characterization of an Oral, $LPA_1$-selective Antagonist", Journal of Pharmacology and Experimental Therapeutics, DOI:10.1124/jpet.110.175901, published Dec. 15, 2010.
Tager, A.M. et al., "The lysophosphatidic acid receptor $LPA_1$ links pulmonary fibrosis to lung injury by mediating fibroblast recruitment and vascular leak", Nature Medicine, vol. 14, No. 1, pp. 45-54 (2008).
Toews, M.L. et al., "Lysophosphatidic acid in airway function and disease", Biochimica et Biophysica Acta, vol. 1582, pp. 240-250 (2002).
Watanabe, N. et al., "Both Plasma Lysophosphatidic Acid and Serum Autotaxin Levels are Increased in Chronic Hepatitis C", J. Clin. Gastroenterol., vol. 41, No. 6, pp. 616-623 (2007).
Watanabe, N. et al., "Plasma lysophosphatidic acid level and serum autotaxin activity are increased in liver injury in rats in relation to its severity", Life Sciences, vol. 81, pp. 1009-1015 (2007).
Watterson, K.R. et al., "Regulation of fibroblast functions by lysophospholipid mediators: Potential roles in wound healing", Wound Repair and Regeneration, vol. 15, pp. 607-616 (2007).
Yamamoto, T. et al., "Synthesis and evaluation of isoxazole derivatives as lysophosphatidic acid (LPA) antagonists", Bioorganic & Medicinal Chemistry Letters, vol. 17, pp. 3736-3740 (2007).
Yang, A.H. et al., "In vivo roles of lysophospholipid receptors revealed by gene targeting studies in mice", Biochimica et Biophysica Acta, vol. 1582, pp. 197-203 (2002).
Yang, M. et al., "G protein-coupled lysophosphatidic acid receptors stimulate proliferation of colon cancer cells through the β-catenin pathway", Proceedings of the National Academy of Sciences, vol. 102, No. 17, pp. 6027-6032 (2005).
Yokoyama, K. et al., "Stereochemical properties of lysophosphatidic acid receptor activation and metabolism", Biochimica et Biophysica Acta, vol. 1582, pp. 295-308 (2002).
Zhao, Y. et al., "Lysophosphatidic acid signaling in airway epithelium: Role in airway inflammation and remodeling", Cellular Signaling, vol. 21, pp. 367-377 (2009).
GB0921606.0 Search Report, dated Dec. 23, 2009.
PCT/US2009/068105 Search Report and Written Opinion, mailed Aug. 13, 2010.
PCT/US2009/068106 Search Report and Written Opinion, mailed Jun. 23, 2010.
PCT/US2010/037309 Search Report and Written Opinion, mailed Feb. 28, 2011.

(56) References Cited

OTHER PUBLICATIONS

PCT/US2010/037316 Search Report and Written Opinion, mailed Feb. 9, 2011.
PCT/US2010/044284 Search Report and Written Opinion, mailed Apr. 26, 2011.
PCT/US2010/050786 Search Report and Written Opinion, mailed Jun. 24, 2011.
PCT/US2010/050787 Search Report and Written Opinion, mailed Jun. 15, 2011.
PCT/US2010/051150 Search Report and Written Opinion, mailed Jun. 21, 2011.
PCT/US2010/051199 Search Report and Written Opinion, mailed Jun. 15, 2011.

* cited by examiner

POLYCYCLIC COMPOUNDS AS LYSOPHOSPHATIDIC ACID RECEPTOR ANTAGONISTS

RELATED APPLICATIONS

This application claims benefit of U.S. Provisional Application No. 61/247,877, entitled "POLYCYCLIC COMPOUNDS AS LYSOPHOSPHATIDIC ACID RECEPTOR ANTAGONISTS" filed on Oct. 1, 2009, which is herein incorporated by reference.

FIELD OF THE INVENTION

Described herein are compounds, methods of making such compounds, pharmaceutical compositions and medicaments comprising such compounds, and methods of using such compounds to treat, prevent or diagnose diseases, disorders or conditions associated with one or more of the lysophosphatidic acid (LPA) receptors.

BACKGROUND OF THE INVENTION

Lysophospholipids are membrane-derived bioactive lipid mediators. Lysophospholipids affect fundamental cellular functions that include proliferation, differentiation, survival, migration, adhesion, invasion, and morphogensis. These functions influence many biological processes that include, but are not limited to, neurogensis, angiogenesis, wound healing, fibrosis, immunity, and carcinogenesis.

Lysophosphatidic acid (LPA) is a lysophospholipid that has been shown to act through sets of specific G protein-coupled receptors (GPCRs) in an autocrine and paracrine fashion. LPA binding to its cognate GPCRs ($LPA_1$, $LPA_2$, $LPA_3$, $LPA_4$, $LPA_5$, $LPA_6$) activates intracellular signaling pathways to produce a variety of biological responses. Antagonists of the LPA receptors find use in the treatment of diseases, disorders or conditions in which LPA plays a role.

SUMMARY OF THE INVENTION

In one aspect, presented herein is a compound of Formula (I), (Ia), (II), (IIa), (III), (IIIa), (IV) or (V) that inhibit the physiological activity of lysophosphatidic acid (LPA), and therefore, are useful as agents for the treatment or prevention of diseases in which inhibition of the physiological activity of LPA is useful, such as diseases in which an LPA receptor participates, is involved in the etiology or pathology of the disease, or is otherwise associated with at least one symptom of the disease.

In one aspect, a compound of Formula (I), (Ia), (II), (IIa), (III), (IIIa), (IV) or (V) is useful for the treatment of fibrosis of organs (liver, kidney, lung, heart and the like), liver diseases (acute hepatatis, chronic hepatitis, liver fibrosis, liver cirrhosis, portal hypertension, regenerative failure, non-alcoholic steatohepatitis (NASH), liver hypofunction, hepatic blood flow disorder, and the like), cell proliferative disease (cancer (solid tumor, solid tumor metastasis, vascular fibroma, myeloma, multiple myeloma, Kaposi's sarcoma, leukemia, chronic lymphocytic leukemia (CLL) and the like) and invasive metastasis of cancer cell, and the like), inflammatory disease (psoriasis, nephropathy, pneumonia and the like), gastrointestinal tract disease (irritable bowel syndrome (IBS), inflammatory bowel disease (IBD), abnormal pancreatic secretion, and the like), renal disease, urinary tract-associated disease (benign prostatic hyperplasia or symptoms associated with neuropathic bladder disease, spinal cord tumor, hernia of intervertebral disk, spinal canal stenosis, symptoms derived from diabetes, lower urinary tract disease (obstruction of lower urinary tract, and the like), inflammatory disease of lower urinary tract, dysuria, frequent urination, and the like), pancreas disease, abnormal angiogenesis-associated disease (arterial obstruction and the like), scleroderma, brain-associated disease (cerebral infarction, cerebral hemorrhage, and the like), neuropathic pain, peripheral neuropathy, and the like, ocular disease (age-related macular degeneration (AMD), diabetic retinopathy, proliferative vitreoretinopathy (PVR), cicatricial pemphigoid, glaucoma filtration surgery scarring, and the like). In one aspect, a compound of Formula (I), (Ia), (II), (IIa), (III), (IIIa), (IV) or (V) is used in the treatment of fibrotic diseases or conditions.

In one aspect, described herein are compounds of Formula (I), (Ia), (II), (IIa), (III), (IIIa), (IV) and (V), pharmaceutically acceptable salts, pharmaceutically acceptable solvates, and prodrugs thereof. In some embodiments, compounds of Formula (I), (Ia), (II), (IIa), (III), (IIIa), (IV) and (V) are antagonists of at least one of the LPA receptors selected from $LPA_1$, $LPA_2$, $LPA_3$, $LPA_4$, $LPA_5$ and $LPA_6$. In one embodiment, compounds of Formula (I), (Ia), (II), (IIa), (III), (IIIa), (IV) and (V) are antagonists of $LPA_1$. In one embodiment, compounds of Formula (I), (Ia), (II), (IIa), (III), (IIIa), (IV) and (V) are antagonists of $LPA_1$ and/or $LPA_3$. In some embodiments, compounds of Formula (I), (Ia), (II), (IIa), (III), (IIIa), (IV) and (V) are antagonists of $LPA_1$ and/or $LPA_2$. In some embodiments, compounds of Formula (I), (Ia), (II), (IIa), (III), (IIIa), (IV) and (V) are selective antagonists for one of the LPA receptors relative to the other LPA receptors. In some embodiments, such a selective antagonist is selective for the $LPA_1$ receptor. In some embodiments, such a selective antagonist is selective for the $LPA_2$ receptor. In some embodiments, such a selective antagonist is selective for the $LPA_3$ receptor.

In some embodiments, a compound of Formula (I), (Ia), (II), (IIa), (III), (IIIa), (IV) or (V) is used in the treatment of diseases, disorders, or conditions in which activation of at least one LPA receptor by LPA contributes to the symptomology or progression of the disease, disorder or condition. These diseases, disorders, or conditions may arise from one or more of a genetic, iatrogenic, immunological, infectious, metabolic, oncological, toxic, surgical, and/or traumatic etiology. In one aspect, the methods, compounds, pharmaceutical compositions, and medicaments described herein comprise antagonists of LPA receptors. In one aspect, the methods, compounds, pharmaceutical compositions, and medicaments described herein comprise antagonists of $LPA_1$.

In one aspect, provided herein is a compound of Formula (Ia), pharmaceutically acceptable salts, pharmaceutically acceptable solvates, or prodrugs thereof:

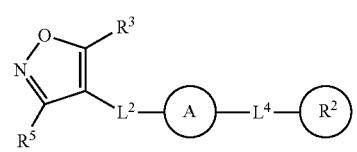

Formula (Ia)

wherein,
$R^3$ is

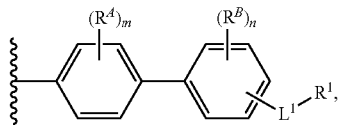

and $R^5$ is H, $C_1$-$C_4$ alkyl, or $C_1$-$C_4$ fluoroalkyl;
or
$R^5$ is

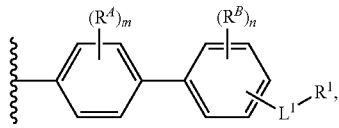

and $R^3$ is H, $C_1$-$C_4$ alkyl, or $C_1$-$C_4$ fluoroalkyl;

$R^1$ is —$CO_2R^D$, —C(=O)NHSO$_2R^E$, —C(=O)N($R^D$)$_2$, —CN, tetrazolyl, or carboxylic acid bioisostere;

$R^D$ is H or $C_1$-$C_6$ alkyl;

$R^E$ is $C_1$-$C_6$ alkyl or a substituted or unsubstituted phenyl;

$L^1$ is absent, $C_1$-$C_4$alkylene, $C_1$-$C_4$fluoroalkylene, $C_3$-$C_6$cycloalkylene, $C_3$-$C_6$cycloalkylene-$C_1$-$C_4$alkylene-, or —C($R^{1a}$)($R^{1b}$)—;

$R^{1a}$ and $R^{1b}$ are each independently selected from H, $C_1$-$C_4$ alkyl and substituted or unsubstituted benzyl;

each of $R^A$ and $R^B$ is independently selected from halogen, —CN, —OH, —$OR^9$, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;

$L^2$ is absent, —C(=O)—, —S—, —S(O)—, —S(O)$_2$—, —N($R^D$)—, —N($R^D$)C(=O)—, substituted or unsubstituted $C_1$-$C_4$alkylene, substituted or unsubstituted $C_1$-$C_4$fluoroalkylene, or a substituted or unsubstituted $C_1$-$C_4$heteroalkylene, where if $L^2$ is substituted, then $L^2$ is substituted with 1 or 2 $R^{12}$, where each $R^{12}$ is F, $C_1$-$C_4$alkyl, —OH, —$OR^D$, or —N($R^D$)$_2$;

ring A is a substituted or unsubstituted cyclic group selected from a substituted or unsubstituted $C_3$-$C_6$cycloalkylene, a substituted or unsubstituted $C_2$-$C_5$heterocycloalkylene, a substituted or unsubstituted monocyclic $C_1$-$C_5$heteroarylene, and a substituted or unsubstituted phenylene, where if ring A is substituted, then ring A is substituted with 1 or 2 $R^{14}$, each $R^{14}$ is independently selected from halogen, —CN, —OH, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;

$L^4$ is absent, a substituted or unsubstituted $C_1$-$C_4$alkylene, substituted or unsubstituted $C_1$-$C_4$fluoroalkylene, substituted or unsubstituted $C_1$-$C_4$heteroalkylene, —O—, —S—, —S(O)—, SO$_2$, —N($R^D$)—, or —C(=O)—N($R^D$)—$C_1$-$C_4$alkylene-, where if $L^4$ is substituted, then $L^4$ is substituted with 1 or 2 $R^{13}$, where each $R^{13}$ is F, $C_1$-$C_4$alkyl, —OH, —$OR^D$, or —N($R^D$)$_2$;

$R^2$ is a substituted or unsubstituted cyclic group selected from a substituted or unsubstituted $C_3$-$C_{10}$cycloalkyl, a substituted or unsubstituted $C_2$-$C_{10}$heterocycloalkyl, a substituted or unsubstituted $C_1$-$C_9$heteroaryl, a substituted or unsubstituted phenyl, and a substituted or unsubstituted naphthyl, wherein if $R^2$ is substituted, then $R^2$ is substituted with 1, 2 or 3 $R^C$, each $R^C$ is independently selected from halogen, —CN, —NO$_2$, —OH, —$OR^9$, —$SR^9$, —S(=O)$R^{10}$, —S(=O)$_2R^{10}$, —N($R^9$)S(=O)$_2R^{10}$, —S(=O)$_2$N($R^9$)$_2$, —C(=O)$R^{10}$, —OC(=O)$R^{10}$, —$CO_2R^9$, —$OCO_2R^{10}$, —N($R^9$)$_2$, —C(=O)N($R^9$)$_2$, —OC(=O)N($R^9$)$_2$, —$NR^9$C(=O)N($R^9$)$_2$, —$NR^9$C(=O)$R^{10}$, $NR^9$C(=O)$OR^{10}$, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;

$R^5$ is H, $C_1$-$C_4$ alkyl, or $C_1$-$C_4$ fluoroalkyl;

each $R^9$ is independently selected from H, $C_1$-$C_6$alkyl, $C_1$-$C_6$heteroalkyl, $C_1$-$C_6$fluoroalkyl, a substituted or unsubstituted $C_3$-$C_6$cycloalkyl, a substituted or unsubstituted $C_2$-$C_6$heterocycloalkyl, a substituted or unsubstituted phenyl, a substituted or unsubstituted monocyclic $C_1$-$C_5$heteroaryl, —$C_1$-$C_4$alkylene-(substituted or unsubstituted $C_3$-$C_6$cycloalkyl), —$C_1$-$C_4$alkylene-(substituted or unsubstituted $C_2$-$C_6$heterocycloalkyl), —$C_1$-$C_4$alkylene-(substituted or unsubstituted phenyl), or —$C_1$-$C_4$alkylene-(substituted or unsubstituted $C_1$-$C_5$heteroaryl); or two $R^9$ groups attached to the same N atom are taken together with the N atom to which they are attached to form a substituted or unsubstituted heterocycle;

$R^{10}$ is selected from $C_1$-$C_6$alkyl, $C_1$-$C_6$heteroalkyl, $C_1$-$C_6$fluoroalkyl, a substituted or unsubstituted $C_3$-$C_6$cycloalkyl, a substituted or unsubstituted $C_2$-$C_6$heterocycloalkyl, a substituted or unsubstituted phenyl, a substituted or unsubstituted monocyclic $C_1$-$C_5$heteroaryl, —$C_1$-$C_4$alkylene-(substituted or unsubstituted $C_3$-$C_6$cycloalkyl), —$C_1$-$C_4$alkylene-(substituted or unsubstituted $C_2$-$C_6$heterocycloalkyl), —$C_1$-$C_4$alkylene-(substituted or unsubstituted phenyl), and —$C_1$-$C_4$alkylene-(substituted or unsubstituted $C_1$-$C_5$heteroaryl);

m is 0, 1 or 2; n is 0, 1 or 2.

For any and all of the embodiments, substituents are selected from among from a subset of the listed alternatives. For example, in some embodiments, $R^1$ is —$CO_2R^D$ or —C(=O)NHSO$_2R^E$. In some embodiments, $R^1$ is —$CO_2R^D$. In some embodiments, $R^1$ is —$CO_2$H. In some embodiments, $R^1$ is —C(=O)NHSO$_2R^E$. In some embodiments, $R^E$ is $C_1$-$C_6$ alkyl. In some embodiments, $R^E$ is —CH$_3$ or —CH$_2$CH$_3$. In some embodiments, $R^D$ is H, —CH$_3$ or —CH$_2$CH$_3$. In some embodiments, $R^D$ is H.

In some embodiments, the compound of Formula (Ia) has the structure of Formula (IIa):

Formula (IIa)

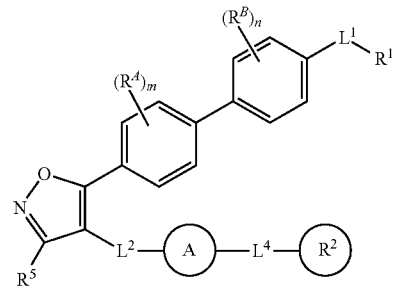

wherein,
$R^1$ is —$CO_2R^D$, —C(=O)NHSO$_2R^E$, —C(=O)N($R^D$)$_2$, —CN, or tetrazolyl;

$R^D$ is H or $C_1$-$C_6$ alkyl; $R^E$ is $C_1$-$C_6$ alkyl;

L¹ is absent, —C₁-C₄alkylene-, —C₃-C₆cycloalkylene-, —C₃-C₆cycloalkylene-C₁-C₂ alkylene-, or —C(R¹ᵃ)(R¹ᵇ)—;

each of $R^A$ and $R^B$ is independently selected from halogen, —CN, —OH, C₁-C₄alkyl, C₁-C₄fluoroalkyl, C₁-C₄fluoroalkoxy, and C₁-C₄alkoxy;

$R^5$ is H or C₁-C₄ alkyl;

m is 0 or 1; n is 0 or 1.

In some embodiments, the compound of Formula (Ia) has the structure of Formula (IIIa):

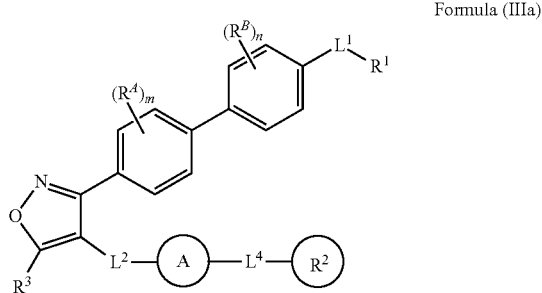

Formula (IIIa)

wherein, $R^1$ is —CO₂$R^D$, —C(=O)NHSO₂$R^E$, —C(=O)N($R^D$)₂, —CN, or tetrazolyl;

$R^D$ is H or C₁-C₆ alkyl; $R^E$ is C₁-C₆ alkyl;

L¹ is absent, —C₁-C₄alkylene-, —C₃-C₆cycloalkylene-, —C₃-C₆cycloalkylene-C₁-C₂ alkylene-, or —C(R¹ᵃ)(R¹ᵇ)—;

each of $R^A$ and $R^B$ is independently selected from halogen, —CN, —OH, C₁-C₄alkyl, C₁-C₄fluoroalkyl, C₁-C₄fluoroalkoxy, and C₁-C₄alkoxy;

$R^3$ is H or C₁-C₄ alkyl;

m is 0 or 1; n is 0 or 1.

In some embodiments, L² is absent, —C(=O)—, —S—, —S(O)—, —S(O)₂—, —N($R^D$)—, substituted or unsubstituted C₁-C₄ alkylene, and substituted or unsubstituted C₁-C₄ heteroalkylene, where if L² is substituted, then L² is substituted with R¹², where R¹² is F, —CH₃, —CH₂CH₃, —OH, —OCH₃, or —OCH₂CH₃; L⁴ is absent, a substituted or unsubstituted C₁-C₄alkylene, substituted or unsubstituted C₁-C₄heteroalkylene, —O—, —S—, —S(O)—, SO₂, —N($R^D$)—, or —C(=O)—N($R^D$)—C₁-C₄ alkylene-, where if L⁴ is substituted, then L⁴ is substituted with R¹³, where each R¹³ is F, C₁-C₄alkyl, —OH, —O$R^D$, or —N($R^D$)₂; R² is a substituted or unsubstituted C₃-C₆cycloalkyl, a substituted or unsubstituted monocyclic C₂-C₅heterocycloalkyl, a substituted or unsubstituted monocyclic C₁-C₅heteroaryl, and a substituted or unsubstituted phenyl, wherein if R² is substituted, then R² is substituted with 1 or 2 $R^C$, each $R^C$ is independently selected from halogen, —CN, —OH, —S(=O)₂R¹⁰, —C(=O)R¹⁰, —CO₂R⁹, —N(R⁹)₂, —C(=O)N(R⁹)₂, —NR⁹C(=O)R¹⁰, C₁-C₄alkyl, C₁-C₄fluoroalkyl, C₁-C₄fluoroalkoxy, C₁-C₄alkoxy, and C₁-C₄heteroalkyl.

In some embodiments, R¹ is —CO₂$R^D$ or —C(=O)NHSO₂$R^E$; L¹ is absent, —CH₂—, —CH(CH₃)—, —CH(substituted or unsubstituted benzyl)-, —C(CH₃)₂—, —CH₂CH₂—, —CH₂CH₂CH₂—, cyclopropyl-1,1-diyl, cyclopropyl-1,2-diyl, cyclobutyl-1,1-diyl, cyclopentyl-1,1-diyl, cyclohexyl-1,1-diyl, or —C(CH₂CH₂)CH₂—.

In some embodiments, L² is absent, —C(=O)—, —NH—, —N(CH₃)—, —CH₂—, —CH₂CH₂—, —CH (CH₃)—, —CH₂CH(CH₃)—, —CH(CH₃)CH₂—, —CH (OH)—, —CH(O$R^D$)—, —CH₂CH(OH)—, —CH₂CH(O$R^D$)—, —CH(OH)CH₂—, —CH(O$R^D$)CH₂—, —CH₂NH—, —CH(CH₃)NH—, —NHCH₂— or —NHCH(CH₃)—; ring A is a substituted or unsubstituted monocyclic C₁-C₅heteroarylene, or a substituted or unsubstituted phenylene, where if ring A is substituted, then ring A is substituted with 1 or 2 R¹⁴, each R¹⁴ is halogen, —CN, —OH, C₁-C₄alkyl, C₁-C₄fluoroalkyl, C₁-C₄fluoroalkoxy, or C₁-C₄alkoxy; L⁴ is absent, —CH₂—, —CH(CH₃)—, —CH₂CH₂—, —CH₂CH(CH₃)—, —CH(CH₃)CH₂—, —CH(OH)—, —O—, —OCH₂—, —CH₂O—, —S—, —S(O)—, SO₂, —CH₂S—, —CH₂S(O)—, —CH₂SO₂, —SCH₂—, —S(O)CH₂—, —SO₂CH₂—, —NH—, —N(CH₃)—, —NHCH₂—, —CH₂NH—, —C(=O)—NH—CH₂—, —C(=O)—NH—CH(CH₃)— or —C(=O)—N(CH₃)—CH(CH₃)—; R² is a substituted or unsubstituted monocyclic C₁-C₅heteroaryl, or a substituted or unsubstituted phenyl, wherein if R² is substituted, then R² is substituted with 1 or 2 $R^C$.

In some embodiments, L¹ is cyclopropyl-1,1-diyl, cyclopropyl-1,2-diyl, cyclobutyl-1,1-diyl, cyclopentyl-1,1-diyl, cyclohexyl-1,1-diyl, or —C(CH₂CH₂)CH₂—; L² is —NH—, —N(CH₃)—, —CH₂—, —CH(CH₃)—, —CH(OH)—, —CH(O$R^D$)—, —NHCH₂— or —NHCH(CH₃)—; L⁴ is absent, —CH₂—, —CH(CH₃)—, —CH(OH)—, —O—, —OCH₂—, —CH₂O—, —S—, —S(O)—, SO₂, —CH₂S—, —CH₂S(O)—, —CH₂SO₂, —SCH₂—, —S(O)CH₂—, —SO₂CH₂—, —NHCH₂—, —CH₂NH—.

In some embodiments, ring A is a substituted or unsubstituted phenylene, where if ring A is substituted, then ring A is substituted with R¹⁴, R¹⁴ is halogen, —CN, —OH, C₁-C₄alkyl, C₁-C₄fluoroalkyl, C₁-C₄fluoroalkoxy, or C₁-C₄alkoxy.

In some embodiments, ring A is a substituted or unsubstituted monocyclic C₁-C₅heteroarylene containing 0-4 N atoms, 0 or 1 O atoms and 0 or 1 S atoms, where if ring A is substituted, then ring A is substituted with R¹⁴, R¹⁴ is halogen, —CN, —OH, C₁-C₄alkyl, C₁-C₄fluoroalkyl, C₁-C₄fluoroalkoxy, or C₁-C₄alkoxy.

In some embodiments, ring A is a substituted or unsubstituted furanylene, substituted or unsubstituted thienylene, substituted or unsubstituted pyrrolylene, substituted or unsubstituted oxazolylene, substituted or unsubstituted thiazolylene, imidazolylene, substituted or unsubstituted pyrazolylene, substituted or unsubstituted triazolylene, substituted or unsubstituted tetrazolylene, substituted or unsubstituted isoxazolylene, substituted or unsubstituted isothiazolylene, substituted or unsubstituted oxadiazolylene, substituted or unsubstituted thiadiazolylene, substituted or unsubstituted pyridinylene, substituted or unsubstituted pyrimidinylene, substituted or unsubstituted pyrazinylene, substituted or unsubstituted pyridazinylene, or a substituted or unsubstituted triazinylene, where if ring A is substituted, then ring A is substituted with R¹⁴, R¹⁴ is halogen, —CN, —OH, C₁-C₄alkyl, C₁-C₄fluoroalkyl, C₁-C₄fluoroalkoxy, or C₁-C₄alkoxy.

In some embodiments, ring A is a substituted or unsubstituted 5-membered monocyclic C₁-C₄heteroarylene containing 1-4 N atoms, 0 or 1 O atoms and 0 or 1 S atoms, where if ring A is substituted, then ring A is substituted with 1 or 2 R¹⁴, each R¹⁴ is independently selected from halogen, —CN, —OH, —CH₃, —CH₂CH₃, —CF₃, —OCF₃, —OCH₃ and —OCH₂CH₃.

In some embodiments, ring A is
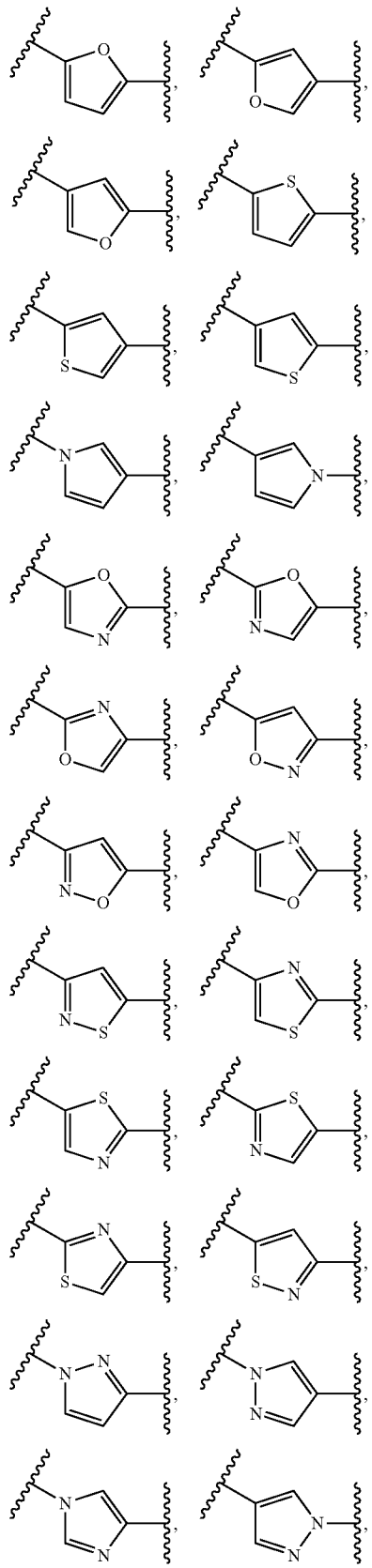
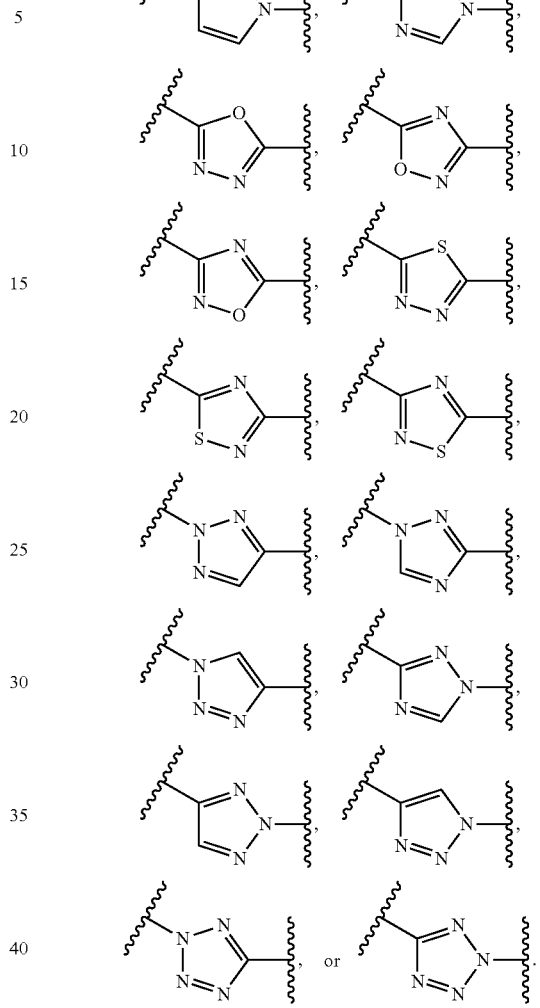
In some embodiments, ring A is a substituted or unsubstituted 6-membered monocyclic $C_3$-$C_5$ heteroarylene containing 1-3 N atoms, where if ring A is substituted, then ring A is substituted with 1 or 2 $R^{14}$, each $R^{14}$ is independently selected from halogen, —CN, —OH, —$CH_3$, —$CH_2CH_3$, —$CF_3$, —$OCF_3$, —$OCH_3$ and —$OCH_2CH_3$.
In some embodiments, ring A is
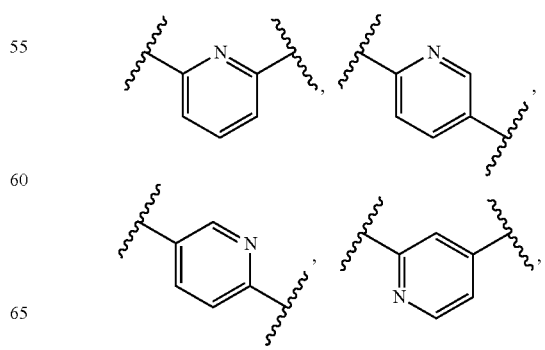

-continued

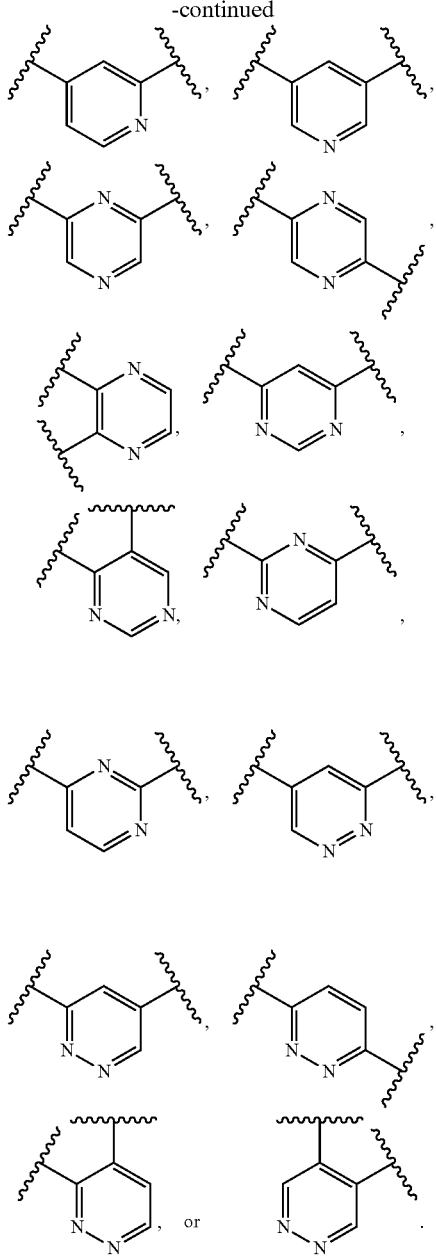

In some embodiments, the compound of Formula (Ia) has the structure of Formula (IV):

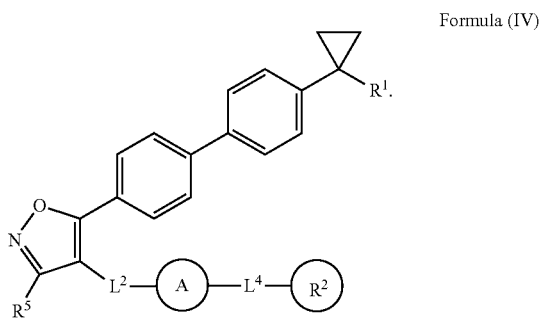

In some embodiments, the compound of Formula (Ia) has the structure of Formula (V):

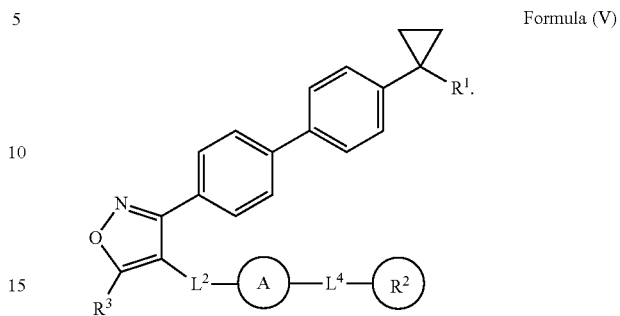

In some embodiments, $R^1$ is —$CO_2R^D$, or —C(=O)NHSO$_2R^E$; $R^D$ is H or $C_1$-$C_4$ alkyl; $R^E$ is $C_1$-$C_4$ alkyl; $L^2$ is —CH$_2$—, —CH(CH$_3$)—, or —CH(OH)—; ring A is a substituted or unsubstituted 5-membered monocyclic $C_1$-$C_4$heteroarylene containing 1-3 N atoms, 0 or 1 O atoms and 0 or 1 S atoms, where if ring A is substituted, then ring A is substituted with $R^{14}$, $R^{14}$ is halogen, —CN, —OH, —CH$_3$, —CH$_2$CH$_3$, —CF$_3$, —OCF$_3$, —OCH$_3$ or —OCH$_2$CH$_3$; $L^4$ is —CH$_2$— or —CH(CH$_3$)—; $R^2$ is a substituted or unsubstituted phenyl, wherein if $R^2$ is substituted, then $R^2$ is substituted with 1 or 2 $R^C$, each $R^C$ is halogen, —CN, —OH, $C_1$-$C_4$alkyl, $C_1$-$C_4$fluoroalkyl, $C_1$-$C_4$fluoroalkoxy, or $C_1$-$C_4$alkoxy.

In some embodiments, $R^1$ is —CO$_2$H or —C(=O)NHSO$_2$CH$_3$; $L^2$ is —CH$_2$— or —CH(OH)—; $L^4$ is —CH$_2$—.

In some embodiments, $R^1$ is —$CO_2R^D$, or —C(=O)NHSO$_2R^E$; $R^D$ is H or $C_1$-$C_4$alkyl; $R^E$ is $C_1$-$C_4$alkyl; $L^2$ is —NH—, —CH$_2$—, —CH(CH$_3$)—, —CH(OH)—, —NHCH$_2$— or —NHCH(CH$_3$)—; ring A is a substituted or unsubstituted pyridinylene, where if ring A is substituted, then ring A is substituted with $R^{14}$, $R^{14}$ is halogen, —CN, —OH, —CH$_3$, —CH$_2$CH$_3$, —CF$_3$, —OCF$_3$, —OCH$_3$ or —OCH$_2$CH$_3$; $L^4$ is absent, —CH$_2$—, or —CH(CH$_3$)—; $R^2$ is a substituted or unsubstituted phenyl, wherein if $R^2$ is substituted, then $R^2$ is substituted with 1 or 2 $R^C$, $R^C$ is halogen, —CN, —OH, $C_1$-$C_4$alkyl, $C_1$-$C_4$fluoroalkyl, $C_1$-$C_4$fluoroalkoxy, or $C_1$-$C_4$alkoxy.

In some embodiments, $R^1$ is or —CO$_2$H or —C(=O)NHSO$_2$CH$_3$; $L^2$ is —NH—; $L^4$ is absent or —CH$_2$—.

Any combination of the groups described above for the various variables is contemplated herein. Throughout the specification, groups and substituents thereof are chosen by one skilled in the field to provide stable moieties and compounds.

In some embodiments, provided is a compound described in Table 1, 2, and/or 3, or a pharmaceutically acceptable salt thereof.

In some embodiments, the compound of Formula (I), (Ia), (II), (IIa), (III), (IIIa), (IV) or (V) is an antagonist of a LPA receptor.

In some embodiments, the compound of Formula (I), (Ia), (II), (IIa), (III), (IIIa), (IV) or (V) is an antagonist of LPA$_1$.

In some embodiments, the compound of Formula (I), (Ia), (II), (IIa), (III), (IIIa), (IV) or (V) is an antagonist of LPA$_2$.

In some embodiments, the compound of Formula (I), (Ia), (II), (IIa), (III), (IIIa), (IV) or (V) is an antagonist of LPA$_3$.

In some embodiments, presented herein are compounds selected from active metabolites, tautomers, pharmaceutically acceptable solvates, pharmaceutically acceptable salts or prodrugs of a compound of Formula (I), (Ia), (II), (IIa), (III), (IIIa), (IV) or (V).

In some embodiments, provided is a pharmaceutical composition comprising a therapeutically effective amount of a compound of Formula (I), (Ia), (II), (IIa), (III), (IIIa), (IV) or (V). In some embodiments, the pharmaceutical composition also contains at least one pharmaceutically acceptable inactive ingredient.

In some embodiments, provided is a pharmaceutical composition comprising a therapeutically effective amount of a compound of Formula (I), (Ia), (II), (IIa), (III), (IIIa), (IV) or (V), or a pharmaceutically acceptable salt thereof, and at least one pharmaceutically acceptable inactive ingredient. In one aspect, the pharmaceutical composition is formulated for intravenous injection, subcutaneous injection, oral administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the pharmaceutical composition further comprises one or more additional therapeutically active agents selected from: corticosteroids, immunosuppresants, analgesics, anti-cancer agent, anti-inflammatories, chemokine receptor antagonists, bronchodilators, leukotriene receptor antagonists, leukotriene formation inhibitors, monoacylglycerol kinase inhibitors, phospholipase $A_1$ inhibitors, phospholipase $A_2$ inhibitors, and lysophospholipase D (lysoPLD) inhibitors, autotaxin inhibitors, decongestants, antihistamines, mucolytics, anticholinergics, antitussives, expectorants, and β-2 agonists.

In some embodiments, provided is a method comprising administering a compound of Formula (I), (Ia), (II), (IIa), (III), (IIIa), (IV) or (V) to a human with a LPA-dependent or LPA-mediated disease or condition. In some embodiments, the human is already being administered one or more additional therapeutically active agents other than a compound of Formula (I), (Ia), (II), (IIa), (III), (IIIa), (IV) or (V). In some embodiments, the method further comprises administering one or more additional therapeutically active agents other than a compound of Formula (I), (Ia), (II), (IIa), (III), (IIIa), (IV) or (V).

In some embodiments, the one or more additional therapeutically active agents other than a compound of Formula (I), (Ia), (II), (IIa), (III), (IIIa), (IV) or (V) are selected from: corticosteroids, immunosuppresants, analgesics, anti-cancer agent, anti-inflammatories, chemokine receptor antagonists, bronchodilators, leukotriene receptor antagonists, leukotriene formation inhibitors, monoacylglycerol kinase inhibitors, phospholipase $A_1$ inhibitors, phospholipase $A_2$ inhibitors, and lysophospholipase D (lysoPLD) inhibitors, autotaxin inhibitors, decongestants, antihistamines, mucolytics, anticholinergics, antitussives, expectorants, and β-2 agonists.

Pharmaceutical formulations described herein are administerable to a subject in a variety of ways by multiple administration routes, including but not limited to, oral, parenteral (e.g., intravenous, subcutaneous, intramuscular), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compound of Formula (I), (Ia), (II), (IIa), (III), (IIIa), (IV) or (V) is administered orally.

In some embodiments, the compound of Formula (I), (Ia), (II), (IIa), (III), (IIIa), (IV) or (V) is administered topically. In such embodiments, the compound of Formula (I), (Ia), (II), (IIa), (III), (IIIa), (IV) or (V) is formulated into a variety of topically administrable compositions, such as solutions, suspensions, lotions, gels, pastes, shampoos, scrubs, rubs, smears, medicated sticks, medicated bandages, balms, creams or ointments. Such pharmaceutical compounds can contain solubilizers, stabilizers, tonicity enhancing agents, buffers and preservatives. In one aspect, the compound of Formula (I), (Ia), (II), (IIa), (III), (IIIa), (IV) or (V) is administered topically to the skin.

In another aspect, the compound of Formula (I), (Ia), (II), (IIa), (III), (IIIa), (IV) or (V) is administered by inhalation. In one embodiment, the compound of Formula (I), (Ia), (II), (IIa), (III), (IIIa), (IV) or (V) is administered by inhalation that directly targets the pulmonary system.

In another aspect, the compound of Formula (I), (Ia), (II), (IIa), (III), (IIIa), (IV) or (V) is formulated for intranasal administration. Such formulations include nasal sprays, nasal mists, and the like.

In another aspect, the compound of Formula (I), (Ia), (II), (IIa), (III), (IIIa), (IV) or (V) is formulated as eye drops.

In another aspect is the use of a compound of Formula (I), (Ia), (II), (IIa), (III), (IIIa), (IV) or (V) in the manufacture of a medicament for treating a disease, disorder or conditions in which the activity of at least one LPA receptor contributes to the pathology and/or symptoms of the disease or condition. In one embodiment of this aspect, the LPA is selected from $LPA_1$, $LPA_2$, $LPA_3$, $LPA_4$, $LPA_5$ and $LPA_6$. In one aspect, the LPA receptor is $LPA_1$. In one aspect, the disease or condition is any of the diseases or conditions specified herein.

In any of the aforementioned aspects are further embodiments in which: (a) the effective amount of the compound of Formula (I), (Ia), (II), (IIa), (III), (IIIa), (IV) or (V) is systemically administered to the mammal; and/or (b) the effective amount of the compound is administered orally to the mammal; and/or (c) the effective amount of the compound is intravenously administered to the mammal; and/or (d) the effective amount of the compound is administered by inhalation; and/or (e) the effective amount of the compound is administered by nasal administration; or and/or (f) the effective amount of the compound is administered by injection to the mammal; and/or (g) the effective amount of the compound is administered topically to the mammal; and/or (h) the effective amount of the compound is administered by ophthalmic administration; and/or (i) the effective amount of the compound is administered rectally to the mammal; and/or (j) the effective amount is adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Also provided is a method of inhibiting the physiological activity of LPA in a mammal comprising administering a therapuetically effective amount of a compound of Formula (I), (Ia), (II), (IIa), (III), (IIIa), (IV) or (V) or a pharmaceutically acceptable salt thereof to the mammal in need thereof.

In one aspect, provided is a medicament for treating a LPA-dependent or LPA-mediated disease or condition in a mammal comprising a therapuetically effective amount of a compound of Formula (I), (Ia), (II), (IIa), (III), (IIIa), (IV) or (V).

In some cases disclosed herein is the use of a compound of Formula (I), (Ia), (II), (IIa), (III), (IIIa), (IV) or (V) in the manufacture of a medicament for the treatment of a LPA-dependent or LPA-mediated disease or condition.

In some cases disclosed herein is the use of a compound of Formula (I), (Ia), (II), (IIa), (III), (IIIa), (IV) or (V) in the treatment or prevention of a LPA-dependent or LPA-mediated disease or condition.

In one aspect, is a method for treating or preventing a LPA-dependent or LPA-mediated disease or condition in a mammal comprising administering a therapuetically effective amount of a compound of Formula (I), (Ia), (II), (IIa), (III), (IIIa), (IV) or (V).

In one aspect, LPA-dependent or LPA-mediated diseases or conditions include, but are not limited to, fibrosis of organs or tissues, scarring, liver diseases, dermatological conditions, cancer, cardiovascular disease, respiratory diseases or conditions, inflammatory disease, gastrointestinal tract disease, renal disease, urinary tract-associated disease, inflammatory disease of lower urinary tract, dysuria, frequent urination, pancreas disease, arterial obstruction, cerebral infarction, cerebral hemorrhage, pain, peripheral neuropathy, and fibromyalgia.

In one aspect, the LPA-dependent or LPA-mediated disease or condition is a respiratory disease or condition. In some embodiments, the respiratory disease or condition is asthma, chronic obstructive pulmonary disease (COPD), pulmonary fibrosis, pulmonary arterial hypertension or acute respiratory distress syndrome.

In some embodiments, the LPA-dependent or LPA-mediated disease or condition is selected from idiopathic pulmonary fibrosis; other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease); radiation induced fibrosis; chronic obstructive pulmonary disease (COPD); scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; focal segmental glomerular sclerosis; IgA nephropathy; hypertension; Alport; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; and autoimmune hepatitis; corneal scarring; hypertrophic scarring; Duputren disease, keloids, cutaneous fibrosis; cutaneous scleroderma; spinal cord injury/fibrosis; myelofibrosis; vascular restenosis; atherosclerosis; arteriosclerosis; Wegener's granulomatosis; Peyronie's disease, chronic lymphocytic leukemia, tumor metastasis, transplant organ rejection, endometreosis, neonatal respiratory distress syndrome and neuropathic pain.

In one aspect, the LPA-dependent or LPA-mediated disease or condition is described herein.

In one aspect, provided is a method for the treatment or prevention of organ fibrosis in a mammal comprising administering a therapeutically effective amount of a compound of Formula (I), (Ia), (II), (IIa), (III), (IIIa), (IV) or (V) or a pharmaceutically acceptable salt thereof to a mammal in need thereof.

In one aspect, the organ fibrosis comprises lung fibrosis, renal fibrosis, or hepatic fibrosis.

In one aspect, provided is a method of improving lung function in a mammal comprising administering a therapeutically effective amount of a compound of Formula (I), (Ia), (II), (IIa), (III), (IIIa), (IV) or (V) or a pharmaceutically acceptable salt thereof to the mammal in need thereof. In one aspect, the mammal has been diagnosed as having lung fibrosis.

In one aspect, compounds disclosed herein are used to treat idiopathic pulmonary fibrosis (usual interstitial pneumonia) in a mammal.

In some embodiments, compounds disclosed herein are used to treat diffuse parenchymal interstitial lung diseases in mammal: iatrogenic drug induced, occupational/environmental (Farmer lung), granulomatous diseases (sarcoidosis, hypersensitivity pneumonia), collagen vascular disease (scleroderma and others), alveolar proteinosis, langerhans cell granulonmatosis, lymphangioleiomyomatosis, Hermansky-Pudlak Syndrome, Tuberous sclerosis, neurofibromatosis, metabolic storage disorders, familial interstitial lung disease.

In some embodiments, compounds disclosed herein are used to treat post-transplant fibrosis associated with chronic rejection in a mammal: Bronchiolitis obliterans for lung transplant.

In some embodiments, compounds disclosed herein are used to treat cutaneous fibrosis in a mammal: cutaneous scleroderma, Dupuytren disease, keloids.

In one aspect, compounds disclosed herein are used to treat hepatic fibrosis with or without cirrhosis in a mammal: toxic/drug induced (hemochromatosis), alcoholic liver disease, viral hepatitis (hepatitis B virus, hepatitis C virus, HCV), nonalcoholic liver disease (NASH), metabolic and auto-immune.

In one aspect, compounds disclosed herein are used to treat renal fibrosis in a mammal: tubulointerstitium fibrosis, glomerular sclerosis.

In any of the aforementioned aspects involving the treatment of LPA dependent diseases or conditions are further embodiments comprising administering at least one additional agent in addition to the administartion of a compound having the structure of Formula (I), (Ia), (II), (IIa), (III), (IIIa), (IV) or (V). In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

In some embodiments, compounds provided herein are used as antagonists of at least one LPA receptor. In some embodiments, compounds provided herein are used for inhibiting the activity of at least one LPA receptor or for the treatment of a disease or condition that would benefit from inhibition of the activity of at least one LPA receptor. In one aspect, the LPA receptor is $LPA_1$.

In other embodiments, compounds provided herein are used for the formulation of a medicament for the inhibition of $LPA_1$ activity.

Articles of manufacture, which include packaging material, a compound of Formula (I), (Ia), (II), (IIa), (III), (IIIa), (IV) or (V), within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for inhibiting the activity of at least one LPA receptor, or for the treatment, prevention or amelioration of one or more symptoms of a disease or condition that would benefit from inhibition of the activity of at least one LPA receptor, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description

DETAILED DESCRIPTION OF THE INVENTION

Lysophospholipids are membrane-derived bioactive lipid mediators. Lysophospholipids include, but are not limited to, lysophosphatidic acid (1-acyl-2-hydroxy-sn-glycero-3-phosphate; LPA), sphingosine 1-phosphate (S1P), lysophosphatidylcholine (LPC), and sphingosylphosphorylcholine (SPC). Lysophospholipids affect fundamental cellular functions that include cellular proliferation, differentiation, survival, migration, adhesion, invasion, and morphogensis. These functions influence many biological processes that include neurogensis, angiogenesis, wound healing, immunity, and carcinogenesis.

LPA acts through sets of specific G protein-coupled receptors (GPCRs) in an autocrine and paracrine fashion. LPA binding to its cognate GPCRs ($LPA_1$, $LPA_2$, $LPA_3$, $LPA_4$, $LPA_5$, $LPA_6$) activates intracellular signaling pathways to produce a variety of biological responses.

Lysophospholipids, such as LPA, are quantitatively minor lipid species compared to their major phospholipid counterparts (e.g., phosphatidylcholine, phosphatidylethanolamine, and sphingomyelin). LPA has a role as a biological effector molecule, and has a diverse range of physiological actions such as, but not limited to, effects on blood pressure, platelet activation, and smooth muscle contraction, and a variety of cellular effects, which include cell growth, cell rounding, neurite retraction, and actin stress fiber formation and cell migration. The effects of LPA are predominantly receptor mediated.

Activation of the LPA receptors ($LPA_1$, $LPA_2$, $LPA_3$, $LPA_4$, $LPA_5$, $LPA_6$) with LPA mediates a range of downstream signaling cascades. These include, but are not limited to, mitogen-activated protein kinase (MAPK) activation, adenylyl cyclase (AC) inhibition/activation, phospholipase C (PLC) activation/$Ca^{2+}$ mobilization, arachidonic acid release, Akt/PKB activation, and the activation of small GTPases, Rho, ROCK, Rac, and Ras. Other pathways that are affected by LPA receptor activation include, but are not limited to, cyclic adenosine monophosphate (cAMP), cell division cycle 42/GTP-binding protein (Cdc42), proto-oncogene serine/threonine-protein kinase Raf (c-RAF), proto-oncogene tyrosine-protein kinase Src (c-src), extracellular signal-regulated kinase (ERK), focal adhesion kinase (FAK), guanine nucleotide exchange factor (GEF), glycogen synthase kinase 3b (GSK3b), c-jun amino-terminal kinase (JNK), MEK, myosin light chain II (MLC II), nuclear factor kB (NF-kB), N-methyl-D-aspartate (NMDA) receptor activation, phosphatidylinositol 3-kinase (PI3K), protein kinase A (PKA), protein kinase C (PKC), ras-related C3 botulinum toxin substrate 1 (RAC1). The actual pathway and realized end point are dependent on a range of variables that include receptor usage, cell type, expression level of a receptor or signaling protein, and LPA concentration. Nearly all mammalian cells, tissues and organs co-express several LPA-receptor subtypes, which indicates that LPA receptors signal in a cooperative manner. $LPA_1$, $LPA_2$, and $LPA_3$ share high amino acid sequence similarity.

LPA is produced from activated platelets, activated adipocytes, neuronal cells, and other cell types. Serum LPA is produced by multiple enzymatic pathways that involve monoacylglycerol kinase, phospholipase $A_1$, secretory phospholipase $A_2$, and lysophospholipase D (lysoPLD), including autotaxin. Several enzymes are involved in LPA degradation: lysophospholipase, lipid phosphate phosphatase, and LPA acyl transferase such as endophilin. LPA concentrations in human serum are estimated to be 1-5 µM. Serum LPA is bound to albumin, low-density lipoproteins, or other proteins, which possibly protect LPA from rapid degradation. LPA molecular species with different acyl chain lengths and saturation are naturally occurring, including 1-palmitoyl (16:0), 1-palmitoleoyl (16:1), 1-stearoyl (18:0), 1-oleoyl (18:1), 1-linoleoyl (18:2), and 1-arachidonyl (20:4) LPA. Quantitatively minor alkyl LPA has biological activities similar to acyl LPA, and different LPA species activate LPA receptor subtypes with varied efficacies.

LPA Receptors $LPA_1$ (previously called VZG-1/EDG-2/mrec1.3) couples with three types of G proteins, $G_{i/o}$, $G_q$, and $G_{12/13}$. Through activation of these G proteins, LPA induces a range of cellular responses through $LPA_1$ including but not limited to: cell proliferation, serum-response element (SRE) activation, mitogen-activated protein kinase (MAPK) activation, adenylyl cyclase (AC) inhibition, phospholipase C (PLC) activation, $Ca^{2+}$ mobilization, Akt activation, and Rho activation.

Wide expression of $LPA_1$ is observed in adult mice, with clear presence in testis, brain, heart, lung, small intestine, stomach, spleen, thymus, and skeletal muscle. Similarly, human tissues also express $LPA_1$; it is present in brain, heart, lung, placenta, colon, small intestine, prostate, testis, ovary, pancreas, spleen, kidney, skeletal muscle, and thymus.

$LPA_2$ (EDG-4) also couples with three types of G proteins, $G_{i/o}$, $G_q$, and $G_{12/13}$, to mediate LPA-induced cellular signaling. Expression of $LPA_2$ is observed in the testis, kidney, lung, thymus, spleen, and stomach of adult mice and in the human testis, pancreas, prostate, thymus, spleen, and peripheral blood leukocytes. Expression of $LPA_2$ is upregulated in various cancer cell lines, and several human $LPA_2$ transcriptional variants with mutations in the 3'-untranslated region have been observed. Targeted deletion of $LPA_2$ in mice has not shown any obvious phenotypic abnormalities, but has demonstrated a significant loss of normal LPA signaling (e.g., PLC activation, $Ca^{2+}$ mobilization, and stress fiber formation) in primary cultures of mouse embryonic fibroblasts (MEFs). Creation of lpa1(−/−) lpa2 (−/−) double-null mice has revealed that many LPA-induced responses, which include cell proliferation, AC inhibition, PLC activation, $Ca^{2+}$ mobilization, JNK and Akt activation, and stress fiber formation, are absent or severely reduced in double-null MEFs. All these responses, except for AC inhibition (AC inhibition is nearly abolished in $LPA_1$ (−/−) MEFs), are only partially affected in either $LPA_1$ (−/−) or $LPA_2$ (−/−) MEFs. $LPA_2$ contributes to normal LPA-mediated signaling responses in at least some cell types (Choi et al, *Biochemica et Biophysica Acta* 2008, 1781, p 531-539).

$LPA_3$ (EDG-7) is distinct from $LPA_1$ and $LPA_2$ in its ability to couple with $G_{i/O}$ and $G_q$ but not $G_{12/13}$ and is much less responsive to LPA species with saturated acyl chains. $LPA_3$ can mediate pleiotropic LPA-induced signaling that includes PLC activation, $Ca^{2+}$ mobilization, AC inhibition/activation, and MAPK activation. Overexpression of $LPA_3$ in neuroblastoma cells leads to neurite elongation, whereas that of $LPA_1$ or $LPA_2$ results in neurite retraction and cell rounding when stimulated with LPA. Expression of $LPA_3$ is observed in adult mouse testis, kidney, lung, small intestine, heart, thymus, and brain. In humans, it is found in the heart, pancreas, prostate, testis, lung, ovary, and brain (frontal cortex, hippocampus, and amygdala).

$LPA_4$ (p2y$_9$/GPR23) is of divergent sequence compared to $LPA_1$, $LPA_2$, and $LPA_3$ with closer similarity to the platelet-activating factor (PAF) receptor. $LPA_4$ mediates LPA induced $Ca^{2+}$ mobilization and cAMP accumulation, and functional coupling to the G protein Gs for AC activation, as well as coupling to other G proteins. The $LPA_4$ gene is expressed in the ovary, pancreas, thymus, kidney and skeletal muscle.

$LPA_5$ (GPR92) is a member of the purinocluster of GPCRs and is structurally most closely related to $LPA_4$. $LPA_5$ is expressed in human heart, placenta, spleen, brain, lung and gut. $LPA_5$ also shows very high expression in the CD8+ lymphocyte compartment of the gastrointestinal tract.

$LPA_6$ (p2y5) is a member of the purinocluster of GPCRs and is structurally most closely related to $LPA_4$. $LPA_6$ is an LPA receptor coupled to the G12/13-Rho signaling pathways and is expressed in the inner root sheaths of human hair follicles.

Illustrative Biological Activity

Wound Healing

Normal wound healing occurs by a highly coordinated sequence of events in which cellular, soluble factors and matrix components act in concert to repair the injury. The healing response can be described as taking place in four broad, overlapping phases-hemostasis, inflammation, proliferation, and remodeling. Many growth factors and cytokines are released into a wound site to initiate and perpetuate wound healing processes.

When wounded, damaged blood vessels activate platelets. The activated platelets play pivotal roles in subsequent repair processes by releasing bioactive mediators to induce cell proliferation, cell migration, blood coagulation, and angiogenesis. LPA is one such mediator that is released from activated platelets; this induces platelet aggregation along with mitogenic/migration effects on the surrounding cells, such as endothelial cells, smooth muscle cells, fibroblasts, and keratinocytes.

Topical application of LPA to cutaneous wounds in mice promotes repair processes (wound closure and increased neoepithelial thickness) by increasing cell proliferation/migration without affecting secondary inflammation.

Activation of dermal fibroblasts by growth factors and cytokines leads to their subsequent migration from the edges of the wound into the provisional matrix formed by the fibrin clot whereupon the fibroblasts proliferate and start to restore the dermis by secreting and organizing the characteristic dermal extracellular matrix (ECM). The increasing number of fibroblasts within the wound and continuous precipitation of ECM enhances matrix rigidity by applying small tractional forces to the newly formed granulation tissue. The increase in mechanical stress, in conjunction with transforming growth factor β (TGFβ), induces α-smooth muscle actin (α-SMA) expression and the subsequent transformation of fibroblasts into myofibroblasts. Myofibroblasts facilitate granulation tissue remodeling via myofibroblast contraction and through the production of ECM components.

LPA regulates many important functions of fibroblasts in wound healing, including proliferation, migration, differentiation and contraction. Fibroblast proliferation is required in wound healing in order to fill an open wound. In contrast, fibrosis is characterized by intense proliferation and accumulation of myofibroblasts that actively synthesize ECM and proinflammatory cytokines. LPA can either increase or suppress the proliferation of cell types important in wound healing, such as epithelial and endothelial cells (EC), macrophages, keratinocytes, and fibroblasts. A role for $LPA_1$ in LPA-induced proliferation was provided by the observation that LPA-stimulated proliferation of fibroblasts isolated from $LPA_1$ receptor null mice was attenuated (Mills et al, *Nat Rev. Cancer* 2003; 3: 582-591). LPA induces cytoskeletal changes that are integral to fibroblast adhesion, migration, differentiation and contraction.

Fibrosis

Tissue injury initiates a complex series of host wound-healing responses; if successful, these responses restore normal tissue structure and function. If not, these responses can lead to tissue fibrosis and loss of function.

For the majority of organs and tissues the development of fibrosis involves a multitude of events and factors. Molecules involved in the development of fibrosis include proteins or peptides (profibrotic cytokines, chemokines, metalloproteinases etc.) and phospholipids. Phospholipids involved in the development of fibrosis include platelet activating factor (PAF), phosphatidyl choline, sphingosine-1 phosphate (S1P) and lysophosphatidic acid (LPA).

A number of muscular dystrophies are characterized by a progressive weakness and wasting of musculature, and by extensive fibrosis. It has been shown that LPA treatment of cultured myoblasts induced significant expression of connective tissue growth factor (CTGF). CTGF subsequently induces collagen, fibronectin and integrin expression and induces dedifferentiation of these myoblasts. Treatment of a variety of cell types with LPA induces reproducible and high level induction of CTGF (J. P. Pradere, et al., $LPA_1$ receptor activation promotes renal interstitial fibrosis, *J. Am. Soc. Nephrol.* 18 (2007) 3110-3118; N. Wiedmaier, et al., *Int J Med Microbiol;* 298(3-4):231-43, 2008). CTGF is a profibrotic cytokine, signaling down-stream and in parallel with TGFβ.

CTGF expression by gingival epithelial cells, which are involved in the development of gingival fibromatosis, was found to be exacerbated by LPA treatment (A. Kantarci, et al., *J. Pathol.* 210 (2006) 59-66).

LPA is associated with the progression of liver fibrosis. In vitro, LPA induces stellate cell and hepatocyte proliferation. These activated cells are the main cell type responsible for the accumulation of ECM in the liver. Furthermore, LPA plasma levels rise during $CCl_4$-induced liver fibrosis in rodents, or in hepatitis C virus-induced liver fibrosis in human (N. Watanabe, et al., Plasma lysophosphatidic acid level and serum autotaxin activity are increased in liver injury in rats in relation to its severity, *Life Sci.* 81 (2007) 1009-1015; N. Watanabe, et al., *J. Clin. Gastroenterol.* 41 (2007) 616-623).

An increase of phospholipid concentrations in the bronchoalveolar lavage fluid in rabbits and rodents injected with bleomycin has been reported (K. Kuroda, et al., Phospholipid concentration in lung lavage fluid as biomarker for pulmonary fibrosis, *Inhal. Toxicol.* 18 (2006) 389-393; K. Yasuda, et al., *Lung* 172 (1994) 91-102).

LPA is associated with heart disease and mycocardial remodeling. Serum LPA levels are increased after myocardial infarction in patients and LPA stimulates rat cardiac fibroblast proliferation and collagen production (Chen et al. *FEBS Lett.* 2006 Aug. 21; 580(19):4737-45).

Pulmonary Fibrosis

In the lung, aberrant wound healing responses to injury contribute to the pathogenesis of fibrotic lung diseases. Fibrotic lung diseases, such as idiopathic pulmonary fibrosis (IPF), are associated with high morbidity and mortality.

LPA is an important mediator of fibroblast recruitment in pulmonary fibrosis. LPA and $LPA_1$ play key pathogenic roles in pulmonary fibrosis. Fibroblast chemoattractant activity plays an important role in the lungs in patients with pulmonary fibrosis. Profibrotic effects of $LPA_1$-receptor stimulation is explained by $LPA_1$-receptor-mediated vascular leakage and increased fibroblast recruitment, both profibrotic events. The LPA-$LPA_1$ pathway has a role in mediating fibroblast migration and vascular leakage in IPF. The end result is the aberrant healing process that characterises this fibrotic condition.

The $LPA_1$ receptor is the LPA receptor most highly expressed on fibroblasts obtained from patients with IPF. Furthermore, BAL obtained from IPF patients induced chemotaxis of human foetal lung fibroblasts that was blocked by the dual $LPA_1$-$LPA_3$ receptor antagonist Ki16425. In an experimental bleomycin-induced lung injury mouse model, it was shown that LPA levels were high in bronchoalveolar lavage samples compared with unexposed controls. $LPA_1$ knockout mice are protected from fibrosis after bleomycin challenge with reduced fibroblast accumulation and vascular leakage. In human subjects with IPF, high LPA levels were observed in bronchoalveolar lavage samples compared with healthy controls. Increased fibroblast chemotactic activity in these samples was inhibited by the Ki16425 indicating that fibroblast migration is mediated by the LPA-LPA receptor(s) pathway (Tager et al. *Nature Medicine, vol.* 14, no. 1, 45-54, 2008).

The LPA-$LPA_1$ pathway is crucial in fibroblast recruitment and vascular leakage in pulmonary fibrosis.

Activation of latent TGF-β by the avβ6 integrin plays a critical role in the development of lung injury and fibrosis (Munger et al. *Cell, vol.* 96, 319-328, 1999). LPA induces avβ6-mediated TGF-β activation on human lung epithelial cells (Xu et al. *Am. J. Pathology*, vol. 174, no. 2, 1264-1279, 2009). The LPA-induced avβ6-mediated TGF-β activation is mediated by the LPA2 receptor. Expression of the LPA2 receptor is increased in epithelial cells and mesenchymal cells in areas of lung fibrosis from IPF patients compared to normal human lung tissue. The LPA-LPA2 pathway contributes to the activation of the TGF-β pathway in pulmonary fibrosis. In some embodiments, compounds that inhibit LPA2 show efficacy in the treatment of lung fibrosis. In some embodiments, compounds that inhibit both LPA1 and LPA2 show improved efficacy in the treatment of lung fibrosis compared to compounds which inhibit only LPA1 or LPA2.

Renal Fibrosis

LPA and $LPA_1$ are involved in the etiology of kidney fibrosis. LPA has effects on both proliferation and contraction of glomerular mesangial cells and thus has been implicated in proliferative glomerulonephritis (C. N. Inoue, et al., *Clin. Sci.* (Colch.) 96, 431-436, 1999). In an animal model of renal fibrosis, unilateral ureteral obstruction (UUO), it was found that renal LPA receptors are expressed under basal conditions with an expression order of $LPA_2 > LPA_3 = LPA_1 \gg LPA_4$. This model mimics in an accelerated manner the development of renal fibrosis including renal inflammation, fibroblast activation and accumulation of extracellular matrix in the tubulointerstitium. UUO significantly induced $LPA_1$-receptor expression. This was paralleled by renal LPA production (3.3 fold increase) in conditioned media from kidney explants. Contralateral kidneys exhibited no significant changes in LPA release and LPA-receptors expression. This shows that a prerequisite for an action of LPA in fibrosis is met: production of a ligand (LPA) and induction of one of its receptors (the $LPA_1$ receptor) (J. P. Pradere et al., *Biochimica et Biophysica Acta* (2008), doi:10.1016/j.bbalip.2008.04.001).

In mice invalidated for the $LPA_1$ receptor ($LPA_1$ (−/−), the development of renal fibrosis was significantly attenuated. UUO mice treated with the LPA receptor antagonist Ki16425 closely resembled the $LPA_1$ (−/−) mice.

LPA can participate in intraperitoneal accumulation of monocyte/macrophages and that LPA can induce expression of the profibrotic cytokine CTGF in primary cultures of human fibroblasts (J. S. Koh, et al., *J. Clin. Invest.* 102 (1998) 716-727).

LPA treatment of a mouse epithelial renal cell line, MCT, induced a rapid increase in the expression of the profibrotic cytokine CTGF. CTGF plays a crucial role in UUO-induced tubulointerstitial fibrosis (TIF), and is involved in the profibrotic activity of TGFβ. This induction was almost completely suppressed by co-treatment with the LPA-receptor antagonist Ki16425. In one aspect, the profibrotic activity of LPA in kidney results from a direct action of LPA on kidney cells involving induction of CTGF.

Hepatic Fibrosis

LPA is implicated in liver disease and fibrosis. Plasma LPA levels and serum autotaxin (enzyme responsible for LPA production) are elevated in hepatitis patients and animal models of liver injury in correlation with increased fibrosis. LPA also regulates liver cell function. $LPA_1$ and $LPA_2$ receptors are expressed by mouse hepatic stellate cells and LPA stimulates migration of hepatic myofibroblasts.

Ocular Fibrosis

LPA is in involved in wound healing in the eye. $LPA_1$ and $LPA_3$ receptors are detectable in the normal rabbit corneal epithelial cells, keratocytes and endothelial cells and $LPA_1$ and $LPA_3$ expression are increased in corneal epithelial cells following injury.

LPA and its homologues are present in the aqueous humor and the lacrimal gland fluid of the rabbit eye and these levels are increased in a rabbit corneal injury model.

LPA induces actin stress fiber formation in rabbit corneal endothelial and epithelial cells and promotes contraction corneal fibroblasts. LPA also stimulates proliferation of human retinal pigmented epithelial cells Cardiac Fibrosis LPA is implicated in myocardial infarction and cardiac fibrosis. Serum LPA levels are increased in patients following myocardial infarction (MI) and LPA stimulates proliferation and collagen production (fibrosis) by rat cardiac fibroblasts. Both LPA1 and LPA3 receptors are highly expressed in human heart tissue.

Treatment of Fibrosis

In one aspect, a compound of Formula (I), (Ia), (II), (IIa), (III), (IIIa), (IV) or (V) is used to treat or prevent fibrosis in a mammal. In one aspect, a compound of Formula (I), (Ia), (II), (IIa), (III), (IIIa), (IV) or (V) is used to treat fibrosis of an organ or tissue in a mammal. In one aspect is a method for preventing a fibrosis condition in a mammal, the method comprising administering to the mammal at risk of developing one or more fibrosis conditions a therapeutically effective amount of a compound of Formula (I), (Ia), (II), (IIa), (III), (IIIa), (IV) or (V). In one aspect, the mammal has been exposed to one or more environmental conditions that are known to increase the risk of fibrosis of an organ or tissue. In one aspect, the mammal has been exposed to one or more environmental conditions that are known to increase the risk of lung, liver or kidney fibrosis. In one aspect, the mammal has a genetic predisposition of developing fibrosis of an organ or tissue. In one aspect, a compound of Formula (I), (Ia), (II), (IIa), (III), (IIIa), (IV) or (V) is adminstered to a mammal to prevent or minimize scarring following injury. In one aspect, injury includes surgery.

The terms "fibrosis" or "fibrosing disorder," as used herein, refers to conditions that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract.

Exemplary diseases, disorders, or conditions that involve fibrosis include, but are not limited to: Lung diseases associated with fibrosis, e.g., idiopathic pulmonary fibrosis, pulmonary fibrosis secondary to systemic inflammatory disease such as rheumatoid arthritis, scleroderma, lupus, cryptogenic fibrosing alveolitis, radiation induced fibrosis, chronic obstructive pulmonary disease (COPD), scleroderma, chronic asthma, silicosis, asbestos induced pulmonary or pleural fibrosis, acute lung injury and acute respiratory distress (including bacterial pneumonia induced, trauma induced, viral pneumonia induced, ventilator induced, non-pulmonary sepsis induced, and aspiration induced); Chronic nephropathies associated with injury/fibrosis (kidney fibrosis), e.g., glomerulonephritis secondary to systemic inflammatory diseases such as lupus and scleroderma, diabetes, glomerular nephritis, focal segmental glomerular sclerosis, IgA nephropathy, hypertension, allograft and Alport; Gut fibrosis, e.g., scleroderma, and radiation induced gut fibrosis; Liver fibrosis, e.g., cirrhosis, alcohol induced liver fibrosis, nonalcoholic steatohepatitis (NASH), biliary duct injury, primary biliary cirrhosis, infection or viral induced liver fibrosis (e.g., chronic HCV infection), and autoimmune hepatitis; Head and neck fibrosis, e.g., radiation induced; Corneal scarring, e.g., LASIK (laser-assisted in situ keratomileusis), corneal transplant, and trabeculectomy; Hypertrophic scarring and keloids, e.g., burn induced or surgical; and Other fibrotic diseases, e.g., sarcoidosis, scleroderma, spinal cord injury/fibrosis, myelofibrosis, vascular restenosis, atherosclerosis, arteriosclerosis, Wegener's granulomatosis, mixed connective tissue disease, and Peyronie's disease.

In one aspect, a mammal suffering from one of the following non-limiting exemplary diseases, disorders, or conditions will benefit from therapy with a compound of Formula (I), (Ia), (II), (IIa), (III), (IIIa), (IV) or (V): atherosclerosis, thrombosis, heart disease, vasculitis, formation of scar tissue, restenosis, phlobitis, COPD (chronic obstructive pulmonary disease), pulmonary hypertension, pulmonary fibrosis, pulmonary inflammation, bowel adhesions, bladder fibrosis and cystitis, fibrosis of the nasal passages, sinusitis, inflammation mediated by neutrophils, and fibrosis mediated by fibroblasts.

In one aspect, a compound of Formula (I), (Ia), (II), (IIa), (III), (IIIa), (IV) or (V) is adminstered to a mammal with fibrosis of an organ or tissue or with a predisposition of developing fibrosis of an organ or tissue with one or more other agents that are used to treat fibrosis. In one aspect, the one or more agents include corticosteroids. In one aspect, the one or more agents include immunosuppresants. In one aspect, the one or more agents include B-cell antagonists. In one aspect, the one or more agents include uteroglobin.

In one aspect, a compound of Formula (I), (Ia), (II), (IIa), (III), (IIIa), (IV) or (V) is used to treat a dermatological disorders in a mammal. The term "dermatological disorder," as used herein refers to a skin disorder. Such dermatological disorders include, but are not limited to, proliferative or inflammatory disorders of the skin such as, atopic dermatitis, bullous disorders, collagenoses, psoriasis, scleroderma, psoriatic lesions, dermatitis, contact dermatitis, eczema, urticaria, rosacea, wound healing, scarring, hypertrophic scarring, keloids, Kawasaki Disease, rosacea, Sjogren-Larsso Syndrome, urticaria. In one aspect, a compound of Formula (I), (Ia), (II), (IIa), (III), (IIIa), (IV) or (V) is used to treat systemic sclerosis.

Pain

Since LPA is released following tissue injury, $LPA_1$ plays an important role in the initiation of neuropathic pain. $LPA_1$, unlike $LPA_2$ or $LPA_3$, is expressed in both dorsal root ganglion (DRG) and dorsal root neurons. Using the antisense oligodeoxynucleotide (AS-ODN) for $LPA_1$ and $LPA_1$-null mice, it was found that LPA-induced mechanical allodynia and hyperalgesia is mediated in an $LPA_1$-dependent manner. $LPA_1$ and downstream Rho-ROCK activation play a role in the initiation of neuropathic pain signaling. Pretreatment with *Clostridium botulinum* C3 exoenzyme (BoTXC3, Rho inhibitor) or Y-27632 (ROCK inhibitor) completely abolished the allodynia and hyperalgesia in nerve-injured mice. LPA also induced demyelination of the dorsal root, which was prevented by BoTXC3. The dorsal root demyelination by injury was not observed in $LPA_1$-null mice or AS-ODN injected wild-type mice. LPA signaling appears to induce important neuropathic pain markers such as protein kinase Cγ (PKCγ) and a voltage-gated calcium channel $\alpha 2\delta 1$ subunit (Ca$\alpha 2\delta 1$) in an $LPA_1$ and Rho-dependent manner (M. Inoue, et al., Initiation of neuropathic pain requires lysophosphatidic acid receptor signaling, *Nat. Med.* 10 (2004) 712-718).

In one aspect, a compound of Formula (I), (Ia), (II), (IIa), (III), (IIIa), (IV) or (V) is used in the treatment of pain in a mammal. In one aspect, the pain is acute pain or chronic pain. In another aspect, the pain is neuropathic pain.

In one aspect, a compound of Formula (I), (Ia), (II), (IIa), (III), (IIIa), (IV) or (V) is used in the treatment of fibromylagia. In one aspect, fibromyalgia stems from the formation of fibrous scar tissue in contractile (voluntary) muscles. Fibrosis binds the tissue and inhibits blood flow, resulting in pain.

Cancer

Lysophospholipid receptor signaling plays a role in the etiology of cancer. Lysophosphatidic acid (LPA) and its G protein-coupled receptors (GPCRs) $LPA_1$, $LPA_2$, and/or LPA$_3$ play a role in the development of several types of cancers. The initiation, progression and metastasis of cancer involve several concurrent and sequential processes including cell proliferation and growth, survival and anti-apoptosis, migration of cells, penetration of foreign cells into defined cellular layers and/or organs, and promotion of angiogenesis. The control of each of these processes by LPA signaling in physiological and pathophysiological conditions underscores the potential therapeutic usefulness of modulating LPA signaling pathways for the treatment of cancer, especially at the level of the LPA receptors or ATX/lysoPLD. Autotaxin (ATX) is a prometastatic enzyme initially isolated from the conditioned medium of human melanoma cells that stimulates a myriad of biological activities, including angiogenesis and the promotion of cell growth, migration, survival, and differentiation through the production of LPA (*Mol Cancer Ther* 2008; 7(10):3352-62).

LPA signals through its own GPCRs leading to activation of multiple downstream effector pathways. Such downstream effector pathways play a role in cancer. LPA and its GPCRs are linked to cancer through major oncogenic signaling pathways.

LPA contributes to tumorigenesis by increasing motility and invasiveness of cells. LPA has been implicated in the initiation or progression of ovarian cancer. LPA is present at significant concentrations (2-80 µM) in the ascitic fluid of ovarian cancer patients. Ovarian cancer cells constitutively produce increased amounts of LPA as compared to normal ovarian surface epithelial cells, the precursor of ovarian epithelial cancer. Elevated LPA levels are also detected in plasma from patients with early-stage ovarian cancers compared with controls. LPA receptors (LPA2 and LPA3) are also overexpressed in ovarian cancer cells as compared to normal ovarian surface epithelial cells. LPA stimulates Cox-2 expression through transcriptional activation and post-transcriptional enhancement of Cox-2 mRNA in ovarian cancer cells. Prostaglandins produced by Cox-2 have been implicated in a number of human cancers and pharmacological inhibition of Cox-2 activity reduces colon cancer development and decreases the size and number of adenomas in patients with familial adenomatous polyposis. LPA has also been implicated in the initiation or progression of prostate cancer, breast cancer, melanoma, head and neck cancer, bowel cancer (colorectal cancer), thyroid cancer and other cancers (Gardell et al, *Trends in Molecular Medicine*, vol. 12, no. 2, p 65-75, 2006; Ishii et al, *Annu. Rev. Biochem*, 73, 321-354, 2004; Mills et al., *Nat. Rev. Cancer,* 3, 582-591, 2003; Murph et al., *Biochimica et Biophysica Acta,* 1781, 547-557, 2008).

The cellular responses to LPA are mediated through the lysophosphatidic acid receptors. For example, LPA receptors mediate both migration of and invasion by pancreatic cancer cell lines: an antagonist of LPA$_1$ and LPA$_3$ (Ki16425) and LPA$_1$-specific siRNA effectively blocked in vitro migration in response to LPA and peritoneal fluid (ascites) from pancreatic cancer patients; in addition, Ki16425 blocked the LPA-induced and ascites-induced invasion activity of a highly peritoneal metastatic pancreatic cancer cell line (Yamada et al, *J. Biol. Chem.,* 279, 6595-6605, 2004).

Colorectal carcinoma cell lines show significant expression of LPA$_1$ mRNA and respond to LPA by cell migration and production of angiogenic factors. Overexpression of LPA receptors has a role in the pathogenesis of thyroid cancer. LPA$_3$ was originally cloned from prostate cancer cells, concordant with the ability of LPA to induce autocrine proliferation of prostate cancer cells.

LPA has stimulatory roles in cancer progression in many types of cancer. LPA is produced from and induces proliferation of prostate cancer cell lines. LPA induces human colon carcinoma DLD1 cell proliferation, migration, adhesion, and secretion of angiogenic factors through LPA$_1$ signalling. In other human colon carcinoma cells lines (HT29 and WiDR), LPA enhances cell proliferation and secretion of angiogenic factors. In other colon cancer cell lines, LPA2 and LPA3 receptor activation results in proliferation of the cells. The genetic or pharmacological manipulation of LPA metabolism, specific blockade of receptor signaling, and/or inhibition of downstream signal transduction pathways, represent approaches for cancer therapies.

In one aspect, a compound of Formula (I), (Ia), (II), (IIa), (III), (IIIa), (IV) or (V) is used in the treatment of cancer. In one aspect, a compound of Formula (I), (Ia), (II), (IIa), (III), (IIIa), (IV) or (V) is used in the treatment of malignant and benign proliferative disease. In one aspect, a compound of Formula (I), (Ia), (II), (IIa), (III), (IIIa), (IV) or (V) is used to prevent or reduce proliferation of tumor cells, invasion and metastasis of carcinomas, pleural mesothelioma (Yamada, *Cancer Sci.,* 2008, 99(8), 1603-1610) or peritoneal mesothelioma, cancer pain, bone metastases (Boucharaba et al, *J. Clin. Invest.,* 2004, 114(12), 1714-1725; Boucharaba et al, *Proc. Natl. acad. Sci.,* 2006, 103(25) 9643-9648). In one aspect is a method of treating cancer in a mammal, the method comprising administering to the mammal a compound of Formula (I), (Ia), (II), (IIa), (III), (IIIa), (IV) or (V) and a second therapeutic agent, wherein the second therapeutic agent is an anti-cancer agent.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma or basal cell cancer) or hematological tumors (such as the leukemias) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenström macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sézary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenström macroglobulinemia, Wilms tumor.

The increased concentrations of LPA and vesicles in ascites from ovarian cancer patients and breast cancer effussions indicate that it could be an early diagnostic marker, a prognostic indicator or an indicator of response to therapy (Mills et al, *Nat. Rev. Cancer.*, 3, 582-591, 2003; Sutphen et al., *Cancer Epidemiol. Biomarkers Prev.* 13, 1185-1191, 2004). LPA concentrations are consistently higher in ascites samples than in matched plasma samples.

Respiratory and Allergic Disorders

In one aspect, LPA is a contributor to the pathogenesis of respiratory diseases. In one aspect the respiratory disease is asthma. Proinflammatory effects of LPA include degranulation of mast cells, contraction of smooth-muscle cells and release of cytokines from dendritic cells. Airway smooth muscle cells, epithelial cells and lung fibroblasts all show responses to LPA. LPA induces the secretion of IL-8 from human bronchial epithelial cells. IL-8 is found in increased concentrations in BAL fluids from patients with asthma, chronic obstructive lung disease, pulmonary sarcoidosis and acute respiratory distress syndrome and I1-8 has been shown to exacerbate airway inflammation and airway remodeling of asthmatics. LPA1, LPA2 and LPA3 receptors have all been shown to contribute to the LPA-induced IL-8 production. Studies cloning multiple GPCRs that are activated by LPA allowed the demonstration of the presence of mRNA for the $LPA_1$, $LPA_2$ and $LPA_3$ in the lung (J. J. A. Contos, et al., *Mol. Pharmacol.* 58, 1188-1196, 2000).

The release of LPA from platelets activated at a site of injury and its ability to promote fibroblast proliferation and contraction are features of LPA as a mediator of wound repair. In the context of airway disease, asthma is an inflammatory disease where inappropriate airway "repair" processes lead to structural "remodeling" of the airway. In asthma, the cells of the airway are subject to ongoing injury due to a variety of insults, including allergens, pollutants, other inhaled environmental agents, bacteria and viruses, leading to the chronic inflammation that characterizes asthma.

In one aspect, in the asthmatic individual, the release of normal repair mediators, including LPA, is exaggerated or the actions of the repair mediators are inappropriately prolonged leading to inappropriate airway remodeling. Major structural features of the remodeled airway observed in asthma include a thickened lamina reticularis (the basement membrane-like structure just beneath the airway epithelial cells), increased numbers and activation of myofibroblasts, thickening of the smooth muscle layer, increased numbers of mucus glands and mucus secretions, and alterations in the connective tissue and capillary bed throughout the airway wall. In one aspect, LPA contributes to these structural changes in the airway. In one aspect, LPA is involved in acute airway hyperresponsiveness in asthma. The lumen of the remodeled asthmatic airway is narrower due to the thickening of the airway wall, thus decreasing airflow. In one aspect, LPA contributes to the long-term structural remodeling and the acute hyperresponsiveness of the asthmatic airway. In one aspect, LPA contributes to the hyper-responsiveness that is a primary feature of acute exacerbations of asthma.

In addition to the cellular responses mediated by LPA, several of the LPA signaling pathway components leading to these responses are relevant to asthma. EGF receptor upregulation is induced by LPA and is also seen in asthmatic airways (M. Amishima, et al., *Am. J. Respir. Crit. Care Med.* 157, 1907-1912, 1998). Chronic inflammation is a contributor to asthma, and several of the transcription factors that are activated by LPA are known to be involved in inflammation (Ediger et al., *Eur Respir J* 21:759-769, 2003).

In one aspect, the fibroblast proliferation and contraction and extracellular matrix secretion stimulated by LPA contributes to the fibroproliferative features of other airway diseases, such as the peribronchiolar fibrosis present in chronic bronchitis, emphysema, and interstitial lung disease. Emphysema is also associated with a mild fibrosis of the alveolar wall, a feature which is believed to represent an attempt to repair alveolar damage. In another aspect, LPA plays a role in the fibrotic interstitial lung diseases and obliterative bronchiolitis, where both collagen and myofibroblasts are increased. In another aspect, LPA is involved in several of the various syndromes that constitute chronic obstructive pulmonary disease.

Administration of LPA in vivo induces airway hyper-responsiveness, itch-scratch responses, infiltration and activation of eosinophils and neutrophils, vascular remodeling, and nociceptive flexor responses. LPA also induces histamine release from mouse and rat mast cells. In an acute allergic reaction, histamine induces various responses, such as contraction of smooth muscle, plasma exudation, and mucus production. Plasma exudation is important in the airway, because the leakage and subsequent airway-wall edema contribute to the development of airway hyperresponsiveness. Plasma exudation progresses to conjunctival swelling in ocular allergic disorder and nasal blockage in allergic rhinitis (Hashimoto et al., *J Pharmacol Sci* 100, 82-87, 2006). In one aspect, plasma exudation induced by LPA is mediated by histamine release from mast cells via one or more LPA receptors. In one aspect, the LPA receptor(s) include $LPA_1$ and/or $LPA_3$. In one aspect, a compound of Formula (I), (Ia), (II), (IIa), (III), (IIIa), (IV) or (V) is used in the treatment of various allergic disorders in a mammal. In one aspect, a compound of Formula (I), (Ia), (II), (IIa), (III), (IIIa), (IV) or (V) is used in the treatment of respiratory diseases, disorders or conditions in a mammal. In one aspect, a compound of Formula (I), (Ia), (II), (IIa), (III), (IIIa), (IV) or (V) is used in the treatment of asthma in a mammal. In one aspect, a compound of Formula (I), (Ia), (II), (IIa), (III), (IIIa), (IV) or (V) is used in the treatment of chronic asthma in a mammal.

The term "respiratory disease," as used herein, refers to diseases affecting the organs that are involved in breathing, such as the nose, throat, larynx, eustachian tubes, trachea, bronchi, lungs, related muscles (e.g., diaphram and intercostals), and nerves. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

In one aspect, presented herein is the use of a compound of Formula (I), (Ia), (II), (IIa), (III), (IIIa), (IV) or (V) in the treatment or prevention of chronic obstructive pulmonary disease in a mammal comprising administering to the mammal at least once an effective amount of at least one compound of Formula (I), (Ia), (II), (IIa), (III), (IIIa), (IV) or (V). In addition, chronic obstructive pulmonary disease includes, but is not limited to, chronic bronchitis or emphysema, pulmonary hypertension, interstitial lung fibrosis and/or airway inflammation, and cystic fibrosis.

Nervous System

The nervous system is a major locus for $LPA_1$ expression; there it is spatially and temporally regulated throughout brain development. Oligodendrocytes, the myelinating cells in the central nervous system (CNS), express $LPA_1$ in mammals. In addition, Schwann cells, the myelinating cells of the peripheral nervous system, also express $LPA_1$, which is involved in regulating Schwann cell survival and morphology. These observations identify important functions for receptor-mediated LPA signaling in neurogenesis, cell survival, and myelination.

Exposure of peripheral nervous system cell lines to LPA produces a rapid refraction of their processes resulting in cell rounding, which was, in part, mediated by polymerization of the actin cytoskeleton. In one aspect, LPA causes neuronal degeneration under pathological conditions when the blood-brain barrier is damaged and serum components leak into the brain (Moolenaar, *Curr. Opin. Cell Biol.* 7:203-10, 1995). Immortalized CNS neuroblast cell lines from the cerebral cortex also display retraction responses to LPA exposure through Rho activation and actomyosin interactions. In one aspect, LPA is associated with post-ischemic neural damage (*J. Neurochem.* 61, 340, 1993; *J. Neurochem.*, 70:66, 1998).

In one aspect, provided is a compound of Formula (I), (Ia), (II), (IIa), (III), (IIIa), (IV) or (V) for use in the treatment or prevention of a nervous system disorder in a mammal. The term "nervous system disorder," as used herein, refers to conditions that alter the structure or function of the brain, spinal cord or peripheral nervous system, including but not limited to Alzheimer's Disease, cerebral edema, cerebral ischemia, stroke, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica.

In one aspect, provided is a compound of Formula (I), (Ia), (II), (IIa), (III), (IIIa), (IV) or (V) for use in the treatment or prevention of a CNS disorder in a mammal. CNS disorders include, but are not limited to, multiple sclerosis, Parkinson's disease, Alzheimer's disease, stroke, cerebral ischemia, retinal ischemia, post-surgical cognitive dysfunction, migraine, peripheral neuropathy/neuropathic pain, spinal cord injury, cerebral edema and head injury.

Cardiovascular Disorders

Cardiovascular phenotypes observed after targeted deletion of lysophospholipid receptors reveal important roles for lysophospholipid signaling in the development and maturation of blood vessels, formation of atherosclerotic plaques and maintenance of heart rate (Ishii, I. et al. *Annu. Rev. Biochem.* 73, 321-354, 2004). Angiogenesis, the formation of new capillary networks from pre-existing vasculature, is normally invoked in wound healing, tissue growth and myocardial angiogenesis after ischemic injury. Peptide growth factors (e.g. vascular endothelial growth factor (VEGF)) and lysophospholipids control coordinated proliferation, migration, adhesion, differentiation and assembly of vascular endothelial cells (VECs) and surrounding vascular smooth-muscle cells (VSMCs). In one aspect, dysregulation of the processes mediating angiogenesis leads to atherosclerosis, hypertension, tumor growth, rheumatoid arthritis and diabetic retinopathy (Osborne, N. and Stainier, D. Y. *Annu. Rev. Physiol.* 65, 23-43, 2003).

Downstream signaling pathways evoked by lysophospholipid receptors include Rac-dependent lamellipodia formation (e.g. $LPA_1$) and Rho-dependent stress-fiber formation (e.g. $LPA_1$), which is important in cell migration and adhesion. Dysfunction of the vascular endothelium can shift the balance from vasodilatation to vasoconstriction and lead to hypertension and vascular remodeling, which are risk factors for atherosclerosis (Maguire, J. J. et al., *Trends Pharmacol. Sci.* 26, 448-454, 2005).

LPA contributes to both the early phase (barrier dysfunction and monocyte adhesion of the endothelium) and the late phase (platelet activation and intra-arterial thrombus formation) of atherosclerosis, in addition to its overall progression. In the early phase, LPA from numerous sources accumulates in lesions and activates its cognate GPCRs ($LPA_1$ and $LPA_3$) expressed on platelets (Siess, W. *Biochim. Biophys. Acta* 1582, 204-215, 2002; Rother, E. et al. *Circulation* 108, 741-747, 2003). This triggers platelet shape change and aggregation, leading to intra-arterial thrombus formation and, potentially, myocardial infarction and stroke. In support of its atherogenic activity, LPA can also be a mitogen and motogen to VSMCs and an activator of endothelial cells and macrophages. In one aspect, mammals with cardiovascular disease benefit from LPA receptor antagonists that prevent thrombus and neointima plaque formation.

The specific effects of LPA are receptor-mediated.

In one aspect, a compound of Formula (I), (Ia), (II), (IIa), (III), (IIIa), (IV) or (V) is used to treat or prevent cardiovascular disease in mammal.

The term "cardiovascular disease," as used herein refers to diseases affecting the heart or blood vessels or both, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

In one aspect, provided herein are methods for preventing or treating vasoconstriction, atherosclerosis and its sequelae myocardial ischemia, myocardial infarction, aortic aneurysm, vasculitis and stroke comprising administering at least once to the mammal an effective amount of at least one compound of Formula (I), (Ia), (II), (IIa), (III), (IIIa), (IV) or (V) or pharmaceutical composition or medicament which includes a compound of Formula (I), (Ia), (II), (IIa), (III), (IIIa), (IV) or (V).

In one aspect, provided herein are methods for reducing cardiac reperfusion injury following myocardial ischemia and/or endotoxic shock comprising administering at least once to the mammal an effective amount of at least one compound of Formula (I), (Ia), (II), (IIa), (III), (IIIa), (IV) or (V).

In one aspect, provided herein are methods for reducing the constriction of blood vessels in a mammal comprising administering at least once to the mammal an effective amount of at least one compound of Formula (I), (Ia), (II), (IIa), (III), (IIIa), (IV) or (V).

In one aspect, provided herein are methods for lowering or preventing an increase in blood pressure of a mammal comprising administering at least once to the mammal an effective amount of at least one compound of Formula (I), (Ia), (II), (IIa), (III), (IIIa), (IV) or (V).

Inflammation

LPA has been shown to regulate immunological responses by modulating activities/functions of immune cells such as T-/B-lymphocytes and macrophages. In activated T cells, LPA activates IL-2 production/cell proliferation through $LPA_1$ (Gardell et al, TRENDS in Molecular Medicine Vol. 12 No. 2 Feb. 2006). Expression of LPA-induced inflammatory response genes is mediated by $LPA_1$ and $LPA_3$ (Biochem Biophys Res Commun. 363(4):1001-8, 2007). In addition, LPA modulates the chemotaxis of inflammatory cells (Biochem Biophys Res Commun., 1993, 15; 193(2), 497). The proliferation and cytokine-secreting activity in response to LPA of immune cells (J. Imuunol. 1999, 162, 2049), platelet aggregation activity in response to LPA, acceleration of migration activity in monocytes, activation of NF-κB in fibroblast, enhancement of fibronectin-binding to the cell surface, and the like are known. Thus, LPA is associated with various inflammatory/immune diseases.

In one aspect, a compound of Formula (I), (Ia), (II), (IIa), (III), (IIIa), (IV) or (V) is used to treat or prevent inflammation in a mammal. In one aspect, antagonists of $LPA_1$ and/or $LPA_3$ find use in the treatment or prevention of inflammatory/immune disorders in a mammal. In one aspect, the antagonist of $LPA_1$ is a compound of Formula (I), (Ia), (II), (IIa), (III), (IIIa), (IV) or (V).

Examples of inflammatory/immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

Other Diseases, Disorders or Conditions

In accordance with one aspect, are methods for treating, preventing, reversing, halting or slowing the progression of LPA-dependent or LPA-mediated diseases or conditions once it becomes clinically evident, or treating the symptoms associated with or related to LPA-dependent or LPA-mediated diseases or conditions, by administering to the mammal a compound of Formula (I), (Ia), (II), (IIa), (III), (IIIa), (IV) or (V). In certain embodiments, the subject already has a LPA-dependent or LPA-mediated disease or condition at the time of administration, or is at risk of developing a LPA-dependent or LPA-mediated disease or condition.

In certain aspects, the activity of $LPA_1$ in a mammal is directly or indirectly modulated by the administration of (at least once) a therapeutically effective amount of at least one compound of Formula (I), (Ia), (II), (IIa), (III), (IIIa), (IV) or (V). Such modulation includes, but is not limited to, reducing and/or inhibiting the activity of $LPA_1$. In additional aspects, the activity of LPA in a mammal is directly or indirectly modulated, including reducing and/or inhibiting, by the administration of (at least once) a therapeutically effective amount of at least one compound of Formula (I), (Ia), (II), (IIa), (III), (IIIa), (IV) or (V). Such modulation includes, but is not limited to, reducing and/or inhibiting the amount and/or activity of a LPA receptor. In one aspect, the LPA receptor is $LPA_1$.

In one aspect, LPA has a contracting action on bladder smooth muscle cell isolated from bladder, and promotes growth of prostate-derived epithelial cell (The Journal of Urology, 1999, vol. 162, pp. 1779-1784; The Journal of Urology, 2000, vol. 163, pp. 1027-1032). In another aspect, LPA contracts the urinary tract and prostate in vitro and increases intraurethral pressure in vivo (WO 02/062389).

In certain aspects, are methods for preventing or treating eosinophil and/or basophil and/or dendritic cell and/or neutrophil and/or monocyte and/or T-cell recruitment comprising administering at least once to the mammal an effective amount of at least one compound of Formula (I), (Ia), (II), (IIa), (III), (IIIa), (IV) or (V).

In certain aspects, are methods for the treatment of cystitis, including, e.g., interstitial cystitis, comprising administering at least once to the mammal a therapeutically effective amount of at least one compound of Formula (I), (Ia), (II), (IIa), (III), (IIIa), (IV) or (V).

In accordance with one aspect, methods described herein include the diagnosis or determination of whether or not a patient is suffering from a LPA-dependent or LPA-mediated disease or condition by administering to the subject a therapeutically effective amount of a compound of Formula (I), (Ia), (II), (IIa), (III), (IIIa), (IV) or (V) and determining whether or not the patient responds to the treatment.

In one aspect provided herein are compounds of Formula (I), (Ia), (II), (IIa), (III), (IIIa), (IV) and (V), pharmaceutically acceptable salts, pharmaceutically acceptable prodrugs, and pharmaceutically acceptable solvates thereof, which are antagonists of $LPA_1$, and are used to treat patients suffering from one or more LPA-dependent or LPA-mediated conditions or diseases, including, but not limited to, lung fibrosis, kindney fibrosis, liver fibrosis, scarring, asthma, rhinitis, chronic obstructive pulmonary disease, pulmonary hypertension, interstitial lung fibrosis, arthritis, allergy, psoriasis, inflammatory bowel disease, adult respiratory distress syndrome, myocardial infarction, aneurysm, stroke, cancer, pain, proliferative disorders and inflammatory conditions. In some embodiments, LPA-dependent conditions or diseases include those wherein an absolute or relative excess of LPA is present and/or observed.

In any of the aforementioned aspects the LPA-dependent or LPA-mediated diseases or conditions include, but are not limited to, organ fibrosis, asthma, allergic disorders, chronic obstructive pulmonary disease, pulmonary hypertension, lung or pleural fibrosis, peritoneal fibrosis, arthritis, allergy, cancer, cardiovascular disease, ult respiratory distress syndrome, myocardial infarction, aneurysm, stroke, and cancer.

In one aspect, a compound of Formula (I), (Ia), (II), (IIa), (III), (IIIa), (IV) or (V) is used to improve the corneal sensitivity decrease caused by corneal operations such as laser-assisted in situ keratomileusis (LASIK) or cataract operation, corneal sensitivity decrease caused by corneal degeneration, and dry eye symptom caused thereby.

In one aspect, presented herein is the use of a compound of Formula (I), (Ia), (II), (IIa), (III), (IIIa), (IV) or (V) in the treatment or prevention of ocular inflammation and allergic conjunctivitis, vernal keratoconjunctivitis, and papillary conjunctivitis in a mammal comprising administering at least once to the mammal an effective amount of at least one compound of Formula (I), (Ia), (II), (IIa), (III), (IIIa), (IV) or (V).

In one aspect, presented herein is the use of a compound of Formula (I), (Ia), (II), (IIa), (III), (IIIa), (IV) or (V) in the treatment or prevention of Sjogren disease or inflammatory disease with dry eyes in a mammal comprising administering at least once to the mammal an effective amount of at least one compound of Formula (I), (Ia), (II), (IIa), (III), (IIIa), (IV) or (V).

In one aspect, LPA and LPA receptors (e.g. $LPA_1$) are involved in the pathogenesis of osteoarthritis (Kotani et al, *Hum. Mol. Genet.*, 2008, 17, 1790-1797). In one aspect, presented herein is the use of a compound of Formula (I), (Ia), (II), (IIa), (III), (IIIa), (IV) or (V) in the treatment or prevention of osteoarthritis in a mammal comprising administering at least once to the mammal an effective amount of at least one compound of Formula (I), (Ia), (II), (IIa), (III), (IIIa), (IV) or (V).

In one aspect, LPA receptors (e.g. $LPA_1$, $LPA_3$) contribute to the pathogenesis of rheumatoid arthritis (Zhao et al, *Mol. Pharmacol.*, 2008, 73(2), 587-600). In one aspect, presented herein is the use of a compound of Formula (I), (Ia), (II), (IIa), (III), (IIIa), (IV) or (V) in the treatment or prevention of rheumatoid arthritis in a mammal comprising administering at least once to the mammal an effective amount of at least one compound of Formula (I), (Ia), (II), (IIa), (III), (IIIa), (IV) or (V).

In one aspect, LPA receptors (e.g. $LPA_1$) contribute to adipogenesis. (Simon et al, *J. Biol. Chem.*, 2005, vol. 280, no. 15, p. 14656). In one aspect, presented herein is the use of a compound of Formula (I), (Ia), (II), (IIa), (III), (IIIa), (IV) or (V) in the promotion of adipose tissue formation in a mammal comprising administering at least once to the mammal an effective amount of at least one compound of Formula (I), (Ia), (II), (IIa), (III), (IIIa), (IV) or (V).

Compounds

Compounds of Formula (I), including pharmaceutically acceptable salts, pharmaceutically acceptable prodrugs, and pharmaceutically acceptable solvates thereof, antagonize or modulate LPA receptor(s) and are used to treat patients suffering from LPA-dependent or LPA-mediated conditions or diseases.

In one aspect, provided herein is a compound of Formula (I), pharmaceutically acceptable salts, pharmaceutically acceptable solvates, or prodrugs thereof:

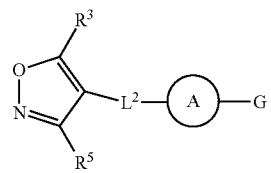

Formula (I)

wherein
$R^3$ is

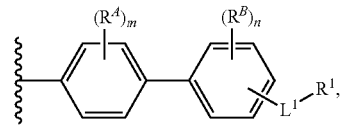

and $R^5$ is H, $C_1$-$C_4$ alkyl, or $C_1$-$C_4$ fluoroalkyl; or
$R^5$ is

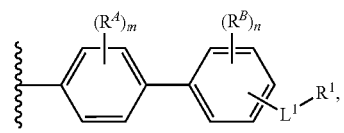

and $R^3$ is H, $C_1$-$C_4$ alkyl, or $C_1$-$C_4$ fluoroalkyl;
m is 0, 1 or 2; n is 0, 1 or 2;
each of $R^A$ and $R^B$ is independently selected from halogen, —CN, —$NO_2$, —OH, —$OR^9$, —$SR^9$, —S(=O)$R^{10}$, —S(=O)$_2R^{10}$, —N($R^9$)S(=O)$_2R^{10}$, —S(=O)$_2$N($R^9$)$_2$, —C(=O)$R^{10}$, —OC(=O)$R^{10}$, —$CO_2R^9$, —$OCO_2R^{10}$, —N($R^9$)$_2$, —C(=O)N($R^9$)$_2$, —OC(=O)N($R^9$)$_2$, —$NR^9$C(=O)N($R^9$)$_2$, —$NR^9$C(=O)$R^{10}$, —$NR^9$C(=O)$OR^{10}$, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl;
$L^1$ is absent, $C_1$-$C_4$ alkylene, $C_1$-$C_4$ fluoroalkylene, $C_3$-$C_6$ cycloalkylene, $C_3$-$C_6$ cycloalkylene-$C_1$-$C_4$alkylene-, or —C($R^{1a}$)($R^{1b}$)—;
$R^{1a}$ and $R^{1b}$ are each independently selected from H, $C_1$-$C_4$ alkyl and substituted or unsubstituted benzyl;
$R^1$ is —$CO_2R^D$, —C(=O)$NHSO_2R^E$, —C(=O)N($R^D$)$_2$, —C(=O)NH—OH, —C(=O)NH—CN, —CN, P(=O)(OH)$_2$, P(=O)(O$R^D$)$_2$, —$OPO_3H_2$, —$SO_2$NHC(=O)$R^E$, tetrazolyl, —C(=NH)$NH_2$, —C(=NH)NHC(=O)$R^E$, or carboxylic acid bioisostere; $R^D$ is H or $C_1$-$C_6$ alkyl; $R^E$ is $C_1$-$C_6$ alkyl or a substituted or unsubstituted phenyl;
$L^2$ is selected from a bond, —C(=O)—, —S—, —S(O)—, —S(O)$_2$—, —N($R^D$)—, substituted or unsubstituted $C_1$-$C_4$ alkylene, substituted or unsubstituted $C_1$-$C_4$ fluoroalkylene, and substituted or unsubstituted $C_1$-$C_4$ heteroalkylene, where if $L^2$ is substituted, then $L^2$ is substituted with 1 or 2 $R^{12}$, where each $R^{12}$ is F, $C_1$-$C_4$alkyl, —OH, —$OR^D$, or —N($R^D$)$_2$;
ring A is a substituted or unsubstituted cyclic group selected from $C_3$-$C_6$cycloalkylene, $C_2$-$C_{10}$heterocycloalkylene, heteroarylene, and arylene;
G is selected from —$R^2$, or -$L^3$-$R^2$;
$R^2$ is selected from a substituted or unsubstituted aryl or a substituted or unsubstituted heteroaryl; and
$L^3$ is selected from substituted or unsubstituted $C_1$-$C_4$ alkylene, substituted or unsubstituted $C_1$-$C_4$ fluoroalkylene, substituted or unsubstituted $C_1$-$C_4$ heteroalkylene, —O—, —S—, —S(O)—, $SO_2$, or —C(=O)—N($R^D$)—$C_1$-$C_4$ alkylene-;
each $R^9$ is independently selected from H, $C_1$-$C_6$alkyl, $C_1$-$C_6$heteroalkyl, $C_1$-$C_6$fluoroalkyl, a substituted or unsubstituted $C_3$-$C_6$cycloalkyl, a substituted or unsubstituted $C_2$-$C_6$heterocycloalkyl, a substituted or unsubstituted phenyl, a substituted or unsubstituted monocyclic heteroaryl, —C₁-C₄alkylene-(substituted or unsubstituted C₃-C₆cycloalkyl), —C₁-C₄alkylene-(substituted or unsubstituted C₂-C₆heterocycloalkyl), —C₁-C₄alkylene-(substituted or unsubstituted phenyl), or —C₁-C₄alkylene-(substituted or unsubstituted heteroaryl); or two R⁹ groups attached to the same N atom are taken together with the N atom to which they are attached to form a substituted or unsubstituted heterocycle;

R¹⁰ is selected from C₁-C₆alkyl, C₁-C₆heteroalkyl, C₁-C₆fluoroalkyl, a substituted or unsubstituted C₃-C₆cycloalkyl, a substituted or unsubstituted C₂-C₆heterocycloalkyl, a substituted or unsubstituted phenyl, a substituted or unsubstituted naphthyl, a substituted or unsubstituted monocyclic heteroaryl, —C₁-C₄alkylene-(substituted or unsubstituted C₃-C₆cycloalkyl), —C₁-C₄alkylene-(substituted or unsubstituted C₂-C₆heterocycloalkyl), —C₁-C₄alkylene-(substituted or unsubstituted phenyl), and —C₁-C₄alkylene-(substituted or unsubstituted heteroaryl).

For any and all of the embodiments, substituents are selected from among from a subset of the listed alternatives. For example, in some embodiments, R¹ is —CO₂R^D or —C(=O)NHSO₂R^E. In some embodiments, R¹ is —CO₂R^D. In some embodiments, R¹ is —CO₂H. In some embodiments, R¹ is —C(=O)NHSO₂R^E. In some embodiments, R^E is C₁-C₆ alkyl. In some embodiments, R^E is —CH₃ or —CH₂CH₃. In some embodiments, R^D is H, —CH₃ or —CH₂CH₃. In some embodiments, R^D is H.

In one aspect, the compound of Formula (I) has the following structure:

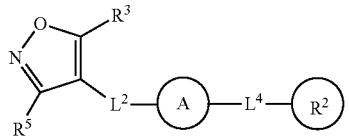

where L⁴ is absent or L³.

In some embodiments, the compound described herein is a compound of Formula (Ia), or a pharmaceutically acceptable salt thereof:

Formula (Ia)

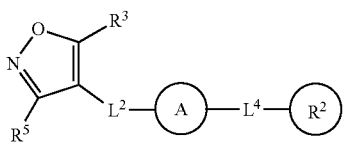

wherein,
R³ is

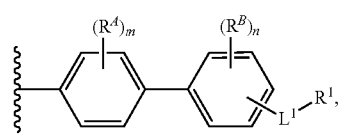

and R⁵ is H, C₁-C₄ alkyl, or C₁-C₄ fluoroalkyl; or

R⁵ is

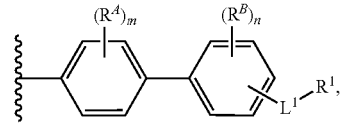

and R³ is H, C₁-C₄ alkyl, or C₁-C₄ fluoroalkyl;

R¹ is —CO₂R^D, —C(=O)NHSO₂R^E, —C(=O)N(R^D)₂, —CN, tetrazolyl, or carboxylic acid bioisostere;

R^D is H or C₁-C₆ alkyl;

R^E is C₁-C₆ alkyl or a substituted or unsubstituted phenyl;

L¹ is absent, C₁-C₄alkylene, C₁-C₄fluoroalkylene, C₃-C₆cycloalkylene, C₃-C₆cycloalkylene-C₁-C₄alkylene-, or —C(R^{1a})(R^{1b})—;

R^{1a} and R^{1b} are each independently selected from H, C₁-C₄ alkyl and substituted or unsubstituted benzyl;

each of R^A and R^B is independently selected from halogen, —CN, —OH, —OR⁹, C₁-C₄alkyl, C₁-C₄fluoroalkyl, C₁-C₄fluoroalkoxy, C₁-C₄alkoxy, and C₁-C₄heteroalkyl;

L² is absent, —C(=O)—, —S—, —S(O)—, —S(O)₂—, —N(R^D)—, —N(R^D)C(=O)—, substituted or unsubstituted C₁-C₄alkylene, substituted or unsubstituted C₁-C₄fluoroalkylene, or a substituted or unsubstituted C₁-C₄heteroalkylene, where if L² is substituted, then L² is substituted with 1 or 2 R¹², where each R¹² is F, C₁-C₄alkyl, —OH, —OR^D, or —N(R^D)₂;

ring A is a substituted or unsubstituted cyclic group selected from a substituted or unsubstituted C₃-C₆cycloalkylene, a substituted or unsubstituted C₂-C₅heterocycloalkylene, a substituted or unsubstituted monocyclic C₁-C₅heteroarylene, and a substituted or unsubstituted phenylene, where if ring A is substituted, then ring A is substituted with 1 or 2 R¹⁴, each R¹⁴ is independently selected from halogen, —CN, —OH, C₁-C₄alkyl, C₁-C₄fluoroalkyl, C₁-C₄fluoroalkoxy, C₁-C₄alkoxy, and C₁-C₄heteroalkyl;

L⁴ is absent, a substituted or unsubstituted C₁-C₄alkylene, substituted or unsubstituted C₁-C₄fluoroalkylene, substituted or unsubstituted C₁-C₄heteroalkylene, —O—, —S—, —S(O)—, SO₂, —N(R^D)—, or —C(=O)—N(R^D)—C₁-C₄alkylene-, where if L⁴ is substituted, then L⁴ is substituted with 1 or 2 R¹³, where each R¹³ is F, C₁-C₄alkyl, —OH, —OR^D, or —N(R^D)₂;

R² is a substituted or unsubstituted cyclic group selected from a substituted or unsubstituted C₃-C₁₀cycloalkyl, a substituted or unsubstituted C₂-C₁₀heterocycloalkyl, a substituted or unsubstituted C₁-C₉heteroaryl, a substituted or unsubstituted phenyl, and a substituted or unsubstituted naphthyl, wherein if R² is substituted, then R² is substituted with 1, 2 or 3 R^C, each R^C is independently selected from halogen, —CN, —NO₂, —OH, —OR⁹, —SR⁹, —S(=O)R¹⁰, —S(=O)₂R¹⁰, —N(R⁹)S(=O)₂R¹⁰, —S(=O)₂N(R⁹)₂, —C(=O)R¹⁰, —OC(=O)R¹⁰, —CO₂R⁹, —OCO₂R¹⁰, —N(R⁹)₂, —C(=O)N(R⁹)₂, —OC(=O)N(R⁹)₂, —NR⁹C(=O)N(R⁹)₂, —NR⁹C(=O)R¹⁰, —NR⁹C(=O)OR¹⁰, C₁-C₄alkyl, C₁-C₄fluoroalkyl, C₁-C₄fluoroalkoxy, C₁-C₄alkoxy, and C₁-C₄heteroalkyl;

R⁵ is H, C₁-C₄ alkyl, or C₁-C₄ fluoroalkyl;

each R⁹ is independently selected from H, C₁-C₆alkyl, C₁-C₆heteroalkyl, C₁-C₆fluoroalkyl, a substituted or unsubstituted $C_3$-$C_6$cycloalkyl, a substituted or unsubstituted $C_2$-$C_6$heterocycloalkyl, a substituted or unsubstituted phenyl, a substituted or unsubstituted monocyclic $C_1$-$C_5$heteroaryl, —$C_1$-$C_4$alkylene-(substituted or unsubstituted $C_3$-$C_6$cycloalkyl), —$C_1$-$C_4$alkylene-(substituted or unsubstituted $C_2$-$C_6$heterocycloalkyl), —$C_1$-$C_4$alkylene-(substituted or unsubstituted phenyl), or —$C_1$-$C_4$alkylene-(substituted or unsubstituted $C_1$-$C_5$heteroaryl); or two $R^9$ groups attached to the same N atom are taken together with the N atom to which they are attached to form a substituted or unsubstituted heterocycle;

$R^{10}$ is selected from $C_1$-$C_6$alkyl, $C_1$-$C_6$heteroalkyl, $C_1$-$C_6$fluoroalkyl, a substituted or unsubstituted $C_3$-$C_6$cycloalkyl, a substituted or unsubstituted $C_2$-$C_6$heterocycloalkyl, a substituted or unsubstituted phenyl, a substituted or unsubstituted monocyclic $C_1$-$C_5$heteroaryl, —$C_1$-$C_4$alkylene-(substituted or unsubstituted $C_3$-$C_6$cycloalkyl), —$C_1$-$C_4$alkylene-(substituted or unsubstituted $C_2$-$C_6$heterocycloalkyl), —$C_1$-$C_4$alkylene-(substituted or unsubstituted phenyl), and —$C_1$-$C_4$alkylene-(substituted or unsubstituted $C_1$-$C_5$heteroaryl);

m is 0, 1 or 2; n is 0, 1 or 2.

In some embodiments, $R^3$ is

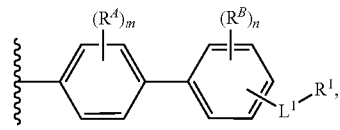

and $R^5$ is H, $C_1$-$C_4$ alkyl, or $C_1$-$C_4$ fluoroalkyl. In some embodiments, $R^3$ is

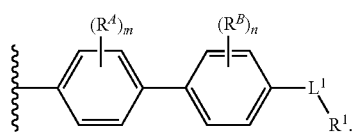

In some embodiments, $R^5$ is $C_1$-$C_4$alkyl. In some embodiments, $R^5$ is H, —$CH_3$, or —$CH_2CH_3$. In some embodiments, $R^5$ is —$CH_3$, or —$CH_2CH_3$. In some embodiments, $R^5$ is —$CH_3$. In some embodiments, $R^5$ is H. In some embodiments, $R^5$ is —H, —$CH_3$ or —$CH_2CH_3$; $R^1$ is —$CO_2R^D$; $R^D$ is H or $C_1$-$C_6$alkyl. In some embodiments, $R^5$ is —$CH_3$; $R^1$ is —$CO_2H$. In some embodiments, the compound of Formula (I) has the structure of Formula (II):

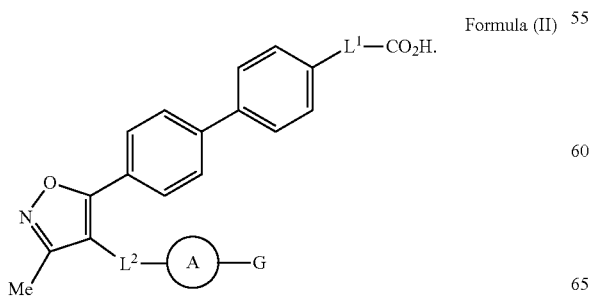

Formula (II)

In some embodiments, the compound of Formula (Ia) has the structure of Formula (IIa):

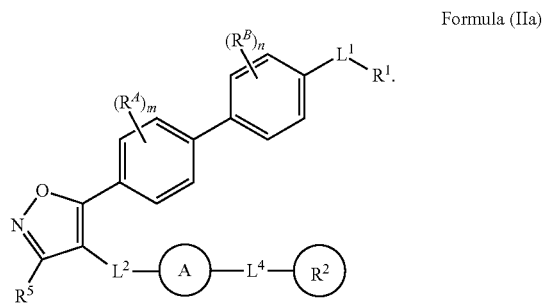

Formula (IIa)

In some embodiments, $R^5$ is

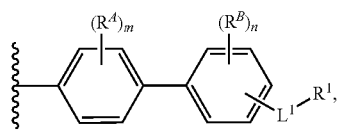

and $R^3$ is H, $C_1$-$C_4$ alkyl, or $C_1$-$C_4$ fluoroalkyl. In some embodiments, $R^5$ is

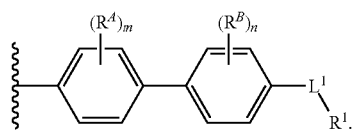

In some embodiments, $R^3$ is $C_1$-$C_4$alkyl. In some embodiments, $R^3$ is H, —$CH_3$, or —$CH_2CH_3$. In some embodiments, $R^3$ is —$CH_3$, or —$CH_2CH_3$. In some embodiments, $R^3$ is —$CH_3$. In some embodiments, $R^3$ is H. In some embodiments, $R^3$ is —H, —$CH_3$ or —$CH_2CH_3$; $R^1$ is —$CO_2R^D$; $R^D$ is H or $C_1$-$C_6$alkyl. In some embodiments, $R^3$ is —$CH_3$; $R^1$ is —$CO_2H$. In some embodiments, the compound of Formula (I) has the structure of Formula (III):

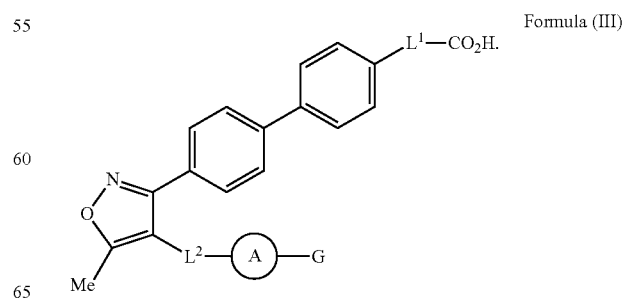

Formula (III)

In some embodiments, the compound of Formula (Ia) has the structure of Formula (IIIa):

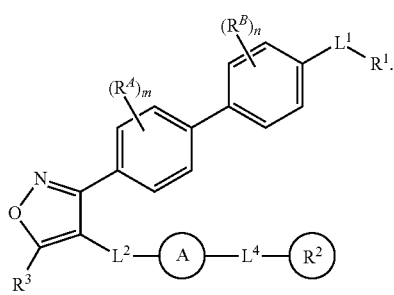

Formula (IIIa)

In some embodiments, L¹ is absent, —CH₂—, —CH(CH₃)—, —CH(substituted or unsubstituted benzyl)-, —C(CH₃)₂—, —CH₂CH₂—, —CH₂CH₂CH₂—, cyclopropyl-1,1-diyl, cyclopropyl-1,2-diyl, cyclobutyl-1,1-diyl, cyclopentyl-1,1-diyl, cyclohexyl-1,1-diyl, or —C(CH₂CH₂)CH₂—.

In some embodiments, L¹ is —CH(CH₃)—, —CH(substituted or unsubstituted benzyl)-, —C(CH₃)₂—, cyclopropyl-1,1-diyl, cyclopropyl-1,2-diyl, or —C(CH₂CH₂)CH₂—.

In some embodiments, L¹ is —CH(CH₃)—, —C(CH₃)₂—, cyclopropyl-1,1-diyl, cyclopropyl-1,2-diyl, cyclobutyl-1,1-diyl, cyclopentyl-1,1-diyl, cyclohexyl-1,1-diyl, or —C(CH₂CH₂)CH₂—.

In some embodiments, L¹ is cyclopropyl-1,1-diyl, cyclopropyl-1,2-diyl, or —C(CH₂CH₂)CH₂—.

In some embodiments, L¹ is cyclopropyl-1,1-diyl.

In some embodiments, L² is selected from a bond, C₁-C₄ alkylene, C₁-C₄ fluoroalkylene, —C(=O)—, —CH(OH)—, —CH(OR^D)—, —S—, —S(O)—, —S(O)₂—, —CH₂CH(OH)—, —CH₂CH(OR^D)—, —CH₂S—, —CH₂S(O)—, —CH₂S(O)₂—, —SCH₂—, —S(O)CH₂—, —S(O)₂CH₂—, —CH(N(R^D)₂)—, —CH₂CH(N(R^D)₂)—, —N(H)—, —CH₂N(H)—, or —N(H)CH₂—.

In some embodiments, L² is absent, —C(=O)—, —N(R^D)—, substituted or unsubstituted C₁-C₄ alkylene, or substituted or unsubstituted C₁-C₄ heteroalkylene, where if L² is substituted, then L² is substituted with R¹². In some embodiments, L² is —N(R^D)—, substituted or unsubstituted C₁-C₂ alkylene, or substituted or unsubstituted C₁-C₂ heteroalkylene, where if L² is substituted, then L² is substituted with R¹². In some embodiments, L² is —N(H)—, —N(CH₃)—, substituted or unsubstituted methylene, or substituted or unsubstituted ethylene, where if L² is substituted, then L² is substituted with R¹². In some embodiments, L² is —N(H)—. In some embodiments, L² is substituted or unsubstituted methylene, where if L² is substituted, then L² is substituted with R¹².

In some embodiments, L² is absent, —C(=O)—, —N(R^D)—, substituted or unsubstituted C₁-C₄ alkylene, or substituted or unsubstituted C₁-C₄ heteroalkylene, where if L² is substituted, then L² is substituted with R¹², where R¹² is F, C₁₋₄ alkyl, —OH, or —OR^D. In some embodiments, L² is absent, C₁-C₄alkylene, —C(=O)—, —CH(OH)—, —CH(OR^D)—, —CH₂CH(OH)—, —CH₂CH(OR^D)—, —CH₂S—, —CH₂S(O)—, —CH₂S(O)₂—, —SCH₂—, —S(O)CH₂—, —S(O)₂CH₂—, —CH₂O—, —OCH₂—, —S(O)₂CH₂—, —N(H)—, —CH₂N(H)—, or —N(H)CH₂—.

In some embodiments, L² is absent, —C(=O)—, —NH—, —N(CH₃)—, —CH₂—, —CH₂CH₂—, —CH(CH₃)—, —CH₂CH(CH₃)—, —CH(CH₃)CH₂—, —CH(OH)—, —CH(OR^D)—, —CH₂CH(OH)—, —CH₂CH(OR^D)—, —CH(OH)CH₂—, —CH(OR^D)CH₂—, —CH₂NH—, —CH(CH₃)NH—, —NHCH₂— or —NHCH(CH₃)—. In some embodiments, L² is —NH—, —N(CH₃)—, —CH₂—, —CH(CH₃)—, —CH(OH)—, —CH(OR^D)—, —CH₂NH—, —CH(CH₃)NH—, —NHCH₂— or —NHCH(CH₃)—. In some embodiments, L² is —NH—, —N(CH₃)—, —CH₂NH—, —CH(CH₃)NH—, —NHCH₂— or —NHCH(CH₃)—. In some embodiments, L² is —NH—, —CH₂NH—, or —NHCH₂—. In some embodiments, L² is —NH— or —NHCH₂—. In some embodiments, L² is —NH—. In some embodiments, L² is —CH₂—, —CH(CH₃)—, —CH(OH)—, —CH(OR^D)—, —CH₂NH—, —CH(CH₃)NH—, —NHCH₂— or —NHCH(CH₃)—. In some embodiments, L² is —CH₂—, —CH(CH₃)—, —CH(OH)—, or —CH(OR^D)—. In some embodiments, L² is —CH₂— or —CH(OH)—. In some embodiments, L² is —CH(OH)—. In some embodiments, L² is —CH₂—.

In some embodiments, R¹² is F, —CH₃, —CH₂CH₃, —OH, —OCH₃, or —OCH₂CH₃. In some embodiments, R¹² is —CH₃, or —OH.

In some embodiments, L² is —CH₂— or —CH(OH)—.

In some embodiments, G is —R².

In some embodiments, G is -L³-R².

In some embodiments, L³ is —CH₂, —CH(Me)—, —CH(OH)—, —CH₂CH₂, —O—, —OCH₂—, CH₂O—, —S—, —S(O)—, SO₂, —CH₂S—, —CH₂S(O)—, —CH₂SO₂₅— SCH₂—, —S(O)CH₂—, —SO₂CH₂, —NHCH₂, —CH₂NH— or —C(=O)—N(Me)—CH(Me)—. In some embodiments, L³ is —CH₂—.

In some embodiments, G is -L⁴-R². In some embodiments, L⁴ is absent or L³.

In some embodiments, L⁴ is absent, a substituted or unsubstituted C₁-C₄alkylene, substituted or unsubstituted C₁-C₄heteroalkylene, —O—, —S—, —S(O)—, SO₂, —N(R^D)—, or —C(=O)—N(R^D)—C₁-C₄ alkylene-, where if L⁴ is substituted, then L⁴ is substituted with R¹³. In some embodiments, L⁴ is absent, —CH₂, —CH(CH₃)—, —CH₂CH₂, —CH₂CH(CH₃)—, —CH(CH₃)CH₂—, —CH(OH)—, —O—, —OCH₂, —CH₂O—, —S—, —S(O)—, SO₂₅—CH₂S—, —CH₂S(O)—, —CH₂SO₂₅—SCH₂—, —S(O)CH₂—, —SO₂CH₂, —NH—, —N(CH₃)—, —NHCH₂—, —CH₂NH—, —C(=O)—NH—CH₂, —C(=O)—NH—CH(CH₃)— or —C(=O)—N(CH₃)—CH(CH₃)—. In some embodiments, L⁴ is absent, —CH₂—, —CH(CH₃)—, —CH₂CH₂, —CH₂CH(CH₃)—, —CH(CH₃)CH₂—, —CH(OH)—, —O—, —OCH₂, —CH₂O—, —S—, —S(O)—, SO₂, —CH₂S—, —CH₂S(O)—, —CH₂SO₂, —SCH₂—, —S(O)CH₂—, —SO₂CH₂, —NH—, —N(CH₃)—, —NHCH₂—, or —CH₂NH—.

In some embodiments, L⁴ is absent, or a substituted or unsubstituted C₁-C₄ alkylene, where if L⁴ is substituted then L⁴ is substituted with R¹³, where R¹³ is F, C₁-C₄alkyl, —OH, or —OR^D. In some embodiments, L⁴ is absent, or a substituted or unsubstituted methylene, or substituted or unsubstituted ethylene, where if L⁴ is substituted, then L⁴ is substituted with R¹³. In some embodiments, L⁴ is absent. In some embodiments, L⁴ is a substituted or unsubstituted methylene, where if L⁴ is substituted, then L⁴ is substituted with R¹³. In some embodiments, L⁴ is a substituted or unsubstituted ethylene, where if L⁴ is substituted, then L⁴ is substituted with R¹³. In some embodiments, R¹³ is F, —CH₃, —CH₂CH₃, —OH, —OCH₃, or —OCH₂CH₃. In some embodiments, R¹³ is —CH₃. In some embodiments, R¹³ is —OH. In some embodiments, L⁴ is absent, —CH₂—, or —CH(CH₃)—. In some embodiments, $L^4$ is absent or —$CH_2$—. In some embodiments, $L^4$ is —$CH_2$—. In some embodiments, $L^4$ is absent.

In some embodiments, $R^2$ is a substituted or unsubstituted cyclic group selected from a substituted or unsubstituted $C_3$-$C_{10}$cycloalkyl, a substituted or unsubstituted $C_2$-$C_{10}$heterocycloalkyl, a substituted or unsubstituted $C_1$-$C_9$heteroaryl, a substituted or unsubstituted phenyl, and a substituted or unsubstituted naphthyl, wherein if $R^2$ is substituted, then $R^2$ is substituted with 1, 2 or 3 $R^C$. In some embodiments, $R^2$ is unsubstituted or monsubstituted. In some embodiments, $R^2$ is unsubstituted. In some embodiments, if $R^2$ is substituted, then $R^2$ is substituted with 1, 2 or 3 $R^C$. In some embodiments, if $R^2$ is substituted, then $R^2$ is substituted with 1 or 2 $R^C$. In some embodiments, $R^2$ is substituted with $R^C$.

In some embodiments, $R^2$ is a substituted or unsubstituted $C_3$-$C_6$cycloalkyl, a substituted or unsubstituted monocyclic $C_2$-$C_5$heterocycloalkyl, a substituted or unsubstituted monocyclic $C_1$-$C_5$heteroaryl, and a substituted or unsubstituted phenyl, wherein if $R^2$ is substituted, then $R^2$ is substituted with 1 or 2 $R^C$.

In some embodiments, $R^2$ is a substituted or unsubstituted monocyclic $C_1$-$C_5$heteroaryl, or a substituted or unsubstituted phenyl, wherein if $R^2$ is substituted, then $R^2$ is substituted with 1 or 2 $R^C$.

In some embodiments, $R^2$ is a substituted or unsubstituted phenyl, wherein if $R^2$ is substituted, then $R^2$ is substituted with 1 or 2 $R^C$.

In some embodiments, $R^2$ is a substituted or unsubstituted aryl. In some embodiments, $R^2$ is a substituted or unsubstituted phenyl.

In some embodiments, $L^3$ is —$CH_2$—.

In some embodiments, G (or -$L^4$-$R^2$) is —$CH_2$— (substituted or unsubstituted aryl).

In some embodiments, G (or -$L^4$-$R^2$) is —$CH_2$— (substituted or unsubstituted phenyl).

In some embodiments, ring A is a cyclic group selected from $C_3$-$C_6$cycloalkylene, $C_2$-$C_{10}$heterocycloalkylene, 5-membered heteroarylene, 6-membered heteroarylene, 9-membered bicyclic heteroarylene, 10-membered bicyclic heteroarylene or arylene.

In some embodiments, ring A is a substituted or unsubstituted phenyl, or a substituted or unsubstituted monocyclic $C_1$-$C_5$heteroarylene, where if ring A is substituted, then ring A is substituted with 1 or 2 $R^{14}$.

In some embodiments, ring A is a substituted or unsubstituted phenyl, or a substituted or unsubstituted monocyclic $C_1$-$C_5$heteroarylene containing 1-4 N atoms, 0 or 1 O atoms and 0 or 1 S atoms, where if ring A is substituted, then ring A is substituted with 1 or 2 $R^{14}$.

In some embodiments, ring A is a substituted or unsubstituted monocyclic $C_1$-$C_5$heteroarylene containing 1-4 N atoms, 0 or 1 O atoms and 0 or 1 S atoms, where if ring A is substituted, then ring A is substituted with 1 or 2 $R^{14}$.

In some embodiments, ring A is a substituted or unsubstituted 5-membered monocyclic $C_1$-$C_4$heteroarylene containing 1-4 N atoms, 0 or 1 O atoms and 0 or 1 S atoms, where if ring A is substituted, then ring A is substituted with 1 or 2 $R^{14}$.

In some embodiments, ring A is a substituted or unsubstituted 6-membered monocyclic $C_3$-$C_5$heteroarylene containing 1-3 N atoms, where if ring A is substituted, then ring A is substituted with 1 or 2 $R^{14}$.

In some embodiments, ring A is a substituted or unsubstituted monocyclic ring wherein the groups -$L^2$- and -$L^4$- are in a 1,2-relationship on ring A (i.e. an ortho relationship).

In some embodiments, ring A is a substituted or unsubstituted monocyclic ring wherein the groups -$L^2$- and -$L^4$- are in a 1,3-relationship on ring A (i.e. a meta relationship).

In some embodiments, ring A is a substituted or unsubstituted monocyclic ring wherein the groups -$L^2$- and -$L^4$- are in a 1,4-relationship on ring A (i.e. a para relationship).

In some embodiments, if ring A is substituted, then ring A is substituted with 1 or 2 $R^{14}$. In some embodiments, ring A is unsubstituted or monosubstituted with $R^{14}$. In some embodiments, ring A is unsubstituted. In some embodiments, ring A is monosubstituted with $R^{14}$.

In some embodiments, ring A is a substituted or unsubstituted phenyl, where if ring A is substituted, then ring A is substituted with 1 or 2 $R^{14}$.

In some embodiments, ring A is a substituted or unsubstituted furanyl, a substituted or unsubstituted thienyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted triazolyl, substituted or unsubstituted tetrazolyl, substituted or unsubstituted isoxazolyl, substituted or unsubstituted isothiazolyl, substituted or unsubstituted oxadiazolyl, or substituted or unsubstituted thiadiazolyl, where if ring A is substituted, then ring A is substituted with 1 or 2 $R^{14}$.

In some embodiments, each $R^{14}$ is independently selected from halogen, —CN, —OH, —$CH_3$, —$CH_2CH_3$, —$CF_3$, —$OCF_3$, —$OCH_3$ and —$OCH_2CH_3$. In some embodiments, each $R^{14}$ is halogen, —CN, —OH, —$CH_3$, —$CH_2CH_3$, —$CF_3$, —$OCF_3$, —$OCH_3$ or —$OCH_2CH_3$. In some embodiments, each $R^{14}$ is independently selected from halogen, —OH, and —$CH_3$. In some embodiments, $R^{14}$ is halogen, —OH, or —$CH_3$. In some embodiments, each $R^{14}$ is independently selected from halogen and —$CH_3$.

In some embodiments, A is a substituted or unsubstituted 5-membered heteroarylene.

In some embodiments, ring A is

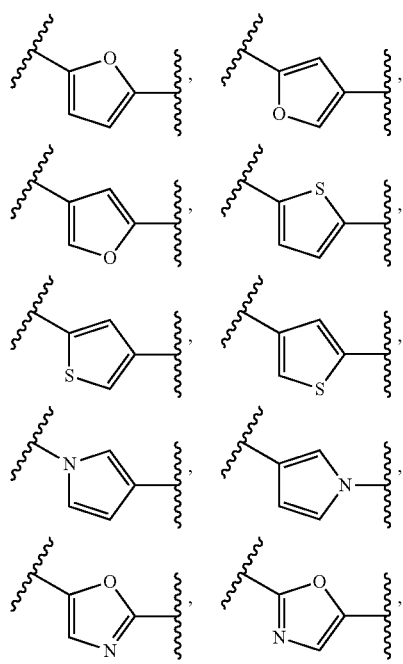

-continued
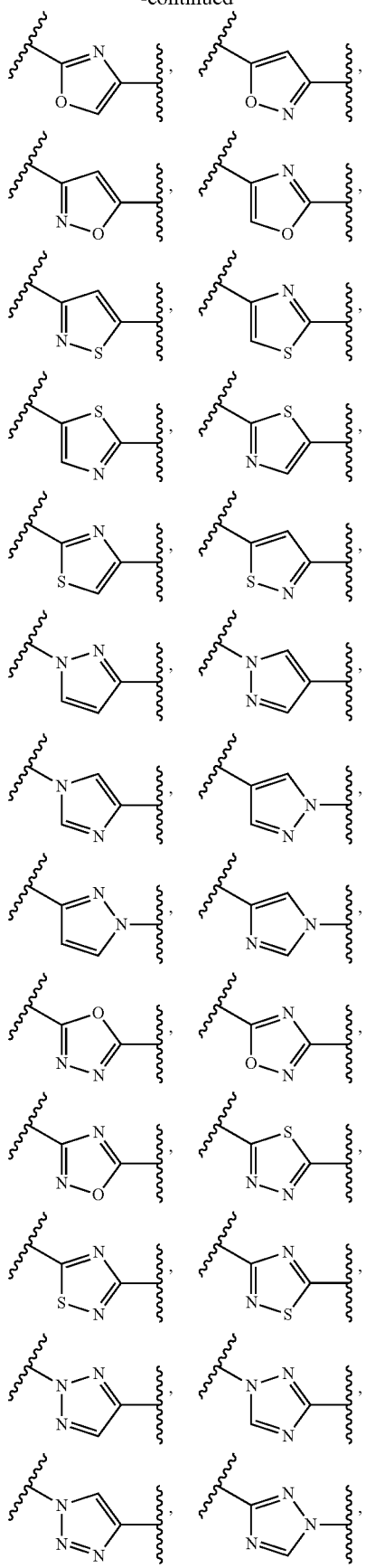
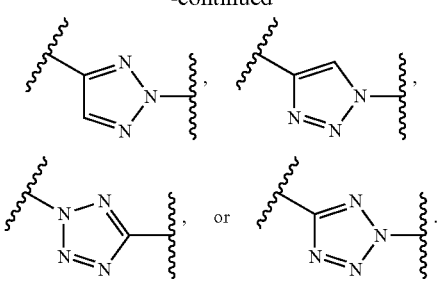
In some embodiments, ring A is:
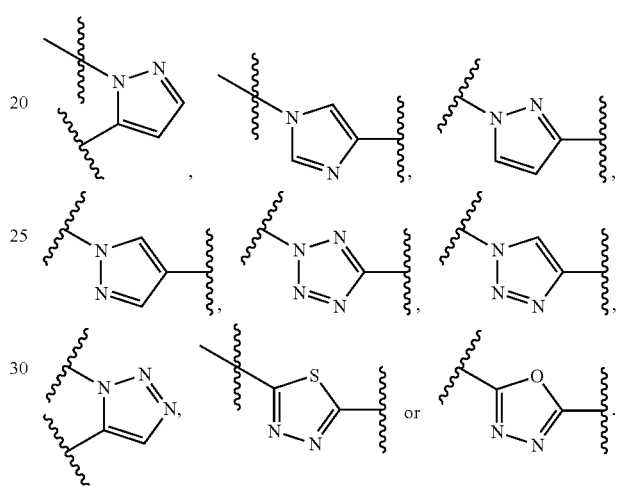
In some embodiments, L² is selected from —CH₂— or —CH(OH)—; G (or -L⁴-R²) is —CH₂— (substituted or unsubstituted phenyl); and A is:
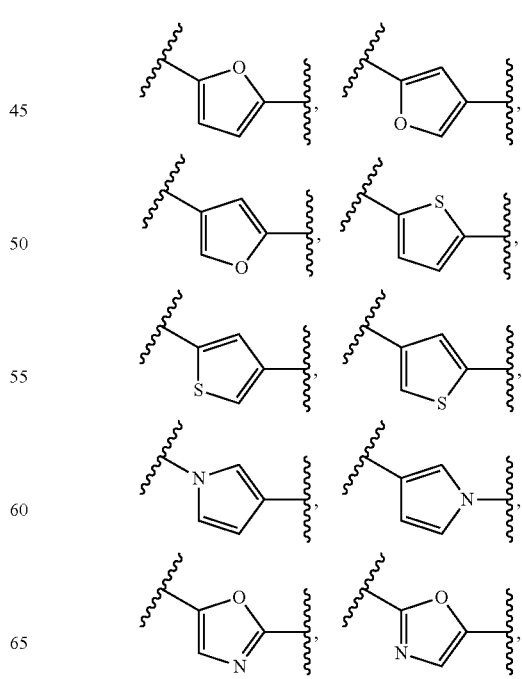

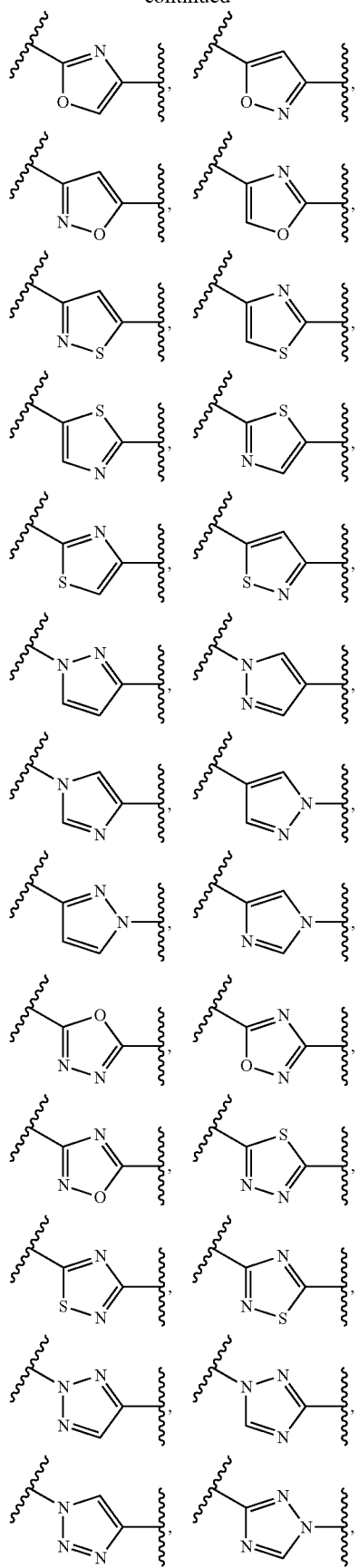

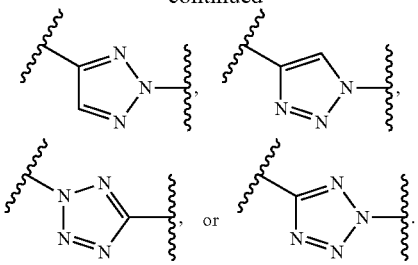

In some embodiments, ring A is a substituted or unsubstituted 6-membered monocyclic $C_3$-$C_5$heteroarylene containing 1-3 N atoms, where if ring A is substituted, then ring A is substituted with 1 or 2 $R^{14}$.

In some embodiments, ring A is a substituted or unsubstituted pyridinylene, a substituted or unsubstituted pyridazinylene, a substituted or unsubstituted pyrimidinylene, a substituted or unsubstituted pyrazinylene, or a substituted or unsubstituted triazinylene, where if ring A is substituted, then ring A is substituted with 1 or 2 $R^{14}$.

In some embodiments, ring A is a substituted or unsubstituted pyridinylene, where if ring A is substituted, then ring A is substituted with 1 or 2 $R^{14}$.

In some embodiments, ring A is

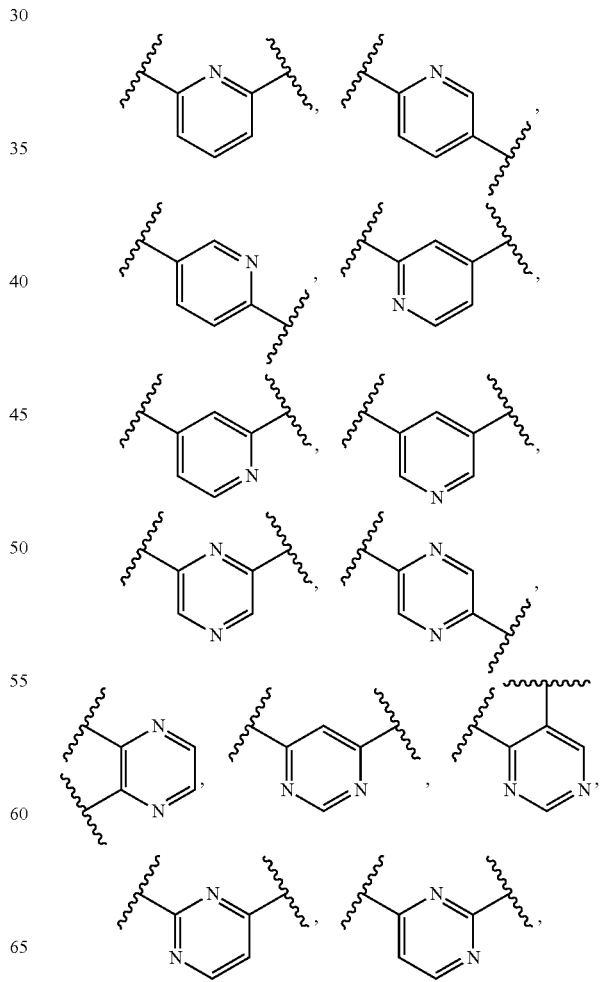

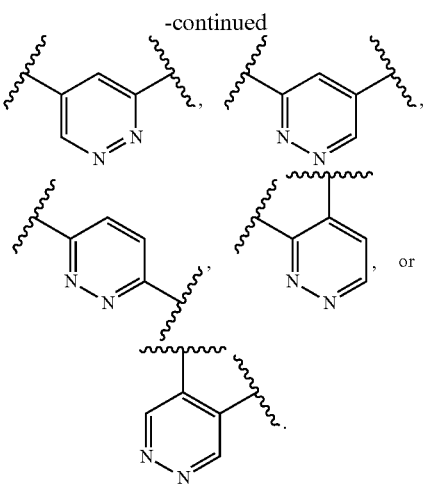

In some embodiments, A is a $C_3$-$C_6$ cycloalkylene.

In some embodiments, A is a substituted or unsubstituted $C_2$-$C_{10}$heterocycloalkylene.

In some embodiments, A is a substituted or unsubstituted 5-membered heteroarylene or substituted or unsubstituted 6-membered heteroarylene.

In some embodiments, the substituted or unsubstituted $C_2$-$C_{10}$heterocycloalkylene is selected from:

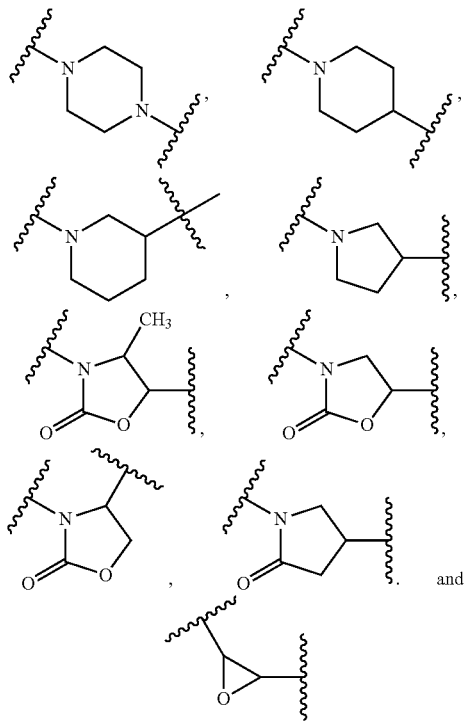

In some embodiments, each $R^A$ is independently selected from halogen, —OH, —$CH_3$, —$CH_2CH_3$, —$CF_3$, —$OCF_3$, —$OCH_3$ and —$OCH_2CH_3$. In some embodiments, each $R^A$ is halogen, —OH, —$CH_3$, —$CH_2CH_3$, —$CF_3$, —$OCF_3$, —$OCH_3$ or —$OCH_2CH_3$.

In some embodiments, each $R^B$ is independently selected from halogen, —OH, —$CH_3$, —$CH_2CH_3$, —$CF_3$, —$OCF_3$, —$OCH_3$ and —$OCH_2CH_3$. In some embodiments, each $R^B$ is halogen, —OH, —$CH_3$, —$CH_2CH_3$, —$CF_3$, —$OCF_3$, —$OCH_3$ or —$OCH_2CH_3$.

In some embodiments, each $R^C$ is independently selected from halogen, —CN, —OH, —$OR^9$, —$SR^9$, —S(=O)$R^{10}$, —S(=O)$_2R^{10}$, —C(=O)$R^{10}$, —$CO_2R^9$, —N($R^9$)$_2$, —C(=O)N($R^9$)$_2$, $C_1$-$C_4$alkyl, $C_1$-$C_4$fluoroalkyl, $C_1$-$C_4$fluoroalkoxy, $C_1$-$C_4$alkoxy, and $C_1$-$C_4$heteroalkyl. In some embodiments, each $R^C$ is independently selected from halogen, —CN, —OH, —S(=O)$_2CH_3$, —C(=O)$CH_3$, —$CO_2H$, —$CO_2CH_3$, —$CO_2CH_2CH_3$, —$NH_2$, —NH($CH_3$), —N($CH_3$)$_2$, —C(=O)$NH_2$, —$CH_3$, —$CH_2CH_3$, —CH($CH_3$)$_2$, —C($CH_3$)$_3$, —$CF_3$, —$CH_2CF_3$, —$OCF_3$, —$OCH_3$, —$OCH_2CH_3$, —$CH_2OCH_3$, —$CH_2OCH_2CH_3$, or —$CH_2N(CH_3)_2$. In some embodiments, each $R^C$ is halogen, —OH, —$CH_3$, —$CH_2CH_3$, —$CF_3$, —$OCF_3$, —$OCH_3$, —$OCH_2CH_3$, —$CH_2OCH_3$, —$CH_2OCH_2CH_3$, or —$CH_2N(CH_3)_2$. In some embodiments, each $R^C$ is independently selected from halogen, —OH, —$CH_3$, —$CH_2CH_3$, —$CF_3$, —$OCF_3$, —$OCH_3$ and —$OCH_2CH_3$.

In some embodiments, m is 0 or 1. In some embodiments, m is 0. In some embodiments, n is 0 or 1. In some embodiments, n is 0.

In some embodiments, $R^2$ is phenyl, 2-fluorophenyl, 2,3-difluorophenyl, 2,4-difluorophenyl, 2,5-difluorophenyl, 2,6-difluorophenyl, 2-chlorophenyl, 2,6-dichlorophenyl, 2-bromophenyl, 3-bromophenyl, 2,4-dichlorophenyl, 2-hydroxyphenyl, 3-hydroxyphenyl, 4-hydroxyphenyl, 2-methoxyphenyl, 3-methoxyphenyl, 4-methoxyphenyl, 2-trifluoromethylphenyl, 3-trifluoromethylphenyl, 4-trifluoromethylphenyl, 2-fluoro-4-methoxyphenyl, 2-methylphenyl, 3-methylphenyl, 4-methylphenyl, 2-cyanophenyl, 3-cyanophenyl, or 4-cyanophenyl.

In some embodiments, the compound of Formula (Ia) has the structure of Formula (IV):

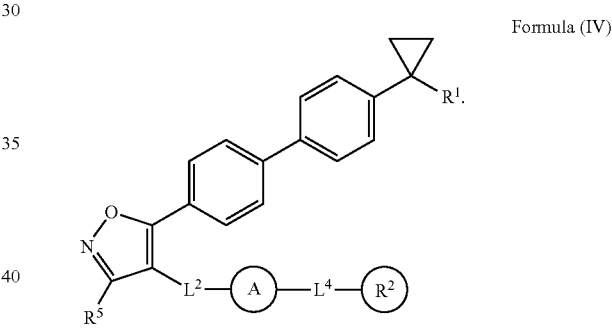

Formula (IV)

In some embodiments, the compound of Formula (Ia) has the structure of Formula (V):

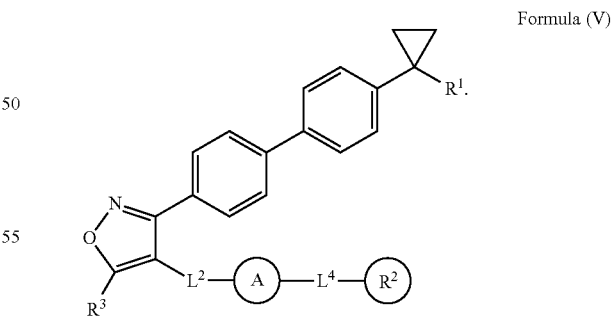

Formula (V)

In some embodiments, $L^1$ is as described in Table 1, 2, and/or 3. In some embodiments, $L^2$ is as described in Table 1, 2, and/or 3. In some embodiments, $R^2$ is as described in Table 1, 2, and/or 3. In some embodiments, $L^4$ is as described in Table 1, 2, and/or 3.

In one aspect, compounds of Formula (I), (Ia), (II), (IIa), (III), (IIIa), (IV) and (V) include, but are not limited to, those described in Table 1, 2, and 3.

TABLE 1

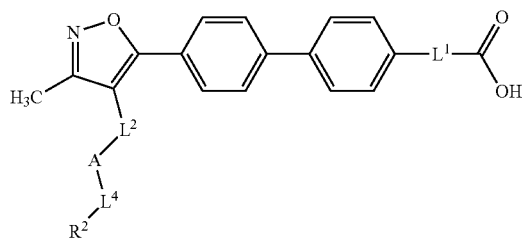

| Cmpd No | L¹ | L² | A | L⁴ | R² | M + H* |
|---|---|---|---|---|---|---|
| 1-1 | Cyclopropyl-1,1-diyl | —NH— | Cyclohexyl-1,2-diyl | —CH₂— | Phenyl | 507 |
| 1-2 | Cyclopropyl-1,1-diyl | —C(=O)— | Piperazinyl-1,4-diyl | — | 2-Methyl-phenyl | 522 |
| 1-3 | Cyclopropyl-1,1-diyl | —C(=O)— | Piperazinyl-1,4-diyl | —S(=O)₂— | 3,4-Dichloro-phenyl | 640 |
| 1-4 | Cyclopropyl-1,1-diyl | — | Oxiran-1,2-diyl | —CH₂CH₂— | Phenyl | 466 |
| 1-5 | Cyclopropyl-1,1-diyl | —CH₂— | Pyrazol-1,3-diyl | — | Phenyl | 476 |
| 1-6 | Cyclopropyl-1,1-diyl | —CH₂— | [1,2,3]Triazol-1,4-diyl | — | Phenyl | 477 |
| 1-7 | Cyclopropyl-1,1-diyl | —CH₂— | 2-Oxo-pyrrolidin-1,4-diyl | — | Phenyl | 493 |
| 1-8 | Cyclopropyl-1,1-diyl | —CH₂— | [1,3,4]Oxadiazol-2,5-diyl | — | Phenyl | 478 |
| 1-9 | Cyclopropyl-1,1-diyl | —CH₂— | [1,2,3]Triazol-1,4-diyl | —CH₂— | Phenyl | 491 |
| 1-10 | Cyclopropyl-1,1-diyl | —CH₂— | Piperidin-1,4-diyl | — | Phenyl | 493 |
| 1-11 | Cyclopropyl-1,1-diyl | —CH₂— | 2-Imino-[1,3,4]oxadiazol-3,5-diyl | — | Phenyl | 493 |
| 1-12 | Cyclopropyl-1,1-diyl | —CH₂— | (S)-2-Oxo-oxazolidin-3,4-diyl | —CH₂— | Phenyl | 509 |
| 1-13 | Cyclopropyl-1,1-diyl | —CH₂— | Pyrazol-1,3-diyl | — | 4-Bromo-phenyl | 554 |
| 1-14 | Cyclopropyl-1,1-diyl | —CH₂— | (S)-2-Oxo-oxazolidin-3,4-diyl | — | Phenyl | 495 |
| 1-15 | Cyclopropyl-1,1-diyl | —CH₂— | (4R,5S)-4-Methyl-2-oxo-oxazolidin-3,5-diyl | — | Phenyl | 509 |
| 1-16 | Cyclopropyl-1,1-diyl | —CH₂— | (4S,5R)-4-Methyl-2-oxo-oxazolidin-3,5-diyl | — | Phenyl | 509 |
| 1-17 | Cyclopropyl-1,1-diyl | —CH₂— | Pyrrolidin-1,3-diyl | — | Phenyl | 479 |
| 1-18 | Cyclopropyl-1,1-diyl | —CH₂— | Piperidin-1,3-diyl | — | Phenyl | 493 |
| 1-19 | Cyclopropyl-1,1-diyl | —CH₂—NH— | [1,3,4]Oxadiazol-2,5-diyl | — | Phenyl | 493 |
| 1-20 | Cyclopropyl-1,1-diyl | —CH₂— | [1,2,3]Triazol-1,5-diyl | — | Phenyl | 477 |
| 1-21 | Cyclopropyl-1,1-diyl | —CH₂— | Tetrazol-2,5-diyl | — | Phenyl | 478 |
| 1-22 | Cyclopropyl-1,1-diyl | —CH₂— | 2-Oxo-oxazolidin-3,5-diyl | — | Phenyl | 495 |
| 1-23 | Cyclopropyl-1,1-diyl | —CH₂— | Pyrazol-1,4-diyl | — | Phenyl | 476 |
| 1-24 | Cyclopropyl-1,1-diyl | — | [1,3,4]Oxadiazol-2,5-diyl | —CH₂— | Phenyl | 478 |
| 1-25 | Cyclopropyl-1,1-diyl | —CH(OH) | 1H-[1,2,3]Triazol-1,4-diyl | —CH₂— | Phenyl | 507 |
| 1-26 | Cyclopropyl-1,1-diyl | — | cis-Cyclopropyl-1,2-diyl | —C(=O)—N(CH₃)—CH(CH₃)— | Phenyl | 521 |
| 1-27 | Cyclopropyl-1,1-diyl | — | trans-Cyclopropyl-1,2-diyl | —C(=O)—N(CH₃)—CH(CH₃)— | Phenyl | 521 |

TABLE 1-continued

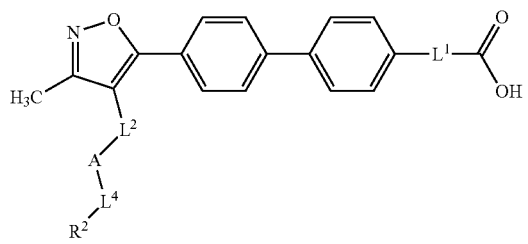

| Cmpd No | L¹ | L² | A | L⁴ | R² | M + H* |
|---|---|---|---|---|---|---|
| 1-28 | Cyclopropyl-1,1-diyl | — | 2-Oxo-oxazolidin-3,5-diyl | —CH₂— | Phenyl | 495 |
| 1-29 | Cyclopropyl-1,1-diyl | —CH₂— | [1,3,4]Oxadiazol-2,5-diyl | —CH₂— | Phenyl | 492 |
| 1-30 | Cyclopropyl-1,1-diyl | —CH(OH)— | [1,3,4]Oxadiazol-2,5-diyl | —CH₂— | Phenyl | 508 |
| 1-31 | Cyclopropyl-1,1-diyl | —CH₂— | 1H-[1,2,3]Triazol-1,4-diyl | —CH₂— | Phenyl | 491 |
| 1-32 | Cyclopropyl-1,1-diyl-methyl | —CH(OH)(CH₂)₃— | Phenyl-1,4-diyl | —CH₂— | Phenyl | 572 |
| 1-33 | Cyclopropyl-1,1-diyl-methyl | —CH(OH)(CH₂)₃— | Phenyl-1,4-diyl | —O— | Phenyl | 574 |
| 1-34 | Cyclopropyl-1,1-diyl | —(S)—CH(OH)— | [1,3,4]Oxadiazol-2,5-diyl | —CH₂— | Phenyl | 508 |
| 1-35 | Cyclopropyl-1,1-diyl | —(R)—CH(OH)— | [1,3,4]Oxadiazol-2,5-diyl | —CH₂— | Phenyl | 508 |
| 1-36 | Cyclopropyl-1,1-diyl | —NH— | Piperidin-1,4-diyl | —CH₂— | Phenyl | 508 |
| 1-37 | Cyclopropyl-1,1-diyl-methyl | —NH— | Piperidin-1,4-diyl | —CH₂— | Phenyl | 522 |
| 1-38 | Cyclopropyl-1,1-diyl | —CH(OH)— | [1,3,4]Oxadiazol-2,5-diyl | — | Phenyl | 494 |
| 1-39 | Cyclopropyl-1,1-diyl-methyl | —CH(OH)— | [1,3,4]Oxadiazol-2,5-diyl | — | Phenyl | 508 |
| 1-40 | Cyclopropyl-1,1-diyl | —(S)—CH(OH)— | 1H-[1,2,3]Triazol-1,4-diyl | —CH₂— | Phenyl | 507 |
| 1-41 | Cyclopropyl-1,1-diyl | —(R)—CH(OH)— | 1H-[1,2,3]Triazol-1,4-diyl | —CH₂— | Phenyl | 507 |
| 1-42 | Cyclopropyl-1,1-diyl-methyl | —NHCH(CH₃)— | Isoxazole-3,5-diyl | — | Phenyl | 520 |
| 1-43 | Cyclopropyl-1,1-diyl-methyl | —NH—(R)—CH(CH₃)— | Isoxazole-3,5-diyl | — | Phenyl | 520 |
| 1-44 | Cyclopropyl-1,1-diyl-methyl | —NH—(S)—CH(CH₃)— | Isoxazole-3,5-diyl | — | Phenyl | 520 |
| 1-45 | Cyclopropyl-1,1-diyl-methyl | —NHCH(CH₃)CH₂— | Phenyl-1,4-diyl | —OCH₂— | 4-Trifluoromethyl-phenyl | 641 |
| 1-46 | Cyclopropyl-1,1-diyl | —CH(OH)— | [1,3,4]Oxadiazol-2,5-diyl | —CH₂— | 4-Trifluoromethyl-phenyl | 576 |
| 1-47 | Cyclopropyl-1,1-diyl | —CH[NH(SO₂Me)]— | 1H-[1,2,3]Triazol-1,4-diyl | —CH₂— | Phenyl | 584 |
| 1-48 | —CH₂— | —CH(OH)— | 1H-[1,2,3]Triazol-1,4-diyl | —CH₂— | Phenyl | 481 |
| 1-49 | —(CH₂)₂— | —CH(OH)— | 1H-[1,2,3]Triazol-1,4-diyl | —CH₂— | Phenyl | 495 |
| 1-50 | Cyclopropyl-1,1-diyl | —CH(OH)— | 1H-[1,2,3]Triazol-1,4-diyl | —CH₂— | 3-Trifluoromethyl-phenyl | 575 |

TABLE 1-continued

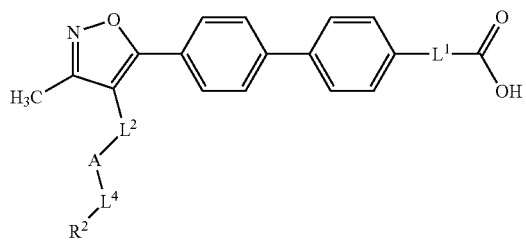

| Cmpd No | L¹ | L² | A | L⁴ | R² | M + H* |
|---|---|---|---|---|---|---|
| 1-51 | —CH₂— | —CH(OH)— | 1H-[1,2,3]Triazol-1,4-diyl | —CH₂— | 3-Trifluoromethyl-phenyl | 549 |
| 1-52 | —(CH₂)₂— | —CH(OH)— | 1H-[1,2,3]Triazol-1,4-diyl | —CH₂— | 3-Trifluoromethyl-phenyl | 563 |
| 1-53 | Cyclopropyl-1,1-diyl | —CH(OH)— | Phenyl-1,3-diyl | — | Phenyl | 502 |
| 1-54 | Cyclopropyl-1,1-diyl | —CH(OH)— | Phenyl-1,4-diyl | —OCH₂— | Phenyl | 532 |
| 1-55 | Cyclopropyl-1,1-diyl | —CH(OH)— | 1H-[1,2,3]Triazol-1,4-diyl | —CH(CH₃)— | Phenyl | 521 |
| 1-56 | Cyclopropyl-1,1-diyl | —CH(OH)— | 1H-[1,2,3]Triazol-1,4-diyl | —CH₂— | 2-Trifluoromethyl-phenyl | 575 |
| 1-57 | Cyclopropyl-1,1-diyl | —CH(OH)— | 1H-[1,2,3]Triazol-1,4-diyl | —CH₂— | 3-Chloro-phenyl | 541 |
| 1-58 | Cyclopropyl-1,1-diyl | —CH(OH)— | Phenyl-1,3-diyl | —CH₂— | Phenyl | 516 |
| 1-59 | Cyclopropyl-1,1-diyl | —CH(OH)— | Pyridine-3,5-diyl | —CH₂— | Phenyl | 517 |
| 1-60 | Cyclopropyl-1,1-diyl | —CH(OH)— | [1,3,4]Oxadiazol-2,5-diyl | — | Phenyl | 522 |
| 1-61 | Cyclopropyl-1,1-diyl | —CH(OH)— | 1H-[1,2,3]Triazol-1,4-diyl | —CH₂— | 2-Chloro-phenyl | 541 |
| 1-62 | Cyclopropyl-1,1-diyl | —CH(OH)— | 1H-[1,2,3]Triazol-1,4-diyl | —CH₂— | 4-Chloro-phenyl | 541 |
| 1-63 | Cyclopropyl-1,1-diyl | —CH(OH)—(R) | 1H-[1,2,3]Triazol-1,4-diyl | —CH₂— | 2-Chloro-phenyl | 541 |
| 1-64 | Cyclopropyl-1,1-diyl | —CH(OH)— | 1H-[1,2,3]Triazol-1,4-diyl | —CH₂— | 3,4-Dichloro-phenyl | 575 |
| 1-65 | —CH₂— | —CH(OH)— | 1H-[1,2,3]Triazol-1,4-diyl | —CH₂— | 3,4-Dichloro-phenyl | 549 |
| 1-66 | Cyclopropyl-1,1-diyl | —NHCH(CH₃)— | Cyclopropyl-1,2-diyl | — | Phenyl | 479 |
| 1-67 | Cyclopropyl-1,1-diyl | —CH(OH)—(R) | 1H-[1,2,3]Triazol-1,4-diyl | —CH(CH₃)—(R) | Phenyl | 521 |
| 1-68 | Cyclopropyl-1,1-diyl | —NH— | Pyridine-2,6-diyl | — | Phenyl | 488 |
| 1-69 | Cyclopropyl-1,1-diyl | —CH(OH)— | Pyridine-2,6-diyl | —CH₂— | Phenyl | 517 |
| 1-70 | Cyclopropyl-1,1-diyl | —CH(OH)— | 1H-[1,2,3]Triazol-1,4-diyl | —CH₂— | 2-Methyl-phenyl | 521 |
| 1-71 | Cyclopropyl-1,1-diyl | —CH(OH)— | 1H-[1,2,3]Triazol-1,4-diyl | —CH₂— | 2-Chloro-6-fluoro-phenyl | 559 |
| 1-72 | Cyclopropyl-1,1-diyl | —CH(OH)— | 1H-[1,2,3]Triazol-1,4-diyl | —CH₂— | 2,6-Dichloro-phenyl | 575 |
| 1-73 | Cyclopropyl-1,1-diyl | —NH— | Pyridine-2,6-diyl | —CH₂— | Phenyl | 502 |
| 1-74 | Cyclopropyl-1,1-diyl | —NH— | Phenyl-1,3-diyl | — | Phenyl | 487 |
| 1-75 | Cyclopropyl-1,1-diyl | —NH— | Phenyl-1,4-diyl | — | Phenyl | 487 |
| 1-76 | —CH₂— | —NH— | Pyridine-2,6-diyl | — | Phenyl | 462 |

TABLE 1-continued

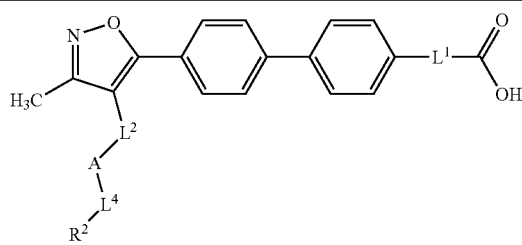

| Cmpd No | L¹ | L² | A | L⁴ | R² | M + H* |
|---|---|---|---|---|---|---|
| 1-77 | Cyclopropyl-1,1-diyl | —NH— | Pyridine-2,6-diyl | — | 3-Trifluoromethyl-phenyl | 556 |
| 1-78 | Cyclopropyl-1,1-diyl | —NH— | Pyrazine-2,6-diyl | — | Phenyl | 489 |
| 1-79 | Cyclopropyl-1,1-diyl | —NH— | Pyridine-2,6-diyl | —O— | Phenyl | 504 |
| 1-80 | Cyclopropyl-1,1-diyl | —NH— | [1,3,4]Oxadiazol-2,5-diyl | — | Phenyl | 479 |
| 1-81 | —(CH₂)₂— | —NH— | [1,3,4]Oxadiazol-2,5-diyl | — | Phenyl | 467 |
| 1-82 | Cyclopropyl-1,1-diyl | —NH— | Phenyl-1,3-diyl | —O— | Phenyl | 503 |
| 1-83 | Cyclopropyl-1,1-diyl | —NH— | [1,3,4]Oxadiazol-2,5-diyl | —CH₂— | Phenyl | 493 |
| 1-84 | Cyclopropyl-1,1-diyl | —NH— | Pyridine-2,6-diyl | —CH₂— | 2-Fluoro-phenyl | 520 |
| 1-85 | Cyclopropyl-1,1-diyl | —NH— | Pyridine-2,6-diyl | —CH₂— | 3-Fluoro-phenyl | 520 |
| 1-86 | Cyclopropyl-1,1-diyl | —NH— | Pyridine-2,6-diyl | —CH₂— | 4-Fluoro-phenyl | 520 |
| 1-87 | Cyclopropyl-1,1-diyl | —NH— | Pyridine-2,6-diyl | — | 2-Ethoxy-pyridine-5-yl | 533 |
| 1-88 | Cyclopropyl-1,1-diyl | —NH— | Pyridine-2,6-diyl | — | 3-Methoxy-pyridine-3-yl | 518 |
| 1-89 | Cyclopropyl-1,1-diyl | —NH— | Phenyl-1,3-diyl | — | 2-Methoxy-pyridine-3-yl | 518 |
| 1-90 | Cyclopropyl-1,1-diyl | —NH— | Phenyl-1,3-diyl | —CH₂— | Phenyl | 501 |
| 1-91 | Cyclopropyl-1,1-diyl | —NH— | Pyridine-2,6-diyl | — | 2-Cyano-phenyl | 513 |
| 1-92 | Cyclopropyl-1,1-diyl | —NH— | Pyridine-2,6-diyl | — | 4-Methoxy-phenyl | 518 |
| 1-93 | Cyclopropyl-1,1-diyl | —NH— | Pyridine-2,6-diyl | — | 3-Fluoro-phenyl | 506 |
| 1-94 | Cyclopropyl-1,1-diyl | —NH— | Pyridine-2,6-diyl | — | 2-Methoxy-phenyl | 518 |
| 1-95 | Cyclopropyl-1,1-diyl | —NH— | Pyridine-2,6-diyl | — | 2-Fluoro-phenyl | 506 |
| 1-96 | Cyclopropyl-1,1-diyl | —NH— | Pyridine-2,6-diyl | — | 2-Trifluoromethyl-phenyl | 556 |
| 1-97 | Cyclopropyl-1,1-diyl | —NH— | Pyridine-2,6-diyl | — | 2-Methoxy-pyridine-3-yl | 519 |
| 1-98 | Cyclopropyl-1,1-diyl | —NH— | Pyridine-2,6-diyl | — | 2-Methoxy-pyridine-5-yl | 519 |
| 1-99 | Cyclopropyl-1,1-diyl | —NH— | Pyridine-2,6-diyl | — | Pyridine-4-yl | 489 |
| 1-100 | Cyclopropyl-1,1-diyl | —NHCH₂— | 1,3-Thiazole-2,5-diyl | — | Phenyl | 508 |
| 1-101 | Cyclopropyl-1,1-diyl | —NH— | Phenyl-1,3-diyl | — | 2-Trifluoromethyl-phenyl | 555 |
| 1-102 | Cyclopropyl-1,1-diyl | —NH— | Phenyl-1,3-diyl | — | 2-Methoxy-pyridine-5-yl | 518 |
| 1-103 | Cyclopropyl-1,1-diyl | —NH— | Phenyl-1,3-diyl | — | Pyridine-3-yl | 488 |
| 1-104 | Cyclopropyl-1,1-diyl | —NH— | Phenyl-1,3-diyl | — | 3-Methoxy-pyridine-5-yl | 518 |
| 1-105 | Cyclopropyl-1,1-diyl | —NH— | Pyridine-2,6-diyl | —N(CH₃)— | Phenyl | 517 |
| 1-106 | Cyclopropyl-1,1-diyl | —NH— | Phenyl-1,3-diyl | —N(CH₃)— | Phenyl | 516 |
| 1-107 | Cyclopropyl-1,1-diyl | —NH— | Pyridine-3,5-diyl | — | Phenyl | 488 |

TABLE 1-continued

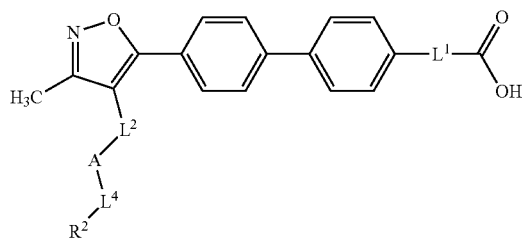

| Cmpd No | L¹ | L² | A | L⁴ | R² | M + H* |
|---|---|---|---|---|---|---|
| 1-108 | Cyclopropyl-1,1-diyl | —NH— | Pyridine-3,5-diyl | — | 3-Fluoro-phenyl | 506 |
| 1-109 | Cyclopropyl-1,1-diyl | —NH— | Pyridine-2,6-diyl | — | 2-Chloro-phenyl | 522 |
| 1-110 | Cyclopropyl-1,1-diyl | —CH(OH)— | Pyridine-2,6-diyl | — | Phenyl | 503 |
| 1-111 | Cyclopropyl-1,1-diyl | —NH— | Pyridine-2,4-diyl | — | Phenyl | 488 |
| 1-112 | Cyclopropyl-1,1-diyl | —NH— | Pyridine-2,4-diyl | — | 3-Fluoro-phenyl | 506 |
| 1-113 | Cyclopropyl-1,1-diyl | —NH— | Pyridine-3,5-diyl | — | 2-Chloro-phenyl | 522 |
| 1-114 | Cyclopropyl-1,1-diyl | —NH— | Pyridine-2,4-diyl | — | 2-Chloro-phenyl | 522 |
| 1-115 | Cyclopropyl-1,1-diyl | —NH— | Pyrimidine-2,6-diyl | — | Phenyl | 489 |
| 1-116 | Cyclopropyl-1,1-diyl | —NH— | Pyridine-2,4-diyl | — | Phenyl | 488 |
| 1-117 | Cyclopropyl-1,1-diyl | —NH— | Phenyl-1,3-diyl | — | 2-(Dimethylamino)-methyl-phenyl | 544 |
| 1-118 | Cyclopropyl-1,1-diyl | —NH— | Pyridine-3,5-diyl | — | 3-Trifluoromethyl-phenyl | 556 |
| 1-119 | Cyclopropyl-1,1-diyl | —NH— | Pyridine-3,5-diyl | — | 4-Trifluoromethyl-phenyl | 556 |
| 1-120 | Cyclopropyl-1,1-diyl | —N— | bis-(Pyridine-2,6-diyl) | —CH₂— | bis-Phenyl | 669 |
| 1-121 | Cyclopropyl-1,1-diyl | —NHC(O)— | Phenyl-1,3-diyl | — | 2-(Dimethylamino)-methyl-phenyl | 572 |
| 1-122 | Cyclopropyl-1,1-diyl | —NH— | Pyridine-2,6-diyl | — | Phenyl | 502 |
| 1-123 | Cyclopropyl-1,1-diyl | —NH— | Pyridine-2,6-diyl | — | Pyrazole-1-yl | 478 |
| 1-124 | Cyclopropyl-1,1-diyl | —NH— | Pyridine-2,6-diyl | — | Morpholine-4-yl | 497 |
| 1-125 | Cyclopropyl-1,1-diyl | —NH— | Pyridine-2,6-diyl | —OCH₂— | Phenyl | 518 |
| 1-126 | Cyclopropyl-1,1-diyl | —NH— | Pyridine-2,6-diyl | —S— | Phenyl | 520 |
| 1-127 | Cyclopropyl-1,1-diyl | —NH— | Pyridine-2,6-diyl | —S(O)— | Phenyl | 536 |
| 1-128 | Cyclopropyl-1,1-diyl | —NH— | Pyridine-2,6-diyl | —S(O)₂— | Phenyl | 552 |
| 1-129 | Cyclopropyl-1,1-diyl | —CH(OH)— | Pyridine-3,5-diyl | — | Phenyl | 503 |
| 1-130 | Cyclopropyl-1,1-diyl | —CH(OH)— | Pyridine-3,5-diyl | — | 3-Trifluoromethyl-phenyl | 571 |
| 1-131 | Cyclopropyl-1,1-diyl | —NH— | Pyridine-2,6-diyl | —C≡C— | Phenyl | 512 |
| 1-132 | —(CH₂)₂— | —NH— | Pyridine-2,6-diyl | — | Phenyl | 476 |
| 1-133 | —C(CH₃)₂— | —NH— | Pyridine-2,6-diyl | — | Phenyl | 490 |
| 1-134 | Cyclopropyl-1,1-diyl-methyl | —NH— | Pyridine-2,6-diyl | — | Phenyl | 502 |
| 1-135 | Cyclopropyl-1,1-diyl | —NH— | Pyridine-2,6-diyl | —C≡C— | Cyclopentyl | 504 |
| 1-136 | Cyclopropyl-1,1-diyl | —NH— | Pyridine-2,6-diyl | —C(O)— | Pyrrolidine-1-yl | 509 |
| 1-137 | Cyclopropyl-1,1-diyl | —NH— | Pyridine-2,6-diyl | —C(O)NH— | Cyclopropyl | 495 |

TABLE 1-continued

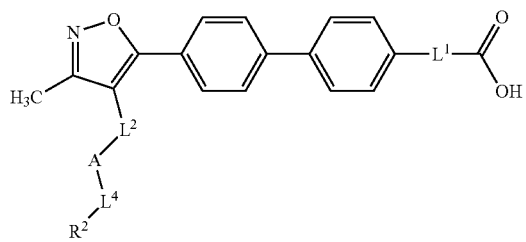

| Cmpd No | L¹ | L² | A | L⁴ | R² | M + H* |
|---|---|---|---|---|---|---|
| 1-138 | Cyclopropyl-1,1-diyl | —NH— | Pyridine-2,6-diyl | —O— | Cyclohexyl | 510 |
| 1-139 | Cyclopropyl-1,1-diyl | —NH— | Pyridine-2,6-diyl | —O— | Cyclobutyl | 482 |
| 1-140 | Cyclopropyl-1,1-diyl | —NH— | Pyridine-2,6-diyl | —OCH(CH₃)— | Cyclohexyl | 538 |
| 1-141 | Cyclopropyl-1,1-diyl | —NH— | Pyridine-2,6-diyl | —O(CH₂)₂— | Phenyl | 532 |
| 1-142 | — | —NH— | [1,3,4]Oxadiazol-2,5-diyl | — | Phenyl | 439 |
| 1-143 | Cyclopropyl-1,1-diyl | —NH— | Pyridine-2,6-diyl | — | Oxazolidin-2-one-3-yl | 497 |
| 1-144 | Cyclopropyl-1,1-diyl | —NH— | Pyridine-2,6-diyl | — | 3-Benzamidyl | 531 |
| 1-145 | Cyclopropyl-1,1-diyl | —NH— | Pyridine-2,6-diyl | — | 3-Cyano-phenyl | 513 |
| 1-146 | Cyclopropyl-1,1-diyl | —NH— | Pyridine-2,6-diyl | — | 5-Fluoro-2-methoxy-phenyl | 536 |
| 1-147 | Cyclopropyl-1,1-diyl | —NH— | Pyridine-2,6-diyl | — | 3-Chloro-5-fluoro-phenyl | 540 |
| 1-148 | Cyclopropyl-1,1-diyl | —NH— | Pyridine-2,6-diyl | — | 2,5-Difluoro-phenyl | 524 |
| 1-149 | Cyclopropyl-1,1-diyl | —NH— | Pyridine-2,6-diyl | — | Tetrazolyl | 480 |
| 1-150 | Cyclopropyl-1,1-diyl | —NH— | Pyridine-2,6-diyl | — | 2,6-Dichloro-phenyl | 556 |
| 1-151 | Cyclopropyl-1,1-diyl | —NH— | Pyridine-2,6-diyl | — | 2-Chloro-5-fluoro-phenyl | 540 |
| 1-152 | Cyclopropyl-1,1-diyl | —NH— | Pyridine-2,6-diyl | — | 2,3-Difluoro-phenyl | 524 |
| 1-153 | Cyclopropyl-1,1-diyl | —NH— | Pyridine-2,6-diyl | — | 2-Chloro-3-fluoro-phenyl | 540 |
| 1-154 | Cyclopropyl-1,1-diyl | —NH— | Pyridine-2,6-diyl | —OCH₂— | Cyclopropyl | 482 |
| 1-155 | Cyclopropyl-1,1-diyl | —NH— | Pyridine-3,5-diyl | — | 2-Chloro-3-fluoro-phenyl | 540 |
| 1-156 | Cyclopropyl-1,1-diyl | —NH— | Pyridine-2,6-diyl | — | 3-Fluoro-2-methyl-phenyl | 520 |
| 1-157 | Cyclopropyl-1,1-diyl | —NH— | Pyridine-2,6-diyl | — | 2-Chloro-3-trifluoromethyl-phenyl | 590 |
| 1-158 | Cyclopropyl-1,1-diyl | —NH— | Pyridine-2,6-diyl | — | 2,3-Dichloro-phenyl | 556 |
| 1-159 | Cyclopropyl-1,1-diyl | —NH— | Pyridine-2,6-diyl | — | 3-Fluoro-2-methoxy-phenyl | 536 |
| 1-160 | Cyclopropyl-1,1-diyl | —NH— | Pyridine-3,5-diyl | — | 3-Chloro-phenyl | 522 |
| 1-161 | Cyclopropyl-1,1-diyl | —NH— | Pyridine-3,5-diyl | — | 2,5-Difluoro-phenyl | 524 |
| 1-162 | Cyclopropyl-1,1-diyl | —NH— | Pyridine-2,6-diyl | — | 3-Chloro-phenyl | 522 |

*mass spectrometric data

Compounds in Table 1 are named:
1-{4'-[4-(2-Benzyl-cyclohexylamino)-3-methyl-isoxazol-5-yl]-biphenyl-4-yl}-cyclopropanecarboxylic acid (Compound 1-1); 1-{4'-[3-Methyl-4-(4-o-tolyl-piperazine-1-carbonyl)-isoxazol-5-yl]-biphenyl-4-yl}-cyclopropanecarboxylic acid (Compound 1-2); 1-(4'-{4-[4-(3,4-Dichloro-benzenesulfonyl)-piperazine-1-carbonyl]-3-methyl-isoxazol-5-yl}-biphenyl-4-yl)-cyclopropanecarboxylic acid (Compound 1-3); 1-{4'-[3-Methyl-4-(3-phenethyl-oxiranyl)-isoxazol-5-yl]-biphenyl-4-yl}-cyclopropanecarboxylic acid (Compound 1-4); 1-{4'-[3-Methyl-4-(3-phenyl-pyrazol-1-ylmethyl)-isoxazol-5-yl]-biphenyl-4-yl}-cyclopropanecarboxylic acid (Compound 1-5); 1-{4'-[3-Methyl-4-(4-phenyl-[1,2,3]triazol-1-ylmethyl)-isoxazol-5-yl]-biphenyl-4-yl}-cyclopropanecarboxylic acid (Compound 1-6); 1-{4'-[3-Methyl-4-(2-oxo-4-phenyl-pyrrolidin-1-ylmethyl)-isoxazol-5-yl]-biphenyl-4-yl}-cyclopropanecarboxylic acid (Compound 1-7); 1-{4'-[3-Methyl-4-(5-phenyl-[1,3,4]oxadiazol-2-ylmethyl)-isoxazol-5-yl]-biphenyl-4-yl}-cyclopropanecarboxylic acid (Compound 1-8); 1-{4'-[4-(4-Benzyl-[1,2,3]triazol-1-ylmethyl)-3-methyl-isoxazol-5-yl]-biphenyl-4-yl}-cyclopropanecarboxylic acid (Compound 1-9); 1-{4'-[3-Methyl-4-(4-phenyl-piperidin-1-ylmethyl)-isoxazol-5-yl]-biphenyl-4-yl}-cyclopropanecarboxylic acid (Compound 1-10); 1-{4'-[4-(2-Imino-5-phenyl-[1,3,4]oxadiazol-3-ylmethyl)-3-methyl-isoxazol-5-yl]-biphenyl-4-yl}-cyclopropanecarboxylic acid (Compound 1-11); 1-{4'-[4-((S)-4-Benzyl-2-oxo-oxazolidin-3-ylmethyl)-3-methyl-isoxazol-5-yl]-biphenyl-4-yl}-cyclopropanecarboxylic acid (Compound 1-12); 1-(4'-{4-[3-(4-Bromo-phenyl)-pyrazol-1-ylmethyl]-3-methyl-isoxazol-5-yl}-biphenyl-4-yl)-cyclopropanecarboxylic acid (Compound 1-13); 1-{4'-[3-Methyl-4-((S)-2-oxo-4-phenyl-oxazolidin-3-ylmethyl)-isoxazol-5-yl]-biphenyl-4-yl}-cyclopropanecarboxylic acid (Compound 1-14); 1-{4'-[3-Methyl-4-((4R,5S)-4-methyl-2-oxo-5-phenyl-oxazolidin-3-ylmethyl)-isoxazol-5-yl]-biphenyl-4-yl}-cyclopropanecarboxylic acid (Compound 1-15); 1-{4'-[3-Methyl-4-((4S,5R)-4-methyl-2-oxo-5-phenyl-oxazolidin-3-ylmethyl)-isoxazol-5-yl]-biphenyl-4-yl}-cyclopropanecarboxylic acid (Compound 1-16); 1-{4'-[3-Methyl-4-(3-phenyl-pyrrolidin-1-ylmethyl)-isoxazol-5-yl]-biphenyl-4-yl}-cyclopropanecarboxylic acid (Compound 1-17); 1-{4'-[3-Methyl-4-(3-phenyl-piperidin-1-ylmethyl)-isoxazol-5-yl]-biphenyl-4-yl}-cyclopropanecarboxylic acid (Compound 1-18); 1-(4'-{3-Methyl-4-[(5-phenyl-[1,3,4]oxadiazol-2-ylamino)-methyl]-isoxazol-5-yl}-biphenyl-4-yl)-cyclopropanecarboxylic acid (Compound 1-19); 1-{4'-[3-Methyl-4-(5-phenyl-[1,2,3]triazol-1-ylmethyl)-isoxazol-5-yl]-biphenyl-4-yl}-cyclopropanecarboxylic acid (Compound 1-20); 1-{4'-[3-Methyl-4-(5-phenyl-tetrazol-2-ylmethyl)-isoxazol-5-yl]-biphenyl-4-yl}-cyclopropanecarboxylic acid (Compound 1-21); 1-{4'-[3-Methyl-4-(2-oxo-5-phenyl-oxazolidin-3-ylmethyl)-isoxazol-5-yl]-biphenyl-4-yl}-cyclopropanecarboxylic acid (Compound 1-22); 1-{4'-[3-Methyl-4-(4-phenyl-pyrazol-1-ylmethyl)-isoxazol-5-yl]-biphenyl-4-yl}-cyclopropanecarboxylic acid (Compound 1-23); 1-{4'-[4-(5-Benzyl-[1,3,4]oxadiazol-2-yl)-3-methyl-isoxazol-5-yl]-biphenyl-4-yl}-cyclopropanecarboxylic acid (Compound 1-24); 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid (Compound 1-25); 1-[4'-(3-Methyl-4-{2-[methyl-((R)-1-phenyl-ethyl)-carbamoyl]-cyclopropyl}-isoxazol-5-yl)-biphenyl-4-yl]-cyclopropanecarboxylic acid (Compound 1-26); 1-[4'-(3-Methyl-4-{2-[methyl-((R)-1-phenyl-ethyl)-carbamoyl]-cyclopropyl}-isoxazol-5-yl)-biphenyl-4-yl]-cyclopropanecarboxylic acid (Compound 1-27); 1-{4'-[4-(3-Benzyl-2-oxo-oxazolidin-5-yl)-3-methyl-isoxazol-5-yl]-biphenyl-4-yl}-cyclopropanecarboxylic acid (Compound 1-28); 1-{4'-[4-(5-Benzyl-[1,3,4]oxadiazol-2-ylmethyl)-3-methyl-isoxazol-5-yl]-biphenyl-4-yl}-cyclopropanecarboxylic acid (Compound 1-29); 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid (Compound 1-30); 1-{4'-[4-(1-Benzyl-1H-[1,2,3]triazol-4-ylmethyl)-3-methyl-isoxazol-5-yl]-biphenyl-4-yl}-cyclopropanecarboxylic acid (Compound 1-31); [1-(4'-{4-[4-(4-Benzyl-phenyl)-1-hydroxy-butyl]-3-methyl-isoxazol-5-yl}-biphenyl-4-yl)-cyclopropyl]-acetic acid (Compound 1-32); [1-(4'-{4-[1-Hydroxy-4-(4-phenoxy-phenyl)-butyl]-3-methyl-isoxazol-5-yl}-biphenyl-4-yl)-cyclopropyl]-acetic acid (Compound 1-33); 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid (Enantiomer A) (Compound 1-34); 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid (Enantiomer B) (Compound 1-35); 1-{4'-[4-(1-Benzyl-piperidin-4-ylamino)-3-methyl-isoxazol-5-yl]-biphenyl-4-yl}-cyclopropanecarboxylic acid (Compound 1-36); (1-{4'-[4-(1-Benzyl-piperidin-4-ylamino)-3-methyl-isoxazol-5-yl]-biphenyl-4-yl}-cyclopropyl)-acetic acid (Compound 1-37); 1-(4'-{4-[Hydroxy-(5-phenyl-[1,3,4]oxadiazol-2-yl)-methyl]-3-methyl-isoxazol-5-yl}-biphenyl-4-yl)-cyclopropanecarboxylic acid (Compound 1-38); [1-(4'-{4-[Hydroxy-(5-phenyl-[1,3,4]oxadiazol-2-yl)-methyl]-3-methyl-isoxazol-5-yl}-biphenyl-4-yl)-cyclopropyl]-acetic acid (Compound 1-39); 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid (Enantiomer A) (Compound 1-40); 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid (Enantiomer B) (Compound 1-41); [1-(4'-{3-Methyl-4-[1-(3-phenyl-isoxazol-5-yl)-ethylamino]-isoxazol-5-yl}-biphenyl-4-yl)-cyclopropyl]-acetic acid (Compound 1-42); [1-(4'-{3-Methyl-4-[1-(3-phenyl-isoxazol-5-yl)-ethylamino]-isoxazol-5-yl}-biphenyl-4-yl)-cyclopropyl]-acetic acid (Enantiomer A) (Compound 1-43); [1-(4'-{3-Methyl-4-[1-(3-phenyl-isoxazol-5-yl)-ethylamino]-isoxazol-5-yl}-biphenyl-4-yl)-cyclopropyl]-acetic acid (Enantiomer B) (Compound 1-44); {1-[4'-(3-Methyl-4-{1-methyl-2-[4-(4-trifluoromethyl-benzyloxy)-phenyl]-ethylamino}-isoxazol-5-yl)-biphenyl-4-yl]-cyclopropyl}-acetic acid (Compound 1-45); 1-[4'-(4-{Hydroxy-[5-(3-trifluoromethyl-benzyl)-[1,3,4]oxadiazol-2-yl]-methyl}-3-methyl-isoxazol-5-yl)-biphenyl-4-yl]-cyclopropanecarboxylic acid (Compound 1-46); 1-(4'-{4-[(1-Benzyl-1H-[1,2,3]triazol-4-yl)-methanesulfonylamino-methyl]-3-methyl-isoxazol-5-yl}-biphenyl-4-yl)-cyclopropanecarboxylic acid (Compound 1-47); (4'-{4-[(1-Benzyl-1H-[1,2,3]triazol-4-yl)-hydroxy-methyl]-3-methyl-isoxazol-5-yl}-biphenyl-4-yl)-acetic acid (Compound 1-48); 3-(4'-{4-[(1-Benzyl-1H-[1,2,3]triazol-4-yl)-hydroxy-methyl]-3-methyl-isoxazol-5-yl}-biphenyl-4-yl)-propionic acid (Compound 1-49); 1-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-cyclopropanecarboxylic acid (Compound 1-50); [4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-acetic acid (Compound 1-51); 3-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-propionic acid (Compound 1-52); 1-{4'-[4-(Biphenyl-3-yl-hydroxy-methyl)-3-methyl-isoxazol-5-yl]-biphenyl-4-yl}-cyclopropanecarboxylic acid (Compound 1-53); 1-(4'-{4-[(4-Benzyloxy-phenyl)-hydroxy-methyl]-3-methyl-isoxazol-5-yl}-biphenyl-4-yl)-cyclopropanecarboxylic acid (Compound 1-54); 1-[4'-(4-{Hydroxy-[1-(1-phenyl-ethyl)-1H-[1,2,3]triazol-4-yl]-methyl}-3-methyl-isoxazol-5-yl)-biphenyl-4-yl]-cyclopropanecarboxylic acid (Compound 1-55); 1-[4'-(4-{Hydroxy-[1-(2-trifluoromethyl-benzyl)-1H-[1,2,3]triazol-4-yl]-methyl}-3-methyl-isoxazol-5-yl)-biphenyl-4-yl]-cyclopropanecarboxylic acid (Compound 1-56); 1-[4'-(4-{[1-(3-Chloro-benzyl)-1H-[1,2,3]triazol-4-yl]-hydroxy-methyl}-3-methyl-isoxazol-5-yl)-biphenyl-4-yl]-cyclopropanecarboxylic acid (Compound 1-57); 1-(4'-{4-[(3-Benzyl-phenyl)-hydroxy-methyl]-3-methyl-isoxazol-5-yl}-biphenyl-4-yl)-cyclopropanecarboxylic acid (Compound 1-58); 1-(4'-{4-[(5-Benzyl-pyridin-3-yl)-hydroxy-methyl]-3-methyl-isoxazol-5-yl}-biphenyl-4-yl)-cyclopropanecarboxylic acid (Compound 1-59); [1-(4'-{4-[(5-Benzyl-[1,3,4]oxadiazol-2-yl)-hydroxy-methyl]-3-methyl-isoxazol-5-yl}-biphenyl-4-yl)-cyclopropyl]-acetic acid (Compound 1-60); 1-[4'-(4-{[1-(2-Chloro-benzyl)-1H-[1,2,3]triazol-4-yl]-hydroxy-methyl}-3-methyl-isoxazol-5-yl)-biphenyl-4-yl]-cyclopropanecarboxylic acid (Compound 1-61); 1-[4'-(4-{[1-(4-Chloro-benzyl)-1H-[1,2,3]triazol-4-yl]-hydroxy-methyl}-3-methyl-isoxazol-5-yl)-biphenyl-4-yl]-cyclopropanecarboxylic acid (Compound 1-62); 1-[4'-(4-{(R)-[1-(2-Chloro-benzyl)-1H-[1,2,3]triazol-4-yl]-hydroxy-methyl}-3-methyl-isoxazol-5-yl)-biphenyl-4-yl]-cyclopropanecarboxylic acid (Compound 1-63); 1-[4'-(4-{[1-(3,4-Dichloro-benzyl)-1H-[1,2,3]triazol-4-yl]-hydroxy-methyl}-3-methyl-isoxazol-5-yl)-biphenyl-4-yl]-cyclopropanecarboxylic acid (Compound 1-64); [4'-(4-{[1-(3,4-Dichloro-benzyl)-1H-[1,2,3]triazol-4-yl]-hydroxy-methyl}-3-methyl-isoxazol-5-yl)-biphenyl-4-yl]-acetic acid (Compound 1-65); 1-(4'-{3-Methyl-4-[trans-1-(2-phenyl-cyclopropyl)-ethylamino]-isoxazol-5-yl}-biphenyl-4-yl)-cyclopropanecarboxylic acid (Compound 1-66); 1-[4'-(4-{(R)-Hydroxy-[1-((R)-1-phenyl-ethyl)-1H-[1,2,3]triazol-4-yl]-methyl}-3-methyl-isoxazol-5-yl)-biphenyl-4-yl]-cyclopropanecarboxylic acid (Compound 1-67); 1-{4'-[3-Methyl-4-(6-phenyl-pyridin-2-ylamino)-isoxazol-5-yl]-biphenyl-4-yl}-cyclopropanecarboxylic acid (Compound 1-68); 1-(4'-{4-[(6-Benzyl-pyridin-2-yl)-hydroxy-methyl]-3-methyl-isoxazol-5-yl}-biphenyl-4-yl)-cyclopropanecarboxylic acid (Compound 1-69); 1-[4'-(4-{Hydroxy-[1-(2-methyl-benzyl)-1H-[1,2,3]triazol-4-yl]-methyl}-3-methyl-isoxazol-5-yl)-biphenyl-4-yl]-cyclopropanecarboxylic acid (Compound 1-70); 1-[4'-(4-{[1-(2-Chloro-6-fluoro-benzyl)-1H-[1,2,3]triazol-4-yl]-hydroxy-methyl}-3-methyl-isoxazol-5-yl)-biphenyl-4-yl]-cyclopropanecarboxylic acid (Compound 1-71); 1-[4'-(4-{[1-(2,6-Dichloro-benzyl)-1H-[1,2,3]triazol-4-yl]-hydroxy-methyl}-3-methyl-isoxazol-5-yl)-biphenyl-4-yl]-cyclopropanecarboxylic acid (Compound 1-72); 1-{4'-[4-(6-Benzyl-pyridin-2-ylamino)-3-methyl-isoxazol-5-yl]-biphenyl-4-yl}-cyclopropanecarboxylic acid (Compound 1-73); 1-{4'-[4-(Biphenyl-3-ylamino)-3-methyl-isoxazol-5-yl]-biphenyl-4-yl}-cyclopropanecarboxylic acid (Compound 1-74); 1-{4'-[4-(Biphenyl-4-ylamino)-3-methyl-isoxazol-5-yl]-biphenyl-4-yl}-cyclopropanecarboxylic acid (Compound 1-75); {4'-[3-Methyl-4-(6-phenyl-pyridin-2-ylamino)-isoxazol-5-yl]-biphenyl-4-yl}-acetic acid (Compound 1-76); 1-(4'-{3-Methyl-4-[6-(3-trifluoromethyl-phenyl)-pyridin-2-ylamino]-isoxazol-5-yl}-biphenyl-4-yl)-cyclopropanecarboxylic acid (Compound 1-77); 1-{4'-[3-Methyl-4-(6-phenyl-pyrazin-2-ylamino)-isoxazol-5-yl]-biphenyl-4-yl}-cyclopropanecarboxylic acid (Compound 1-78); 1-{4'-[3-Methyl-4-(6-phenoxy-pyridin-2-ylamino)-isoxazol-5-yl]-biphenyl-4-yl}-cyclopropanecarboxylic acid (Compound 1-79); 1-{4'-[3-Methyl-4-(5-phenyl-[1,3,4]oxadiazol-2-ylamino)-isoxazol-5-yl]-biphenyl-4-yl}-cyclopropanecarboxylic acid (Compound 1-80); 3-{4'-[3-Methyl-4-(5-phenyl-[1,3,4]oxadiazol-2-ylamino)-isoxazol-5-yl]-biphenyl-4-yl}-propionic acid (Compound 1-81); 1-{4'-[3-Methyl-4-(3-phenoxy-phenylamino)-isoxazol-5-yl]-biphenyl-4-yl}-cyclopropanecarboxylic acid (Compound 1-82); 1-{4'-[4-(5-Benzyl-[1,3,4]oxadiazol-2-ylamino)-3-methyl-isoxazol-5-yl]-biphenyl-4-yl}-cyclopropanecarboxylic acid (Compound 1-83); 1-(4'-{4-[6-(2-Fluoro-benzyl)-pyridin-2-ylamino]-3-methyl-isoxazol-5-yl}-biphenyl-4-yl)-cyclopropanecarboxylic acid (Compound 1-84); 1-(4'-{4-[6-(3-Fluoro-benzyl)-pyridin-2-ylamino]-3-methyl-isoxazol-5-yl}-biphenyl-4-yl)-cyclopropanecarboxylic acid (Compound 1-85); 1-(4'-{4-[6-(4-Fluoro-benzyl)-pyridin-2-ylamino]-3-methyl-isoxazol-5-yl}-biphenyl-4-yl)-cyclopropanecarboxylic acid (Compound 1-86); 1-{4'-[4-(6'-Ethoxy-[2,3']bipyridinyl-6-ylamino)-3-methyl-isoxazol-5-yl]-biphenyl-4-yl}-cyclopropanecarboxylic acid (Compound 1-87); 1-(4'-{4-[6-(3-Methoxy-phenyl)-pyridin-2-ylamino]-3-methyl-isoxazol-5-yl}-biphenyl-4-yl)-cyclopropanecarboxylic acid (Compound 1-88); 1-(4'-{4-[3-(2-Methoxy-pyridin-3-yl)-phenylamino]-3-methyl-isoxazol-5-yl}-biphenyl-4-yl)-cyclopropanecarboxylic acid (Compound 1-89); 1-{4'-[4-(3-Benzyl-phenylamino)-3-methyl-isoxazol-5-yl]-biphenyl-4-yl}-cyclopropanecarboxylic acid (Compound 1-90); 1-(4'-{4-[6-(2-Cyano-phenyl)-pyridin-2-ylamino]-3-methyl-isoxazol-5-yl}-biphenyl-4-yl)-cyclopropanecarboxylic acid (Compound 1-91); 1-(4'-{4-[6-(4-Methoxy-phenyl)-pyridin-2-ylamino]-3-methyl-isoxazol-5-yl}-biphenyl-4-yl)-cyclopropanecarboxylic acid (Compound 1-92); 1-(4'-{4-[6-(3-Fluoro-phenyl)-pyridin-2-ylamino]-3-methyl-isoxazol-5-yl}-biphenyl-4-yl)-cyclopropanecarboxylic acid (Compound 1-93); 1-(4'-{4-[6-(2-Methoxy-phenyl)-pyridin-2-ylamino]-3-methyl-isoxazol-5-yl}-biphenyl-4-yl)-cyclopropanecarboxylic acid (Compound 1-94); 1-(4'-{4-[6-(2-Fluoro-phenyl)-pyridin-2-ylamino]-3-methyl-isoxazol-5-yl}-biphenyl-4-yl)-cyclopropanecarboxylic acid (Compound 1-95); 1-(4'-{3-methyl-4-[6-(2-trifluoromethyl-phenyl)-pyridin-2-ylamino]-isoxazol-5-yl}-biphenyl-4-yl)-cyclopropanecarboxylic acid (Compound 1-96); 1-{4'-[4-(2'-Methoxy-[2,3']bipyridinyl-6-ylamino)-3-methyl-isoxazol-5-yl]-biphenyl-4-yl}-cyclopropanecarboxylic acid (Compound 1-97); 1-{4'-[4-(6'-Methoxy-[2,3']bipyridinyl-6-ylamino)-3-methyl-isoxazol-5-yl]-biphenyl-4-yl}-cyclopropanecarboxylic acid (Compound 1-98); 1-{4'-[4-([2,4']Bipyridinyl-6-ylamino)-3-methyl-isoxazol-5-yl]-biphenyl-4-yl}-cyclopropanecarboxylic acid (Compound 1-99); 1-(4'-{3-Methyl-4-[(2-phenyl-thiazol-5-ylmethyl)-amino]-isoxazol-5-yl}-biphenyl-4-yl)-cyclopropanecarboxylic acid (Compound 1-100); 1-{4'-[3-Methyl-4-(2'-trifluoromethyl-biphenyl-3-ylamino)-isoxazol-5-yl]-biphenyl-4-yl}-cyclopropanecarboxylic acid (Compound 1-101); 1-(4'-{4-[3-(6-Methoxy-pyridin-3-yl)-phenylamino]-3-methyl-isoxazol-5-yl}-biphenyl-4-yl)-cyclopropanecarboxylic acid (Compound 1-102); 1-{4'-[3-Methyl-4-(3-pyridin-3-yl-phenylamino)-isoxazol-5-yl]-biphenyl-4-yl}-cyclopropanecarboxylic acid (Compound 1-103); 1-(4'-{4-[3-(5-Methoxy-pyridin-3-yl)-phenylamino]-3-methyl-isoxazol-5-yl}-biphenyl-4-yl)-cyclopropanecarboxylic acid (Compound 1-104); 1-(4'-{3-Methyl-4-[6-(methyl-phenyl-amino)-pyridin-2-ylamino]-isoxazol-5-yl}-biphenyl-4-yl)-cyclopropanecarboxylic acid (Compound 1-105); 1-(4'-{3-Methyl-4-[3-(methyl-phenyl-amino)-phenylamino]-isoxazol-5-yl}-biphenyl-4-yl)-cyclopropanecarboxylic acid (Compound 1-106); 1-{4'-[3-Methyl-4-(5-phenyl-pyridin-3-ylamino)-isoxazol-5-yl]-biphenyl-4-yl}-cyclopropanecarboxylic acid (Compound 1-107); 1-(4'-{4-[5-(3-Fluoro-phenyl)-pyridin-3-ylamino]-3-methyl-isoxazol-5-yl}-biphenyl-4-yl)-cyclopropanecarboxylic acid (Compound 1-108); 1-(4'-{4-[6-(2-Chloro-phenyl)-pyridin-2-ylamino]-3-methyl-isoxazol-5-yl}-biphenyl-4-yl)-cyclopropanecarboxylic acid (Compound 1-109); 1-(4'-{4-[Hydroxy-(6-phenylpyridin-2-yl)-methyl]-3-methyl-isoxazol-5-yl}-biphenyl-4-yl)-cyclopropanecarboxylic acid (Compound 1-110); 1-{4'-[3-Methyl-4-(2-phenyl-pyridin-4-ylamino)-isoxazol-5-yl]-biphenyl-4-yl}-cyclopropanecarboxylic acid (Compound 1-111); 1-(4'-{4-[2-(3-Fluoro-phenyl)-pyridin-4-ylamino]-3-methyl-isoxazol-5-yl}-biphenyl-4-yl)-cyclopropanecarboxylic acid (Compound 1-112); 1-(4'-{4-[5-(2-Chloro-phenyl)-pyridin-3-ylamino]-3-methyl-isoxazol-5-yl}-biphenyl-4-yl)-cyclopropanecarboxylic acid (Compound 1-113); 1-(4'-{4-[2-(2-Chloro-phenyl)-pyridin-4-ylamino]-3-methyl-isoxazol-5-yl}-biphenyl-4-yl)-cyclopropanecarboxylic acid (Compound 1-114); 1-{4'-[3-Methyl-4-(4-phenyl-pyrimidin-2-ylamino)-isoxazol-5-yl]-biphenyl-4-yl}-cyclopropanecarboxylic acid (Compound 1-115); 1-{4'-[3-Methyl-4-(4-phenyl-pyridin-2-ylamino)-isoxazol-5-yl]-biphenyl-4-yl}-cyclopropanecarboxylic acid (Compound 1-116); 1-{4'-[4-(2'-Dimethylaminomethyl-biphenyl-3-ylamino)-3-methyl-isoxazol-5-yl]-biphenyl-4-yl}-cyclopropanecarboxylic acid (Compound 1-117); 1-(4'-{3-Methyl-4-[5-(3-trifluoromethyl-phenyl)-pyridin-3-ylamino]-isoxazol-5-yl}-biphenyl-4-yl)-cyclopropanecarboxylic acid (Compound 1-118); 1-(4'-{3-Methyl-4-[5-(4-trifluoromethyl-phenyl)-pyridin-3-ylamino]-isoxazol-5-yl}-biphenyl-4-yl)-cyclopropanecarboxylic acid (Compound 1-119); 1-(4'-{4-[Bis-(6-benzyl-pyridin-2-yl)-amino]-3-methyl-isoxazol-5-yl}-biphenyl-4-yl)-cyclopropanecarboxylic acid (Compound 1-120); 1-(4'-{4-[(2'-Dimethylaminomethyl-biphenyl-3-carbonyl)-amino]-3-methyl-isoxazol-5-yl}-biphenyl-4-yl)-cyclopropanecarboxylic acid (Compound 1-121); 1-{4'-[3-Methyl-4-(6-phenyl-pyridin-2-ylamino)-isoxazol-5-yl]-biphenyl-4-yl}-cyclobutanecarboxylic acid (Compound 1-122); 1-{4'-[3-Methyl-4-(6-pyrazol-1-yl-pyridin-2-ylamino)-isoxazol-5-yl]-biphenyl-4-yl}-cyclopropanecarboxylic acid (Compound 1-123); 1-{4'-[3-Methyl-4-(6-morpholin-4-yl-pyridin-2-ylamino)-isoxazol-5-yl]-biphenyl-4-yl}-cyclopropanecarboxylic acid (Compound 1-124); 1-{4'-[4-(6-Benzyloxy-pyridin-2-ylamino)-3-methyl-isoxazol-5-yl]-biphenyl-4-yl}-cyclopropanecarboxylic acid (Compound 1-125); 1-{4'-[3-Methyl-4-(6-phenylsulfanyl-pyridin-2-ylamino)-isoxazol-5-yl]-biphenyl-4-yl}-cyclopropanecarboxylic acid (Compound 1-126); 1-{4'-[4-(6-Benzenesulfinyl-pyridin-2-ylamino)-3-methyl-isoxazol-5-yl]-biphenyl-4-yl}-cyclopropanecarboxylic acid (Compound 1-127); 1-{4'-[4-(6-Benzenesulfonyl-pyridin-2-ylamino)-3-methyl-isoxazol-5-yl]-biphenyl-4-yl}-cyclopropanecarboxylic acid (Compound 1-128); 1-(4'-{4-[Hydroxy-(5-phenyl-pyridin-3-yl)-methyl]-3-methyl-isoxazol-5-yl}-biphenyl-4-yl)-cyclopropanecarboxylic acid (Compound 1-129); 1-[4'-(4-{Hydroxy-[5-(3-trifluoromethyl-phenyl)-pyridin-3-yl]-methyl}-3-methyl-isoxazol-5-yl)-biphenyl-4-yl]-cyclopropanecarboxylic acid (Compound 1-130); 1-{4'-[3-Methyl-4-(6-phenylethynyl-pyridin-2-ylamino)-isoxazol-5-yl]-biphenyl-4-yl}-cyclopropanecarboxylic acid (Compound 1-131); 3-{4'-[3-Methyl-4-(6-phenyl-pyridin-2-ylamino)-isoxazol-5-yl]-biphenyl-4-yl}-propionic acid (Compound 1-132); 2-Methyl-2-{4'-[3-methyl-4-(6-phenyl-pyridin-2-ylamino)-isoxazol-5-yl]-biphenyl-4-yl}-propionic acid (Compound 1-133); (1-{4'-[3-Methyl-4-(6-phenyl-pyridin-2-ylamino)-isoxazol-5-yl]-biphenyl-4-yl}-cyclopropyl)-acetic acid (Compound 1-134); 1-{4'-[4-(6-Cyclopentylethynyl-pyridin-2-ylamino)-3-methyl-isoxazol-5-yl]-biphenyl-4-yl}-cyclopropanecarboxylic acid (Compound 1-135); 1-{4'-[3-Methyl-4-[6-(pyrrolidine-1-carbonyl)-pyridin-2-ylamino]-isoxazol-5-yl]-biphenyl-4-yl}-cyclopropanecarboxylic acid (Compound 1-136); 1-{4'-[4-(6-Cyclopropylcarbamoyl-pyridin-2-ylamino)-3-methyl-isoxazol-5-yl]-biphenyl-4-yl}-cyclopropanecarboxylic acid (Compound 1-137); 1-{4'-[4-(6-Cyclohexyloxy-pyridin-2-ylamino)-3-methyl-isoxazol-5-yl]-biphenyl-4-yl}-cyclopropanecarboxylic acid (Compound 1-138); 1-{4'-[4-(6-Cyclobutoxy-pyridin-2-ylamino)-3-methyl-isoxazol-5-yl]-biphenyl-4-yl}-cyclopropanecarboxylic acid (Compound 1-139); 1-(4'-{4-[6-(1-Cyclohexyl-ethoxy)-pyridin-2-ylamino]-3-methyl-isoxazol-5-yl}-biphenyl-4-yl)-cyclopropanecarboxylic acid (Compound 1-140); 1-{4'-[3-Methyl-4-(6-phenethyloxy-pyridin-2-ylamino)-isoxazol-5-yl]-biphenyl-4-yl}-cyclopropanecarboxylic acid (Compound 1-141); 4'-[3-Methyl-4-(5-phenyl-[1,3,4]oxadiazol-2-ylamino)-isoxazol-5-yl]-biphenyl-4-carboxylic acid (Compound 1-142); 1-(4'-{3-Methyl-4-[6-(2-oxo-oxazolidin-3-yl)-pyridin-2-ylamino]-isoxazol-5-yl}-biphenyl-4-yl)-cyclopropanecarboxylic acid (Compound 1-143); 1-(4'-{4-[6-(3-Carbamoyl-phenyl)-pyridin-2-ylamino]-3-methyl-isoxazol-5-yl}-biphenyl-4-yl)-cyclopropanecarboxylic acid (Compound 1-144); 1-(4'-{4-[6-(3-Cyano-phenyl)-pyridin-2-ylamino]-3-methyl-isoxazol-5-yl}-biphenyl-4-yl)-cyclopropanecarboxylic acid (Compound 1-145); 1-(4'-{4-[6-(5-Fluoro-2-methoxy-phenyl)-pyridin-2-ylamino]-3-methyl-isoxazol-5-yl}-biphenyl-4-yl)-cyclopropanecarboxylic acid (Compound 1-146); 1-(4'-{4-[6-(3-Chloro-5-fluoro-phenyl)-pyridin-2-ylamino]-3-methyl-isoxazol-5-yl}-biphenyl-4-yl)-cyclopropanecarboxylic acid (Compound 1-147); 1-(4'-{4-[6-(2,5-Difluoro-phenyl)-pyridin-2-ylamino]-3-methyl-isoxazol-5-yl}-biphenyl-4-yl)-cyclopropanecarboxylic acid (Compound 1-148); 1-(4'-{3-Methyl-4-[6-(2H-tetrazol-5-yl)-pyridin-2-ylamino]-isoxazol-5-yl}-biphenyl-4-yl)-cyclopropanecarboxylic acid (Compound 1-149); 1-(4'-{4-[6-(2,6-Dichloro-phenyl)-pyridin-2-ylamino]-3-methyl-isoxazol-5-yl}-biphenyl-4-yl)-cyclopropanecarboxylic acid (Compound 1-150); 1-(4'-{4-[6-(2-Chloro-5-fluoro-phenyl)-pyridin-2-ylamino]-3-methyl-isoxazol-5-yl}-biphenyl-4-yl)-cyclopropanecarboxylic acid (Compound 1-151); 1-(4'-{4-[6-(2,3-Difluoro-phenyl)-pyridin-2-ylamino]-3-methyl-isoxazol-5-yl}-biphenyl-4-yl)-cyclopropanecarboxylic acid (Compound 1-152); 1-(4'-{4-[6-(2-Chloro-3-fluoro-phenyl)-pyridin-2-ylamino]-3-methyl-isoxazol-5-yl}-biphenyl-4-yl)-cyclopropanecarboxylic acid (Compound 1-153); 1-{4'-[4-(6-Cyclopropylmethoxy-pyridin-2-ylamino)-3-methyl-isoxazol-5-yl]-biphenyl-4-yl}-cyclopropanecarboxylic acid (Compound 1-154); 1-(4'-{4-[5-(2-Chloro-3-fluoro-phenyl)-pyridin-3-ylamino]-3-methyl-isoxazol-5-yl}-biphenyl-4-yl)-cyclopropanecarboxylic acid (Compound 1-155); 1-(4'-{4-[6-(3-Fluoro-2-methyl-phenyl)-pyridin-2-ylamino]-3-methyl-isoxazol-5-yl}-biphenyl-4-yl)-cyclopropanecarboxylic acid (Compound 1-156); 1-(4'-{4-[6-(2-Chloro-3-trifluoromethyl-phenyl)-pyridin-2-ylamino]-3-methyl-isoxazol-5-yl}-biphenyl-4-yl)-cyclopropanecarboxylic acid (Compound 1-157); 1-(4'-{4-[6-(2,3-Dichloro-phenyl)-pyridin-2-ylamino]-3-methyl-isoxazol-5-yl}-biphenyl-4-yl)-cyclopropanecarboxylic acid (Compound 1-158); 1-(4'-{4-[6-(3-Fluoro-2-methoxy-phenyl)-pyridin-2-ylamino]-3-methyl-isoxazol-5-yl}-biphenyl-4-yl)-cyclopropanecarboxylic acid (Compound 1-159); 1-(4'-{4-[5-(3-Chloro-phenyl)-pyridin-3-ylamino]-3-methyl-isoxazol-5-yl}-biphenyl-4-yl)-cyclopropanecarboxylic acid (Compound 1-160); 1-(4'-{4-[5-(2,5-Difluoro-phenyl)-pyridin-3-ylamino]-3-methyl-isoxazol-5-yl}-biphenyl-4-yl)-cyclopropanecarboxylic acid (Compound 1-161); 1-(4'-{4-[6-(3-Chloro-phenyl)-pyridin-2-ylamino]-3-methyl-isoxazol-5-yl}-biphenyl-4-yl)-cyclopropanecarboxylic acid (Compound 1-162).

TABLE 2

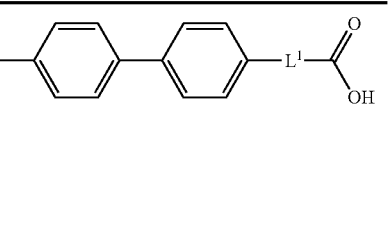

| Cmpd No | L¹ | L² | A | L⁴ | R² | M + H* |
|---|---|---|---|---|---|---|
| 2-1 | Cyclopropyl-1,1-diyl | —NH— | Pyridine-2,6-diyl | — | Phenyl | 502 |
| 2-2 | Cyclopropyl-1,1-diyl | —NH— | [1,3,4]Oxadiazol-2,5-diyl | — | Phenyl | 493 |

*mass spectrometric data

Compounds in Table 2 are named:
1-{4'-[3-Ethyl-4-(6-phenyl-pyridin-2-ylamino)-isoxazol-5-yl]-biphenyl-4-yl}-cyclopropanecarboxylic acid (Compound 2-1); 1-{4'-[3-Ethyl-4-(5-phenyl-[1,3,4]oxadiazol-2-ylamino)-isoxazol-5-yl]-biphenyl-4-yl}-cyclopropanecarboxylic acid (Compound 2-2).

(Compound 3-3); N-(1-{4'-[3-Methyl-4-(5-phenyl-[1,3,4]oxadiazol-2-ylamino)-isoxazol-5-yl]-biphenyl-4-yl}-cyclopropanecarbonyl)-methanesulfonamide (Compound 3-4); N-(1-{4'-[4-(6-Benzyl-pyridin-2-ylamino)-3-methyl-isoxazol-5-yl]-biphenyl-4-yl}-cyclopropanecarbonyl)-methanesulfonamide (Compound 3-5); N-(1-{4'-[3-Methyl-4-(6-phenyl-pyridin-2-ylamino)-isoxazol-5-yl]-biphenyl-4-yl}-cyclopropanecarbonyl)-methanesulfonamide (Compound 3-6).

Any combination of the groups described above for the various variables is contemplated herein. Throughout the specification, groups and substituents thereof are chosen by one skilled in the field to provide stable moieties and compounds.

Synthesis of Compounds

Compounds of Formula (I), (Ia), (II), (IIa), (III), (IIIa), (IV) and (V) described herein are synthesized using standard synthetic techniques or using methods known in the art in combination with methods described herein. In addition, solvents, temperatures and other reaction conditions presented herein may vary.

The starting material used for the synthesis of the compounds of Formula (I), (Ia), (II), (IIa), (III), (IIIa), (IV) and (V) are either synthesized or obtained from commercial sources, such as, but not limited to, Sigma-Aldrich, Fluka, Acros Organics, Alfa Aesar, and the like. The compounds described herein, and other related compounds having different substituents are synthesized using techniques and materials described herein or otherwise known, including those found in March, ADVANCED ORGANIC CHEMISTRY 4th Ed., (Wiley 1992); Carey and Sundberg, ADVANCED ORGANIC CHEMISTRY 4th

TABLE 3

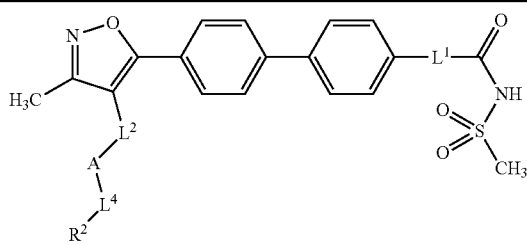

| Cmpd No | L¹ | L² | A | L⁴ | R² | M + H* |
|---|---|---|---|---|---|---|
| 3-1 | Cyclopropyl-1,1-diyl | —CH(OH)— | [1,2,3]Triazol-1,4-diyl | —CH₂— | Phenyl | 584 |
| 3-2 | Cyclopropyl-1,1-diyl | —CH(OH)— | [1,3,4]Oxadiazol-2,5-diyl | —CH₂— | Phenyl | 585 |
| 3-3 | Cyclopropyl-1,1-diyl | —CH(OH)— | [1,2,3]Triazol-1,4-diyl | —CH₂— | 3-Trifluoromethyl-phenyl | 652 |
| 3-4 | Cyclopropyl-1,1-diyl | —NH— | [1,3,4]Oxadiazol-2,5-diyl | — | Phenyl | 556 |
| 3-5 | Cyclopropyl-1,1-diyl | —NH— | Pyridine-2,6-diyl | —CH₂— | Phenyl | 579 |
| 3-6 | Cyclopropyl-1,1-diyl | —NH— | Pyridine-2,6-diyl | — | Phenyl | 565 |

*mass spectrometric data

Compounds in Table 3 are named:
N-[1-(4'-{4-[(1-Benzyl-1H-[1,2,3]triazol-4-yl)-hydroxy-methyl]-3-methyl-isoxazol-5-yl}-biphenyl-4-yl)-cyclopropanecarbonyl]-methanesulfonamide (Enantiomer B) (Compound 3-1); N-[1-(4'-{4-[(5-Benzyl-[1,3,4]oxadiazol-2-yl)-hydroxy-methyl]-3-methyl-isoxazol-5-yl}-biphenyl-4-yl)-cyclopropanecarbonyl]-methanesulfonamide (Enantiomer A) (Compound 3-2); N-{1-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-cyclopropanecarbonyl}-methanesulfonamide Ed., Vols. A and B (Plenum 2000, 2001), and Green and Wuts, PROTECTIVE GROUPS IN ORGANIC SYNTHESIS 3rd Ed., (Wiley 1999). General methods for the preparation of compounds can be modified by the use of appropriate reagents and conditions for the introduction of the various moieties found in the formulae as provided herein.

In one aspect, the compounds of Formula (I), (Ia), (II), (IIa), (III), (IIIa), (IV) and (V) are prepared as outlined in the following Schemes.

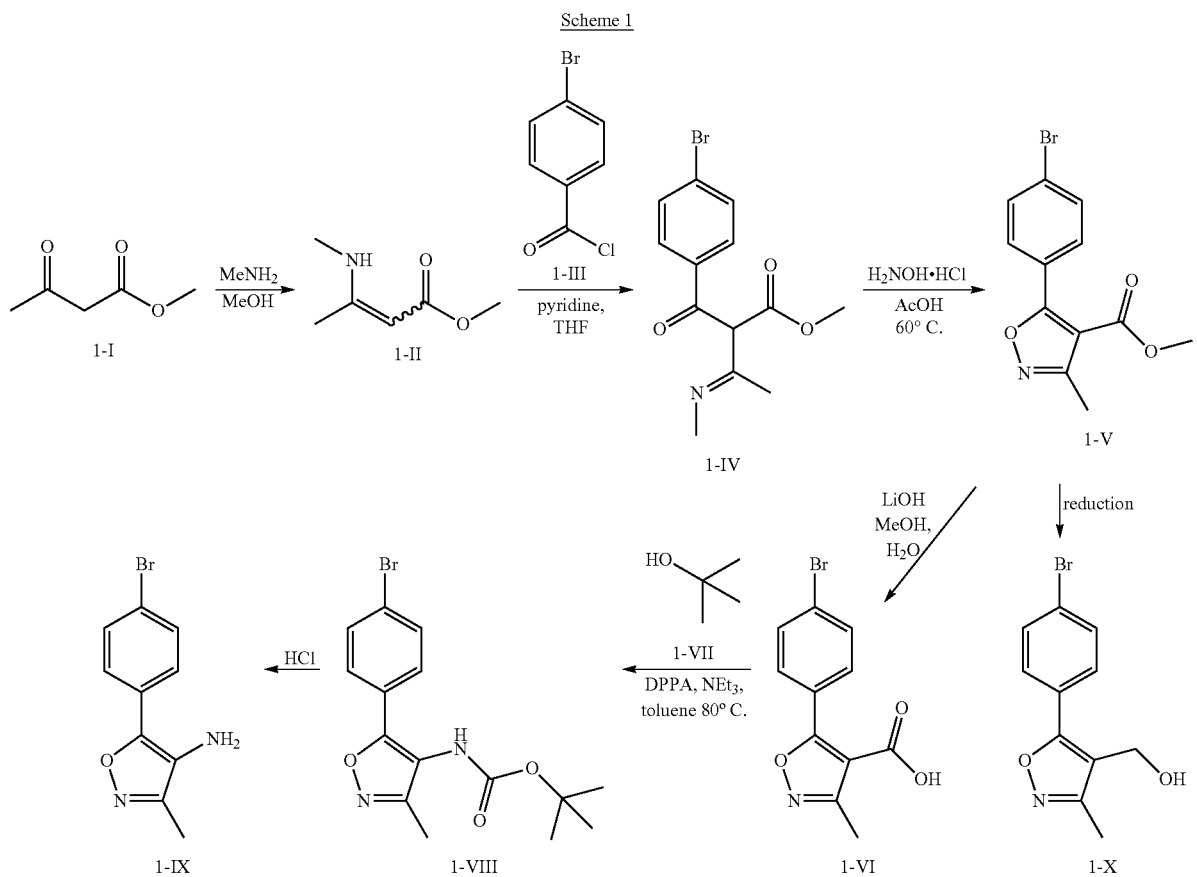

In one aspect, the synthesis of compounds of Formula (I), (Ia), (II), (IIa), (III), (IIIa), (IV) and (V) described herein begins with the reaction of an alkyl acetoacetate with methylamine to provide a compound of structure 1-II. Compounds of structure 1-II are reacted with a substituted or unsubstituted 4-halo-benzoyl chloride (structure I-III) to provide compounds of structure 1-IV. Treatment of compounds of structure 1-IV with hydroxylamine and acetic acid provides isoxazoles of structure 1-V. Hydrolysis of the ester group of isoxazoles of structure 1-V provides carboxylic acids of structure 1-VI. A Curtius rearrangement of carboxylic acids of structure 1-VI in the presence of hydroxy compounds of structure 1-VII provides carbamate compounds of structure 1-VIII. Deprotection of the tert-butoxycarbonyl group provides amines of structure 1-IX which are further functionalized into compounds of Formula (I), (Ia), (II), (IIa), (III), (IIIa), (IV) and (V). In some embodiments, compounds of 1-V are reduced to the alcohol and then further functionalized into compounds of Formula (I), (Ia), (II), (IIa), (III), (IIIa), (IV) and (V).

In some embodiments, the isoxazole in any of the schemes described herein are prepared as outlined in Scheme 2.

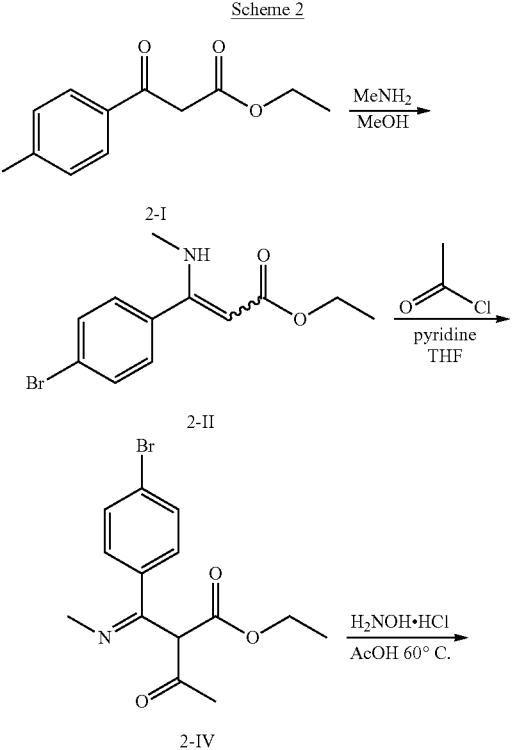

-continued

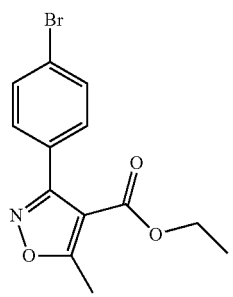

1-V

In some embodiments, the synthesis of compounds of Formula (I), (Ia), (II), (IIa), (III), (IIIa), (IV) and (V) described herein begins with the reaction of an alkyl acetoacetate with methylamine to provide a compound of structure 2-II. Reaction of 2-II provides compounds 2-IV which are then treated with hydroxylamine to provide isoxazoles of structure 1-V. Isoxazoles of structure 2-V are then elaborated into compounds of Formula (I), (Ia), (II), (IIa), (III), (IIIa), (IV) and (V) as described herein.

In some embodiments, compounds of Formula (I), (Ia), (II), (IIa), (III), (IIIa), (IV) and (V) are prepared as described in Scheme 3.

Scheme 3

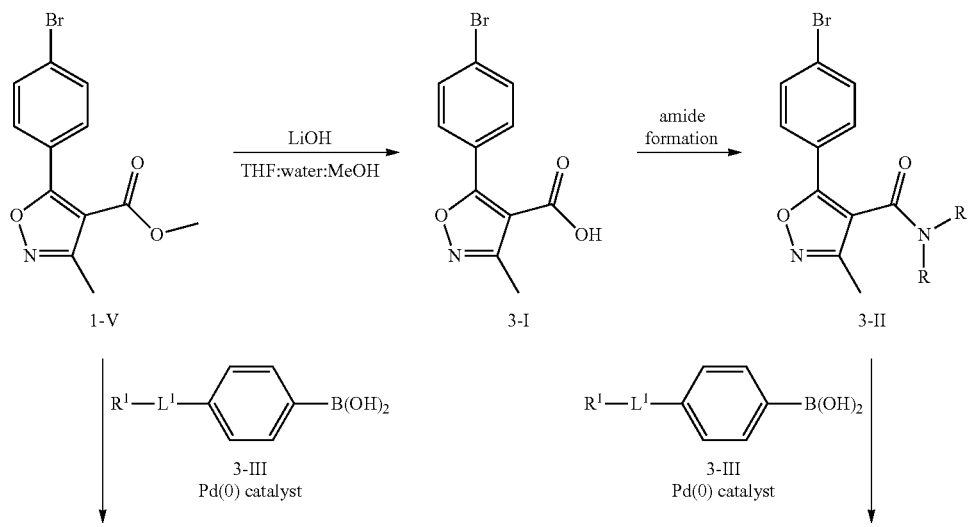

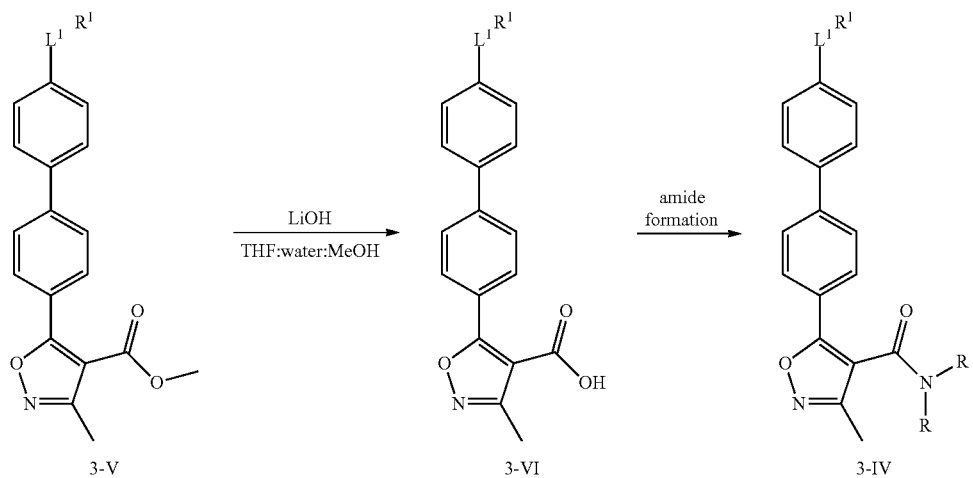

In some embodiments, ester 1-V is hydrolysized to the acid 3-I and this acid is coupled with an amine providing amide 3-II. In some embodiments, compounds 3-II are subjected to a palladium-catalyzed coupling with boronic acid deriviatives 3-III to provide amide derivates 3-IV. Alternatively, in some embodiments, compounds 1-V are subjected to a palladium-catalyzed coupling with boronic acid deriviatives 3-III to provide ester derivates 3-V. Hydrolysis and amide formation provides amide derivatives 3-IV.

In some embodiments, compounds of Formula (I), (Ia), (II), (IIa), (III), (IIIa), (IV) and (V) are prepared as described in Scheme 4.

Scheme 4

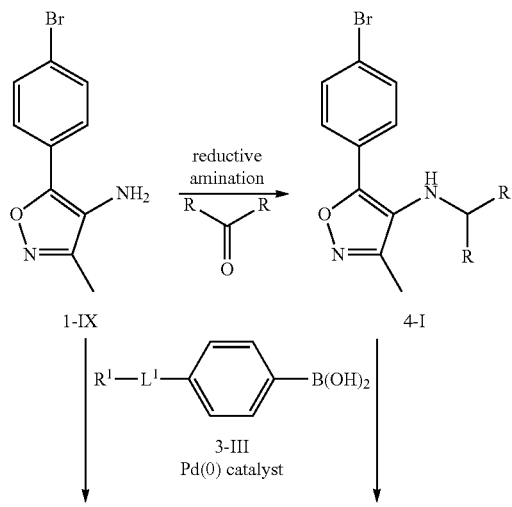

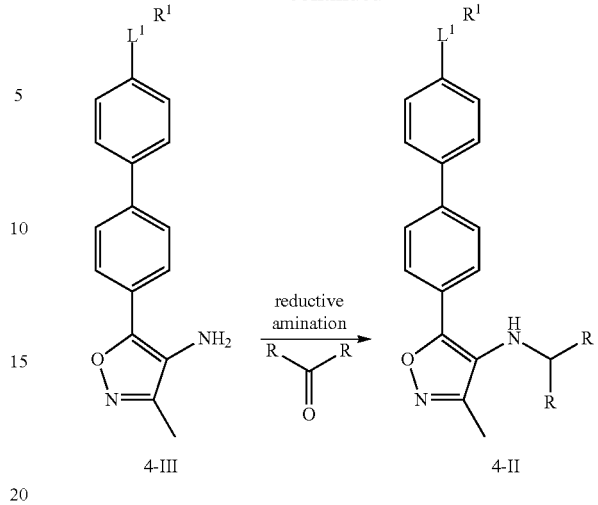

In some embodiments, amine 1-IX is subjected to a reductive amination to provide substituted amine 4-I. In some embodiments, compounds 4-I are subjected to a palladium-catalyzed coupling with boronic acid deriviatives 3-III to provide amine derivates 4-II. Alternatively, in some embodiments, compounds 1-V are subjected to a palladium-catalyzed coupling with boronic acid deriviatives 3-III to provide amine derivates 4-III. Reductive amination provides substituted amine 4-II.

In some embodiments, compounds of Formula (I), (Ia), (II), (IIa), (III), (IIIa), (IV) and (V) are prepared as described in Scheme 5.

Scheme 5

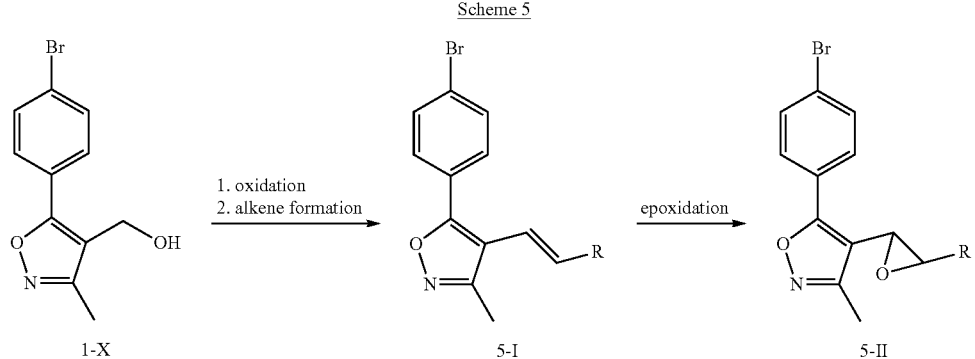

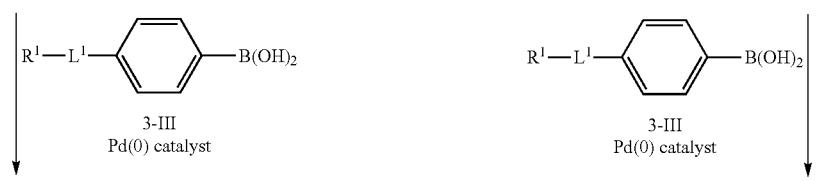

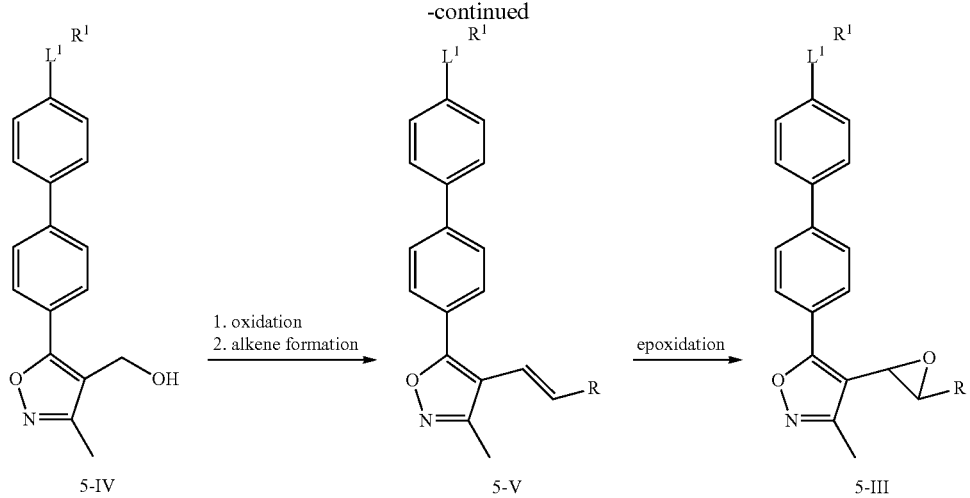

In some embodiments, alcohol 1-X is oxidized to the aldehyde and subjected to an alkene forming reaction, such as a Wittig reaction or a Horner-Emmons reaction as known to one skilled in the art, to provide alkene 5-I. Epoxidation of alkene 5-I affords epoxide 5-II. In some embodiments the epoxidation occurs with induction of sterochemistry by employing methods known in the art for such a transformation, such as the method of Jacobsen and co-workers, or Shi and co-workers. In some embodiments, compounds 5-II are subjected to a palladium-catalyzed coupling with boronic acid deriviatives 3-III to provide derivates 5-III. Alternatively, in some embodiments, compounds 1-X are subjected to a palladium-catalyzed coupling with boronic acid deriviatives 3-III to provide compounds 5-IV. Oxidation to the aldehyde and subjecting to an alkene forming reaction, such as a Wittig reaction or a Horner-Emmons reaction provides alkene 5-V. Epoxidation of alkene 5-V affords epoxide 5-111. In some embodiments the epoxidation occurs with induction of sterochemistry by employing methods known in the art for such a transformation, such as the method of Jacobsen and co-workers, or Shi and co-workers.

In some embodiments, compounds of Formula (I), (Ia), (II), (IIa), (III), (IIIa), (IV) and (V) are prepared as described in Scheme 6.

Scheme 6

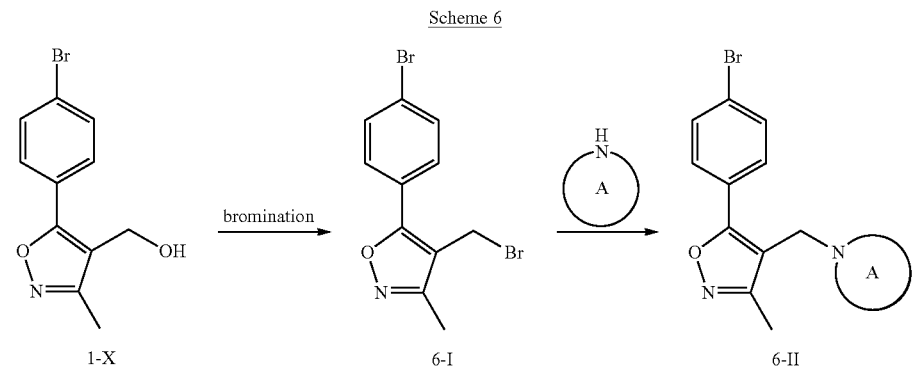

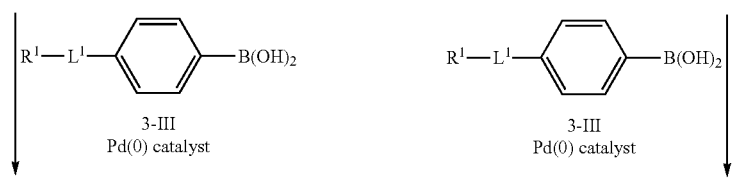

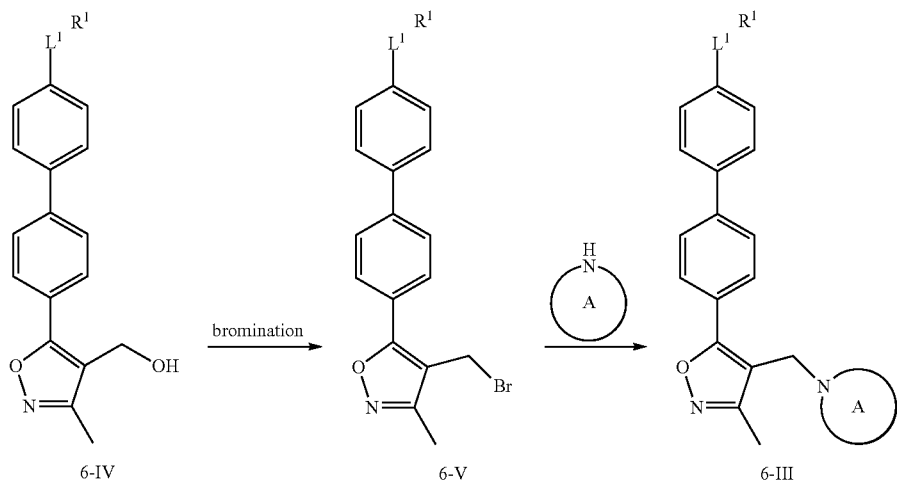

In some embodiments, alcohol 1-X is converted to bromide 6-I. Displacement of the bromine with a nucleophilic nitrogen heterocycle affords intermediate 6-II. Palladium-catalyzed coupling with aryl boronic acids yields compound 6-III. Alternatively, in some embodiments, compounds 1-X are subjected to a palladium-catalyzed coupling with boronic acid deriviatives 3-III to provide compounds 6-IV. Bromination followed by displacement with nucleophilic heterocycle A provides compound 6-III.

In some embodiments, compounds of Formula (I), (Ia), (II), (IIa), (III), (IIIa), (IV) and (V) are prepared as described in Scheme 7.

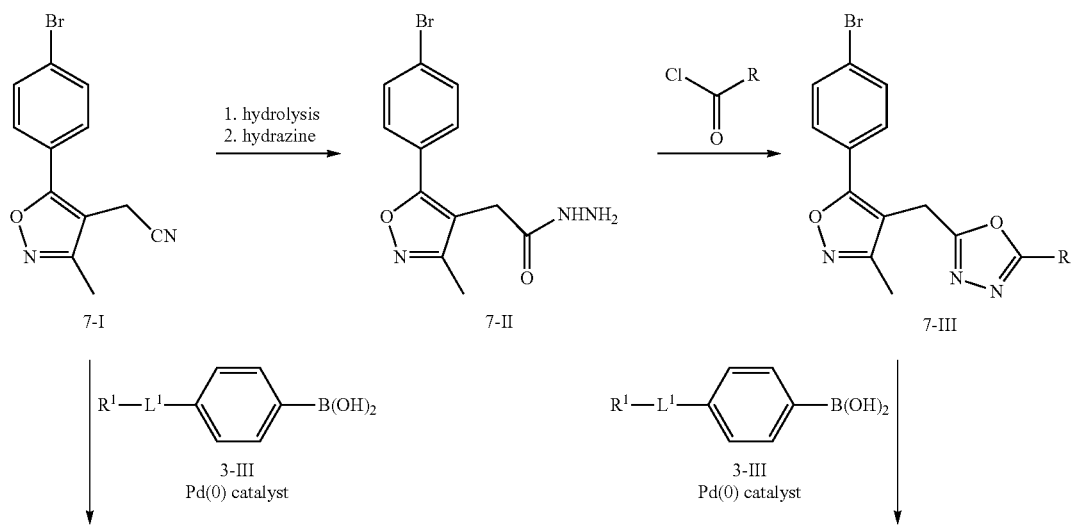

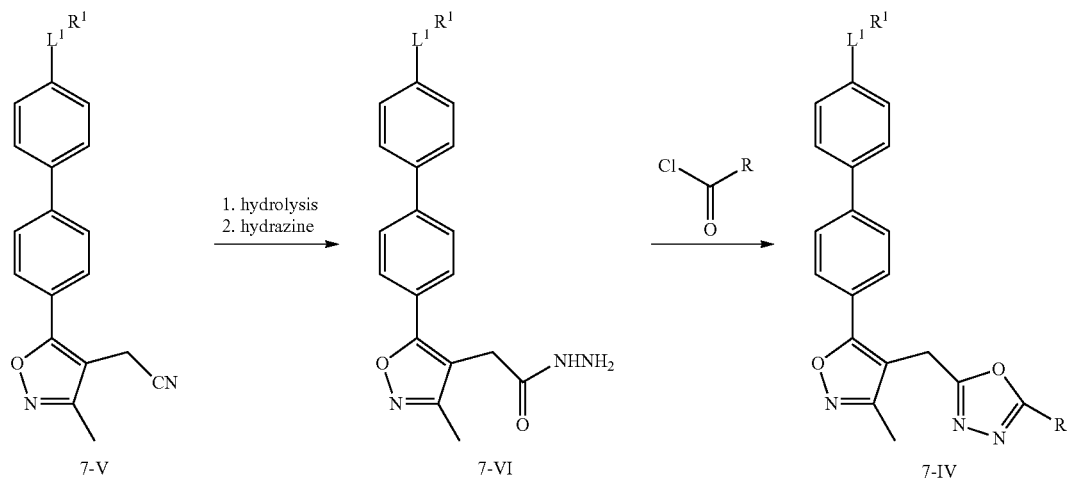

In some embodiments, nitrile 7-I is obtained from bromide 6-I by displacement with cyanide. Nitrile 7-I is hydrolysized and condensed with hydrazine to give the acyl hydrazide 7-II. Condensation of 7-II with an acid chloride, or other suitable carboxylic acid derivative, provides oxadiazole 7-III. Palladium-catalyzed coupling with aryl boronic acids yields compound 7-IV. Alternatively, in some embodiments, compounds 7-I are subjected to a palladium-catalyzed coupling with boronic acid deriviatives 3-III to provide compounds 7-V. Nitrile 7-V is hydrolysized and condensed with hydrazine to give the acyl hydrazide 7-VI. Condensation of 7-VI with an acid chloride, or other suitable carboxylic acid derivative, provides oxadiazole 7-IV.

In some embodiments, compounds of Formula (I), (Ia), (II), (IIa), (III), (IIIa), (IV) and (V) are prepared as described in Scheme 8.

Scheme 8

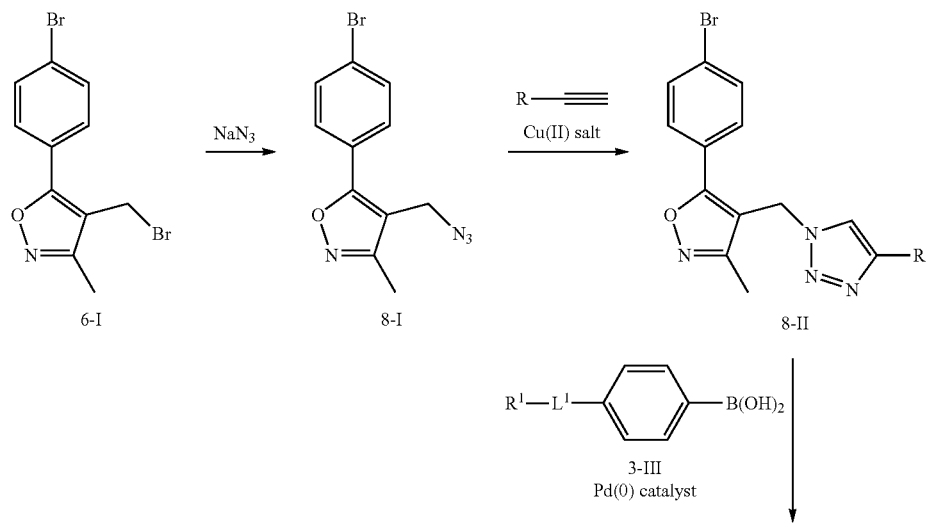

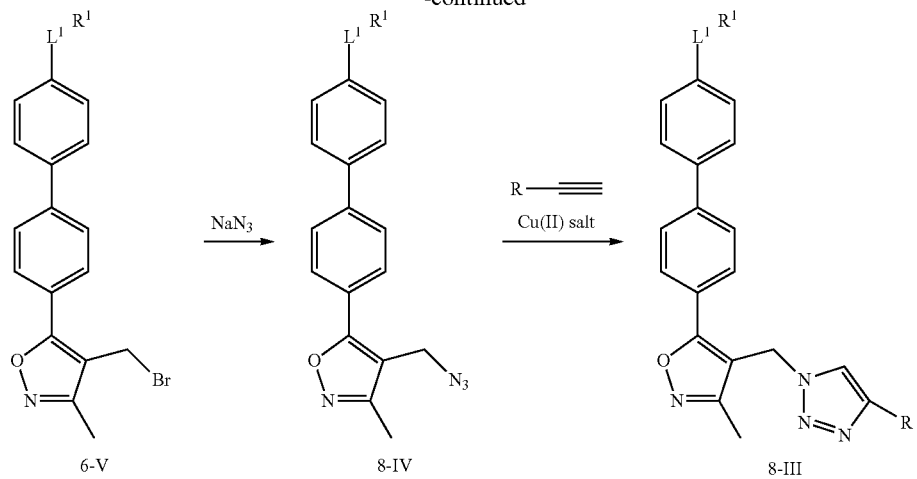

In some embodiments, azide 8-I is obtained from bromide 6-I by treatment with sodium azide. Treatment of azide 8-I with a terminal alkyne in the presence of a copper (II) salt yields triazole 8-II via a Huisgen-Sharpless cycloaddition (Kolb and Sharpless, Drug Discovery Today (2003), 8:1128). Palladium-catalyzed coupling with aryl boronic acids yields compound 8-III. Alternatively, in some embodiments, compound 6-V is treated with sodium azide to provide compounds 8-IV. Treatment of azide 8-IV with a terminal alkyne in the presence of a copper (II) salt yields triazole 8-III via a Huisgen-Sharpless cycloaddition.

In some embodiments, compounds of Formula (I), (Ia), (II), (IIa), (III), (IIIa), (IV) and (V) are synthesized as outlined in the Examples.

A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Further Forms of Compounds

In one aspect, a compound of Formula (I), (Ia), (II), (IIa), (III), (IIIa), (IV) or (V) possess one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, a compound of Formula (I), (Ia), (II), (IIa), (III), (IIIa), (IV) or (V) is prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are seprated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

The methods and compositions described herein include the use of amorphous forms as well as crystalline forms (also known as polymorphs). In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In some embodiments, compounds described herein are prepared as prodrugs. A "prodrug" refers to an agent that is converted into the parent drug in vivo. Prodrugs are often useful because, in some situations, they may be easier to administer than the parent drug.

They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design prodrugs of the compound is possible. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Rooseboom et al., *Pharmacological Reviews,* 56:53-102, 2004; Aesop Cho, "Recent Advances in Oral Prodrug Discovery", *Annual Reports in Medicinal Chemistry*, Vol. 41, 395-407, 2006; T. Higuchi and V. Stella, *Pro-drugs as Novel Delivery Systems*, Vol. 14 of the A.C.S. Symposium Series).

Prodrug forms of the herein described compounds, wherein the prodrug is metabolized in vivo to produce a compound of Formula (I), (Ia), (II), (IIa), (III), (IIIa), (IV) or (V) as set forth herein are included within the scope of the claims. In some cases, some of the herein-described compounds may be a prodrug for another derivative or active compound.

In some embodiments, sites on the aromatic ring portion of a compound of Formula (I), (Ia), (II), (IIa), (III), (IIIa), (IV) or (V) are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^2$H, $^3$H, $^{13}$C, $^{14}$C, $^{15}$N, $^{18}$O, $^{17}$O, $^{35}$S, $^{18}$F, $^{36}$Cl. In one aspect, isotopically-labeled compounds described herein, for example those into which radioactive isotopes such as $^3$H and $^{14}$C are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I), (Ia), (II), (IIa), (III), (IIIa), (IV) or (V) with acids. Pharmaceutically acceptable salts are also obtained by reacting a compound of Formula (I), (Ia), (II), (IIa), (III), (IIIa), (IV) or (V) with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like. In some embodiments, compounds described herein are prepared as a sodium salt.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Compounds described herein, such as a compound of Formula (I), (Ia), (II), (IIa), (III), (IIIa), (IV) or (V), may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility. Various factors such as the recrystallization solvent, rate of crystallization, and storage temperature may cause a single crystal form to dominate.

Throughout the specification, groups and substituents thereof can be chosen by one skilled in the field to provide stable moieties and compounds.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting. The section headings used herein are for organizational purposes only and are not to be construed as limiting the subject matter described.

An "alkyl" group refers to an aliphatic hydrocarbon group. The alkyl group may be a saturated alkyl group (which means that it does not contain any carbon-carbon double bonds or carbon-carbon triple bonds) or the alkyl group may be an unsaturated alkyl group (which means that it contains at least one carbon-carbon double bonds or carbon-carbon triple bond). The alkyl moiety, whether saturated or unsaturated, may be branched or straight chain.

The "alkyl" group may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_6$ alkyl" or similar designations. By way of example only, "$C_1$-$C_6$ alkyl" indicates that there are one, two, three, four, five, or six carbon atoms in the alkyl chain. In one aspect the alkyl is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, sec-butyl, tertiary butyl, pentyl, neopentyl, hexyl, allyl, but-2-enyl, but-3-enyl, and the like. In one aspect, an alkyl is a $C_1$-$C_6$ alkyl.

The term "alkylene" refers to a divalent alkyl radical. Any of the above mentioned monovalent alkyl groups may be an alkylene by abstraction of a second hydrogen atom from the alkyl. In one aspect, an alkelene is a $C_1$-$C_6$alkylene. In some embodiments, an alkylene is a $C_1$-$C_4$alkylene. In some embodiments, an alkylene is methylene, ethylene, propylene or butylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

An "alkoxy" group refers to a (alkyl)O— group, where alkyl is as defined herein.

The term "alkylamine" refers to the —$N(alkyl)_xH_y$ group, where x and y are selected from the group x=1, y=1 and x=2, y=0. In some embodiments, when x=2 and y=0, the alkyl groups taken together with the nitrogen atom to which they are attached form a cyclic ring system.

The term "aromatic" refers to a planar ring having a delocalized π-electron system containing 4n+2 π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from heterocyclic rings in which the ring backbone contains at least one atom which is different from carbon.

As used herein, the term "aryl" refers to an aromatic ring wherein each of the atoms forming the ring is a carbon atom. Aryl rings are formed by five, six, seven, eight, nine, or more than nine carbon atoms. Aryl groups are optionally substituted. In one aspect, an aryl is a phenyl or a naphthalenyl. In one aspect, an aryl is a phenyl. In one aspect, an aryl is a $C_6$-$C_{10}$aryl. Depending on the structure, an aryl group can be a monoradical or a diradical (i.e., an arylene group). In one aspect, an arylene is a $C_6$-$C_{10}$ arylene. Examplary arylenes include, but are not limited to, phenyl-1,2-ene, phenyl-1,3-ene, and phenyl-1,4-ene.

The term "cycloalkyl" refers to a monocyclic or polycyclic aliphatic, non-aromatic radical, wherein each of the atoms forming the ring (i.e. skeletal atoms) is a carbon atom. Cycloalkyls may be saturated, or partially unsaturated. Cycloalkyls may be fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, and cyclooctyl. Cycloalkyl groups may be substituted or unsubstituted. Depending on the structure, a cycloalkyl group can be a monoradical or a diradical (i.e., an cycloalkylene group, such as, but not limited to, cyclopropan-1,1-diyl, cyclobutan-1,1-diyl, cyclopentan-1,1-diyl, cyclohexan-1,1-diyl, cyclohexan-1,4-diyl, cycloheptan-1,1-diyl, and the like). In one aspect, a cycloalkyl is a $C_3$-$C_6$cycloalkyl.

The term "halo" or, alternatively, "halogen" or "halide" means fluoro, chloro, bromo or iodo.

The term "haloalkyl" refers to an alkyl group in which one or more hydrogen atoms are replaced by one or more halide atoms. In one aspect, a haloalkyl is a $C_1$-$C_4$haloalkyl.

The term "haloalkylene" refers to an alkylene group in which one or more hydrogen atoms are replaced by one or more halide atoms. In one aspect, a haloalkylene is a $C_1$-$C_6$haloalkylene. In another aspect, a haloalkylene is a $C_1$-$C_4$haloalkylene.

The term "fluoroalkyl" refers to an alkyl in which one or more hydrogen atoms are replaced by a fluorine atom. In one aspect, a fluoralkyl is a $C_1$-$C_4$fluoroalkyl.

The term "fluoroalkylene" refers to an alkylene in which one or more hydrogen atoms are replaced by a fluorine atom. In one aspect, a fluoralkylene is a $C_1$-$C_6$fluoroalkylene. In another aspect, a fluoralkylene is a $C_1$-$C_4$fluoroalkylene.

The term "heteroalkyl" refers to an alkyl group in which one or more skeletal atoms of the alkyl are selected from an atom other than carbon, e.g., oxygen, nitrogen, sulfur, phosphorus or combinations thereof. In one aspect, a heteroalkyl is a $C_1$-$C_6$heteroalkyl.

The term "heteroalkylene" refers to an alkylene group in which one or more skeletal atoms of the alkyl are selected from an atom other than carbon, e.g., oxygen, nitrogen, sulfur, phosphorus or combinations thereof. In one aspect, a heteroalkylene is a $C_1$-$C_6$heteroalkylene. In another aspect, a heteroalkylene is a $C_1$-$C_4$heteroalkylene. Examplary heteroalkylenes include, but are not limited to, —OCH$_2$—, —OCH(CH$_3$)—, —OC(CH$_3$)$_2$—, —OCH$_2$CH$_2$—, —CH$_2$O—, —CH(CH$_3$)O—, —C(CH$_3$)$_2$O—, —CH$_2$CH$_2$O—, —CH$_2$OCH$_2$—, —CH$_2$OCH$_2$CH$_2$—, —CH$_2$CH$_2$OCH$_2$, —SCH$_2$, —SCH(CH$_3$)—, —SC(CH$_3$)$_2$, —SCH$_2$CH$_2$, —CH$_2$S—, —CH(CH$_3$)S—, —C(CH$_3$)$_2$S—, —CH$_2$CH$_2$S—, —CH$_2$SCH$_2$—, —CH$_2$SCH$_2$CH$_2$—, —CH$_2$CH$_2$SCH$_2$—, —SO$_2$CH$_2$—, —SO$_2$CH(CH$_3$)—, —SO$_2$C(CH$_3$)$_2$—, —SO$_2$CH$_2$CH$_2$—, —CH$_2$SO$_2$—, —CH(CH$_3$)SO$_2$—, —C(CH$_3$)$_2$SO$_2$—, —CH$_2$CH$_2$SO$_2$—, —CH$_2$SO$_2$CH$_2$—, —CH$_2$SO$_2$CH$_2$CH$_2$—, —CH$_2$CH$_2$SO$_2$CH$_2$—, —NHCH$_2$—, —NHCH(CH$_3$)—, —NHC(CH$_3$)$_2$—, —NHCH$_2$CH$_2$—, —CH$_2$NH—, —CH(CH$_3$)NH—, —C(CH$_3$)$_2$NH—, —CH$_2$CH$_2$NH—, —CH$_2$NHCH$_2$, —CH$_2$NHCH$_2$CH$_2$, —CH$_2$CH$_2$NHCH$_2$—, and the like.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo [3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may ber substituted with one or two oxo (=O) moieties, such as pyrrolidin-2-one.

The terms "heteroaryl" or, alternatively, "heteroaromatic" refers to an aryl group that includes one or more ring heteroatoms selected from nitrogen, oxygen and sulfur. Illustrative examples of heteroaryl groups include the following moieties:

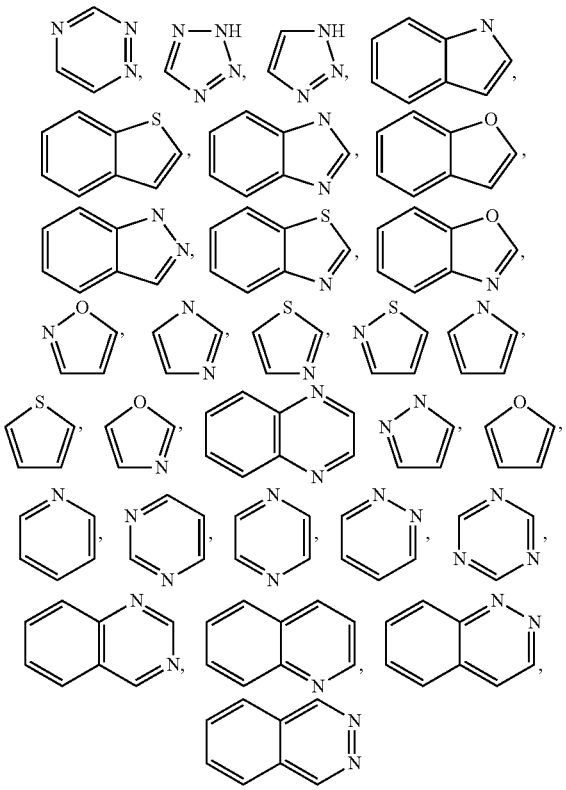

and the like. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. In one aspect, a heteroaryl contains 0-3 N atoms. In another aspect, a heteroaryl contains 1-3 N atoms. In another aspect, a heteroaryl contains 0-3 N atoms, 0-1 O atoms, and 0-1 S atoms. In another aspect, a heteroaryl is a monocyclic or bicyclic heteroaryl. In one aspect, heteroaryl is a $C_1$-$C_9$heteroaryl. In one aspect, monocyclic heteroaryl is a $C_1$-$C_5$heteroaryl. In one aspect, monocyclic heteroaryl is a 5-membered or 6-membered heteroaryl. In one aspect, bicyclic heteroaryl is a $C_6$-$C_9$heteroaryl. Depending on the structure, a heteroaryl group can be a monoradical or a diradical (i.e., a heteroarylene group).

The term "heteroarylene" refers to a divalent heteroaryl radical. Any of the above mentioned monovalent heteroaryl groups may be a heteroarylene by abstraction of a second hydrogen atom from the heteroaryl group. The divalent heteroaryl radical may be attached through two carbon atoms, or through one carbon atom and one heteroatom, or through two heteroatoms.

A "heterocycloalkyl" or "heteroalicyclic" group refers to a cycloalkyl group that includes at least one heteroatom selected from nitrogen, oxygen and sulfur. The radicals may be fused with an aryl or heteroaryl. Illustrative examples of heterocycloalkyl groups, also referred to as non-aromatic heterocycles, include:

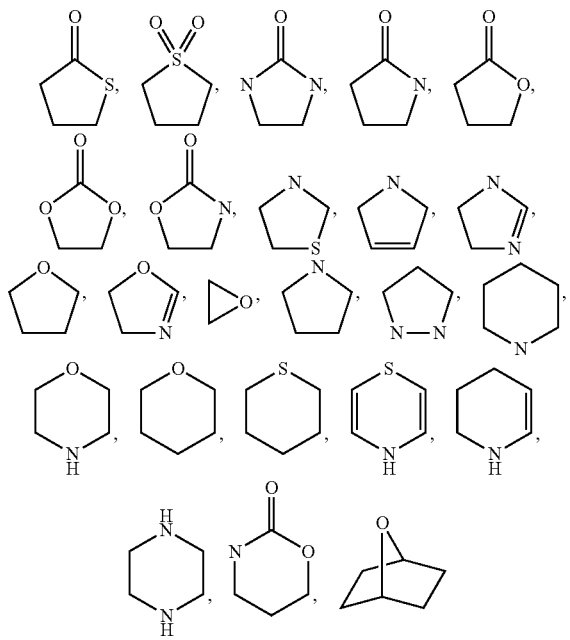

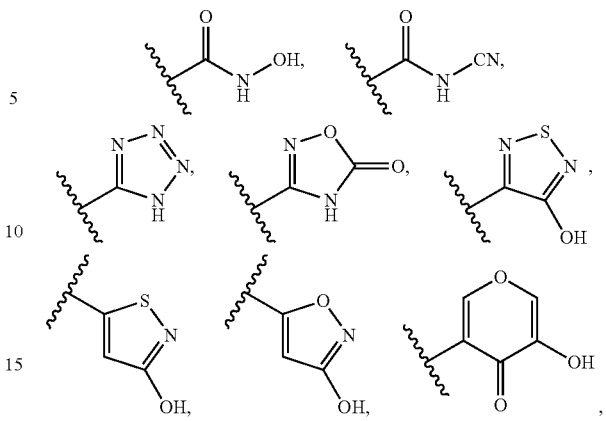

and the like. In some embodiments, the heterocycloalkyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In one aspect, a heterocycloalkyl contains 0-2 N atoms. In another aspect, a heterocycloalkyl contains 0-4 N atoms, 0-2 O atoms or 0-1 S atoms.

The term "heterocycloalkylene" refers to a divalent heterocycloalkyl radical. Any of the above mentioned monovalent heterocycloalkyl groups may be a heterocycloalkylene by abstraction of a second hydrogen atom from the heterocycloalkyl group. The divalent heterocycloalkyl radical may be attached through two carbon atoms, or through one carbon atom and one heteroatom, or through two heteroatoms.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

A "cyano" group refers to a —CN group.

The term "membered ring" includes any cyclic structure. The term "membered" is meant to denote the number of skeletal atoms that constitute the ring. Thus, for example, cyclohexyl, pyridinyl, pyranyl and thiopyranyl are 6-membered rings and cyclopentyl, pyrrolyl, furanyl, and thienyl are 5-membered rings.

The term "moiety" refers to a specific segment or functional group of a molecule. Chemical moieties are often recognized chemical entities embedded in or appended to a molecule.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to, and the like.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, nitro, haloalkyl, fluoroalkyl, fluoroalkoxy, and amino, including mono- and di-substituted amino groups, and the protected derivatives thereof. By way of example an optional substituents may be halide, —CN, —NO$_2$, or $L_sR_s$, wherein each $L_s$ is independently selected from a bond, —O—, —C(=O)—, —C(=O)O—, —S—, —S(=O)—, —S(=O)$_2$—, —NH—, —NHC(=O)—, —C(=O)NH—, S(=O)$_2$NH—, —NHS (=O)$_2$, —OC(=O)NH—, —NHC(=O)O—, or —(C$_1$-C$_6$ alkylene)-; and each $R_s$ is selected from H, alkyl, fluoroalkyl, heteroalkyl, cycloalkyl, aryl, heteroaryl, or heterocycloalkyl. The protecting groups that may form the protective derivatives of the above substituents may be found in sources such as Greene and Wuts, above. In some embodiments, optional substituents are selected from halogen, —CN, —NH$_2$, —OH, —N(CH$_3$)$_2$, alkyl, fluoroalkyl, heteroalkyl, cycloalkyl, heterocycloalkyl, aryl, heteroaryl, alkoxy, aryloxy, alkylthio, arylthio, alkylsulfoxide, arylsulfoxide, alkylsulfone, and arylsulfone. In some embodiments, an optional substituents is halogen, —CN, —NH$_2$, —OH, —NH(CH$_3$), —N(CH$_3$)$_2$, alkyl, fluoroalkyl, heteroalkyl, alkoxy, fluoroalkoxy, —S-alkyl, or —S(=O)$_2$alkyl. In some embodiments, an optional substituent is selected from halogen, —CN, —NH$_2$, —OH, —NH(CH$_3$), —N(CH$_3$)$_2$, —CH$_3$, —CH$_2$CH$_3$, —CF$_3$, —OCH$_3$, —OCH$_2$CH$_3$, and —OCF$_3$. In some embodiments, substituted groups are substituted with one or two of the preceding groups. In some embodiments, substituted groups are substituted with one of the preceding groups. In some embodiments, an optional substituent on an aliphatic carbon atom (acyclic or cyclic, saturated or unsaturated carbon atoms, excluding aromatic carbon atoms) includes oxo (=O).

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, stereoselective synthesis and/or the separation of stereoisomers by chiral chromatographic columns.

The methods and formulations described herein include the use of N-oxides (if appropriate), crystalline forms (also known as polymorphs), or pharmaceutically acceptable salts of compounds having the structure of Formula (I), (Ia), (II), (IIa), (III), (IIIa), (IV) or (V), as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

Certain Terminology

The term "acceptable" with respect to a formulation, composition or ingredient, as used herein, means having no persistent detrimental effect on the general health of the subject being treated.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist, partial agonist, an inverse agonist and antagonist. In one embodiment, a modulator is an antagonist.

The term "agonist," as used herein, refers to a molecule such as a compound, a drug, an enzyme activator or a hormone modulator that binds to a specific receptor and triggers a response in the cell. An agonist mimics the action of an endogenous ligand (such as LPA, prostaglandin, hormone or neurotransmitter) that binds to the same receptor.

The term "antagonist," as used herein, refers to a molecule such as a compound, which diminishes, inhibits, or prevents the action of another molecule or the activity of a receptor site. Antagonists include, but are not limited to, competitive antagonists, non-competitive antagonists, uncompetitive antagonists, partial agonists and inverse agonists.

The term "LPA-dependent", as used herein, refers to conditions or disorders that would not occur, or would not occur to the same extent, in the absence of LPA.

The term "LPA-mediated", as used herein, refers to refers to conditions or disorders that might occur in the absence of LPA but can occur in the presence of LPA.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), (Ia), (II), (IIa), (III), (IIIa), (IV) or (V) and a co-agent, are both administered to a patient simultaneously in the form of a single entity or dosage. The term "non-fixed combination" means that the active ingredients, e.g. a compound of Formula (I), (Ia), (II), (IIa), (III), (IIIa), (IV) or (V) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Provided herein are pharmaceutical compositions that include a compound of Formula (I), (Ia), (II), (IIa), (III), (IIIa), (IV) or (V) and at least one pharmaceutically acceptable inactive ingredient. In some embodiments, the compounds described herein are administered as pharmaceutical compositions in which a compound of Formula (I), (Ia), (II), (IIa), (III), (IIIa), (IV) or (V) is mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), (Ia), (II), (IIa), (III), (IIIa), (IV) or (V) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound of Formula (I), (Ia), (II), (IIa), (III), (IIIa), (IV) or (V) are manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound of Formula (I), (Ia), (II), (IIa), (III), (IIIa), (IV) or (V) as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, compounds described herein exist in unsolvated form or in solvated forms with pharmaceutically acceptable solvents such as water, ethanol, and the like. The solvated forms of the compounds presented herein are also considered to be disclosed herein.

In certain embodiments, compositions provided herein include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, formulations described herein benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

The pharmaceutical compositions described herein, which include a compound of Formula (I), (Ia), (II), (IIa), (III), (IIIa), (IV) or (V) are formulated into any suitable dosage form, including but not limited to, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

Pharmaceutical preparations that are administered orally include push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added.

All formulations for oral administration are in dosages suitable for such administration.

In one aspect, solid oral soage forms are prepared by mixing a compound of Formula (I), (Ia), (II), (IIa), (III), (IIIa), (IV) or (V) with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. In still other embodiments, the pharmaceutical formulation is in the form of a tablet. In other embodiments, pharmaceutical formulations of a compound of Formula (I), (Ia), (II), (IIa), (III), (IIIa), (IV) or (V) are in the form of a capsule.

In some embodiments, solid dosage forms, e.g., tablets, effervescent tablets, and capsules, are prepared by mixing particles of a compound of Formula (I), (Ia), (II), (IIa), (III), (IIIa), (IV) or (V) with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

Suitable disintegrants for use in the solid dosage forms described herein include, but are not limited to, natural starch such as corn starch or potato starch, a pregelatinized starch, or sodium starch glycolate, a cellulose such as methylcrystalline cellulose, methylcellulose, microcrystalline cellulose, croscarmellose, or a cross-linked cellulose, such as cross-linked sodium carboxymethylcellulose, cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a gum such as agar, guar, locust bean, Karaya, pectin, or tragacanth, sodium starch glycolate, bentonite, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose, hydroxypropylmethylcellulose, hydroxypropylmethylcellulose acetate stearate, hydroxyethylcellulose, hydroxypropylcellulose, ethylcellulose, and microcrystalline cellulose, microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose, glucose, dextrose, molasses, mannitol, sorbitol, xylitol, lactose, a natural or synthetic gum such as acacia, tragacanth, ghatti gum, mucilage of isapol husks, starch, polyvinylpyrrolidone, larch arabogalactan, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Binder levels of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10°), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms of the pharmaceutical compositions described herein. The amounts of such additives can be readily determined by one skilled in the art, according to the particular properties desired.

Compressed tablets are solid dosage forms prepared by compacting the bulk blend of the formulations described above.

In various embodiments, tablets will include one or more flavoring agents.

In other embodiments, the tablets will include a film surrounding the final compressed tablet. In some embodiments, the film coating can provide a delayed release of the compound of Formula (I), (Ia), (II), (IIa), (III), (IIIa), (IV) or (V) from the formulation. In other embodiments, the film coating aids in patient compliance (e.g., Opadry® coatings or sugar coating). Film coatings including Opadry® typically range from about 1% to about 3% of the tablet weight.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

In various embodiments, the particles of the compound of Formula (I), (Ia), (II), (IIa), (III), (IIIa), (IV) or (V) and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In other embodiments, a powder including a compound of Formula (I), (Ia), (II), (IIa), (III), (IIIa), (IV) or (V) is formulated to include one or more pharmaceutical excipients and flavors. Such a powder is prepared, for example, by mixing the compound of Formula (I), (Ia), (II), (IIa), (III), (IIIa), (IV) or (V) and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared. Effervescent salts have been used to disperse medicines in water for oral administration.

In some embodiments, the pharmaceutical solid oral dosage forms are formulated to provide a controlled release of the compound of Formula (I), (Ia), (II), (IIa), (III), (IIIa), (IV) or (V). Controlled release refers to the release of the compound of Formula (I), (Ia), (II), (IIa), (III), (IIIa), (IV) or (V) from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules, which include a compound of Formula (I), (Ia), (II), (IIa), (III), (IIIa), (IV) or (V), that are coated or uncoated.

Any coatings should be applied to a sufficient thickness such that the entire coating does not dissolve in the gastrointestinal fluids at pH below about 5, but does dissolve at pH about 5 and above. Coatings are typically selected from any of the following:

Shellac—this coating dissolves in media of pH>7; Acrylic polymers—examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine; Poly Vinyl Acetate Phthalate (PVAP)—PVAP dissolves in pH>5, and it is much less permeable to water vapor and gastric fluids.

Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed in U.S. Pat. Nos. 5,011,692, 5,017,381, 5,229,135, 5,840,329 and 5,837,284. In one embodiment, the pulsatile dosage form includes at least two groups of particles, (i.e. multiparticulate) each containing the formulation described herein. The first group of particles provides a substantially immediate dose of the compound of Formula (I), (Ia), (II), (IIa), (III), (IIIa), (IV) or (V) upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or known in the art.

In some embodiments, pharmaceutical formulations are provided that include particles of a compound of Formula (I), (Ia), (II), (IIa), (III), (IIIa), (IV) or (V) and at least one dispersing agent or suspending agent for oral administration to a subject. The formulations may be a powder and/or granules for suspension, and upon admixture with water, a substantially uniform suspension is obtained.

In one aspect, liquid formulation dosage forms for oral administration are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of the compound of Formula (I), (Ia), (II), (IIa), (III), (IIIa), (IV) or (V), the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In one embodiment, the aqueous suspensions and dispersions described herein remain in a homogenous state, as defined in The USP Pharmacists' Pharmacopeia (2005 edition, chapter 905), for at least 4 hours. In one embodiment, an aqueous suspension is re-suspended into a homogenous suspension by physical agitation lasting less than 1 minute. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch, or sodium starch glycolate; a cellulose such as methylcrystalline cellulose, methylcellulose, croscarmellose, or a cross-linked cellulose, such as cross-linked sodium carboxymethylcellulose, cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein include, for example, hydrophilic polymers, electrolytes, Tween® 60 or 80, PEG, polyvinylpyrrolidone, and the carbohydrate-based dispersing agents such as, for example, hydroxypropylcellulose and hydroxypropyl cellulose ethers, hydroxypropyl methylcellulose and hydroxypropyl methylcellulose ethers, carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer, 4-(1,1,3,3-tetramethylbutyl)-phenol polymer with ethylene oxide and formaldehyde (also known as tyloxapol), poloxamers; and poloxamines. In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers; hydroxypropyl methylcellulose and hydroxypropyl methylcellulose ethers; carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers; or poloxamines.

Wetting agents suitable for the aqueous suspensions and dispersions described herein include, but are not limited to, cetyl alcohol, glycerol monostearate, polyoxyethylene sorbitan fatty acid esters (e.g., the commercially available Tweens® such as e.g., Tween 20® and Tween 80®, and polyethylene glycols, oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, aspartame, chocolate, cinnamon, citrus, cocoa, cyclamate, dextrose, fructose, ginger, glycyrrhetinate, glycyrrhiza (licorice) syrup, monoammonium glyrrhizinate (MagnaSweet®), maltol, mannitol, menthol, neohesperidine DC, neotame, Prosweet® Powder, saccharin, sorbitol, stevia, sucralose, sucrose, sodium saccharin, saccharin, aspartame, acesulfame potassium, mannitol, sucralose, tagatose, thaumatin, vanilla, xylitol, or any combination thereof.

In some embodiments, the liquid formulations also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

Representative intranasal formulations are described in, for example, U.S. Pat. Nos. 4,476,116, 5,116,817 and 6,391,452. Formulations that include a compound of Formula (I), (Ia), (II), (IIa), (III), (IIIa), (IV) or (V) are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. Preferably, the nasal dosage form should be isotonic with nasal secretions.

For administration by inhalation, a compound of Formula (I), (Ia), (II), (IIa), (III), (IIIa), (IV) or (V) is formulated for use as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal formulations that include a compound of Formula (I), (Ia), (II), (IIa), (III), (IIIa), (IV) or (V) are administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

In some embodiments, a compound of Formula (I), (Ia), (II), (IIa), (III), (IIIa), (IV) or (V) is prepared as transdermal dosage forms. In one embodiments, the transdermal formulations described herein include at least three components: (1) a formulation of a compound of Formula (I), (Ia), (II), (IIa), (III), (IIIa), (IV) or (V); (2) a penetration enhancer; and (3) an aqueous adjuvant. In some embodiments the transdermal formulations include additional components such as, but not limited to, gelling agents, creams and ointment bases, and the like. In some embodiments, the transdermal formulation further include a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of compounds described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the compounds described herein can be accomplished by means of iontophoretic patches and the like. In one aspect, transdermal patches provide controlled delivery of the compound of Formula (I), (Ia), (II), (IIa), (III), (IIIa), (IV) or (V). In one aspect, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In one aspect, a compound of Formula (I), (Ia), (II), (IIa), (III), (IIIa), (IV) or (V) is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. In some embodiments, formulations suitable for subcutaneous injection also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. In some cases it is desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein are formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

In some embodiments, a compound of Formula (I), (Ia), (II), (IIa), (III), (IIIa), (IV) or (V) is formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Methods of Dosing and Treatment Regimens

In one embodiment, the compound of Formula (I), (Ia), (II), (IIa), (III), (IIIa), (IV) or (V) is used in the preparation of medicaments for the treatment of LPA-dependent or LPA-mediated diseases or conditions. In addition, a method for treating any of the diseases or conditions described herein in a subject in need of such treatment, involves administration of pharmaceutical compositions that include at least one compound of Formula (I), (Ia), (II), (IIa), (III), (IIIa), (IV) or (V) or a pharmaceutically acceptable salt, pharmaceutically active metabolite, pharmaceutically acceptable prodrug, or pharmaceutically acceptable solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician. In one aspect, prophylactic treatments include admistering to a mammal, who previously experienced at least one symtom of the disease being treated and is currently in remission, a pharmaceutical composition comprising a compound of Formula (I), (Ia), (II), (IIa), (III), (IIIa), (IV) or (V) in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In certain embodiments in which the patient is presented with a situation in which the activity of LPA needs to be enhanced, for example, to assist with wound healing, the dose of drug being administered may be temporarily reduced or temporarily suspended for a certain length of time (i.e., a "drug diversion"). In specific embodiments, the length of the drug diversion is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug diversion is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. Once the situation requiring enhanced activity of LPA is alleviated, the normal dosing schedule is optionally reinstated.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated. In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously (or over a short period of time) or at appropriate intervals, for example as two, three, four or more sub-doses per day.

In one embodiment, the daily dosages appropriate for the compound of Formula (I), (Ia), (II), (IIa), (III), (IIIa), (IV) or (V) described herein are from about 0.01 to about 10 mg/kg per body weight. In specific embodiments, an indicated daily dosage in a large mammal, including, but not limited to, humans, is in the range from about 0.5 mg to about 1000 mg, conveniently administered in divided doses, including, but not limited to, up to four times a day. In one embodiment, the daily dosage is administered in extended release form. In certain embodiments, suitable unit dosage forms for oral administration comprise from about 1 to 500 mg active ingredient. In other embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

Patient Selection

In any of the aforementioned aspects involving the prevention or treatment of LPA-mediated diseases or conditions are further embodiments comprising identifying patients by screening for LPA receptor gene SNPs. A SNP located in the promoter region of $LPA_1$ showed significant association with knee osteoarthritis in two independent populations (Mototani et al. *Hum. Mol. Genetics*, vol. 17, no. 12, 2008). Patients can be further selected based on increased LPA receptor expression in the tissue of interest. For example, chronic lymphocytic leukemia (CLL) is characterized by the accumulation of CD19+/CD5+ B-lymphocytes in the peripheral blood, bone marrow and lymphoid organs which occurs as a result of a block in B-lymphocyte apoptosis. LPA can protect some CLL cells from apoptosis and the cells that are protected by LPA have high levels of $LPA_1$ mRNA. In some embodiments, CLL patients are selected based on the expression of the LPA1R. LPA receptor expression are determined by methods including, but not limited to, northern blotting, western blotting, quantitative PCR (qPCR), flow cytometry, autoradiography (using a small molecule radioligand or PET ligand). In some embodiments, patients are selected based on the concentration of serum or tissue LPA measured by mass spectrometry. LPA concentrations are high in ovarian cancer ascites and in some breast cancer effusions. In some embodiments, patients are selected based on a combination of the above markers (increased LPA concentrations and increased LPA receptor expression).

Combination Treatments

In certain instances, it is appropriate to administer at least one compound of Formula (I), (Ia), (II), (IIa), (III), (IIIa), (IV) or (V) in combination with another therapeutic agent. By way of example only, if one of the side effects experienced by a patient upon receiving one of the compounds herein is inflammation, then it may be appropriate to administer an anti-inflammatory agent in combination with the initial therapeutic agent. Or in another example, a patient is presented with a situation in which antagonism of LPA receptors provides potential harm, for example, if the patient is wounded, antagonism of LPA receptors may lead to a delay in wound healing. In such an event, in certain embodiments, the patient benefits by administration of a local wound-healing agent (at the site of the wound) in combination with the co-existing administration of a compound of Formula (I), (Ia), (II), (IIa), (III), (IIIa), (IV) or (V).

Or, in one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit experienced by a patient is increased by administering one of the compounds described herein with another therapeutic agent (which also includes a therapeutic regimen) that also has therapeutic benefit.

In one specific embodiment, a compound of Formula (I), (Ia), (II), (IIa), (III), (IIIa), (IV) or (V) is co-administered with a second therapeutic agent, wherein the compound of Formula (I), (Ia), (II), (IIa), (III), (IIIa), (IV) or (V) and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound of Formula (I), (Ia), (II), (IIa), (III), (IIIa), (IV) or (V) is initiated prior to, during, or after treatment with a second agent described herein, and continues until any time during treatment with the second agent or after termination of treatment with the second agent. It also includes treatments in which a compound of Formula (I), (Ia), (II), (IIa), (III), (IIIa), (IV) or (V) and the second agent being used in combination are administered simultaneously or at different times and/or at decreasing or increasing intervals during the treatment period. Combination treatment further includes periodic treatments that start and stop at various times to assist with the clinical management of the patient.

Compositions and methods for combination therapy are provided herein. In accordance with one aspect, the pharmaceutical compositions disclosed herein are used to treat LPA-dependent or LPA-mediated conditions.

It is understood that the dosage regimen to treat, prevent, or ameliorate the condition(s) for which relief is sought, is modified in accordance with a variety of factors. These factors include the disease, disorder or condition from which the subject suffers, as well as the age, weight, sex, diet, and medical condition of the subject. Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills). In one embodiment, one of the therapeutic agents is given in multiple doses, and in another, two (or more if present) are given as multiple doses. In some embodiments of non-simultaneous administration, the timing between the multiple doses vary from more than zero weeks to less than four weeks. In addition, the combination methods, compositions and formulations are not to be limited to the use of only two agents; the use of multiple therapeutic combinations is also envisioned.

The compounds of Formula (I), (Ia), (II), (IIa), (III), (IIIa), (IV) and (V) and combination therapies are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

By way of example, therapies which combine a compound of Formula (I), (Ia), (II), (IIa), (III), (IIIa), (IV) or (V) with inhibitors of LPA synthesis or LPA receptor antagonists, either acting at the same or other points in the LPA synthesis or signalling pathway, are encompassed herein for treating LPA-dependent or LPA-mediated diseases or conditions.

Exemplary Agent for Use in Combination Therapy

In another embodiment described herein, methods for treatment of LPA-dependent or LPA-mediated conditions or diseases, such as proliferative disorders, including cancer, comprises administration to a mammal a compound of Formula (I), (Ia), (II), (IIa), (III), (IIIa), (IV) or (V) in combination with at least one additional agent selected, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In one aspect, the compound of Formula (I), (Ia), (II), (IIa), (III), (IIIa), (IV) or (V) is administered or formulated in combination with one or more anti-cancer agents. In some embodiments, one or more of the anti-cancer agents are proapoptotic agents. Examples of anti-cancer agents include, but are not limited to, any of the following: gossypol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib, geldanamycin, 17-N-Allylamino-17-Demethoxygeldanamycin (17-AAG), flavopiridol, LY294002, bortezomib, trastuzumab, BAY 11-7082, PKC412, or PD184352, Taxol™ (paclitaxel), and analogs of Taxol™, such as Taxotere™. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with a compound of Formula (I), (Ia), (II), (IIa), (III), (IIIa), (IV) or (V) include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

Other anti-cancer agents for use in combination with the compound of Formula (I), (Ia), (II), (IIa), (III), (IIIa), (IV) or (V) include one or more of the following: Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rIL2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Yet other anticancer agents for use in combination with the compound of Formula (I), (Ia), (II), (IIa), (III), (IIIa), (IV) or (V) include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products for use in combination with the compound of Formula (I), (Ia), (II), (IIa), (III), (IIIa), (IV) or (V) include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents for use in combination with the compound of Formula (I), (Ia), (II), (IIa), (III), (IIIa), (IV) or (V) include, but are not limited to, nitrogen mustards (e.g., mechloroethamine, cyclophosphamide, chlorambucil, meiphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists for use in combination with the compound of Formula (I), (Ia), (II), (IIa), (III), (IIIa), (IV) or (V) include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules include without limitation the following marketed drugs and drugs in development: Erbulozole, Dolastatin 10, Mivobulin isethionate, Vincristine, NSC-639829, Discodermolide, ABT-751, Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride, Epothilones (such as Epothilone A, Epothilone B, Epothilone C, Epothilone D, Epothilone E, Epothilone F, Epothilone B N-oxide, Epothilone A N-oxide, 16-aza-epothilone B, 21-aminoepothilone B, 21-hydroxyepothilone D, 26-fluoroepothilone, Auristatin PE, Soblidotin, Vincristine sulfate, Cryptophycin 52, Vitilevuamide, Tubulysin A, Canadensol, Centaureidin, Oncocidin A1 Fijianolide B, Laulimalide, Narcosine, Nascapine, Hemiasterlin, Vanadocene acetylacetonate, Indanocine Eleutherobins (such as Desmethyleleutherobin, Desaetyleleutherobin, Isoeleutherobin A, and Z-Eleutherobin), Caribaeoside, Caribaeolin, Halichondrin B, Diazonamide A, Taccalonolide A, Diozostatin, (−)-Phenylahistin, Myoseverin B, Resverastatin phosphate sodium.

In one aspect, a compound of Formula (I), (Ia), (II), (IIa), (III), (IIIa), (IV) or (V) is co-administered with thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

Immunosuppresants

In one aspect, a compound of Formula (I), (Ia), (II), (IIa), (III), (IIIa), (IV) or (V) are to treat or reduce fibrosis in a mammal. In one aspect, a compound of Formula (I), (Ia), (II), (IIa), (III), (IIIa), (IV) or (V) are administered in combination with one or more immunosuppresants. Immunosuppressive therapy is clinically used to treat or prevent the rejection of transplanted organs and tissues (e.g. bone marrow, heart, kidney, liver); treatment of autoimmune diseases or diseases that are most likely of autoimmune origin (e.g. rheumatoid arthritis, myasthenia gravis, systemic lupus erythematosus, Crohn's disease, and ulcerative colitis); and treatment of some other non-autoimmune inflammatory diseases (e.g. long term allergic asthma control), and in the treatment of fibrotic conditions.

In some embodiments, a compound of Formula (I), (Ia), (II), (IIa), (III), (IIIa), (IV) or (V) is adminsitered with corticosteroids. In some embodiments, a compound of Formula (I), (Ia), (II), (IIa), (III), (IIIa), (IV) or (V) is adminsitered with an a therapeutic agent selected from among: Calcineurin inhibitors (such as, but not limited to, cyclosporin, tacrolimus); mTOR inhibitors (such as, but not limited to, sirolimus, everolimus); anti-proliferatives (such as, but not limited to, azathioprine, mycophenolic acid); corticosteroids (such as, but not limited to, prednisone, cortisone acetate, prednisolone, methylprednisolone, dexamethasone, betamethasone, triamcinolone, beclometasone, fludrocortisone acetate, deoxycorticosterone acetate, aldosterone, hydrocortisone); antibodies (such as, but not limited to, monoclonal anti-IL-2Rα receptor antibodies (basiliximab, daclizumab), polyclonal anti-T-cell antibodies (anti-thymocyte globulin (ATG), anti-lymphocyte globulin (ALG)), B-cell antagonists, rituximab, natalizumab.

Other therapeutic agents include, but are not limited to: cyclophosphamide, penicillamine, cyclosporine, nitrosoureas, cisplatin, carboplatin, oxaliplatin, methotrexate, azathioprine, mercaptopurine, pyrimidine analogues, protein synthesis inhibitors, dactinomycin, anthracyclines, mitomycin C, bleomycin, mithramycin, Atgam®, Thymoglobuline®, OKT3®, basiliximab, daclizumab, cyclosporin, tacrolimus, sirolimus, Interferons (IFN-β, IFN-γ), opioids, TNF binding proteins (infliximab, etanercept, adalimumab, golimumab), leflunomide, gold thioglucose, gold thiomalate, aurofin, sulfasalazine, hydroxychloroquinine, minocycline, rapamicin, mycophenolic acid, mycophenolate mofetil, FTY720, as well as those listed in U.S. Pat. No. 7,060,697.

In one embodiment, a compound of Formula (I), (Ia), (II), (IIa), (III), (IIIa), (IV) or (V) is administered in combination with Cyclosporin A (CsA) or tacrolimus (FK506). In one embodiment, a compound of Formula (I), (Ia), (II), (IIa), (III), (IIIa), (IV) or (V) is administered to a mammal in combination with an anti-inflammatory agent including, but not limited to, non-steroidal anti-inflammatory drugs (NSAIDs) and corticosteroids (glucocorticoids).

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

Corticosteroids, include, but are not limited to: betamethasone, prednisone, alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In one embodiment, a compound of Formula (I), (Ia), (II), (IIa), (III), (IIIa), (IV) or (V) is administered in combination with leukotriene receptor antagonists including, but are not limited to, BAY u9773 (see EP 00791576; published 27 Aug. 1997), DUO-LT (Tsuji et al, *Org. Biomol. Chem.*, 1, 3139-3141, 2003), zafirlukast, montelukast, prankulast, and derivatives or analogs thereof.

Other Combination Therapies

In another embodiment described herein, methods for treatment of LPA-dependent or LPA-mediated conditions or diseases, such as atherosclerosis, comprises administration to a patient compounds, pharmaceutical compositions, or medicaments described herein in combination with at least one additional agent selected, by way of example only, HMG- CoA reductase inhibitors (e.g., statins in their lactonized or dihydroxy open acid forms and pharmaceutically acceptable salts and esters thereof, including but not limited to lovastatin; simvastatin; dihydroxy open-acid simvastatin, particularly the ammonium or calcium salts thereof; pravastatin, particularly the sodium salt thereof; fluvastatin, particularly the sodium salt thereof; atorvastatin, particularly the calcium salt thereof; nisvastatin, also referred to as NK-104; rosuvastatin); agents that have both lipid-altering effects and other pharmaceutical activities; HMG-CoA synthase inhibitors; cholesterol absorption inhibitors such as ezetimibe; cholesterol ester transfer protein (CETP) inhibitors, for example JTT-705 and CP529, 414; squalene epoxidase inhibitors; squalene synthetase inhibitors (also known as squalene synthase inhibitors); acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists, including the compounds commonly referred to as glitazones, for example troglitazone, pioglitazone and rosiglitazone and including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists such as 5-[(2,4-dioxo-5-thiazolidinyl)methyl]-2-methoxy-N—[[4-(trifluoromethyl)phenyl]methyl]-benzamide, known as KRP-297; vitamin B6 (also known as pyridoxine) and the pharmaceutically acceptable salts thereof such as the HCl salt; vitamin B12 (also known as cyanocobalamin); folic acid or a pharmaceutically acceptable salt or ester thereof such as the sodium salt and the methylglucamine salt; antioxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABC1 gene expression; FXR and LXR ligands including both inhibitors and agonists; bisphosphonate compounds such as alendronate sodium; and cyclooxygenase-2 inhibitors such as rofecoxib and celecoxib.

In another embodiment described herein, methods for treatment of LPA-dependent or LPA-mediated conditions or diseases, such as the therapy of stroke, comprises administration to a patient compounds, pharmaceutical compositions, or medicaments described herein in combination with at least one additional agent selected from, by way of example only, COX-2 inhibitors; nitric oxide synthase inhibitors, such as N-(3-(aminomethyl)benzyl)acetamidine; Rho kinase inhibitors, such as fasudil; angiotension II type-1 receptor antagonists, including candesartan, losartan, irbesartan, eprosartan, telmisartan and valsartan; glycogen synthase kinase 3 inhibitors; sodium or calcium channel blockers, including crobenetine; p38 MAP kinase inhibitors, including SKB 239063; thromboxane AX-synthetase inhibitors, including isbogrel, ozagrel, ridogrel and dazoxiben; statins (HMG CoA reductase inhibitors), including lovastatin, simvastatin, dihydroxy open-acid simvastatin, pravastatin, fluvastatin, atorvastatin, nisvastatin, and rosuvastatin; neuroprotectants, including free radical scavengers, calcium channel blockers, excitatory amino acid antagonists, growth factors, antioxidants, such as edaravone, vitamin C, TROLOX™, citicoline and minicycline, and reactive astrocyte inhibitors, such as (2R)-2-propyloctanoic acid; beta andrenergic blockers, such as propranolol, nadolol, timolol, pindolol, labetalol, metoprolol, atenolol, esmolol and acebutolol; NMDA receptor antagonists, including memantine; NR2B antagonists, such as traxoprodil; 5-HT1A agonists; receptor platelet fibrinogen receptor antagonists, including tirofiban and lamifiban; thrombin inhibitors; antithrombotics, such as argatroban; antihypertensive agents, such as enalapril; vasodilators, such as cyclandelate; nociceptin antagonists; DPIV antagonists; GABA 5 inverse agonists; and selective androgen receptor modulators.

In another embodiment described herein, methods for treatment of LPA-dependent or LPA-mediated conditions or diseases, such as the therapy of interstitial cystitis, comprises administration to a patient compounds, pharmaceutical compositions, or medicaments described herein in combination with at least one additional agent selected from, by way of example only, dimethylsulfoxide, omalizumab, and pentosan polysulfate.

In yet another embodiment described herein, methods for treating LPA-dependent or LPA-mediated conditions or diseases, such as the therapy of respiratory disorders (e.g., asthma, COPD and rhinitis), comprises administration to a patient compounds, pharmaceutical compositions, or medicaments described herein in combination with at least one agent used in the treatment of respiratory conditions. Agents used in the treatment of respiratory conditions include, but are not limited to, bronchodilators (e.g., sympathomimetic agents and xanthine derivatives), leukotriene receptor antagonists, leukotriene formation inhibitors, leukotriene modulators, nasal decongestants, respiratory enzymes, lung surfactants, antihistamines (e.g., mepyramine (pyrilamine), antazoline, diphenhydramine, carbinoxamine, doxylamine, clemastine, dimenhydrinate, pheniramine, chlorphenamine (chlorpheniramine), dexchlorpheniramine, brompheniramine, triprolidine, cetirizine, cyclizine, chlorcyclizine, hydroxyzine, meclizine, loratadine, desloratidine, promethazine, alimemazine (trimeprazine), cyproheptadine, azatadine, ketotifen, acrivastine, astemizole, cetirizine, mizolastine, terfenadine, azelastine, levocabastine, olopatadine, levocetirizine, fexofenadine), mucolytics, corticosteroids, anticholinergics, antitussives, analgesics, expectorants, albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, zafirlukast, ambrisentan, bosentan, enrasentan, sitaxsentan, tezosentan, iloprost, treprostinil, pirfenidone, 5-lipoxygenase-activating protein (FLAP) inhibitors, FLAP modulators and 5-LO inhibitors.

In a specific embodiment described herein, methods for treating LPA-dependent or LPA-mediated conditions or diseases, such as the therapy of asthma and/or COPD, comprises administration to a patient anti-inflammatory agents. In certain embodiments, methods for treating LPA-dependent or LPA-mediated conditions or diseases, such as the therapy of asthma and/or COPD, comprise administration to a patient compounds, pharmaceutical compositions, or medicaments described herein in combination with at least one additional agent selected from, but not limited to, epinephrine, isoproterenol, orciprenaline, bronchodilators, glucocorticoids, leukotriene modifiers, mast-cell stabilizers, xanthines, anticholinergics, β-2 agonists, FLAP inhibitors, FLAP modulators or 5-LO inhibitors. β-2 agonists include, but are not limited to, short-acting β-2 agonists (e.g., salbutamol (albuterol), levalbuterol, terbutaline, pirbuterol, procaterol, metaproterenol, fenoterol and bitolterol mesylate) and long-acting β-2 agonists (e.g., salmeterol, formoterol, bambuterol and clenbuterol). FLAP inhibitors and/or FLAP modulators include, but are not limited to, 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid, 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid, MK-886, MK-0591, BAY-x1005 and compounds found in US 2007/0225285, US 2007/0219206, US 2007/0173508, US 2007/0123522 and US 2007/0105866 (each of which are hereby incorporated by reference). Glucocorticoids include, but are not limited to, beclometasone, budesonide, ciclesonide, fluticasone and mometasone. Anticholinergics include, but are not limited to, ipratropium and tiotropium. Mast cell stabilizers include, but are not limited to, cromoglicate and nedocromil. Xanthines include, but are not limited to, amminophylline, theobromine and theophylline. Leukotriene antagonists include, but are not limited to, montelukast, tomelukast, pranlukast and zafirlukast. 5-LO inhibitors include, but are not limited to, zileuton, VIA-2291 (ABT761), AZ-4407 and ZD-2138 and compounds found in US 2007/0149579, WO2007/016784.

In another specific embodiment described herein, methods for treating LPA-dependent or LPA-mediated conditions or diseases, such as the therapy of allergic diseases or conditions, comprises administration to a patient compounds, pharmaceutical compositions, or medicaments described herein in combination with at least one additional agent selected from, by way of example only, antihistamines, leukotriene antagonists, corticosteroids and decongestants. Leukotriene antagonists include, but are not limited to, montelukast, tomelukast, pranlukast and zafirlukast.

In one aspect, LPA receptor antagonists described herein are admistered in combination with one or more agents used to treat used to treat asthma, including, but not limited to: combination inhalers (fluticasone and salmeterol oral inhalation (e.g. Advair)); inhaled Beta-2 agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled corticosteroids (beclomethasone oral inhalation; budesonide inhalation solution; budesonide inhaler; flunisolide oral inhalation; fluticasone inhalation aerosol; fluticasone powder for oral inhalation; mometasone inhalation powder; triamcinolone oral inhalation); leukotriene modifiers (montelukast; zafirlukast; zileuton); mast cell stabilizers (cromolyn inhaler; nedocromil oral inhalation); monoclonal antibodies (omalizumab); oral Beta-2 agonists (albuterol oral syrup; albuterol oral tablets; metaproterenol; terbutaline); bronchodilator (aminophylline; oxtriphylline; theophylline).

In one aspect, LPA receptor anatogonists described herein are admistered in combination with one or more agents used to treat allergy, including, but not limited to: antihistamine and decongestant combinations (cetirizine and pseudoephedrine; desloratadine and pseudoephedrine ER; fexofenadine and pseudoephedrine; loratadine and pseudoephedrine); antihistamines (azelastine nasal spray; brompheniramine; brompheniramine oral suspension; carbinoxamine; cetirizine; chlorpheniramine; clemastine; desloratadine; dexchlorpheniramine ER; dexchlorpheniramine oral syrup; diphenhydramine oral; fexofenadine; loratadine; promethazine); decongestants (pseudoephedrine); leukotriene modifiers (montelukast; montelukast granules); nasal anticholinergics (ipratropium); nasal corticosteroids (beclomethasone nasal inhalation; budesonide nasal inhaler; flunisolide nasal inhalation; fluticasone nasal inhalation; mometasone nasal spray; triamcinolone nasal inhalation; triamcinolone nasal spray); nasal decongestants (phenylephrine); nasal mast cell stabilizers (cromolyn nasal spray).

In one aspect, LPA receptor anatogonists described herein are admistered in combination with one or more agents used to treat chronic obstructive pulmonary disease (COPD), including, but not limited to: anticholinergics—ipratropium bromide oral inhalation); combination Inhalers (albuterol and ipratropium (e.g. Combivent, DuoNeb); fluticasone and salmeterol oral inhalation (e.g. Advair)); corticosteroids (dexamethasone tablets; fludrocortisone acetate; hydrocortisone tablets; methylprednisolone; prednisolone liquid; prednisone oral; triamcinolone oral); inhaled Beta-2 Agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled Corticosteroids (beclomethasone oral inhalation; budesonide inhalation solution; budesonide inhaler; flunisolide oral inhalation; fluticasone inhalation aerosol; fluticasone powder for oral inhalation; triamcinolone oral inhalation); mukolytics (guaifenesin); oral Beta-2 agonists (albuterol oral syrup; albuterol oral tablets; metaproterenol; terbutaline); bronchodilator (aminophylline; oxtriphylline; theophylline).

In one embodiment, a compound of Formula (I), (Ia), (II), (IIa), (III), (IIIa), (IV) or (V) described herein are administered to a patient in combination with inhaled corticosteroids.

In one embodiment, a compound of Formula (I), (Ia), (II), (IIa), (III), (IIIa), (IV) or (V) described herein are administered to a patient in combination with beta2-adrenergic receptor agonists. In one embodiment, a compounds of Formula (I), (Ia), (II), (IIa), (III), (IIIa), (IV) or (V) is administered to a patient in combination with short acting beta2-adrenergic receptor agonists. In one embodiment, a compound of Formula (I), (Ia), (II), (IIa), (III), (IIIa), (IV) or (V) is administered to a patient in combination with long-acting beta2-adrenergic receptor agonists.

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

EXAMPLES

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

EXAMPLES

These examples are provided for illustrative purposes only and not to limit the scope of the claims provided herein.

Example 1

Synthesis of 1-{4'-[4-(2-Benzyl-cyclohexylamino)-3-methyl-isoxazol-5-yl]-biphenyl-4-yl}-cyclopropanecarboxylic acid (Compound 1-1)

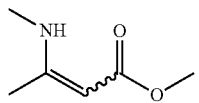

Step 1: 3-Methylamino-but-2-enoic acid methyl ester

To a solution of methyl acetoacetate (29.4 g, 253 mmol) in MeOH (30 mL) was added methylamine (33 wt % in EtOH; 48 mL, 385 mmol) dropwise at room temperature. The reaction was stirred for 1 hour, and then concentrated and dried to give the title compound as a white crystalline solid.

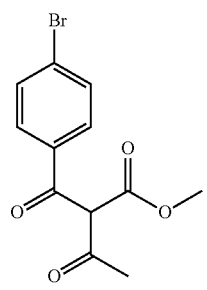 [SMILES: COC(=O)C(C(C)=O)C(=O)c1ccc(Br)cc1]

Step 2: 2-(4-Bromo-benzoyl)-3-oxo-butyric acid methyl ester

To 3-methylamino-but-2-enoic acid methyl ester (5.0 g, 39.1 mmol) in THF (100 mL) was added pyridine (3.7 mL, 47 mmol). The mixture was cooled to 0° C., and 4-bromobenzoyl chloride (8.55 g, 39.1 mmol) in THF (30 mL) was added dropwise over 2 minutes. The reaction was warmed to room temperature over 1 hour and stirred overnight. Aqueous workup provided the title compound.

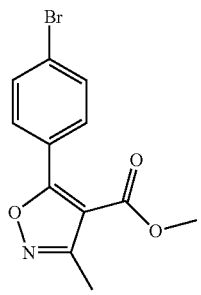 [SMILES: COC(=O)c1c(C)noc1-c1ccc(Br)cc1]

Step 3: 5-(4-Bromo-phenyl)-3-methyl-isoxazole-4-carboxylic acid methyl ester

To a mixture of 2-(4-bromo-benzoyl)-3-oxo-butyric acid methyl ester (11 g, 39 mmol) in acetic acid (50 mL) was added hydroxylamine hydrochloride (2.66 g, 39 mmol), and the reaction was stirred at 115° C. for 1 hour. After cooling, aqueous workup provided the title compound, which was used directly in the hydrolysis step.

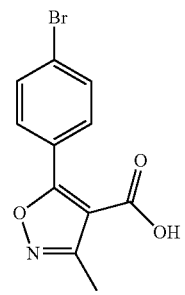 [SMILES: Cc1noc(-c2ccc(Br)cc2)c1C(=O)O]

Step 4: 5-(4-Bromo-phenyl)-3-methyl-isoxazole-4-carboxylic acid 5-(4-Bromo-phenyl)-3-methyl-isoxazole-4-carboxylic acid methyl ester (39 mmol) in MeOH (50 mL) and H$_2$O (10 mL) was treated with lithium hydroxide (2 g, 48 mmol), and the reaction was stirred at 60° C. for 1 hour. The mixture was acidified, and standard workup provided the title compound.

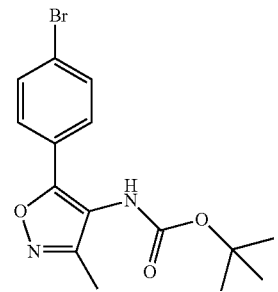 [SMILES: Cc1noc(-c2ccc(Br)cc2)c1NC(=O)OC(C)(C)C]

Step 5: [5-(4-Bromo-phenyl)-3-methyl-isoxazol-4-yl]-carbamic acid tert-butyl ester 5-(4-Bromo-phenyl)-3-methyl-isoxazole-4-carboxylic acid (1.6 g, 6.0 mmol), diphenylphosphoryl azide (1.6 g, 6.0 mmol), and triethylamine (1.3 mL, 9.3 mmol) were combined in t-BuOH and refluxed overnight. After cooling, the mixture was concentrated, and the residue was partitioned between EtOAc and H₂O. The organic layer was separated and concentrated, and the residue was purified by silica gel chromatography (16-18% EtOAc in hexanes) to give the title compound.

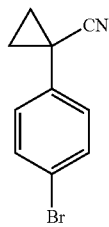

Step 6: 1-(4-Bromo-phenyl)-cyclopropanecarbonitrile

Potassium hydroxide (14.3 g, 255 mmol) was dissolved in H₂O (5 mL) and toluene (40 mL). 4-Bromophenylacetonitrile (5.0 g, 25.5 mmol) and tetrabutylammonium bromide (0.41 g, 1.3 mmol) was added, followed by 1,2-dibromoethane (3.25 mL, 38 mmol) dropwise over 10 minutes. The reaction was stirred at room temperature for 2 hours and then worked-up to give the title compound.

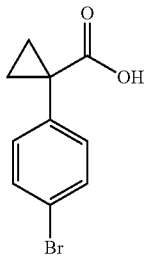

Step 7: 1-(4-Bromo-phenyl)-cyclopropanecarboxylic acid 1-(4-Bromo-phenyl)-cyclopropanecarbonitrile (5 g, 22.5 mmol) and potassium hydroxide (5 g, 89.3 mmol) were combined in ethylene glycol (70 mL), and the reaction was stirred at 180° C. for 4 hours. The mixture was poured into H₂O, acidified, and filtered to give the title compound.

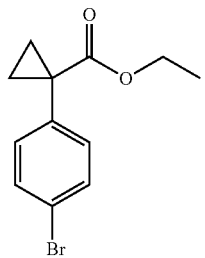

Step 8: 1-(4-Bromo-phenyl)-cyclopropanecarboxylic acid ethyl ester 1-(4-Bromo-phenyl)-cyclopropanecarboxylic acid (5 g, 20.7 mmol) in EtOH (50 mL) was treated with sulfuric acid (2 mL), and the reaction was stirred at 75° C. for 1 hour. The mixture was worked up to give the title compound.

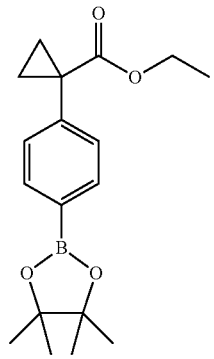 [SMILES: CCOC(=O)C1(c2ccc(B3OC(C)(C)C(C)(C)O3)cc2)CC1]

Step 9: 1-[4-(4,4,5,5-Tetramethyl-[1,3,2]dioxaborolan-2-yl)-phenyl]-cyclopropanecarboxylic acid ethyl ester 1-(4-Bromo-phenyl)-cyclopropanecarboxylic acid ethyl ester (3.6 g, 13.4 mmol), bis(pinacolato)diboron (3.37 g, 16.1 mmol), and potassium acetate (2.8 g, 29.0 mmol) were combined in 1,4-dioxane (30 mL) under N₂ atmosphere. The solution was purged with N₂ (g) for 10 minutes, and then (1,1'-bis(diphenylphosphino)ferrocene)-dichloropalladium (II) (0.50 g, 0.65 mmol) was added and the reaction was heated to 80° C. for 2 hours. After aqueous workup, the crude material was purified by silica gel chromatography (0-30% EtOAc in hexanes) to give the title compound.

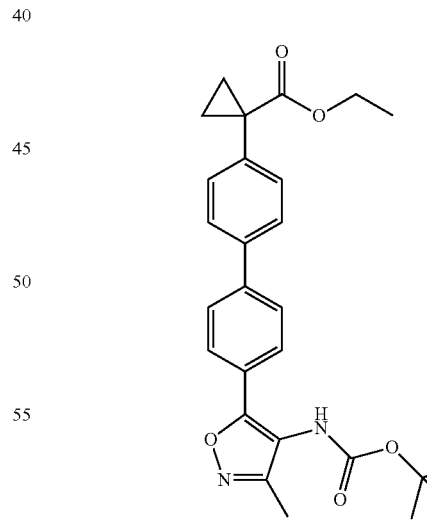

Step 10: 1-[4'-(4-tert-Butoxycarbonylamino-3-methyl-isoxazol-5-yl)-biphenyl-4-yl]-cyclopropanecarboxylic acid ethyl ester

[5-(4-Bromo-phenyl)-3-methyl-isoxazol-4-yl]-carbamic acid tert-butyl ester (2.0 g, 5.6 mmol), 1-[4-(4,4,5,5-tetramethyl-[1,3,2]dioxaborolan-2-yl)-phenyl]-cyclopropanecarboxylic acid ethyl ester (1.78 g, 5.6 mmol), tetrakis(triphenylphosphine)palladium(0) (0.65 g, 0.56 mmol), and sodium bicarbonate (1.4 g, 16.8 mmol) were combined in DME (30 mL) and H₂O (10 mL), and the mixture was purged with N₂ (g). The reaction was stirred at 80° C. overnight, and after aqueous workup, the crude material was purified by silica gel chromatography (0-40% EtOAc in hexanes) to give the title compound.

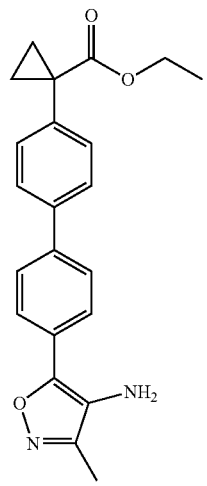 [SMILES: CCOC(=O)C1(c2ccc(-c3ccc(-c4onc(C)c4N)cc3)cc2)CC1]

Step 11: 1-[4'-(4-Amino-3-methyl-isoxazol-5-yl)-biphenyl-4-yl]-cyclopropanecarboxylic acid ethyl ester 1-[4'-(4-tert-Butoxycarbonylamino-3-methyl-isoxazol-5-yl)-biphenyl-4-yl]-cyclopropanecarboxylic acid ethyl ester (1.5 g, 3.2 mmol) in CH₂Cl₂ (10 mL) was treated with trifluoroacetic acid (4 mL), and the reaction was stirred for 1 hour. The mixture was neutralized and worked up to give the title compound.

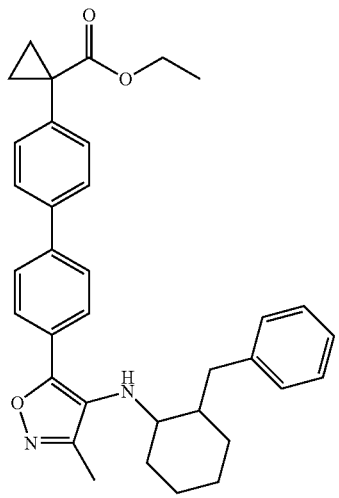 [SMILES: CCOC(=O)C1(c2ccc(-c3ccc(-c4onc(C)c4NC4CCCCC4Cc4ccccc4)cc3)cc2)CC1]

Step 12: 1-{4'-[4-(2-Benzyl-cyclohexylamino)-3-methyl-isoxazol-5-yl]-biphenyl-4-yl}-cyclopropanecarboxylic acid ethyl ester 1-[4'-(4-Amino-3-methyl-isoxazol-5-yl)-biphenyl-4-yl]-cyclopropanecarboxylic acid ethyl ester (0.200 g, 0.55 mmol) and 2-benzylcyclohexanone (0.156 g, 0.83 mmol) were combined in toluene and stirred at 110° C. for 1 hour. After cooling to room temperature, THF was added, followed by sodium cyanoborohydride (0.086 g, 1.37 mmol), and the reaction was stirred at room temperature for 2 hours. The mixture was adsorbed onto silica gel and purified by silica gel chromatography to give the title compound.

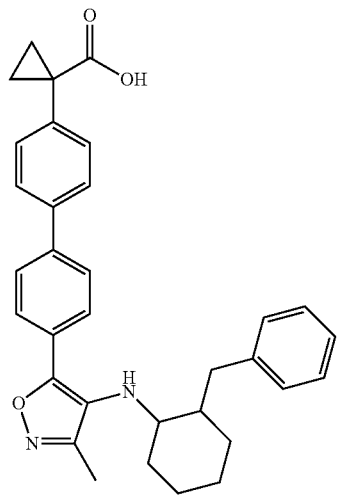 [SMILES: Cc1noc(-c2ccc(-c3ccc(C4(C(=O)O)CC4)cc3)cc2)c1NC1CCCCC1Cc1ccccc1]

Step 13: 1-{4'-[4-(2-Benzyl-cyclohexylamino)-3-methyl-isoxazol-5-yl]-biphenyl-4-yl}-cyclopropanecarboxylic acid To 1-{4'-[4-(2-benzyl-cyclohexylamino)-3-methyl-isoxazol-5-yl]-biphenyl-4-yl}-cyclopropanecarboxylic acid ethyl ester (0.130 g, 0.24 mmol) in 2:1:1 THF:H₂O:MeOH was added lithium hydroxide (0.050 g, 1.19 mmol), and the reaction was stirred at 70° C. for 2 hours. After acidic workup, the crude material was purified by preparative HPLC to give the title compound.

Example 2

Synthesis of 1-{4'-[3-Methyl-4-(4-o-tolyl-piperazine-1-carbonyl)-isoxazol-5-yl]-biphenyl-4-yl}-cyclopropanecarboxylic acid (Compound 1-2)

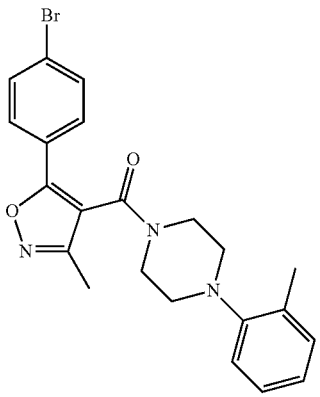 [SMILES: Cc1ccccc1N1CCN(C(=O)c2c(C)noc2-c2ccc(Br)cc2)CC1]

Step 1: [5-(4-Bromo-phenyl)-3-methyl-isoxazol-4-yl]-(4-o-tolyl-piperazin-1-yl)-methanone To a solution of 5-(4-bromo-phenyl)-3-methyl-isoxazole-4-carboxylic acid (0.100 g, 0.35 mmol), 1-(2-methylphenyl)piperazine (0.092 g, 0.52 mmol), and 1-hydroxybenzotriazole (0.096 g, 0.71 mmol) in 5:1 $CH_2Cl_2$:DMF was added N-(3-dimethylaminopropyl)-N'-ethylcarbodiimide hydrochloride (0.136 g, 0.71 mmol), and the reaction was stirred at room temperature overnight. The reaction was diluted with $CH_2Cl_2$ and washed twice with $H_2O$, once with brine, and then dried over $Na_2SO_4$, filtered, and concentrated to give the title compound, which was used directly in the following step.

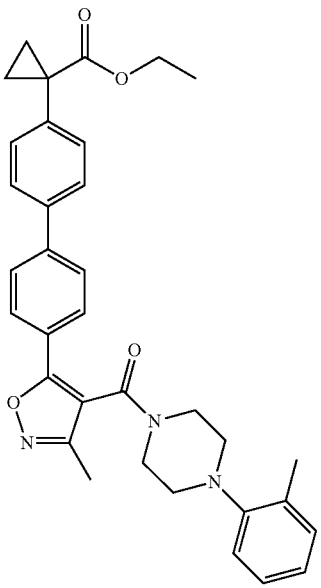 [SMILES: CCOC(=O)C1(c2ccc(-c3ccc(-c4onc(C)c4C(=O)N4CCN(c5ccccc5C)CC4)cc3)cc2)CC1]

Step 2: 1-{4'-[3-Methyl-4-(4-o-tolyl-piperazine-1-carbonyl)-isoxazol-5-yl]-biphenyl-4-yl}-cyclopropanecarboxylic acid ethyl ester

[5-(4-Bromo-phenyl)-3-methyl-isoxazol-4-yl]-(4-o-tolyl-piperazin-1-yl)-methanone (0.156 g, 0.36 mmol), 1-[4-(4,4,5,5-tetramethyl-[1,3,2]dioxaborolan-2-yl)-phenyl]-cyclopropanecarboxylic acid ethyl ester (0.168 g, 0.53 mmol), tetrakis(triphenylphosphine)palladium(0) (0.042 g, 0.04 mmol), and sodium bicarbonate (0.076 g, 0.90 mmol) were combined in 3:1 DME:$H_2O$, and the mixture was purged with $N_2$ (g). The reaction was stirred at 80° C. for 1 hour and then cooled and concentrated. The crude material was purified by silica gel chromatography (0-40% EtOAc in hexanes) to give the title compound.

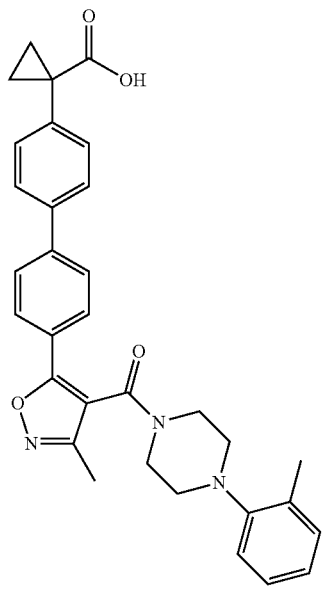 [SMILES: Cc1ccccc1N1CCN(C(=O)c2c(C)noc2-c2ccc(-c3ccc(C4(C(=O)O)CC4)cc3)cc2)CC1]

Step 3: 1-{4'-[3-Methyl-4-(4-o-tolyl-piperazine-1-carbonyl)-isoxazol-5-yl]-biphenyl-4-yl}-cyclopropanecarboxylic acid Prepared according to the procedure described in Example 1, Step 13, using 1-{4'-[3-methyl-4-(4-o-tolyl-piperazine-1-carbonyl)-isoxazol-5-yl]-biphenyl-4-yl}-cyclopropanecarboxylic acid ethyl ester.

Example 3

Synthesis of 1-(4'-{4-[4-(3,4-Dichloro-benzenesulfonyl)-piperazine-1-carbonyl]-3-methyl-isoxazol-5-yl}-biphenyl-4-yl)-cyclopropanecarboxylic acid (Compound 1-3)

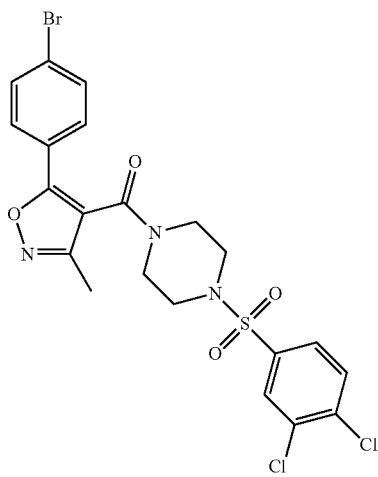 [SMILES: Cc1noc(-c2ccc(Br)cc2)c1C(=O)N1CCN(S(=O)(=O)c2ccc(Cl)c(Cl)c2)CC1]

Step 1: [5-(4-Bromo-phenyl)-3-methyl-isoxazol-4-yl]-[4-(3,4-dichloro-benzenesulfonyl)-piperazin-1-yl]-methanone Prepared according to the procedure described in Example 2, Step 1, using 5-(4-bromo-phenyl)-3-methyl-isoxazole-4-carboxylic acid and 1-[(3,4-dichlorophenyl)sulfonyl]piperazine hydrochloride.

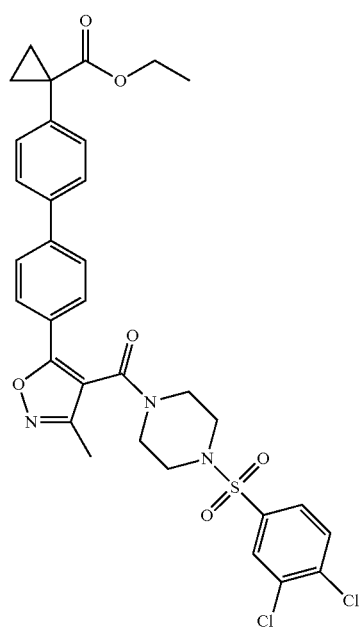 [SMILES: CCOC(=O)C1(c2ccc(-c3ccc(-c4onc(C)c4C(=O)N4CCN(S(=O)(=O)c5ccc(Cl)c(Cl)c5)CC4)cc3)cc2)CC1]

Step 2: 1-(4'-{4-[4-(3,4-Dichloro-benzenesulfonyl)-piperazine-1-carbonyl]-3-methyl-isoxazol-5-yl}-biphenyl-4-yl)-cyclopropanecarboxylic acid ethyl ester Prepared according to the procedure described in Example 2, Step 2, using [5-(4-bromo-phenyl)-3-methyl-isoxazol-4-yl]-[4-(3,4-dichloro-benzenesulfonyl)-piperazin-1-yl]-methanone and 1-[4-(4,4,5,5-tetramethyl-[1,3,2]dioxaborolan-2-yl)-phenyl]-cyclopropanecarboxylic acid ethyl ester.

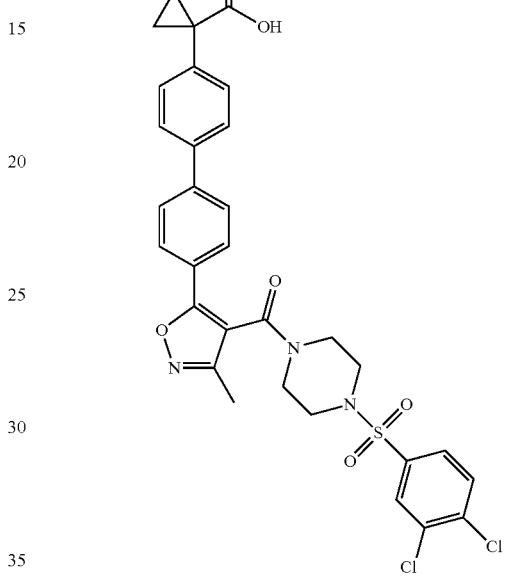

Step 3: 1-(4'-{4-[4-(3,4-Dichloro-benzenesulfonyl)-piperazine-1-carbonyl]-3-methyl-isoxazol-5-yl}-biphenyl-4-yl)-cyclopropanecarboxylic acid Prepared according to the procedure described in Example 1, Step 13, using 1-(4'-{4-[4-(3,4-dichloro-benzenesulfonyl)-piperazine-1-carbonyl]-3-methyl-isoxazol-5-yl}-biphenyl-4-yl)-cyclopropanecarboxylic acid ethyl ester.

Example 4

Synthesis of 1-{4'-[3-Methyl-4-(3-phenethyl-oxiranyl)-isoxazol-5-yl]-biphenyl-4-yl}-cyclopropanecarboxylic acid (Compound 1-4)

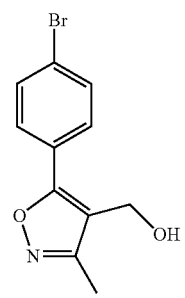

Step 1: [5-(4-Bromo-phenyl)-3-methyl-isoxazol-4-yl]methanol 5-(4-Bromo-phenyl)-3-methyl-isoxazole-4-carboxylic acid methyl ester (5 g, 16.8 mmol) and lithium borohydride (1.85 g, 84.1 mmol) were combined in EtOH and stirred at 60° C. After aqueous workup, the crude material was purified by silica gel chromatography to give the title compound.

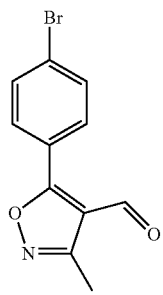

Step 2: 5-(4-Bromo-phenyl)-3-methyl-isoxazole-4-carbaldehyde

[5-(4-Bromo-phenyl)-3-methyl-isoxazol-4-yl]-methanol (1.2 g, 4.5 mmol) was treated with 4-methylmorpholine N-oxide (0.786 g, 6.7 mmol) and tetrapropylammonium perruthenate (catalytic) in $CH_2Cl_2$. The reaction was monitored by analytical LCMS and when complete it was filtered through Celite then submitted to silica gel chromatography to give the title compound.

Step 3: 5-(4-Bromo-phenyl)-3-methyl-4-(4-phenyl-but-1-enyl)-isoxazole

To a solution of (3-phenylpropyl)triphenylphosphonium bromide (0.956 g, 2.07 mmol) in THF (5 mL) at −78° C. was slowly added n-butyllithium (2.5M in hexanes; 0.83 mL, 2.07 mmol), and the mixture was stirred for 15 minutes. 5-(4-Bromo-phenyl)-3-methyl-isoxazole-4-carbaldehyde (0.500 g, 1.88 mmol) in THF (3 mL) was added, and the reaction was warmed to 0° C. and stirred for 1 hour. The solution was diluted with 1N aqueous HCl and extracted twice with EtOAc. The combined organic layers were dried over $Na_2SO_4$, decanted, and concentrated. The residue was purified by silica gel chromatography (0-20% EtOAc in hexanes) to give the title compound.

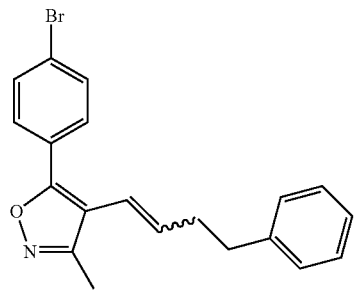 [SMILES: Cc1noc(-c2ccc(Br)cc2)c1C=CCCc1ccccc1]

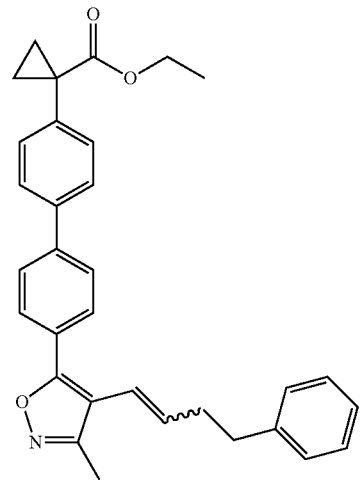 [SMILES: CCOC(=O)C1(c2ccc(-c3ccc(-c4onc(C)c4C=CCCc4ccccc4)cc3)cc2)CC1]

Step 4: 1-{4'-[3-Methyl-4-(4-phenyl-but-1-enyl)-isoxazol-5-yl]-biphenyl-4-yl}-cyclopropanecarboxylic acid ethyl ester Prepared according to the procedure described in Example 2, Step 2, using 5-4-bromo-phenyl)-3-methyl-4-(4-phenyl-but-1-enyl)-isoxazole and 1-[4-(4,4,5,5-tetramethyl-[1,3,2]dioxaborolan-2-yl)-phenyl]-cyclopropanecarboxylic acid ethyl ester.

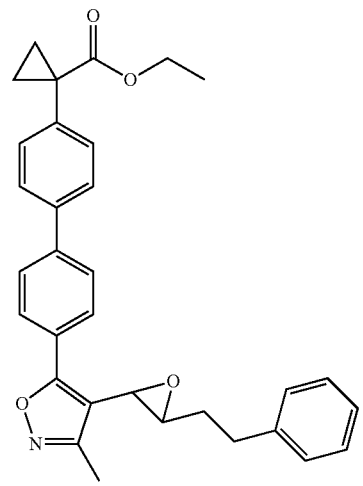 [SMILES: CCOC(=O)C1(c2ccc(-c3ccc(-c4onc(C)c4C4OC4CCc4ccccc4)cc3)cc2)CC1]

Step 5: 1-{4'-[3-Methyl-4-(3-phenethyl-oxiranyl)-isoxazol-5-yl]-biphenyl-4-yl}-cyclopropanecarboxylic acid ethyl ester To a solution of 1-{4'-[3-methyl-4-(4-phenyl-but-1-enyl)-isoxazol-5-yl]-biphenyl-4-yl}-cyclopropanecarboxylic acid ethyl ester (0.343 g, 0.72 mmol) in $CH_2Cl_2$ (3.5 mL) was added meta-chloroperoxybenzoic acid (0.181 g, 0.79 mmol), and the reaction was stirred at room temperature overnight. Analytical LCMS indicated the starting material was still present, so additional meta-chloroperoxybenzoic acid was added, and the reaction was stirred overnight at room temperature. After aqueous workup, the organic layer was dried over MgSO₄, filtered, and concentrated, and the crude material was purified by silica gel chromatography to give the title compound.

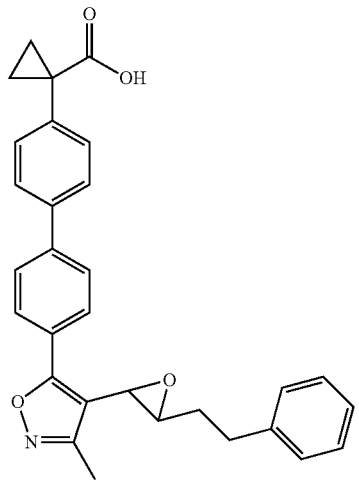 [SMILES: Cc1noc(-c2ccc(-c3ccc(C4(C(=O)O)CC4)cc3)cc2)c1C1OC1CCc1ccccc1]

Step 6: 1-{4'-[3-Methyl-4-(3-phenethyl-oxiranyl)-isoxazol-5-yl]-biphenyl-4-yl}-cyclopropanecarboxylic acid Prepared according to the procedure described in Example 1, Step 13, using 1-{4'-[3-methyl-4-(3-phenethyl-oxiranyl)-isoxazol-5-yl]-biphenyl-4-yl}-cyclopropanecarboxylic acid ethyl ester.

Example 5

Synthesis of 1-{4'-[3-Methyl-4-(3-phenyl-pyrazol-1-ylmethyl)-isoxazol-5-yl]-biphenyl-4-yl}-cyclopropanecarboxylic acid (Compound 1-5)

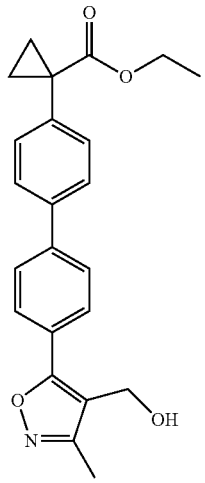 [SMILES: CCOC(=O)C1(c2ccc(-c3ccc(-c4onc(C)c4CO)cc3)cc2)CC1]

Step 1: 1-[4'-(4-Hydroxymethyl-3-methyl-isoxazol-5-yl)-biphenyl-4-yl]-cyclopropanecarboxylic acid ethyl ester Prepared according to the procedure described in Example 2, Step 2, using [5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester.

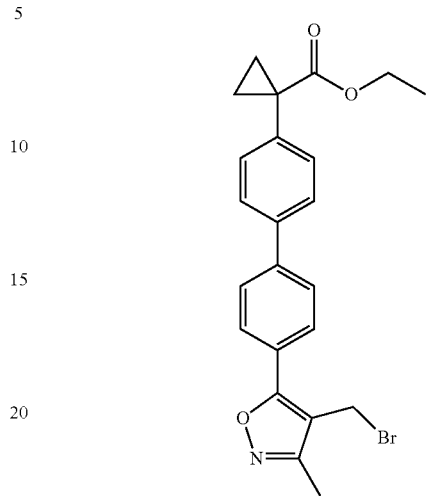

Step 2: 1-[4'-(4-Bromomethyl-3-methyl-isoxazol-5-yl)-biphenyl-4-yl]-cyclopropanecarboxylic acid ethyl ester Phosphorus tribromide (0.43 mL, 4.53 mmol) was added to a solution of 1-[4'-(4-hydroxymethyl-3-methyl-isoxazol-5-yl)-biphenyl-4-yl]-cyclopropanecarboxylic acid ethyl ester (1.14 g, 3.02 mmol) in DME (30 mL) at 0° C. The reaction was stirred overnight at room temperature, and then cooled to 0° C. and neutralized with saturated aqueous NaHCO₃ to pH 7. The mixture was partitioned between CH₂Cl₂ and H₂O, and the aqueous layer was extracted with CH₂Cl₂. The combined organic layers were dried over MgSO₄, filtered, and concentrated, and the residue was purified by silica gel chromatography to give the title compound.

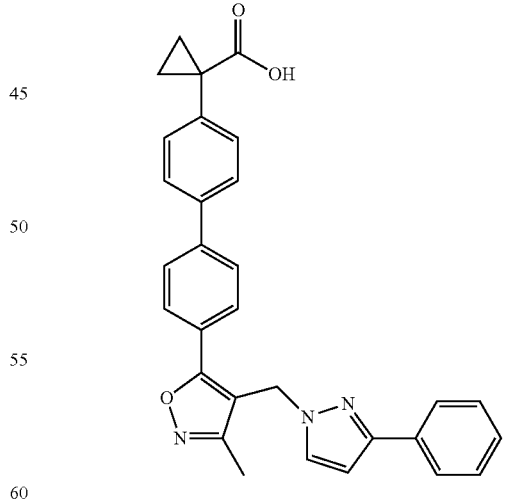

Step 3: 1-{4'-[3-Methyl-4-(3-phenyl-pyrazol-1-ylmethyl)-isoxazol-5-yl]-biphenyl-4-yl}-cyclopropanecarboxylic acid 1-[4'-(4-Bromomethyl-3-methyl-isoxazol-5-yl)-biphenyl-4-yl]-cyclopropanecarboxylic acid ethyl ester (0.132 g, 0.3 mmol) and 3-phenyl-1H-pyrazole (0.043 g, 0.3 mmol) were combined in DMF. Sodium hydride (60% in mineral oil; 0.014 g, 0.35 mmol) was added, and the reaction was stirred at room temperature for 1.5 hours. Once no starting material was seen by analytical LCMS, the mixture was diluted with EtOAc and 1N aqueous HCl. The aqueous layer was extracted with EtOAc, and the combined organic layers were washed with H$_2$O and brine, and then dried over Na$_2$SO$_4$, filtered, and concentrated. The residue was purified by preparative HPLC to give the title compound.

Example 6

Synthesis of 1-{4'-[3-Methyl-4-(4-phenyl-[1,2,3]triazol-1-ylmethyl)-isoxazol-5-yl]-biphenyl-4-yl}-cyclopropanecarboxylic acid (Compound 1-6)

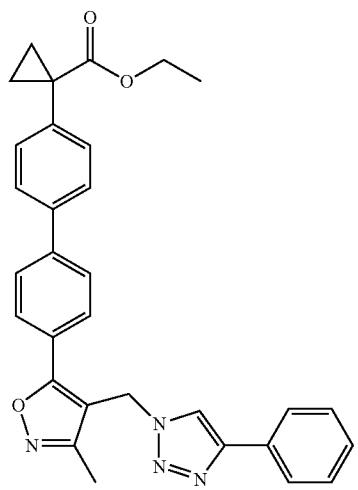 [SMILES: CCOC(=O)C1(c2ccc(-c3ccc(-c4onc(C)c4Cn4cc(-c5ccccc5)nn4)cc3)cc2)CC1]

Step 1: 1-{4'-[3-Methyl-4-(4-phenyl-[1,2,3]triazol-1-ylmethyl)-isoxazol-5-yl]-biphenyl-4-yl}-cyclopropanecarboxylic acid ethyl ester Prepared according to the procedure described in Example 5, Step 3, using 1-[4'-(4-bromomethyl-3-methyl-isoxazol-5-yl)-biphenyl-4-yl]-cyclopropanecarboxylic acid ethyl ester and 4-phenyl-1H-1,2,3-triazole.

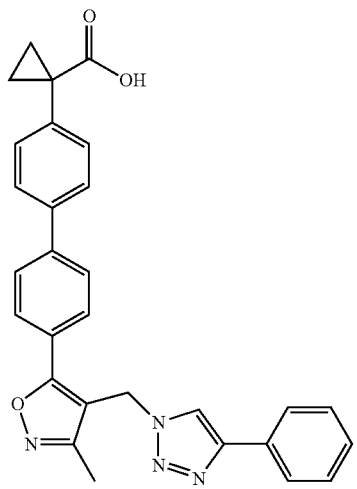 [SMILES: Cc1noc(-c2ccc(-c3ccc(C4(C(=O)O)CC4)cc3)cc2)c1Cn1cc(-c2ccccc2)nn1]

Step 2: 1-{4'-[3-Methyl-4-(4-phenyl-[1,2,3]triazol-1-ylmethyl)-isoxazol-5-yl]-biphenyl-4-yl}-cyclopropanecarboxylic acid Prepared according to the procedure described in Example 1, Step 13, using 1-{4'-[3-methyl-4-(4-phenyl-[1,2,3]triazol-1-ylmethyl)-isoxazol-5-yl]-biphenyl-4-yl}-cyclopropanecarboxylic acid ethyl ester.

Example 7

Synthesis of 1-{4'-[3-Methyl-4-(2-oxo-4-phenyl-pyrrolidin-1-ylmethyl)-isoxazol-5-yl]-biphenyl-4-yl}-cyclopropanecarboxylic acid (Compound 1-7)

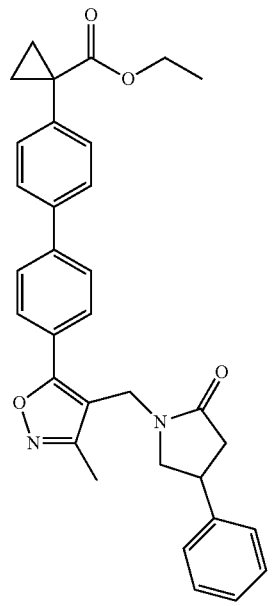 [SMILES: CCOC(=O)C1(c2ccc(-c3ccc(-c4onc(C)c4CN4CC(c5ccccc5)CC4=O)cc3)cc2)CC1]

Step 1: 1-{4'-[3-Methyl-4-(2-oxo-4-phenyl-pyrrolidin-1-ylmethyl)-isoxazol-5-yl]-biphenyl-4-yl}-cyclopropanecarboxylic acid ethyl ester Prepared according to the procedure described in Example 5, Step 3, using 1-[4'-(4-bromomethyl-3-methyl-isoxazol-5- yl)-biphenyl-4-yl]-cyclopropanecarboxylic acid ethyl ester and 4-phenyl-2-pyrollidinone.

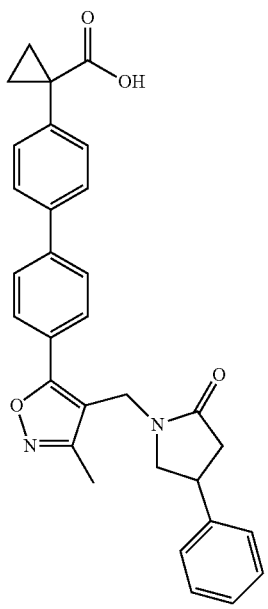 [SMILES: Cc1noc(-c2ccc(-c3ccc(C4(C(=O)O)CC4)cc3)cc2)c1CN1CC(c2ccccc2)CC1=O]

Step 2: 1-{4'-[3-Methyl-4-(2-oxo-4-phenyl-pyrrolidin-1-ylmethyl)-isoxazol-5-yl]-biphenyl-4-yl}-cyclopropanecarboxylic acid Prepared according to the procedure described in Example 1, Step 13, using 1-{4'-[3-methyl-4-(2-oxo-4-phenyl-pyrrolidin-1-ylmethyl)-isoxazol-5-yl]-biphenyl-4-yl}-cyclopropanecarboxylic acid ethyl ester.

Example 8

Synthesis of 1-{4'-[3-Methyl-4-(5-phenyl[1,3,4]oxadiazol-2-ylmethyl)-isoxazol-5-yl]-biphenyl-4-yl}-cyclopropanecarboxylic acid (Compound 1-8)

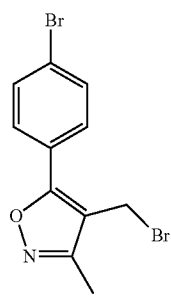

Step 1: 4-Bromomethyl-5-(4-bromo-phenyl)-3-methyl-isoxazole

[5-(4-Bromo-phenyl)-3-methyl-isoxazol-4-yl]-methanol (2.88 g, 10.74 mmol) in DME (23 mL) was treated with phosphorus tribromide (1.5 mL, 16.11 mmol), and the reaction was stirred at room temperature for 1 hour. Aqueous workup provided the title compound.

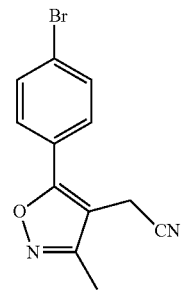 [SMILES: Cc1noc(-c2ccc(Br)cc2)c1CC#N]

Step 2: [5-(4-Bromo-phenyl)-3-methyl-isoxazol-4-yl]acetonitrile

To 4-bromomethyl-5-(4-bromo-phenyl)-3-methyl-isoxazole (10.74 mmol) in DMF (30 mL) was added potassium cyanide (0.729 g, 10.74 mmol), and the reaction was stirred at 65° C. overnight. After aqueous workup, the crude material was purified by silica gel chromatography (0-70% EtOAc in hexanes) to give the title compound.

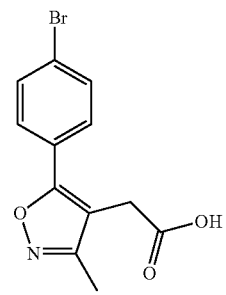 [SMILES: Cc1noc(-c2ccc(Br)cc2)c1CC(=O)O]

Step 3: [5-(4-Bromo-phenyl)-3-methyl-isoxazol-4-yl]acetic acid

[5-(4-Bromo-phenyl)-3-methyl-isoxazol-4-yl]-acetonitrile (1.652 g, 5.96 mmol) in EtOH (9 mL) was treated with 4N aqueous NaOH (6 mL, 23.85 mmol), and the reaction was stirred at 75° C. for 3 hours. The mixture was acidified with 2N aqueous HCl (12 mL) and a precipitate formed as the solution cooled to room temperature. The mixture was filtered, and the solid material was dried to give the title compound.

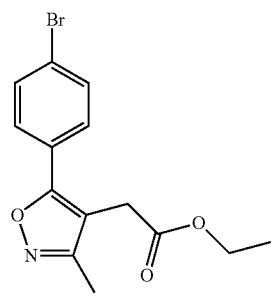 [SMILES: CCOC(=O)Cc1c(C)noc1-c1ccc(Br)cc1]

Step 4: [5-(4-Bromo-phenyl)-3-methyl-isoxazol-4-yl]acetic acid ethyl ester

To [5-(4-bromo-phenyl)-3-methyl-isoxazol-4-yl]-acetic acid (0.200 g, 0.68 mmol) in EtOH (3 mL) was added thionyl chloride (0.10 mL, 1.35 mmol), and the reaction was stirred for 1 hour. The mixture was quenched with saturated aqueous NH₄Cl and diluted with EtOAc and H₂O. After standard aqueous workup, the crude material was purified by silica gel chromatography to give the title compound.

Step 5: [5-(4-Bromo-phenyl)-3-methyl-isoxazol-4-yl]-acetic acid hydrazide

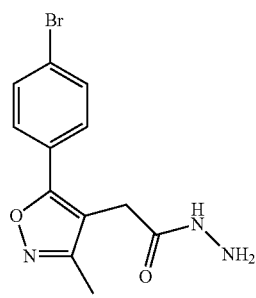 [SMILES: Cc1noc(-c2ccc(Br)cc2)c1CC(=O)NN]

To [5-(4-bromo-phenyl)-3-methyl-isoxazol-4-yl]-acetic acid ethyl ester (0.114 g, 0.37 mmol) in EtOH (4 mL) was added hydrazine (1M in THF; 2 mL), and the reaction was sealed and stirred at 80° C. overnight. The mixture was poured into brine and extracted with EtOAc. The combined organic layers were washed with H₂O and brine, and then dried over MgSO₄, filtered, and concentrated to give the title compound.

Step 6: 2-[5-(4-Bromo-phenyl)-3-methyl-isoxazol-4-ylmethyl]-5-phenyl-[1,3,4]oxadiazole

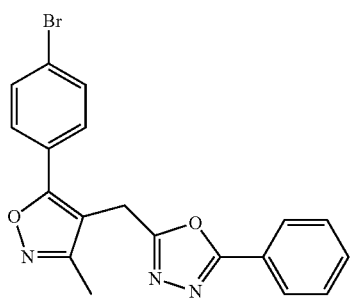 [SMILES: Cc1noc(-c2ccc(Br)cc2)c1Cc1nnc(-c2ccccc2)o1]

To [5-(4-bromo-phenyl)-3-methyl-isoxazol-4-yl]-acetic acid hydrazide (0.142 g, 0.46 mmol) in CH₂Cl₂ (2.3 mL) at 0° C. was added triethylamine (0.19 mL, 1.37 mmol) and benzoyl chloride (0.05 mL, 0.46 mmol), and the reaction was stirred at room temperature for 3 hours. Toluenesulfonyl chloride (0.088 g, 0.46 mmol) was added, and the reaction was stirred overnight. After aqueous workup, the crude material was purified by silica gel chromatography to give the title compound.

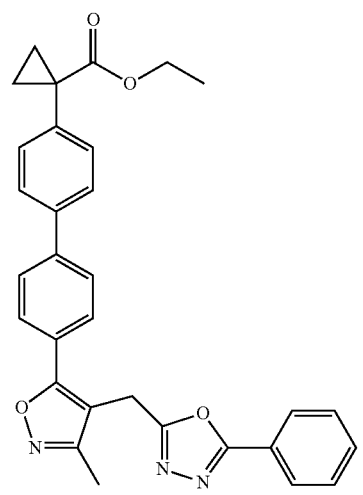 [SMILES: CCOC(=O)C1(c2ccc(-c3ccc(-c4onc(C)c4Cc4nnc(-c5ccccc5)o4)cc3)cc2)CC1]

Step 7: 1-{4'-[3-Methyl-4-(5-phenyl-[1,3,4]oxadiazol-2-ylmethyl)-isoxazol-5-yl]-biphenyl-4-yl}-cyclopropanecarboxylic acid ethyl ester Prepared according to the procedure described in Example 2, Step 2, using 2-[5-(4-bromo-phenyl)-3-methyl-isoxazol-4-ylmethyl]-5-phenyl-[1,3,4]oxadiazole and 1-[4-(4,4,5,5-tetramethyl-[1,3,2]dioxaborolan-2-yl)-phenyl]-cyclopropanecarboxylic acid ethyl ester.

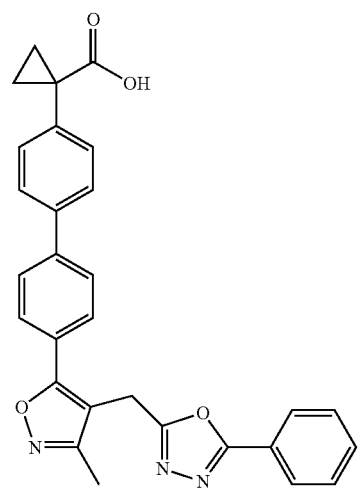 [SMILES: Cc1noc(-c2ccc(-c3ccc(C4(C(=O)O)CC4)cc3)cc2)c1Cc1nnc(-c2ccccc2)o1]

Step 8: 1-{4'-[3-Methyl-4-(5-phenyl-[1,3,4]oxadiazol-2-ylmethyl)-isoxazol-5-yl]-biphenyl-4-yl}-cyclopropanecarboxylic acid Prepared according to the procedure described in Example 1, Step 13, using 1-{4'-[3-methyl-4-(5-phenyl-[1,3,4]oxadiazol-2-ylmethyl)-isoxazol-5-yl]-biphenyl-4-yl}-cyclopropanecarboxylic acid ethyl ester.

Example 9

Synthesis of 1-{4'-[4-(4-Benzyl-[1,2,3]triazol-1-ylmethyl)-3-methyl-isoxazol-5-yl]-biphenyl-4-yl}-cyclopropanecarboxylic acid (Compound 1-9)

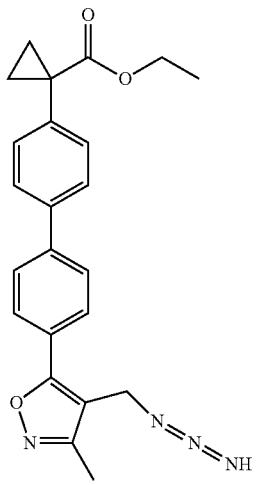

Step 1: 1-[4'-(4-Azidomethyl-3-methyl-isoxazol-5-yl)-biphenyl-4-yl]-cyclopropanecarboxylic acid ethyl ester Sodium nitrile (0.060 g, 0.91 mmol) was dissolved in H$_2$O (0.5 mL). DMF (2 mL) was added, followed by 1-[4'-(4-Bromomethyl-3-methyl-isoxazol-5-yl)-biphenyl-4-yl]-cyclopropanecarboxylic acid ethyl ester (0.200 g, 0.45 mmol), and the reaction was stirred overnight. The mixture was diluted with H$_2$O and extracted with EtOAc. The combined organic layers were dried over Na$_2$SO$_4$, filtered, and concentrated to give the title compound.

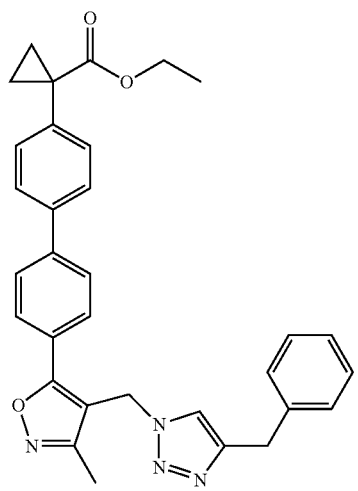 [SMILES: CCOC(=O)C1(c2ccc(-c3ccc(-c4onc(C)c4Cn4cc(Cc5ccccc5)nn4)cc3)cc2)CC1]

Step 2: 1-{4'-[4-(4-Benzyl-[1,2,3]triazol-1-ylmethyl)-3-methyl-isoxazol-5-yl]-biphenyl-4-yl}-cyclopropanecarboxylic acid ethyl ester To a solution of 1-[4'-(4-azidomethyl-3-methyl-isoxazol-5-yl)-biphenyl-4-yl]-cyclopropanecarboxylic acid ethyl ester (0.183 g, 0.45 mmol) in tBuOH (1.5 mL) and H$_2$O (1.5 mL) was added 3-phenyl-1-propyne (0.053 g, 0.45 mmol), followed by sodium ascorbate (0.009 g, 0.045 mmol) and copper (II) sulfate pentahydrate (0.001 g, 0.005 mmol), and the reaction was stirred overnight. After aqueous workup, the crude material was purified by silica gel chromatography to give the title compound.

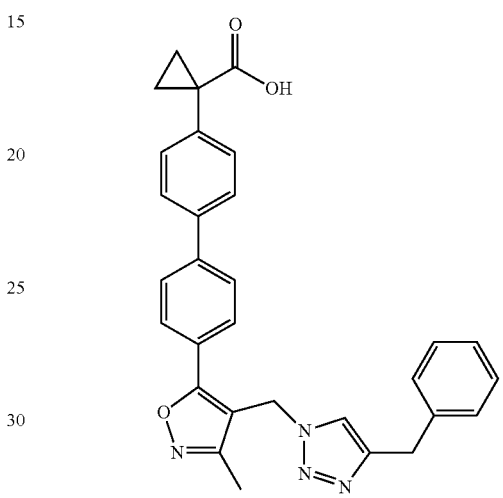

Step 3: 1-{4'-[4-(4-Benzyl-[1,2,3]triazol-1-ylmethyl)-3-methyl-isoxazol-5-yl]-biphenyl-4-yl}-cyclopropanecarboxylic acid Prepared according to the procedure described in Example 1, Step 13, using 1-{4'-[4-(4-benzyl-[1,2,3]triazol-1-ylmethyl)-3-methyl-isoxazol-5-yl]-biphenyl-4-yl}-cyclopropanecarboxylic acid ethyl ester.

Example 10

Synthesis of 1-{4'-[3-Methyl-4-(4-phenyl-piperidin-1-ylmethyl)-isoxazol-5-yl]-biphenyl-4-yl}-cyclopropanecarboxylic acid (Compound 1-10)

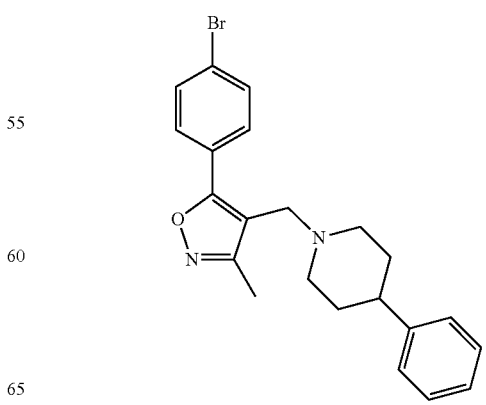

Step 1: 1-[5-(4-Bromo-phenyl)-3-methyl-isoxazol-4-ylmethyl]-4-phenyl-piperidine Prepared according to the procedure described in Example 1, Step 12, using 5-4-bromo-phenyl)-3-methyl-isoxazole-4-carbaldehyde and 4-phenyl-piperidine.

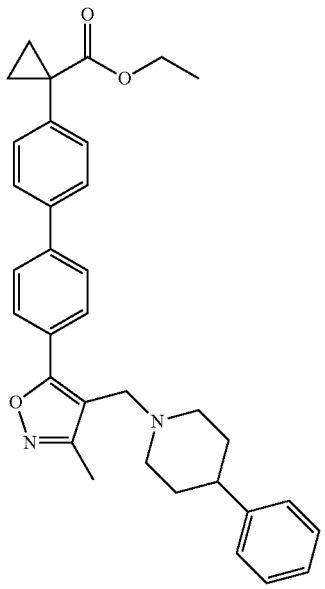 [SMILES: CCOC(=O)C1(c2ccc(-c3ccc(-c4onc(C)c4CN4CCC(c5ccccc5)CC4)cc3)cc2)CC1]

Step 2: 1-{4'-[3-Methyl-4-(4-phenyl-piperidin-1-ylmethyl)-isoxazol-5-yl]-biphenyl-4-yl}-cyclopropanecarboxylic acid ethyl ester Prepared according to the procedure described in Example 1, Step 10, using 1-[5-(4-bromo-phenyl)-3-methyl-isoxazol-4-ylmethyl]-4-phenyl-piperidine and 1-[4-(4,4,5,5-tetramethyl-[1,3,2]dioxaborolan-2-yl)-phenyl]-cyclopropanecarboxylic acid ethyl ester.

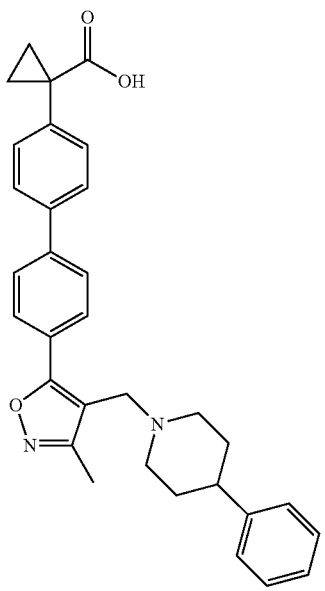 [SMILES: Cc1noc(-c2ccc(-c3ccc(C4(C(=O)O)CC4)cc3)cc2)c1CN1CCC(c2ccccc2)CC1]

Step 3: 1-{4'-[3-Methyl-4-(4-phenyl-piperidin-1-ylmethyl)-isoxazol-5-yl]-biphenyl-4-yl}-cyclopropanecarboxylic acid Prepared according to the procedure described in Example 1, Step 13, using 1-{4'-[3-methyl-4-(4-phenyl-piperidin-1-ylmethyl)-isoxazol-5-yl]-biphenyl-4-yl}-cyclopropanecarboxylic acid ethyl ester.

Example 11

Synthesis of 1-{4'-[4-(2-Imino-5-phenyl-[1,3,4]oxadiazol-3-ylmethyl)-3-methyl-isoxazol-5-yl]-biphenyl-4-yl}-cyclopropanecarboxylic acid (Compound 1-11)

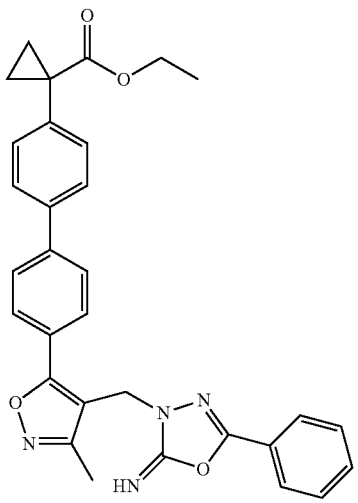 [SMILES: CCOC(=O)C1(c2ccc(-c3ccc(-c4onc(C)c4Cn4nc(-c5ccccc5)oc4=N)cc3)cc2)CC1]

Step 1: 1-{4'-[4-(2-Imino-5-phenyl-[1,3,4]oxadiazol-3-ylmethyl)-3-methyl-isoxazol-5-yl]-biphenyl-4-yl}-cyclopropanecarboxylic acid ethyl ester Prepared according to the procedure described in Example 5, Step 3, using 1-[4'-(4-bromomethyl-3-methyl-isoxazol-5-yl)-biphenyl-4-yl]-cyclopropanecarboxylic acid ethyl ester and 5-phenyl-[1,3,4]oxadiazol-2-ylamine.

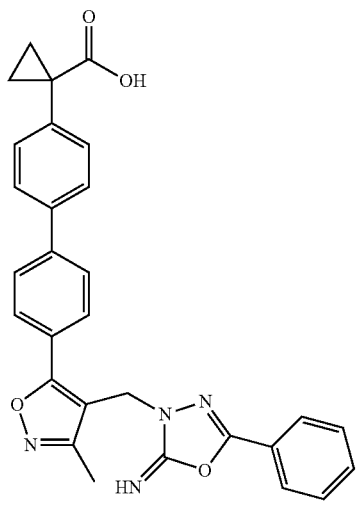 [SMILES: Cc1noc(-c2ccc(-c3ccc(C4(C(=O)O)CC4)cc3)cc2)c1Cn1nc(-c2ccccc2)oc1=N]

Step 2: 1-{4'-[4-(2-Imino-5-phenyl-[1,3,4]oxadiazol-3-ylmethyl)-3-methyl-isoxazol-5-yl]-biphenyl-4-yl}-cyclopropanecarboxylic acid Prepared according to the procedure described in Example 1, Step 13, using 1-{4'-[4-(2-imino-5-phenyl-[1,3,4]oxadiazol-3-ylmethyl)-3-methyl-isoxazol-5-yl]-biphenyl-4-yl}-cyclopropanecarboxylic acid ethyl ester.

Example 12

Synthesis of 1-{4'-[4-((S)-4-Benzyl-2-oxo-oxazolidin-3-ylmethyl)-3-methyl-isoxazol-5-yl]-biphenyl-4-yl}-cyclopropanecarboxylic acid (Compound 1-12)

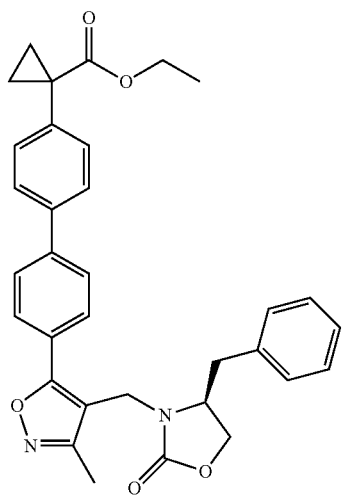 [SMILES: CCOC(=O)C1(c2ccc(-c3ccc(-c4onc(C)c4CN4C(=O)OC[C@@H]4Cc4ccccc4)cc3)cc2)CC1]

Step 1: 1-{4'-[4-((S)-4-Benzyl-2-oxo-oxazolidin-3-ylmethyl)-3-methyl-isoxazol-5-yl]-biphenyl-4-yl}-cyclopropanecarboxylic acid ethyl ester Prepared according to the procedure described in Example 5, Step 3, using 1-[4'-(4-bromomethyl-3-methyl-isoxazol-5-yl)-biphenyl-4-yl]-cyclopropanecarboxylic acid ethyl ester and (S)-4-benzyl-oxazolidin-2-one.

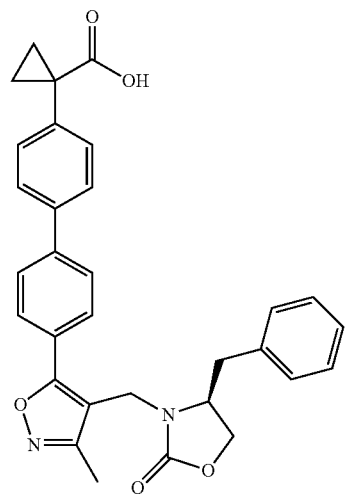 [SMILES: Cc1noc(-c2ccc(-c3ccc(C4(C(=O)O)CC4)cc3)cc2)c1CN1C(=O)OC[C@@H]1Cc1ccccc1]

Step 2: 1-{4'-[4-((S)-4-Benzyl-2-oxo-oxazolidin-3-ylmethyl)-3-methyl-isoxazol-5-yl]-biphenyl-4-yl}-cyclopropanecarboxylic acid Prepared according to the procedure described in Example 1, Step 13, using 1-{4'-[4-((S)-4-benzyl-2-oxo-oxazolidin-3-ylmethyl)-3-methyl-isoxazol-5-yl]-biphenyl-4-yl}-cyclopropanecarboxylic acid ethyl ester.

Example 13

Synthesis of 1-(4'-{4-[3-(4-Bromo-phenyl)-pyrazol-1-ylmethyl]-3-methyl-isoxazol-5-yl}-biphenyl-4-yl)-cyclopropanecarboxylic acid (Compound 1-13)

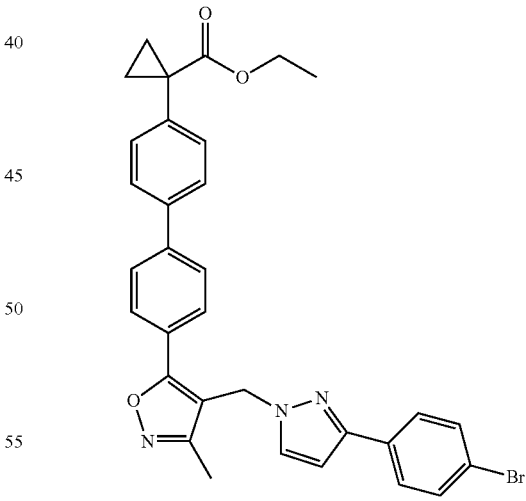

Step 1: 1-(4'-{4-[3-(4-Bromo-phenyl)-pyrazol-1-ylmethyl]-3-methyl-isoxazol-5-yl}-biphenyl-4-yl)-cyclopropanecarboxylic acid ethyl ester Prepared according to the procedure described in Example 5, Step 3, using 1-[4'-(4-bromomethyl-3-methyl-isoxazol-5-yl)-biphenyl-4-yl]-cyclopropanecarboxylic acid ethyl ester and 3-(4-bromo-phenyl)-1H-pyrazole.

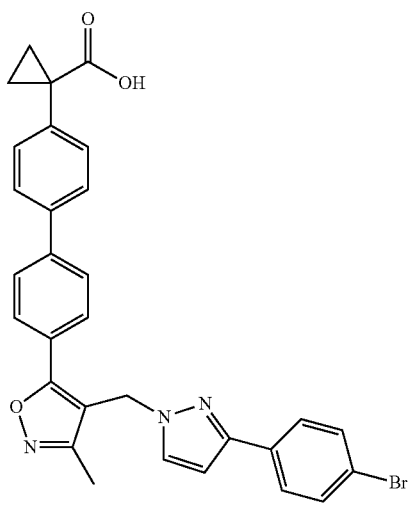 [SMILES: Cc1noc(-c2ccc(-c3ccc(C4(C(=O)O)CC4)cc3)cc2)c1Cn1ccc(-c2ccc(Br)cc2)n1]

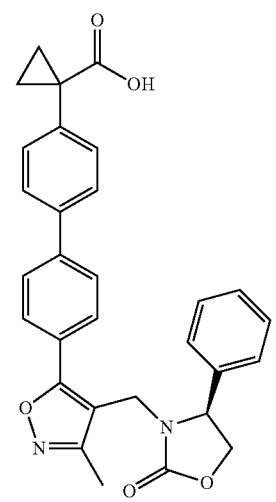

Step 2: 1-(4'-{4-[3-(4-Bromo-phenyl)-pyrazol-1-ylmethyl]-3-methyl-isoxazol-5-yl}-biphenyl-4-yl)-cyclopropanecarboxylic acid Prepared according to the procedure described in Example 1, Step 13, using 1-(4'-{4-[3-(4-bromo-phenyl)-pyrazol-1-ylmethyl]-3-methyl-isoxazol-5-yl}-biphenyl-4-yl)-cyclopropanecarboxylic acid ethyl ester.

Step 2: 1-{4'-[3-Methyl-4-((S)-2-oxo-4-phenyl-oxazolidin-3-ylmethyl)-isoxazol-5-yl]-biphenyl-4-yl}-cyclopropanecarboxylic acid Prepared according to the procedure described in Example 1, Step 13, using 1-{4'-[3-methyl-4-((S)-2-oxo-4-phenyl-oxazolidin-3-ylmethyl)-isoxazol-5-yl]-biphenyl-4-yl}-cyclopropanecarboxylic acid ethyl ester.

Example 14

Synthesis of 1-{4'-[3-Methyl-4-((S)-2-oxo-4-phenyl-oxazolidin-3-ylmethyl)-isoxazol-5-yl]-biphenyl-4-yl}-cyclopropanecarboxylic acid (Compound 1-14)

Example 15

Synthesis of 1-{4'-[3-Methyl-4-((4R,5S)-4-methyl-2-oxo-5-phenyl-oxazolidin-3-ylmethyl)-isoxazol-5-yl]-biphenyl-4-yl}-cyclopropanecarboxylic acid (Compound 1-15)

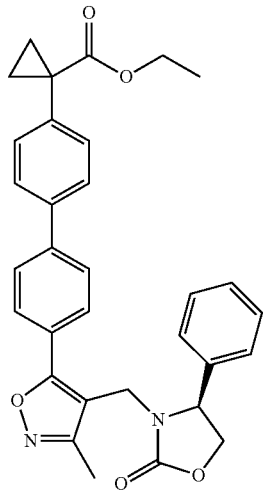 [SMILES: CCOC(=O)C1(c2ccc(-c3ccc(-c4onc(C)c4CN4C(=O)OC[C@@H]4c4ccccc4)cc3)cc2)CC1]

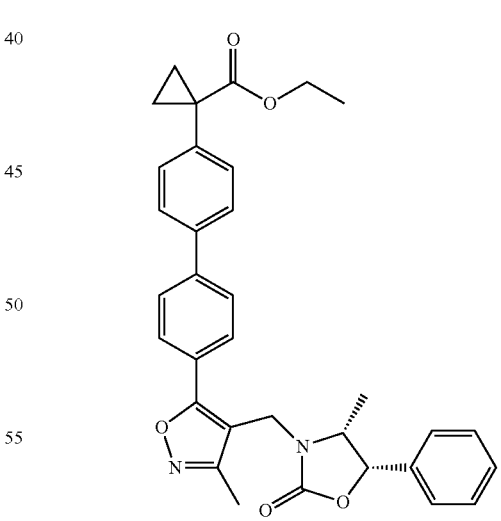

Step 1: 1-{4'-[3-Methyl-4-((S)-2-oxo-4-phenyl-oxazolidin-3-ylmethyl)-isoxazol-5-yl]-biphenyl-4-yl}-cyclopropanecarboxylic acid ethyl ester Prepared according to the procedure described in Example 5, Step 3, using 1-[4'-(4-bromomethyl-3-methyl-isoxazol-5-yl)-biphenyl-4-yl]-cyclopropanecarboxylic acid ethyl ester and (S)-4-phenyl-oxazolidin-2-one.

Step 1: 1-{4'-[3-Methyl-4-((4R,5S)-4-methyl-2-oxo-5-phenyl-oxazolidin-3-ylmethyl)-isoxazol-5-yl]-biphenyl-4-yl}-cyclopropanecarboxylic acid ethyl ester Prepared according to the procedure described in Example 5, Step 3, using 1-[4'-(4-bromomethyl-3-methyl-isoxazol-5- yl)-biphenyl-4-yl]-cyclopropanecarboxylic acid ethyl ester and (4R,5S)-4-methyl-5-phenyl-oxazolidin-2-one.

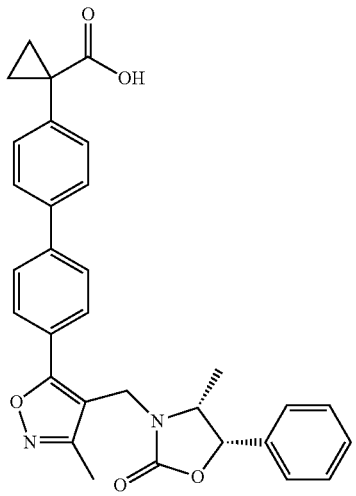 [SMILES: Cc1noc(-c2ccc(-c3ccc(C4(C(=O)O)CC4)cc3)cc2)c1CN1C(=O)O[C@@H](c2ccccc2)[C@H]1C]

Step 2: 1-{4'-[3-Methyl-4-((4R,5S)-4-methyl-2-oxo-5-phenyl-oxazolidin-3-ylmethyl)-isoxazol-5-yl]-biphenyl-4-yl}-cyclopropanecarboxylic acid Prepared according to the procedure described in Example 1, Step 13, using 1-{4'-[3-methyl-4-((4R,5S)-4-methyl-2-oxo-5-phenyl-oxazolidin-3-ylmethyl)-isoxazol-5-yl]-biphenyl-4-yl}-cyclopropanecarboxylic acid ethyl ester.

Example 16

Synthesis of 1-{4'-[3-Methyl-4-((4S,5R)-4-methyl-2-oxo-5-phenyl-oxazolidin-3-ylmethyl)-isoxazol-5-yl]-biphenyl-4-yl}-cyclopropanecarboxylic acid (Compound 1-16)

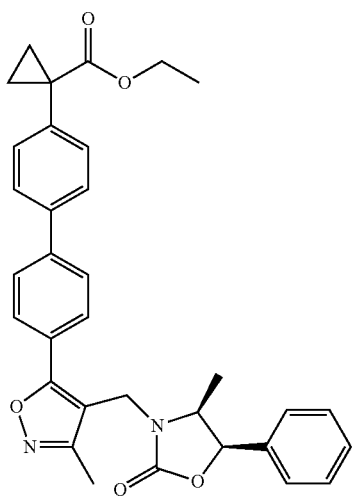 [SMILES: CCOC(=O)C1(c2ccc(-c3ccc(-c4onc(C)c4CN4C(=O)O[C@H](c5ccccc5)[C@@H]4C)cc3)cc2)CC1]

Step 1: 1-{4'-[3-Methyl-4-((4S,5R)-4-methyl-2-oxo-5-phenyl-oxazolidin-3-ylmethyl)-isoxazol-5-yl]-biphenyl-4-yl}-cyclopropanecarboxylic acid ethyl ester Prepared according to the procedure described in Example 5, Step 3, using 1-[4'-(4-bromomethyl-3-methyl-isoxazol-5-yl)-biphenyl-4-yl]-cyclopropanecarboxylic acid ethyl ester and (4S,5R)-4-methyl-5-phenyl-oxazolidin-2-one.

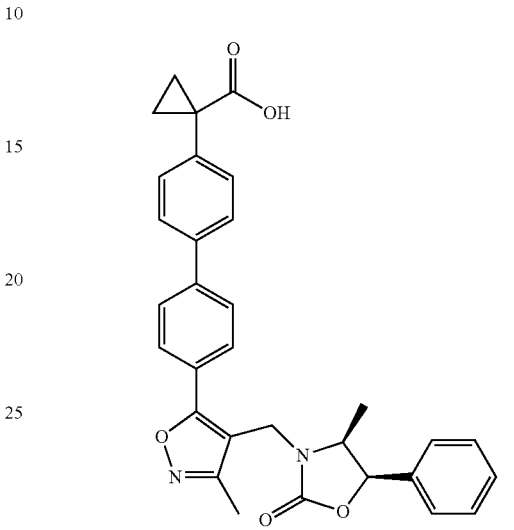

Step 2: 1-{4'-[3-Methyl-4-((4S,5R)-4-methyl-2-oxo-5-phenyl-oxazolidin-3-ylmethyl)-isoxazol-5-yl]-biphenyl-4-yl}-cyclopropanecarboxylic acid Prepared according to the procedure described in Example 1, Step 13, using 1-{4'-[3-methyl-4-((4S,5R)-4-methyl-2-oxo-5-phenyl-oxazolidin-3-ylmethyl)-isoxazol-5-yl]-biphenyl-4-yl}-cyclopropanecarboxylic acid ethyl ester.

Example 17

Synthesis of 1-{4'-[3-Methyl-4-(3-phenyl-pyrrolidin-1-ylmethyl)-isoxazol-5-yl]-biphenyl-4-yl}-cyclopropanecarboxylic acid (Compound 1-17)

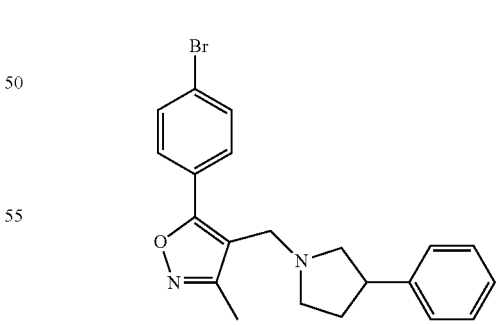

Step 1: 5-(4-Bromo-phenyl)-3-methyl-4-(3-phenyl-pyrrolidin-1-ylmethyl)-isoxazole Prepared according to the procedure described in Example 1, Step 12, using 5-(4-bromo-phenyl)-3-methyl-isoxazole-4-carbaldehyde and 3-phenyl-pyrrolidine.

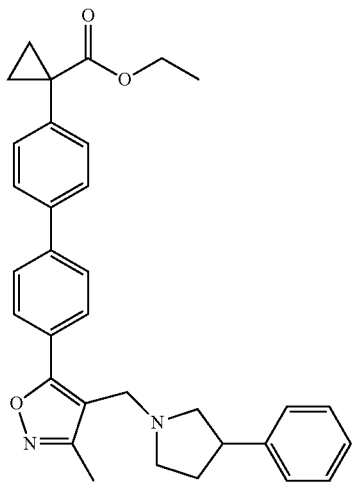 [SMILES: CCOC(=O)C1(c2ccc(-c3ccc(-c4onc(C)c4CN4CCC(c5ccccc5)C4)cc3)cc2)CC1]

Step 2: 1-{4'-[3-Methyl-4-(3-phenyl-pyrrolidin-1-ylmethyl)-isoxazol-5-yl]-biphenyl-4-yl}-cyclopropanecarboxylic acid ethyl ester Prepared according to the procedure described in Example 1, Step 10, using 5-(4-bromo-phenyl)-3-methyl-4-(3-phenyl-pyrrolidin-1-ylmethyl)-isoxazole and 1-[4-(4,4,5,5-tetramethyl-[1,3,2]dioxaborolan-2-yl)-phenyl]-cyclopropanecarboxylic acid ethyl ester.

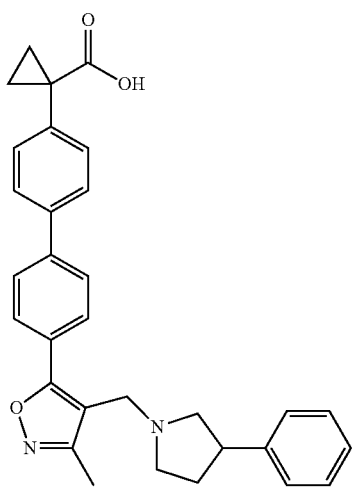 [SMILES: Cc1noc(-c2ccc(-c3ccc(C4(C(=O)O)CC4)cc3)cc2)c1CN1CCC(c2ccccc2)C1]

Step 3: 1-{4'-[3-Methyl-4-(3-phenyl-pyrrolidin-1-ylmethyl)-isoxazol-5-yl]-biphenyl-4-yl}-cyclopropanecarboxylic acid Prepared according to the procedure described in Example 1, Step 13, using 1-{-4'-[3-methyl-4-(3-phenyl-pyrrolidin-1-ylmethyl)-isoxazol-5-yl]-biphenyl-4-yl}-cyclopropanecarboxylic acid ethyl ester.

Example 18

Synthesis of 1-{4'-[3-Methyl-4-(3-phenyl-piperidin-1-ylmethyl)-isoxazol-5-yl]-biphenyl-4-yl}-cyclopropanecarboxylic acid (Compound 1-18)

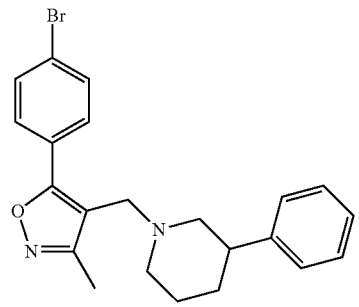 [SMILES: Cc1noc(-c2ccc(Br)cc2)c1CN1CCCC(c2ccccc2)C1]

Step 1: 1-[5-(4-Bromo-phenyl)-3-methyl-isoxazol-4-ylmethyl]-3-phenyl-piperidine

Prepared according to the procedure described in Example 1, Step 12, using 5-(4-bromo-phenyl)-3-methyl-isoxazole-4-carbaldehyde and 3-phenyl-piperidine.

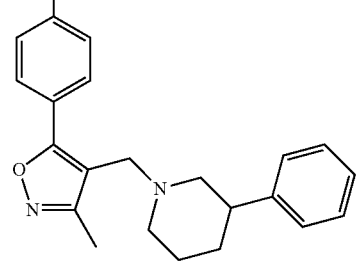

Step 2: 1-{4'-[3-Methyl-4-(3-phenyl-piperidin-1-ylmethyl)-isoxazol-5-yl]-biphenyl-4-yl}-cyclopropanecarboxylic acid ethyl ester Prepared according to the procedure described in Example 1, Step 10, using 1-[5-(4-bromo-phenyl)-3-methyl-isoxazol-4-ylmethyl]-3-phenyl-piperidine and 1-[4-(4,4,5,5-tetramethyl-[1,3,2]dioxaborolan-2-yl)-phenyl]-cyclopropanecarboxylic acid ethyl ester.

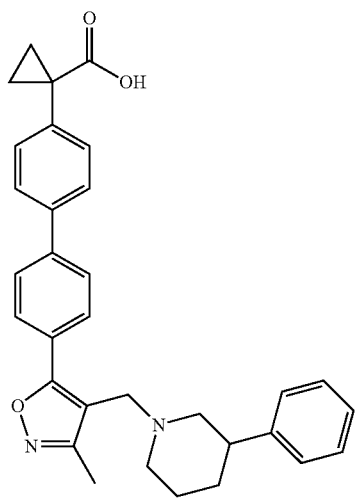 [SMILES: Cc1noc(-c2ccc(-c3ccc(C4(C(=O)O)CC4)cc3)cc2)c1CN1CCCC(c2ccccc2)C1]

Step 3: 1-{4'-[3-Methyl-4-(3-phenyl-piperidin-1-ylmethyl)-isoxazol-5-yl]-biphenyl-4-yl}-cyclopropanecarboxylic acid Prepared according to the procedure described in Example 1, Step 13, using 1-{4'-[3-methyl-4-(3-phenyl-piperidin-1-ylmethyl)-isoxazol-5-yl]-biphenyl-4-yl}-cyclopropanecarboxylic acid ethyl ester.

Example 19

Synthesis of 1-(4'-{3-Methyl-4-[(5-phenyl-[1,3,4]oxadiazol-2-ylamino)-methyl]-isoxazol-5-yl}-biphenyl-4-yl)-cyclopropanecarboxylic acid (Compound 1-19)

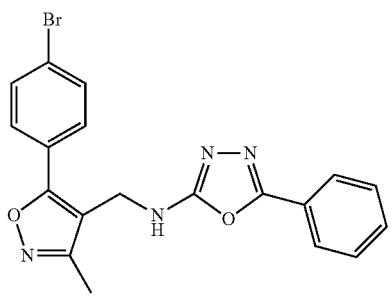 [SMILES: Cc1noc(-c2ccc(Br)cc2)c1CNc1nnc(-c2ccccc2)o1]

Step 1: [5-(4-Bromo-phenyl)-3-methyl-isoxazol-4-ylmethyl]-(5-phenyl-[1,3,4]oxadiazol-2-yl)-amine Prepared according to the procedure described in Example 1, Step 12, using 5-(4-bromo-phenyl)-3-methyl-isoxazole-4-carbaldehyde and 5-phenyl-[1,3,4]oxadiazol-2-ylamine.

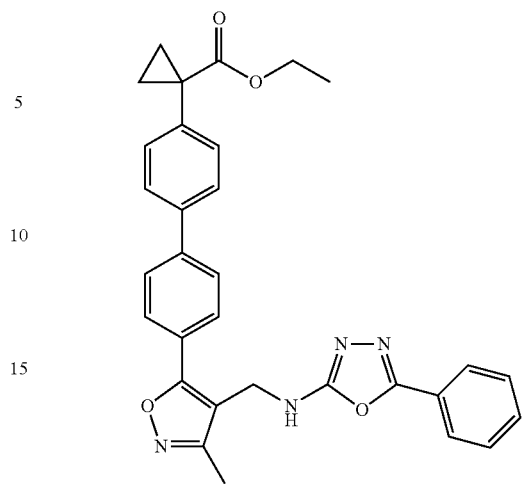

Step 2: 1-(4'-{3-Methyl-4-[(5-phenyl-[1,3,4]oxadiazol-2-ylamino)-methyl]-isoxazol-5-yl}-biphenyl-4-yl)-cyclopropanecarboxylic acid ethyl ester Prepared according to the procedure described in Example 1, Step 10, using [5-(4-bromo-phenyl)-3-methyl-isoxazol-4-ylmethyl]-(5-phenyl-[1,3,4]oxadiazol-2-yl)-amine and 1-[4-(4,4,5,5-tetramethyl-[1,3,2]dioxaborolan-2-yl)-phenyl]-cyclopropanecarboxylic acid ethyl ester.

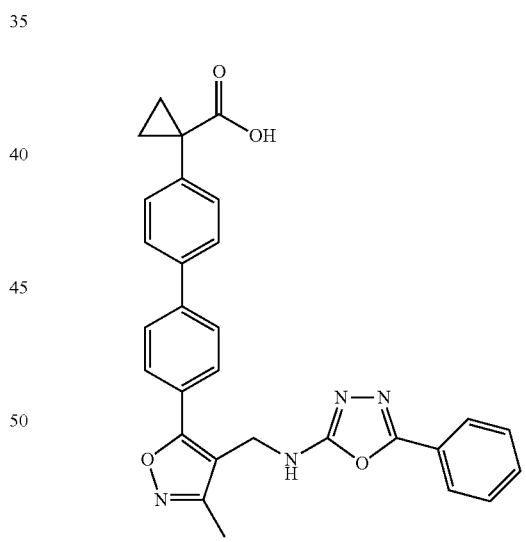

Step 3: 1-(4'-{3-Methyl-4-[(5-phenyl-[1,3,4]oxadiazol-2-ylamino)-methyl]-isoxazol-5-yl}-biphenyl-4-yl)-cyclopropanecarboxylic acid Prepared according to the procedure described in Example 1, Step 13, using 1-(4'-{3-methyl-4-[(5-phenyl-[1,3,4]oxadiazol-2-ylamino)-methyl]-isoxazol-5-yl}-biphenyl-4-yl)-cyclopropanecarboxylic acid ethyl ester.

Example 20

Synthesis of 1-{4'-[3-Methyl-4-(5-phenyl-[1,2,3]triazol-1-ylmethyl)-isoxazol-5-yl]-biphenyl-4-yl}-cyclopropanecarboxylic acid (Compound 1-20)

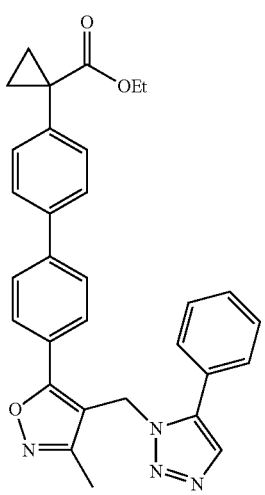 [SMILES: CCOC(=O)C1(c2ccc(-c3ccc(-c4onc(C)c4Cn4nncc4-c4ccccc4)cc3)cc2)CC1]

Step 1: 1-{4'-[3-Methyl-4-(5-phenyl-[1,2,3]triazol-1-ylmethyl)-isoxazol-5-yl]-biphenyl-4-yl}-cyclopropanecarboxylic acid ethyl ester Prepared according to the procedure described in Example 5, Step 3, using 1-[4'-(4-bromomethyl-3-methyl-isoxazol-5-yl)-biphenyl-4-yl]-cyclopropanecarboxylic acid ethyl ester and 5-phenyl-1H-[1,2,3]triazole.

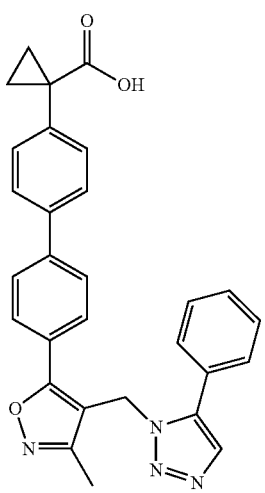 [SMILES: Cc1noc(-c2ccc(-c3ccc(C4(C(=O)O)CC4)cc3)cc2)c1Cn1nncc1-c1ccccc1]

Step 2: 1-{4'-[3-Methyl-4-(5-phenyl-[1,2,3]triazol-1-ylmethyl)-isoxazol-5-yl]-biphenyl-4-yl}-cyclopropanecarboxylic acid Prepared according to the procedure described in Example 1, Step 13, using 1-{4'-[3-methyl-4-(5-phenyl-[1,2,3]triazol-1-ylmethyl)-isoxazol-5-yl]-biphenyl-4-yl}-cyclopropanecarboxylic acid ethyl ester.

Example 21

Synthesis of 1-{4'-[3-Methyl-4-(5-phenyl-tetrazol-2-ylmethyl)-isoxazol-5-yl]-biphenyl-4-yl}-cyclopropanecarboxylic acid (Compound 1-21)

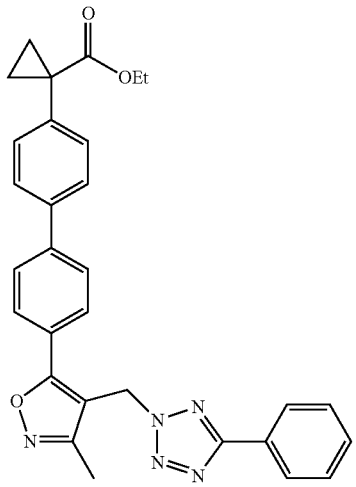 [SMILES: CCOC(=O)C1(c2ccc(-c3ccc(-c4onc(C)c4Cn4nnc(-c5ccccc5)n4)cc3)cc2)CC1]

Step 1: 1-{4'-[3-Methyl-4-(5-phenyl-tetrazol-2-ylmethyl)-isoxazol-5-yl]-biphenyl-4-yl}-cyclopropanecarboxylic acid ethyl ester Prepared according to the procedure described in Example 5, Step 3, using 1-[4'-(4-bromomethyl-3-methyl-isoxazol-5-yl)-biphenyl-4-yl]-cyclopropanecarboxylic acid ethyl ester and 5-phenyl-2H-tetrazole.

151

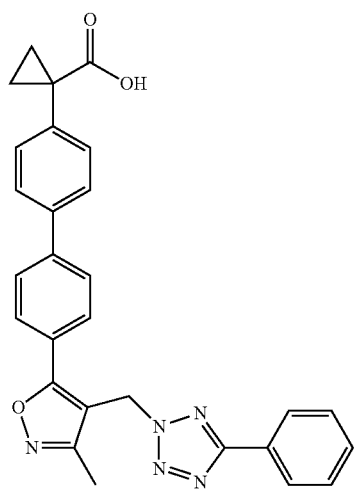

Step 2: 1-{4'-[3-Methyl-4-(5-phenyl-[1,2,3]triazol-1-ylmethyl)-isoxazol-5-yl]-biphenyl-4-yl}-cyclopropanecarboxylic acid Prepared according to the procedure described in Example 1, Step 13, using 1-{4'-[3-Methyl-4-(5-phenyl-tetrazol-2-ylmethyl)-isoxazol-5-yl]-biphenyl-4-yl}-cyclopropanecarboxylic acid ethyl ester.

Example 22

Synthesis of 1-{4'-[3-Methyl-4-(2-oxo-5-phenyl-oxazolidin-3-ylmethyl)-isoxazol-5-yl]-biphenyl-4-yl}-cyclopropanecarboxylic acid (Compound 1-22)

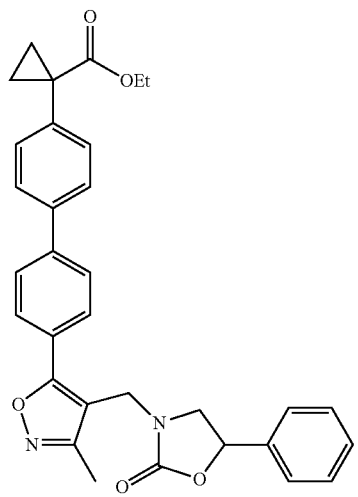 [SMILES: CCOC(=O)C1(c2ccc(-c3ccc(-c4onc(C)c4CN4CC(c5ccccc5)OC4=O)cc3)cc2)CC1]

Step 1: 1-{4'-[3-Methyl-4-(2-oxo-5-phenyl-oxazolidin-3-ylmethyl)-isoxazol-5-yl]-biphenyl-4-yl}-cyclopropanecarboxylic acid ethyl ester Prepared according to the procedure described in Example 5, Step 3, using 1-[4'-(4-bromomethyl-3-methyl-isoxazol-5-yl)-biphenyl-4-yl]-cyclopropanecarboxylic acid ethyl ester and 5-phenyl-oxazolidin-2-one.

152

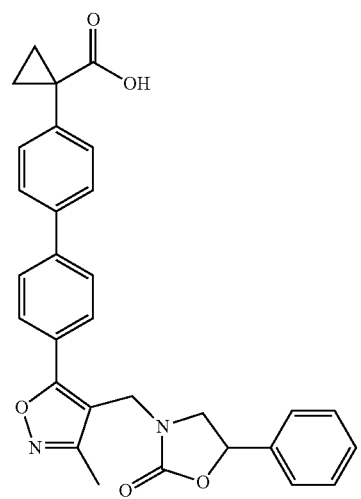 [SMILES: Cc1noc(-c2ccc(-c3ccc(C4(C(=O)O)CC4)cc3)cc2)c1CN1CC(c2ccccc2)OC1=O]

Step 2: 1-{4'-[3-Methyl-4-(2-oxo-5-phenyl-oxazolidin-3-ylmethyl)-isoxazol-5-yl]-biphenyl-4-yl}-cyclopropanecarboxylic acid Prepared according to the procedure described in Example 1, Step 13, using 1-{4'-[3-Methyl-4-(2-oxo-5-phenyl-oxazolidin-3-ylmethyl)-isoxazol-5-yl]-biphenyl-4-yl}-cyclopropanecarboxylic acid ethyl ester.

Example 23

Synthesis of 1-{4'-[3-Methyl-4-(4-phenyl-pyrazol-1-ylmethyl)-isoxazol-5-yl]-biphenyl-4-yl}-cyclopropanecarboxylic acid (Compound 1-23)

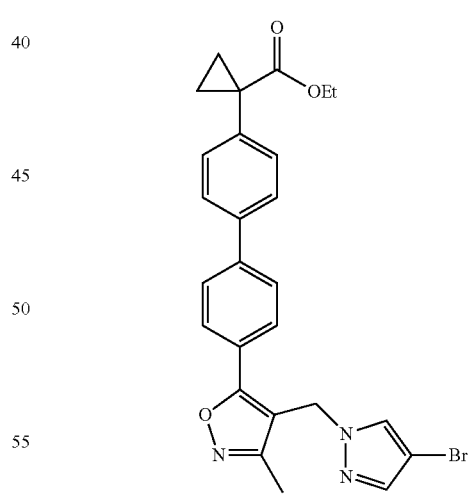

Step 1: 1-{4'-[4-(4-Bromo-pyrazol-1-ylmethyl)-3-methyl-isoxazol-5-yl]-biphenyl-4-yl}-cyclopropanecarboxylic acid ethyl ester Prepared according to the procedure described in Example 5, Step 3, using 1-[4'-(4-bromomethyl-3-methyl-isoxazol-5-yl)-biphenyl-4-yl]-cyclopropanecarboxylic acid ethyl ester and 4-Bromo-1H-pyrazole.

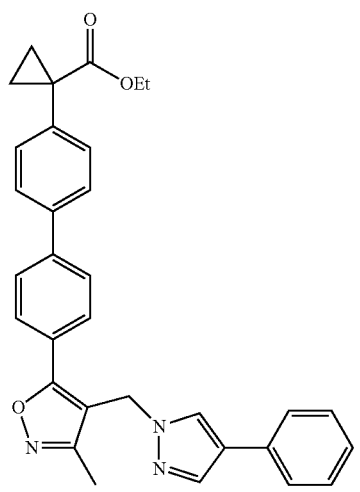

Step 2: 1-{4'-[3-Methyl-4-(4-phenyl-pyrazol-1-ylmethyl)-isoxazol-5-yl]-biphenyl-4-yl}-cyclopropanecarboxylic acid ethyl ester 1-{4'-[4-(4-Bromo-pyrazol-1-ylmethyl)-3-methyl-isoxazol-5-yl]-biphenyl-4-yl}-cyclopropanecarboxylic acid ethyl ester (0.062 g, 0.122 mmol), phenylboronic acid (0.018 g, 0.146 mmol), tri(o-tolyl)phosphine (0.004 g, 0.0122 mmol) and sodium bicarbonate (0.041 g, 0.488 mmol) were dissolved in DME (1.5 mL) and $H_2O$ (0.5 mL) and $N_2$ (g) was bubbled through the mixture for 10 minutes. Palladium(II) acetate (1 mg, 0.002 mmol) was added and the reaction was heated to 90° C. for 1 hour. The reaction was cooled and purified via silica gel chromatography to afford the title compound.

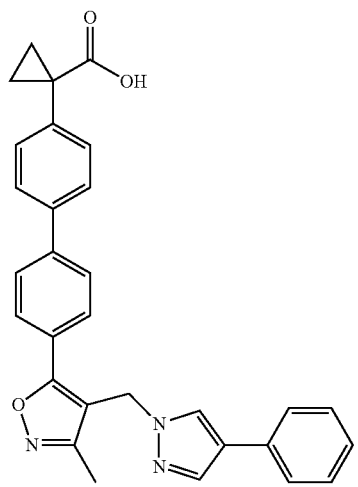

Step 3: 1-{4'-[3-Methyl-4-(4-phenyl-pyrazol-1-ylmethyl)-isoxazol-5-yl]-biphenyl-4-yl}-cyclopropanecarboxylic acid 1-{4'-[3-Methyl-4-(4-phenyl-pyrazol-1-ylmethyl)-isoxazol-5-yl]-biphenyl-4-yl}-cyclopropanecarboxylic acid ethyl ester (0.051 g, 0.101 mmol) was dissolved in THF (1 mL) then MeOH (0.5 mL) and NaOH (3N aq., 0.5 mL) was added and the reaction stirred at room temperature. After 8 hours the reaction was acidified with 1N aq. HCl then submitted to standard workup procedures to give the title compound.

Example 24

Synthesis of 1-{4'-[4-(5-Benzyl-[1,3,4]oxadiazol-2-yl)-3-methyl-isoxazol-5-yl]-biphenyl-4-yl}-cyclopropanecarboxylic acid (Compound 1-24)

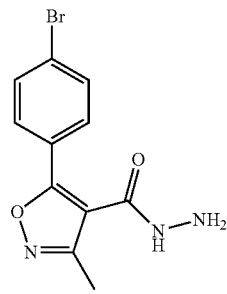 [SMILES: Cc1noc(-c2ccc(Br)cc2)c1C(=O)NN]

Step 1:
5-(4-Bromo-phenyl)-3-methyl-isoxazole-4-carboxylic acid hydrazide 5-(4-Bromo-phenyl)-3-methyl-isoxazole-4-carboxylic acid (0.061 g, 2.16 mmol) was dissolved in THF (5 mL) then 1,1'-carbonyldiimidazole (0.390 g, 2.38 mmol) was added and the reaction was heated to 70° C. for 40 minutes. The reaction was then cooled to 0° C. and hydrazine monohydrate (0.220 mL, 4.32 mmol) was added. The reaction was then allowed to slowly warm to room temperature and stirred overnight. Standard aqueous workup afforded the title compound, which was brought to the next step without further purification.

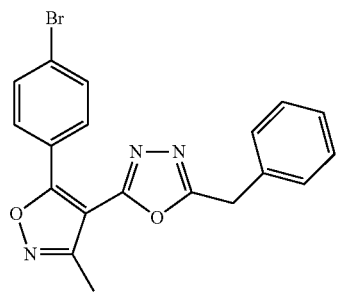 [SMILES: Cc1noc(-c2ccc(Br)cc2)c1-c1nnc(Cc2ccccc2)o1]

Step 2: 2-Benzyl-5-[5-(4-bromo-phenyl)-3-methyl-isoxazol-4-yl]-[1,3,4]oxadiazole Prepared according to the procedure described in Example 8, Step 6, using 5-(4-bromo-phenyl)-3-methyl-isoxazole-4-carboxylic acid hydrazide and phenylacetyl chloride.

Step 3: 1-{4'-[4-(5-Benzyl-[1,3,4]oxadiazol-2-yl)-3-methyl-isoxazol-5-yl]-biphenyl-4-yl}-cyclopropanecarboxylic acid ethyl ester

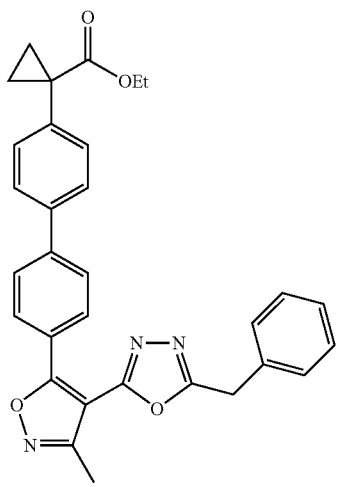 [SMILES: CCOC(=O)C1(c2ccc(-c3ccc(-c4onc(C)c4-c4nnc(Cc5ccccc5)o4)cc3)cc2)CC1]

Prepared according to the procedure described in Example 1, Step 10, using 2-benzyl-5-[5-(4-bromo-phenyl)-3-methyl-isoxazol-4-yl]-[1,3,4]oxadiazole and 1-[4-(4,4,5,5-tetramethyl-[1,3,2]dioxaborolan-2-yl)-phenyl]-cyclopropanecarboxylic acid ethyl ester.

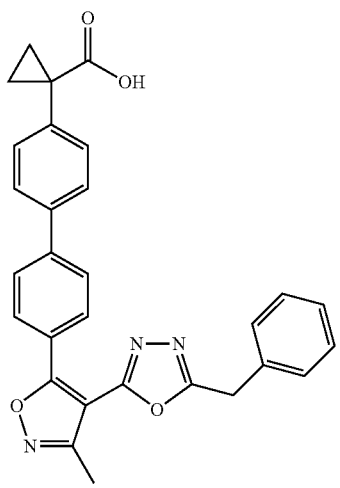 [SMILES: Cc1noc(-c2ccc(-c3ccc(C4(C(=O)O)CC4)cc3)cc2)c1-c1nnc(Cc2ccccc2)o1]

Step 4: 1-{4'-[4-(5-Benzyl-[1,3,4]oxadiazol-2-yl)-3-methyl-isoxazol-5-yl]-biphenyl-4-yl}-cyclopropanecarboxylic acid

Prepared according to the procedure described in Example 23, Step 3, using 1-{4'-[4-(5-Benzyl-[1,3,4]oxadiazol-2-yl)-3-methyl-isoxazol-5-yl]-biphenyl-4-yl}-cyclopropanecarboxylic acid ethyl ester.

Example 25

Synthesis of 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid (Compound 1-25)

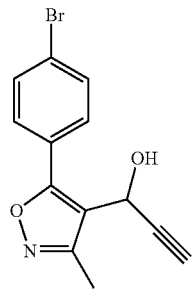 [SMILES: C#CC(O)c1c(C)noc1-c1ccc(Br)cc1]

Step 1: 1-[5-(4-Bromo-phenyl)-3-methyl-isoxazol-4-yl]-prop-2-yn-1-ol

5-(4-Bromo-phenyl)-3-methyl-isoxazole-4-carbaldehyde (0.285 g, 1.07 mmol) was dissolved in THF (8 mL) and the solution was cooled to –78° C. Ethynylmagnesium bromide (0.5M in THF, 2.6 mL, 1.28 mmol) was added dropwise and the reaction was allowed to warm to room temperature. After 1 hour the reaction was quenched with aqueous ammonium chloride the submitted to standard workup to yield the title compound.

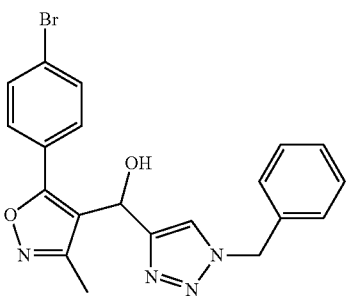 [SMILES: Cc1noc(-c2ccc(Br)cc2)c1C(O)c1cn(Cc2ccccc2)nn1]

Step 2: (1-Benzyl-1H-[1,2,3]triazol-4-yl)-[5-(4-bromo-phenyl)-3-methyl-isoxazol-4-yl]-methanol

Prepared according to the procedure described in Example 9, Step 2, using 1-[5-(4-bromo-phenyl)-3-methyl-isoxazol-4-yl]-prop-2-yn-1-ol and azidomethyl-benzene.

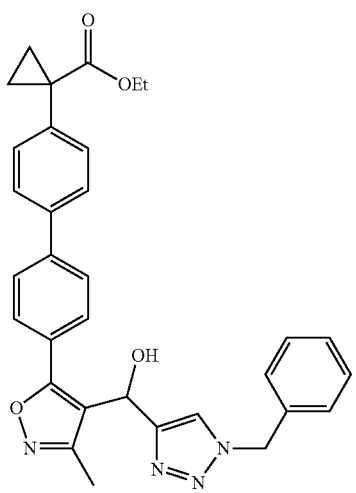 [SMILES: CCOC(=O)C1(c2ccc(-c3ccc(-c4onc(C)c4C(O)c4cn(Cc5ccccc5)nn4)cc3)cc2)CC1]

Step 3: 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid ethyl ester Prepared according to the procedure described in Example 1, Step 10, using (1-benzyl-1H-[1,2,3]triazol-4-yl)-[5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester.

Step 4: 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid

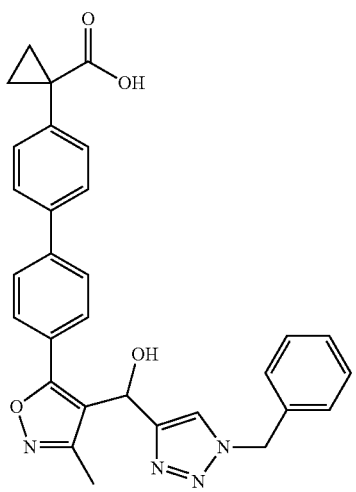

Prepared according to the procedure described in Example 23, Step 3, using 1-(4'-{4-[(1-benzyl-1H-[1,2,3]triazol-4-yl)-hydroxy-methyl]-3-methyl-isoxazol-5-yl}-biphenyl-4-yl)-cyclopropanecarboxylic acid ethyl ester.

Example 26

Synthesis of 1-[4'-(3-Methyl-4-{2-[methyl-((R)-1-phenyl-ethyl)-carbamoyl]-cyclopropyl}-isoxazol-5-yl)-biphenyl-4-yl]-cyclopropanecarboxylic acid (Compound 1-26)

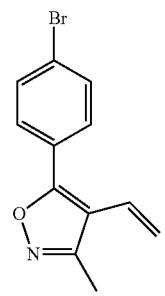

Step 1:
5-(4-Bromo-phenyl)-3-methyl-4-vinyl-isoxazole

Potassium tert-butoxide (1.0M in THF, 13.53 mL, 13.53 mmol) was added to a suspension of methyltriphenylphosphonium bromide (4.8 g, 13.53 mmol) in THF (40 mL) at 0° C. 5-(4-Bromo-phenyl)-3-methyl-isoxazole-4-carbaldehyde (1.8 g, 6.76 mmol) in THF (40 mL) was then added and the reaction stirred at 0° C. for 30 minutes. The reaction was then submitted to standard aqueous workup and purified on silica gel to afford the title compound.

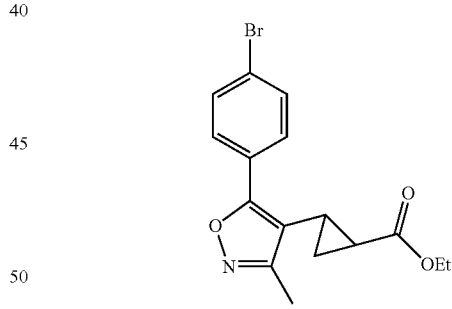

Step 2: 2-[5-(4-Bromo-phenyl)-3-methyl-isoxazol-4-yl]-cyclopropanecarboxylic acid ethyl ester 5-(4-Bromo-phenyl)-3-methyl-4-vinyl-isoxazole (0.805 g, 3.05 mmol) was dissolved in toluene (10 mL) and rhodium (II) acetate dimer (0.070 g, 0.15 mmol) was added. Ethyldiazo acetate (0.800 mL, 7.62 mmol) in toluene (5 mL) was then added and the reaction stirred at room temperature overnight. Additional portions of rhodium(II) acetate dimer and ethyldiazo acetate were added and the reaction stirred for 4 hours. Aqueous workup followed by silica gel chromatography afforded the title compound as a separable mixture of isomers.

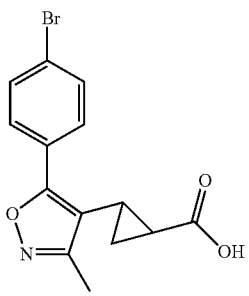 [SMILES: Cc1noc(-c2ccc(Br)cc2)c1C1CC1C(=O)O]

Step 3: 2-[5-(4-Bromo-phenyl)-3-methyl-isoxazol-4-yl]-cyclopropanecarboxylic acid 2-[5-(4-Bromo-phenyl)-3-methyl-isoxazol-4-yl]-cyclopropanecarboxylic acid ethyl ester (more polar isomer, 0.164 g, 0.468 mmol) was dissolved in THF (3 mL) then MeOH (1 mL) and NaOH (1N aq., 1 mL) were added. The reaction stirred at room temperature overnight and was then acidified with 1N aq. HCl and submitted to standard aqueous workup to afford the title compound.

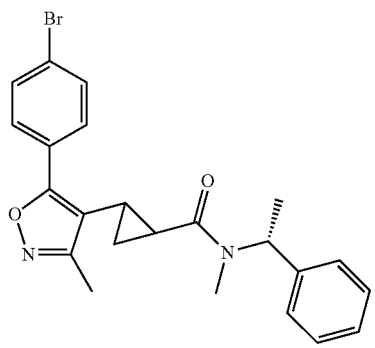 [SMILES: Cc1noc(-c2ccc(Br)cc2)c1C1CC1C(=O)N(C)[C@H](C)c1ccccc1]

Step 4: 2-[5-(4-Bromo-phenyl)-3-methyl-isoxazol-4-yl]-cyclopropanecarboxylic acid methyl-((R)-1-phenyl-ethyl)-amide Prepared according to the procedure described in Example 2, Step 1, using 2-[5-(4-bromo-phenyl)-3-methyl-isoxazol-4-yl]-cyclopropanecarboxylic acid and methyl-((R)-1-phenyl-ethyl)-amine

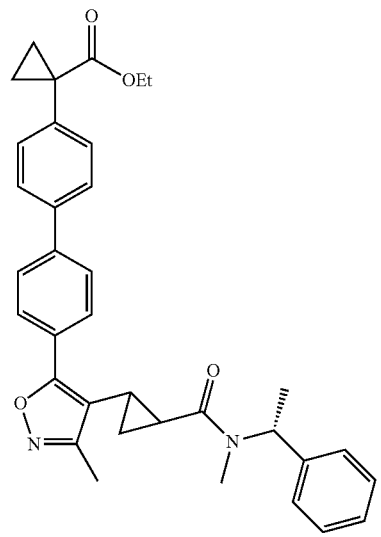 [SMILES: CCOC(=O)C1(c2ccc(-c3ccc(-c4onc(C)c4C4CC4C(=O)N(C)[C@H](C)c4ccccc4)cc3)cc2)CC1]

Step 5: 1-[4'-(3-Methyl-4-{2-[methyl-((R)-1-phenyl-ethyl)-carbamoyl]-cyclopropyl}-isoxazol-5-yl)-biphenyl-4-yl]-cyclopropanecarboxylic acid ethyl ester Prepared according to the procedure described in Example 1, Step 10, using 2-[5-(4-bromo-phenyl)-3-methyl-isoxazol-4-yl]-cyclopropanecarboxylic acid methyl-((R)-1-phenyl-ethyl)-amide and 1-[4-(4,4,5,5-tetramethyl-[1,3,2]dioxaborolan-2-yl)-phenyl]-cyclopropanecarboxylic acid ethyl ester.

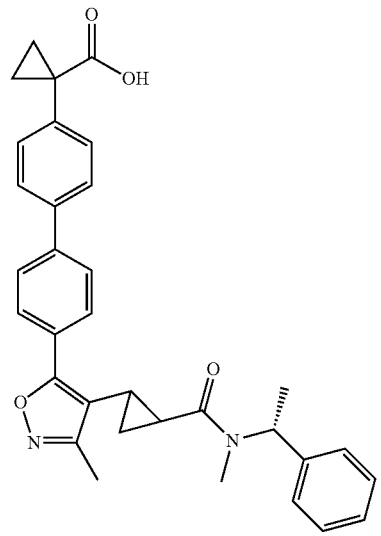 [SMILES: Cc1noc(-c2ccc(-c3ccc(C4(C(=O)O)CC4)cc3)cc2)c1C1CC1C(=O)N(C)[C@H](C)c1ccccc1]

Step 6: 1-[4'-(3-Methyl-4-{2-[methyl-((R)-1-phenyl-ethyl)-carbamoyl]-cyclopropyl}-isoxazol-5-yl)-biphenyl-4-yl]-cyclopropanecarboxylic acid Prepared according to the procedure described in Example 23, Step 3, using 1-[4'-(3-methyl-4-{2-[methyl-((R)-1-phenyl-ethyl)-carbamoyl]-cyclopropyl}-isoxazol-5-yl)-biphenyl-4-yl]-cyclopropanecarboxylic acid ethyl ester.

Example 27

Synthesis of 1-[4'-(3-Methyl-4-{2-[methyl-((R)-1-phenyl-ethyl)-carbamoyl]-cyclopropyl}-isoxazol-5-yl)-biphenyl-4-yl]-cyclopropanecarboxylic acid (Compound 1-27)

Step 1: 2-[5-(4-Bromo-phenyl)-3-methyl-isoxazol-4-yl]-cyclopropanecarboxylic acid

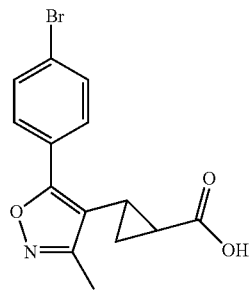 [SMILES: Cc1noc(-c2ccc(Br)cc2)c1C1CC1C(=O)O]

Prepared according to the procedure described in Example 26, Step 3, using 2-[5-(4-bromo-phenyl)-3-methyl-isoxazol-4-yl]-cyclopropanecarboxylic acid ethyl ester (more polar isomer).

Step 2: 2-[5-(4-Bromo-phenyl)-3-methyl-isoxazol-4-yl]-cyclopropanecarboxylic acid methyl-((R)-1-phenyl-ethyl)-amide

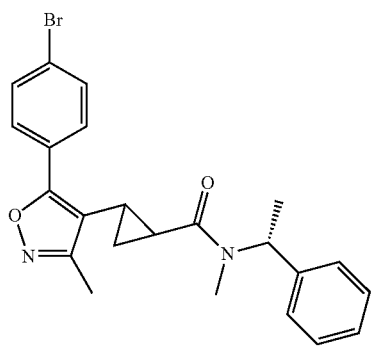 [SMILES: Cc1noc(-c2ccc(Br)cc2)c1C1CC1C(=O)N(C)[C@H](C)c1ccccc1]

Prepared according to the procedure described in Example 2, Step 1, using 2-[5-(4-bromo-phenyl)-3-methyl-isoxazol-4-yl]-cyclopropanecarboxylic acid and methyl-((R)-1-phenyl-ethyl)-amine.

Step 3: 1-[4'-(3-Methyl-4-{2-[methyl-((R)-1-phenyl-ethyl)-carbamoyl]-cyclopropyl}-isoxazol-5-yl)-biphenyl-4-yl]-cyclopropanecarboxylic acid ethyl ester

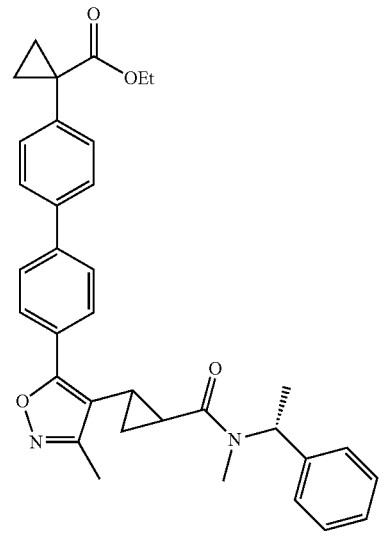 [SMILES: CCOC(=O)C1(c2ccc(-c3ccc(-c4onc(C)c4C4CC4C(=O)N(C)[C@H](C)c4ccccc4)cc3)cc2)CC1]

Prepared according to the procedure described in Example 1, Step 10, using 2-[5-(4-bromo-phenyl)-3-methyl-isoxazol-4-yl]-cyclopropanecarboxylic acid methyl-((R)-1-phenyl-ethyl)-amide and 1-[4-(4,4,5,5-tetramethyl-[1,3,2]dioxaborolan-2-yl)-phenyl]-cyclopropanecarboxylic acid ethyl ester.

Step 4: 1-[4'-(3-Methyl-4-{2-[methyl-((R)-1-phenyl-ethyl)-carbamoyl]-cyclopropyl}-isoxazol-5-yl)-biphenyl-4-yl]-cyclopropanecarboxylic acid

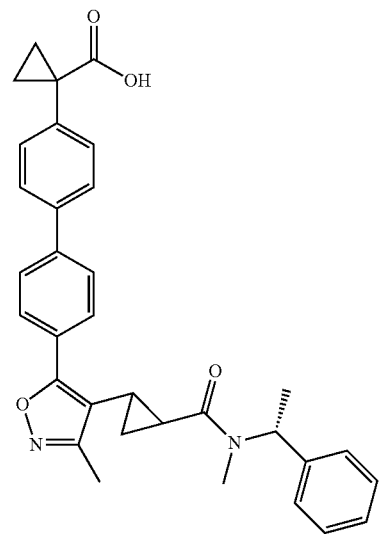 [SMILES: Cc1noc(-c2ccc(-c3ccc(C4(C(=O)O)CC4)cc3)cc2)c1C1CC1C(=O)N(C)[C@H](C)c1ccccc1]

Prepared according to the procedure described in Example 23, Step 3, using 1-[4'-(3-methyl-4-{2-[methyl-((R)-1-phenyl-ethyl)-carbamoyl]-cyclopropyl}-isoxazol-5-yl)-biphenyl-4-yl]-cyclopropanecarboxylic acid ethyl ester.

Example 28

Synthesis of 1-{4'-[4-(3-Benzyl-2-oxo-oxazolidin-5-yl)-3-methyl-isoxazol-5-yl]-biphenyl-4-yl}-cyclopropanecarboxylic acid (Compound 1-28)

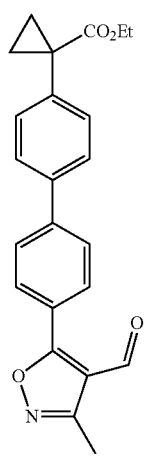

Step 1: 1-[4'-(4-Formyl-3-methyl-isoxazol-5-yl)-biphenyl-4-yl]-cyclopropanecarboxylic acid ethyl ester 5-(4-Bromo-phenyl)-3-methyl-isoxazole-4-carbaldehyde (0.5 g, 1.88 mmol) was mixed with 1-[4-(4,4,5,5-Tetramethyl-[1,3,2]dioxaborolan-2-yl)-phenyl]-cyclopropanecarboxylic acid ethyl ester (0.72 g, 2.07 mmol) and sodium bicarbonate (0.553 g, 6.58 mmol) in DME (5 mL) and H₂O (2.5 mL). The reaction was purged with N₂ (g) then bis(triphenylphosphine)palladium(II) dichloride (0.066 g, 0.094 mmol) was added and the reaction was heated to 85° C. overnight. After cooling to room temperature the reaction was submitted to standard aqueous workup the purified by silica gel chromatograph (0-20% EtOAc in hexanes) to give the title compound.

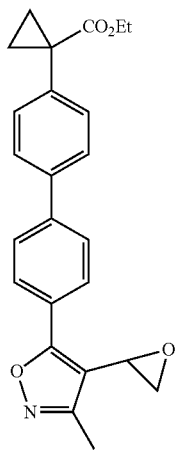 [SMILES: CCOC(=O)C1(c2ccc(-c3ccc(-c4onc(C)c4C4CO4)cc3)cc2)CC1]

Step 2: 1-[4'-(3-Methyl-4-oxiranyl-isoxazol-5-yl)-biphenyl-4-yl]-cyclopropanecarboxylic acid ethyl ester n-Butyllithium (1.6M in hexanes, 2.30 mL, 3.69 mmol) was placed in a flask along with DMSO (8 mL) and the solution was placed under N₂ atmosphere. Trimethyl sulfoxonium iodide (0.963 g, 4.29 mmol) was added and stirred for 5 minutes. 1-[4'-(4-Formyl-3-methyl-isoxazol-5-yl)-biphenyl-4-yl]-cyclopropanecarboxylic acid ethyl ester (0.46 g, 1.23 mmol) in DMSO (8 mL) was then added and the reaction was stirred. After 40 minutes the reaction was quenched with ice then submitted to standard aqueous workup and purified on silica gel (0-40% EtOAc in hexanes) to afford the title compound.

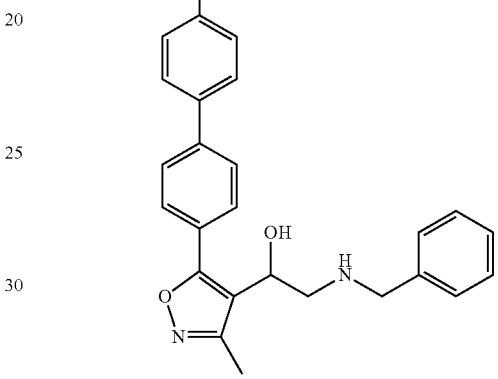

Step 3: 1-{4'-[4-(2-Benzylamino-1-hydroxy-ethyl)-3-methyl-isoxazol-5-yl]-biphenyl-4-yl}-cyclopropanecarboxylic acid ethyl ester 1-[4'-(3-Methyl-4-oxiranyl-isoxazol-5-yl)-biphenyl-4-yl]-cyclopropanecarboxylic acid ethyl ester (0.100 g, 0.26 mmol), benzylamine (0.034 mL, 0.31 mmol) and N-methylpyrrolidine (5 mL) were combined in a flask and stirred at 85° C. overnight. An additional portion of benzylamine (0.050 mL) was added and the reaction continued to stir at 85° C. for 48 hours. The reaction mixture was cooled and submitted to standard aqueous workup to give the title compound.

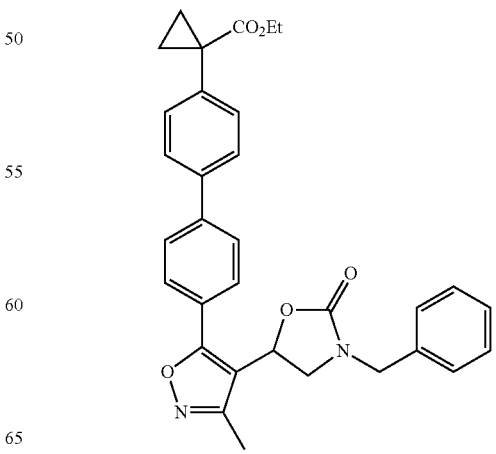

Step 4: 1-{4'-[4-(3-Benzyl-2-oxo-oxazolidin-5-yl)-3-methyl-isoxazol-5-yl]-biphenyl-4-yl}-cyclopropanecarboxylic acid ethyl ester 1-{4'-[4-(2-Benzylamino-1-hydroxy-ethyl)-3-methyl-isoxazol-5-yl]-biphenyl-4-yl}-cyclopropanecarboxylic acid ethyl ester (0.190 g, 0.38 mmol) was dissolved in toluene (4 mL) then placed under N₂ atmosphere at 0° C. Triethylamine (0.159 mL, 1.14 mmol) and phosgene (1.9M in toluene, 0.201 mL, 0.38 mmol) were added and the reaction stirred at 0° C. After two hours an additional portion of each of triethylamine (0.160 mL) and phosgene (0.200 mL) were added and the reaction stirred an additional 20 minutes. The reaction was submitted to standard workup procedures and silica gel chromatography (0-40% EtOAc in hexanes) to yield the title compound.

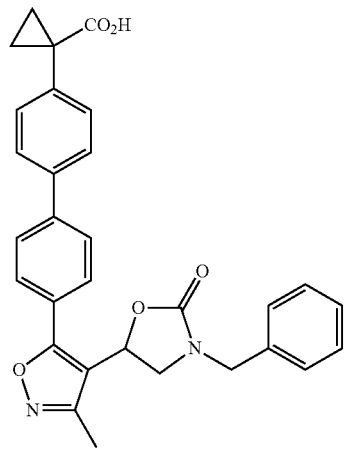 [SMILES: CCOC(=O)C1(c2ccc(-c3ccc(-c4onc(C)c4C4CN(Cc5ccccc5)C(=O)O4)cc3)cc2)CC1]

Step 5: 1-{4'-[4-(3-Benzyl-2-oxo-oxazolidin-5-yl)-3-methyl-isoxazol-5-yl]-biphenyl-4-yl}-cyclopropanecarboxylic acid Prepared according to the procedure described in Example 23, Step 3, using 1-{4'-[4-(3-benzyl-2-oxo-oxazolidin-5-yl)-3-methyl-isoxazol-5-yl]-biphenyl-4-yl}-cyclopropanecarboxylic acid ethyl ester.

Example 29

Synthesis of 1-{4'-[4-(5-Benzyl-[1,3,4]oxadiazol-2-ylmethyl)-3-methyl-isoxazol-5-yl]-biphenyl-4-yl}-cyclopropanecarboxylic acid (Compound 1-29)

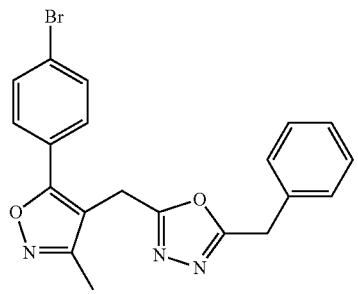 [SMILES: Cc1noc(-c2ccc(Br)cc2)c1Cc1nnc(Cc2ccccc2)o1]

Step 1: 2-Benzyl-5-[5-(4-bromo-phenyl)-3-methyl-isoxazol-4-ylmethyl]-[1,3,4]oxadiazole Prepared according to the procedure described in Example 8, Step 6, using [5-(4-bromo-phenyl)-3-methyl-isoxazol-4-yl]-acetic acid hydrazide and phenylacetyl chloride.

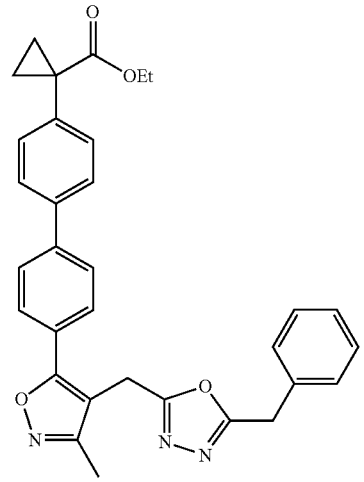 [SMILES: CCOC(=O)C1(c2ccc(-c3ccc(-c4onc(C)c4Cc4nnc(Cc5ccccc5)o4)cc3)cc2)CC1]

Step 2: 1-{4'-[4-(5-Benzyl-[1,3,4]oxadiazol-2-ylmethyl)-3-methyl-isoxazol-5-yl]-biphenyl-4-yl}-cyclopropanecarboxylic acid ethyl ester Prepared according to the procedure described in Example 1, Step 10, using 2-benzyl-5-[5-(4-bromo-phenyl)-3-methyl-isoxazol-4-ylmethyl]-[1,3,4]oxadiazole and 1-[4-(4,4,5,5-tetramethyl-[1,3,2]dioxaborolan-2-yl)-phenyl]-cyclopropanecarboxylic acid ethyl ester.

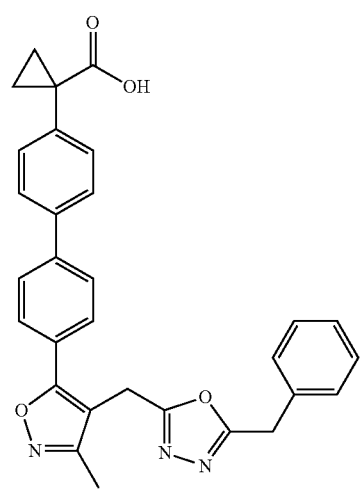 [SMILES: Cc1noc(-c2ccc(-c3ccc(C4(C(=O)O)CC4)cc3)cc2)c1Cc1nnc(Cc2ccccc2)o1]

Step 3: 1-{4'-[4-(5-Benzyl-[1,3,4]oxadiazol-2-ylmethyl)-3-methyl-isoxazol-5-yl]-biphenyl-4-yl}-cyclopropanecarboxylic acid Prepared according to the procedure described in Example 23, Step 3, using 1-{4'-[4-(5-benzyl-[1,3,4]oxadiazol-2-ylmethyl)-3-methyl-isoxazol-5-yl]-biphenyl-4-yl}-cyclopropanecarboxylic acid ethyl ester.

Example 30

1-(4'-{4-[(5-Benzyl-[1,3,4]oxadiazol-2-yl)-hydroxymethyl]-3-methyl-isoxazol-5-yl}-biphenyl-4-yl)-cyclopropanecarboxylic acid (Compound 1-30)

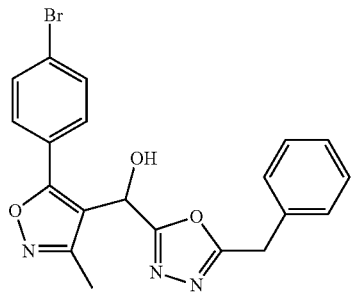 [SMILES: Cc1noc(-c2ccc(Br)cc2)c1C(O)c1nnc(Cc2ccccc2)o1]

Step 1: (5-Benzyl-[1,3,4]oxadiazol-2-yl)-[5-(4-bromo-phenyl)-3-methyl-isoxazol-4-yl]-methanol 2-Benzyl-[1,3,4]oxadiazole (0.500 g, 3.12 mmol) was dissolved in THF and cooled to −70° C. then n-butyllithium (1.5M in THF, 2.1 mL, 3.12 mmol) was added and the reaction stirred for 1.5 hours. Magnesium bromide ethyl etherate (0.631 g, 3.43 mmol) was added and the reaction was allowed to warm to −45° C. After 45 minutes 5-(4-bromo-phenyl)-3-methyl-isoxazole-4-carbaldehyde (0.415 g, 1.56 mmol) in THF (2 mL) was added and the reaction was allowed to stir overnight. The reaction was quenched with aqueous ammonium chloride then submitted to standard workup and purification via silica gel chromatography (0-60% EtOAc in hexanes) to give the title compound.

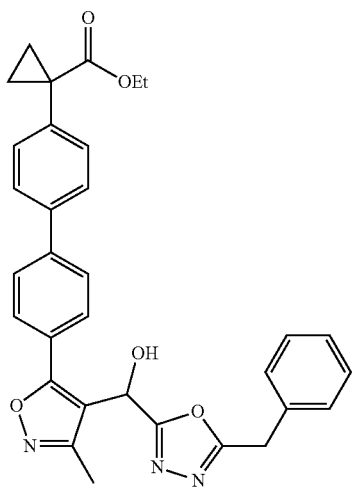 [SMILES: CCOC(=O)C1(c2ccc(-c3ccc(-c4onc(C)c4C(O)c4nnc(Cc5ccccc5)o4)cc3)cc2)CC1]

Step 2: 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid ethyl ester Prepared according to the procedure described in Example 1, Step 10, using (5-benzyl-[1,3,4]oxadiazol-2-yl)-[5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester.

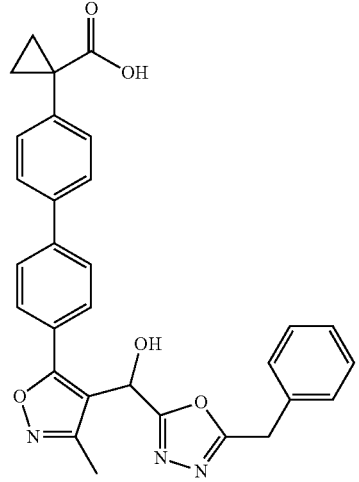 [SMILES: Cc1noc(-c2ccc(-c3ccc(C4(C(=O)O)CC4)cc3)cc2)c1C(O)c1nnc(Cc2ccccc2)o1]

Step 3: 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid Prepared according to the procedure described in Example 23, Step 3, using 1-(4'-{4-[(5-benzyl-[1,3,4]oxadiazol-2-yl)-hydroxy-methyl]-3-methyl-isoxazol-5-yl}-biphenyl-4-yl)-cyclopropanecarboxylic acid ethyl ester.

Example 31

1-{4'-[4-(1-Benzyl-1H-[1,2,3]triazol-4-ylmethyl)-3-methyl-isoxazol-5-yl]-biphenyl-4-yl}-cyclopropanecarboxylic acid (Compound 1-31)

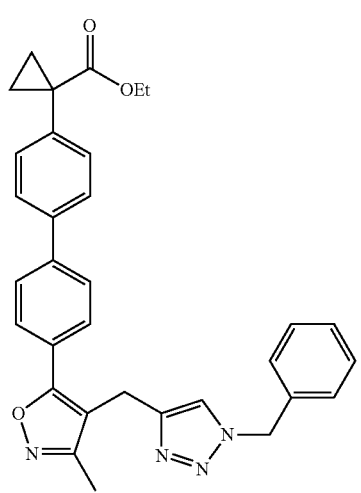 [SMILES: CCOC(=O)C1(c2ccc(-c3ccc(-c4onc(C)c4Cc4cn(Cc5ccccc5)nn4)cc3)cc2)CC1]

Step 1: 1-{4'-[4-(1-Benzyl-1H-[1,2,3]triazol-4-ylmethyl)-3-methyl-isoxazol-5-yl]-biphenyl-4-yl}-cyclopropanecarboxylic acid ethyl ester 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid ethyl ester (0.123 g, 0.230 mmol) and triethylsilane (0.044 mL, 0.276 mmol) were dissolved in CH₂Cl₂ (0.5 mL) then trifluoromethanesulfonic acid (0.5 mL) was slowly added. After stirring for 1 hour at room temperature, an additional portion of triethylsilane (0.050 mL) was added and the reaction was heated to 50° C. for 3.5 hours. An additional portion of triethylsilane (1 mL) was added and the reaction continued to stir at 50° C. for 1 hour. The reaction mixture was concentrated, dissolved in CH₂Cl₂, and filtered through a plug of silica gel. The crude material was then purified via preparatory HPLC to afford the title compound.

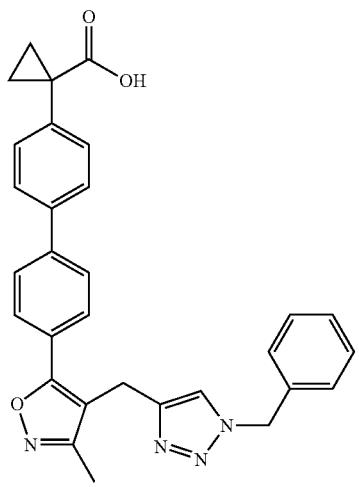 [SMILES: Cc1noc(-c2ccc(-c3ccc(C4(C(=O)O)CC4)cc3)cc2)c1Cc1cn(Cc2ccccc2)nn1]

Step 2: 1-{4'-[4-(1-Benzyl-1H-[1,2,3]triazol-4-ylmethyl)-3-methyl-isoxazol-5-yl]-biphenyl-4-yl}-cyclopropanecarboxylic acid Prepared according to the procedure described in Example 23, Step 3, using 1-{4'-[4-(1-benzyl-1H-[1,2,3]triazol-4-ylmethyl)-3-methyl-isoxazol-5-yl]-biphenyl-4-yl}-cyclopropanecarboxylic acid ethyl ester.

Example 32

[1-(4'-{4-[4-(4-Benzyl-phenyl)-1-hydroxy-butyl]-3-methyl-isoxazol-5-yl}-biphenyl-4-yl)-cyclopropyl]-acetic acid (Compound 1-32)

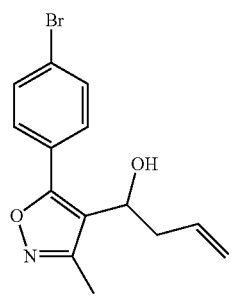 [SMILES: C=CCC(O)c1c(C)noc1-c1ccc(Br)cc1]

Step 1: 1-[5-(4-Bromo-phenyl)-3-methyl-isoxazol-4-yl]-but-3-en-1-ol

Prepared according to the procedure described in Example 25, Step 1, using 5-(4-bromo-phenyl)-3-methyl-isoxazole-4-carbaldehyde and allyl magnesium bromide.

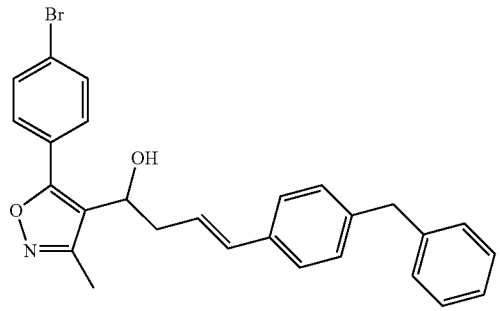

Step 2: (E)-4-(4-Benzyl-phenyl)-1-[5-(4-bromo-phenyl)-3-methyl-isoxazol-4-yl]-but-3-en-1-ol 1-[5-(4-Bromo-phenyl)-3-methyl-isoxazol-4-yl]-but-3-en-1-ol (0.380 g, 1.233 mmol) in acetonitrile (4 mL) was added to a flask containing 1-benzyl-4-iodo-benzene (0.3649 g, 1.233 mmol) and cesium carbonate (0.4102 g, 1.233 mmol). Palladium(II) acetate (0.030 g, 0.1233 mmol) was added and the reaction was heated to 85° C. and stirred overnight. The reaction was then cooled and submitted to standard aqueous workup followed by silica gel chromatography (0-50% EtOAc in hexanes) to yield the title compound.

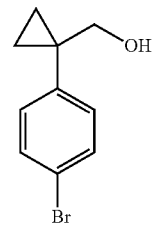

Step 3: [1-(4-Bromo-phenyl)-cyclopropyl]-methanol 1-(4-Bromo-phenyl)-cyclopropanecarboxylic acid ethyl ester (25 g, 92.89 mmol) was dissolved in THF (175 mL) and was stirred under N₂ atmosphere at −4° C. Lithium aluminum hydride (4.58 g, 120.75 mmol) was added in portions and the reaction stirred between 2 to 8° C. for 1 hour. The reaction was worked up using the Fieser method, filtered and concentrated to afford the title compound.

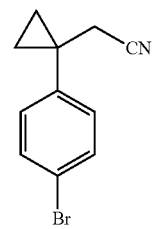 [SMILES: N#CCC1(c2ccc(Br)cc2)CC1]

Step 4: [1-(4-Bromo-phenyl)-cyclopropyl]-acetonitrile

[1-(4-Bromo-phenyl)-cyclopropyl]-methanol (11.42 g, 50.29 mmol) was dissolved in CH₂Cl₂ (171 mL) and the solution was cooled to −78° C. Triethylamine (8.41 mL, 60.35 mmol) was added followed by methanesulfonyl chloride (4.30 mL, 55.31 mmol) and the reaction stirred at −78° C. for 1 hour. The reaction was allowed to slowly warm to 0° C. while stirring for an addition 1.5 hours. The reaction was submitted to standard aqueous workup and was then diluted with DMF (90 mL) and evaporated to remove any residual CH$_2$Cl$_2$. Sodium cyanide (7.39 g, 150.8 mmol) and DMF (20 mL) were added and the reaction was heated to 70° C. for 3 hours. The reaction was cooled and submitted to standard aqueous workup to give the title compound.

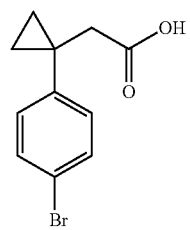 [SMILES: O=C(O)CC1(c2ccc(Br)cc2)CC1]

Step 5: [1-(4-Bromo-phenyl)-cyclopropyl]-acetic acid

[1-(4-Bromo-phenyl)-cyclopropyl]-acetonitrile (7.56 g, 32.2 mmol) and KOH (7.56 g, 128.7 mmol) were dissolved in EtOH (54 mL) and H$_2$O (6.75 mL) then the reaction was heated to 110° C. for 16 hours. The reaction was cooled then submitted to acidic aqueous workup to obtain the title compound which was used in the next step without further purification.

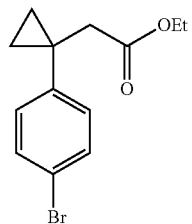 [SMILES: CCOC(=O)CC1(c2ccc(Br)cc2)CC1]

Step 6: [1-(4-Bromo-phenyl)-cyclopropyl]-acetic acid ethyl ester

[1-(4-Bromo-phenyl)-cyclopropyl]-acetic acid (from the previous step) was dissolved in EtOH (80 mL) and conc. H$_2$SO$_4$ (2 mL) was added. The reaction was heated to 80° C. overnight then concentrated and submitted to standard aqueous workup to afford the title compound.

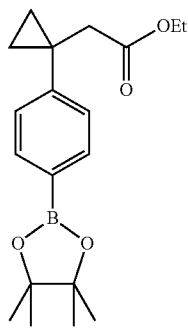

Step 7: {1-[4-(4,4,5,5-Tetramethyl-[1,3,2]dioxaborolan-2-yl)-phenyl]-cyclopropyl}-acetic acid ethyl ester Prepared according to the procedure described in Example 1, Step 9, using [1-(4-bromo-phenyl)-cyclopropyl]-acetic acid ethyl ester and bis(pinacolato)diboron.

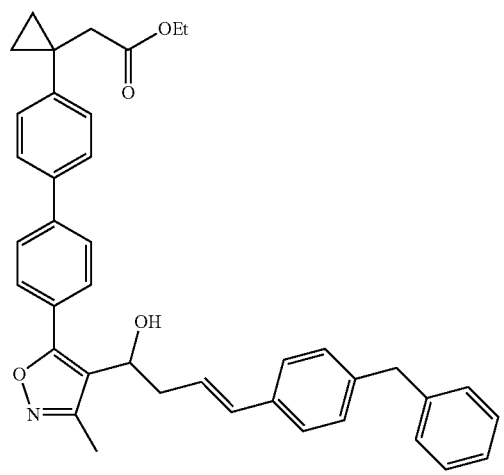 [SMILES: CCOC(=O)CC1(c2ccc(-c3ccc(-c4onc(C)c4C(O)C/C=C/c4ccc(Oc5ccccc5)cc4)cc3)cc2)CC1]

Step 8: [1-(4'-{4-[(E)-4-(4-Benzyl-phenyl)-1-hydroxy-but-3-enyl]-3-methyl-isoxazol-5-yl}-biphenyl-4-yl)-cyclopropyl]-acetic acid ethyl ester Prepared according to the procedure described in Example 28, Step 1, using (E)-4-(4-benzyl-phenyl)-1-[5-(4-bromo-phenyl)-3-methyl-isoxazol-4-yl]-but-3-en-1-ol and {1-[4-(4,4,5,5-tetramethyl-[1,3,2]dioxaborolan-2-yl)-phenyl]-cyclopropyl}-acetic acid ethyl ester.

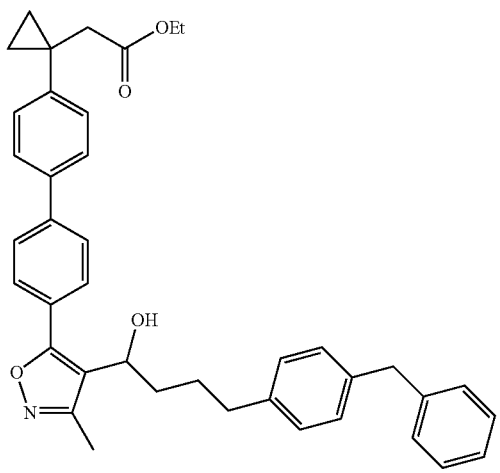

Step 9: [1-(4'-{4-[4-(4-Benzyl-phenyl)-1-hydroxy-butyl]-3-methyl-isoxazol-5-yl}-biphenyl-4-yl)-cyclopropyl]-acetic acid ethyl ester

[1-(4'-{4-[(E)-4-(4-Benzyl-phenyl)-1-hydroxy-but-3-enyl]-3-methyl-isoxazol-5-yl}-biphenyl-4-yl)-cyclopropyl]-acetic acid ethyl ester (0.203 g, 0.340 mmol) was dissolved in EtOH and palladium on carbon (0.020 g, 10% wt., wet: 50% w/w H$_2$O) was added. The reaction was stirred under H$_2$ (g) atmosphere overnight then filtered through Celite to afford the title compound in EtOH solution, which was brought to the next step without further purification.

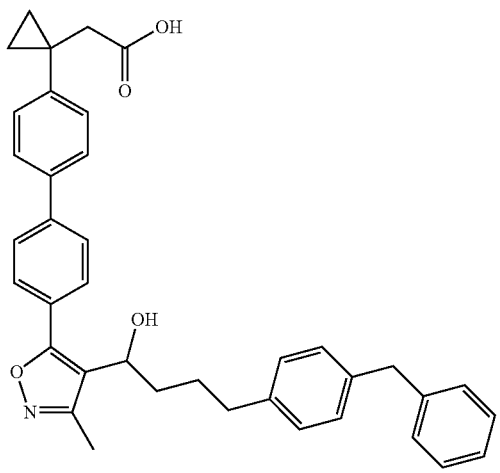 [SMILES: CCOC(=O)CC1(c2ccc(-c3ccc(-c4onc(C)c4C(O)CCCc4ccc(Oc5ccccc5)cc4)cc3)cc2)CC1]

Step 10: [1-(4'-{4-[4-(4-Benzyl-phenyl)-1-hydroxy-butyl]-3-methyl-isoxazol-5-yl}-biphenyl-4-yl)-cyclopropyl]-acetic acid Prepared according to the procedure described in Example 23, Step 3, using [1-(4'-{4-[4-(4-benzyl-phenyl)-1-hydroxy-butyl]-3-methyl-isoxazol-5-yl}-biphenyl-4-yl)-cyclopropyl]-acetic acid ethyl ester.

Example 33

[1-(4'-{-4-[1-Hydroxy-4-(4-phenoxy-phenyl)-butyl]-3-methyl-isoxazol-5-yl}-biphenyl-4-yl)-cyclopropyl]-acetic acid (Compound 1-33)

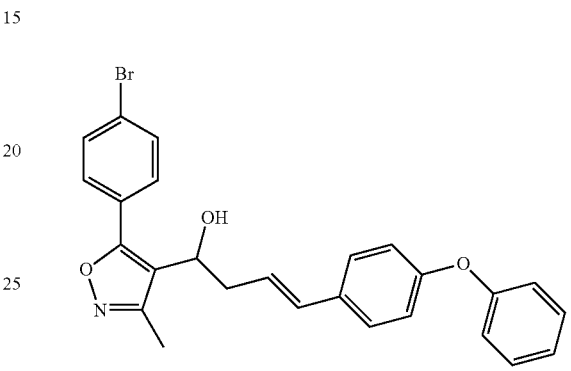

Step 1: (E)-1-[5-(4-Bromo-phenyl)-3-methyl-isoxazol-4-yl]-4-(4-phenoxy-phenyl)-but-3-en-1-ol Prepared according to the procedure described in Example 32, Step 2, using 1-[5-(4-bromo-phenyl)-3-methyl-isoxazol-4-yl]-but-3-en-1-ol and 1-iodo-4-phenoxy-benzene.

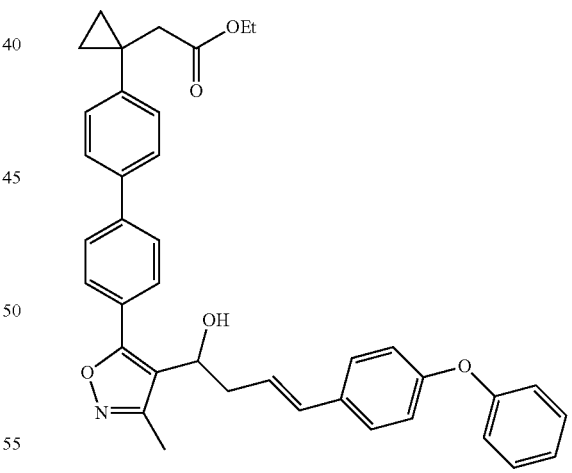

Step 2: [1-(4'-{4-[(E)-1-Hydroxy-4-(4-phenoxy-phenyl)-but-3-enyl]-3-methyl-isoxazol-5-yl}-biphenyl-4-yl)-cyclopropyl]-acetic acid ethyl ester Prepared according to the procedure described in Example 28, Step 1, using (E)-1-[5-(4-bromo-phenyl)-3-methyl-isoxazol-4-yl]-4-(4-phenoxy-phenyl)-but-3-en-1-ol and {1-[4-(4,4,5,5-tetramethyl-[1,3,2]dioxaborolan-2-yl)-phenyl]-cyclopropyl}-acetic acid ethyl ester.

Step 3: [1-(4'-{-4-[1-Hydroxy-4-(4-phenoxy-phenyl)-butyl]-3-methyl-isoxazol-5-yl}-biphenyl-4-yl)-cyclopropyl]-acetic acid ethyl ester

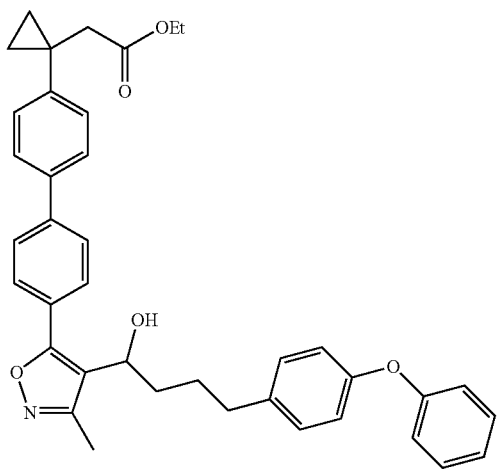 [SMILES: Cc1noc(-c2ccc(-c3ccc(C4(CC(=O)O)CC4)cc3)cc2)c1C(O)CCCc1ccc(Oc2ccccc2)cc1]

Prepared according to the procedure described in Example 32, Step 9, using [1-(4'-{4-[(E)-1-hydroxy-4-(4-phenoxy-phenyl)-but-3-enyl]-3-methyl-isoxazol-5-yl}-biphenyl-4-yl)-cyclopropyl]-acetic acid ethyl ester.

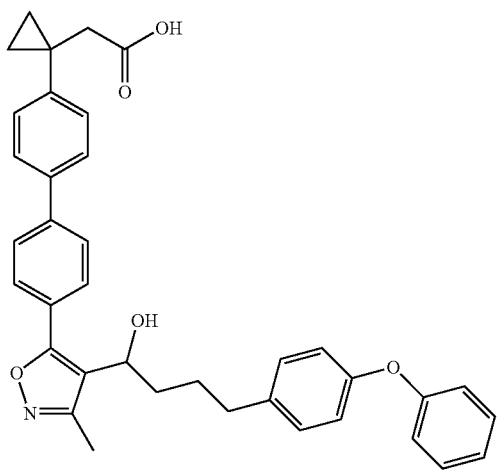

Step 4: [1-(4'-{-4-[1-Hydroxy-4-(4-phenoxy-phenyl)-butyl]-3-methyl-isoxazol-5-yl}-biphenyl-4-yl)-cyclopropyl]-acetic acid Prepared according to the procedure described in Example 23, Step 3, using [1-(4'-{4-[4-(4-benzyl-phenyl)-1-hydroxy-butyl]-3-methyl-isoxazol-5-yl}-biphenyl-4-yl)-cyclopropyl]-acetic acid ethyl ester.

Example 34

1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid (Enantiomer A) (Compound 1-34)

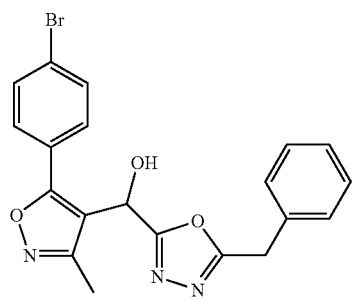 [SMILES: Cc1noc(-c2ccc(Br)cc2)c1C(O)c1nnc(Cc2ccccc2)o1]

Step 1: (5-Benzyl-[1,3,4]oxadiazol-2-yl)-[5-(4-bromo-phenyl)-3-methyl-isoxazol-4-yl]-methanol Prepared according to the procedure described in Example 30, Step 1, using 5-(4-Bromo-phenyl)-3-methyl-isoxazole-4-carbaldehyde and 2-benzyl-[1,3,4]oxadiazole.

The recovered material was purified by silica gel chromatography (0-60% EtOAc in hexanes) then the by preparatory chiral HPLC (Chiralpak AD column, 95:5 hexanes:EtOH) to give enantiomer A (first to elute) and enantiomer B (second to elute) with undetermined absolute stereochemistry.

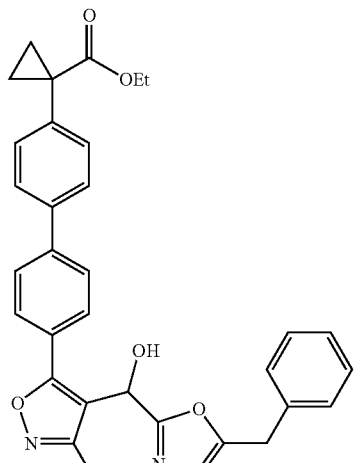

Step 2: 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid ethyl ester (Enantiomer A)

Prepared according to the procedure described in Example 1, Step 10, using (5-benzyl-[1,3,4]oxadiazol-2-yl)-[5-(4-bromo-phenyl)-3-methyl-isoxazol-4-yl]-methanol (Enantiomer A) and 1-[4-(4,4,5,5-tetramethyl-[1,3,2]dioxaborolan-2-yl)-phenyl]-cyclopropanecarboxylic acid ethyl ester.

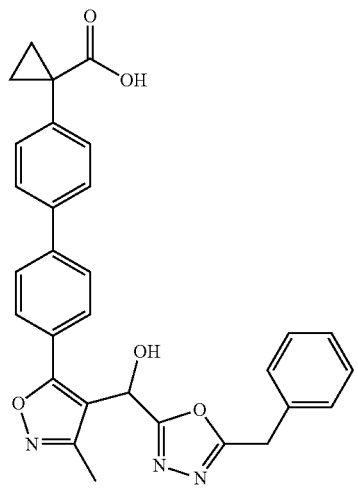

Step 3: 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid (Enantiomer A)

Prepared according to the procedure described in Example 23, Step 3, using 1-(4'-{4-[(5-benzyl-[1,3,4]oxadiazol-2-yl)-hydroxy-methyl]-3-methyl-isoxazol-5-yl}-biphenyl-4-yl)-cyclopropanecarboxylic acid ethyl ester (Enantiomer A).

Example 35

1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid (Enantiomer B) (Compound 1-35)

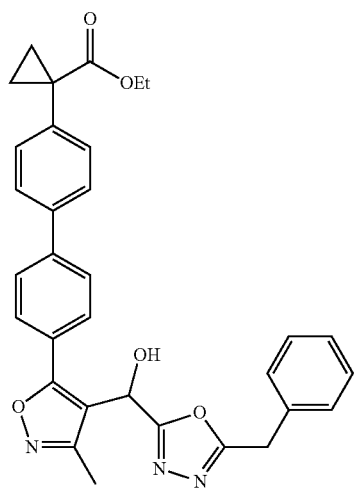

Step 1: 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid ethyl ester (Enantiomer B)

Prepared according to the procedure described in Example 1, Step 10, using (5-benzyl-[1,3,4]oxadiazol-2-yl)-[5-(4-bromo-phenyl)-3-methyl-isoxazol-4-yl]-methanol (Enantiomer B) and 1-[4-(4,4,5,5-tetramethyl-[1,3,2]dioxaborolan-2-yl)-phenyl]-cyclopropanecarboxylic acid ethyl ester.

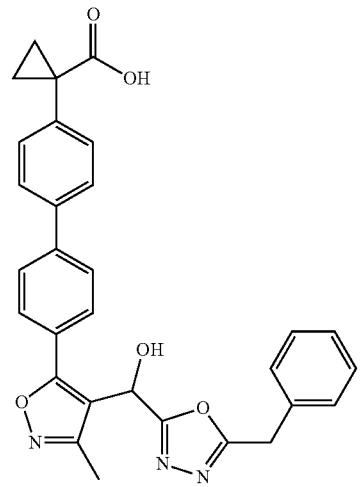

Step 2: 1-(4'-{4-[(5-Benzyl-[1,3,4]oxadiazol-2-yl)-hydroxy-methyl]-3-methyl-isoxazol-5-yl}-biphenyl-4-yl)-cyclopropanecarboxylic acid (Enantiomer B)

Prepared according to the procedure described in Example 23, Step 3, using 1-(4'-{4-[(5-benzyl-[1,3,4]oxadiazol-2-yl)-hydroxy-methyl]-3-methyl-isoxazol-5-yl}-biphenyl-4-yl)-cyclopropanecarboxylic acid ethyl ester (Enantiomer B).

Example 36

1-{4'-[4-(1-Benzyl-piperidin-4-ylamino)-3-methyl-isoxazol-5-yl]-biphenyl-4-yl}-cyclopropanecarboxylic acid (Compound 1-36)

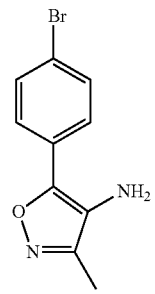

Step 1: 5-(4-Bromo-phenyl)-3-methyl-isoxazol-4-ylamine

Prepared according to the procedure described in Example 1, Step 11, using [5-(4-bromo-phenyl)-3-methyl-isoxazol-4-yl]-carbamic acid tert-butyl ester.

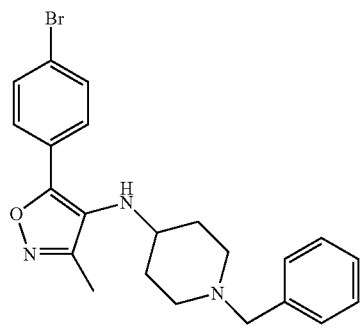 [SMILES: Cc1noc(-c2ccc(Br)cc2)c1NC1CCN(Cc2ccccc2)CC1]

Step 2: (1-Benzyl-piperidin-4-yl)-[5-(4-bromo-phenyl)-3-methyl-isoxazol-4-yl]-amine 5-(4-Bromo-phenyl)-3-methyl-isoxazol-4-ylamine (0.500 g, 1.73 mmol) and 1-benzyl-piperidin-4-one were mixed with acetic acid (0.200 mL) in MeOH (8 mL). The reaction was cooled to 0° C. and stirred for one hour before sodium cyanoborohydride (0.108 g, 1.74 mmol) was added. The reaction was allowed to warm to room temperature and was monitored by analytical LCMS. When complete, the reaction was quenched with aqueous sodium bicarbonate then submitted to standard workup procedures. The crude material was purified by silica gel chromatography (0-100% EtOAc in hexanes) to afford the title compound

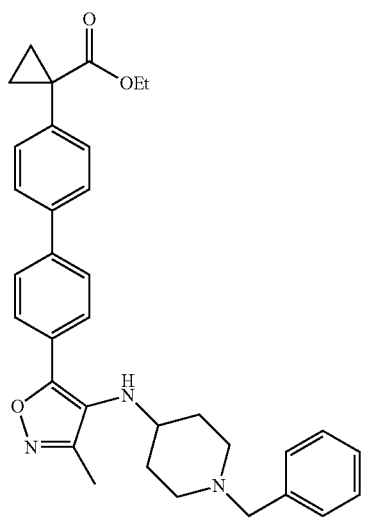 [SMILES: CCOC(=O)C1(c2ccc(-c3ccc(-c4onc(C)c4NC4CCN(Cc5ccccc5)CC4)cc3)cc2)CC1]

Step 3: 1-{4'-[4-(1-Benzyl-piperidin-4-ylamino)-3-methyl-isoxazol-5-yl]-biphenyl-4-yl}-cyclopropanecarboxylic acid ethyl ester Prepared according to the procedure described in Example 1, Step 10, using (1-benzyl-piperidin-4-yl)-[5-(4-bromo-phenyl)-3-methyl-isoxazol-4-yl]-amine and 1-[4-(4,4,5,5-tetramethyl-[1,3,2]dioxaborolan-2-yl)-phenyl]-cyclopropanecarboxylic acid ethyl ester.

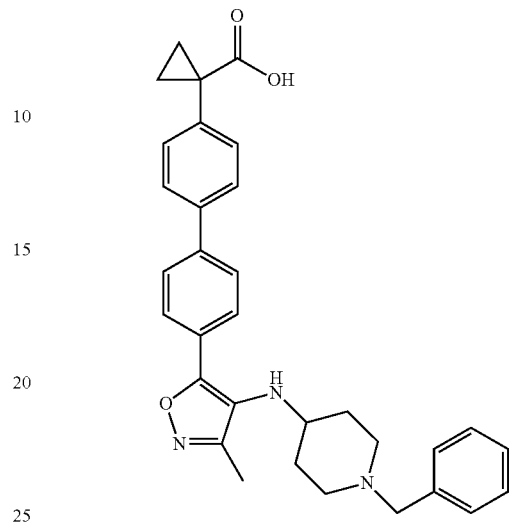

Step 4: 1-{4'-[4-(1-Benzyl-piperidin-4-ylamino)-3-methyl-isoxazol-5-yl]-biphenyl-4-yl}-cyclopropanecarboxylic acid Prepared according to the procedure described in Example 1, Step 13, using 1-{4'-[4-(1-benzyl-piperidin-4-ylamino)-3-methyl-isoxazol-5-yl]-biphenyl-4-yl}-cyclopropanecarboxylic acid ethyl ester.

Example 37

(1-{4'-[4-(1-Benzyl-piperidin-4-ylamino)-3-methyl-isoxazol-5-yl]-biphenyl-4-yl}-cyclopropyl)-acetic acid (Compound 1-37)

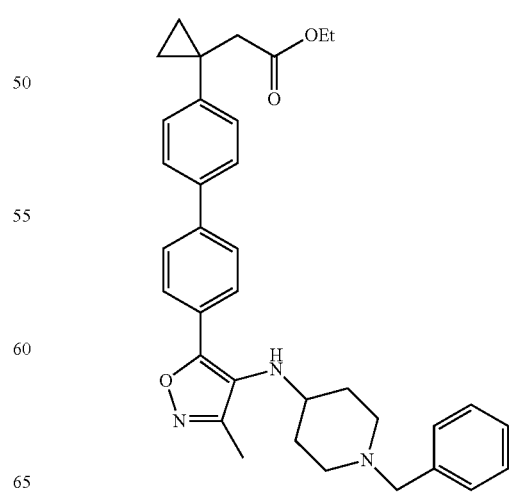

Step 1: (1-{4'-[4-(1-Benzyl-piperidin-4-ylamino)-3-methyl-isoxazol-5-yl]-biphenyl-4-yl}-cyclopropyl)-acetic acid ethyl ester Prepared according to the procedure described in Example 1, Step 10, using (1-benzyl-piperidin-4-yl)-[5-(4-bromo-phenyl)-3-methyl-isoxazol-4-yl]-amine and {1-[4-(4,4,5,5-tetramethyl-[1,3,2]dioxaborolan-2-yl)-phenyl]-cyclopropyl}-acetic acid ethyl ester.

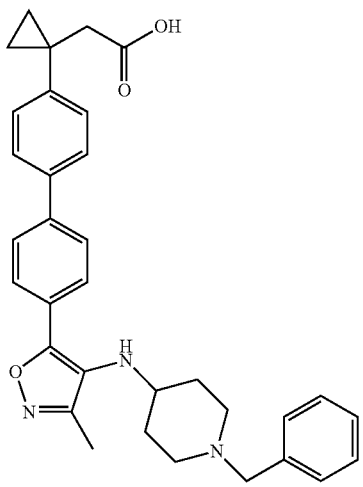 [SMILES: Cc1noc(-c2ccc(-c3ccc(C4(CC(=O)O)CC4)cc3)cc2)c1NC1CCN(Cc2ccccc2)CC1]

Step 2: (1-{4'-[4-(1-Benzyl-piperidin-4-ylamino)-3-methyl-isoxazol-5-yl]-biphenyl-4-yl}-cyclopropyl)-acetic acid Prepared according to the procedure described in Example 1, Step 13, using (1-{4'-[4-(1-benzyl-piperidin-4-ylamino)-3-methyl-isoxazol-5-yl]-biphenyl-4-yl}-cyclopropyl)-acetic acid ethyl ester.

Example 38

1-(4'-{4-[Hydroxy-(5-phenyl-[1,3,4]oxadiazol-2-yl)-methyl]-3-methyl-isoxazol-5-yl}-biphenyl-4-yl)-cyclopropanecarboxylic acid (Compound 1-38)

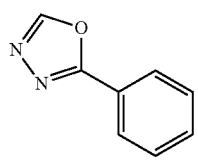 [SMILES: c1ccc(-c2nnco2)cc1]

Step 1: 2-Phenyl-[1,3,4]oxadiazole

Benzoic acid methyl ester (1.01 g, 7.34 mmol) and hydrazine monohydrate (10 mL) were dissolved in EtOH (20 mL) then heated in a sealed tube to 80° C. for 23 hours. The reaction was allowed to cool and then triethylorthoformate (25 mL) and p-toluenesulfonic acid (0.100 g, 0.526 mmol) were added, the tube was re-sealed, and the reaction was heated to 120° C. for 26 hours. The reaction mixture was then submitted to standard aqueous workup and purified on silica gel (0-70% EtOAc in hexanes) to afford the title compound.

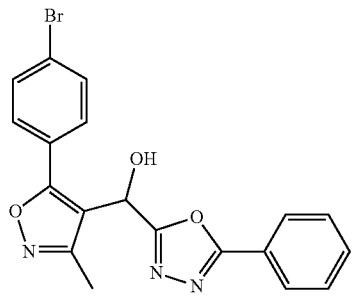 [SMILES: Cc1noc(-c2ccc(Br)cc2)c1C(O)c1nnc(-c2ccccc2)o1]

Step 2: [5-(4-Bromo-phenyl)-3-methyl-isoxazol-4-yl]-(5-phenyl-[1,3,4]oxadiazol-2-yl)-methanol Prepared according to the procedure described in Example 30, Step 1, using 5-(4-Bromo-phenyl)-3-methyl-isoxazole-4-carbaldehyde and 2-phenyl-[1,3,4]oxadiazole.

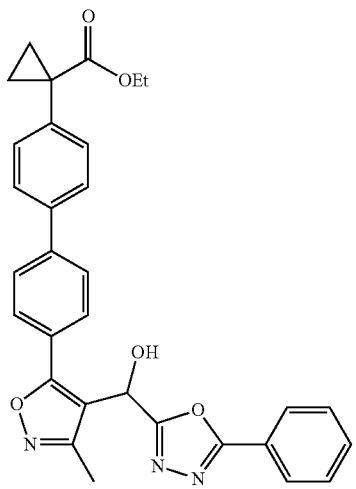 [SMILES: CCOC(=O)C1(c2ccc(-c3ccc(-c4onc(C)c4C(O)c4nnc(-c5ccccc5)o4)cc3)cc2)CC1]

Step 3: 1-(4'-{4-[Hydroxy-(5-phenyl-[1,3,4]oxadiazol-2-yl)-methyl]-3-methyl-isoxazol-5-yl}-biphenyl-4-yl)-cyclopropanecarboxylic acid ethyl ester Prepared according to the procedure described in Example 28, Step 1, using [5-(4-bromo-phenyl)-3-methyl-isoxazol-4-yl]-(5-phenyl-[1,3,4]oxadiazol-2-yl)-methanol and 1-[4-(4,4,5,5-tetramethyl-[1,3,2]dioxaborolan-2-yl)-phenyl]-cyclopropanecarboxylic acid ethyl ester.

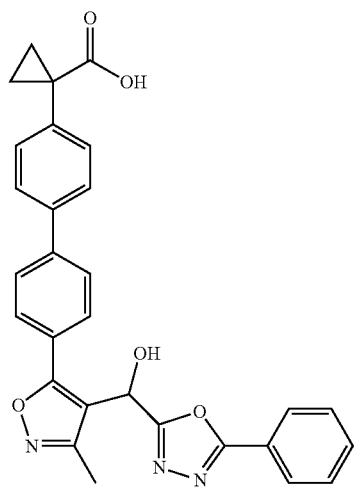 [SMILES: Cc1noc(-c2ccc(-c3ccc(C4(C(=O)O)CC4)cc3)cc2)c1C(O)c1nnc(-c2ccccc2)o1]

Step 4: 1-(4'-{4-[Hydroxy-(5-phenyl-[1,3,4]oxadiazol-2-yl)-methyl]-3-methyl-isoxazol-5-yl}-biphenyl-4-yl)-cyclopropanecarboxylic acid Prepared according to the procedure described in Example 23, Step 3, using 1-(4'-{4-[hydroxy-(5-phenyl-[1,3,4]oxadiazol-2-yl)-methyl]-3-methyl-isoxazol-5-yl}-biphenyl-4-yl)-cyclopropanecarboxylic acid ethyl ester.

Example 39

[1-(4'-{4-[Hydroxy-(5-phenyl-[1,3,4]oxadiazol-2-yl)-methyl]-3-methyl-isoxazol-5-yl}-biphenyl-4-yl)-cyclopropyl]-acetic acid (Compound 1-39)

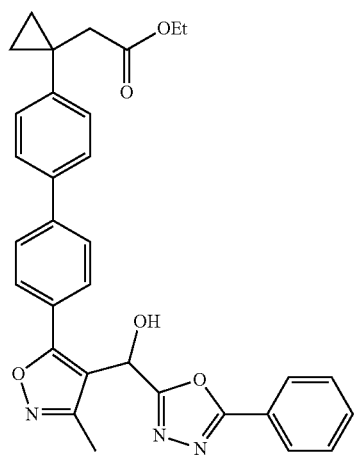 [SMILES: CCOC(=O)CC1(c2ccc(-c3ccc(-c4onc(C)c4C(O)c4nnc(-c5ccccc5)o4)cc3)cc2)CC1]

Step 1: [1-(4'-{4-[Hydroxy-(5-phenyl-[1,3,4]oxadiazol-2-yl)-methyl]-3-methyl-isoxazol-5-yl}-biphenyl-4-yl)-cyclopropyl]-acetic acid ethyl ester Prepared according to the procedure described in Example 28, Step 1, using [5-(4-bromo-phenyl)-3-methyl-isoxazol-4-yl]-(5-phenyl-[1,3,4]oxadiazol-2-yl)-methanol and {1-[4-(4,4,5,5-tetramethyl-[1,3,2]dioxaborolan-2-yl)-phenyl]-cyclopropyl}-acetic acid ethyl ester.

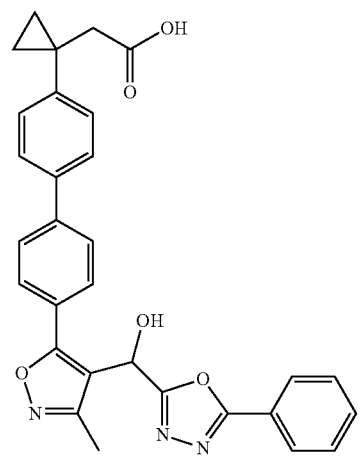 [SMILES: Cc1noc(-c2ccc(-c3ccc(C4(CC(=O)O)CC4)cc3)cc2)c1C(O)c1nnc(-c2ccccc2)o1]

Step 2: [1-(4'-{4-[Hydroxy-(5-phenyl-[1,3,4]oxadiazol-2-yl)-methyl]-3-methyl-isoxazol-5-yl}-biphenyl-4-yl)-cyclopropyl]-acetic acid Prepared according to the procedure described in Example 23, Step 3, using [1-(4'-{4-[hydroxy-(5-phenyl-[1,3,4]oxadiazol-2-yl)-methyl]-3-methyl-isoxazol-5-yl}-biphenyl-4-yl)-cyclopropyl]-acetic acid ethyl ester.

Example 40

1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid (Enantiomer A) (Compound 1-40)

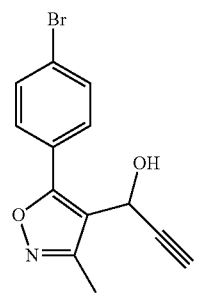 [SMILES: C#CC(O)c1c(C)noc1-c1ccc(Br)cc1]

Step 1: 1-[5-(4-Bromo-phenyl)-3-methyl-isoxazol-4-yl]-prop-2-yn-1-ol

Prepared according to the procedure described in Example 25, Step 1, and after the reaction the material was purified via preparatory chiral HPLC (Chiralcel AD column, 85:15 hexanes:EtOH) to give enantiomer A (first to elute) and enantiomer B (second to elute) with undetermined absolute stereochemistry.

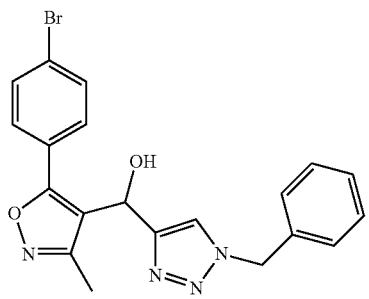 [SMILES: Cc1noc(-c2ccc(Br)cc2)c1C(O)c1cn(Cc2ccccc2)nn1]

Step 2: (1-Benzyl-1H-[1,2,3]triazol-4-yl)-[5-(4-bromo-phenyl)-3-methyl-isoxazol-4-yl]-methanol (Enantiomer A)

To a solution of 1-[5-(4-Bromo-phenyl)-3-methyl-isoxazol-4-yl]-prop-2-yn-1-ol (Enantiomer A) (0.530 g, 1.81 mmol) in DMSO (4 mL) and $H_2O$ (4 mL) was added azidomethyl-benzene (0.242 g, 1.81 mmol), followed by sodium ascorbate (0.036 g, 0.181 mmol) and copper(II) sulfate pentahydrate (0.005 g, 0.018 mmol), and the reaction was stirred overnight. After aqueous workup the crude material was purified by silica gel chromatography (15-100% EtOAc in hexanes) to give the title compound.

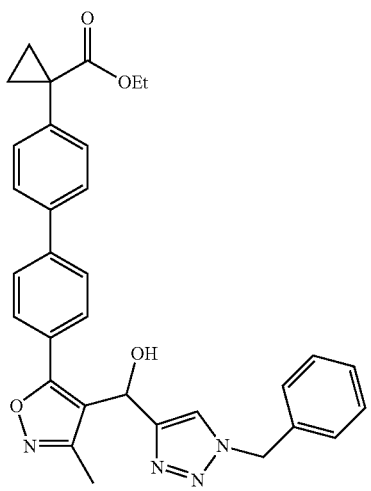

Step 3: 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid ethyl ester (Enantiomer A)

Prepared according to the procedure described in Example 1, Step 10, using (1-benzyl-1H-[1,2,3]triazol-4-yl)-[5-(4-bromo-phenyl)-3-methyl-isoxazol-4-yl]-methanol (Enantiomer A) and 1-[4-(4,4,5,5-tetramethyl-[1,3,2]dioxaborolan-2-yl)-phenyl]-cyclopropanecarboxylic acid ethyl ester.

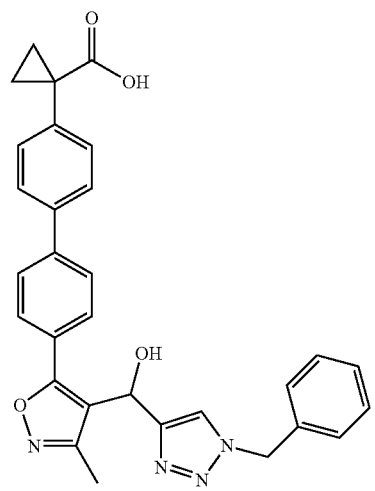 [SMILES: Cc1noc(-c2ccc(-c3ccc(C4(C(=O)O)CC4)cc3)cc2)c1C(O)c1cn(Cc2ccccc2)nn1]

Step 4: 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid (Enantiomer A)

Prepared according to the procedure described in Example 23, Step 3, using 1-(4'-{4-[(1-benzyl-1H-[1,2,3]triazol-4-yl)-hydroxy-methyl]-3-methyl-isoxazol-5-yl}-biphenyl-4-yl)-cyclopropanecarboxylic acid ethyl ester (Enantiomer A).

Example 41

1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid (Enantiomer B) (Compound 1-41)

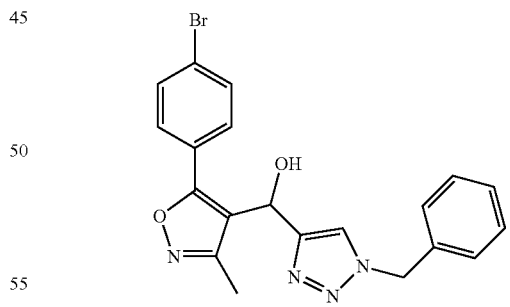

Step 1: (1-Benzyl-1H-[1,2,3]triazol-4-yl)-[5-(4-bromo-phenyl)-3-methyl-isoxazol-4-yl]-methanol (Enantiomer B)

Prepared according to the procedure described in Example 40, Step 2, using 1-[5-(4-Bromo-phenyl)-3-methyl-isoxazol-4-yl]-prop-2-yn-1-ol (Enantiomer B) and azidomethyl-benzene.

187

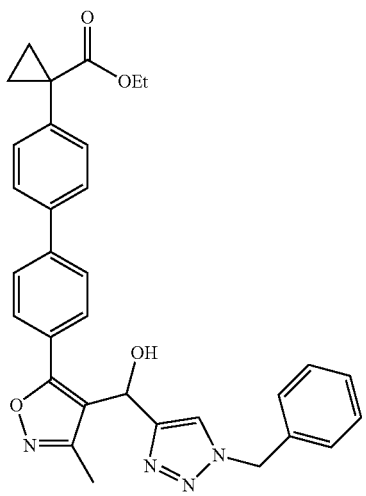

Step 2: 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid ethyl ester (Enantiomer B)

Prepared according to the procedure described in Example 1, Step 10, using (1-benzyl-1H-[1,2,3]triazol-4-yl)-[5-(4-bromo-phenyl)-3-methyl-isoxazol-4-yl]-methanol (Enantiomer B) and 1-[4-(4,4,5,5-tetramethyl-[1,3,2]dioxaborolan-2-yl)-phenyl]-cyclopropanecarboxylic acid ethyl ester.

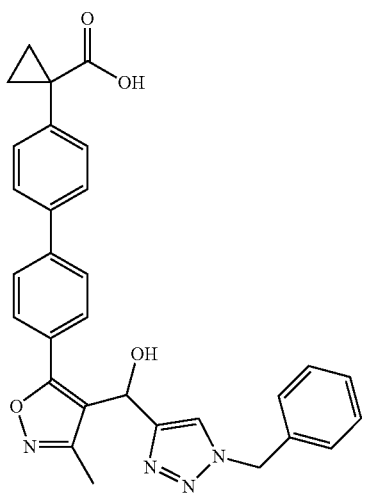 [SMILES: Cc1noc(-c2ccc(-c3ccc(C4(C(=O)O)CC4)cc3)cc2)c1C(O)c1cn(Cc2ccccc2)nn1]

Step 3: 1-(4'-{4-[(1-Benzyl-1H-[1,2,3]triazol-4-yl)-hydroxy-methyl]-3-methyl-isoxazol-5-yl}-biphenyl-4-yl)-cyclopropanecarboxylic acid (Enantiomer B)

Prepared according to the procedure described in Example 23, Step 3, using 1-(4'-{4-[(1-benzyl-1H-[1,2,3]triazol-4-yl)-hydroxy-methyl]-3-methyl-isoxazol-5-yl}-biphenyl-4-yl)-cyclopropanecarboxylic acid ethyl ester (Enantiomer B).

Example 42

[1-(4'-{3-Methyl-4-[1-(3-phenyl-isoxazol-5-yl)-ethylamino]-isoxazol-5-yl}-biphenyl-4-yl)-cyclopropyl]-acetic acid (Compound 1-42)

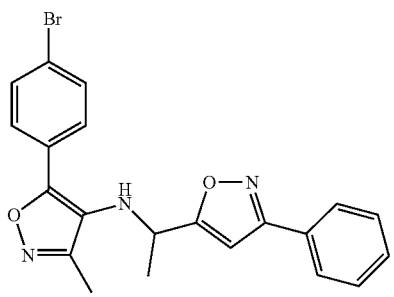 [SMILES: Cc1noc(-c2ccc(Br)cc2)c1NC(C)c1cc(-c2ccccc2)no1]

Step 1: [5-(4-Bromo-phenyl)-3-methyl-isoxazol-4-yl]-[1-(3-phenyl-isoxazol-5-yl)-ethyl]-amine Prepared according to the procedure described in Example 1, Step 12, using 5-(4-bromo-phenyl)-3-methyl-isoxazol-4-ylamine and 1-(3-phenyl-isoxazol-5-yl)-ethanone.

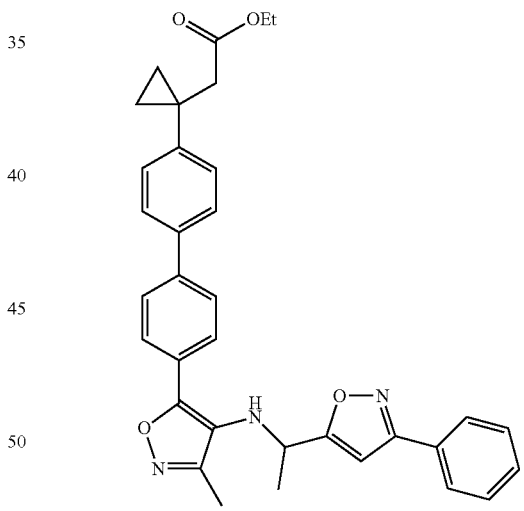

Step 2: [1-(4'-{3-Methyl-4-[1-(3-phenyl-isoxazol-5-yl)-ethylamino]-isoxazol-5-yl}-biphenyl-4-yl)-cyclopropyl]-acetic acid ethyl ester Prepared according to the procedure described in Example 1, Step 10, using [5-(4-bromo-phenyl)-3-methyl-isoxazol-4-yl]-[1-(3-phenyl-isoxazol-5-yl)-ethyl]-amine and {1-[4-(4,4,5,5-tetramethyl-[1,3,2]dioxaborolan-2-yl)-phenyl]-cyclopropyl}-acetic acid ethyl ester. Additionally, (1,1'-bis(diphenylphosphino)ferrocene)-dichloropalladium(II) was used as the catalyst in place of tetrakis(triphenylphosphine)palladium(0).

189

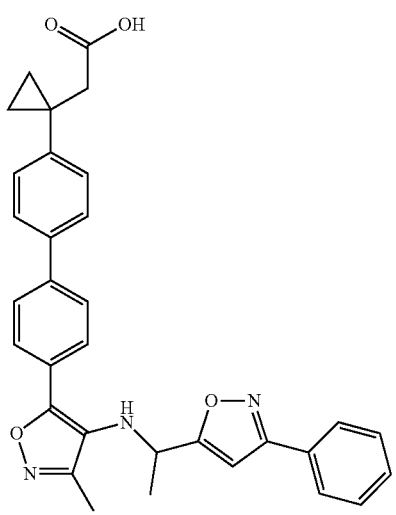 [SMILES: Cc1noc(-c2ccc(-c3ccc(C4(CC(=O)O)CC4)cc3)cc2)c1NC(C)c1cc(-c2ccccc2)no1]

Step 3: [1-(4'-{3-Methyl-4-[1-(3-phenyl-isoxazol-5-yl)-ethylamino]-isoxazol-5-yl}-biphenyl-4-yl)-cyclopropyl]-acetic acid

[1-(4'-{3-Methyl-4-[1-(3-phenyl-isoxazol-5-yl)-ethylamino]-isoxazol-5-yl}-biphenyl-4-yl)-cyclopropyl]-acetic acid ethyl ester (0.0861 g, 0.157 mmol) was dissolved in THF (2 mL) then EtOH (1 mL) and NaOH (3N aq., 0.157 mL, 0.472 mmol) was added and the reaction stirred at 60° C. overnight. The reaction was submitted to standard workup procedure and purified via preparatory HPLC (0.1% TFA/ H₂O/ACN) to afford the title compound.

Example 43

[1-(4'-{3-Methyl-4-[1-(3-phenyl-isoxazol-5-yl)-ethylamino]-isoxazol-5-yl}-biphenyl-4-yl)-cyclopropyl]-acetic acid (Enantiomer A) (Compound 1-43)

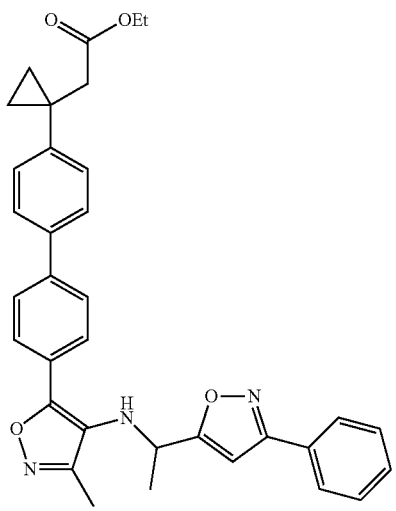 [SMILES: CCOC(=O)CC1(c2ccc(-c3ccc(-c4onc(C)c4NC(C)c4cc(-c5ccccc5)no4)cc3)cc2)CC1]

190

Step 1: [1-(4'-{3-Methyl-4-[1-(3-phenyl-isoxazol-5-yl)-ethylamino]-isoxazol-5-yl}-biphenyl-4-yl)-cyclopropyl]-acetic acid ethyl ester Prepared according to the procedure described in Example 42, Step 2, using the same starting materials and after the reaction the material was purified on preparatory chiral HPLC (Chiralpak AD column, 78% EtOH in hexanes over 30 minutes) to afford enantiomer A (first to elute) and enantiomer B (second to elute) with undetermined absolute stereochemistry

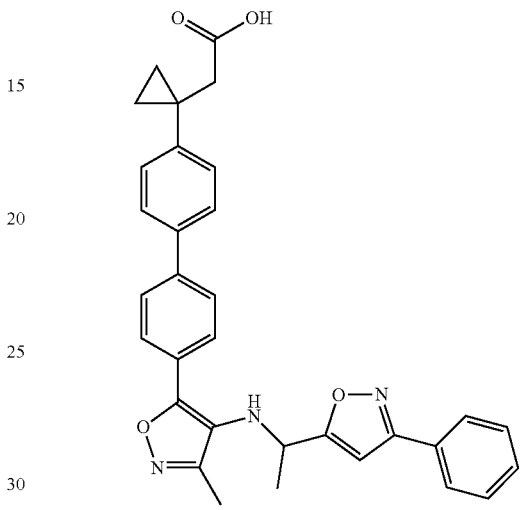

Step 2: [1-(4'-{3-Methyl-4-[1-(3-phenyl-isoxazol-5-yl)-ethylamino]-isoxazol-5-yl}-biphenyl-4-yl)-cyclopropyl]-acetic acid (Enantiomer A)

Prepared according to the procedure described in Example 42, Step 3, using [1-(4'-{3-methyl-4-[1-(3-phenyl-isoxazol-5-yl)-ethylamino]-isoxazol-5-yl}-biphenyl-4-yl)-cyclopropyl]-acetic acid ethyl ester (enantiomer A).

Example 44

[1-(4'-{3-Methyl-4-[1-(3-phenyl-isoxazol-5-yl)-ethylamino]-isoxazol-5-yl}-biphenyl-4-yl)-cyclopropyl]-acetic acid (Enantiomer B) (Compound 1-44)

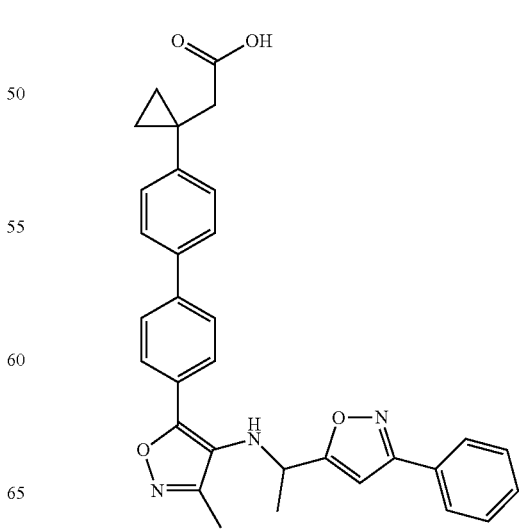

Step 1: [1-(4'-{3-Methyl-4-[1-(3-phenyl-isoxazol-5-yl)-ethylamino]-isoxazol-5-yl}-biphenyl-4-yl)-cyclopropyl]-acetic acid (Enantiomer B)

Prepared according to the procedure described in Example 42, Step 3, using [1-(4'-{3-methyl-4-[1-(3-phenyl-isoxazol-5-yl)-ethylamino]-isoxazol-5-yl}-biphenyl-4-yl)-cyclopropyl]-acetic acid ethyl ester (enantiomer B).

Example 45

{1-[4'-(3-Methyl-4-{1-methyl-2-[4-(4-trifluoromethyl-benzyloxy)-phenyl]-ethylamino}-isoxazol-5-yl)-biphenyl-4-yl]-cyclopropyl}-acetic acid (Compound 1-45)

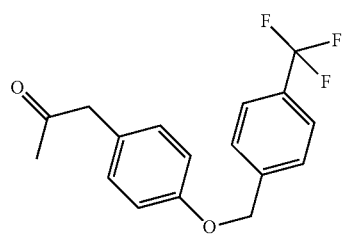 [SMILES: CC(=O)Cc1ccc(OCc2ccc(C(F)(F)F)cc2)cc1]

Step 1: 1-[4-(4-Trifluoromethyl-benzyloxy)-phenyl]-propan-2-one

1-Bromomethyl-4-trifluoromethyl-benzene (1.55 g, 6.49 mmol) and 1-(4-hydroxy-phenyl)-propan-2-one (1.46 g, 9.74 mmol) were stirred in acetonitrile (65 mL) along with cesium carbonate (5.3 g, 16.23 mmol). After stirring at room temperature for two days the reaction was heated to 60° C. for 3 hours. After cooling the reaction was submitted to standard aqueous workup then purified on silica gel (0-100% (2% MeOH in EtOAC) to hexanes) to yield the title compound.

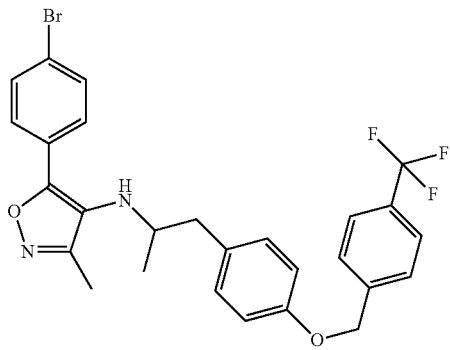 [SMILES: Cc1noc(-c2ccc(Br)cc2)c1NC(C)Cc1ccc(OCc2ccc(C(F)(F)F)cc2)cc1]

Step 2: [5-(4-Bromo-phenyl)-3-methyl-isoxazol-4-yl]-{1-methyl-2-[4-(4-trifluoromethyl-benzyloxy)-phenyl]-ethyl}-amine Prepared according to the procedure described in Example 36, Step 2, using 5-(4-bromo-phenyl)-3-methyl-isoxazol-4-ylamine and 1-[4-(4-trifluoromethyl-benzyloxy)-phenyl]-propan-2-one.

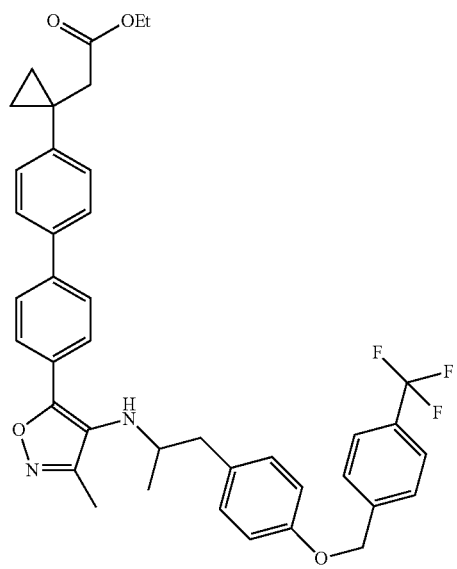 [SMILES: CCOC(=O)CC1(c2ccc(-c3ccc(-c4onc(C)c4NC(C)Cc4ccc(OCc5ccc(C(F)(F)F)cc5)cc4)cc3)cc2)CC1]

Step 3: {1-[4'-(3-Methyl-4-{1-methyl-2-[4-(4-trifluoromethyl-benzyloxy)-phenyl]-ethylamino}-isoxazol-5-yl)-biphenyl-4-yl]-cyclopropyl}-acetic acid ethyl ester Prepared according to the procedure described in Example 42, Step 2, using [5-(4-bromo-phenyl)-3-methyl-isoxazol-4-yl]-{1-methyl-2-[4-(4-trifluoromethyl-benzyloxy)-phenyl]-ethyl}-amine and {1-[4-(4,4,5,5-tetramethyl-[1,3,2]dioxaborolan-2-yl)-phenyl]-cyclopropyl}-acetic acid ethyl ester.

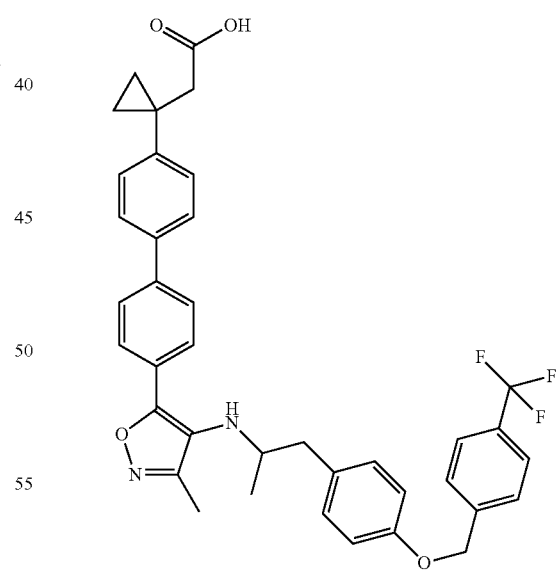

Step 4: {1-[4'-(3-Methyl-4-{1-methyl-2-[4-(4-trifluoromethyl-benzyloxy)-phenyl]-ethylamino}-isoxazol-5-yl)-biphenyl-4-yl]-cyclopropyl}-acetic acid Prepared according to the procedure described in Example 42, Step 3, using {1-[4'-(3-methyl-4-{1-methyl-2-[4-(4-trifluoromethyl-benzyloxy)-phenyl]-ethylamino}-isoxazol-5-yl)-biphenyl-4-yl]-cyclopropyl}-acetic acid ethyl ester.

Example 46

1-[4'-(4-{Hydroxy-[5-(3-trifluoromethyl-benzyl)-[1,3,4]oxadiazol-2-yl]-methyl}-3-methyl-isoxazol-5-yl)-biphenyl-4-yl]-cyclopropanecarboxylic acid (Compound 1-46)

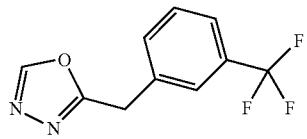 [SMILES: FC(F)(F)c1cccc(Cc2nnco2)c1]

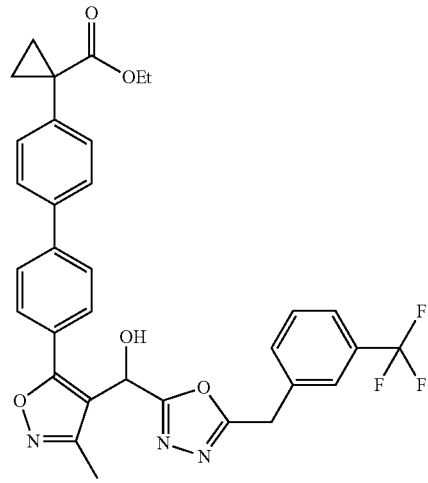

Step 1:
2-(3-Trifluoromethyl-benzyl)-[1,3,4]oxadiazole (3-Trifluoromethyl-phenyl)-acetic acid methyl ester (0.720 g, 3.30 mmol) was dissolved in hydrazine (7 mL) and EtOH (15 mL) and heated to 90° C. overnight. Analytical LCMS indicated complete reaction so the mixture was concentrated and azeotroped two time with toluene. The crude material was dissolved in triethylorthoformate and heated to 135° C. for 20 hours then allowed to cool. The reaction mixture was concentrated to afford the title compound.

Step 3: 1-[4'-(4-{Hydroxy-[5-(3-trifluoromethyl-benzyl)[1,3,4]oxadiazol-2-yl]-methyl}-3-methyl-isoxazol-5-yl)-biphenyl-4-yl]-cyclopropanecarboxylic acid ethyl ester Prepared according to the procedure described in Example 1, Step 10, using [5-(4-bromo-phenyl)-3-methyl-isoxazol-4-yl]-[5-(3-trifluoromethyl-benzyl)-[1,3,4]oxadiazol-2-yl]-methanol and 1-[4-(4,4,5,5-tetramethyl-[1,3,2]dioxaborolan-2-yl)-phenyl]-cyclopropanecarboxylic acid ethyl ester.

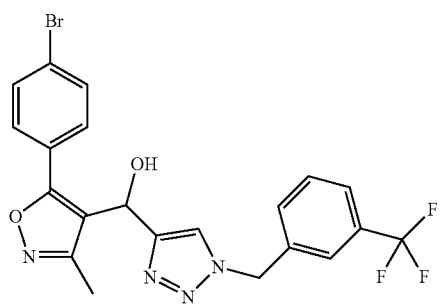 [SMILES: Cc1noc(-c2ccc(Br)cc2)c1C(O)c1cn(Cc2cccc(C(F)(F)F)c2)nn1]

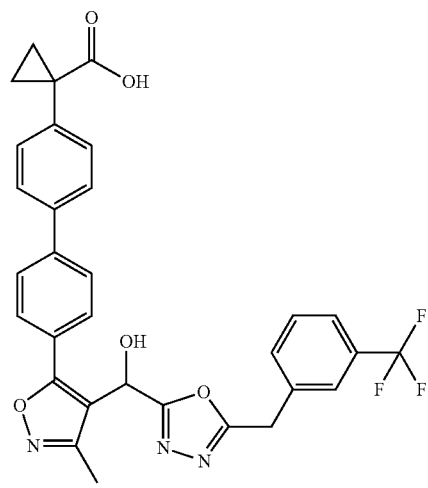 [SMILES: Cc1noc(-c2ccc(-c3ccc(C4(C(=O)O)CC4)cc3)cc2)c1C(O)c1nnc(Cc2cccc(C(F)(F)F)c2)o1]

Step 2: [5-(4-Bromo-phenyl)-3-methyl-isoxazol-4-yl]-[5-(3-trifluoromethyl-benzyl)-[1,3,4]oxadiazol-2-yl]-methanol Prepared according to the procedure described in Example 30, Step 1, using 5-(4-Bromo-phenyl)-3-methyl-isoxazole-4-carbaldehyde and 2-(3-trifluoromethyl-benzyl)-[1,3,4]oxadiazole.

Step 4: 1-[4'-(4-{Hydroxy-[5-(3-trifluoromethyl-benzyl)-[1,3,4]oxadiazol-2-yl]-methyl}-3-methyl-isoxazol-5-yl)-biphenyl-4-yl]-cyclopropanecarboxylic acid Prepared according to the procedure described in Example 23, Step 3, using 1-[4'-(4-{hydroxy-[5-(3-trifluoromethylbenzyl)-[1,3,4]oxadiazol-2-yl]-methyl}-3-methyl-isoxazol-5-yl)-biphenyl-4-yl]-cyclopropanecarboxylic acid ethyl ester.

Example 47

1-(4'-{4-[(1-Benzyl-1H-[1,2,3]triazol-4-yl)-methane-sulfonylamino-methyl]-3-methyl-isoxazol-5-yl}-biphenyl-4-yl)-cyclopropanecarboxylic acid (Compound 1-47)

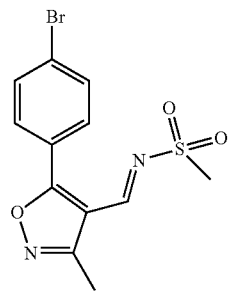 [SMILES: Cc1noc(-c2ccc(Br)cc2)c1/C=N/S(C)(=O)=O]

Step 1: N-[1-[5-(4-Bromo-phenyl)-3-methyl-isoxazol-4-yl]-meth-(E)-ylidene]-methanesulfonamide 5-(4-Bromo-phenyl)-3-methyl-isoxazole-4-carbaldehyde (2 g, 7.5 mmol) was mixed with methanesulfonamide (0.714 g, 7.5 mmol) and p-toluenesulfonic acid monohydrate (0.010 g, 0.053 mmol) in toluene. The reaction was heated to reflux for 24 hours with Dean-Stark apparatus in place. Upon cooling the product precipitated from the reaction mixture and was isolated by filtration to afford the title compound.

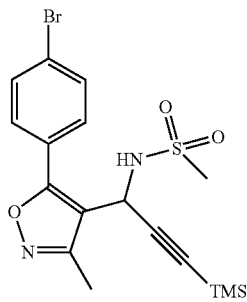 [SMILES: Cc1noc(-c2ccc(Br)cc2)c1C(C#C[Si](C)(C)C)NS(C)(=O)=O]

Step 2: N-{1-[5-(4-Bromo-phenyl)-3-methyl-isoxazol-4-yl]-3-trimethylsilanyl-prop-2-ynyl}-methane-sulfonamide (Trimethylsilyl)acetylene (0.6926 mL, 5 mmol) and diethylzinc (1.1M in toluene, 4.54 mL, 5 mmol) were dissolved in toluene (15.5 mL) and stirred for 1 hour at room temperature. Then, N-[1-[5-(4-Bromo-phenyl)-3-methyl-isoxazol-4-yl]-meth-(E)-ylidene]-methanesulfonamide (1 g, 0.291 mmol) was added and the reaction was heated to 60° C. for 20 hours. The reaction was quenched with H₂O and submitted to aqueous workup then purified via silica gel chromatography to yield the title compound which was brought directly to the next step.

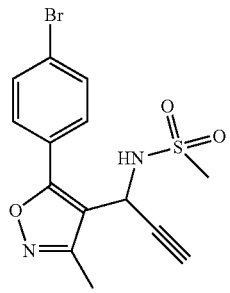 [SMILES: C#CC(NS(C)(=O)=O)c1c(C)noc1-c1ccc(Br)cc1]

Step 3: N-{1-[5-(4-Bromo-phenyl)-3-methyl-isoxazol-4-yl]-prop-2-ynyl}-methanesulfonamide N-{1-[5-(4-Bromo-phenyl)-3-methyl-isoxazol-4-yl]-3-trimethylsilanyl-prop-2-ynyl}-methanesulfonamide (from previous step) was dissolved in THF (10 mL) and the mixture was cooled to 0° C. Tetrabutylammonium fluoride (1.0M in THF, 0.3 mL, 0.3 mmol) was added and the reaction stirred at 0° C. for 1 hour. The reaction was then submitted to standard aqueous workup and purified on silica gel (0-70% EtOAc in hexanes) to afford the title compound.

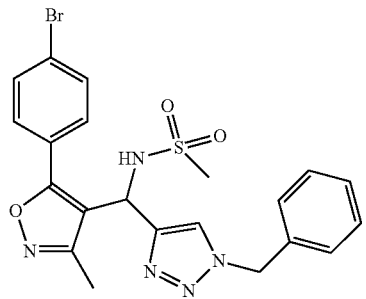 [SMILES: Cc1noc(-c2ccc(Br)cc2)c1C(NS(C)(=O)=O)c1cn(Cc2ccccc2)nn1]

Step 4: N-{(1-Benzyl-1H-[1,2,3]triazol-4-yl)-[5-(4-bromo-phenyl)-3-methyl-isoxazol-4-yl]-methyl}-methanesulfonamide Prepared according to the procedure described in Example 40, Step 2, using N-{1-[5-(4-bromo-phenyl)-3-methyl-isoxazol-4-yl]-prop-2-ynyl}-methanesulfonamide and benzyl azide.

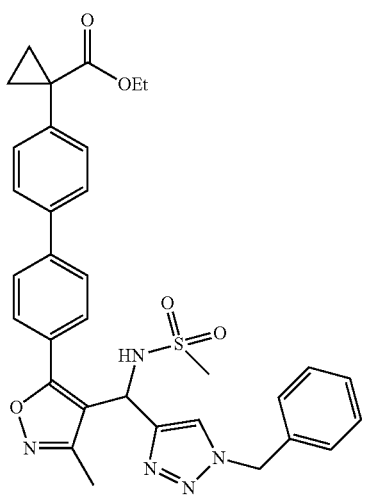

Step 5: 1-(4'-{4-[(1-Benzyl-1H-[1,2,3]triazol-4-yl)-methanesulfonylamino-methyl]-3-methyl-isoxazol-5-yl}-biphenyl-4-yl)-cyclopropanecarboxylic acid ethyl ester Prepared according to the procedure described in Example 42, Step 2, using N-{(1-benzyl-1H-[1,2,3]triazol-4-yl)-[5-(4-bromo-phenyl)-3-methyl-isoxazol-4-yl]-methyl}-methanesulfonamide and 1-[4-(4,4,5,5-tetramethyl-[1,3,2]dioxaborolan-2-yl)-phenyl]-cyclopropanecarboxylic acid ethyl ester.

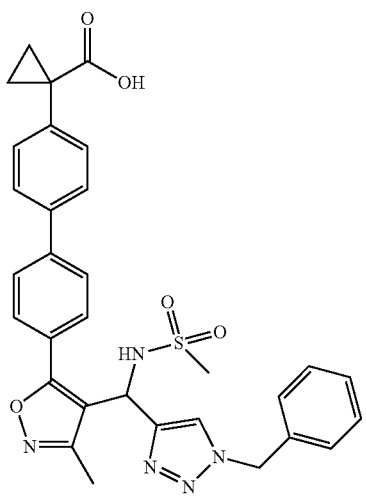 [SMILES: Cc1noc(-c2ccc(-c3ccc(C4(C(=O)O)CC4)cc3)cc2)c1C(NS(C)(=O)=O)c1cn(Cc2ccccc2)nn1]

Step 6: 1-(4'-{4-[(1-Benzyl-1H-[1,2,3]triazol-4-yl)-methanesulfonylamino-methyl]-3-methyl-isoxazol-5-yl}-biphenyl-4-yl)-cyclopropanecarboxylic acid Prepared according to the procedure described in Example 1, Step 13, using 1-(4'-{4-[(1-benzyl-1H-[1,2,3]triazol-4-yl)-methanesulfonylamino-methyl]-3-methyl-isoxazol-5-yl}-biphenyl-4-yl)-cyclopropanecarboxylic acid ethyl ester.

Example 48

(4'-{4-[(1-Benzyl-1H-[1,2,3]triazol-4-yl)-hydroxy-methyl]-3-methyl-isoxazol-5-yl}-biphenyl-4-yl)-acetic acid (Compound 1-48)

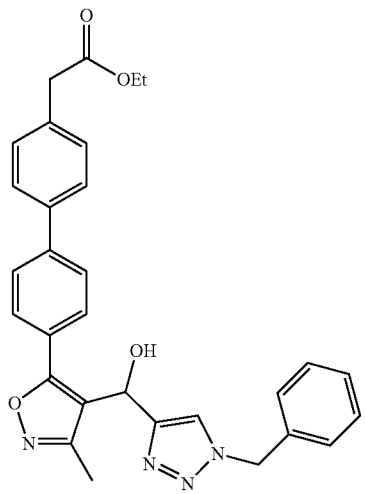 [SMILES: CCOC(=O)Cc1ccc(-c2ccc(-c3onc(C)c3C(O)c3cn(Cc4ccccc4)nn3)cc2)cc1]

Step 1: (4'-{4-[(1-Benzyl-1H-[1,2,3]triazol-4-yl)-hydroxy-methyl]-3-methyl-isoxazol-5-yl}-biphenyl-4-yl)-acetic acid ethyl ester Prepared according to the procedure described in Example 1, Step 10, using (1-benzyl-1H-[1,2,3]triazol-4-yl)-[5-(4-bromo-phenyl)-3-methyl-isoxazol-4-yl]-methanol and [4-(4,4,5,5-tetramethyl-[1,3,2]dioxaborolan-2-yl)-phenyl]-acetic acid ethyl ester.

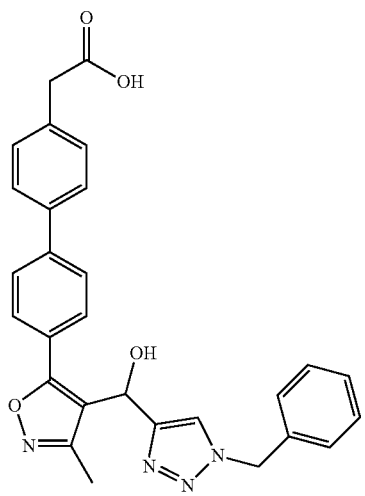 [SMILES: Cc1noc(-c2ccc(-c3ccc(CC(=O)O)cc3)cc2)c1C(O)c1cn(Cc2ccccc2)nn1]

Step 2: (4'-{4-[(1-Benzyl-1H-[1,2,3]triazol-4-yl)-hydroxy-methyl]-3-methyl-isoxazol-5-yl}-biphenyl-4-yl)-acetic acid Prepared according to the procedure described in Example 1, Step 13, using (4'-{4-[(1-benzyl-1H-[1,2,3]triazol-4-yl)-hydroxy-methyl]-3-methyl-isoxazol-5-yl}-biphenyl-4-yl)-acetic acid ethyl ester.

Example 49

3-(4'-{4-[(1-Benzyl-1H-[1,2,3]triazol-4-yl)-hydroxy-methyl]-3-methyl-isoxazol-5-yl}-biphenyl-4-yl)-propionic acid (Compound 1-49)

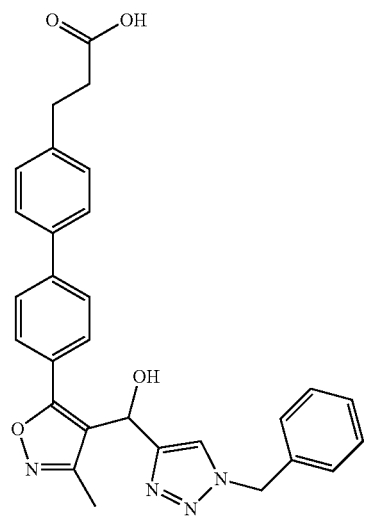 [SMILES: Cc1noc(-c2ccc(-c3ccc(CCC(=O)O)cc3)cc2)c1C(O)c1cn(Cc2ccccc2)nn1]

Step 1: 3-(4'-{4-[(1-Benzyl-1H-[1,2,3]triazol-4-yl)-hydroxy-methyl]-3-methyl-isoxazol-5-yl}-biphenyl-4-yl)-propionic acid ethyl ester Prepared according to the procedure described in Example 1, Step 10, using (1-benzyl-1H-[1,2,3]triazol-4-yl)-[5-(4-bromo-phenyl)-3-methyl-isoxazol-4-yl]-methanol and [4-(2-ethoxycarbonylethyl)phenyl]boronic acid.

Step 2: 3-(4'-{4-[(1-Benzyl-1H-[1,2,3]triazol-4-yl)-hydroxy-methyl]-3-methyl-isoxazol-5-yl}-biphenyl-4-yl)-propionic acid Prepared according to the procedure described in Example 1, Step 13, using 3-(4'-{4-[(1-benzyl-1H-[1,2,3]triazol-4-yl)-hydroxy-methyl]-3-methyl-isoxazol-5-yl}-biphenyl-4-yl)-propionic acid ethyl ester.

Example 50

1-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-cyclopropanecarboxylic acid (Compound 1-50)

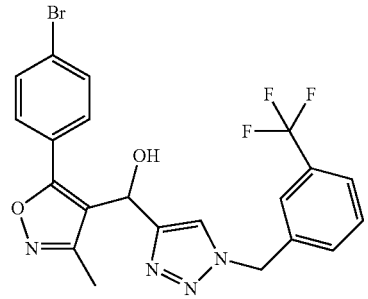 [SMILES: Cc1noc(-c2ccc(Br)cc2)c1C(O)c1cn(Cc2cccc(C(F)(F)F)c2)nn1]

Step 1: [5-(4-Bromo-phenyl)-3-methyl-isoxazol-4-yl]-[1-(3-trifluoromethyl-benzyl)-1H-[1,2,3]triazol-4-yl]-methanol 1-Bromomethyl-3-trifluoromethyl-benzene (0.0491 g, 0.205 mmol) and sodium azide (0.0222 g, 0.342 mmol) were combined in DMSO and stirred at room temperature for 2 hours. Then, 1-[5-(4-bromo-phenyl)-3-methyl-isoxazol-4-yl]-prop-2-yn-1-ol (0.500 g, 0.171 mmol), copper(II)sulfate pentahydrate (0.0043 g, 0.017 mmol) and sodium ascorbate (0.0034 g, 0.017 mmol) were added and the reaction stirred at room temperature for 2 days. The reaction was submitted to standard aqueous workup and purified on silica gel to afford the title compound.

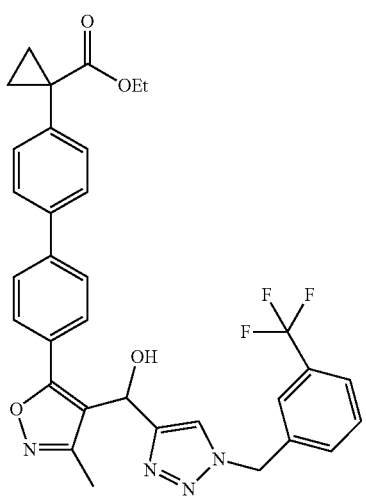

Step 2: 1-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-cyclopropanecarboxylic acid ethyl ester Prepared according to the procedure described in Example 1, Step 10, using [5-(4-bromo-phenyl)-3-methyl-isoxazol-4-yl]-[1-(3-trifluoromethyl-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

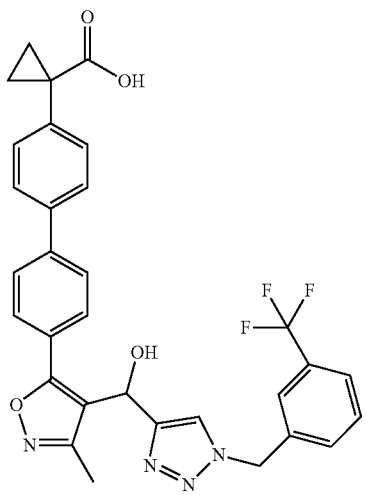 [SMILES: Cc1noc(-c2ccc(-c3ccc(C4(C(=O)O)CC4)cc3)cc2)c1C(O)c1cn(Cc2cccc(C(F)(F)F)c2)nn1]

Step 3: 1-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-cyclopropanecarboxylic acid Prepared according to the procedure described in Example 1, Step 13, using 1-[4'-(4-{hydroxy-[1-(3-trifluoromethyl-benzyl)-1H-[1,2,3]triazol-4-yl]-methyl}-3-methyl-isoxazol-5-yl)-biphenyl-4-yl]-cyclopropanecarboxylic acid ethyl ester.

Example 51

[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]acetic acid (Compound 1-51)

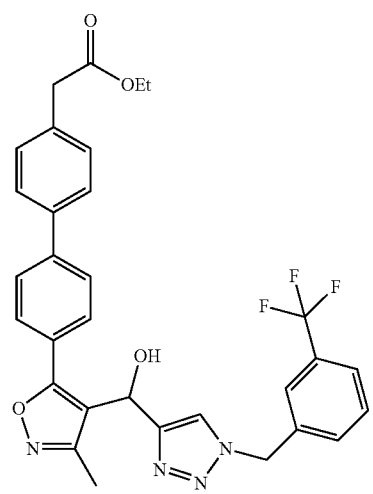 [SMILES: CCOC(=O)Cc1ccc(-c2ccc(-c3onc(C)c3C(O)c3cn(Cc4cccc(C(F)(F)F)c4)nn3)cc2)cc1]

Step 1: [4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-acetic acid ethyl ester Prepared according to the procedure described in Example 1, Step 10, using [5-(4-bromo-phenyl)-3-methyl-isoxazol-4-yl]-[1-(3-trifluoromethyl-benzyl)-1H-[1,2,3]triazol-4-yl]-methanol and [4-(4,4,5,5-tetramethyl-[1,3,2]dioxaborolan-2-yl)-phenyl]-acetic acid ethyl ester.

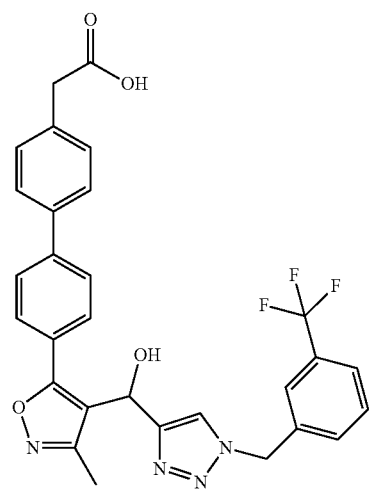 [SMILES: Cc1noc(-c2ccc(-c3ccc(CC(=O)O)cc3)cc2)c1C(O)c1cn(Cc2cccc(C(F)(F)F)c2)nn1]

Step 2: [4'-(4-{Hydroxy-[1-(3-trifluoromethyl-benzyl)-1H-[1,2,3]triazol-4-yl]-methyl}-3-methyl-isoxazol-5-yl)-biphenyl-4-yl]acetic acid Prepared according to the procedure described in Example 1, Step 13, using [4'-(4-{hydroxy-[1-(3-trifluoromethyl-benzyl)-1H-[1,2,3]triazol-4-yl]-methyl}-3-methyl-isoxazol-5-yl)-biphenyl-4-yl]-acetic acid ethyl ester.

Example 52

3-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]propionic acid (Compound 1-52)

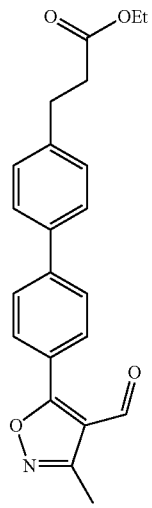 [SMILES: CCOC(=O)CCc1ccc(-c2ccc(-c3onc(C)c3C=O)cc2)cc1]

Step 1: 3-[4'-(4-Formyl-3-methyl-isoxazol-5-yl)-biphenyl-4-yl]-propionic acid ethyl ester Prepared according to the procedure described in Example 1, Step 10, using 5-(4-bromo-phenyl)-3-methyl-isoxazole-4-carbaldehyde and [4-(2-ethoxycarbonylethyl)phenyl]boronic acid.

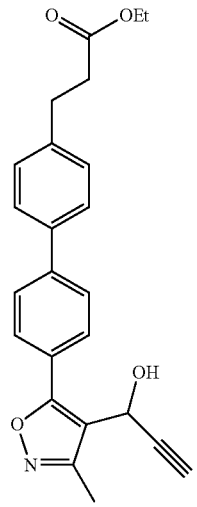 [SMILES: C#CC(O)c1c(C)noc1-c1ccc(-c2ccc(CCC(=O)OCC)cc2)cc1]

Step 2: 3-{4'-[4-(1-Hydroxy-prop-2-ynyl)-3-methyl-isoxazol-5-yl]-biphenyl-4-yl}-propionic acid ethyl ester Prepared according to the procedure described in Example 25, Step 1, using 3-[4'-(4-formyl-3-methyl-isoxazol-5-yl)-biphenyl-4-yl]-propionic acid ethyl ester and ethynylmagnesium bromide.

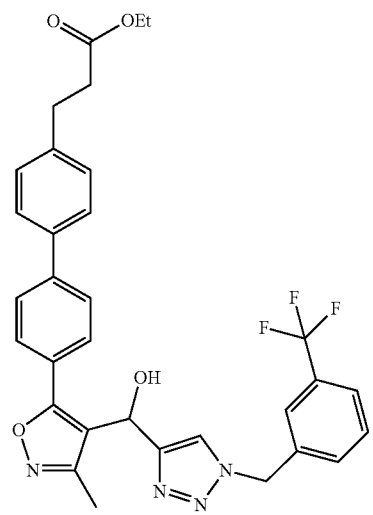 [SMILES: CCOC(=O)CCc1ccc(-c2ccc(-c3onc(C)c3C(O)c3cn(Cc4cccc(C(F)(F)F)c4)nn3)cc2)cc1]

Step 3: 3-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-propionic acid ethyl ester Prepared according to the procedure described in Example 50, Step 1, using 3-{4'-[4-(1-hydroxy-prop-2-ynyl)-3-methyl-isoxazol-5-yl]-biphenyl-4-yl}-propionic acid ethyl ester and 1-bromomethyl-3-trifluoromethyl-benzene.

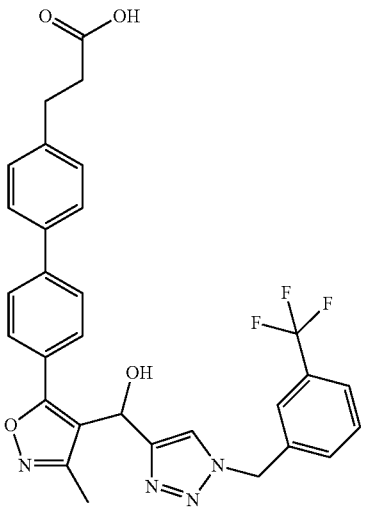 [SMILES: Cc1noc(-c2ccc(-c3ccc(CCC(=O)O)cc3)cc2)c1C(O)c1cn(Cc2cccc(C(F)(F)F)c2)nn1]

Step 4: 3-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-propionic acid Prepared according to the procedure described in Example 1, Step 13, using 3-[4'-(4-{hydroxy-[1-(3-trifluoromethyl-benzyl)-1H-[1,2,3]triazol-4-yl]-methyl}-3-methyl-isoxazol-5-yl)-biphenyl-4-yl]-propionic acid ethyl ester.

Example 53

1-{4'-[4-(Biphenyl-3-yl-hydroxy-methyl)-3-methyl-isoxazol-5-yl]-biphenyl-4-yl}-cyclopropanecarboxylic acid (Compound 1-53)

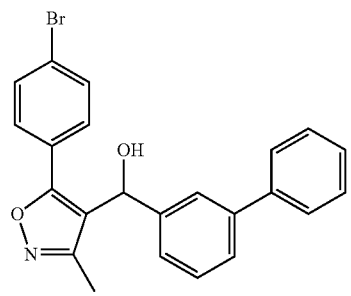 [SMILES: Cc1noc(-c2ccc(Br)cc2)c1C(O)c1cccc(-c2ccccc2)c1]

Step 1: Biphenyl-3-yl-[5-(4-bromo-phenyl)-3-methyl-isoxazol-4-yl]-methanol

Prepared according to the procedure described in Example 25, Step 1, using 5-(4-bromo-phenyl)-3-methyl-isoxazole-4-carbaldehyde and 3-(biphenyl)magnesium bromide.

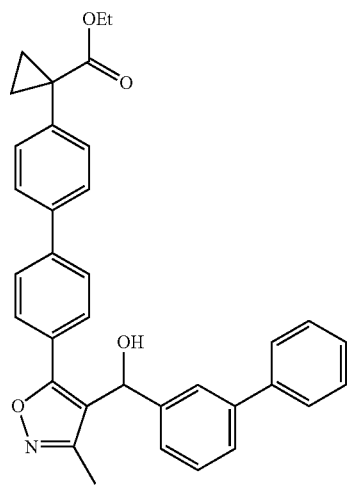 [SMILES: CCOC(=O)C1(c2ccc(-c3ccc(-c4onc(C)c4C(O)c4cccc(-c5ccccc5)c4)cc3)cc2)CC1]

Step 2: 1-{4'-[4-(Biphenyl-3-yl-hydroxy-methyl)-3-methyl-isoxazol-5-yl]-biphenyl-4-yl}-cyclopropanecarboxylic acid ethyl ester Prepared according to the procedure described in Example 42, Step 2, using biphenyl-3-yl-[5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester.

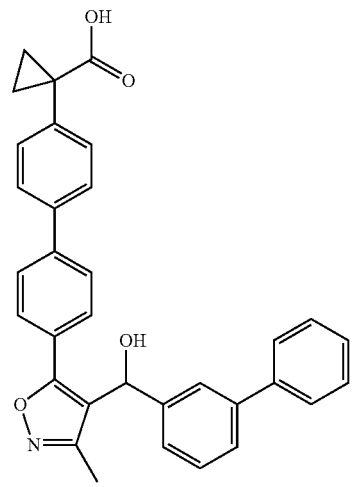 [SMILES: Cc1noc(-c2ccc(-c3ccc(C4(C(=O)O)CC4)cc3)cc2)c1C(O)c1cccc(-c2ccccc2)c1]

Step 3: 1-{4'-[4-(Biphenyl-3-yl-hydroxy-methyl)-3-methyl-isoxazol-5-yl]-biphenyl-4-yl}-cyclopropanecarboxylic acid Prepared according to the procedure described in Example 42, Step 3, using 1-{4'-[4-(biphenyl-3-yl-hydroxy-methyl)-3-methyl-isoxazol-5-yl]-biphenyl-4-yl}-cyclopropanecarboxylic acid ethyl ester.

Example 54

1-(4'-{4-[(4-Benzyloxy-phenyl)-hydroxy-methyl]-3-methyl-isoxazol-5-yl}-biphenyl-4-yl)-cyclopropanecarboxylic acid (Compound 1-54)

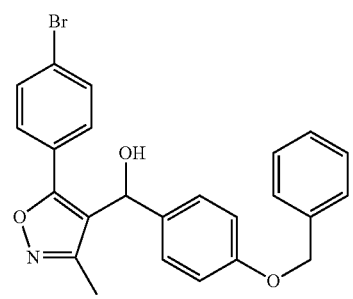 [SMILES: Cc1noc(-c2ccc(Br)cc2)c1C(O)c1ccc(OCc2ccccc2)cc1]

Step 1: (4-Benzyloxy-phenyl)-[5-(4-bromo-phenyl)-3-methyl-isoxazol-4-yl]-methanol Prepared according to the procedure described in Example 25, Step 1, using 5-(4-bromo-phenyl)-3-methyl-isoxazole-4-carbaldehyde and 4-(benzyloxy)phenyl magnesium bromide.

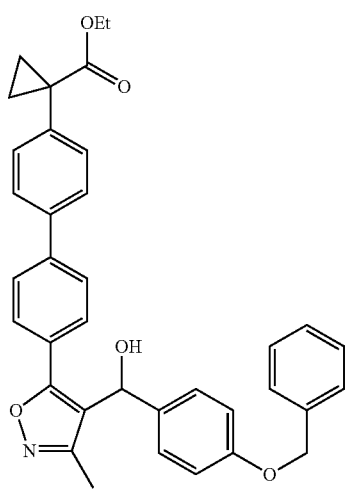 [SMILES: CCOC(=O)C1(c2ccc(-c3ccc(-c4onc(C)c4C(O)c4ccc(OCc5ccccc5)cc4)cc3)cc2)CC1]

Step 2: 1-(4'-{4-[(4-Benzyloxy-phenyl)-hydroxy-methyl]-3-methyl-isoxazol-5-yl}-biphenyl-4-yl)-cyclopropanecarboxylic acid ethyl ester Prepared according to the procedure described in Example 42, Step 2, using (4-benzyloxy-phenyl)-[5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester.

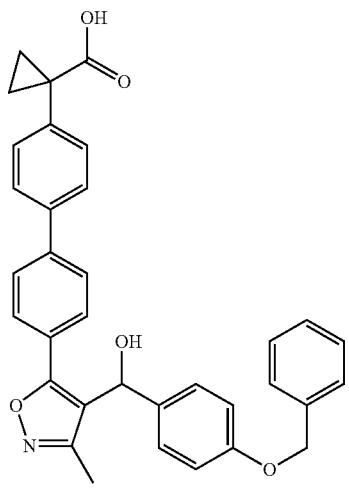 [SMILES: Cc1noc(-c2ccc(-c3ccc(C4(C(=O)O)CC4)cc3)cc2)c1C(O)c1ccc(OCc2ccccc2)cc1]

Step 3: 1-(4'-{4-[(4-Benzyloxy-phenyl)-hydroxy-methyl]-3-methyl-isoxazol-5-yl}-biphenyl-4-yl)-cyclopropanecarboxylic acid Prepared according to the procedure described in Example 42, Step 3, using 1-(4'-{4-[(4-benzyloxy-phenyl)-hydroxy-methyl]-3-methyl-isoxazol-5-yl}-biphenyl-4-yl)-cyclopropanecarboxylic acid ethyl ester.

Example 55

1-[4'-(4-{Hydroxy-[1-(1-phenyl-ethyl)-1H-[1,2,3]triazol-4-yl]-methyl}-3-methyl-isoxazol-5-yl)-biphenyl-4-yl]-cyclopropanecarboxylic acid (Compound 1-55)

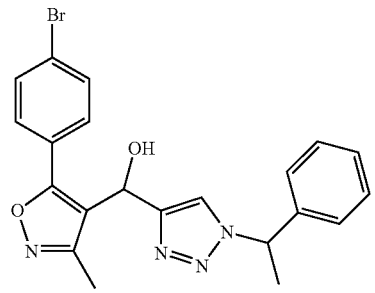 [SMILES: Cc1noc(-c2ccc(Br)cc2)c1C(O)c1cn(C(C)c2ccccc2)nn1]

Step 1: [5-(4-Bromo-phenyl)-3-methyl-isoxazol-4-yl]-[1-(1-phenyl-ethyl)-1H-[1,2,3]triazol-4-yl]-methanol Prepared according to the procedure described in Example 50, Step 1, using 1-[5-(4-bromo-phenyl)-3-methyl-isoxazol-4-yl]-prop-2-yn-1-ol and (1-bromo-ethyl)-benzene.

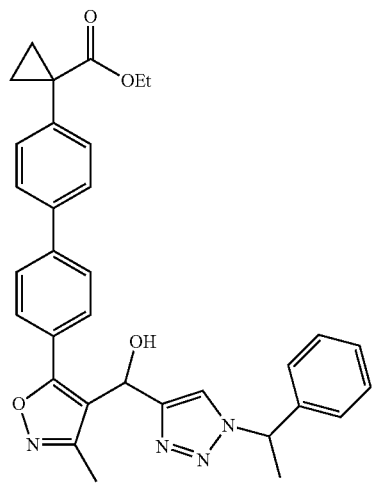 [SMILES: CCOC(=O)C1(c2ccc(-c3ccc(-c4onc(C)c4C(O)c4cn(C(C)c5ccccc5)nn4)cc3)cc2)CC1]

Step 2: 1-[4'-(4-{Hydroxy-[1-(1-phenyl-ethyl)-1H-[1,2,3]triazol-4-yl-]methyl}-3-methyl-isoxazol-5-yl)-biphenyl-4-yl]-cyclopropanecarboxylic acid ethyl ester Prepared according to the procedure described in Example 1, Step 10, using [5-(4-bromo-phenyl)-3-methyl-isoxazol-4-yl]-[1-(1-phenyl-ethyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

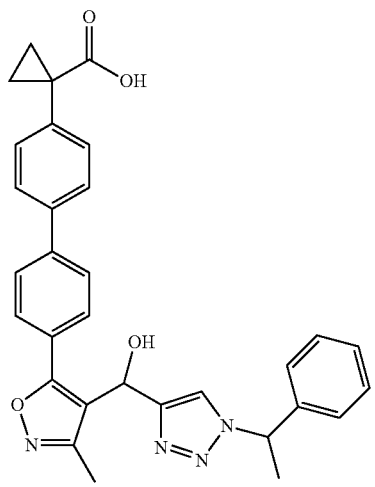 [SMILES: Cc1noc(-c2ccc(-c3ccc(C4(C(=O)O)CC4)cc3)cc2)c1C(O)c1cn(C(C)c2ccccc2)nn1]

Step 3: 1-[4'-(4-{Hydroxy-[1-(1-phenyl-ethyl)-1H-[1,2,3]triazol-4-yl-]methyl}-3-methyl-isoxazol-5-yl)-biphenyl-4-yl]-cyclopropanecarboxylic acid Prepared according to the procedure described in Example 1, Step 13, using 1-[4'-(4-{hydroxy-[1-(1-phenyl-ethyl)-1H-[1,2,3]triazol-4-yl]-methyl}-3-methyl-isoxazol-5-yl)-biphenyl-4-yl]-cyclopropanecarboxylic acid ethyl ester.

Example 56

1-[4'-(4-{Hydroxy-[1-(2-trifluoromethyl-benzyl)-1H-[1,2,3]triazol-4-yl]-methyl}-3-methyl-isoxazol-5-yl)-biphenyl-4-yl]-cyclopropanecarboxylic acid (Compound 1-56)

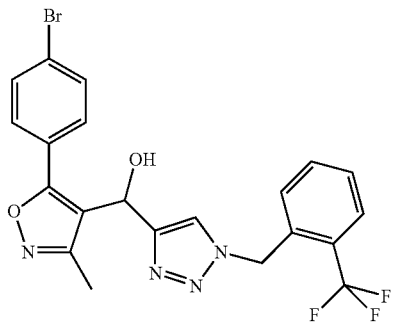 [SMILES: Cc1noc(-c2ccc(Br)cc2)c1C(O)c1cn(Cc2ccccc2C(F)(F)F)nn1]

Step 1: [5-(4-Bromo-phenyl)-3-methyl-isoxazol-4-yl]-[1-(2-trifluoromethyl-benzyl)-1H-[1,2,3]triazol-4-yl]-methanol Prepared according to the procedure described in Example 50, Step 1, using 1-[5-(4-bromo-phenyl)-3-methyl-isoxazol-4-yl]-prop-2-yn-1-ol and 1-bromomethyl-2-trifluoromethyl-benzene.

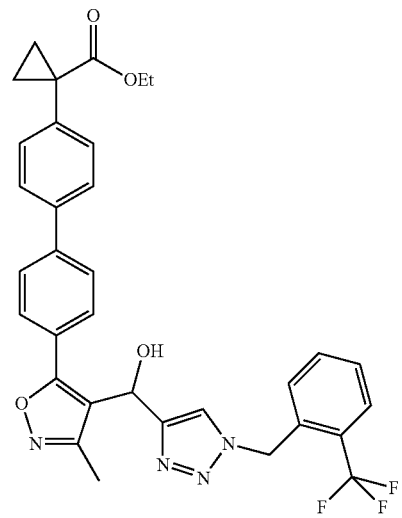 [SMILES: Cc1noc(-c2ccc(-c3ccc(C4(C(=O)O)CC4)cc3)cc2)c1C(O)c1cn(Cc2ccccc2C(F)(F)F)nn1]

Step 2: 1-[4'-(4-{Hydroxy-[1-(2-trifluoromethyl-benzyl)-1H-[1,2,3]triazol-4-yl]-methyl}-3-methyl-isoxazol-5-yl)-biphenyl-4-yl]-cyclopropanecarboxylic acid ethyl ester Prepared according to the procedure described in Example 1, Step 10, using [5-(4-bromo-phenyl)-3-methyl-isoxazol-4-yl]-[1-(2-trifluoromethyl-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

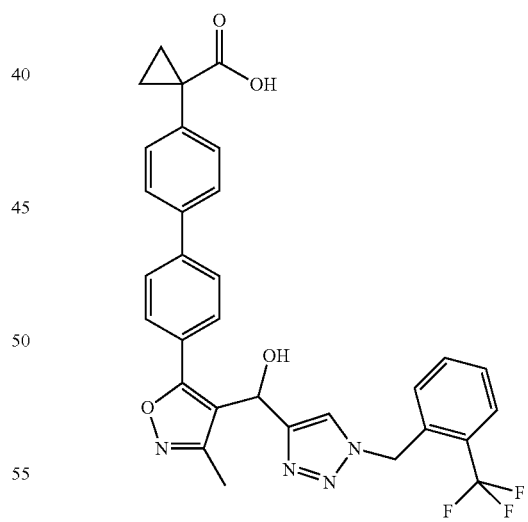

Step 3: 1-[4'-(4-{Hydroxy-[1-(2-trifluoromethyl-benzyl)-1H-[1,2,3]triazol-4-yl]-methyl}-3-methyl-isoxazol-5-yl)-biphenyl-4-yl]-cyclopropanecarboxylic acid Prepared according to the procedure described in Example 1, Step 13, using 1-[4'-(4-{hydroxy-[1-(2-trifluoromethylbenzyl)-1H-[1,2,3]triazol-4-yl]-methyl}-3-methyl-isoxazol-5-yl)-biphenyl-4-yl]-cyclopropanecarboxylic acid ethyl ester.

Example 57

1-[4'-(4-{[1-(3-Chloro-benzyl)-1H-[1,2,3]triazol-4-yl]-hydroxy-methyl}-3-methyl-isoxazol-5-yl)-biphenyl-4-yl]-cyclopropanecarboxylic acid (Compound 1-57)

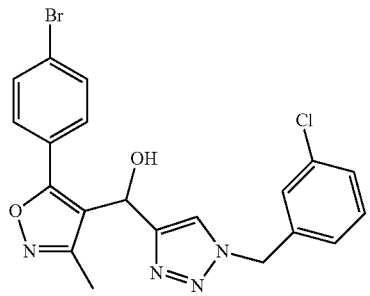 [SMILES: Cc1noc(-c2ccc(Br)cc2)c1C(O)c1cn(Cc2cccc(Cl)c2)nn1]

Step 1: [5-(4-Bromo-phenyl)-3-methyl-isoxazol-4-yl]-[1-(3-chloro-benzyl)-1H-[1,2,3]triazol-4-yl]-methanol Prepared according to the procedure described in Example 50, Step 1, using 1-[5-(4-bromo-phenyl)-3-methyl-isoxazol-4-yl]-prop-2-yn-1-ol and 1-bromomethyl-3-chloro-benzene.

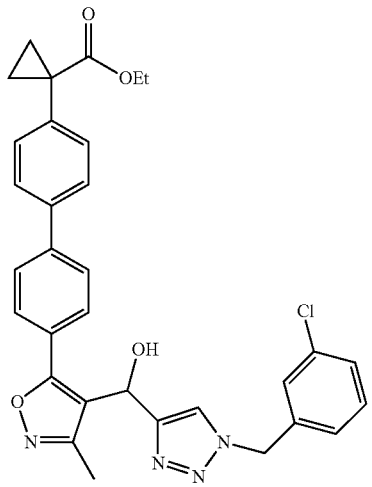 [SMILES: CCOC(=O)C1(c2ccc(-c3ccc(-c4onc(C)c4C(O)c4cn(Cc5cccc(Cl)c5)nn4)cc3)cc2)CC1]

Step 2: 1-[4'-(4-{[1-(3-Chloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester Prepared according to the procedure described in Example 1, Step 10, using [5-(4-bromo-phenyl)-3-methyl-isoxazol-4-yl]-[1-(3-chloro-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

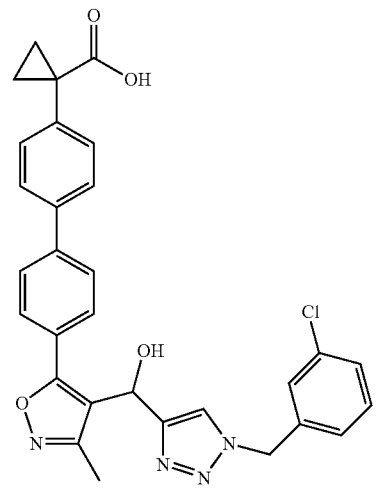 [SMILES: Cc1noc(-c2ccc(-c3ccc(C4(C(=O)O)CC4)cc3)cc2)c1C(O)c1cn(Cc2cccc(Cl)c2)nn1]

Step 3: 1-[4'-(4-{[1-(3-Chloro-benzyl)-1H-[1,2,3]triazol-4-yl]-hydroxy-methyl}-3-methyl-isoxazol-5-yl)-biphenyl-4-yl]-cyclopropanecarboxylic acid Prepared according to the procedure described in Example 1, Step 13, using 1-[4'-(4-{[1-(3-chloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester.

Example 58

1-(4'-{4-[(3-Benzyl-phenyl)-hydroxy-methyl]-3-methyl-isoxazol-5-yl}-biphenyl-4-yl)-cyclopropanecarboxylic acid (Compound 1-58)

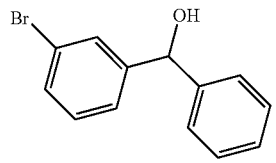

Step 1: (3-Bromo-phenyl)-phenyl-methanol

Prepared according to the procedure described in Example 25, Step 1, using 3-bromobenzaldehyde and phenylmagnesium bromide.

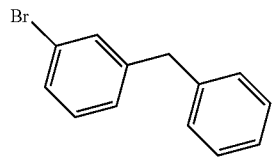

Step 2: 1-Benzyl-3-bromo-benzene (3-Bromo-phenyl)-phenyl-methanol (from previous step) was dissolved in diethyl ether (10 mL) and the solution was added dropwise to a suspension of lithium aluminum hydride (0.607 g, 16 mmol) and aluminum chloride (2.11 g, 16 mmol) stirring in THF (15 mL). The reaction was heated to 40° C. for 1 hour then cooled to 0° C., quenched with H₂O, and submitted to standard aqueous workup. The crude product was purified via silica gel chromatography (0-5% EtOAc in hexanes) to afford the title compound.

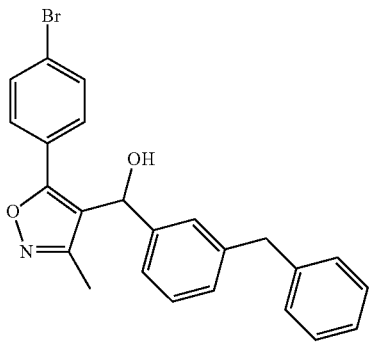 [SMILES: Cc1noc(-c2ccc(Br)cc2)c1C(O)c1cccc(Cc2ccccc2)c1]

Step 3: (3-Benzyl-phenyl)-[5-(4-bromo-phenyl)-3-methyl-isoxazol-4-yl]-methanol

1-Benzyl-3-bromo-benzene (0.811 g, 3.3 mmol) was dissolved in THF (2 mL), cooled to −78° C. and then n-butyllithium (2.0 M in THF, 1.65 mL, 3.3 mmol) was added dropwise. The reaction was stirred for 15 minutes then warmed to 0° C. and 5-(4-bromo-phenyl)-3-methyl-isoxazole-4-carbaldehyde (1.05 g, 3.96 mmol) was added. The reaction was allowed to warm to room temperature while stirring for 1 hour. The reaction was quenched with aqueous ammonium chloride then submitted to standard aqueous workup and silica gel chromatography to give the title compound.

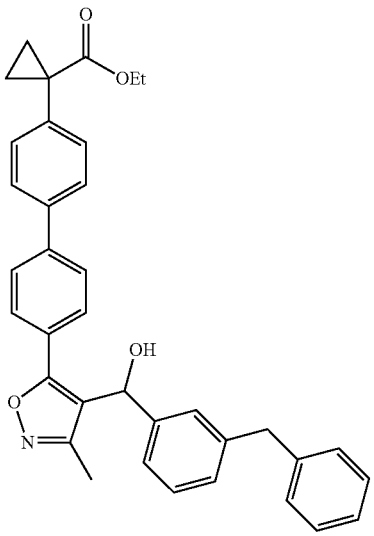

Step 4: 1-(4'-{4-[(3-Benzyl-phenyl)-hydroxy-methyl]-3-methyl-isoxazol-5-yl}-biphenyl-4-yl)-cyclopropanecarboxylic acid ethyl ester Prepared according to the procedure described in Example 28, Step 1, using (3-benzyl-phenyl)-[5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester.

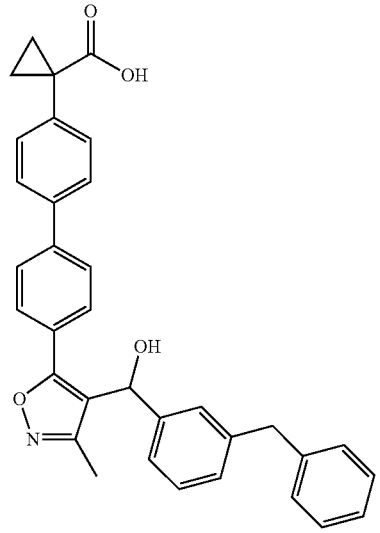 [SMILES: Cc1noc(-c2ccc(-c3ccc(C4(C(=O)O)CC4)cc3)cc2)c1C(O)c1cccc(Cc2ccccc2)c1]

Step 5: 1-(4'-{4-[(3-Benzyl-phenyl)-hydroxy-methyl]-3-methyl-isoxazol-5-yl}-biphenyl-4-yl)-cyclopropanecarboxylic acid Prepared according to the procedure described in Example 1, Step 13, using 1-(4'-{4-[(3-benzyl-phenyl)-hydroxy-methyl]-3-methyl-isoxazol-5-yl}-biphenyl-4-yl)-cyclopropanecarboxylic acid ethyl ester.

Example 59

1-(4'-{4-[(5-Benzyl-pyridin-3-yl)-hydroxy-methyl]-3-methyl-isoxazol-5-yl}-biphenyl-4-yl)-cyclopropanecarboxylic acid (Compound 1-59)

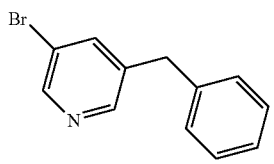 [SMILES: Brc1cncc(Cc2ccccc2)c1]

Step 1: 3-Benzyl-5-bromo-pyridine

Benzylmagnesium bromide (1.0 M in THF, 20 mL, 20 mmol) was added to a solution of zinc chloride (2.73 g, 20 mmol) in THF (20 mL) and the reaction was heated to 50° C. for 2.5 hours. The solution was then added by canula to a solution of 3,5-dibromo-pyridine (3.07 g, 13 mmol), copper (I) iodide (0.0148 g, 0.78 mmol), and (1,1'-bis(diphenylphosphino)ferrocene)-dichloropalladium(II) (0.048 g, 0.65 mmol) in THF (20 mL). The reaction was heated to 50° C. for 48 hours then quenched with H₂O, submitted to standard aqueous workup, and purified via silica gel chromatography (0-50% EtOAc in hexanes) to give the title compound.

Step 2: (5-Benzyl-pyridin-3-yl)-[5-(4-bromo-phenyl)-3-methyl-isoxazol-4-yl]-methanol

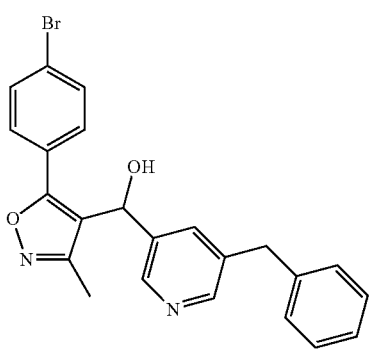 [SMILES: Cc1noc(-c2ccc(Br)cc2)c1C(O)c1cncc(Cc2ccccc2)c1]

3-Benzyl-5-bromo-pyridine (0.474 g, 1.91 mmol) was dissolved in THF (10 mL) and cooled to 0° C. Isopropylmagnesium chloride (2 M in THF, 0.96 mL, 1.91 mmol) was added dropwise and the reaction was allowed to warm to room temperature and stirred for 1 hour. Analytical LCMS indicated no reaction so an additional portion of isopropylmagnesium chloride (1.91 mmol) was added and the reaction stirred for 1 hour at room temperature. Analytical LCMS still indicated no progress so the reaction was cooled to −78° C. and n-butyllithium (2.5 M in hexanes, 0.764 mL, 1.91 mL) was added. The reaction was allowed to slowly warm to 0° C. then 5-(4-bromo-phenyl)-3-methyl-isoxazole-4-carbaldehyde (0.610 g, 2.29 mmol) was added and the reaction was allowed to warm to room temperature. The reaction was quenched with $H_2O$, submitted to standard aqueous workup and then purified via silica gel chromatography to yield the title compound.

Step 3: 1-(4'-{4-[(5-Benzyl-pyridin-3-yl)-hydroxy-methyl]-3-methyl-isoxazol-5-yl}-biphenyl-4-yl)-cyclopropanecarboxylic acid ethyl ester

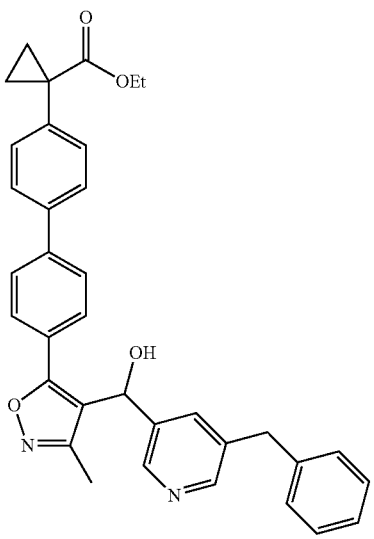 [SMILES: Cc1noc(-c2ccc(-c3ccc(C4(C(=O)O)CC4)cc3)cc2)c1C(O)c1cncc(Cc2ccccc2)c1]

Prepared according to the procedure described in Example 28, Step 1, using (5-benzyl-pyridin-3-yl)-[5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester.

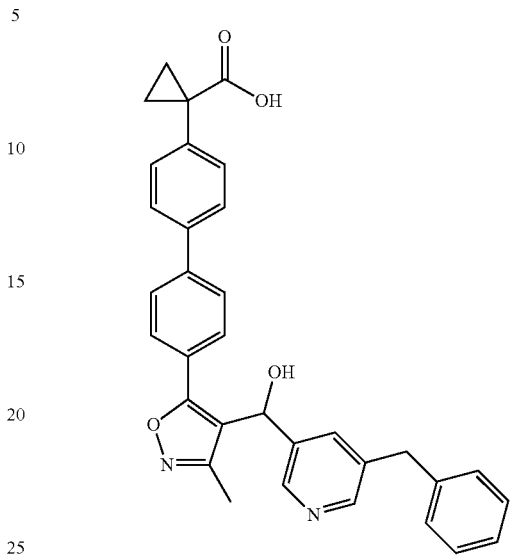

Step 4: 1-(4'-{4-[(5-Benzyl-pyridin-3-yl)-hydroxy-methyl]-3-methyl-isoxazol-5-yl}-biphenyl-4-yl)-cyclopropanecarboxylic acid Prepared according to the procedure described in Example 1, Step 13, using 1-(4'-{4-[(5-benzyl-pyridin-3-yl)-hydroxy-methyl]-3-methyl-isoxazol-5-yl}-biphenyl-4-yl)-cyclopropanecarboxylic acid ethyl ester.

Example 60

[1-(4'-{4-[(5-Benzyl-[1,3,4]oxadiazol-2-yl)-hydroxy-methyl]-3-methyl-isoxazol-5-yl}-biphenyl-4-yl)-cyclopropyl]-acetic acid (Compound 1-60)

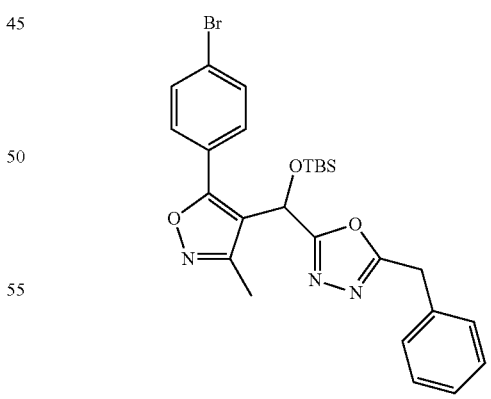

Step 1: 2-Benzyl-5-[[5-(4-bromo-phenyl)-3-methyl-isoxazol-4-yl]-(tert-butyl-dimethyl-silanyloxy)-methyl]-[1,3,4]oxadiazole (5-Benzyl-[1,3,4]oxadiazol-2-yl)-[5-(4-bromo-phenyl)-3-methyl-isoxazol-4-yl]-methanol (0.537 g, 1.26 mmol), tertbutyldimethylsilyl chloride (0.209 g, 3.78 mmol) and imidazole (0.095 g, 3.78 mmol) were combined in DMF (8 mL) and stirred at room temperature for 72 hours. Standard aqueous workup and silica gel chromatography (0-10% EtOAc in hexanes) gave the title compound.

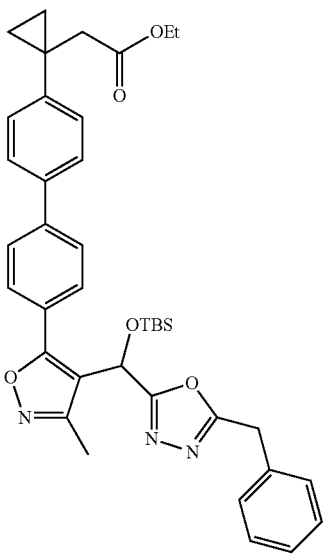 [SMILES: CCOC(=O)CC1(c2ccc(-c3ccc(-c4onc(C)c4C(O[Si](C)(C)C(C)(C)C)c4nnc(Cc5ccccc5)o4)cc3)cc2)CC1]

Step 2: [1-(4'-{4-[(5-Benzyl-[1,3,4]oxadiazol-2-yl)-(tert-butyl-dimethyl-silanyloxy)-methyl]-3-methyl-isoxazol-5-yl}-biphenyl-4-yl)-cyclopropyl]-acetic acid ethyl ester Prepared according to the procedure described in Example 1, Step 10, using 2-benzyl-5-[[5-(4-bromo-phenyl)-3-methyl-isoxazol-4-yl]-(tert-butyl-dimethyl-silanyloxy)-methyl]-[1,3,4]oxadiazole and {1-[4-(4,4,5,5-tetramethyl-[1,3,2]dioxaborolan-2-yl)-phenyl]-cyclopropyl}-acetic acid ethyl ester.

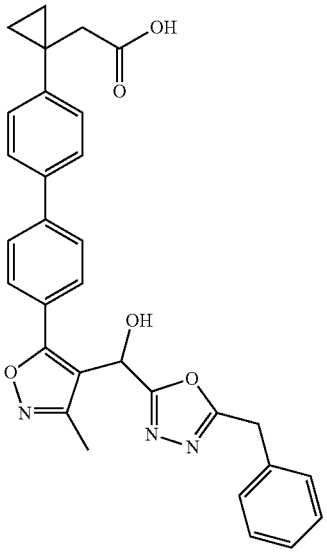 [SMILES: Cc1noc(-c2ccc(-c3ccc(C4(CC(=O)O)CC4)cc3)cc2)c1C(O)c1nnc(Cc2ccccc2)o1]

Step 3: [1-(4'-{4-[(5-Benzyl-[1,3,4]oxadiazol-2-yl)-hydroxy-methyl]-3-methyl-isoxazol-5-yl}-biphenyl-4-yl)-cyclopropyl]-acetic acid Prepared according to the procedure described in Example 1, Step 13, using [1-(4'-{4-[(5-Benzyl-[1,3,4]oxadiazol-2-yl)-(tert-butyl-dimethyl-silanyloxy)-methyl]-3-methyl-isoxazol-5-yl}-biphenyl-4-yl)-cyclopropyl]-acetic acid ethyl ester.

Example 61

1-[4'-(4-{[1-(2-Chloro-benzyl)-1H-[1,2,3]triazol-4-yl]-hydroxy-methyl}-3-methyl-isoxazol-5-yl)-biphenyl-4-yl]-cyclopropanecarboxylic acid (Compound 1-61)

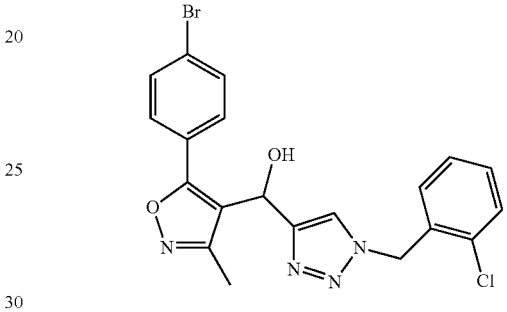

Step 1: [5-(4-Bromo-phenyl)-3-methyl-isoxazol-4-yl]-[1-(2-chloro-benzyl)-1H-[1,2,3]triazol-4-yl]-methanol Prepared according to the procedure described in Example 50, Step 1, using 1-[5-(4-bromo-phenyl)-3-methyl-isoxazol-4-yl]-prop-2-yn-1-ol and 1-bromomethyl-2-chloro-benzene.

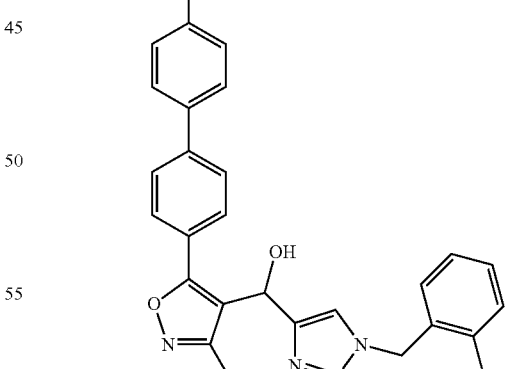

Step 2: 1-[4'-(4-{[1-(2-Chloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester Prepared according to the procedure described in Example 1, Step 10, using [5-(4-Bromo-phenyl)-3-methyl-isoxazol-4- yl]-[1-(2-chloro-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

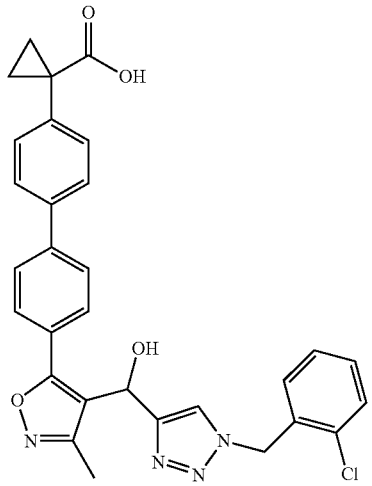 [SMILES: Cc1noc(-c2ccc(-c3ccc(C4(C(=O)O)CC4)cc3)cc2)c1C(O)c1cn(Cc2ccccc2Cl)nn1]

Step 3: 1-[4'-(4-{[1-(2-Chloro-benzyl)-1H-[1,2,3]triazol-4-yl]-hydroxy-methyl}-3-methyl-isoxazol-5-yl)-biphenyl-4-yl]-cyclopropanecarboxylic acid Prepared according to the procedure described in Example 1, Step 13, using [1-(4'-{4-[(5-Benzyl-[1,3,4]oxadiazol-2-yl)-(tert-butyl-dimethyl-silanyloxy)-methyl]-3-methyl-isoxazol-5-yl}-biphenyl-4-yl)-cyclopropyl]-acetic acid ethyl ester.

Example 62

1-[4'-(4-{[1-(4-Chloro-benzyl)-1H-[1,2,3]triazol-4-yl]-hydroxy-methyl}-3-methyl-isoxazol-5-yl)-biphenyl-4-yl]-cyclopropanecarboxylic acid (Compound 1-62)

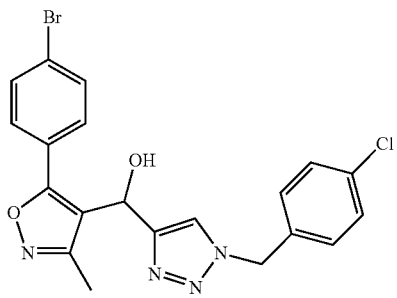 [SMILES: Cc1noc(-c2ccc(Br)cc2)c1C(O)c1cn(Cc2ccc(Cl)cc2)nn1]

Step 1: [5-(4-Bromo-phenyl)-3-methyl-isoxazol-4-yl]-[1-(4-chloro-benzyl)-1H-[1,2,3]triazol-4-yl]-methanol Prepared according to the procedure described in Example 50, Step 1, using 1-[5-(4-bromo-phenyl)-3-methyl-isoxazol-4-yl]-prop-2-yn-1-ol and 1-bromomethyl-4-chloro-benzene.

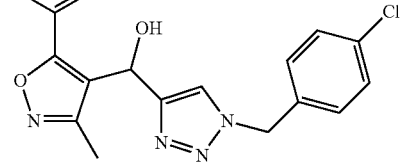

Step 2: 1-[4'-(4-{[1-(4-Chloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester Prepared according to the procedure described in Example 1, Step 10, using [5-(4-Bromo-phenyl)-3-methyl-isoxazol-4-yl]-[1-(4-chloro-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

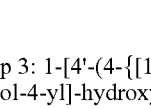

Step 3: 1-[4'-(4-{[1-(4-Chloro-benzyl)-1H-[1,2,3]triazol-4-yl]-hydroxy-methyl}-3-methyl-isoxazol-5-yl)-biphenyl-4-yl]-cyclopropanecarboxylic acid Prepared according to the procedure described in Example 1, Step 13, using 1-[4'-(4-{[1-(4-chloro-benzyl)-1H-[1,2,3]

triazol-4-yl]-hydroxy-methyl}-3-methyl-isoxazol-5-yl)-biphenyl-4-yl]-cyclopropanecarboxylic acid ethyl ester.

Example 63

1-[4'-(4-{(R)-[1-(2-Chloro-benzyl)-1H-[1,2,3]triazol-4-yl]-hydroxy-methyl}-3-methyl-isoxazol-5-yl)-biphenyl-4-yl]-cyclopropanecarboxylic acid (Compound 1-63)

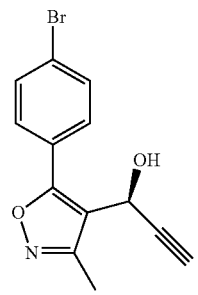 [SMILES: C#C[C@H](O)c1c(C)noc1-c1ccc(Br)cc1]

Step 1: (S)-1-[5-(4-Bromo-phenyl)-3-methyl-isoxazol-4-yl]-prop-2-yn-1-ol

Zinc triflate (0.75 g, 2.1 mmol), (1S,2R)-(+)-N-methylephedrine (0.41 g, 2.3 mmol) and triethylamine (0.23 g, 2.3 mmol) were stirred in toluene (10 mL) at room temperature for 2 hours. (Trimethylsilyl)acetylene (0.32 g, 2.3 mmol) was added and the reaction stirred for 15 minute then 5-(4-bromophenyl)-3-methyl-isoxazole-4-carbaldehyde (0.5 g, 1.9 mmol) was added and the reaction stirred at room temperature for 2 weeks. The reaction mixture was purified on by silica gel chromatography (0-20% EtOAc in hexanes) to afford the title product with 97.5% ee as measured by analytical chiral HPLC.

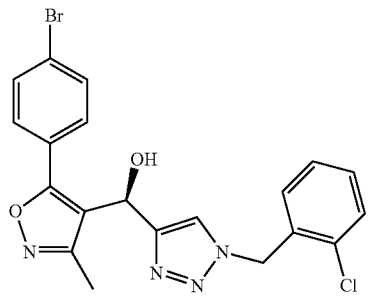 [SMILES: Cc1noc(-c2ccc(Br)cc2)c1[C@@H](O)c1cn(Cc2ccccc2Cl)nn1]

Step 2: (R)-[5-(4-Bromo-phenyl)-3-methyl-isoxazol-4-yl]-[1-(2-chloro-benzyl)-1H-[1,2,3]triazol-4-yl]methanol Prepared according to the procedure described in Example 50, Step 1, using (S)-1-[5-(4-bromo-phenyl)-3-methyl-isoxazol-4-yl]-prop-2-yn-1-ol and 1-bromomethyl-2-chlorobenzene.

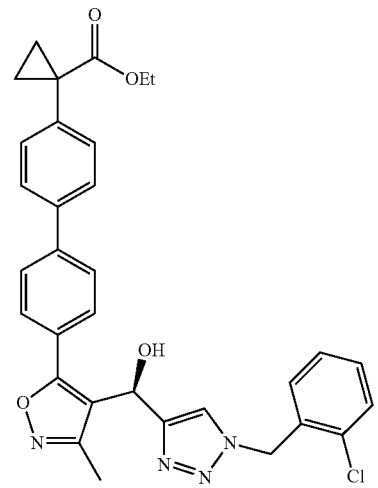 [SMILES: CCOC(=O)C1(c2ccc(-c3ccc(-c4onc(C)c4[C@@H](O)c4cn(Cc5ccccc5Cl)nn4)cc3)cc2)CC1]

Step 3: 1-[4'-(4-{(R)-[1-(2-Chloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester Prepared according to the procedure described in Example 1, Step 10, using (R)-[5-(4-bromo-phenyl)-3-methyl-isoxazol-4-yl]-[1-(2-chloro-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

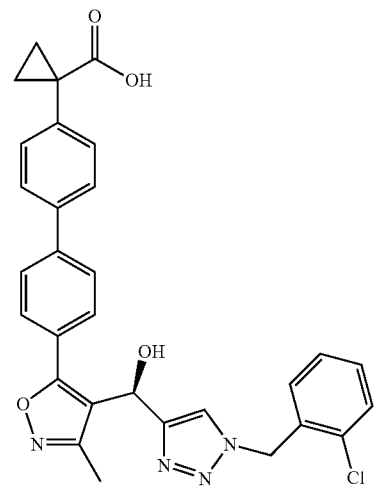 [SMILES: Cc1noc(-c2ccc(-c3ccc(C4(C(=O)O)CC4)cc3)cc2)c1[C@@H](O)c1cn(Cc2ccccc2Cl)nn1]

Step 4: 1-[4'-(4-{(R)-[1-(2-Chloro-benzyl)-1H-[1,2,3]triazol-4-yl]-hydroxy-methyl}-3-methyl-isoxazol-5-yl)-biphenyl-4-yl]-cyclopropanecarboxylic acid Prepared according to the procedure described in Example 1, Step 13, using 1-[4'-(4-{(R)-[1-(2-Chloro-benzyl)-1H-[1, 2,3]triazol-4-yl]-hydroxy-methyl}-3-methyl-isoxazol-5-yl)-biphenyl-4-yl]-cyclopropanecarboxylic acid ethyl ester.

Example 64

1-[4'-(4-{[1-(3,4-Dichloro-benzyl)-1H-[1,2,3]triazol-4-yl]-hydroxy-methyl}-3-methyl-isoxazol-5-yl)-biphenyl-4-yl]-cyclopropanecarboxylic acid (Compound 1-64)

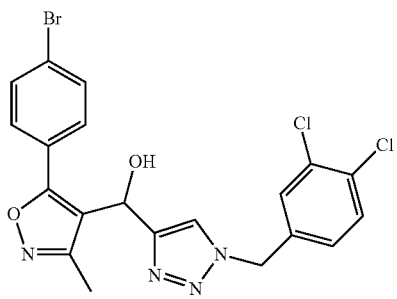 [SMILES: Cc1noc(-c2ccc(Br)cc2)c1C(O)c1cn(Cc2ccc(Cl)c(Cl)c2)nn1]

Step 1: [5-(4-Bromo-phenyl)-3-methyl-isoxazol-4-yl]-[1-(3,4-dichloro-benzyl)-1H-[1,2,3]triazol-4-yl]methanol Prepared according to the procedure described in Example 50, Step 1, using 1-[5-(4-bromo-phenyl)-3-methyl-isoxazol-4-yl]-prop-2-yn-1-ol and 4-bromomethyl-1,2-dichloro-benzene.

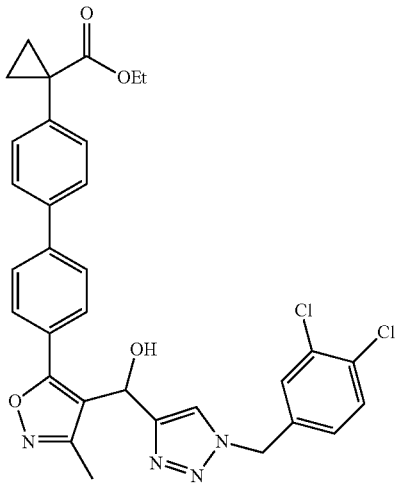

Step 2: 1-[4'-(4-{[1-(3,4-Dichloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester Prepared according to the procedure described in Example 1, Step 10, using [5-(4-bromo-phenyl)-3-methyl-isoxazol-4-yl]-[1-(3,4-dichloro-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

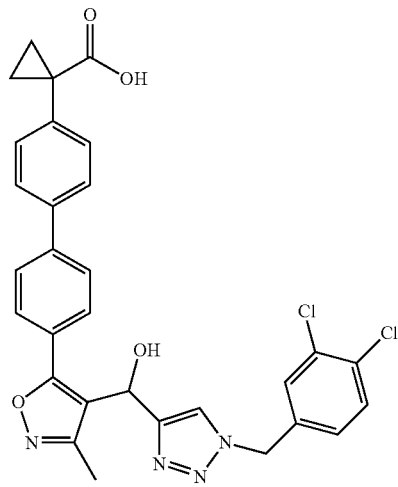 [SMILES: Cc1noc(-c2ccc(-c3ccc(C4(C(=O)O)CC4)cc3)cc2)c1C(O)c1cn(Cc2ccc(Cl)c(Cl)c2)nn1]

Step 3: 1-[4'-(4-{[1-(3,4-Dichloro-benzyl)-1H-[1,2,3]triazol-4-yl]-hydroxy-methyl}-3-methyl-isoxazol-5-yl)-biphenyl-4-yl]-cyclopropanecarboxylic acid Prepared according to the procedure described in Example 1, Step 13, using 1-[4'-(4-{[1-(3,4-dichloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester.

Example 65

[4'-(4-{[1-(3,4-Dichloro-benzyl)-1H-[1,2,3]triazol-4-yl]-hydroxy-methyl}-3-methyl-isoxazol-5-yl)-biphenyl-4-yl]-acetic acid (Compound 1-65)

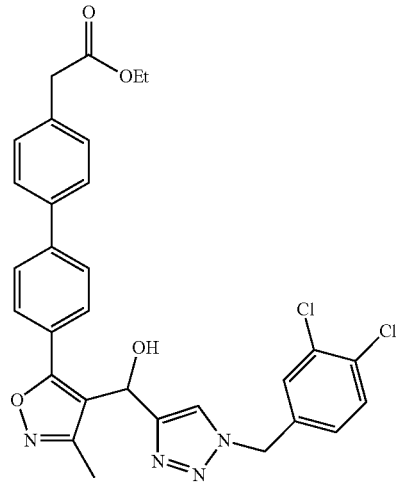 [SMILES: Cc1noc(-c2ccc(-c3ccc(CC(=O)O)cc3)cc2)c1C(O)c1cn(Cc2ccc(Cl)c(Cl)c2)nn1]

Step 1: [4'-(4-{[1-(3,4-Dichloro-benzyl)-1H-[1,2,3]triazol-4-yl]-hydroxy-methyl}-3-methyl-isoxazol-5-yl)-biphenyl-4-yl]acetic acid ethyl ester Prepared according to the procedure described in Example 1, Step 10, using [5-(4-bromo-phenyl)-3-methyl-isoxazol-4-yl]-[1-(3,4-dichloro-benzyl)-1H-[1,2,3]triazol-4-yl]-methanol and [4-(4,4,5,5-tetramethyl-[1,3,2]dioxaborolan-2-yl)-phenyl]-acetic acid ethyl ester.

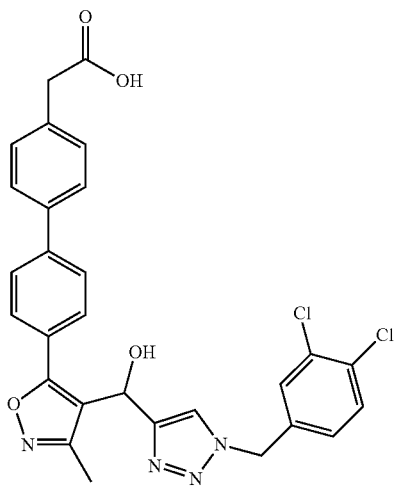

Step 2: [4'-(4-{[1-(3,4-Dichloro-benzyl)-1H-[1,2,3]triazol-4-yl]-hydroxy-methyl}-3-methyl-isoxazol-5-yl)-biphenyl-4-yl]-acetic acid Prepared according to the procedure described in Example 1, Step 13, using [4'-(4-{[1-(3,4-dichloro-benzyl)-1H-[1,2,3]triazol-4-yl]-hydroxy-methyl}-3-methyl-isoxazol-5-yl)-biphenyl-4-yl]-acetic acid ethyl ester.

Example 66

1-(4'-{3-Methyl-4-[trans-1-(2-phenyl-cyclopropyl)-ethylamino]-isoxazol-5-yl}-biphenyl-4-yl)-cyclopropanecarboxylic acid (Compound 1-66)

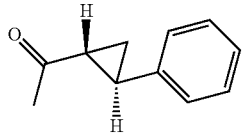

Step 1: trans-1-(2-Phenyl-cyclopropyl)-ethanone trans-2-Phenyl-1-cyclopropanecarboxylic acid (2.0 g, 12.3 mmol) was dissolved in diethyl ether (40 mL) and cooled to 0° C. Methyllithium (1.6 M in hexanes, 16.8 mL, 27 mmol) was added dropwise and then the reaction stirred for 1 hour. The reaction was quenched with MeOH then submitted to standard aqueous workup and silica gel chromatography (0-40% EtOAc in hexanes) to afford the title compound.

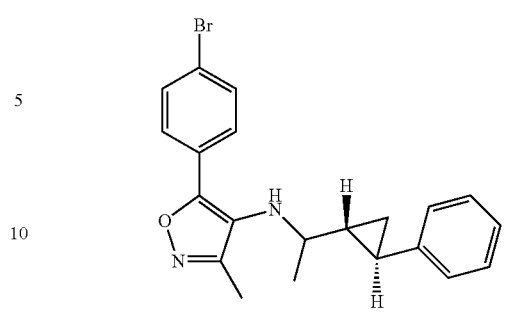

Step 2: [5-(4-Bromo-phenyl)-3-methyl-isoxazol-4-yl]-[trans-1-(2-phenyl-cyclopropyl)-ethyl]-amine Prepared according to the procedure described in Example 1, Step 12, using 5-(4-bromo-phenyl)-3-methyl-isoxazol-4-ylamine and trans-1-(2-phenyl-cyclopropyl)-ethanone.

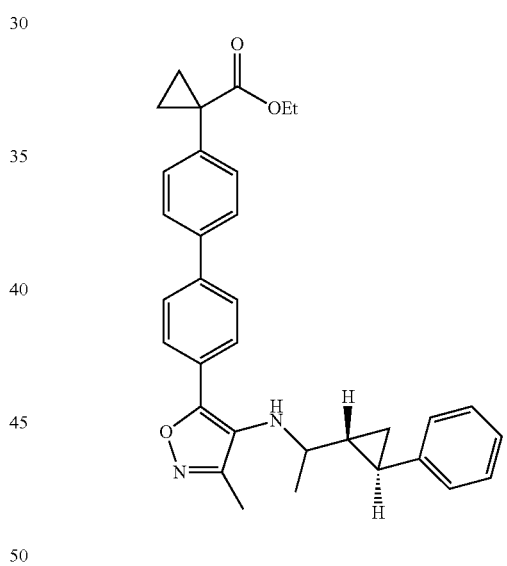

Step 3: 1-(4'-{3-Methyl-4-[trans-1-(2-phenyl-cyclopropyl)-ethylamino]-isoxazol-5-yl}-biphenyl-4-yl)-cyclopropanecarboxylic acid ethyl ester Prepared according to the procedure described in Example 42, Step 2, using [5-(4-bromo-phenyl)-3-methyl-isoxazol-4-yl]-[trans-1-(2-phenyl-cyclopropyl)-ethyl]-amine and 1-[4-(4,4,5,5-tetramethyl-[1,3,2]dioxaborolan-2-yl)-phenyl]-cyclopropanecarboxylic acid ethyl ester.

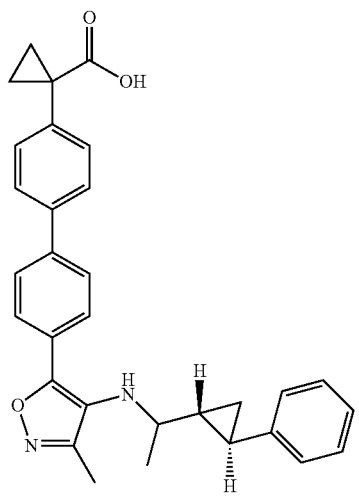 [SMILES: Cc1noc(-c2ccc(-c3ccc(C4(C(=O)O)CC4)cc3)cc2)c1NC(C)[C@@H]1C[C@H]1c1ccccc1]

Step 4: 1-(4'-{3-Methyl-4-[trans-1-(2-phenyl-cyclopropyl)-ethylamino]-isoxazol-5-yl}-biphenyl-4-yl)-cyclopropanecarboxylic acid ethyl ester Prepared according to the procedure described in Example 1, Step 13, using 1-(4'-{3-Methyl-4-[trans-1-(2-phenyl-cyclopropyl)-ethylamino]-isoxazol-5-yl}-biphenyl-4-yl)-cyclopropanecarboxylic acid ethyl ester.

Example 67

1-[4'-(4-{(R)-Hydroxy-[1-((R)-1-phenyl-ethyl)-1H-[1,2,3]triazol-4-yl]-methyl}-3-methyl-isoxazol-5-yl)-biphenyl-4-yl]-cyclopropanecarboxylic acid (Compound 1-67)

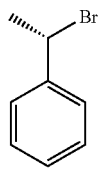

Step 1: ((S)-1-Bromo-ethyl)-benzene

Bromine (3.2 g, 20.0 mmol) was added to a suspension of triphenylphosphine (5.2 g, 19.8 mmol) stirring in ACN at −15° C. The reaction was warmed to room temperature and stirred for 50 minutes then cooled to −35° C. and (R)-(+)-1-phenylethanol (1.6 g, 13.1 mmol) was added. The reaction was allowed to warm to −10° C. over 70 minutes and was then quenched with $H_2O$ and submitted to standard aqueous workup to afford the title compound which was used without further purification.

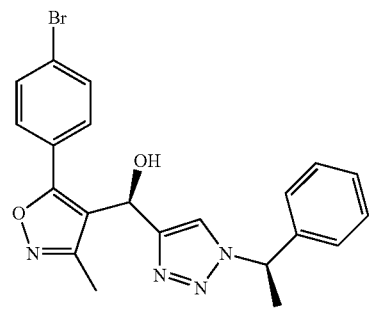 [SMILES: Cc1noc(-c2ccc(Br)cc2)c1[C@@H](O)c1cn([C@H](C)c2ccccc2)nn1]

Step 2: (R)-[5-(4-Bromo-phenyl)-3-methyl-isoxazol-4-yl]-[1-((R)-1-phenyl-ethyl)-1H-[1,2,3]triazol-4-yl]-methanol Prepared according to the procedure described in Example 50, Step 1, using (S)-1-[5-(4-bromo-phenyl)-3-methyl-isoxazol-4-yl]-prop-2-yn-1-ol and ((R)-1-bromo-ethyl)-benzene.

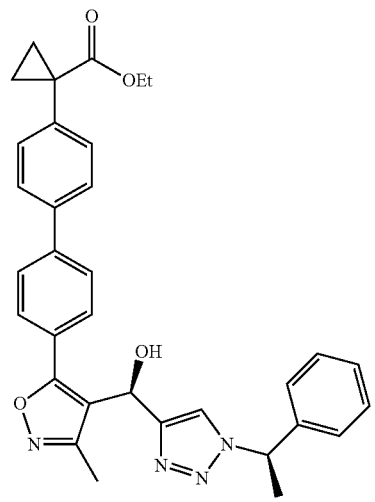 [SMILES: CCOC(=O)C1(c2ccc(-c3ccc(-c4onc(C)c4[C@@H](O)c4cn([C@H](C)c5ccccc5)nn4)cc3)cc2)CC1]

Step 3: 1-[4'-(4-{(R)-Hydroxy-[1-((R)-1-phenyl-ethyl)-1H-[1,2,3]triazol-4-yl]-methyl}-3-methyl-isoxazol-5-yl)-biphenyl-4-yl]-cyclopropanecarboxylic acid ethyl ester Prepared according to the procedure described in Example 1, Step 10, using (R)-[5-(4-Bromo-phenyl)-3-methyl-isoxazol-4-yl]-[1-((R)-1-phenyl-ethyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

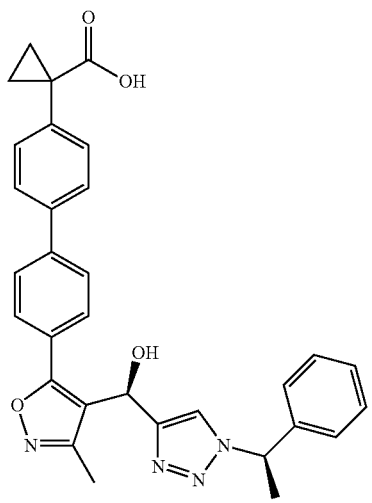 [SMILES: Cc1noc(-c2ccc(-c3ccc(C4(C(=O)O)CC4)cc3)cc2)c1[C@@H](O)c1cn([C@H](C)c2ccccc2)nn1]

Step 4: 1-[4'-(4-{(R)-Hydroxy-[1-((R)-1-phenyl-ethyl)-1H-[1,2,3]triazol-4-yl]-methyl}-3-methyl-isoxazol-5-yl)-biphenyl-4-yl]-cyclopropanecarboxylic acid Prepared according to the procedure described in Example 1, Step 13, using 1-[4'-(4-{(R)-hydroxy-[1-((R)-1-phenyl-ethyl)-1H-[1,2,3]triazol-4-yl]-methyl}-3-methyl-isoxazol-5-yl)-biphenyl-4-yl]-cyclopropanecarboxylic acid ethyl ester.

Example 68

1-{4'-[3-Methyl-4-(6-phenyl-pyridin-2-ylamino)-isoxazol-5-yl]-biphenyl-4-yl}-cyclopropanecarboxylic acid (Compound 1-68)

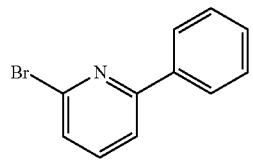

Step 1: 2-Bromo-6-phenyl-pyridine 2,6-Dibromo-pyridine (1.2 g, 0.508 mmol), phenylboronic acid (0.620 g, 0.508 mmol) and sodium carbonate (2 M aq., 30 mL) were dissolved in MeOH (10 mL) and toluene (30 mL) and the solution was degassed with bubbling $N_2$ (g). Tetrakis(triphenylphosphine)palladium(0) (0.172 g, 0.149 mmol) was added and the reaction was heated to 100° C. overnight. After cooling the reaction was submitted to standard aqueous workup and purified by silica gel chromatography to give the title compound

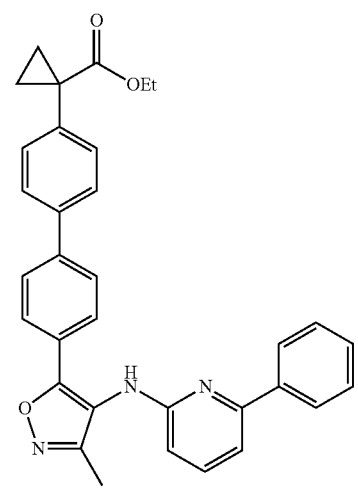 [SMILES: CCOC(=O)C1(c2ccc(-c3ccc(-c4onc(C)c4Nc4cccc(-c5ccccc5)n4)cc3)cc2)CC1]

Step 2: 1-{4'-[3-Methyl-4-(6-phenyl-pyridin-2-ylamino)-isoxazol-5-yl]-biphenyl-4-yl}-cyclopropanecarboxylic acid ethyl ester 1-[4'-(4-Amino-3-methyl-isoxazol-5-yl)-biphenyl-4-yl]-cyclopropanecarboxylic acid ethyl ester (0.250 g, 0.689 mmol), 2-bromo-6-phenyl-pyridine (0.1457 g, 0.62 mmol), cesium carbonate (0.2694 g, 0.826 mmol) and (±)-2,2'-bis(diphenylphosphino)-1,1'-binaphthyl (0.032 g, 0.052 mmol) were dissolved in toluene (3 mL) and the solution was degassed with bubbling $N_2$ (g). Tris(dibenzylideneacetone)dipalladium(0) (0.0158 g, 0.017 mmol) was added and the reaction was heated to 110° C. for 24 hours. After cooling the reaction was submitted to standard aqueous workup and silica gel chromatography to afford the title compound.

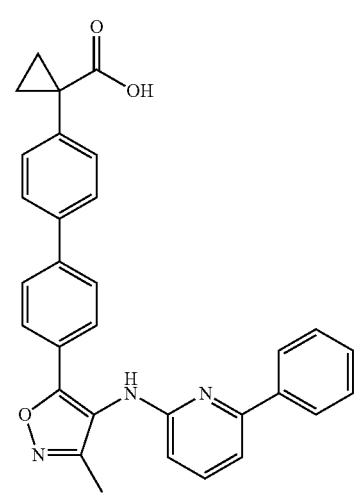 [SMILES: Cc1noc(-c2ccc(-c3ccc(C4(C(=O)O)CC4)cc3)cc2)c1Nc1cccc(-c2ccccc2)n1]

Step 3: 1-{4'-[3-Methyl-4-(6-phenyl-pyridin-2-ylamino)-isoxazol-5-yl]-biphenyl-4-yl}-cyclopropanecarboxylic acid Prepared according to the procedure described in Example 1, Step 13, using 1-{4'-[3-methyl-4-(6-phenyl-pyridin-2-ylamino)-isoxazol-5-yl]-biphenyl-4-yl}-cyclopropanecarboxylic acid ethyl ester.

Example 69

1-(4'-{4-[(6-Benzyl-pyridin-2-yl)-hydroxy-methyl]-3-methyl-isoxazol-5-yl}-biphenyl-4-yl)-cyclopropanecarboxylic acid (Compound 1-69)

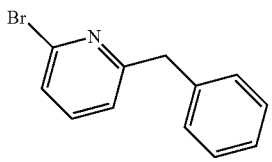 [SMILES: Brc1cccc(Cc2ccccc2)n1]

Step 1: 2-Benzyl-6-bromo-pyridine 2,6-Dibromopyridine (2.36 g, 1 mmol), benzylzinc bromide (0.9 M in THF, 1.05 mL, 0.95 mmol) and tetrakis(triphenylphosphine)palladium(0) (0.012 g, 0.01 mmol) were placed in THF (75 mL) and heated to 60° C. for 20 hours. The reaction mixture was cooled, submitted to standard aqueous workup and purified on silica gel to afford the title compound.

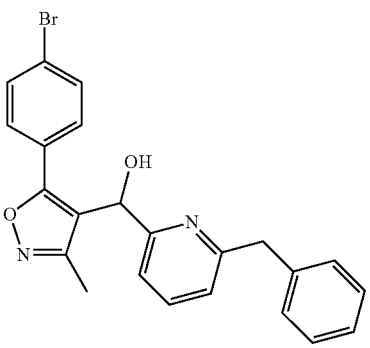 [SMILES: Cc1noc(-c2ccc(Br)cc2)c1C(O)c1cccc(Cc2ccccc2)n1]

Step 2: (6-Benzyl-pyridin-2-yl)-[5-(4-bromo-phenyl)-3-methyl-isoxazol-4-yl]-methanol Prepared according to the procedure described in Example 58, Step, using 5-(4-bromo-phenyl)-3-methyl-isoxazole-4-carbaldehyde and 2-benzyl-6-bromo-pyridine.

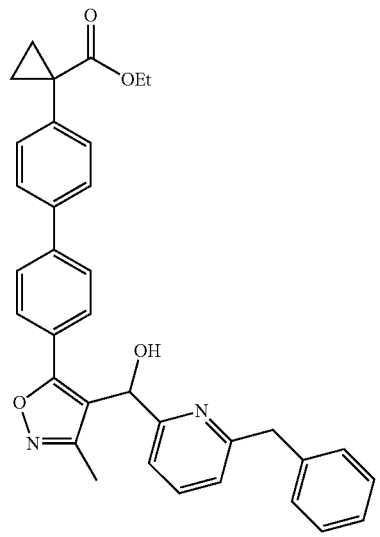 [SMILES: CCOC(=O)C1(c2ccc(-c3ccc(-c4onc(C)c4C(O)c4cccc(Cc5ccccc5)n4)cc3)cc2)CC1]

Step 3: 1-(4'-{4-[(6-Benzyl-pyridin-2-yl)-hydroxy-methyl]-3-methyl-isoxazol-5-yl}-biphenyl-4-yl)-cyclopropanecarboxylic acid ethyl ester Prepared according to the procedure described in Example 42, Step 2, using (6-benzyl-pyridin-2-yl)-[5-(4-bromo-phenyl)-3-methyl-isoxazol-4-yl]-methanol and 1-[4-(4,4,5,5-tetramethyl-[1,3,2]dioxaborolan-2-yl)-phenyl]-cyclopropanecarboxylic acid ethyl ester.

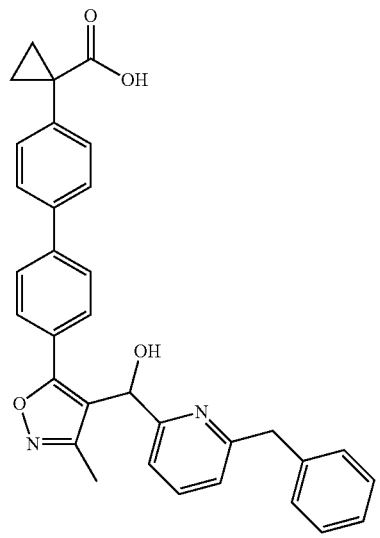 [SMILES: Cc1noc(-c2ccc(-c3ccc(C4(C(=O)O)CC4)cc3)cc2)c1C(O)c1cccc(Cc2ccccc2)n1]

Step 4: 1-(4'-{4-[(6-Benzyl-pyridin-2-yl)-hydroxy-methyl]-3-methyl-isoxazol-5-yl}-biphenyl-4-yl)-cyclopropanecarboxylic acid Prepared according to the procedure described in Example 1, Step 13, using 1-(4'-{4-[(6-benzyl-pyridin-2-yl)-hydroxymethyl]-3-methyl-isoxazol-5-yl}-biphenyl-4-yl)-cyclopropanecarboxylic acid ethyl ester.

Example 70

1-[4'-(4-{Hydroxy-[1-(2-methyl-benzyl)-1H-[1,2,3]triazol-4-yl]-methyl}-3-methyl-isoxazol-5-yl)-biphenyl-4-yl]-cyclopropanecarboxylic acid (Compound 1-70)

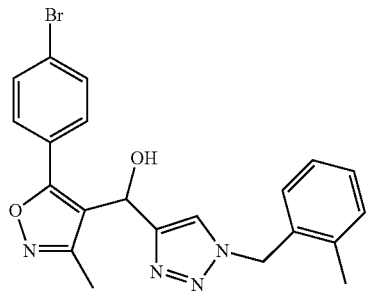 [SMILES: Cc1ccccc1Cn1cc(C(O)c2c(C)noc2-c2ccc(Br)cc2)nn1]

Step 1: [5-(4-Bromo-phenyl)-3-methyl-isoxazol-4-yl]-[1-(2-methyl-benzyl)-1H-[1,2,3]triazol-4-yl]methanol Prepared according to the procedure described in Example 50, Step 1, using 1-[5-(4-bromo-phenyl)-3-methyl-isoxazol-4-yl]-prop-2-yn-1-ol and 1-bromomethyl-2-methyl-benzene.

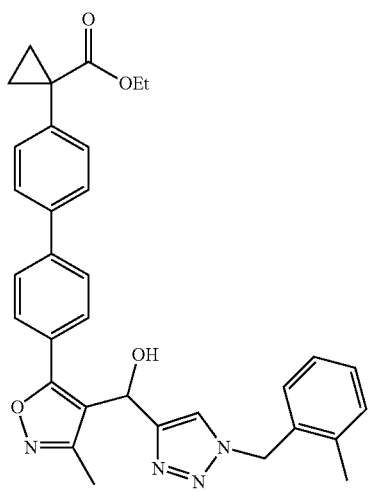 [SMILES: CCOC(=O)C1(c2ccc(-c3ccc(-c4onc(C)c4C(O)c4cn(Cc5ccccc5C)nn4)cc3)cc2)CC1]

Step 2: 1-[4'-(4-{Hydroxy-[1-(2-methyl-benzyl)-1H-[1,2,3]triazol-4-yl-]methyl}-3-methyl-isoxazol-5-yl)-biphenyl-4-yl]-cyclopropanecarboxylic acid ethyl ester Prepared according to the procedure described in Example 1, Step 10, using [5-(4-bromo-phenyl)-3-methyl-isoxazol-4-yl]-[1-(2-methyl-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

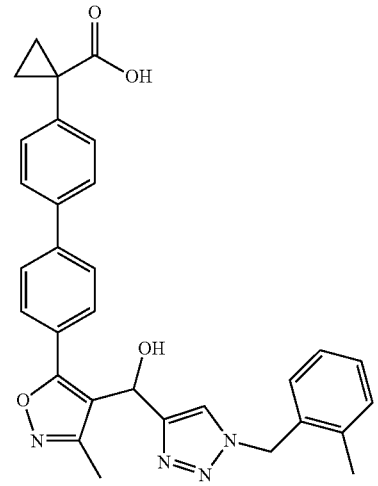

Step 3: 1-[4'-(4-{Hydroxy-[1-(1-phenyl-ethyl)-1H-[1,2,3]triazol-4-yl]-methyl}-3-methyl-isoxazol-5-yl)-biphenyl-4-yl]-cyclopropanecarboxylic acid Prepared according to the procedure described in Example 1, Step 13, using 1-[4'-(4-{hydroxy-[1-(2-methyl-benzyl)-1H-[1,2,3]triazol-4-yl]-methyl}-3-methyl-isoxazol-5-yl)-biphenyl-4-yl]-cyclopropanecarboxylic acid ethyl ester.

Example 71

1-[4'-(4-{[1-(2-Chloro-6-fluoro-benzyl)-1H-[1,2,3]triazol-4-yl]-hydroxy-methyl}-3-methyl-isoxazol-5-yl)-biphenyl-4-yl]-cyclopropanecarboxylic acid (Compound 1-71)

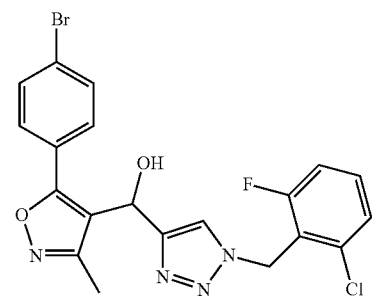 [SMILES: Cc1noc(-c2ccc(Br)cc2)c1C(O)c1cn(Cc2c(F)cccc2Cl)nn1]

Step 1: [5-(4-Bromo-phenyl)-3-methyl-isoxazol-4-yl]-[1-(2-chloro-6-fluoro-benzyl)-1H-[1,2,3]triazol-4-yl]-methanol Prepared according to the procedure described in Example 50, Step 1, using 1-[5-(4-bromo-phenyl)-3-methyl-isoxazol-4-yl]-prop-2-yn-1-ol and 2-bromomethyl-1-chloro-3-fluoro-benzene.

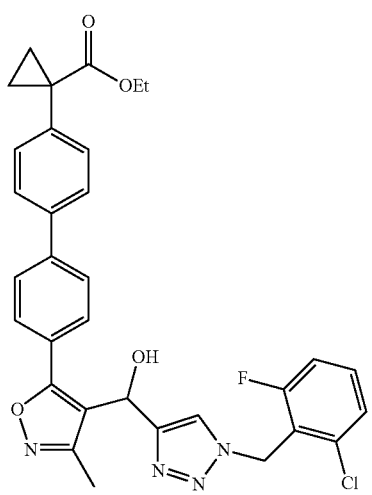

Step 2: 1-[4'-(4-{[1-(2-Chloro-6-fluoro-benzyl)-1H-[1,2,3]triazol-4-yl]-hydroxy-methyl}-3-methyl-isoxazol-5-yl)-biphenyl-4-yl]-cyclopropanecarboxylic acid ethyl ester Prepared according to the procedure described in Example 1, Step 10, using [5-(4-bromo-phenyl)-3-methyl-isoxazol-4-yl]-[1-(2-chloro-6-fluoro-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

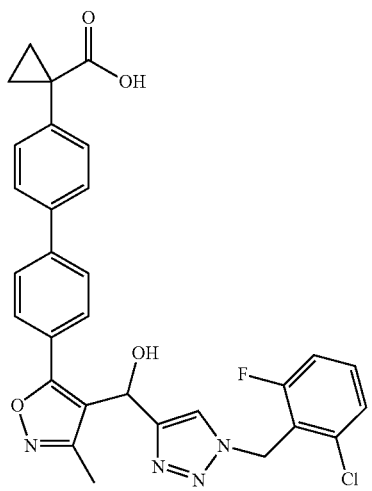 [SMILES: Cc1noc(-c2ccc(-c3ccc(C4(C(=O)O)CC4)cc3)cc2)c1C(O)c1cn(Cc2c(F)cccc2Cl)nn1]

Step 3: 1-[4'-(4-{[1-(2-Chloro-6-fluoro-benzyl)-1H-[1,2,3]triazol-4-yl]-hydroxy-methyl}-3-methyl-isoxazol-5-yl)-biphenyl-4-yl]-cyclopropanecarboxylic acid Prepared according to the procedure described in Example 1, Step 13, using 1-[4'-(4-{[1-(2-Chloro-6-fluoro-benzyl)-1H-[1,2,3]triazol-4-yl]-hydroxy-methyl}-3-methyl-isoxazol-5-yl)-biphenyl-4-yl]-cyclopropanecarboxylic acid ethyl ester.

Example 72

1-[4'-(4-{[1-(2,6-Dichloro-benzyl)-1H-[1,2,3]triazol-4-yl]-hydroxy-methyl}-3-methyl-isoxazol-5-yl)-biphenyl-4-yl]-cyclopropanecarboxylic acid (Compound 1-72)

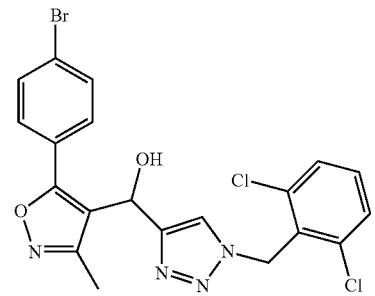 [SMILES: Cc1noc(-c2ccc(Br)cc2)c1C(O)c1cn(Cc2c(Cl)cccc2Cl)nn1]

Step 1: [5-(4-Bromo-phenyl)-3-methyl-isoxazol-4-yl]-[1-(2,6-dichloro-benzyl)-1H-[1,2,3]triazol-4-yl]methanol Prepared according to the procedure described in Example 50, Step 1, using 1-[5-(4-bromo-phenyl)-3-methyl-isoxazol-4-yl]-prop-2-yn-1-ol and 2-bromomethyl-1,3-dichloro-benzene.

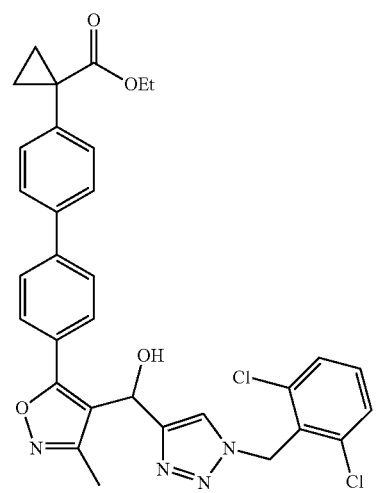 [SMILES: CCOC(=O)C1(c2ccc(-c3ccc(-c4onc(C)c4C(O)c4cn(Cc5c(Cl)cccc5Cl)nn4)cc3)cc2)CC1]

Step 2: 1-[4'-(4-{[1-(2,6-Dichloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester Prepared according to the procedure described in Example 1, Step 10, using [5-(4-bromo-phenyl)-3-methyl-isoxazol-4-yl]-[1-(2,6-dichloro-benzyl)-1H-[1,2,3]triazol-4-yl]-methanol and 1-[4-(4,4,5,5-tetramethyl-[1,3,2]dioxaborolan-2-yl)-phenyl]-cyclopropanecarboxylic acid ethyl ester.

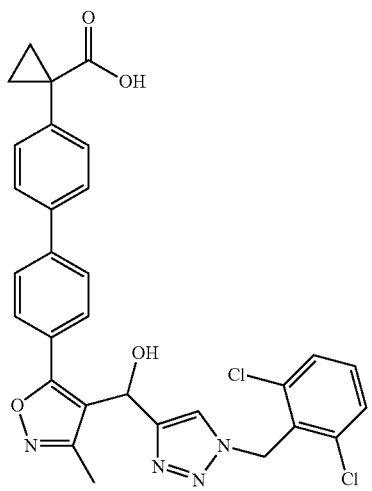 [SMILES: Cc1noc(-c2ccc(-c3ccc(C4(C(=O)O)CC4)cc3)cc2)c1C(O)c1cn(Cc2c(Cl)cccc2Cl)nn1]

Step 3: 1-[4'-(4-{[1-(2,6-Dichloro-benzyl)-1H-[1,2,3]triazol-4-yl]-hydroxy-methyl}-3-methyl-isoxazol-5-yl)-biphenyl-4-yl]-cyclopropanecarboxylic acid Prepared according to the procedure described in Example 1, Step 13, using 1-[4'-(4-{[1-(2,6-dichloro-benzyl)-1H-[1,2,3]triazol-4-yl]-hydroxy-methyl}-3-methyl-isoxazol-5-yl)-biphenyl-4-yl]-cyclopropanecarboxylic acid ethyl ester.

Example 73

1-{4'-[4-(6-Benzyl-pyridin-2-ylamino)-3-methyl-isoxazol-5-yl]-biphenyl-4-yl}-cyclopropanecarboxylic acid (Compound 1-73)

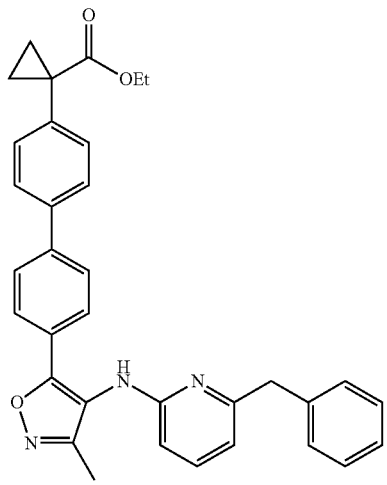

Step 1: 1-{4'-[4-(6-Benzyl-pyridin-2-ylamino)-3-methyl-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-benzyl-6-bromo-pyridine.

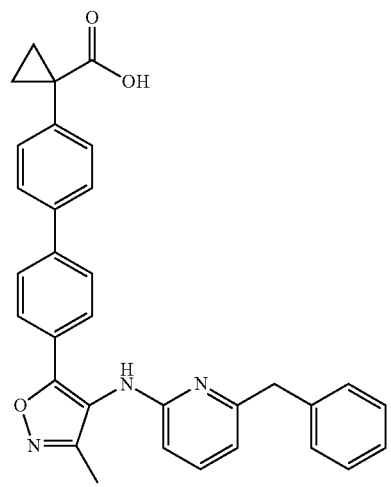

Step 2: 1-{4'-[4-(6-Benzyl-pyridin-2-ylamino)-3-methyl-isoxazol-5-yl]-biphenyl-4-yl}-cyclopropanecarboxylic acid Prepared according to the procedure described in Example 1, Step 13, using 1-{4'-[4-(6-benzyl-pyridin-2-ylamino)-3-methyl-isoxazol-5-yl]-biphenyl-4-yl}-cyclopropanecarboxylic acid ethyl ester.

Example 74

1-{4'-[4-(Biphenyl-3-ylamino)-3-methyl-isoxazol-5-yl]-biphenyl-4-yl}-cyclopropanecarboxylic acid (Compound 1-74)

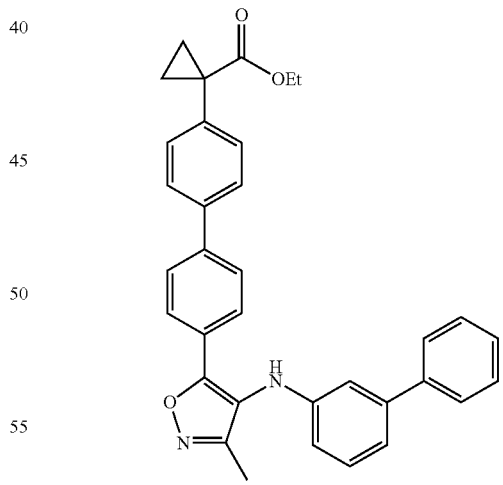

Step 1: 1-{4'-[4-(Biphenyl-3-ylamino)-3-methyl-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 3-bromo-biphenyl.

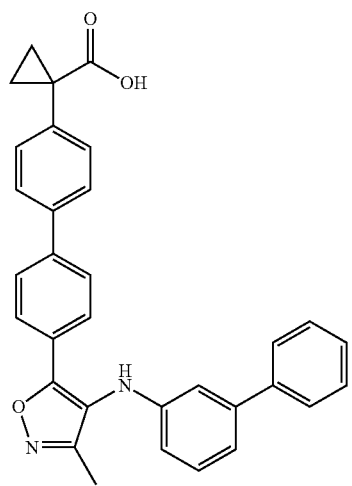 [SMILES: CCOC(=O)C1(c2ccc(-c3ccc(-c4onc(C)c4Nc4cccc(-c5ccccc5)c4)cc3)cc2)CC1]

Step 2: 1-{4'-[4-(Biphenyl-3-ylamino)-3-methyl-isoxazol-5-yl]-biphenyl-4-yl}-cyclopropanecarboxylic acid Prepared according to the procedure described in Example 1, Step 13, using 1-{4'-[4-(biphenyl-3-ylamino)-3-methyl-isoxazol-5-yl]-biphenyl-4-yl}-cyclopropanecarboxylic acid ethyl ester.

Example 75

1-{4'-[4-(Biphenyl-4-ylamino)-3-methyl-isoxazol-5-yl]-biphenyl-4-yl}-cyclopropanecarboxylic acid (Compound 1-75)

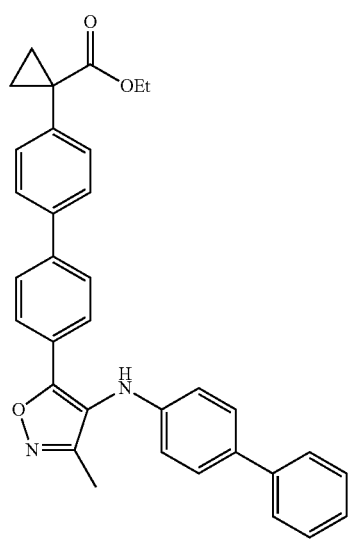 [SMILES: Cc1noc(-c2ccc(-c3ccc(C4(C(=O)O)CC4)cc3)cc2)c1Nc1ccc(-c2ccccc2)cc1]

Step 1: 1-{4'-[4-(Biphenyl-4-ylamino)-3-methyl-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 4-bromo-biphenyl.

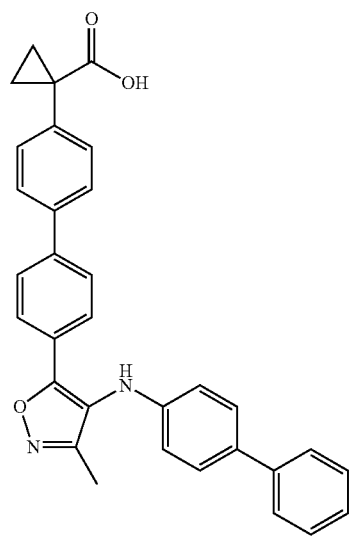

Step 2: 1-{4'-[4-(Biphenyl-4-ylamino)-3-methyl-isoxazol-5-yl]-biphenyl-4-yl}-cyclopropanecarboxylic acid Prepared according to the procedure described in Example 1, Step 13, using 1-{4'-[4-(biphenyl-4-ylamino)-3-methyl-isoxazol-5-yl]-biphenyl-4-yl}-cyclopropanecarboxylic acid ethyl ester.

Example 76

{4'-[3-Methyl-4-(6-phenyl-pyridin-2-ylamino)-isoxazol-5-yl]-biphenyl-4-yl}-acetic acid (Compound 1-76)

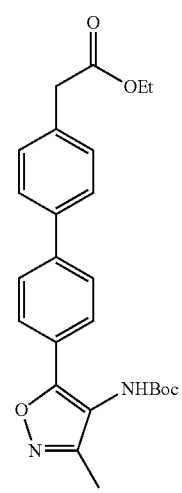 [SMILES: CCOC(=O)Cc1ccc(-c2ccc(-c3onc(C)c3NC(=O)OC(C)(C)C)cc2)cc1]

Step 1: [4'-(4-tert-Butoxycarbonylamino-3-methyl-isoxazol-5-yl)-biphenyl-4-yl]-acetic acid ethyl ester Prepared according to the procedure described in Example 42, Step 2, using [5-(4-bromo-phenyl)-3-methyl-isoxazol-4- yl]-carbamic acid tert-butyl ester and [4-(4,4,5,5-tetramethyl-[1,3,2]dioxaborolan-2-yl)-phenyl]-acetic acid ethyl ester.

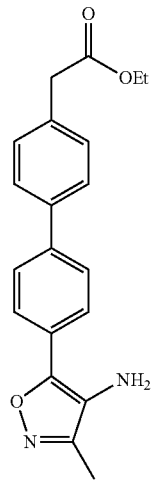 [SMILES: CCOC(=O)Cc1ccc(-c2ccc(-c3onc(C)c3N)cc2)cc1]

Step 2: [4'-(4-Amino-3-methyl-isoxazol-5-yl)-biphenyl-4-yl]acetic acid ethyl ester Prepared according to the procedure described in Example 1, Step 11, using [4'-(4-tert-butoxycarbonylamino-3-methyl-isoxazol-5-yl)-biphenyl-4-yl]-acetic acid ethyl ester.

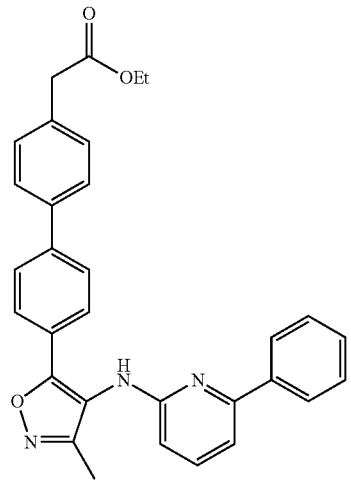 [SMILES: CCOC(=O)Cc1ccc(-c2ccc(-c3onc(C)c3Nc3cccc(-c4ccccc4)n3)cc2)cc1]

Step 3: {4'-[3-Methyl-4-(6-phenyl-pyridin-2-ylamino)-isoxazol-5-yl]-biphenyl-4-yl}-acetic acid ethyl ester Prepared according to the procedure described in Example 68, Step 2, using [4'-(4-amino-3-methyl-isoxazol-5-yl)-biphenyl-4-yl]-acetic acid ethyl ester and 2-bromo-6-phenyl-pyridine.

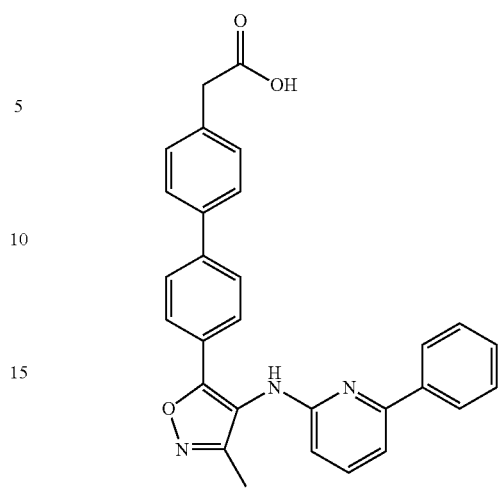

Step 4: {4'-[3-Methyl-4-(6-phenyl-pyridin-2-ylamino)-isoxazol-5-yl]-biphenyl-4-yl}-acetic acid Prepared according to the procedure described in Example 1, Step 13, using {4'-[3-methyl-4-(6-phenyl-pyridin-2-ylamino)-isoxazol-5-yl]-biphenyl-4-yl}-acetic acid ethyl ester.

Example 77

1-(4'-{3-Methyl-4-[6-(3-trifluoromethyl-phenyl)-pyridin-2-ylamino]-isoxazol-5-yl}-biphenyl-4-yl)-cyclopropanecarboxylic acid (Compound 1-77)

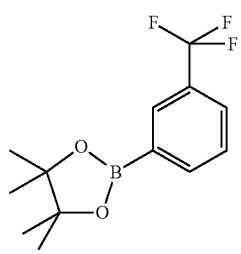 [SMILES: CC1(C)OB(c2cccc(C(F)(F)F)c2)OC1(C)C]

Step 1: 4,4,5,5-Tetramethyl-2-(3-trifluoromethyl-phenyl)-[1,3,2]dioxaborolane

Prepared according to the procedure described in Example 1, Step 9, using 1-bromo-3-trifluoromethyl-benzene and bis(pinacolato)diboron.

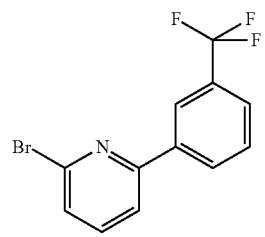 [SMILES: FC(F)(F)c1cccc(-c2cccc(Br)n2)c1]

Step 2: 2-Bromo-6-(3-trifluoromethyl-phenyl)-pyridine

Prepared according to the procedure described in Example 42, Step 2, using 4,4,5,5-tetramethyl-2-(3-trifluoromethyl-phenyl)-[1,3,2]dioxaborolane and 2,6-dibromo-pyridine.

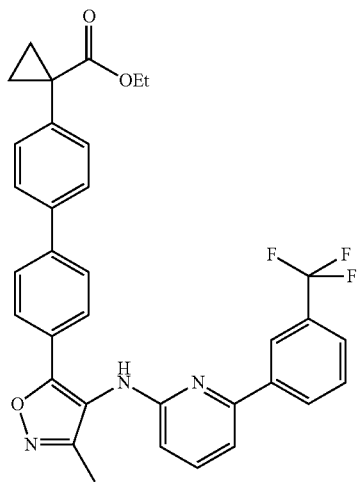 [SMILES: Cc1noc(-c2ccc(-c3ccc(C4(C(=O)O)CC4)cc3)cc2)c1Nc1cccc(-c2cccc(C(F)(F)F)c2)n1]

Step 3: 1-(4'-{3-Methyl-4-[6-(3-trifluoromethyl-phenyl)-pyridin-2-ylamino]-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-bromo-6-(3-trifluoromethyl-phenyl)-pyridine.

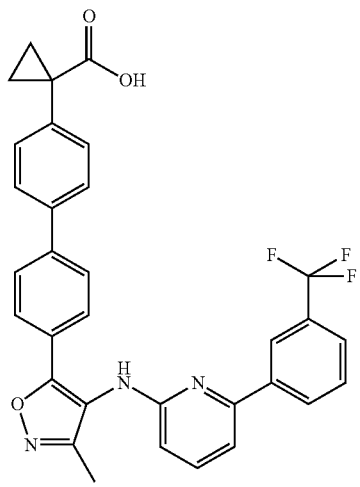

Step 4: 1-(4'-{3-Methyl-4-[6-(3-trifluoromethyl-phenyl)-pyridin-2-ylamino]-isoxazol-5-yl}-biphenyl-4-yl)-cyclopropanecarboxylic acid Prepared according to the procedure described in Example 1, Step 13, using 1-(4'-{3-methyl-4-[6-(3-trifluoromethyl-phenyl)-pyridin-2-ylamino]-isoxazol-5-yl}-biphenyl-4-yl)-cyclopropanecarboxylic acid ethyl ester.

Example 78

1-{4'-[3-Methyl-4-(6-phenyl-pyrazin-2-ylamino)-isoxazol-5-yl]-biphenyl-4-yl}-cyclopropanecarboxylic acid (Compound 1-78)

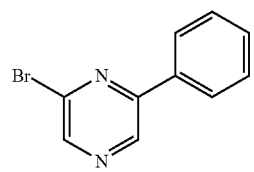 [SMILES: Brc1cncc(-c2ccccc2)n1]

Step 1: 2-Bromo-6-phenyl-pyrazine

Prepared according to the procedure described in Example 42, Step 2, using 2,6-dibromo-pyrazine and phenylboronic acid.

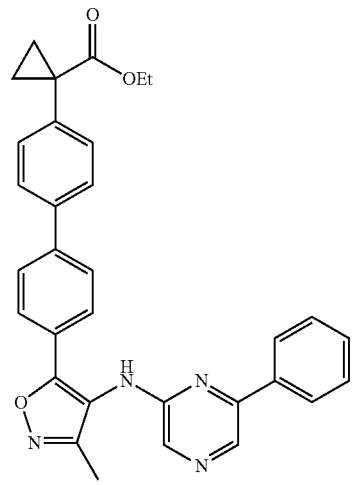

Step 2: 1-{4'-[3-Methyl-4-(6-phenyl-pyrazin-2-ylamino)-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-bromo-6-phenyl-pyrazine.

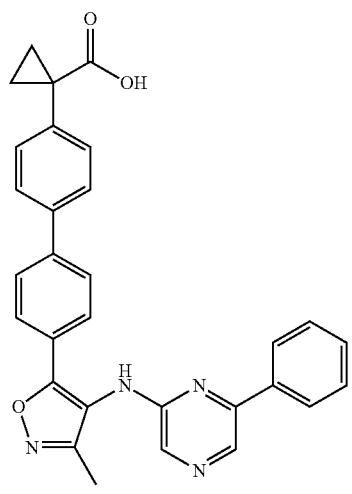

Step 3: 1-{4'-[3-Methyl-4-(6-phenyl-pyrazin-2-ylamino)-isoxazol-5-yl]-biphenyl-4-yl}-cyclopropanecarboxylic acid Prepared according to the procedure described in Example 1, Step 13, using 1-{4'-[3-methyl-4-(6-phenyl-pyrazin-2-ylamino)-isoxazol-5-yl]-biphenyl-4-yl}-cyclopropanecarboxylic acid ethyl ester.

Example 79

1-{4'-[3-Methyl-4-(6-phenoxy-pyridin-2-ylamino)-isoxazol-5-yl]-biphenyl-4-yl}-cyclopropanecarboxylic acid (Compound 1-79)

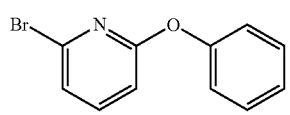

Step 1: 2-Bromo-6-phenoxy-pyridine 2,6-Dibromo-pyridine (2 g, 8.44 mmol) and phenol (0.794 g, 8.44 mmol) were dissolved in DMSO (20 mL) and potassium tert-butoxide (0.947 g, 8.44 mmol) was added. The reaction was heated to 160° C. overnight then allowed to cool to room temperature. The reaction was submitted to aqueous workup and silica gel chromatography to afford the title compound.

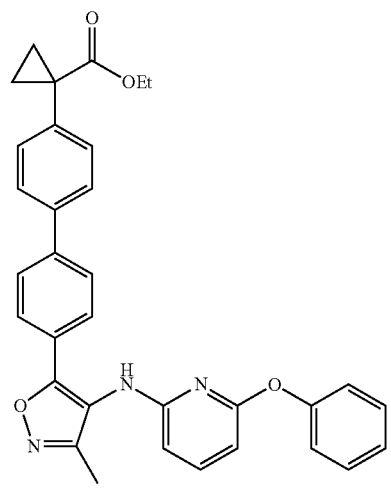

Step 2: 1-{4'-[3-Methyl-4-(6-phenoxy-pyridin-2-ylamino)-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-bromo-6-phenoxy-pyridine.

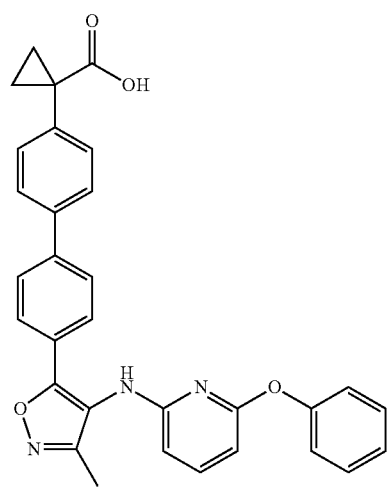

Step 3: 1-{4'-[3-Methyl-4-(6-phenoxy-pyridin-2-ylamino)-isoxazol-5-yl]-biphenyl-4-yl}-cyclopropanecarboxylic acid Prepared according to the procedure described in Example 1, Step 13, using 1-{4'-[3-methyl-4-(6-phenyl-pyrazin-2-ylamino)-isoxazol-5-yl]-biphenyl-4-yl}-cyclopropanecarboxylic acid ethyl ester.

Example 80

1-{4'-[3-Methyl-4-(5-phenyl-[1,3,4]oxadiazol-2-ylamino)-isoxazol-5-yl]-biphenyl-4-yl}-cyclopropanecarboxylic acid (Compound 1-80)

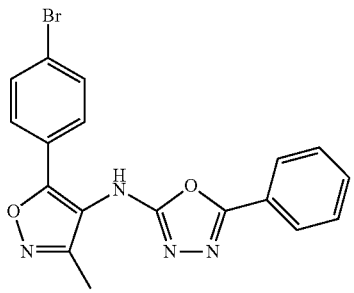 [SMILES: Cc1noc(-c2ccc(Br)cc2)c1Nc1nnc(-c2ccccc2)o1]

Step 1: [5-(4-Bromo-phenyl)-3-methyl-isoxazol-4-yl]-(5-phenyl-[1,3,4]oxadiazol-2-yl)-amine 5-(4-Bromo-phenyl)-3-methyl-isoxazole-4-carboxylic acid (1 g, 3.6 mmol), triethylamine (1 mL, 7.2 mmol) and diphenylphosphoryl azide (1.98 g, 7.2 mmol) were placed in toluene (20 mL) and heated to 60° C. for 20 minutes. Benzoic acid hydrazide (0.98 g, 7.2 mmol) was added in a single portion and the reaction was heated and stirred for 2 hours. The reaction was cooled and submitted to aqueous workup. The crude material was dissolved in dioxane (100 mL), phosphorous(V) oxychloride was added and the reaction was heated to 100° C. overnight. The reaction was cooled and worked up and the residue was purified on silica gel (0-80% EtOAc in hexanes) to yield the title compound.

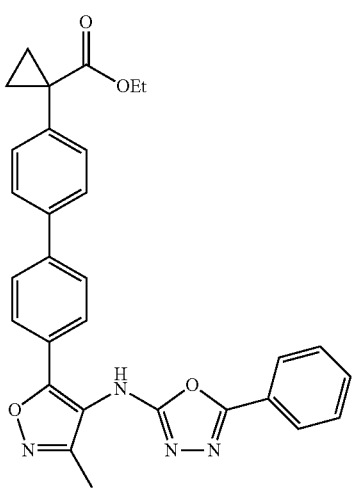 [SMILES: Cc1noc(-c2ccc(-c3ccc(C4(C(=O)O)CC4)cc3)cc2)c1Nc1nnc(-c2ccccc2)o1]

Step 2: 1-{4'-[3-Methyl-4-(5-phenyl-[1,3,4]oxadiazol-2-ylamino)-isoxazol-5-yl]-biphenyl-4-yl}-cyclopropanecarboxylic acid ethyl ester Prepared according to the procedure described in Example 42, Step 2, using [5-(4-bromo-phenyl)-3-methyl-isoxazol-4-yl]-(5-phenyl-[1,3,4]oxadiazol-2-yl)-amine and 1-[4-(4,4,5,5-tetramethyl-[1,3,2]dioxaborolan-2-yl)-phenyl]-cyclopropanecarboxylic acid ethyl ester.

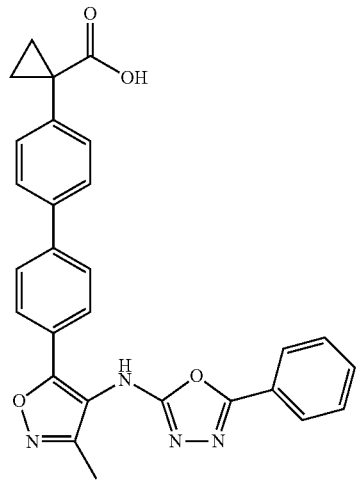

Step 3: 1-{4'-[3-Methyl-4-(5-phenyl[1,3,4]oxadiazol-2-ylamino)-isoxazol-5-yl]-biphenyl-4-yl}-cyclopropanecarboxylic acid Prepared according to the procedure described in Example 1, Step 13, using 1-{4'-[3-methyl-4-(5-phenyl-[1,3,4]oxadiazol-2-ylamino)-isoxazol-5-yl]-biphenyl-4-yl}-cyclopropanecarboxylic acid ethyl ester.

Example 81

3-{4'-[3-Methyl-4-(5-phenyl[1,3,4]oxadiazol-2-ylamino)-isoxazol-5-yl]-biphenyl-4-yl}-propionic acid (Compound 1-81)

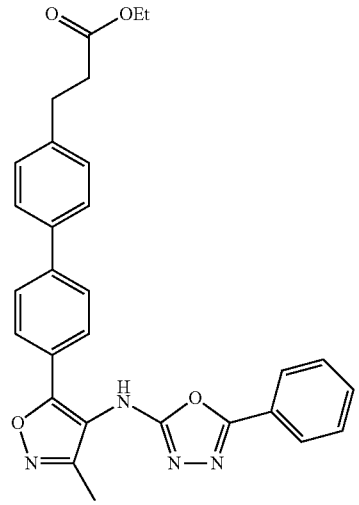

249

Step 1: 3-{4'-[3-Methyl-4-(5-phenyl[1,3,4]oxadiazol-2-ylamino)-isoxazol-5-yl]-biphenyl-4-yl}-propionic acid ethyl ester

Prepared according to the procedure described in Example 42, Step 2, using [5-(4-bromo-phenyl)-3-methyl-isoxazol-4-yl]-(5-phenyl-[1,3,4]oxadiazol-2-yl)-amine and [4-(2-ethoxycarbonylethyl)phenyl]boronic acid.

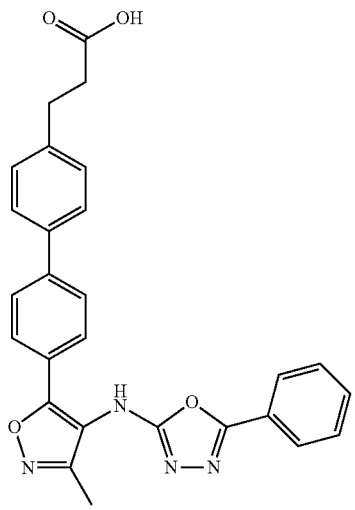 [SMILES: Cc1noc(-c2ccc(-c3ccc(CCC(=O)O)cc3)cc2)c1Nc1nnc(-c2ccccc2)o1]

Step 2: 3-{4'-[3-Methyl-4-(5-phenyl-[1,3,4]oxadiazol-2-ylamino)-isoxazol-5-yl]-biphenyl-4-yl}-propionic acid

Prepared according to the procedure described in Example 1, Step 13, using 3-{4'-[3-methyl-4-(5-phenyl-[1,3,4]oxadiazol-2-ylamino)-isoxazol-5-yl]-biphenyl-4-yl}-propionic acid ethyl ester.

Example 82

1-{4'-[3-Methyl-4-(3-phenoxy-phenylamino)-isoxazol-5-yl]-biphenyl-4-yl}-cyclopropanecarboxylic acid (Compound 1-82)

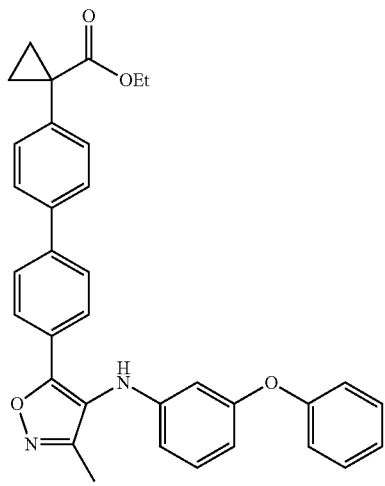

250

Step 1: 1-{4'-[3-Methyl-4-(3-phenoxy-phenylamino)-isoxazol-5-yl]-biphenyl-4-yl}-cyclopropanecarboxylic acid ethyl ester

Prepared according to the procedure described in Example 68, Step 2, using 1-[4'-(4-amino-3-methyl-isoxazol-5-yl)-biphenyl-4-yl]-cyclopropanecarboxylic acid ethyl ester and 1-bromo-3-phenoxy-benzene.

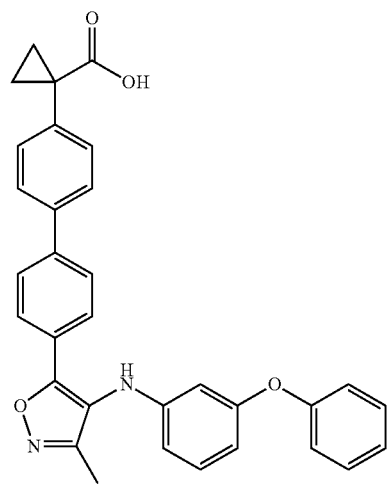

Step 2: 1-{4'-[3-Methyl-4-(3-phenoxy-phenylamino)-isoxazol-5-yl]-biphenyl-4-yl}-cyclopropanecarboxylic acid

Prepared according to the procedure described in Example 1, Step 13, using 1-{4'-[3-methyl-4-(3-phenoxy-phenylamino)-isoxazol-5-yl]-biphenyl-4-yl}-cyclopropanecarboxylic acid ethyl ester.

Example 83

1-{4'-[4-(5-Benzyl-[1,3,4]oxadiazol-2-ylamino)-3-methyl-isoxazol-5-yl]-biphenyl-4-yl}-cyclopropanecarboxylic acid (Compound 1-83)

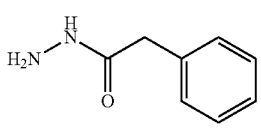

Step 1: Phenyl-acetic acid hydrazide

Phenyl-acetic acid methyl ester (5 g, 33.3 mmol) was dissolved in hydrazine hydrate (25 mL) and EtOH (50 mL) and the reaction was heated in a sealed tube to 80° C. overnight. After cooling the reaction was concentrated to afford the title compound.

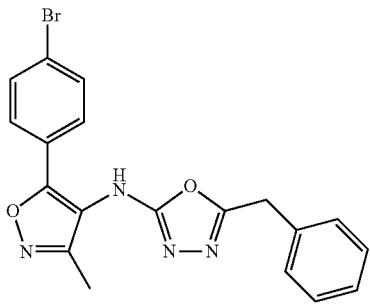 [SMILES: Cc1noc(-c2ccc(Br)cc2)c1Nc1nnc(Cc2ccccc2)o1]

Step 2: (5-Benzyl-[1,3,4]oxadiazol-2-yl)-[5-(4-bromo-phenyl)-3-methyl-isoxazol-4-yl]-amine Prepared according to the procedure described in Example 80, Step 1, using 5-(4-bromo-phenyl)-3-methyl-isoxazole-4-carboxylic acid and phenyl-acetic acid hydrazide.

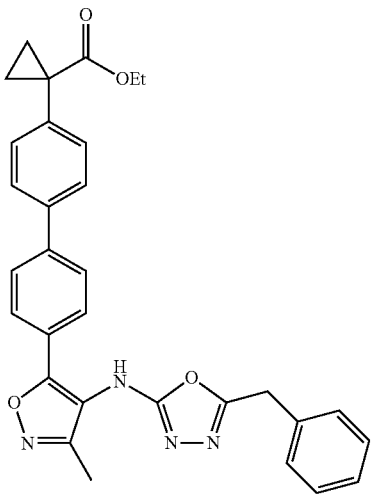

Step 3: 1-{4'-[4-(5-Benzyl-[1,3,4]oxadiazol-2-ylamino)-3-methyl-isoxazol-5-yl]-biphenyl-4-yl}-cyclopropanecarboxylic acid ethyl ester Prepared according to the procedure described in Example 42, Step 2, using (5-benzyl-[1,3,4]oxadiazol-2-yl)-[5-(4-bromo-phenyl)-3-methyl-isoxazol-4-yl]-amine and 1-[4-(4,4,5,5-tetramethyl-[1,3,2]dioxaborolan-2-yl)-phenyl]-cyclopropanecarboxylic acid ethyl ester.

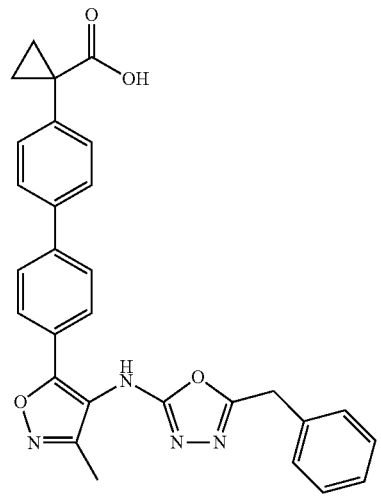 [SMILES: Cc1noc(-c2ccc(-c3ccc(C4(C(=O)O)CC4)cc3)cc2)c1Nc1nnc(Cc2ccccc2)o1]

Step 4: 1-{4'-[4-(5-Benzyl-[1,3,4]oxadiazol-2-ylamino)-3-methyl-isoxazol-5-yl]-biphenyl-4-yl}-cyclopropanecarboxylic acid Prepared according to the procedure described in Example 1, Step 13, using 1-{4'-[4-(5-benzyl-[1,3,4]oxadiazol-2-ylamino)-3-methyl-isoxazol-5-yl]-biphenyl-4-yl}-cyclopropanecarboxylic acid ethyl ester.

Example 84

1-(4'-{4-[6-(2-Fluoro-benzyl)-pyridin-2-ylamino]-3-methyl-isoxazol-5-yl}-biphenyl-4-yl)-cyclopropanecarboxylic acid (Compound 1-84)

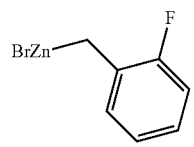

Step 1: 2-Fluoro-benzylzinc bromide

2-Fluoro-benzyl bromide (1 g, 5.29 mmol), zinc (0.380 g, 5.82 mmol) and 1,2-dibromoethane (0.050 mL, 0.58 mmol) were mixed in THF (10 mL) and heated to reflux overnight. After cooling a solution of the title compound was obtained that was used directly and immediately in the next step.

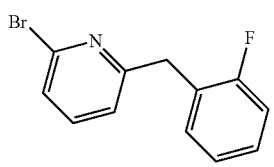 [SMILES: Fc1ccccc1Cc1cccc(Br)n1]

Step 2: 2-Bromo-6-(2-fluoro-benzyl)-pyridine

A solution of 2-fluoro-benzylzinc bromide was added to 2,6-dibromo-pyridine (1.25 g, 5.27 mmol) then tetrakis(triphenylphosphine)palladium(0) (0.122 g, 0.106 mmol) was added and the reaction was heated to 68° C. for 4 hours. After cooling, silica gel was added to the reaction and it was concentrated to near-dryness. The silica gel was loaded onto a column of silica gel for purification to afford thet title compound.

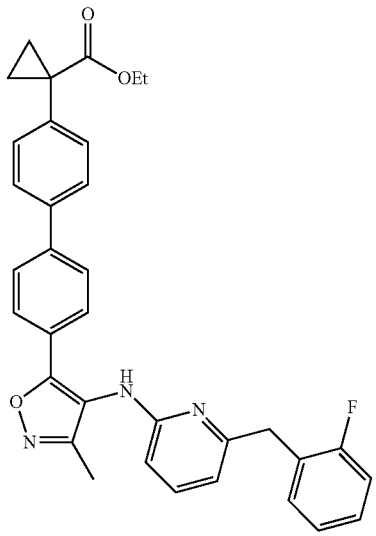 [SMILES: Cc1noc(-c2ccc(-c3ccc(C4(C(=O)O)CC4)cc3)cc2)c1Nc1cccc(Cc2ccccc2F)n1]

Step 3: 1-(4'-{4-[6-(2-Fluoro-benzyl)-pyridin-2-ylamino]-3-methyl-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-bromo-6-(2-fluoro-benzyl)-pyridine.

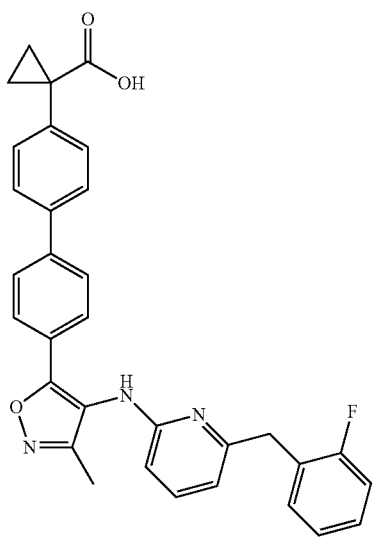

Step 4: 1-(4'-{4-[6-(2-Fluoro-benzyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(2-fluoro-benzyl)-pyridin-2-ylamino]-3-methyl-isoxazol-5-yl}-biphenyl-4-yl)-cyclopropanecarboxylic acid ethyl ester.

Example 85

1-(4'-{4-[6-(3-Fluoro-benzyl)-pyridin-2-ylamino]-3-methyl-isoxazol-5-yl}-biphenyl-4-yl)-cyclopropanecarboxylic acid (Compound 1-85)

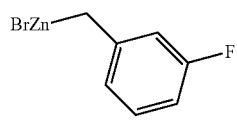

Step 1: 3-Fluoro-benzylzinc bromide

Prepared according to the procedure described in Example 84, Step 1, using 3-fluoro-benzyl bromide.

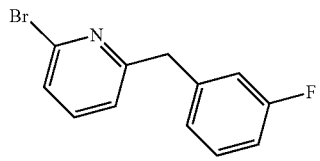 [SMILES: Fc1cccc(Cc2cccc(Br)n2)c1]

Step 2: 2-Bromo-6-(3-fluoro-benzyl)-pyridine

Prepared according to the procedure described in Example 84, Step 2, using 2,6-dibromo-pyridine and 3-fluoro-benzylzinc bromide.

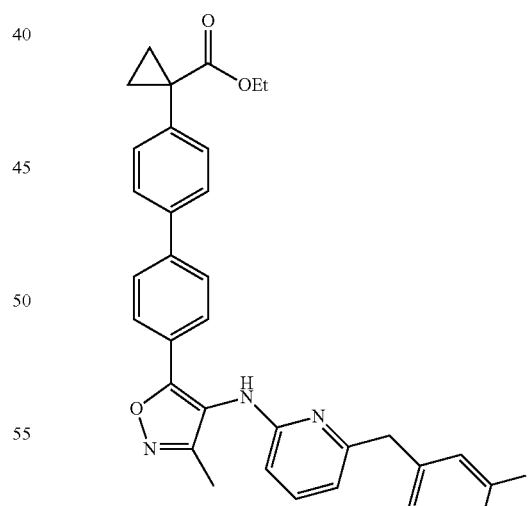

Step 3: 1-(4'-{4-[6-(3-Fluoro-benzyl)-pyridin-2-ylamino]-3-methyl-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-bromo-6-(3-fluoro-benzyl)-pyridine.

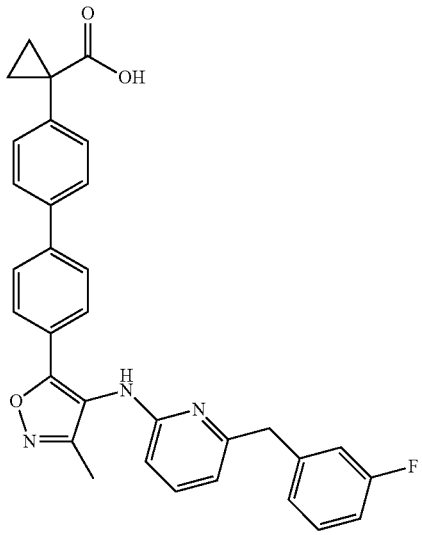 [SMILES: Cc1noc(-c2ccc(-c3ccc(C4(C(=O)O)CC4)cc3)cc2)c1Nc1cccc(Cc2cccc(F)c2)n1]

Step 4: 1-(4'-{4-[6-(3-Fluoro-benzyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(3-fluoro-benzyl)-pyridin-2-ylamino]-3-methyl-isoxazol-5-yl}-biphenyl-4-yl)-cyclopropanecarboxylic acid ethyl ester.

Example 86

1-(4'-{4-[6-(4-Fluoro-benzyl)-pyridin-2-ylamino]-3-methyl-isoxazol-5-yl}-biphenyl-4-yl)-cyclopropanecarboxylic acid (Compound 1-86)

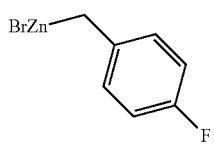

Step 1: 4-Fluoro-benzylzinc bromide

Prepared according to the procedure described in Example 84, Step 1, using 4-fluoro-benzyl bromide.

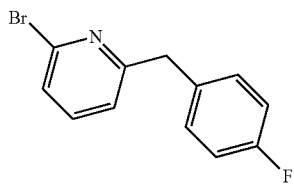 [SMILES: Fc1ccc(Cc2cccc(Br)n2)cc1]

Step 2: 2-Bromo-6-(4-fluoro-benzyl)-pyridine

Prepared according to the procedure described in Example 84, Step 2, using 2,6-dibromo-pyridine and 4-fluoro-benzylzinc bromide.

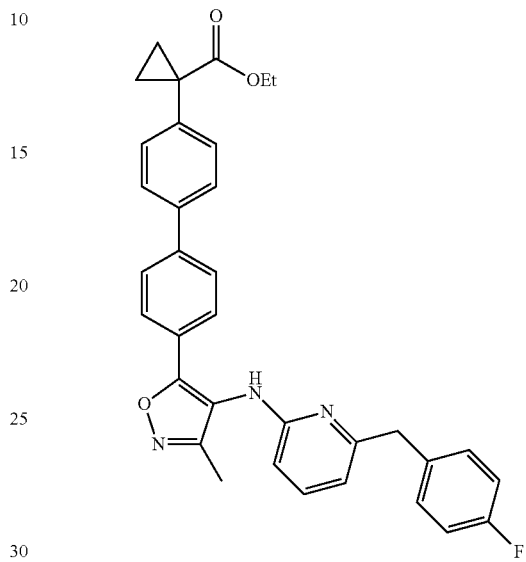

Step 3: 1-(4'-{4-[6-(4-Fluoro-benzyl)-pyridin-2-ylamino]-3-methyl-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-bromo-6-(4-fluoro-benzyl)-pyridine.

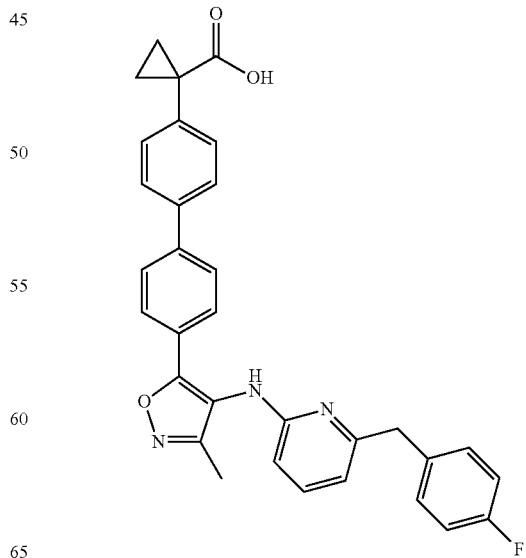

Step 4: 1-(4'-{4-[6-(4-Fluoro-benzyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(4-fluoro-benzyl)-pyridin-2-ylamino]-3-methyl-isoxazol-5-yl}-biphenyl-4-yl)-cyclopropanecarboxylic acid ethyl ester.

Example 87

1-{4'-[4-(6'-Ethoxy-[2,3]bipyridinyl-6-ylamino)-3-methyl-isoxazol-5-yl]-biphenyl-4-yl}-cyclopropanecarboxylic acid (Compound 1-87)

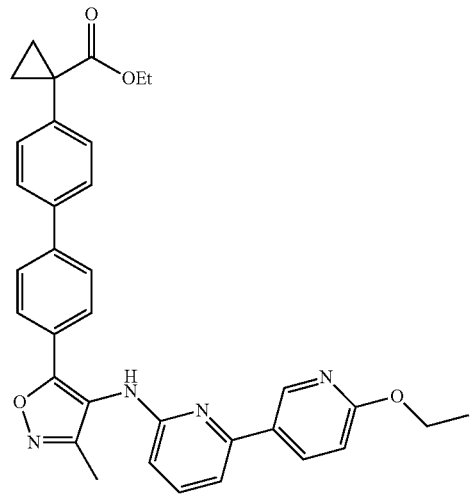

Step 2: 1-{4'-[4-(6'-Ethoxy-[2,3']bipyridinyl-6-ylamino)-3-methyl-isoxazol-5-yl]-biphenyl-4-yl}-cyclopropanecarboxylic acid ethyl ester Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2-ethoxy-5-pyridineboronic acid.

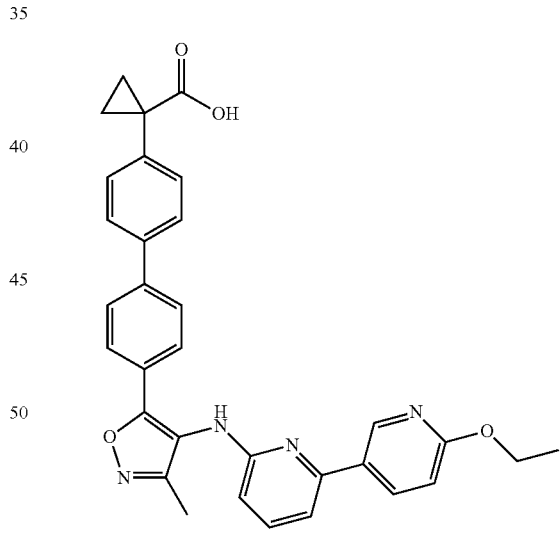

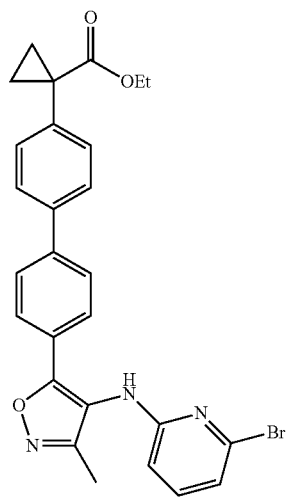 [SMILES: CCOC(=O)C1(c2ccc(-c3ccc(-c4onc(C)c4Nc4cccc(Br)n4)cc3)cc2)CC1]

Step 1: 1-{4'-[4-(6-Bromo-pyridin-2-ylamino)-3-methyl-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2,6-dibromo-pyridine.

Step 3: 1-{4'-[4-(6'-Ethoxy-[2,3']bipyridinyl-6-ylamino)-3-methyl-isoxazol-5-yl]-biphenyl-4-yl}-cyclopropanecarboxylic acid Prepared according to the procedure described in Example 1, Step 13, using 1-{4'-[4-(6'-ethoxy-[2,3']bipyridinyl-6- ylamino)-3-methyl-isoxazol-5-yl]-biphenyl-4-yl}-cyclopropanecarboxylic acid ethyl ester.

Example 88

1-(4'-{4-[6-(3-Methoxy-phenyl)-pyridin-2-ylamino]-3-methyl-isoxazol-5-yl}-biphenyl-4-yl)-cyclopropanecarboxylic acid (Compound 1-88)

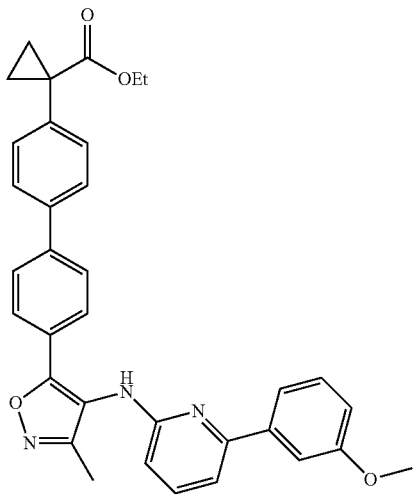 [SMILES: CCOC(=O)C1(c2ccc(-c3ccc(-c4onc(C)c4Nc4cccc(-c5cccc(OC)c5)n4)cc3)cc2)CC1]

Step 1: 1-(4'-{4-[6-(3-Methoxy-phenyl)-pyridin-2-ylamino]-3-methyl-isoxazol-5-yl}-biphenyl-4-yl)-cyclopropanecarboxylic acid ethyl ester Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 3-methoxyphenylboronic acid.

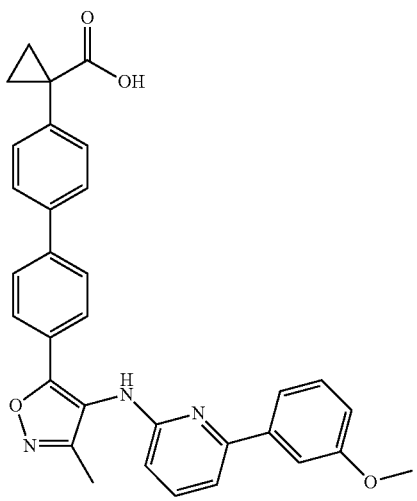 [SMILES: COc1cccc(-c2cccc(Nc3c(C)noc3-c3ccc(-c4ccc(C5(C(=O)O)CC5)cc4)cc3)n2)c1]

Step 2: 1-(4'-{4-[6-(3-Methoxy-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(3-methoxy-phenyl)-pyridin-2-ylamino]-3-methyl-isoxazol-5-yl}-biphenyl-4-yl)-cyclopropanecarboxylic acid ethyl ester.

Example 89

1-(4'-{4-[3-(2-Methoxy-pyridin-3-yl)-phenylamino]-3-methyl-isoxazol-5-yl}-biphenyl-4-yl)-cyclopropanecarboxylic acid (Compound 1-89)

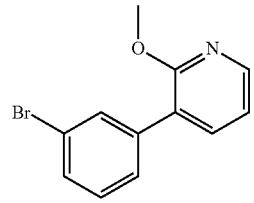

Step 1: 3-(3-Bromo-phenyl)-2-methoxy-pyridine

Prepared according to the procedure described in Example 42, Step 2, using 1,3-dibromo-benzene and 2-methoxy-3-pyridineboronic acid.

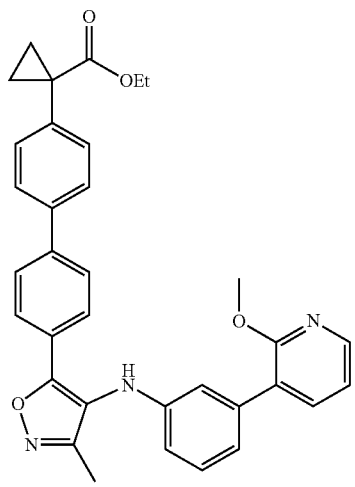 [SMILES: CCOC(=O)C1(c2ccc(-c3ccc(-c4onc(C)c4Nc4cccc(-c5cccnc5OC)c4)cc3)cc2)CC1]

Step 2: 1-(4'-{4-[3-(2-Methoxy-pyridin-3-yl)-phenylamino]-3-methyl-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 3-(3-bromo-phenyl)-2-methoxy-pyridine.

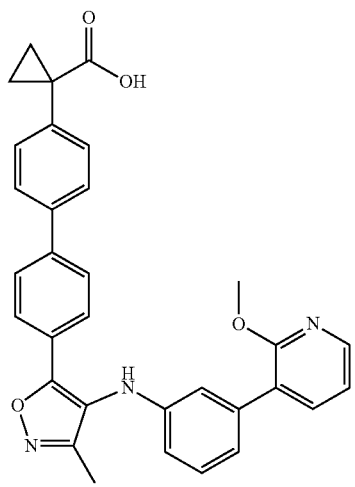 [SMILES: COc1ncccc1-c1cccc(Nc2c(C)noc2-c2ccc(-c3ccc(C4(C(=O)O)CC4)cc3)cc2)c1]

Step 3: 1-(4'-{4-[3-(2-Methoxy-pyridin-3-yl)-phenylamino]-3-methyl-isoxazol-5-yl}-biphenyl-4-yl)-cyclopropanecarboxylic acid Prepared according to the procedure described in Example 1, Step 13, using 1-(4'-{4-[3-(2-methoxy-pyridin-3-yl)-phenylamino]-3-methyl-isoxazol-5-yl}-biphenyl-4-yl)-cyclopropanecarboxylic acid ethyl ester.

Example 90

1-{4'-[4-(3-Benzyl-phenylamino)-3-methyl-isoxazol-5-yl]-biphenyl-4-yl}-cyclopropanecarboxylic acid (Compound 1-90)

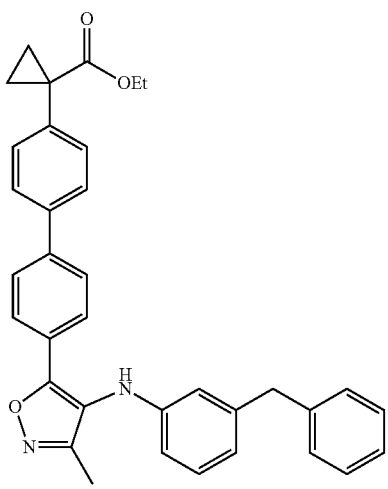

Step 1: 1-{4'-[4-(3-Benzyl-phenylamino)-3-methyl-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 1-benzyl-3-bromo-benzene.

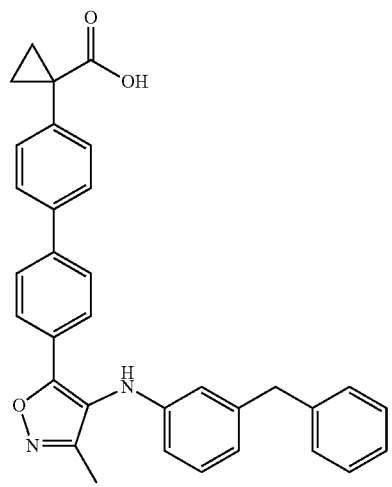 [SMILES: Cc1noc(-c2ccc(-c3ccc(C4(C(=O)O)CC4)cc3)cc2)c1Nc1cccc(Cc2ccccc2)c1]

Step 2: 1-{4'-[4-(3-Benzyl-phenylamino)-3-methyl-isoxazol-5-yl]-biphenyl-4-yl}-cyclopropanecarboxylic acid Prepared according to the procedure described in Example 1, Step 13, using 1-{4'-[4-(3-benzyl-phenylamino)-3-methyl-isoxazol-5-yl]-biphenyl-4-yl}-cyclopropane carboxylic acid ethyl ester.

Example 91

1-(4'-{4-[6-(2-Cyano-phenyl)-pyridin-2-ylamino]-3-methyl-isoxazol-5-yl}-biphenyl-4-yl)-cyclopropanecarboxylic acid (Compound 1-91)

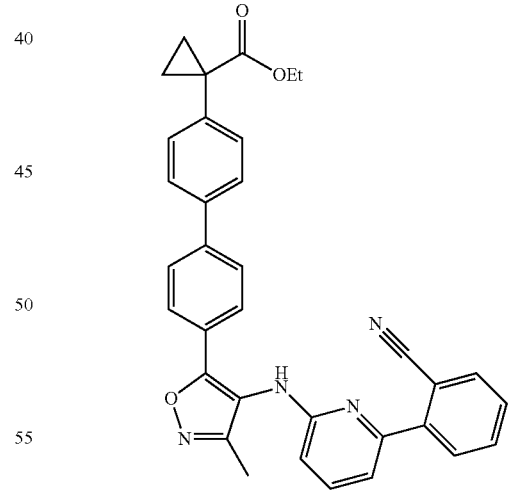

Step 1: 1-(4'-{4-[6-(2-Cyano-phenyl)-pyridin-2-ylamino]-3-methyl-isoxazol-5-yl}-biphenyl-4-yl)-cyclopropanecarboxylic acid ethyl ester Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2-cyanophenylboronic acid.

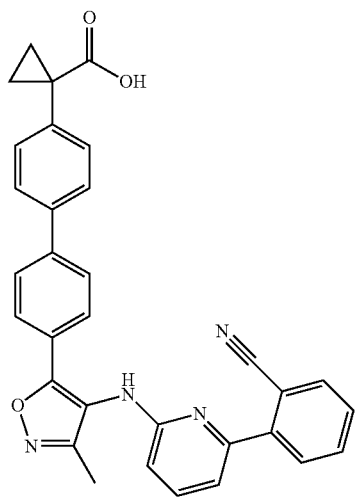 [SMILES: Cc1noc(-c2ccc(-c3ccc(C4(C(=O)O)CC4)cc3)cc2)c1Nc1cccc(-c2ccccc2C#N)n1]

Step 2: 1-(4'-{4-[6-(2-Cyano-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(2-cyano-phenyl)-pyridin-2-ylamino]-3-methyl-isoxazol-5-yl}-biphenyl-4-yl)-cyclopropanecarboxylic acid ethyl ester.

Example 92

1-(4'-{4-[6-(4-Methoxy-phenyl)-pyridin-2-ylamino]-3-methyl-isoxazol-5-yl}-biphenyl-4-yl)-cyclopropanecarboxylic acid (Compound 1-92)

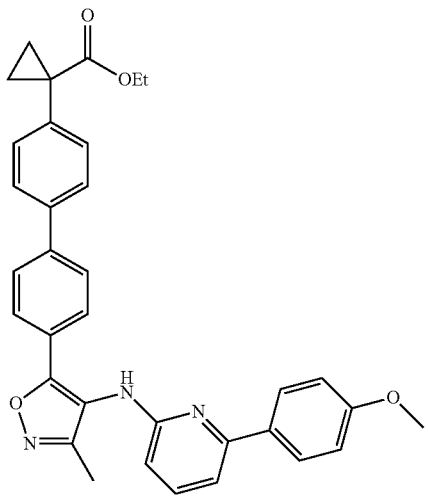 [SMILES: CCOC(=O)C1(c2ccc(-c3ccc(-c4onc(C)c4Nc4cccc(-c5ccc(OC)cc5)n4)cc3)cc2)CC1]

Step 1: 1-(4'-{4-[6-(4-Methoxy-phenyl)-pyridin-2-ylamino]-3-methyl-isoxazol-5-yl}-biphenyl-4-yl)-cyclopropanecarboxylic acid ethyl ester Prepared according to the procedure described in Example 1, Step 10, using 1-(4'-[4-(6-bromo-pyridin-2-ylamino)-3-methyl-isoxazol-5-yl]-biphenyl-4-yl}-cyclopropanecarboxylic acid ethyl ester and 4-methoxyphenylboronic acid.

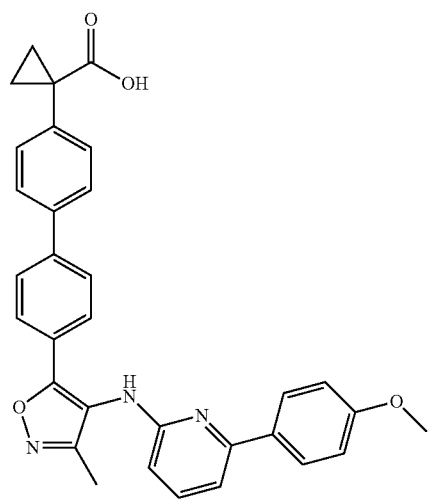

Step 2: 1-(4'-{4-[6-(4-Methoxy-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(4-methoxy-phenyl)-pyridin-2-ylamino]-3-methyl-isoxazol-5-yl}-biphenyl-4-yl)-cyclopropanecarboxylic acid ethyl ester.

Example 93

1-(4'-{4-[6-(3-Fluoro-phenyl)-pyridin-2-ylamino]-3-methyl-isoxazol-5-yl}-biphenyl-4-yl)-cyclopropanecarboxylic acid (Compound 1-93)

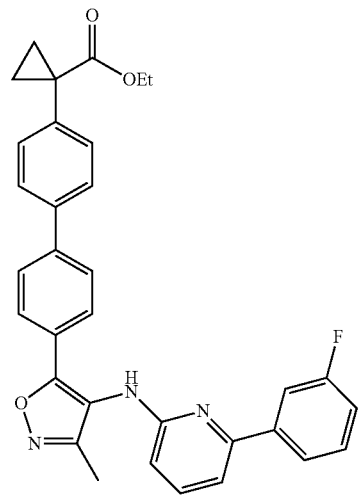 [SMILES: CCOC(=O)C1(c2ccc(-c3ccc(-c4onc(C)c4Nc4cccc(-c5cccc(F)c5)n4)cc3)cc2)CC1]

Step 1: 1-(4'-{4-[6-(3-Fluoro-phenyl)-pyridin-2-ylamino]-3-methyl-isoxazol-5-yl}-biphenyl-4-yl)-cyclopropanecarboxylic acid ethyl ester Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 3-fluorophenylboronic acid.

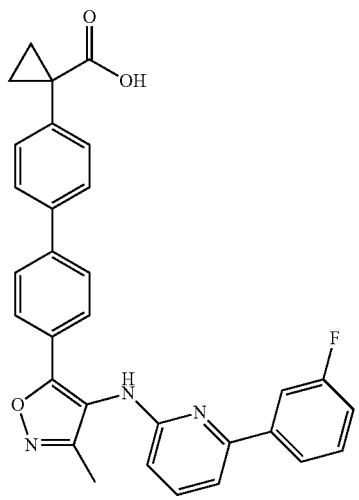 [SMILES: Cc1noc(-c2ccc(-c3ccc(C4(C(=O)O)CC4)cc3)cc2)c1Nc1cccc(-c2cccc(F)c2)n1]

Step 2: 1-(4'-{4-[6-(3-Fluoro-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(3-fluoro-phenyl)-pyridin-2-ylamino]-3-methyl-isoxazol-5-yl}-biphenyl-4-yl)-cyclopropanecarboxylic acid ethyl ester.

Example 94

1-(4'-{4-[6-(2-Methoxy-phenyl)-pyridin-2-ylamino]-3-methyl-isoxazol-5-yl}-biphenyl-4-yl)-cyclopropanecarboxylic acid (Compound 1-94)

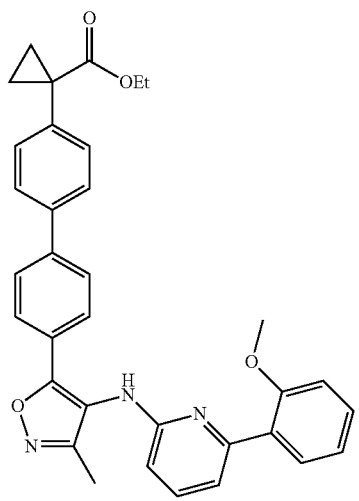 [SMILES: CCOC(=O)C1(c2ccc(-c3ccc(-c4onc(C)c4Nc4cccc(-c5ccccc5OC)n4)cc3)cc2)CC1]

Step 1: 1-(4'-{4-[6-(2-Methoxy-phenyl)-pyridin-2-ylamino]-3-methyl-isoxazol-5-yl}-biphenyl-4-yl)-cyclopropanecarboxylic acid ethyl ester Prepared according to the procedure described in Example 1, Step 10, using 1-[4'-(4-amino-3-methyl-isoxazol-5-yl)-biphenyl-4-yl]-cyclopropanecarboxylic acid ethyl ester and 3-(3-bromo-phenyl)-2-methoxy-pyridine.

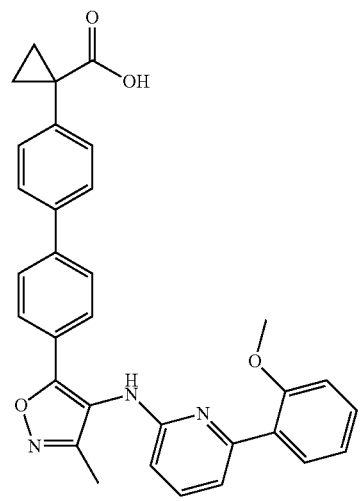 [SMILES: COc1ccccc1-c1cccc(Nc2c(C)noc2-c2ccc(-c3ccc(C4(C(=O)O)CC4)cc3)cc2)n1]

Step 2: 1-(4'-{4-[6-(2-Methoxy-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(2-methoxy-phenyl)-pyridin-2-ylamino]-3-methyl-isoxazol-5-yl}-biphenyl-4-yl)-cyclopropanecarboxylic acid ethyl ester.

Example 95

1-(4'-{4-[6-(2-Fluoro-phenyl)-pyridin-2-ylamino]-3-methyl-isoxazol-5-yl}-biphenyl-4-yl)-cyclopropanecarboxylic acid (Compound 1-95)

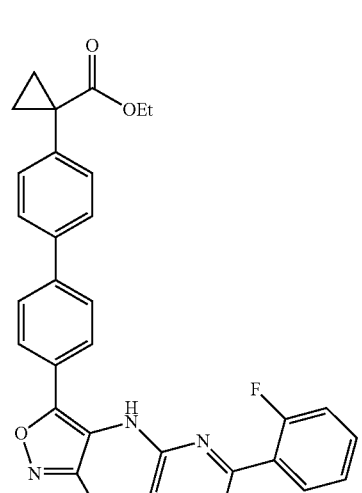

Step 1: 1-(4'-{4-[6-(2-Fluoro-phenyl)-pyridin-2-ylamino]-3-methyl-isoxazol-5-yl}-biphenyl-4-yl)-cyclopropanecarboxylic acid ethyl ester Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2-(2-fluoro-phenyl)-4,4,5,5-tetramethyl-[1,3,2]dioxaborolane.

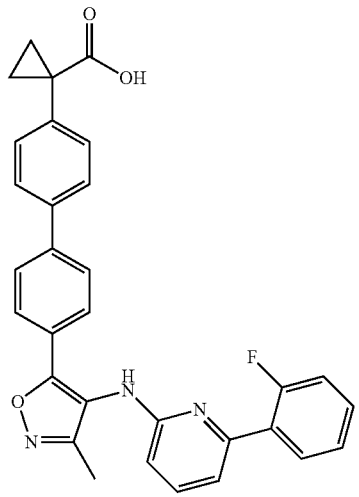 [SMILES: Cc1noc(-c2ccc(-c3ccc(C4(C(=O)O)CC4)cc3)cc2)c1Nc1cccc(-c2ccccc2F)n1]

Step 2: 1-(4'-{4-[6-(2-Fluoro-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(2-fluoro-phenyl)-pyridin-2-ylamino]-3-methyl-isoxazol-5-yl}-biphenyl-4-yl)-cyclopropanecarboxylic acid ethyl ester.

Example 96

1-(4'-{3-methyl-4-[6-(2-trifluoromethyl-phenyl)-pyridin-2-ylamino]-isoxazol-5-yl}-biphenyl-4-yl)-cyclopropanecarboxylic acid (Compound 1-96)

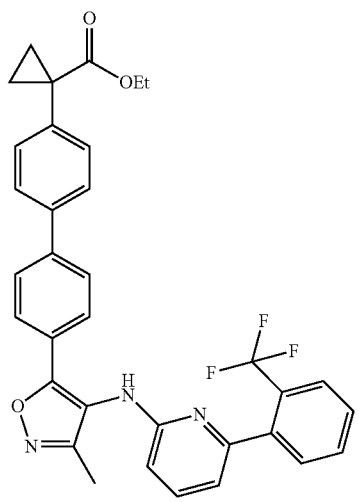 [SMILES: CCOC(=O)C1(c2ccc(-c3ccc(-c4onc(C)c4Nc4cccc(-c5ccccc5C(F)(F)F)n4)cc3)cc2)CC1]

Step 1: 1-(4'-{3-Methyl-4-[6-(2-trifluoromethyl-phenyl)-pyridin-2-ylamino]-isoxazol-5-yl}-biphenyl-4-yl)-cyclopropanecarboxylic acid ethyl ester Prepared according to the procedure described in Example 1, Step 10, using 1-{4'-[4-(6-bromo-pyridin-2-ylamino)-3- methyl-isoxazol-5-yl]-biphenyl-4-yl}-cyclopropanecarboxylic acid ethyl ester and 4,4,5,5-tetramethyl-2-(2-trifluoromethyl-phenyl)-[1,3,2]dioxaborolane.

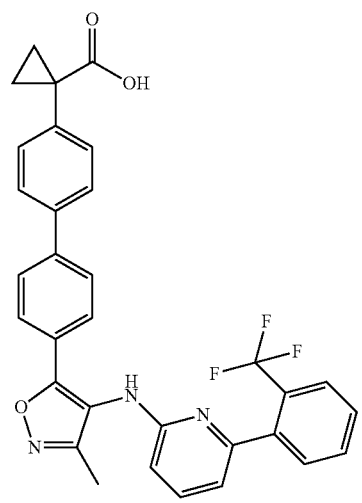 [SMILES: Cc1noc(-c2ccc(-c3ccc(C4(C(=O)O)CC4)cc3)cc2)c1Nc1cccc(-c2ccccc2C(F)(F)F)n1]

Step 2: 1-(4'-{3-Methyl-4-[6-(2-trifluoromethyl-phenyl)-pyridin-2-ylamino]-isoxazol-5-yl}-biphenyl-4-yl)-cyclopropanecarboxylic acid Prepared according to the procedure described in Example 1, Step 13, using 1-(4'-{3-methyl-4-[6-(2-trifluoromethyl-phenyl)-pyridin-2-ylamino]-isoxazol-5-yl}-biphenyl-4-yl)-cyclopropanecarboxylic acid ethyl ester.

Example 97

1-{4'-[4-(2'-Methoxy-[2,3']bipyridinyl-6-ylamino)-3-methyl-isoxazol-5-yl]-biphenyl-4-yl}-cyclopropanecarboxylic acid (Compound 1-97)

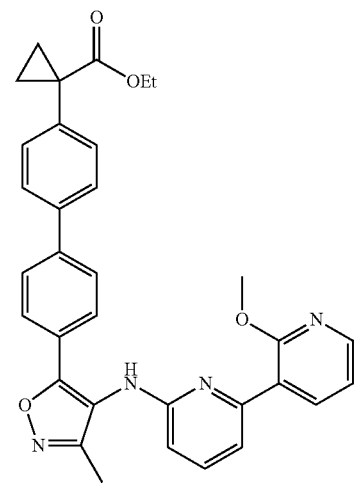 [SMILES: CCOC(=O)C1(c2ccc(-c3ccc(-c4onc(C)c4Nc4cccc(-c5cccnc5OC)n4)cc3)cc2)CC1]

Step 1: 1-{4'-[4-(2'-Methoxy-[2,3']bipyridinyl-6-ylamino)-3-methyl-isoxazol-5-yl]-biphenyl-4-yl}-cyclopropanecarboxylic acid ethyl ester Prepared according to the procedure described in Example 42, Step 2, using 1-{4'-[4-(6-bromo-pyridin-2-ylamino)-3- methyl-isoxazol-5-yl]-biphenyl-4-yl}-cyclopropanecarboxylic acid ethyl ester and 2-methoxypyridine-3-boronic acid.

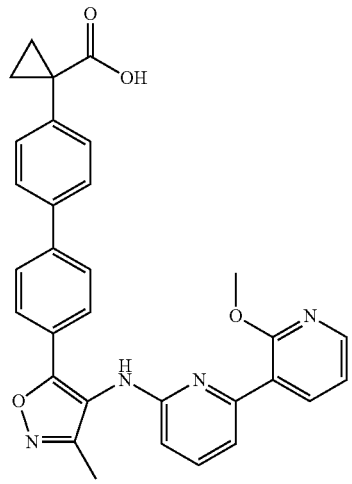 [SMILES: COc1ncccc1-c1cccc(Nc2c(C)noc2-c2ccc(-c3ccc(C4(C(=O)O)CC4)cc3)cc2)n1]

Step 2: 1-{4'-[4-(2'-Methoxy-[2,3']bipyridinyl-6-ylamino)-3-methyl-isoxazol-5-yl]-biphenyl-4-yl}-cyclopropanecarboxylic acid Prepared according to the procedure described in Example 1, Step 13, using 1-{4'-[4-(2'-methoxy-[2,3']bipyridinyl-6-ylamino)-3-methyl-isoxazol-5-yl]-biphenyl-4-yl}-cyclopropanecarboxylic acid ethyl ester.

Example 98

1-{4'-[4-(6'-Methoxy-[2,3']bipyridinyl-6-ylamino)-3-methyl-isoxazol-5-yl]-biphenyl-4-yl}-cyclopropanecarboxylic acid (Compound 1-98)

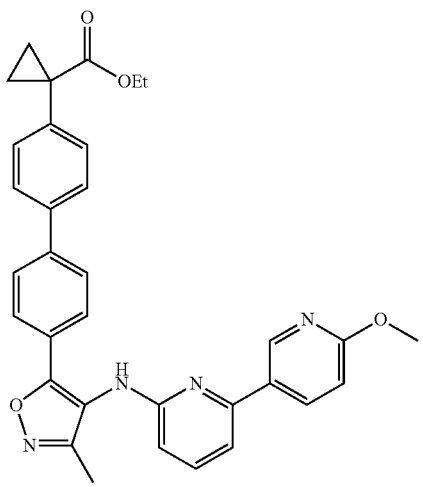 [SMILES: COc1ccc(-c2cccc(Nc3c(C)noc3-c3ccc(-c4ccc(C5(C(=O)O)CC5)cc4)cc3)n2)cn1]

Step 1: 1-{4'-[4-(6'-Methoxy-[2,3']bipyridinyl-6-ylamino)-3-methyl-isoxazol-5-yl]-biphenyl-4-yl}-cyclopropanecarboxylic acid ethyl ester Prepared according to the procedure described in Example 42, Step 2, using 1-{4'-[4-(6-bromo-pyridin-2-ylamino)-3- methyl-isoxazol-5-yl]-biphenyl-4-yl}-cyclopropanecarboxylic acid ethyl ester and 2-methoxypyridine-5-boronic acid.

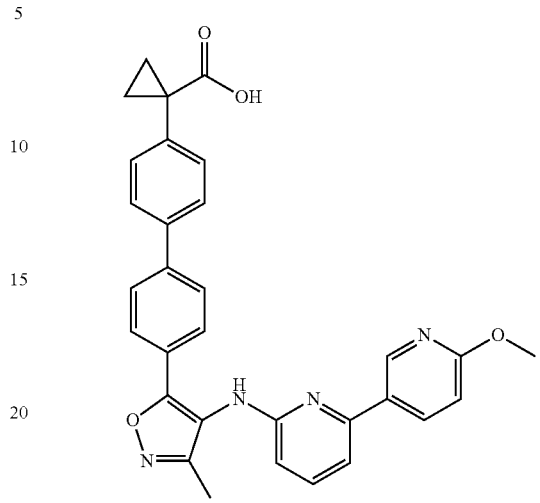

Step 2: 1-{4'-[4-(6'-Methoxy-[2,3']bipyridinyl-6-ylamino)-3-methyl-isoxazol-5-yl]-biphenyl-4-yl}-cyclopropanecarboxylic acid Prepared according to the procedure described in Example 1, Step 13, using 1-{4'-[4-(6'-methoxy-[2,3']bipyridinyl-6-ylamino)-3-methyl-isoxazol-5-yl]-biphenyl-4-yl}-cyclopropanecarboxylic acid ethyl ester.

Example 99

1-{4'-[4-([2,4']Bipyridinyl-6-ylamino)-3-methyl-isoxazol-5-yl]-biphenyl-4-yl}-cyclopropanecarboxylic acid (Compound 1-99)

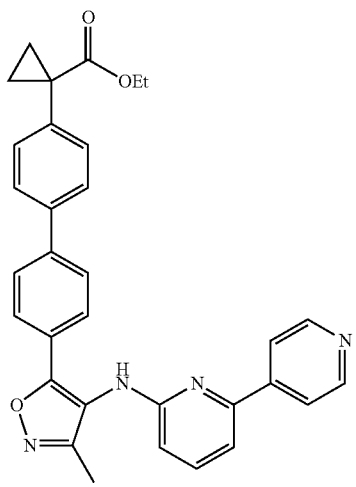

Step 1: 1-{4'-[4-([2,4']Bipyridinyl-6-ylamino)-3-methyl-isoxazol-5-yl]-biphenyl-4-yl}-cyclopropanecarboxylic acid ethyl ester Prepared according to the procedure described in Example 42, Step 2, using 1-{4'-[4-(6-bromo-pyridin-2-ylamino)-3- methyl-isoxazol-5-yl]-biphenyl-4-yl}-cyclopropanecarboxylic acid ethyl ester and pyridine-4-boronic acid.

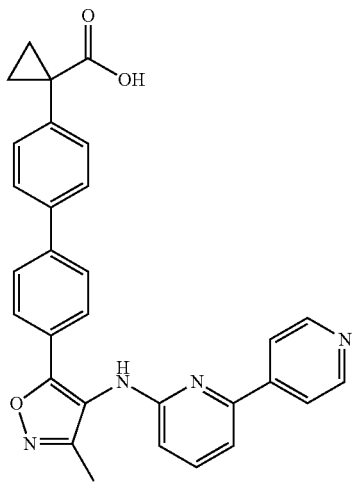 [SMILES: CCOC(=O)C1(c2ccc(-c3ccc(-c4onc(C)c4Nc4cccc(-c5ccncc5)n4)cc3)cc2)CC1]

Step 2: 1-{4'-[4-([2,4']Bipyridinyl-6-ylamino)-3-methyl-isoxazol-5-yl]-biphenyl-4-yl}-cyclopropanecarboxylic acid Prepared according to the procedure described in Example 1, Step 13, using 1-{4'-[4-([2,4']bipyridinyl-6-ylamino)-3-methyl-isoxazol-5-yl]-biphenyl-4-yl}-cyclopropanecarboxylic acid ethyl ester.

Example 100

1-(4'-{3-Methyl-4-[(2-phenyl-thiazol-5-ylmethyl)-amino]-isoxazol-5-yl}-biphenyl-4-yl)-cyclopropanecarboxylic acid (Compound 1-100)

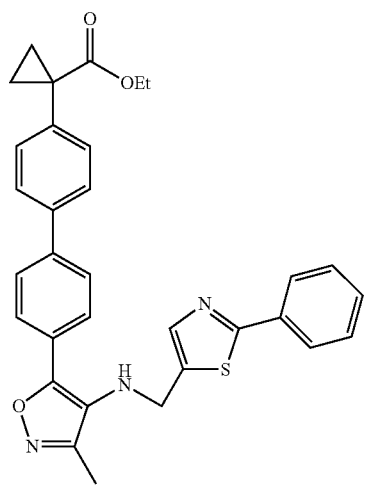 [SMILES: Cc1noc(-c2ccc(-c3ccc(C4(C(=O)O)CC4)cc3)cc2)c1NCc1cnc(-c2ccccc2)s1]

Step 1: 1-(4'-{3-Methyl-4-[(2-phenyl-thiazol-5-ylmethyl)-amino]-isoxazol-5-yl}-biphenyl-4-yl)-cyclopropanecarboxylic acid ethyl ester Prepared according to the procedure described in Example 1, Step 12, using 1-[4'-(4-amino-3-methyl-isoxazol-5-yl)-bi-phenyl-4-yl]-cyclopropanecarboxylic acid ethyl ester and 2-phenyl-thiazole-5-carbaldehyde.

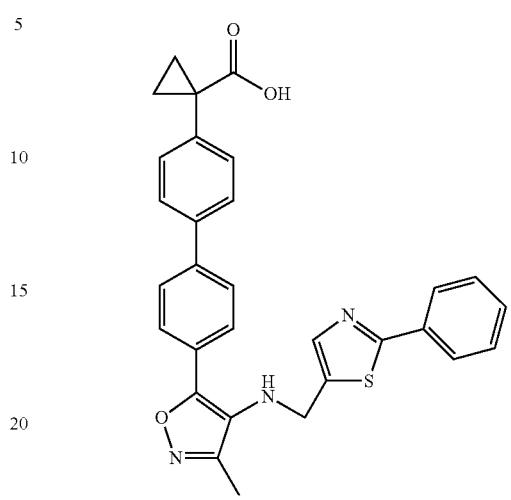

Step 2: 1-(4'-{3-Methyl-4-[(2-phenyl-thiazol-5-ylmethyl)-amino]-isoxazol-5-yl}-biphenyl-4-yl)-cyclopropanecarboxylic acid Prepared according to the procedure described in Example 1, Step 13, using 1-(4'-{3-methyl-4-[(2-phenyl-thiazol-5-ylmethyl)-amino]-isoxazol-5-yl}-biphenyl-4-yl)-cyclopropanecarboxylic acid ethyl ester.

Example 101

1-{4'-[3-Methyl-4-(2'-trifluoromethyl-biphenyl-3-ylamino)-isoxazol-5-yl]-biphenyl-4-yl}-cyclopropanecarboxylic acid (Compound 1-101)

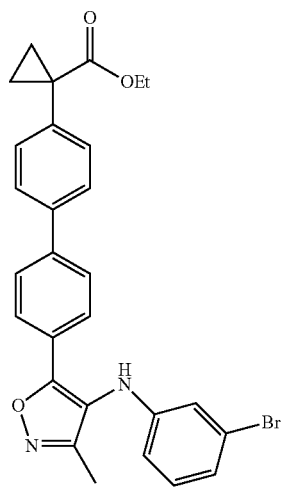 [SMILES: CCOC(=O)C1(c2ccc(-c3ccc(-c4onc(C)c4Nc4cccc(Br)c4)cc3)cc2)CC1]

Step 1: 1-{4'-[4-(3-Bromo-phenylamino)-3-methyl-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 1,3-dibromo-benzene.

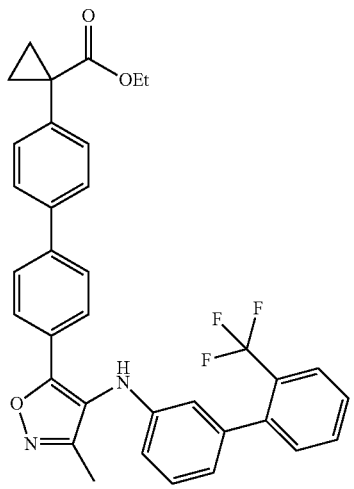 [SMILES: CCOC(=O)C1(c2ccc(-c3ccc(-c4onc(C)c4Nc4cccc(-c5ccccc5C(F)(F)F)c4)cc3)cc2)CC1]

Step 2: 1-{4'-[3-Methyl-4-(2'-trifluoromethyl-biphenyl-3-ylamino)-isoxazol-5-yl]-biphenyl-4-yl}-cyclopropanecarboxylic acid ethyl ester Prepared according to the procedure described in Example 1, Step 10, using 1-{4'-[4-(3-bromo-phenylamino)-3-methyl-isoxazol-5-yl]-biphenyl-4-yl}-cyclopropanecarboxylic acid ethyl ester and 2-(trifluoromethyl)phenylboronic acid.

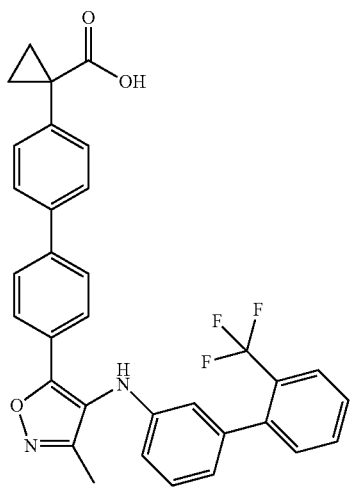 [SMILES: Cc1noc(-c2ccc(-c3ccc(C4(C(=O)O)CC4)cc3)cc2)c1Nc1cccc(-c2ccccc2C(F)(F)F)c1]

Step 3: 1-{4'-[3-Methyl-4-(2'-trifluoromethyl-biphenyl-3-ylamino)-isoxazol-5-yl]-biphenyl-4-yl}-cyclopropanecarboxylic acid Prepared according to the procedure described in Example 1, Step 13, using 1-{4'-[3-methyl-4-(2'-trifluoromethyl-biphenyl-3-ylamino)-isoxazol-5-yl]-biphenyl-4-yl}-cyclopropanecarboxylic acid ethyl ester.

Example 102

1-(4'-{4-[3-(6-Methoxy-pyridin-3-yl)-phenylamino]-3-methyl-isoxazol-5-yl}-biphenyl-4-yl)-cyclopropanecarboxylic acid (Compound 1-102)

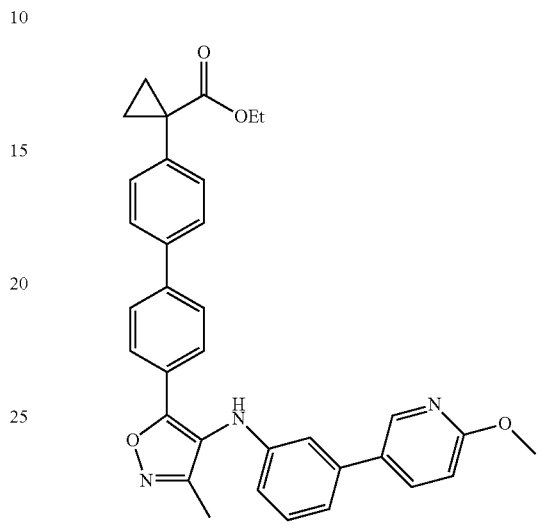

Step 1: 1-(4'-{4-[3-(6-Methoxy-pyridin-3-yl)-phenylamino]-3-methyl-isoxazol-5-yl}-biphenyl-4-yl)-cyclopropanecarboxylic acid ethyl ester Prepared according to the procedure described in Example 1, Step 10, using 1-{4'-[4-(3-bromo-phenylamino)-3-methyl-isoxazol-5-yl]-biphenyl-4-yl}-cyclopropanecarboxylic acid ethyl ester and 2-methoxy-5-pyridineboronic acid.

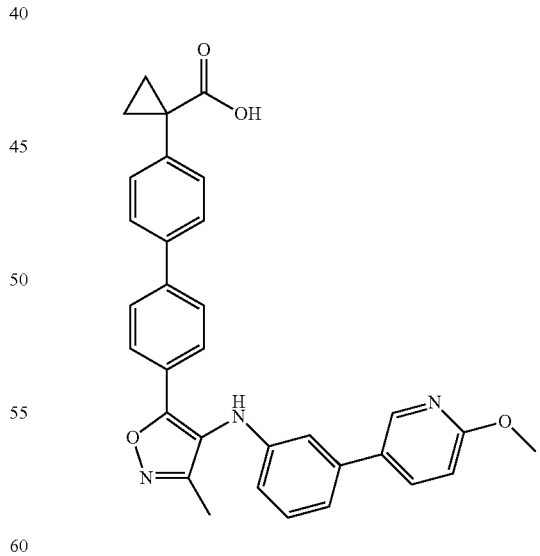

Step 2: 1-(4'-{4-[3-(6-Methoxy-pyridin-3-yl)-phenylamino]-3-methyl-isoxazol-5-yl}-biphenyl-4-yl)-cyclopropanecarboxylic acid Prepared according to the procedure described in Example 1, Step 13, using 1-(4'-{4-[3-(6-methoxy-pyridin-3-yl)-phenylamino]-3-methyl-isoxazol-5-yl}-biphenyl-4-yl)-cyclopropanecarboxylic acid ethyl ester.

Example 103

1-{4'-[3-Methyl-4-(3-pyridin-3-yl-phenylamino)-isoxazol-5-yl]-biphenyl-4-yl}-cyclopropanecarboxylic acid (Compound 1-103)

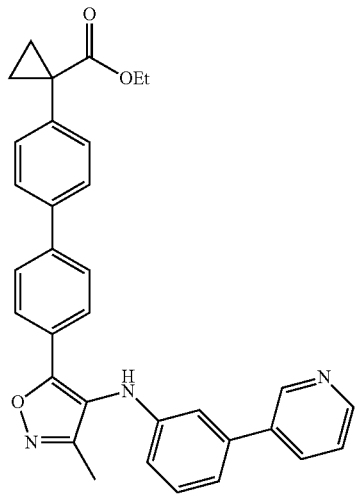 [SMILES: CCOC(=O)C1(c2ccc(-c3ccc(-c4onc(C)c4Nc4cccc(-c5cccnc5)c4)cc3)cc2)CC1]

Step 1: 1-{4'-[3-Methyl-4-(3-pyridin-3-yl-phenylamino)-isoxazol-5-yl]-biphenyl-4-yl}-cyclopropanecarboxylic acid ethyl ester Prepared according to the procedure described in Example 1, Step 10, using 1-{4'-[4-(3-bromo-phenylamino)-3-methyl-isoxazol-5-yl]-biphenyl-4-yl}-cyclopropanecarboxylic acid ethyl ester and pyridine-3-boronic acid.

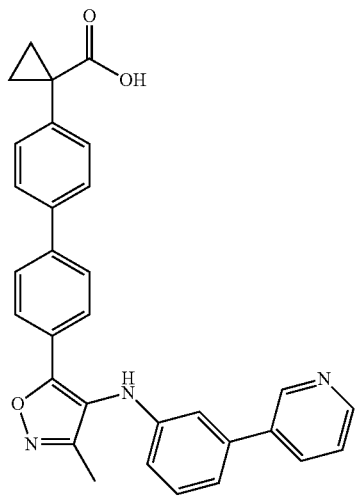 [SMILES: Cc1noc(-c2ccc(-c3ccc(C4(C(=O)O)CC4)cc3)cc2)c1Nc1cccc(-c2cccnc2)c1]

Step 2: 1-{4'-[3-Methyl-4-(3-pyridin-3-yl-phenylamino)-isoxazol-5-yl]-biphenyl-4-yl}-cyclopropanecarboxylic acid Prepared according to the procedure described in Example 1, Step 13, using 1-{4'-[3-methyl-4-(3-pyridin-3-yl-phenylamino)-isoxazol-5-yl]-biphenyl-4-yl}-cyclopropanecarboxylic acid ethyl ester.

Example 104

1-(4'-{4-[3-(5-Methoxy-pyridin-3-yl)-phenylamino]-3-methyl-isoxazol-5-yl}-biphenyl-4-yl)-cyclopropanecarboxylic acid (Compound 1-104)

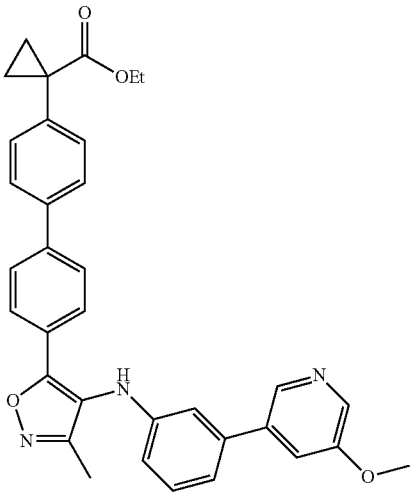 [SMILES: COc1cncc(-c2cccc(Nc3c(C)noc3-c3ccc(-c4ccc(C5(C(=O)O)CC5)cc4)cc3)c2)c1]

Step 1: 1-(4'-{4-[3-(5-Methoxy-pyridin-3-yl)-phenylamino]-3-methyl-isoxazol-5-yl}-biphenyl-4-yl)-cyclopropanecarboxylic acid ethyl ester Prepared according to the procedure described in Example 1, Step 10, using 1-{4'-[4-(3-bromo-phenylamino)-3-methyl-isoxazol-5-yl]-biphenyl-4-yl}-cyclopropanecarboxylic acid ethyl ester and 5-methoxypyridine-3-boronic acid.

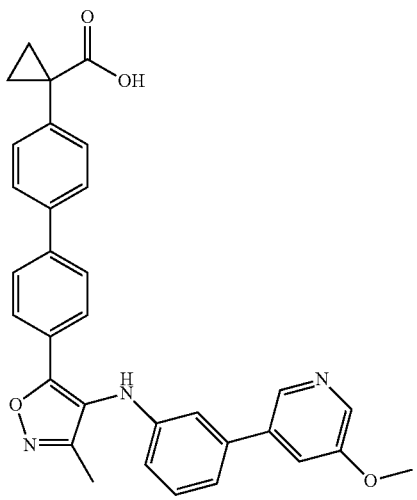

Step 2: 1-(4'-{4-[3-(5-Methoxy-pyridin-3-yl)-phenylamino]-3-methyl-isoxazol-5-yl}-biphenyl-4-yl)-cyclopropanecarboxylic acid Prepared according to the procedure described in Example 1, Step 13, using 1-(4'-{4-[3-(5-methoxy-pyridin-3-yl)-phenylamino]-3-methyl-isoxazol-5-yl}-biphenyl-4-yl)-cyclopropanecarboxylic acid ethyl ester.

Example 105

1-(4'-{3-Methyl-4-[6-(methyl-phenyl-amino)-pyridin-2-ylamino]-isoxazol-5-yl}-biphenyl-4-yl)-cyclopropanecarboxylic acid (Compound 1-105)

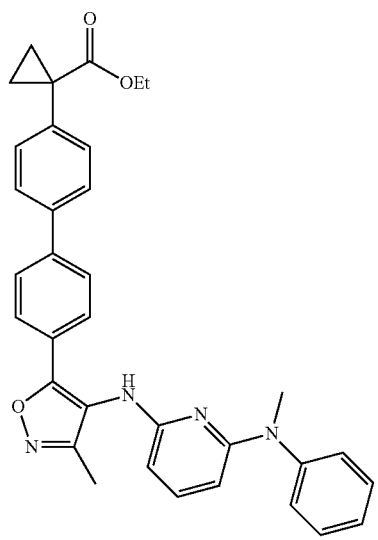 [SMILES: Cc1noc(-c2ccc(-c3ccc(C4(C(=O)O)CC4)cc3)cc2)c1Nc1cccc(N(C)c2ccccc2)n1]

Step 1: 1-(4'-{3-Methyl-4-[6-(methyl-phenyl-amino)-pyridin-2-ylamino]-isoxazol-5-yl}-biphenyl-4-yl)-cyclopropanecarboxylic acid ethyl ester Prepared according to the procedure described in Example 68, Step 2, using 1-{4'-[4-(6-bromo-pyridin-2-ylamino)-3-methyl-isoxazol-5-yl]-biphenyl-4-yl}-cyclopropanecarboxylic acid ethyl ester and N-methylaniline.

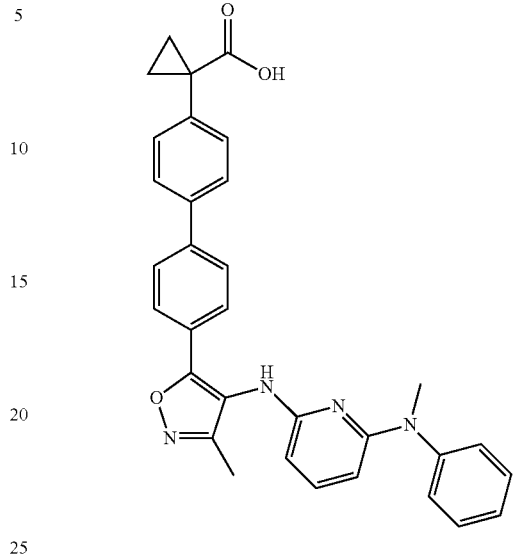

Step 2: 1-(4'-{3-Methyl-4-[6-(methyl-phenyl-amino)-pyridin-2-ylamino]-isoxazol-5-yl}-biphenyl-4-yl)-cyclopropanecarboxylic acid Prepared according to the procedure described in Example 1, Step 13, using 1-(4'-{3-methyl-4-[6-(methyl-phenyl-amino)-pyridin-2-ylamino]-isoxazol-5-yl}-biphenyl-4-yl)-cyclopropanecarboxylic acid ethyl ester.

Example 106

1-(4'-{3-Methyl-4-[3-(methyl-phenyl-amino)-phenylamino]-isoxazol-5-yl}-biphenyl-4-yl)-cyclopropanecarboxylic acid (Compound 1-106)

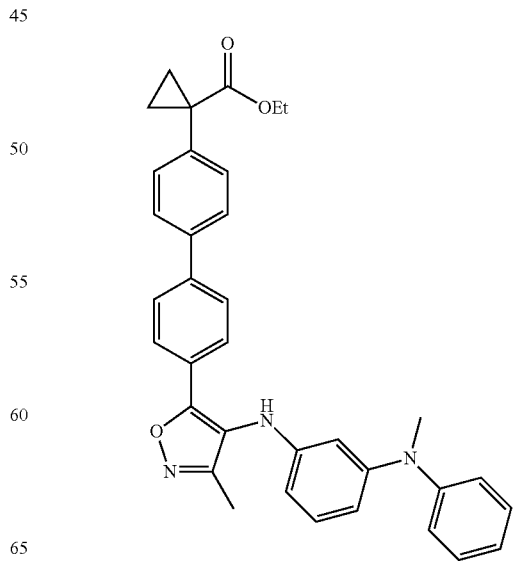

Step 1: 1-(4'-{3-Methyl-4-[3-(methyl-phenyl-amino)-phenylamino]-isoxazol-5-yl}-biphenyl-4-yl)-cyclopropanecarboxylic acid ethyl ester Prepared according to the procedure described in Example 68, Step 2, using 1-{4'-[4-(3-bromo-phenylamino)-3-methyl-isoxazol-5-yl]-biphenyl-4-yl}-cyclopropanecarboxylic acid ethyl ester and N-methylaniline.

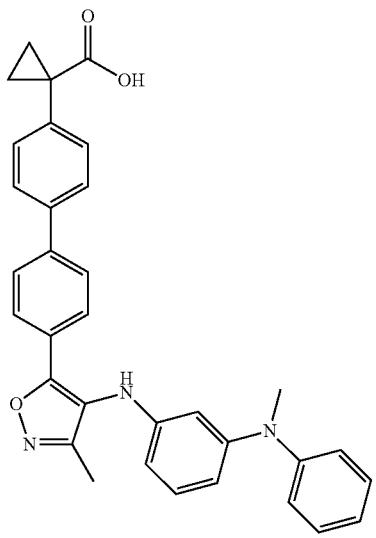 [SMILES: Cc1noc(-c2ccc(-c3ccc(C4(C(=O)O)CC4)cc3)cc2)c1Nc1cccc(N(C)c2ccccc2)c1]

Step 2: 1-(4'-{3-Methyl-4-[3-(methyl-phenyl-amino)-phenylamino]-isoxazol-5-yl}-biphenyl-4-yl)-cyclopropanecarboxylic acid Prepared according to the procedure described in Example 1, Step 13, using 1-(4'-{3-methyl-4-[3-(methyl-phenyl-amino)-phenylamino]-isoxazol-5-yl}-biphenyl-4-yl)-cyclopropanecarboxylic acid ethyl ester.

Example 107

1-{4'-[3-Methyl-4-(5-phenyl-pyridin-3-ylamino)-isoxazol-5-yl]-biphenyl-4-yl}-cyclopropanecarboxylic acid (Compound 1-107)

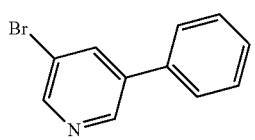 [SMILES: Brc1cncc(-c2ccccc2)c1]

Step 1: 3-Bromo-5-phenyl-pyridine

Prepared according to the procedure described in Example 1, Step 10, using 3,5-dibromo-pyridine and phenylboronic acid.

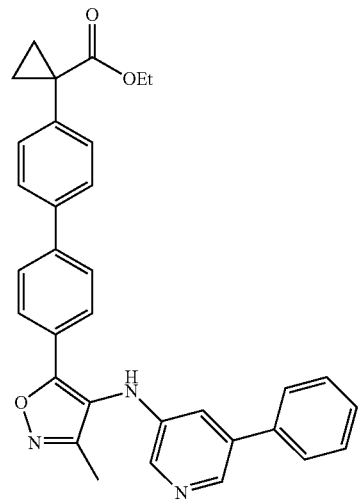 [SMILES: CCOC(=O)C1(c2ccc(-c3ccc(-c4onc(C)c4Nc4cncc(-c5ccccc5)c4)cc3)cc2)CC1]

Step 2: 1-{4'-[3-Methyl-4-(5-phenyl-pyridin-3-ylamino)-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 3-bromo-5-phenyl-pyridine.

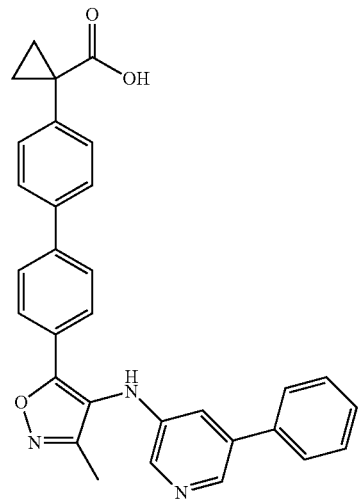 [SMILES: Cc1noc(-c2ccc(-c3ccc(C4(C(=O)O)CC4)cc3)cc2)c1Nc1cncc(-c2ccccc2)c1]

Step 3: 1-{4'-[3-Methyl-4-(5-phenyl-pyridin-3-ylamino)-isoxazol-5-yl]-biphenyl-4-yl}-cyclopropanecarboxylic acid Prepared according to the procedure described in Example 1, Step 13, using 1-{4'-[3-methyl-4-(5-phenyl-pyridin-3-ylamino)-isoxazol-5-yl]-biphenyl-4-yl}-cyclopropanecarboxylic acid ethyl ester.

Example 108

1-(4'-{4-[5-(3-Fluoro-phenyl)-pyridin-3-ylamino]-3-methyl-isoxazol-5-yl}-biphenyl-4-yl)-cyclopropanecarboxylic acid (Compound 1-108)

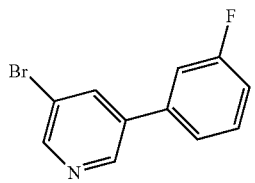 [SMILES: Fc1cccc(-c2cncc(Br)c2)c1]

Step 1: 3-Bromo-5-(3-fluoro-phenyl)-pyridine

Prepared according to the procedure described in Example 1, Step 10, using 3,5-dibromo-pyridine and 3-fluorophenylboronic acid.

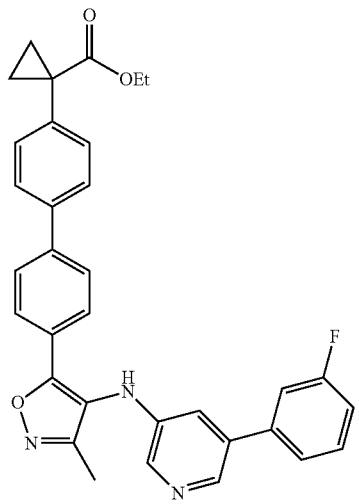 [SMILES: CCOC(=O)C1(c2ccc(-c3ccc(-c4onc(C)c4Nc4cncc(-c5cccc(F)c5)c4)cc3)cc2)CC1]

Step 2: 1-(4'-{4-[5-(3-Fluoro-phenyl)-pyridin-3-ylamino]-3-methyl-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 3-bromo-5-(3-fluoro-phenyl)-pyridine.

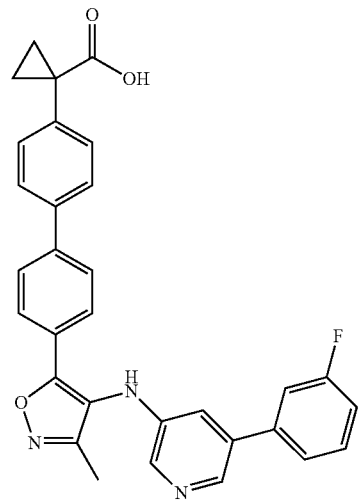 [SMILES: Cc1noc(-c2ccc(-c3ccc(C4(C(=O)O)CC4)cc3)cc2)c1Nc1cncc(-c2cccc(F)c2)c1]

Step 3: 1-(4'-{4-[5-(3-Fluoro-phenyl)-pyridin-3-ylamino]-3-methyl-isoxazol-5-yl}-biphenyl-4-yl)-cyclopropanecarboxylic acid Prepared according to the procedure described in Example 1, Step 13, using 1-(4'-{4-[5-(3-fluoro-phenyl)-pyridin-3-ylamino]-3-methyl-isoxazol-5-yl}-biphenyl-4-yl)-cyclopropanecarboxylic acid ethyl ester.

Example 109

1-(4'-{4-[6-(2-Chloro-phenyl)-pyridin-2-ylamino]-3-methyl-isoxazol-5-yl}-biphenyl-4-yl)-cyclopropanecarboxylic acid (Compound 1-109)

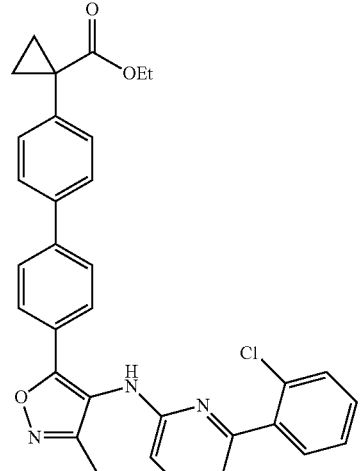

Step 1: 1-(4'-{4-[6-(2-Chloro-phenyl)-pyridin-2-ylamino]-3-methyl-isoxazol-5-yl}-biphenyl-4-yl)-cyclopropanecarboxylic acid ethyl ester Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2-chlorophenylboronic acid.

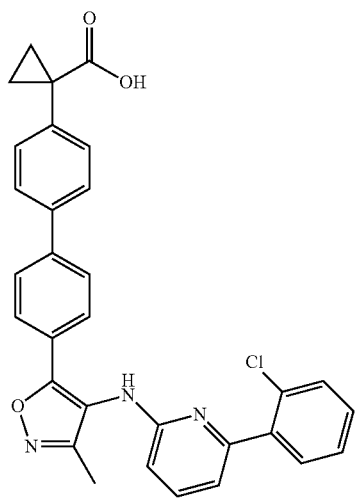

Step 2: 1-(4'-{4-[6-(2-Chloro-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(2-chloro-phenyl)-pyridin-2-ylamino]-3-methyl-isoxazol-5-yl}-biphenyl-4-yl)-cyclopropanecarboxylic acid ethyl ester.

Example 110

1-(4'-{4-[Hydroxy-(6-phenyl-pyridin-2-yl)-methyl]-3-methyl-isoxazol-5-yl}-biphenyl-4-yl)-cyclopropanecarboxylic acid (Compound 1-110)

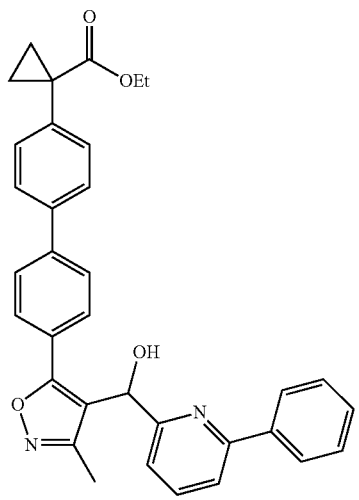 [SMILES: CCOC(=O)C1(c2ccc(-c3ccc(-c4onc(C)c4C(O)c4cccc(-c5ccccc5)n4)cc3)cc2)CC1]

Step 1: 1-(4'-{4-[Hydroxy-(6-phenyl-pyridin-2-yl)-methyl]-3-methyl-isoxazol-5-yl}-biphenyl-4-yl)-cyclopropanecarboxylic acid ethyl ester Prepared according to the procedure described in Example 58, Step 3, using 1-[4'-(4-formyl-3-methyl-isoxazol-5-yl)-biphenyl-4-yl]-cyclopropanecarboxylic acid ethyl ester and 2-bromo-6-phenyl-pyridine.

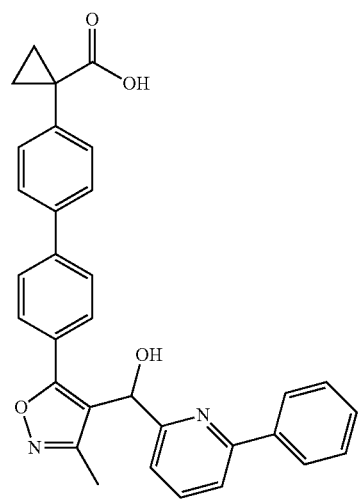 [SMILES: Cc1noc(-c2ccc(-c3ccc(C4(C(=O)O)CC4)cc3)cc2)c1C(O)c1cccc(-c2ccccc2)n1]

Step 2: 1-(4'-{4-[Hydroxy-(6-phenyl-pyridin-2-yl)-methyl]-3-methyl-isoxazol-5-yl}-biphenyl-4-yl)-cyclopropanecarboxylic acid Prepared according to the procedure described in Example 1, Step 13, using 1-(4'-{4-[hydroxy-(6-phenyl-pyridin-2-yl)-methyl]-3-methyl-isoxazol-5-yl}-biphenyl-4-yl)-cyclopropanecarboxylic acid ethyl ester.

Example 111

1-{4'-[3-Methyl-4-(2-phenyl-pyridin-4-ylamino)-isoxazol-5-yl]-biphenyl-4-yl}-cyclopropanecarboxylic acid (Compound 1-111)

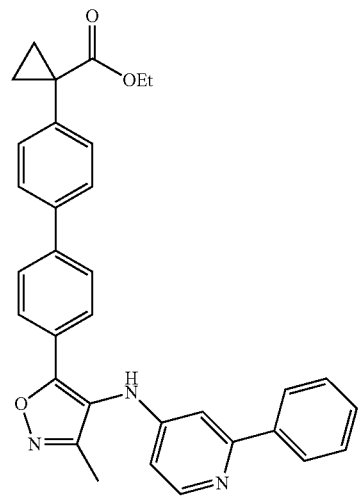 [SMILES: CCOC(=O)C1(c2ccc(-c3ccc(-c4onc(C)c4Nc4ccnc(-c5ccccc5)c4)cc3)cc2)CC1]

Step 1: 1-{4'-[3-Methyl-4-(2-phenyl-pyridin-4-ylamino)-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 4-bromo-2-phenyl-pyridine.

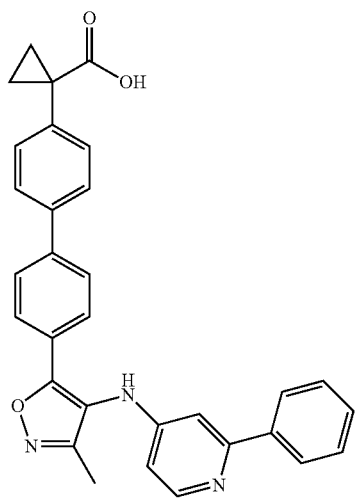 [SMILES: Cc1noc(-c2ccc(-c3ccc(C4(C(=O)O)CC4)cc3)cc2)c1Nc1ccnc(-c2ccccc2)c1]

Step 2: 1-{4'-[3-Methyl-4-(2-phenyl-pyridin-4-ylamino)-isoxazol-5-yl]-biphenyl-4-yl}-cyclopropanecarboxylic acid Prepared according to the procedure described in Example 1, Step 13, using 1-{4'-[3-methyl-4-(2-phenyl-pyridin-4-ylamino)-isoxazol-5-yl]-biphenyl-4-yl}-cyclopropanecarboxylic acid ethyl ester.

Example 112

1-(4'-{4-[2-(3-Fluoro-phenyl)-pyridin-4-ylamino]-3-methyl-isoxazol-5-yl}-biphenyl-4-yl)-cyclopropanecarboxylic acid (Compound 1-112)

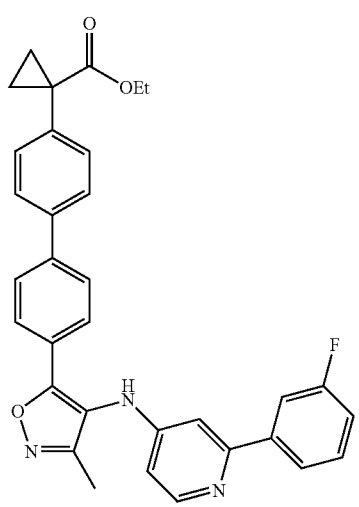 [SMILES: CCOC(=O)C1(c2ccc(-c3ccc(-c4onc(C)c4Nc4ccnc(-c5cccc(F)c5)c4)cc3)cc2)CC1]

Step 1: 1-(4'-{4-[2-(3-Fluoro-phenyl)-pyridin-4-ylamino]-3-methyl-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 4-bromo-2-(3-fluoro-phenyl)-pyridine.

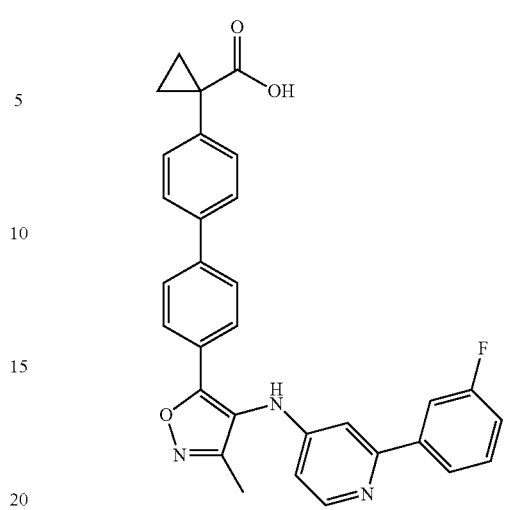

Step 2: 1-(4'-{4-[2-(3-Fluoro-phenyl)-pyridin-4-ylamino]-3-methyl-isoxazol-5-yl}-biphenyl-4-yl)-cyclopropanecarboxylic acid Prepared according to the procedure described in Example 1, Step 13, using 1-(4'-{4-[2-(3-fluoro-phenyl)-pyridin-4-ylamino]-3-methyl-isoxazol-5-yl}-biphenyl-4-yl)-cyclopropanecarboxylic acid ethyl ester.

Example 113

1-(4'-{4-[5-(2-Chloro-phenyl)-pyridin-3-ylamino]-3-methyl-isoxazol-5-yl}-biphenyl-4-yl)-cyclopropanecarboxylic acid (Compound 1-113)

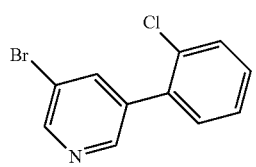 [SMILES: Clc1ccccc1-c1cncc(Br)c1]

Step 1: 3-Bromo-5-(2-chloro-phenyl)-pyridine

Prepared according to the procedure described in Example 1, Step 10, using 3,5-dibromo-pyridine and 2-chlorophenyl-boronic acid.

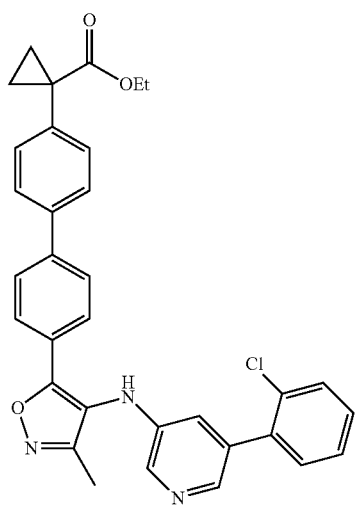 [SMILES: Cc1noc(-c2ccc(-c3ccc(C4(C(=O)O)CC4)cc3)cc2)c1Nc1cncc(-c2ccccc2Cl)c1]

Step 2: 1-(4'-{4-[5-(2-Chloro-phenyl)-pyridin-3-ylamino]-3-methyl-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 3-bromo-5-(2-chloro-phenyl)-pyridine.

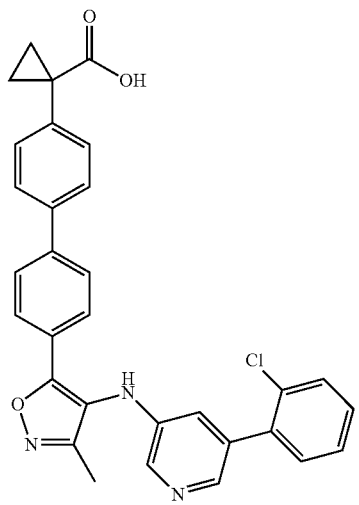

Step 3: 1-(4'-{4-[5-(2-Chloro-phenyl)-pyridin-3-ylamino]-3-methyl-isoxazol-5-yl}-biphenyl-4-yl)-cyclopropanecarboxylic acid Prepared according to the procedure described in Example 1, Step 13, using 1-(4'-{4-[5-(2-chloro-phenyl)-pyridin-3-ylamino]-3-methyl-isoxazol-5-yl}-biphenyl-4-yl)-cyclopropanecarboxylic acid ethyl ester.

Example 114

1-(4'-{4-[2-(2-Chloro-phenyl)-pyridin-4-ylamino]-3-methyl-isoxazol-5-yl}-biphenyl-4-yl)-cyclopropanecarboxylic acid (Compound 1-114)

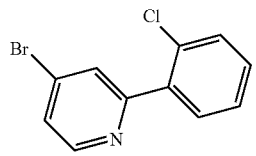

Step 1: 4-Bromo-2-(2-chloro-phenyl)-pyridine

Prepared according to the procedure described in Example 1, Step 10, using 2,4-dibromo-pyridine and 2-chlorophenyl-boronic acid.

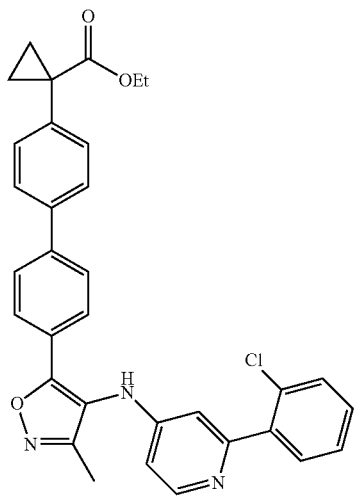

Step 2: 1-(4'-{4-[2-(2-Chloro-phenyl)-pyridin-4-ylamino]-3-methyl-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 4-bromo-2-(2-chloro-phenyl)-pyridine.

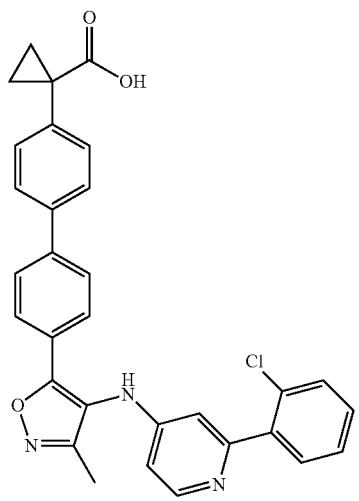 [SMILES: CCOC(=O)C1(c2ccc(-c3ccc(-c4onc(C)c4Nc4ccnc(-c5ccccc5Cl)c4)cc3)cc2)CC1]

Step 3: 1-(4'-{4-[2-(2-Chloro-phenyl)-pyridin-4-ylamino]-3-methyl-isoxazol-5-yl}-biphenyl-4-yl)-cyclopropanecarboxylic acid Prepared according to the procedure described in Example 1, Step 13, using 1-(4'-{4-[2-(2-chloro-phenyl)-pyridin-4-ylamino]-3-methyl-isoxazol-5-yl}-biphenyl-4-yl)-cyclopropanecarboxylic acid ethyl ester.

Example 115

1-{4'-[3-Methyl-4-(4-phenyl-pyrimidin-2-ylamino)-isoxazol-5-yl]-biphenyl-4-yl}-cyclopropanecarboxylic acid (Compound 1-115)

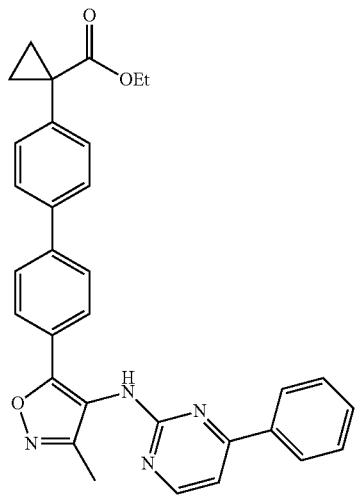

Step 1: 1-{4'-[3-Methyl-4-(4-phenyl-pyrimidin-2-ylamino)-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-bromo-4-phenyl-pyrimidine.

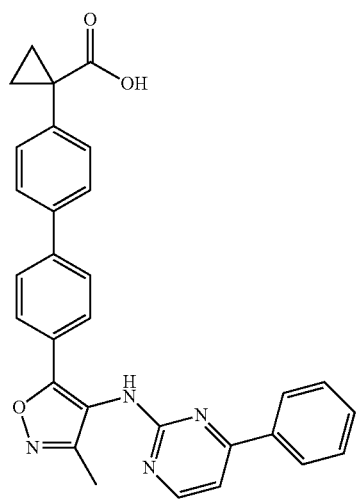

Step 2: 1-{4'-[3-Methyl-4-(4-phenyl-pyrimidin-2-ylamino)-isoxazol-5-yl]-biphenyl-4-yl}-cyclopropanecarboxylic acid Prepared according to the procedure described in Example 1, Step 13, using 1-{4'-[3-methyl-4-(4-phenyl-pyrimidin-2-ylamino)-isoxazol-5-yl]-biphenyl-4-yl}-cyclopropanecarboxylic acid ethyl ester.

Example 116

1-{4'-[3-Methyl-4-(4-phenyl-pyridin-2-ylamino)-isoxazol-5-yl]-biphenyl-4-yl}-cyclopropanecarboxylic acid (Compound 1-116)

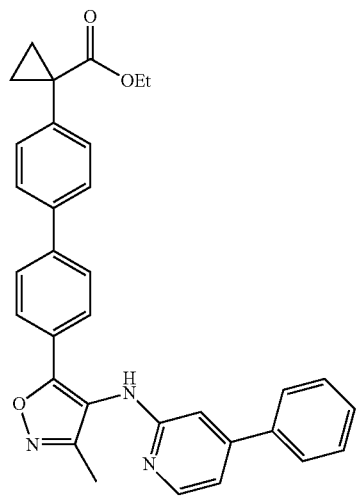 [SMILES: Cc1noc(-c2ccc(-c3ccc(C4(C(=O)O)CC4)cc3)cc2)c1Nc1cc(-c2ccccc2)ccn1]

Step 1: 1-{4'-[3-Methyl-4-(4-phenyl-pyridin-2-ylamino)-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-bromo-4-phenyl-pyridine.

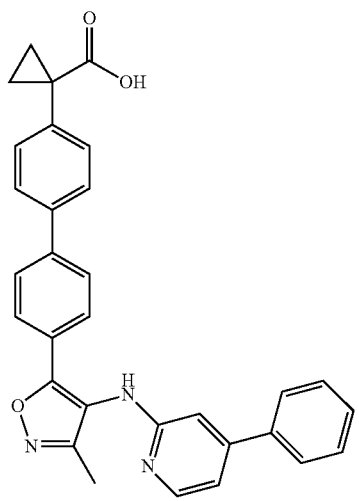

Step 2: 1-{4'-[3-Methyl-4-(4-phenyl-pyridin-2-ylamino)-isoxazol-5-yl]-biphenyl-4-yl}-cyclopropanecarboxylic acid Prepared according to the procedure described in Example 1, Step 13, using 1-{4'-[3-methyl-4-(4-phenyl-pyridin-2-ylamino)-isoxazol-5-yl]-biphenyl-4-yl}-cyclopropanecarboxylic acid ethyl ester.

Example 117

1-{4'-[4-(2'-Dimethylaminomethyl-biphenyl-3-ylamino)-3-methyl-isoxazol-5-yl]-biphenyl-4-yl}-cyclopropanecarboxylic acid (Compound 1-117)

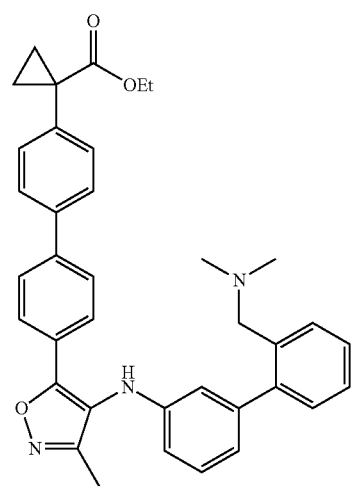 [SMILES: CCOC(=O)C1(c2ccc(-c3ccc(-c4onc(C)c4Nc4cccc(-c5ccccc5CN(C)C)c4)cc3)cc2)CC1]

Step 1: 1-{4'-[4-(2'-Dimethylaminomethyl-biphenyl-3-ylamino)-3-methyl-isoxazol-5-yl]-biphenyl-4-yl}-cyclopropanecarboxylic acid ethyl ester Prepared according to the procedure described in Example 42, Step 2, using 1-{4'-[4-(3-bromo-phenylamino)-3-methyl-isoxazol-5-yl]-biphenyl-4-yl}-cyclopropanecarboxylic acid ethyl ester and 2-(N,N-dimethylaminomethyl)-phenylboronic acid.

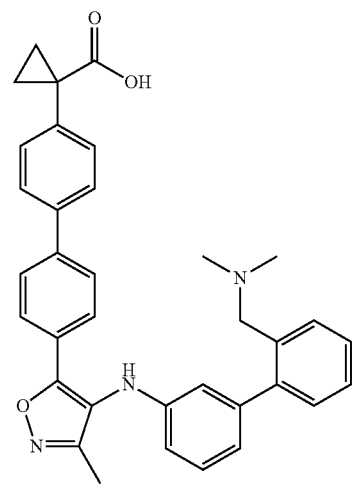 [SMILES: Cc1noc(-c2ccc(-c3ccc(C4(C(=O)O)CC4)cc3)cc2)c1Nc1cccc(-c2ccccc2CN(C)C)c1]

Step 2: 1-{4'-[4-(2'-Dimethylaminomethyl-biphenyl-3-ylamino)-3-methyl-isoxazol-5-yl]-biphenyl-4-yl}-cyclopropanecarboxylic acid Prepared according to the procedure described in Example 1, Step 13, using 1-{4'-[4-(2'-dimethylaminomethyl-biphenyl-3-ylamino)-3-methyl-isoxazol-5-yl]-biphenyl-4-yl}-cyclopropanecarboxylic acid ethyl ester.

Example 118

1-(4'-{3-Methyl-4-[5-(3-trifluoromethyl-phenyl)-pyridin-3-ylamino]-isoxazol-5-yl}-biphenyl-4-yl)-cyclopropanecarboxylic acid (Compound 1-118)

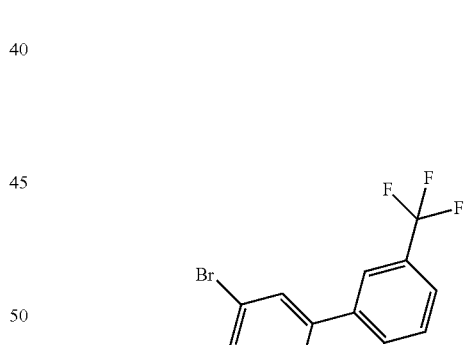

Step 1:
3-Bromo-5-(3-trifluoromethyl-phenyl)-pyridine

Prepared according to the procedure described in Example 1, Step 10, using 3,5-dibromo-pyridine and 3-(trifluoromethyl)-phenylboronic acid.

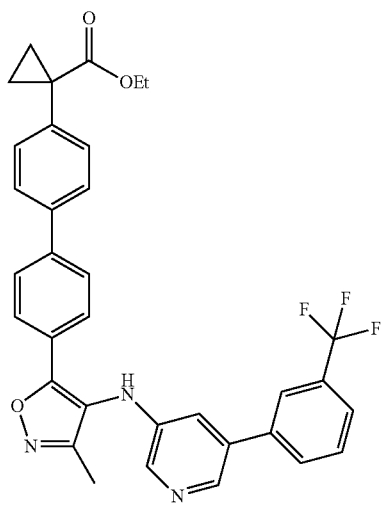 [SMILES: CCOC(=O)C1(c2ccc(-c3ccc(-c4onc(C)c4Nc4cncc(-c5cccc(C(F)(F)F)c5)c4)cc3)cc2)CC1]

Step 2: 1-(4'-{3-Methyl-4-[5-(3-trifluoromethyl-phenyl)-pyridin-3-ylamino]-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 3-bromo-5-(3-trifluoromethyl-phenyl)-pyridine.

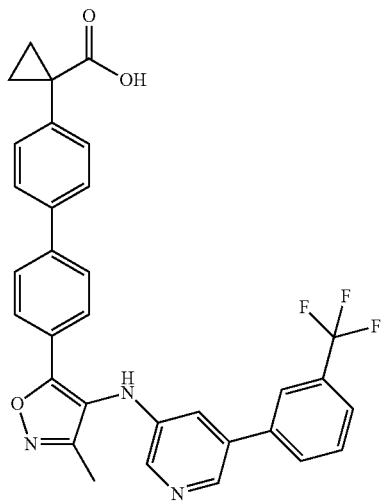 [SMILES: Cc1noc(-c2ccc(-c3ccc(C4(C(=O)O)CC4)cc3)cc2)c1Nc1cncc(-c2cccc(C(F)(F)F)c2)c1]

Step 3: 1-(4'-{3-Methyl-4-[5-(3-trifluoromethyl-phenyl)-pyridin-3-ylamino]-isoxazol-5-yl}-biphenyl-4-yl)-cyclopropanecarboxylic acid Prepared according to the procedure described in Example 1, Step 13, using 1-(4'-{3-Methyl-4-[5-(3-trifluoromethyl-phenyl)-pyridin-3-ylamino]-isoxazol-5-yl}-biphenyl-4-yl)-cyclopropanecarboxylic acid ethyl ester.

Example 119

1-(4'-{3-Methyl-4-[5-(4-trifluoromethyl-phenyl)-pyridin-3-ylamino]-isoxazol-5-yl}-biphenyl-4-yl)-cyclopropanecarboxylic acid (Compound 1-119)

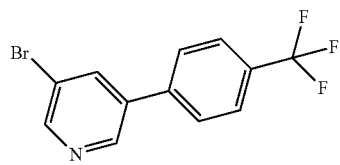 [SMILES: FC(F)(F)c1ccc(-c2cncc(Br)c2)cc1]

Step 1:
3-Bromo-5-(4-trifluoromethyl-phenyl)-pyridine

Prepared according to the procedure described in Example 1, Step 10, using 3,5-dibromo-pyridine and 4-(trifluoromethyl)-phenylboronic acid.

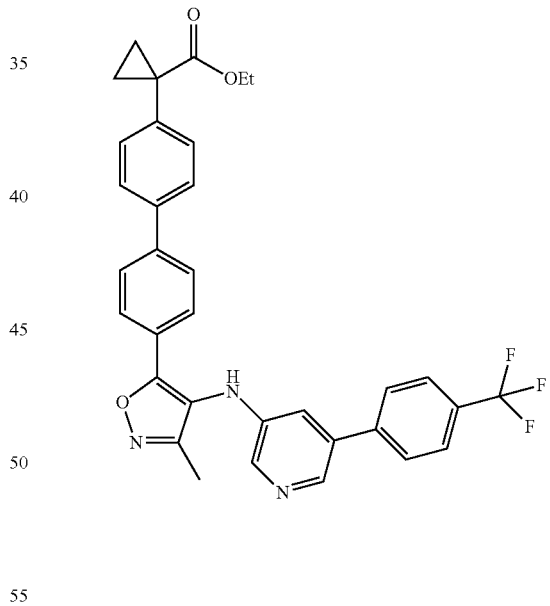

Step 2: 1-(4'-{3-Methyl-4-[5-(4-trifluoromethyl-phenyl)-pyridin-3-ylamino]-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 3-bromo-5-(4-trifluoromethyl-phenyl)-pyridine.

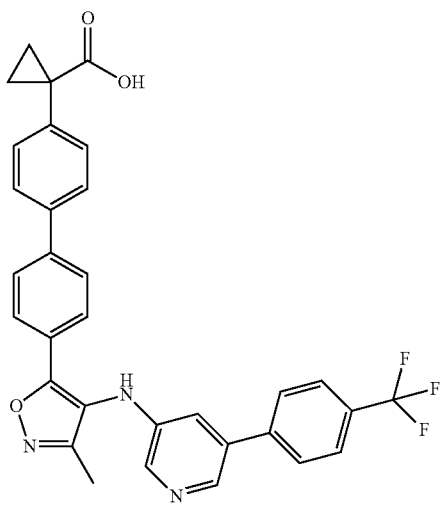 [SMILES: Cc1noc(-c2ccc(-c3ccc(C4(C(=O)O)CC4)cc3)cc2)c1Nc1cncc(-c2ccc(C(F)(F)F)cc2)c1]

Step 3: 1-(4'-{3-Methyl-4-[5-(4-trifluoromethyl-phenyl)-pyridin-3-ylamino]-isoxazol-5-yl}-biphenyl-4-yl)-cyclopropanecarboxylic acid Prepared according to the procedure described in Example 1, Step 13, using 1-(4'-{3-Methyl-4-[5-(4-trifluoromethyl-phenyl)-pyridin-3-ylamino]-isoxazol-5-yl}-biphenyl-4-yl)-cyclopropanecarboxylic acid ethyl ester.

Example 120

1-(4'-{4-[Bis-(6-benzyl-pyridin-2-yl)-amino]-3-methyl-isoxazol-5-yl}-biphenyl-4-yl)-cyclopropanecarboxylic acid (Compound 1-120)

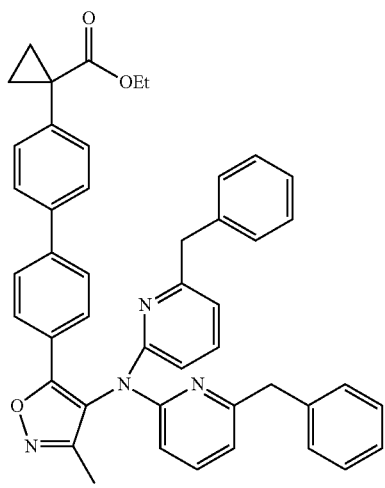 [SMILES: CCOC(=O)C1(c2ccc(-c3ccc(-c4onc(C)c4N(c4cccc(Cc5ccccc5)n4)c4cccc(Cc5ccccc5)n4)cc3)cc2)CC1]

Step 1: 1-(4'-{4-[Bis-(6-benzyl-pyridin-2-yl)-amino]-3-methyl-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-benzyl-6-bromo-pyridine.

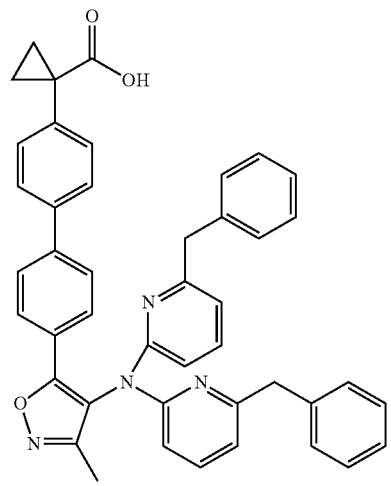 [SMILES: Cc1noc(-c2ccc(-c3ccc(C4(C(=O)O)CC4)cc3)cc2)c1N(c1cccc(Cc2ccccc2)n1)c1cccc(Cc2ccccc2)n1]

Step 2: 1-(4'-{4-[Bis-(6-benzyl-pyridin-2-yl)-amino]-3-methyl-isoxazol-5-yl}-biphenyl-4-yl)-cyclopropanecarboxylic acid Prepared according to the procedure described in Example 1, Step 13, using 1-(4'-{4-[bis-(6-benzyl-pyridin-2-yl)-amino]-3-methyl-isoxazol-5-yl}-biphenyl-4-yl)-cyclopropanecarboxylic acid ethyl ester.

Example 121

1-(4'-{4-[(2'-Dimethylaminomethyl-biphenyl-3-carbonyl)-amino]-3-methyl-isoxazol-5-yl}-biphenyl-4-yl)-cyclopropanecarboxylic acid (Compound 1-121)

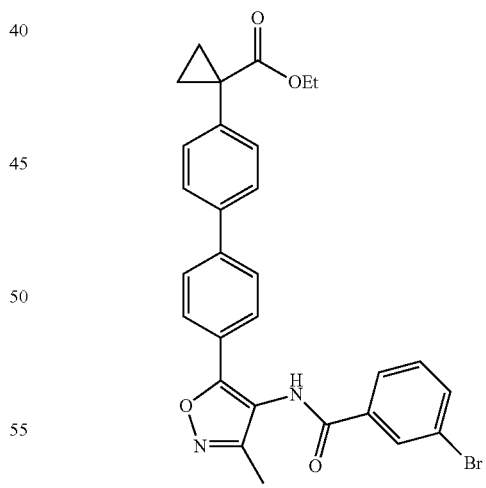

Step 1: 1-{4'-[4-(3-Bromo-benzoylamino)-3-methyl-isoxazol-5-yl]-biphenyl-4-yl}-cyclopropanecarboxylic acid ethyl ester 1-[4'-(4-Amino-3-methyl-isoxazol-5-yl)-biphenyl-4-yl]-cyclopropanecarboxylic acid ethyl ester (0.181 g, 0.5 mmol), 3-bromo-benzoic acid (0.100 g, 0.5 mmol), O-(7-azabenzotriazol-1-yl)-N,N,N',N'-tetramethyl uronium hexafluorophosphate (0.228 g, 0.6 mmol) and N-methylmorpholine (0.110 mL, 1.0 mmol) were combined in DMF and stirred at room temperature for 2 days. The reaction was submitted to standard aqueous workup and purified by silica gel chromatography to afford the title compound.

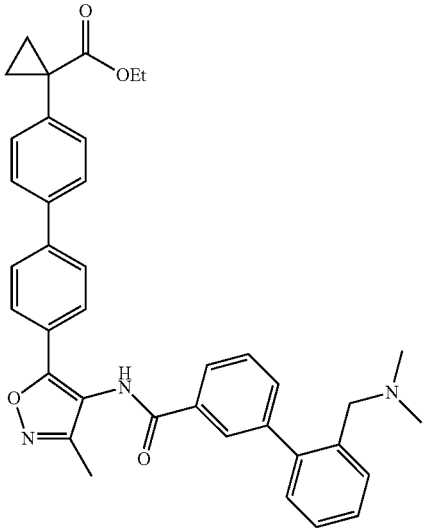 [SMILES: Cc1noc(-c2ccc(-c3ccc(C4(C(=O)O)CC4)cc3)cc2)c1NC(=O)c1cccc(-c2ccccc2CN(C)C)c1]

Step 2: 1-(4'-{4-[(2'-Dimethylaminomethyl-biphenyl-3-carbonyl)-amino]-3-methyl-isoxazol-5-yl}-biphenyl-4-yl)-cyclopropanecarboxylic acid ethyl ester Prepared according to the procedure described in Example 1, Step 10, using 1-{4'-[4-(3-bromo-benzoylamino)-3-methyl-isoxazol-5-yl]-biphenyl-4-yl}-cyclopropanecarboxylic acid ethyl ester and 2-(N,N-dimethylaminomethyl)-phenylboronic acid.

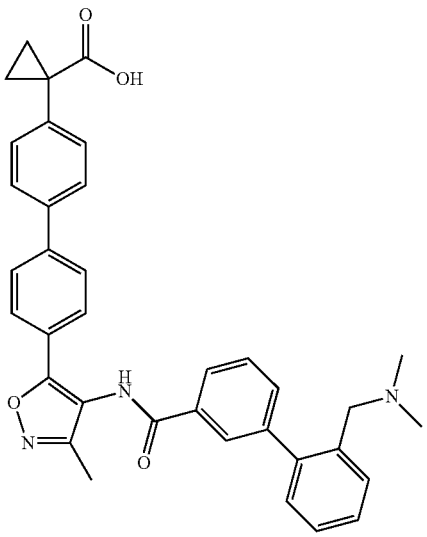

Step 3: 1-(4'-{4-[(2'-Dimethylaminomethyl-biphenyl-3-carbonyl)-amino]-3-methyl-isoxazol-5-yl}-biphenyl-4-yl)-cyclopropanecarboxylic acid Prepared according to the procedure described in Example 1, Step 13, using 1-(4'-{4-[(2'-dimethylaminomethyl-biphenyl-3-carbonyl)-amino]-3-methyl-isoxazol-5-yl}-biphenyl-4-yl)-cyclopropanecarboxylic acid ethyl ester.

Example 122

1-{4'-[3-Methyl-4-(6-phenyl-pyridin-2-ylamino)-isoxazol-5-yl]-biphenyl-4-yl}-cyclobutanecarboxylic acid (Compound 1-122)

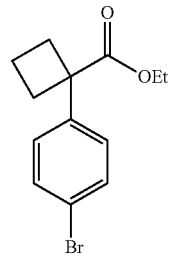 [SMILES: CCOC(=O)C1(c2ccc(Br)cc2)CCC1]

Step 1: 1-(4-Bromo-phenyl)-cyclobutanecarboxylic acid ethyl ester

Ethyl 4-bromophenyl acetate (2 g, 8.2 mmol) was dissolved in DMF (20 mL) and cooled to 0° C. under $N_2$ atmosphere. Sodium hydride (60% in mineral oil, 0.72 g, 18.1 mmol) was added and the reaction was allowed to warm to room temperature. After 10 minutes the ice bath was replaced and 1,3-dibromopropane (0.92 mL, 9.0 mmol) was added, and the reaction was again allowed to warm to room temperature. After 30 minutes the reaction was submitted to aqueous workup and purified on silica gel to give the title compound.

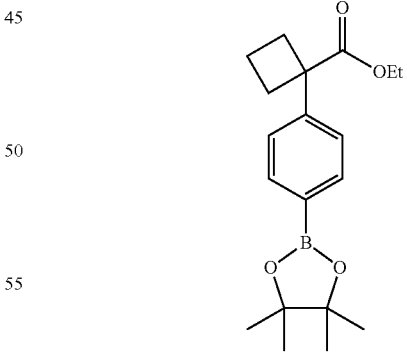

Step 2: 1-[4-(4,4,5,5-Tetramethyl-[1,3,2]dioxaborolan-2-yl)-phenyl]-cyclobutanecarboxylic acid ethyl ester Prepared according to the procedure described in Example 1, Step 9, using 1-(4-bromo-phenyl)-cyclobutanecarboxylic acid ethyl ester and bis(pinacolato)diboron.

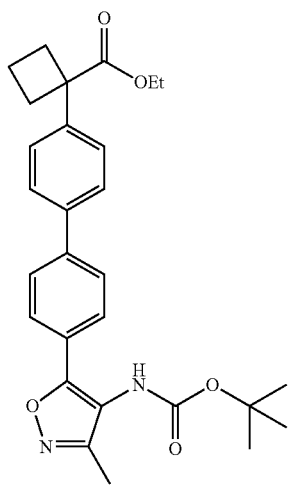 [SMILES: CCOC(=O)C1(c2ccc(-c3ccc(-c4onc(C)c4NC(=O)OC(C)(C)C)cc3)cc2)CCC1]

Step 3: 1-[4'-(4-tert-Butoxycarbonylamino-3-methyl-isoxazol-5-yl)-biphenyl-4-yl]-cyclobutanecarboxylic acid ethyl ester Prepared according to the procedure described in Example 42, Step 2, using [5-(4-bromo-phenyl)-3-methyl-isoxazol-4-yl]-carbamic acid tert-butyl ester and 1-[4-(4,4,5,5-tetramethyl-[1,3,2]dioxaborolan-2-yl)-phenyl]-cyclobutanecarboxylic acid ethyl ester.

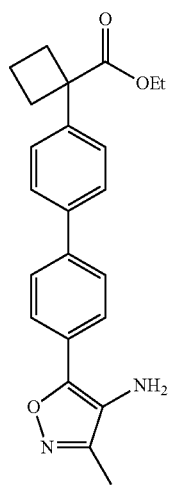 [SMILES: CCOC(=O)C1(c2ccc(-c3ccc(-c4onc(C)c4N)cc3)cc2)CCC1]

Step 4: 1-[4'-(4-Amino-3-methyl-isoxazol-5-yl)-biphenyl-4-yl]-cyclobutanecarboxylic acid ethyl ester Prepared according to the procedure described in Example 1, Step 9, using 1-[4'-(4-tert-butoxycarbonylamino-3-methyl-isoxazol-5-yl)-biphenyl-4-yl]-cyclobutanecarboxylic acid ethyl ester.

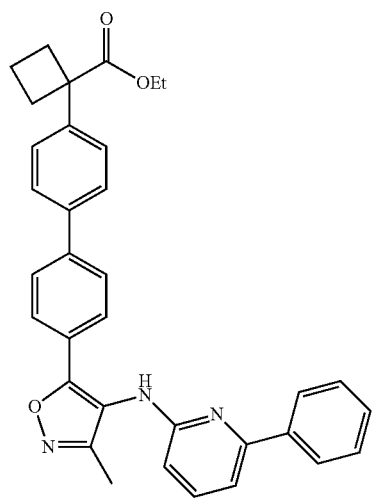

Step 5: 1-{4'-[3-Methyl-4-(6-phenyl-pyridin-2-ylamino)-isoxazol-5-yl]-biphenyl-4-yl}-cyclobutanecarboxylic acid ethyl ester Prepared according to the procedure described in Example 68, Step 2, using 1-[4'-(4-amino-3-methyl-isoxazol-5-yl)-biphenyl-4-yl]-cyclobutanecarboxylic acid ethyl ester and 2-bromo-6-phenyl-pyridine.

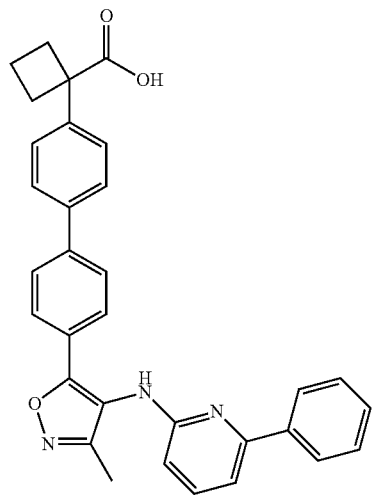 [SMILES: Cc1noc(-c2ccc(-c3ccc(C4(C(=O)O)CCC4)cc3)cc2)c1Nc1cccc(-c2ccccc2)n1]

Step 6: 1-{4'-[3-Methyl-4-(6-phenyl-pyridin-2-ylamino)-isoxazol-5-yl]-biphenyl-4-yl}-cyclobutanecarboxylic acid Prepared according to the procedure described in Example 1, Step 13, using 1-{4'-[3-methyl-4-(6-phenyl-pyridin-2-ylamino)-isoxazol-5-yl]-biphenyl-4-yl}-cyclobutanecarboxylic acid ethyl ester.

Example 123

1-{4'-[3-Methyl-4-(6-pyrazol-1-yl-pyridin-2-ylamino)-isoxazol-5-yl]-biphenyl-4-yl}-cyclopropanecarboxylic acid (Compound 1-123)

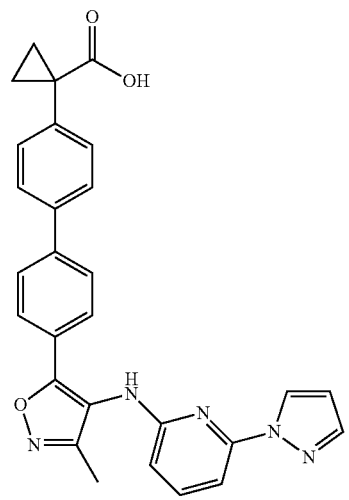

Step 2: 1-{4'-[3-Methyl-4-(6-pyrazol-1-yl-pyridin-2-ylamino)-isoxazol-5-yl]-biphenyl-4-yl}-cyclopropanecarboxylic acid Prepared according to the procedure described in Example 1, Step 13, using 1-{4'-[3-methyl-4-(6-pyrazol-1-yl-pyridin-2-ylamino)-isoxazol-5-yl]-biphenyl-4-yl}-cyclopropanecarboxylic acid ethyl ester.

Example 124

1-{4'-[3-Methyl-4-(6-morpholin-4-yl-pyridin-2-ylamino)-isoxazol-5-yl]-biphenyl-4-yl}-cyclopropanecarboxylic acid (Compound 1-124)

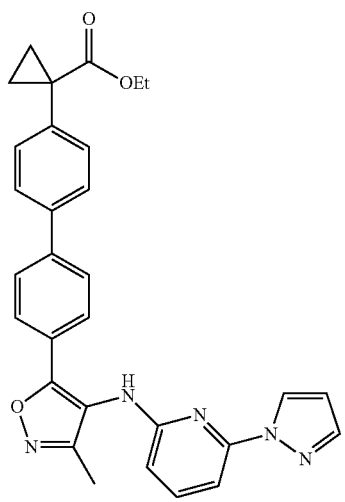 [SMILES: Cc1noc(-c2ccc(-c3ccc(C4(C(=O)O)CC4)cc3)cc2)c1Nc1cccc(-n2cccn2)n1]

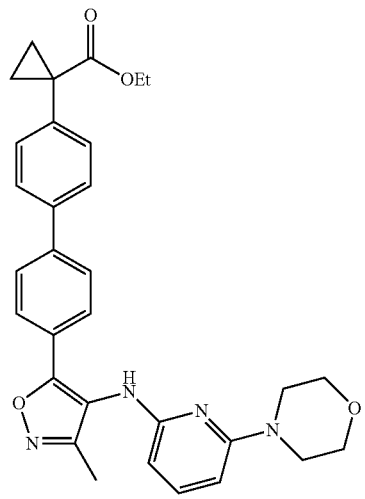 [SMILES: Cc1noc(-c2ccc(-c3ccc(C4(C(=O)O)CC4)cc3)cc2)c1Nc1cccc(N2CCOCC2)n1]

Step 1: 1-{4'-[3-Methyl-4-(6-pyrazol-1-yl-pyridin-2-ylamino)-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-bromo-6-pyrazol-1-yl-pyridine.

Step 1: 1-{4'-[3-Methyl-4-(6-morpholin-4-yl-pyridin-2-ylamino)-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 4-(6-bromo-pyridin-2-yl)-morpholine.

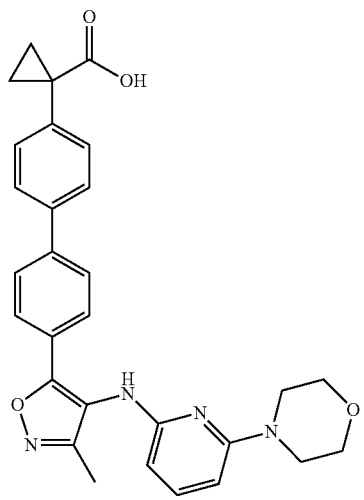

Step 2: 1-{4'-[3-Methyl-4-(6-morpholin-4-yl-pyridin-2-ylamino)-isoxazol-5-yl]-biphenyl-4-yl}-cyclopropanecarboxylic acid Prepared according to the procedure described in Example 1, Step 13, using 1-{4'-[3-methyl-4-(6-morpholin-4-yl-pyridin-2-ylamino)-isoxazol-5-yl]-biphenyl-4-yl}-cyclopropanecarboxylic acid ethyl ester.

Example 125

1-{4'-[4-(6-Benzyloxy-pyridin-2-ylamino)-3-methyl-isoxazol-5-yl]-biphenyl-4-yl}-cyclopropanecarboxylic acid (Compound 1-125)

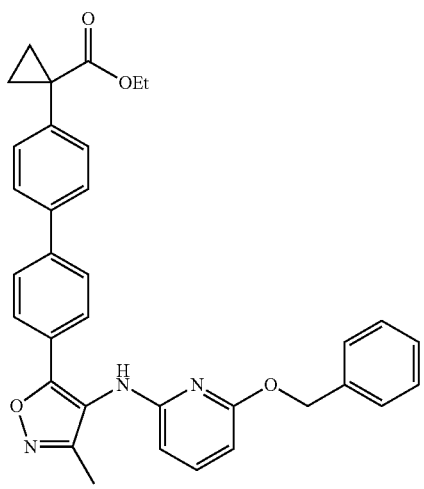 [SMILES: Cc1noc(-c2ccc(-c3ccc(C4(C(=O)O)CC4)cc3)cc2)c1Nc1cccc(OCc2ccccc2)n1]

Step 1: 1-{4'-[4-(6-Benzyloxy-pyridin-2-ylamino)-3-methyl-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-benzyloxy-6-bromo-pyridine.

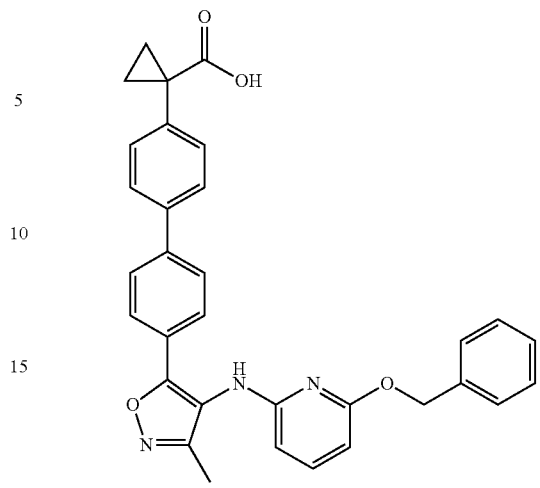

Step 2: 1-{4'-[4-(6-Benzyloxy-pyridin-2-ylamino)-3-methyl-isoxazol-5-yl]-biphenyl-4-yl}-cyclopropanecarboxylic acid Prepared according to the procedure described in Example 1, Step 13, using 1-{4'-[4-(6-benzyloxy-pyridin-2-ylamino)-3-methyl-isoxazol-5-yl]-biphenyl-4-yl}-cyclopropanecarboxylic acid ethyl ester.

Example 126

1-{4'-[3-Methyl-4-(6-phenylsulfanyl-pyridin-2-ylamino)-isoxazol-5-yl]-biphenyl-4-yl}-cyclopropanecarboxylic acid (Compound 1-126)

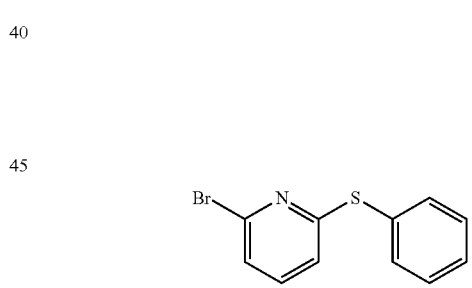

Step 1: 2-Bromo-6-phenylsulfanyl-pyridine 2,6-Dibromo-pyridine (3.6 g, 15 mmol) was dissolved in THF (20 mL) and cooled to −78° C. under $N_2$ atmosphere. n-Butyllithium (2.5M in THF, 6.4 mL, 16 mmol) was added and the reaction stirred for 1 hour before diphenyl disulfide (15 mmol) in THF (2 mL) was added. The reaction was allowed to warm to room temperature and stirred for 2 hours. The reaction was quenched with $H_2O$ and submitted to aqueous workup. The crude residue was purified on silica gel to afford the title compound.

Step 2: 1-{4'-[3-Methyl-4-(6-phenylsulfanyl-pyridin-2-ylamino)-isoxazol-5-yl]-biphenyl-4-yl}-cyclopropanecarboxylic acid ethyl ester

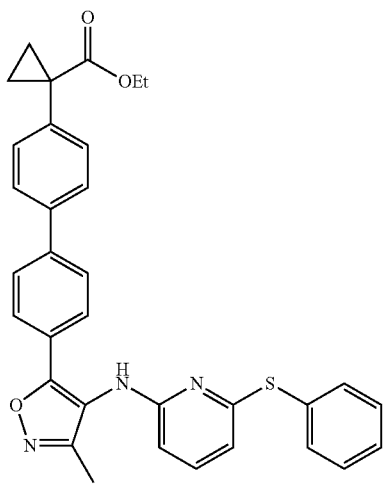 [SMILES: CCOC(=O)C1(c2ccc(-c3ccc(-c4onc(C)c4Nc4cccc(Sc5ccccc5)n4)cc3)cc2)CC1]

Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-bromo-6-phenylsulfanyl-pyridine.

Step 3: 1-{4'-[3-Methyl-4-(6-phenylsulfanyl-pyridin-2-ylamino)-isoxazol-5-yl]-biphenyl-4-yl}-cyclopropanecarboxylic acid

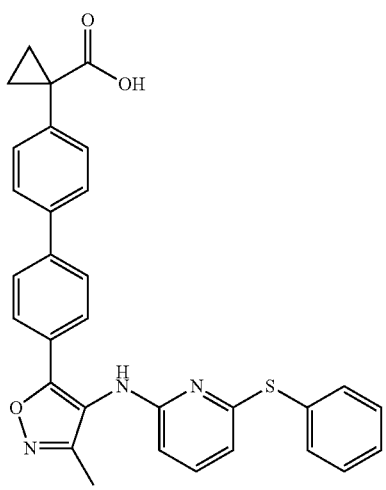 [SMILES: Cc1noc(-c2ccc(-c3ccc(C4(C(=O)O)CC4)cc3)cc2)c1Nc1cccc(Sc2ccccc2)n1]

Prepared according to the procedure described in Example 1, Step 13, using 1-{4'-[3-methyl-4-(6-phenylsulfanyl-pyridin-2-ylamino)-isoxazol-5-yl]-biphenyl-4-yl}-cyclopropanecarboxylic acid ethyl ester.

Example 127

1-{4'-[4-(6-Benzenesulfinyl-pyridin-2-ylamino)-3-methyl-isoxazol-5-yl]-biphenyl-4-yl}-cyclopropanecarboxylic acid (Compound 1-127)

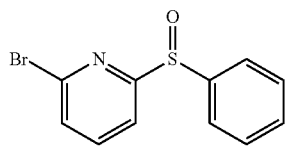 [SMILES: O=S(c1ccccc1)c1cccc(Br)n1]

Step 1: 2-Benzenesulfinyl-6-bromo-pyridine

2-Bromo-6-phenylsulfanyl-pyridine (0.5323 g, 2 mmol) was dissolved in CH$_2$Cl$_2$ (20 mL) and m-chloroperbenzoic acid (0.345 g, 2 mmol) was added. The reaction was stirred at room temperature overnight then submitted to aqueous workup and purification on silica gel to give the title compound.

Step 2: 1-{4'-[4-(6-Benzenesulfinyl-pyridin-2-ylamino)-3-methyl-isoxazol-5-yl]-biphenyl-4-yl}-cyclopropanecarboxylic acid ethyl ester

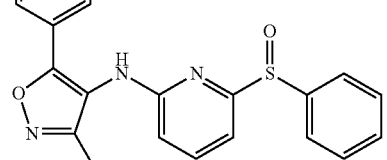

Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-benzenesulfinyl-6-bromo-pyridine.

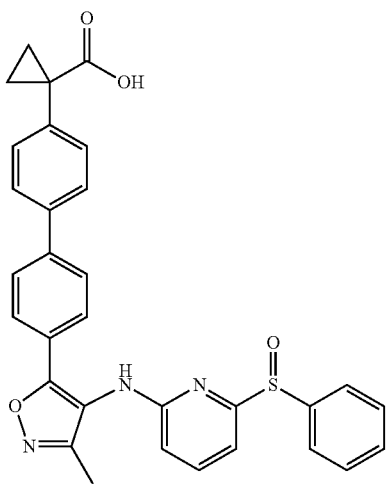 [SMILES: Cc1noc(-c2ccc(-c3ccc(C4(C(=O)O)CC4)cc3)cc2)c1Nc1cccc(S(=O)c2ccccc2)n1]

Step 3: 1-{4'-[4-(6-Benzenesulfinyl-pyridin-2-ylamino)-3-methyl-isoxazol-5-yl]-biphenyl-4-yl}-cyclopropanecarboxylic acid Prepared according to the procedure described in Example 1, Step 13, using 1-{4'-[4-(6-benzenesulfinyl-pyridin-2-ylamino)-3-methyl-isoxazol-5-yl]-biphenyl-4-yl}-cyclopropanecarboxylic acid ethyl ester.

Example 128

1-{4'-[4-(6-Benzenesulfonyl-pyridin-2-ylamino)-3-methyl-isoxazol-5-yl]-biphenyl-4-yl}-cyclopropanecarboxylic acid (Compound 1-128)

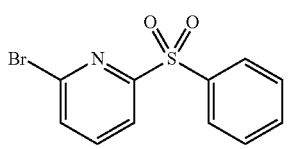 [SMILES: O=S(=O)(c1ccccc1)c1cccc(Br)n1]

Step 1: 2-Benzenesulfonyl-6-bromo-pyridine

2-Bromo-6-phenylsulfanyl-pyridine (0.5323 g, 2 mmol) was dissolved in $CH_2Cl_2$ (20 mL) and m-chloroperbenzoic acid (1.38 g, 8 mmol) was added. The reaction was stirred at room temperature overnight then submitted to aqueous workup and purification on silica gel to give the title compound.

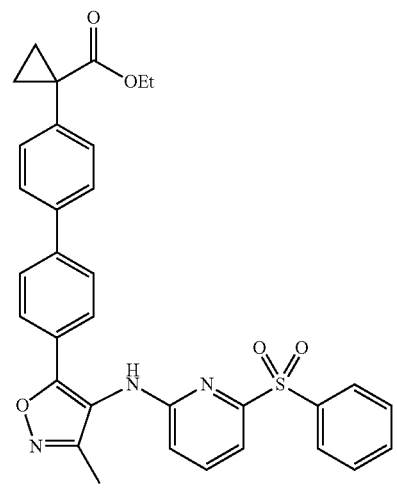 [SMILES: CCOC(=O)C1(c2ccc(-c3ccc(-c4onc(C)c4Nc4cccc(S(=O)(=O)c5ccccc5)n4)cc3)cc2)CC1]

Step 2: 1-{4'-[4-(6-Benzenesulfonyl-pyridin-2-ylamino)-3-methyl-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-benzenesulfonyl-6-bromo-pyridine.

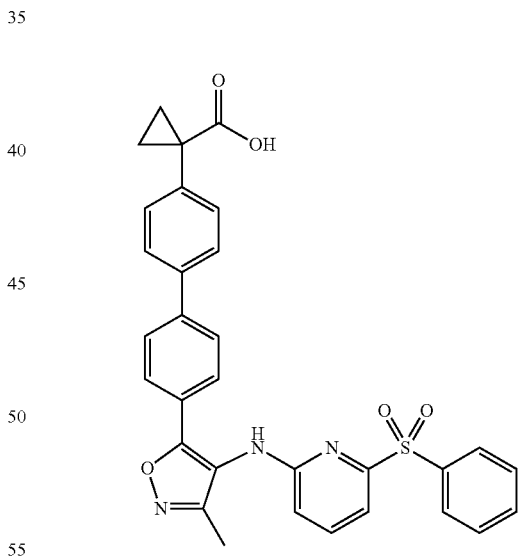

Step 3: 1-{4'-[4-(6-Benzenesulfonyl-pyridin-2-ylamino)-3-methyl-isoxazol-5-yl]-biphenyl-4-yl}-cyclopropanecarboxylic acid Prepared according to the procedure described in Example 1, Step 13, using 1-{4'-[4-(6-benzenesulfonyl-pyridin-2- ylamino)-3-methyl-isoxazol-5-yl]-biphenyl-4-yl}-cyclopropanecarboxylic acid ethyl ester.

Example 129

1-(4'-{4-[Hydroxy-(5-phenyl-pyridin-3-yl)-methyl]-3-methyl-isoxazol-5-yl}-biphenyl-4-yl)-cyclopropanecarboxylic acid (Compound 1-129)

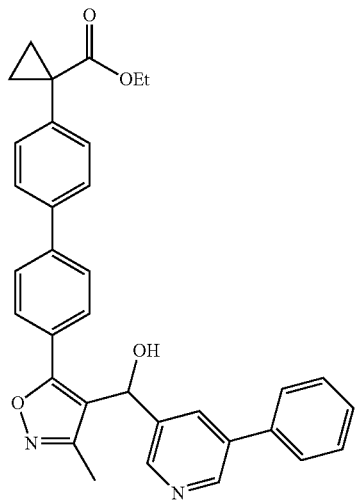

Step 1: 1-(4'-{4-[Hydroxy-(5-phenyl-pyridin-3-yl)-methyl]-3-methyl-isoxazol-5-yl}-biphenyl-4-yl)-cyclopropanecarboxylic acid ethyl ester Prepared according to the procedure described in Example 30, Step 1, using 1-[4'-(4-formyl-3-methyl-isoxazol-5-yl)-biphenyl-4-yl]-cyclopropanecarboxylic acid ethyl ester and 3-bromo-5-phenyl-pyridine.

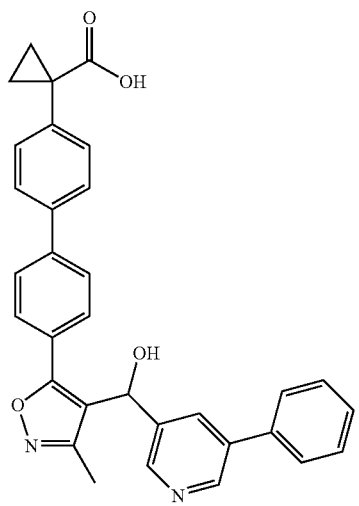 [SMILES: Cc1noc(-c2ccc(-c3ccc(C4(C(=O)O)CC4)cc3)cc2)c1C(O)c1cncc(-c2ccccc2)c1]

Step 2: 1-(4'-{4-[Hydroxy-(5-phenyl-pyridin-3-yl)-methyl]-3-methyl-isoxazol-5-yl}-biphenyl-4-yl)-cyclopropanecarboxylic acid Prepared according to the procedure described in Example 1, Step 13, using 1-(4'-{4-[hydroxy-(5-phenyl-pyridin-3-yl)-methyl]-3-methyl-isoxazol-5-yl}-biphenyl-4-yl)-cyclopropanecarboxylic acid ethyl ester.

Example 130

1-[4'-(4-{Hydroxy-[5-(3-trifluoromethyl-phenyl)-pyridin-3-yl]-methyl}-3-methyl-isoxazol-5-yl)-biphenyl-4-yl]-cyclopropanecarboxylic acid (Compound 1-130)

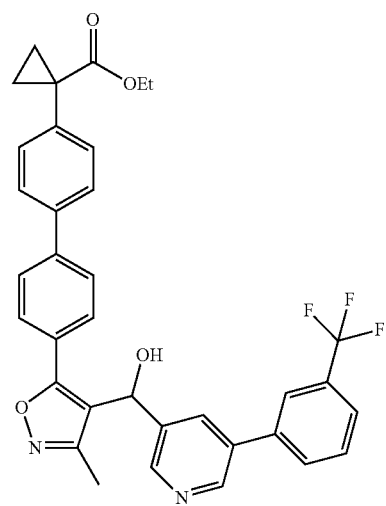 [SMILES: CCOC(=O)C1(c2ccc(-c3ccc(-c4onc(C)c4C(O)c4cncc(-c5cccc(C(F)(F)F)c5)c4)cc3)cc2)CC1]

Step 1: 1-[4'-(4-{Hydroxy-[5-(3-trifluoromethyl-phenyl)-pyridin-3-yl]-methyl}-3-methyl-isoxazol-5-yl)-biphenyl-4-yl]-cyclopropanecarboxylic acid ethyl ester Prepared according to the procedure described in Example 30, Step 1, using 1-[4'-(4-formyl-3-methyl-isoxazol-5-yl)-biphenyl-4-yl]-cyclopropanecarboxylic acid ethyl ester and 3-bromo-5-(3-trifluoromethyl-phenyl)-pyridine.

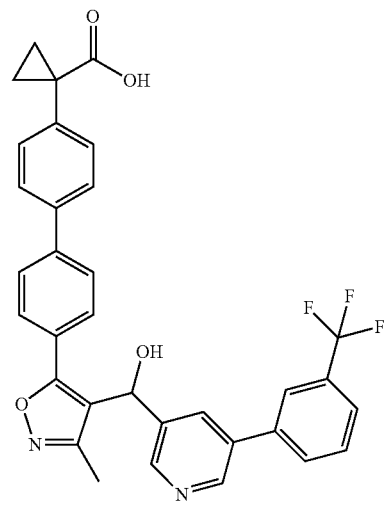

Step 2: 1-[4'-(4-{Hydroxy-[5-(3-trifluoromethyl-phenyl)-pyridin-3-yl]-methyl}-3-methyl-isoxazol-5-yl)-biphenyl-4-yl]-cyclopropanecarboxylic acid Prepared according to the procedure described in Example 1, Step 13, using 1-[4'-(4-{hydroxy-[5-(3-trifluoromethyl-phenyl)-pyridin-3-yl]-methyl}-3-methyl-isoxazol-5-yl)-biphenyl-4-yl]-cyclopropanecarboxylic acid ethyl ester.

Example 131

1-{4'-[3-Methyl-4-(6-phenylethynyl-pyridin-2-ylamino)-isoxazol-5-yl]-biphenyl-4-yl}-cyclopropanecarboxylic acid (Compound 1-131)

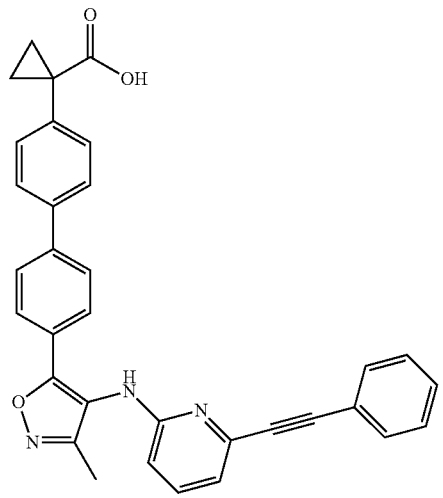 [SMILES: CCOC(=O)C1(c2ccc(-c3ccc(-c4onc(C)c4Nc4cccc(C#Cc5ccccc5)n4)cc3)cc2)CC1]

Step 2: 1-{4'-[3-Methyl-4-(6-phenylethynyl-pyridin-2-ylamino)-isoxazol-5-yl]-biphenyl-4-yl}-cyclopropanecarboxylic acid Prepared according to the procedure described in Example 1, Step 13, using 1-{4'-[3-methyl-4-(6-phenylethynyl-pyridin-2-ylamino)-isoxazol-5-yl]-biphenyl-4-yl}-cyclopropanecarboxylic acid ethyl ester.

Example 132

3-{4'-[3-Methyl-4-(6-phenyl-pyridin-2-ylamino)-isoxazol-5-yl]-biphenyl-4-yl}-propionic acid (Compound 1-132)

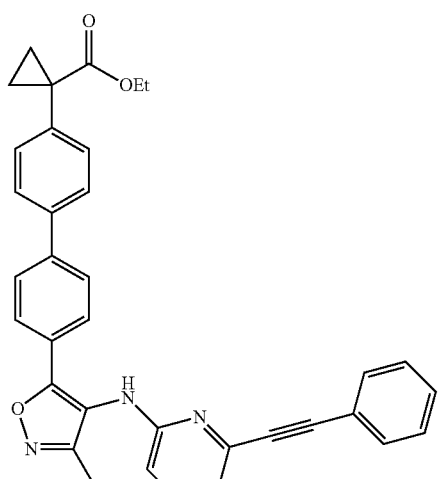

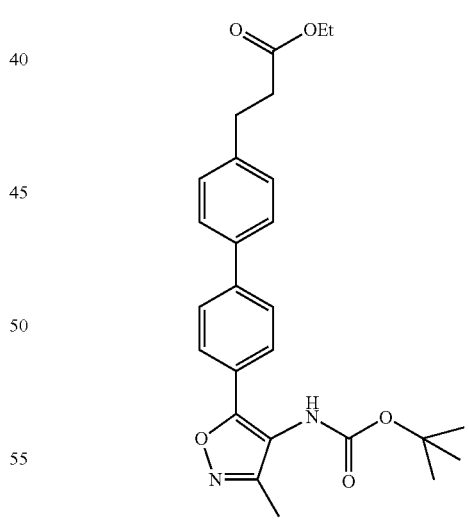

Step 1: 1-{4'-[3-Methyl-4-(6-phenylethynyl-pyridin-2-ylamino)-isoxazol-5-yl]-biphenyl-4-yl}-cyclopropanecarboxylic acid ethyl ester 1-{4'-[4-(6-Bromo-pyridin-2-ylamino)-3-methyl-isoxazol-5-yl]-biphenyl-4-yl}-cyclopropanecarboxylic acid ethyl ester (0.200 g, 0.386 mmol) was dissolved in toluene along with phenylacetylene (0.051 mL, 0.46 mmol), copper (I) iodide (0.367 g, 1.93 mmol), triethylamine (0.269 mL, 1.93 mmol) and bis(triphenylphosphine)palladium(II) dichloride (0.032 g, 0.039 mmol). The reaction was heated to 40° C. for 3 days then cooled, diluted with EtOAc and filtered through a plug of silica gel. The crude material was purified on silica gel to yield the title compound.

Step 1: 3-[4'-(4-tert-Butoxycarbonylamino-3-methyl-isoxazol-5-yl)-biphenyl-4-yl]-propionic acid ethyl ester Prepared according to the procedure described in Example 42, Step 2, using [5-(4-bromo-phenyl)-3-methyl-isoxazol-4-yl]-carbamic acid tert-butyl ester and [4-(2-ethoxycarbonyl-ethyl)phenyl]boronic acid.

313

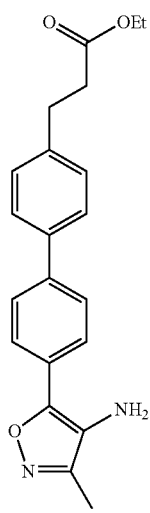

Step 2: 3-[4'-(4-Amino-3-methyl-isoxazol-5-yl)-biphenyl-4-yl]propionic acid ethyl ester Prepared according to the procedure described in Example 1, Step 11, using 3-[4'-(4-tert-Butoxycarbonylamino-3-methyl-isoxazol-5-yl)-biphenyl-4-yl]-propionic acid ethyl ester.

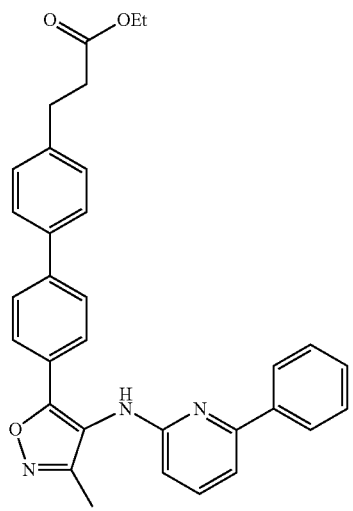 [SMILES: CCOC(=O)CCc1ccc(-c2ccc(-c3onc(C)c3Nc3cccc(-c4ccccc4)n3)cc2)cc1]

Step 3: 3-{4'-[3-Methyl-4-(6-phenyl-pyridin-2-ylamino)-isoxazol-5-yl]-biphenyl-4-yl}-propionic acid ethyl ester Prepared according to the procedure described in Example 68, Step 2, using 3-[4'-(4-amino-3-methyl-isoxazol-5-yl)-biphenyl-4-yl]-propionic acid ethyl ester and 2-bromo-6-phenyl-pyridine. Additionally, palladium(II) acetate was used as the catalyst in place of tris(dibenzylideneacetone)dipalladium(0).

314

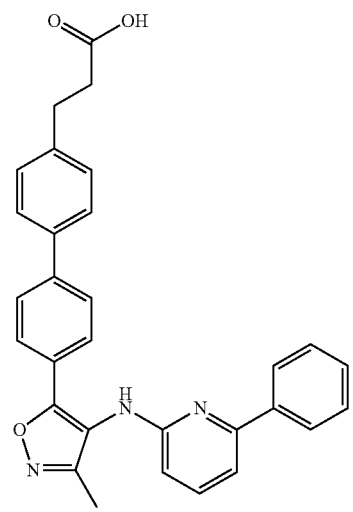 [SMILES: Cc1noc(-c2ccc(-c3ccc(CCC(=O)O)cc3)cc2)c1Nc1cccc(-c2ccccc2)n1]

Step 4: 3-{4'-[3-Methyl-4-(6-phenyl-pyridin-2-ylamino)-isoxazol-5-yl]-biphenyl-4-yl}-propionic acid Prepared according to the procedure described in Example 1, Step 13, using 3-{4'-[3-methyl-4-(6-phenyl-pyridin-2-ylamino)-isoxazol-5-yl]-biphenyl-4-yl}-propionic acid ethyl ester.

Example 133

2-Methyl-2-{4'-[3-methyl-4-(6-phenyl-pyridin-2-ylamino)-isoxazol-5-yl]-biphenyl-4-yl}-propionic acid (Compound 1-133)

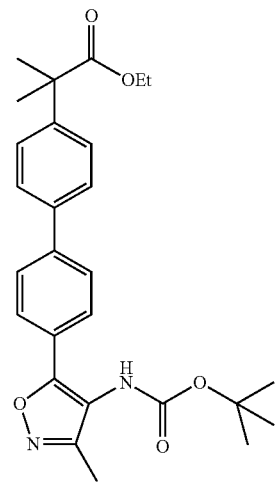 [SMILES: CCOC(=O)C(C)(C)c1ccc(-c2ccc(-c3onc(C)c3NC(=O)OC(C)(C)C)cc2)cc1]

Step 1: 2-[4'-(4-tert-Butoxycarbonylamino-3-methyl-isoxazol-5-yl)-biphenyl-4-yl]-2-methyl-propionic acid ethyl ester Prepared according to the procedure described in Example 42, Step 2, using [5-(4-bromo-phenyl)-3-methyl-isoxazol-4- yl]-carbamic acid tert-butyl ester and 2-methyl-2-[4-(4,4,5,5-tetramethyl-[1,3,2]dioxaborolan-2-yl)-phenyl]-propionic acid ethyl ester.

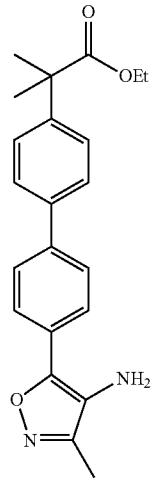

Step 2: 2-[4'-(4-Amino-3-methyl-isoxazol-5-yl)-biphenyl-4-yl]-2-methyl-propionic acid ethyl ester Prepared according to the procedure described in Example 1, Step 11, using 2-[4'-(4-tert-butoxycarbonylamino-3-methyl-isoxazol-5-yl)-biphenyl-4-yl]-2-methyl-propionic acid ethyl ester.

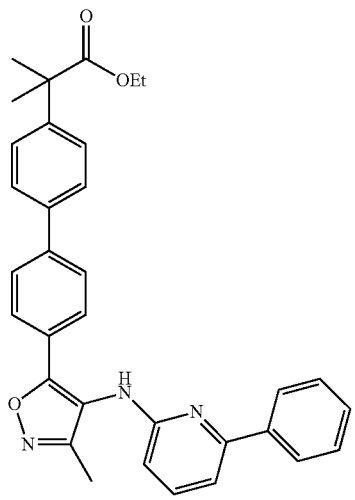 [SMILES: Cc1noc(-c2ccc(-c3ccc(C(C)(C)C(=O)O)cc3)cc2)c1Nc1cccc(-c2ccccc2)n1]

Step 3: 2-Methyl-2-{4'-[3-methyl-4-(6-phenyl-pyridin-2-ylamino)-isoxazol-5-yl]-biphenyl-4-yl}-propionic acid ethyl ester Prepared according to the procedure described in Example 134, Step 3, using 2-[4'-(4-amino-3-methyl-isoxazol-5-yl)-biphenyl-4-yl]-2-methyl-propionic acid ethyl ester and 2-bromo-6-phenyl-pyridine.

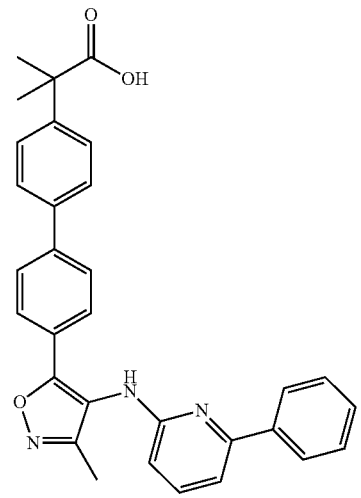

Step 4: 2-Methyl-2-{4'-[3-methyl-4-(6-phenyl-pyridin-2-ylamino)-isoxazol-5-yl]-biphenyl-4-yl}-propionic acid ethyl ester Prepared according to the procedure described in Example 1, Step 13, using (1-{4'-[3-methyl-4-(6-phenyl-pyridin-2-ylamino)-isoxazol-5-yl]-biphenyl-4-yl}-cyclopropyl)-acetic acid ethyl ester.

Example 134

(1-{4'-[3-Methyl-4-(6-phenyl-pyridin-2-ylamino)-isoxazol-5-yl]-biphenyl-4-yl}-cyclopropyl)-acetic acid (Compound 1-134)

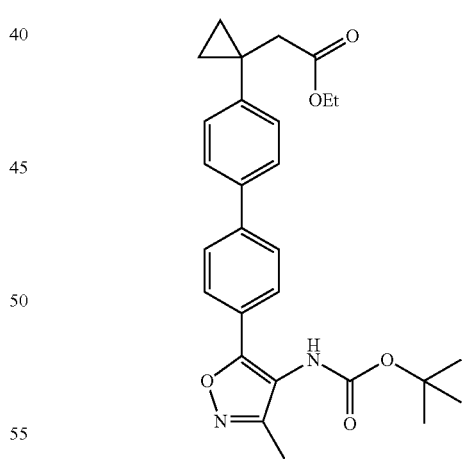

Step 1: {1-[4'-(4-tert-Butoxycarbonylamino-3-methyl-isoxazol-5-yl)-biphenyl-4-yl]-cyclopropyl}-acetic acid ethyl ester Prepared according to the procedure described in Example 42, Step 2, using [5-(4-bromo-phenyl)-3-methyl-isoxazol-4-yl]-carbamic acid tert-butyl ester and {1-[4-(4,4,5,5-tetramethyl-[1,3,2]dioxaborolan-2-yl)-phenyl]-cyclopropyl}-acetic acid ethyl ester.

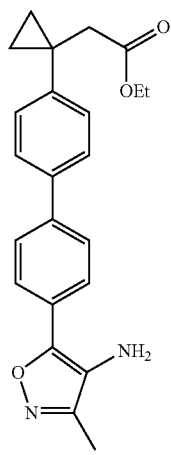 [SMILES: CCOC(=O)CC1(c2ccc(-c3ccc(-c4onc(C)c4N)cc3)cc2)CC1]

Step 2: {1-[4'-(4-Amino-3-methyl-isoxazol-5-yl)-biphenyl-4-yl]-cyclopropyl}-acetic acid ethyl ester Prepared according to the procedure described in Example 1, Step 11, using {1-[4'-(4-tert-butoxycarbonylamino-3-methyl-isoxazol-5-yl)-biphenyl-4-yl]-cyclopropyl}-acetic acid ethyl ester.

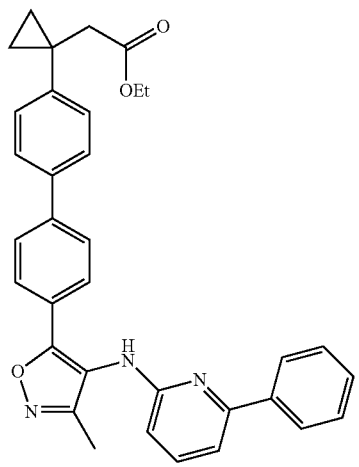 [SMILES: CCOC(=O)CC1(c2ccc(-c3ccc(-c4onc(C)c4Nc4cccc(-c5ccccc5)n4)cc3)cc2)CC1]

Step 3: (1-{4'-[3-Methyl-4-(6-phenyl-pyridin-2-ylamino)-isoxazol-5-yl]-biphenyl-4-yl}-cyclopropyl)-acetic acid ethyl ester Prepared according to the procedure described in Example 68, Step 2, using {1-[4'-(4-amino-3-methyl-isoxazol-5-yl)-biphenyl-4-yl]-cyclopropyl}-acetic acid ethyl ester and 2-bromo-6-phenyl-pyridine. Additionally, palladium(II) acetate was used as the catalyst in place of tris(dibenzylideneacetone)dipalladium(0).

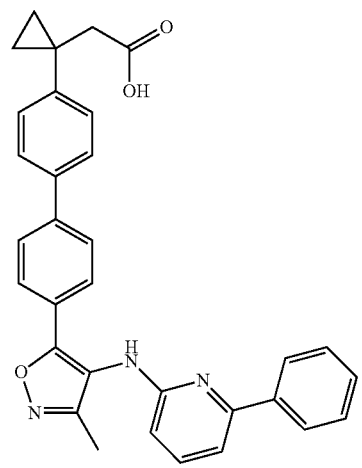 [SMILES: Cc1noc(-c2ccc(-c3ccc(C4(CC(=O)O)CC4)cc3)cc2)c1Nc1cccc(-c2ccccc2)n1]

Step 4: (1-{4'-[3-Methyl-4-(6-phenyl-pyridin-2-ylamino)-isoxazol-5-yl]-biphenyl-4-yl}-cyclopropyl)-acetic acid Prepared according to the procedure described in Example 1, Step 13, using (1-{4'-[3-methyl-4-(6-phenyl-pyridin-2-ylamino)-isoxazol-5-yl]-biphenyl-4-yl}-cyclopropyl)-acetic acid ethyl ester.

Example 135

1-{4'-[4-(6-Cyclopentylethynyl-pyridin-2-ylamino)-3-methyl-isoxazol-5-yl]-biphenyl-4-yl}-cyclopropanecarboxylic acid (Compound 1-135)

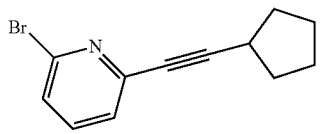 [SMILES: Brc1cccc(C#CC2CCCC2)n1]

Step 1: 2-Bromo-6-cyclopentylethynyl-pyridine 2,6-Dibromo-pyridine (0.544 g, 2.34 mmol), cyclopentylacetylene (0.220 g, 2.34 mmol), copper(I) iodide (0.445 g, 2.34 mmol), triethylamine (0.98 mL, 7.01 mmol) and bis(triphenylphosphine)palladium(II) dichloride (0.164 g, 0.023 mmol) were combined in DMF and stirred at room temperature for 2 days. The reaction was purified via silica gel chromatography to afford the title compound.

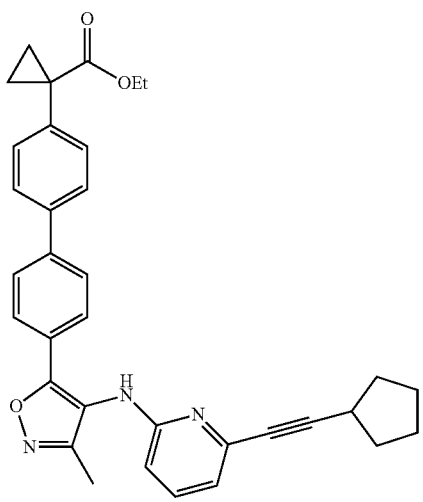 [SMILES: Cc1noc(-c2ccc(-c3ccc(C4(C(=O)O)CC4)cc3)cc2)c1Nc1cccc(C#CC2CCCC2)n1]

Step 2: 1-{4'-[4-(6-Cyclopentylethynyl-pyridin-2-ylamino)-3-methyl-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 2-bromo-6-cyclopentylethynyl-pyridine.

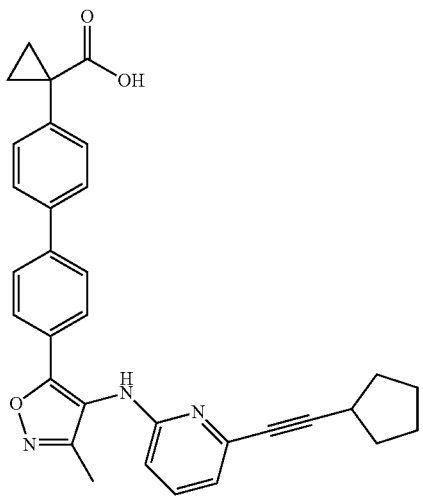

Step 3: 1-{4'-[4-(6-Cyclopentylethynyl-pyridin-2-ylamino)-3-methyl-isoxazol-5-yl]-biphenyl-4-yl}-cyclopropanecarboxylic acid Prepared according to the procedure described in Example 1, Step 13, using 1-{4'-[4-(6-cyclopentylethynyl-pyridin-2-ylamino)-3-methyl-isoxazol-5-yl]-biphenyl-4-yl}-cyclopropanecarboxylic acid ethyl ester.

Example 136

1-(4'-{3-Methyl-4-[6-(pyrrolidine-1-carbonyl)-pyridin-2-ylamino]-isoxazol-5-yl}-biphenyl-4-yl)-cyclopropanecarboxylic acid (Compound 1-136)

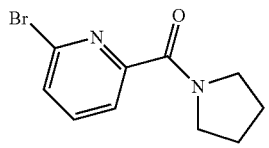 [SMILES: O=C(c1cccc(Br)n1)N1CCCC1]

Step 1: (6-Bromo-pyridin-2-yl)-pyrrolidin-1-yl-methanone

Prepared according to the procedure described in Example 121, Step 1, using 6-bromo-pyridine-2-carboxylic acid and pyrrolidine.

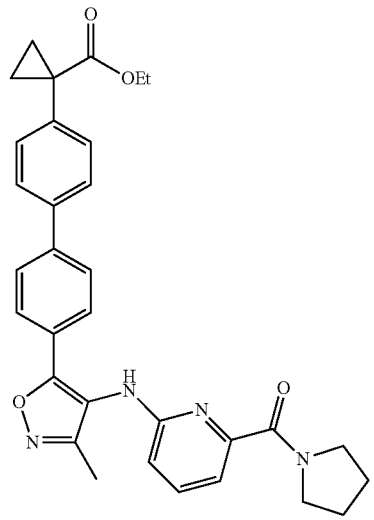 [SMILES: Cc1noc(-c2ccc(-c3ccc(C4(C(=O)O)CC4)cc3)cc2)c1Nc1cccc(C(=O)N2CCCC2)n1]

Step 2: 1-(4'-{3-Methyl-4-[6-(pyrrolidine-1-carbonyl)-pyridin-2-ylamino]-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and (6-bromo-pyridin-2-yl)-pyrrolidin-1-yl-methanone.

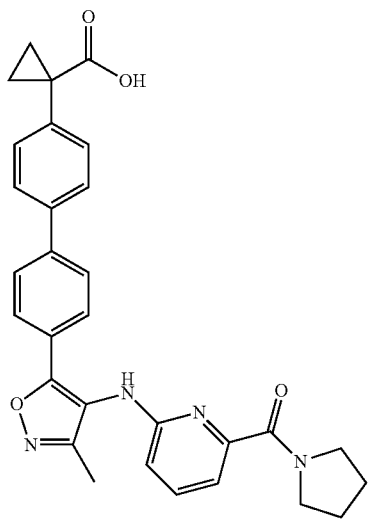

Step 3: 1-(4'-{3-Methyl-4-[6-(pyrrolidine-1-carbonyl)-pyridin-2-ylamino]-isoxazol-5-yl}-biphenyl-4-yl)-cyclopropanecarboxylic acid Prepared according to the procedure described in Example 1, Step 13, using 1-(4'-{3-methyl-4-[6-(pyrrolidine-1-carbonyl)-pyridin-2-ylamino]-isoxazol-5-yl}-biphenyl-4-yl)-cyclopropanecarboxylic acid ethyl ester.

Example 137

1-{4'-[4-(6-Cyclopropylcarbamoyl-pyridin-2-ylamino)-3-methyl-isoxazol-5-yl]-biphenyl-4-yl}-cyclopropanecarboxylic acid (Compound 1-137)

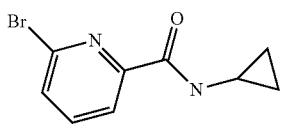 [SMILES: O=C(NC1CC1)c1cccc(Br)n1]

Step 1: 6-Bromo-pyridine-2-carboxylic acid cyclopropylamide

Prepared according to the procedure described in Example 121, Step 1, using 6-bromo-pyridine-2-carboxylic acid and cyclopropylamine.

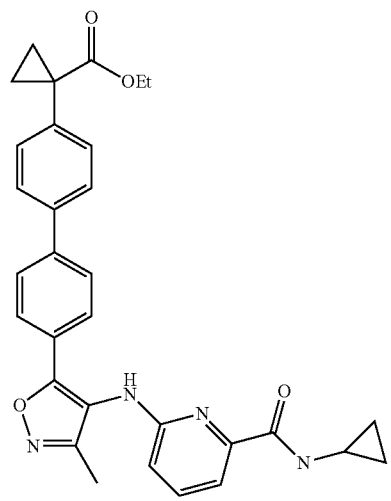 [SMILES: CCOC(=O)C1(c2ccc(-c3ccc(-c4onc(C)c4Nc4cccc(C(=O)NC5CC5)n4)cc3)cc2)CC1]

Step 2: 1-{4'-[4-(6-Cyclopropylcarbamoyl-pyridin-2-ylamino)-3-methyl-isoxazol-5-yl]-biphenyl-4-yl}-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 6-bromo-pyridine-2-carboxylic acid cyclopropylamide.

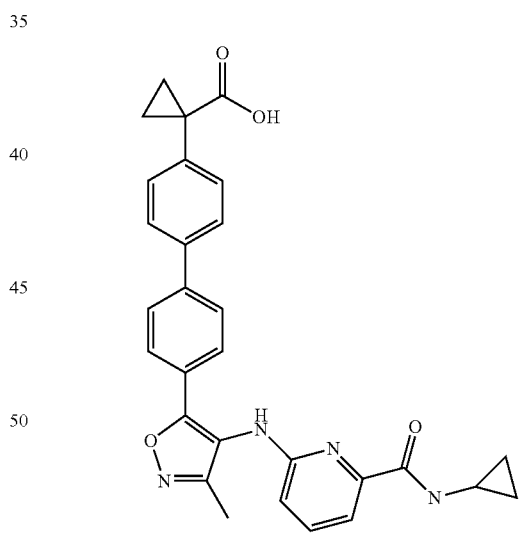

Step 3: 1-{4'-[4-(6-Cyclopropylcarbamoyl-pyridin-2-ylamino)-3-methyl-isoxazol-5-yl]-biphenyl-4-yl}-cyclopropanecarboxylic acid Prepared according to the procedure described in Example 1, Step 13, using 1-{4'-[4-(6-cyclopropylcarbamoyl-pyridin- 2-ylamino)-3-methyl-isoxazol-5-yl]-biphenyl-4-yl}-cyclopropanecarboxylic acid ethyl ester.

Example 138

1-{4'-[4-(6-Cyclohexyloxy-pyridin-2-ylamino)-3-methyl-isoxazol-5-yl]-biphenyl-4-yl}-cyclopropanecarboxylic acid (Compound 1-138)

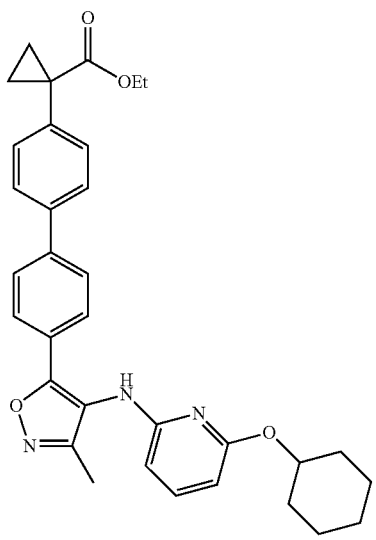 [SMILES: Cc1noc(-c2ccc(-c3ccc(C4(C(=O)O)CC4)cc3)cc2)c1Nc1cccc(OC2CCCCC2)n1]

Step 1: 1-{4'-[4-(6-Cyclohexyloxy-pyridin-2-ylamino)-3-methyl-isoxazol-5-yl]-biphenyl-4-yl}-cyclopropanecarboxylic acid ethyl ester Prepared according to the procedure described in Example 134, Step 3, using 1-[4'-(4-amino-3-methyl-isoxazol-5-yl)-biphenyl-4-yl]-cyclopropanecarboxylic acid ethyl ester and 2-bromo-6-cyclohexyloxy-pyridine.

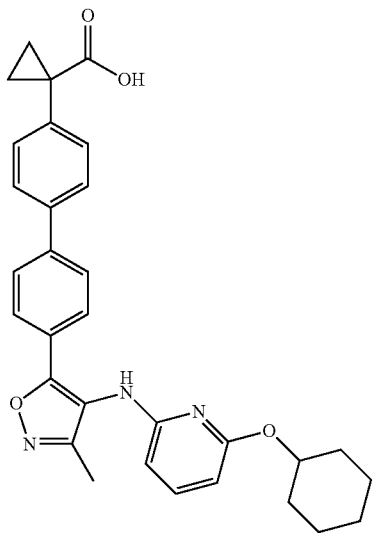

Step 2: 1-{4'-[4-(6-Cyclohexyloxy-pyridin-2-ylamino)-3-methyl-isoxazol-5-yl]-biphenyl-4-yl}-cyclopropanecarboxylic acid Prepared according to the procedure described in Example 1, Step 13, using 1-{4'-[4-(6-cyclohexyloxy-pyridin-2-ylamino)-3-methyl-isoxazol-5-yl]-biphenyl-4-yl}-cyclopropanecarboxylic acid ethyl ester.

Example 139

1-{4'-[4-(6-Cyclobutoxy-pyridin-2-ylamino)-3-methyl-isoxazol-5-yl]-biphenyl-4-yl}-cyclopropanecarboxylic acid (Compound 1-139)

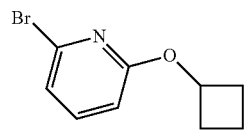

Step 1: 2-Bromo-6-cyclobutoxy-pyridine

Cyclobutanol (0.470 mL, 6 mmol) was dissolved in toluene (2 mL) and sodium hydride (60% in mineral oil, 0.240 g, 6 mmol) was added. The reaction was stirred at room temperature for 10 minutes then 2,6-dibromo-pyridine (0.710 g, 3 mmol) was added. The reaction was heated to 110° C. for 16 hours then cooled to room temperature, filtered through Celite, and purified on silica gel (0-5% EtOAc in hexanes) to give the title compound.

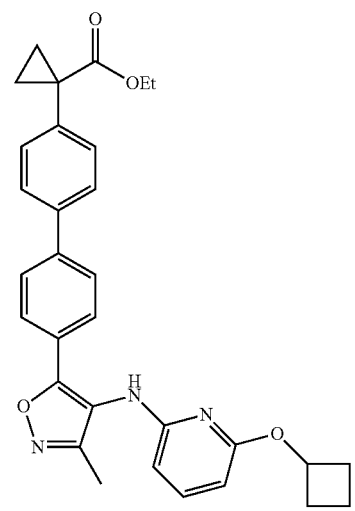

Step 2: 1-{4'-[4-(6-Cyclobutoxy-pyridin-2-ylamino)-3-methyl-isoxazol-5-yl]-biphenyl-4-yl}-cyclopropanecarboxylic acid ethyl ester Prepared according to the procedure described in Example 134, Step 3, using 1-[4'-(4-amino-3-methyl-isoxazol-5-yl)-biphenyl-4-yl]-cyclopropanecarboxylic acid ethyl ester and 2-bromo-6-cyclobutoxy-pyridine.

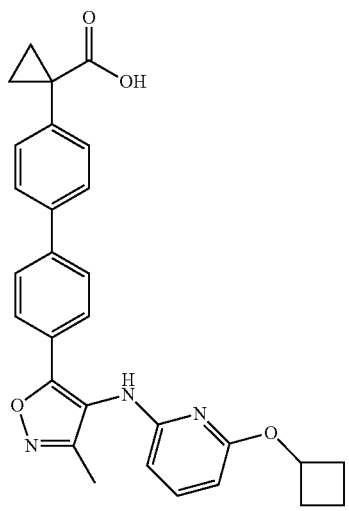 [SMILES: Cc1noc(-c2ccc(-c3ccc(C4(C(=O)O)CC4)cc3)cc2)c1Nc1cccc(OC2CCC2)n1]

Step 3: 1-{4'-[4-(6-Cyclobutoxy-pyridin-2-ylamino)-3-methyl-isoxazol-5-yl]-biphenyl-4-yl}-cyclopropanecarboxylic acid Prepared according to the procedure described in Example 1, Step 13, using 1-{4'-[4-(6-cyclobutoxy-pyridin-2-ylamino)-3-methyl-isoxazol-5-yl]-biphenyl-4-yl}-cyclopropanecarboxylic acid ethyl ester.

Example 140

1-(4'-{4-[6-(1-Cyclohexyl-ethoxy)-pyridin-2-ylamino]-3-methyl-isoxazol-5-yl}-biphenyl-4-yl)-cyclopropanecarboxylic acid (Compound 1-140)

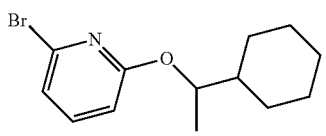 [SMILES: CC(Oc1cccc(Br)n1)C1CCCCC1]

Step 1: 6-Bromo-pyridine-2-carboxylic acid cyclopropylamide

Prepared according to the procedure described in Example 139, Step 1, using 2,6-dibromo-pyridine and 1-cyclohexyl-ethanol.

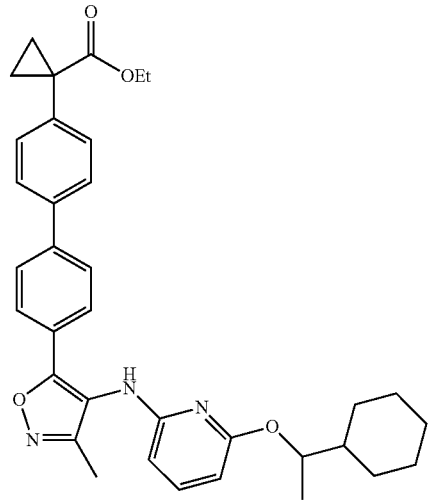 [SMILES: CCOC(=O)C1(c2ccc(-c3ccc(-c4onc(C)c4Nc4cccc(OC(C)C5CCCCC5)n4)cc3)cc2)CC1]

Step 2: 1-(4'-{4-[6-(1-Cyclohexyl-ethoxy)-pyridin-2-ylamino]-3-methyl-isoxazol-5-yl}-biphenyl-4-yl)-cyclopropanecarboxylic acid ethyl ester Prepared according to the procedure described in Example 134, Step 3, using 1-[4'-(4-amino-3-methyl-isoxazol-5-yl)-biphenyl-4-yl]-cyclopropanecarboxylic acid ethyl ester and 2-bromo-6-(1-cyclohexyl-ethoxy)-pyridine.

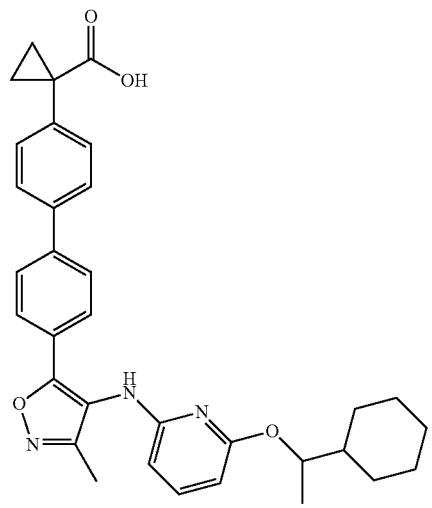 [SMILES: Cc1noc(-c2ccc(-c3ccc(C4(C(=O)O)CC4)cc3)cc2)c1Nc1cccc(OC(C)C2CCCCC2)n1]

Step 3: 1-(4'-{4-[6-(1-Cyclohexyl-ethoxy)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(1-cyclohexyl-ethoxy)-pyridin- 2-ylamino]-3-methyl-isoxazol-5-yl}-biphenyl-4-yl)-cyclopropanecarboxylic acid ethyl ester.

Example 141

1-{4'-[3-Methyl-4-(6-phenethyloxy-pyridin-2-ylamino)-isoxazol-5-yl]-biphenyl-4-yl}-cyclopropanecarboxylic acid (Compound 1-141)

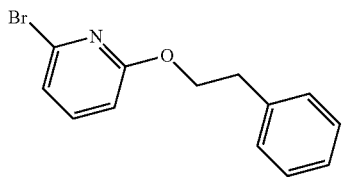 [SMILES: Brc1cccc(OCCc2ccccc2)n1]

Step 1: 2-Bromo-6-phenethyloxy-pyridine

Prepared according to the procedure described in Example 139, Step 1, using 2,6-dibromo-pyridine and 2-phenyl-ethanol.

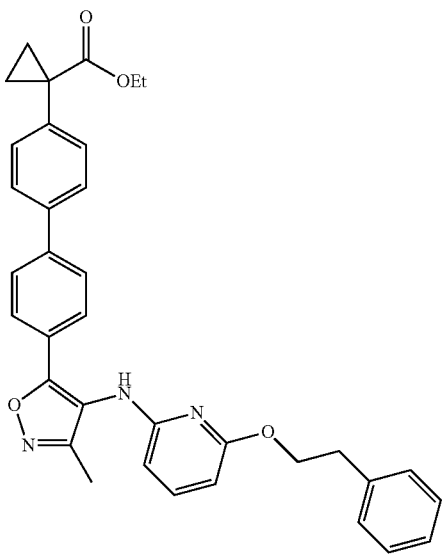 [SMILES: CCOC(=O)C1(c2ccc(-c3ccc(-c4onc(C)c4Nc4cccc(OCCc5ccccc5)n4)cc3)cc2)CC1]

Step 2: 1-{4'-[3-Methyl-4-(6-phenethyloxy-pyridin-2-ylamino)-isoxazol-5-yl]-biphenyl-4-yl}-cyclopropanecarboxylic acid ethyl ester Prepared according to the procedure described in Example 134, Step 3, using 1-[4'-(4-amino-3-methyl-isoxazol-5-yl)-biphenyl-4-yl]-cyclopropanecarboxylic acid ethyl ester and 2-bromo-6-phenethyloxy-pyridine.

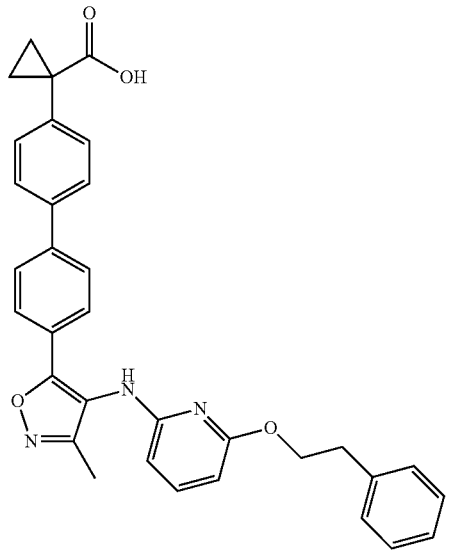 [SMILES: Cc1noc(-c2ccc(-c3ccc(C4(C(=O)O)CC4)cc3)cc2)c1Nc1cccc(OCCc2ccccc2)n1]

Step 3: 1-{4'-[3-Methyl-4-(6-phenethyloxy-pyridin-2-ylamino)-isoxazol-5-yl]-biphenyl-4-yl}-cyclopropanecarboxylic acid Prepared according to the procedure described in Example 1, Step 13, using 1-{4'-[3-methyl-4-(6-phenethyloxy-pyridin-2-ylamino)-isoxazol-5-yl]-biphenyl-4-yl}-cyclopropanecarboxylic acid ethyl ester.

Example 142

4'-[3-Methyl-4-(5-phenyl-[1,3,4]oxadiazol-2-ylamino)-isoxazol-5-yl]-biphenyl-4-carboxylic acid (Compound 1-142)

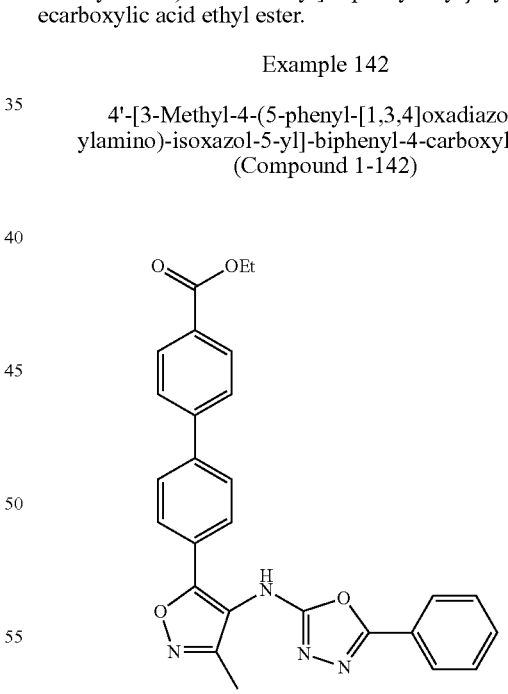

Step 1: 4'-[3-Methyl-4-(5-phenyl-[1,3,4]oxadiazol-2-ylamino)-isoxazol-5-yl]-biphenyl-4-carboxylic acid ethyl ester Prepared according to the procedure described in Example 42, Step 2, using [5-(4-bromo-phenyl)-3-methyl-isoxazol-4-yl]-(5-phenyl-[1,3,4]oxadiazol-2-yl)-amine and 4-ethoxycarbonylphenylboronic acid.

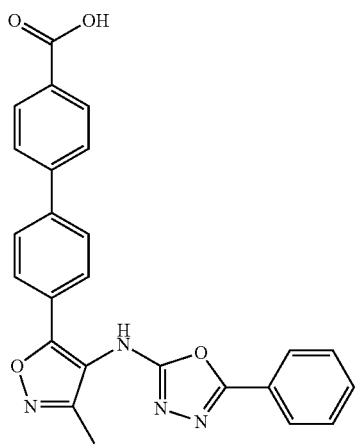 [SMILES: Cc1noc(-c2ccc(-c3ccc(C(=O)O)cc3)cc2)c1Nc1nnc(-c2ccccc2)o1]

Step 2: 4'-[3-Methyl-4-(5-phenyl-[1,3,4]oxadiazol-2-ylamino)-isoxazol-5-yl]-biphenyl-4-carboxylic acid Prepared according to the procedure described in Example 1, Step 13, using 4'-[3-methyl-4-(5-phenyl-[1,3,4]oxadiazol-2-ylamino)-isoxazol-5-yl]-biphenyl-4-carboxylic acid ethyl ester.

Example 143

1-(4'-{3-Methyl-4-[6-(2-oxo-oxazolidin-3-yl)-pyridin-2-ylamino]-isoxazol-5-yl}-biphenyl-4-yl)-cyclopropanecarboxylic acid (Compound 1-143)

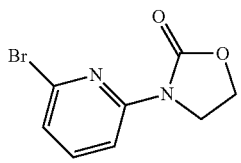 [SMILES: O=C1OCCN1c1cccc(Br)n1]

Step 1: 3-(6-Bromo-pyridin-2-yl)-oxazolidin-2-one

Prepared according to the procedure described in Example 139, Step 1, using 2,6-dibromo-pyridine and oxazolidin-2-one.

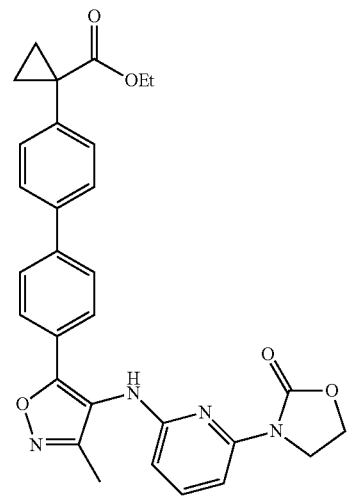 [SMILES: CCOC(=O)C1(c2ccc(-c3ccc(-c4onc(C)c4Nc4cccc(N5CCOC5=O)n4)cc3)cc2)CC1]

Step 2: 1-(4'-{3-Methyl-4-[6-(2-oxo-oxazolidin-3-yl)-pyridin-2-ylamino]-isoxazol-5-yl}-biphenyl-4-yl)-cyclopropanecarboxylic acid ethyl ester Prepared according to the procedure described in Example 134, Step 3, using 1-[4'-(4-amino-3-methyl-isoxazol-5-yl)-biphenyl-4-yl]-cyclopropanecarboxylic acid ethyl ester and 3-(6-bromo-pyridin-2-yl)-oxazolidin-2-one.

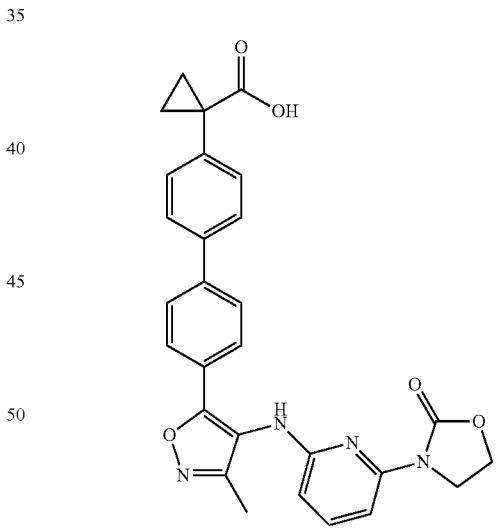

Step 3: 1-(4'-{3-Methyl-4-[6-(2-oxo-oxazolidin-3-yl)-pyridin-2-ylamino]-isoxazol-5-yl}-biphenyl-4-yl)-cyclopropanecarboxylic acid Prepared according to the procedure described in Example 1, Step 13, using 1-(4'-{3-methyl-4-[6-(2-oxo-oxazolidin-3- yl)-pyridin-2-ylamino]-isoxazol-5-yl}-biphenyl-4-yl)-cyclopropanecarboxylic acid ethyl ester.

Example 144

1-(4'-{4-[6-(3-Carbamoyl-phenyl)-pyridin-2-ylamino]-3-methyl-isoxazol-5-yl}-biphenyl-4-yl)-cyclopropanecarboxylic acid (Compound 1-144)

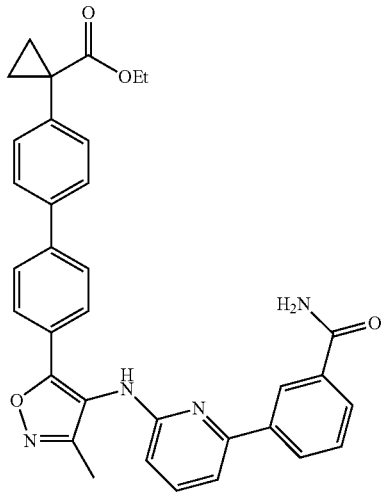 [SMILES: CCOC(=O)C1(c2ccc(-c3ccc(-c4onc(C)c4Nc4cccc(-c5cccc(C(N)=O)c5)n4)cc3)cc2)CC1]

Step 1: 1-(4'-{4-[6-(3-Carbamoyl-phenyl)-pyridin-2-ylamino]-3-methyl-isoxazol-5-yl}-biphenyl-4-yl)-cyclopropanecarboxylic acid ethyl ester Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 3-aminocarbonyl-phenylboronic acid.

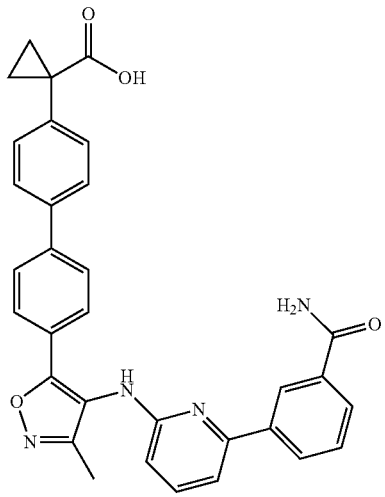

Step 2: 1-(4'-{4-[6-(3-Carbamoyl-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(3-carbamoyl-phenyl)-pyridin-2-ylamino]-3-methyl-isoxazol-5-yl}-biphenyl-4-yl)-cyclopropanecarboxylic acid ethyl ester.

Example 145

1-(4'-{4-[6-(3-Cyano-phenyl)-pyridin-2-ylamino]-3-methyl-isoxazol-5-yl}-biphenyl-4-yl)-cyclopropanecarboxylic acid (Compound 1-145)

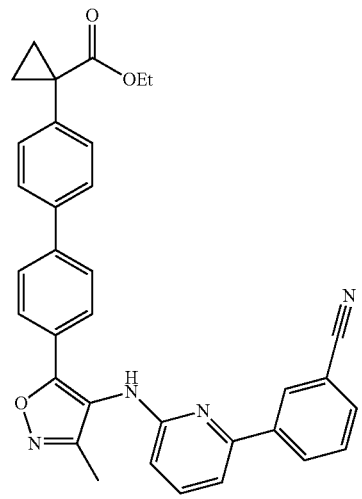

Step 1: 1-(4'-{4-[6-(3-Cyano-phenyl)-pyridin-2-ylamino]-3-methyl-isoxazol-5-yl}-biphenyl-4-yl)-cyclopropanecarboxylic acid ethyl ester Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 3-cyano-phenylboronic acid.

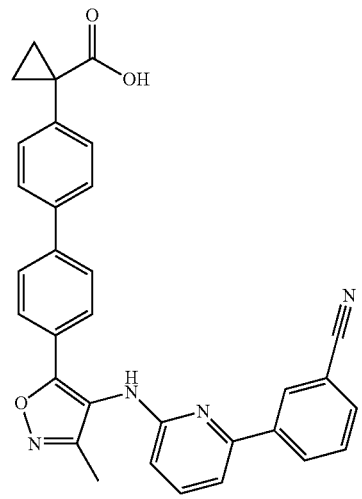 [SMILES: Cc1noc(-c2ccc(-c3ccc(C4(C(=O)O)CC4)cc3)cc2)c1Nc1cccc(-c2cccc(C#N)c2)n1]

Step 2: 1-(4'-{4-[6-(3-Cyano-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(3-cyano-phenyl)-pyridin-2-ylamino]-3-methyl-isoxazol-5-yl}-biphenyl-4-yl)-cyclopropanecarboxylic acid ethyl ester.

Example 146

1-(4'-{4-[6-(5-Fluoro-2-methoxy-phenyl)-pyridin-2-ylamino]-3-methyl-isoxazol-5-yl}-biphenyl-4-yl)-cyclopropanecarboxylic acid (Compound 1-146)

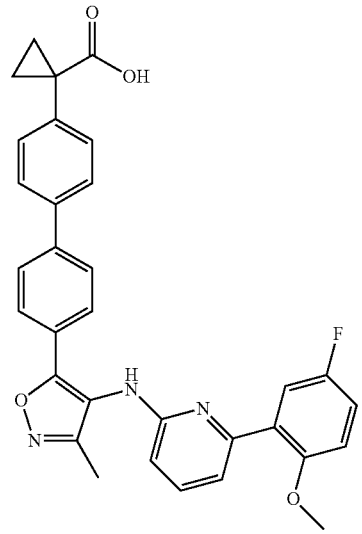 [SMILES: COc1ccc(F)cc1-c1cccc(Nc2c(C)noc2-c2ccc(-c3ccc(C4(C(=O)O)CC4)cc3)cc2)n1]

Step 2: 1-(4'-{4-[6-(5-Fluoro-2-methoxy-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(5-fluoro-2-methoxy-phenyl)-pyridin-2-ylamino]-3-methyl-isoxazol-5-yl}-biphenyl-4-yl)-cyclopropanecarboxylic acid ethyl ester.

Example 147

1-(4'-{4-[6-(3-Chloro-5-fluoro-phenyl)-pyridin-2-ylamino]-3-methyl-isoxazol-5-yl}-biphenyl-4-yl)-cyclopropanecarboxylic acid (Compound 1-147)

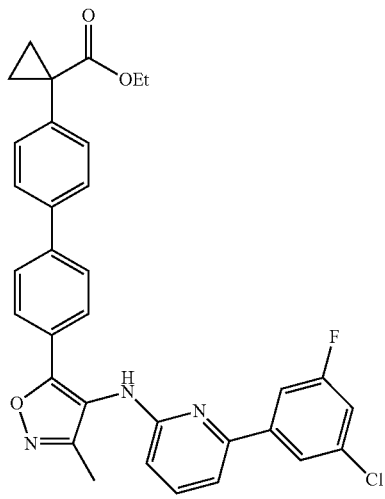 [SMILES: CCOC(=O)C1(c2ccc(-c3ccc(-c4onc(C)c4Nc4cccc(-c5cc(F)cc(Cl)c5)n4)cc3)cc2)CC1]

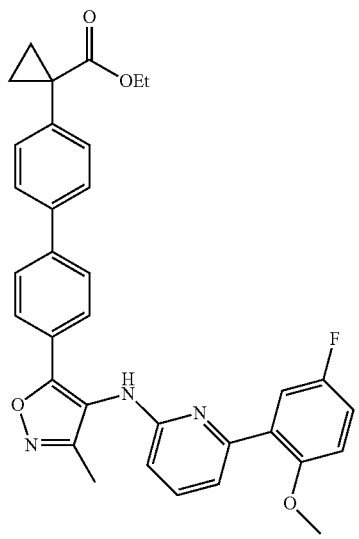

Step 1: 1-(4'-{4-[6-(5-Fluoro-2-methoxy-phenyl)-pyridin-2-ylamino]-3-methyl-isoxazol-5-yl}-biphenyl-4-yl)-cyclopropanecarboxylic acid ethyl ester Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 5-fluoro-2-methoxy-phenylboronic acid.

Step 1: 1-(4'-{4-[6-(3-Chloro-5-fluoro-phenyl)-pyridin-2-ylamino]-3-methyl-isoxazol-5-yl}-biphenyl-4-yl)-cyclopropanecarboxylic acid ethyl ester Prepared according to the procedure described in Example 1, Step 10, using 1-{4'-[4-(6-bromo-pyridin-2-ylamino)-3- methyl-isoxazol-5-yl]-biphenyl-4-yl}-cyclopropanecarboxylic acid ethyl ester and 3-chloro-5-fluorophenylboronic acid.

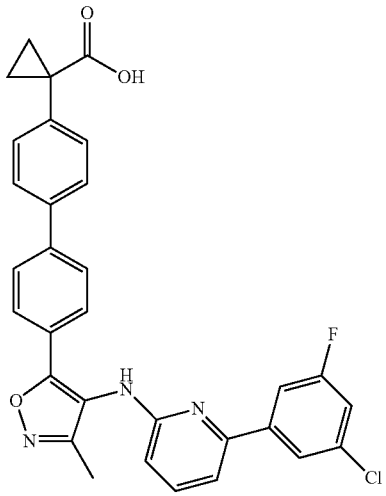 [SMILES: Cc1noc(-c2ccc(-c3ccc(C4(C(=O)O)CC4)cc3)cc2)c1Nc1cccc(-c2cc(F)cc(Cl)c2)n1]

Step 2: 1-(4'-{4-[6-(3-Chloro-5-fluoro-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(3-chloro-5-fluoro-phenyl)-pyridin-2-ylamino]-3-methyl-isoxazol-5-yl}-biphenyl-4-yl)-cyclopropanecarboxylic acid ethyl ester.

Example 148

1-(4'-{4-[6-(2,5-Difluoro-phenyl)-pyridin-2-ylamino]-3-methyl-isoxazol-5-yl}-biphenyl-4-yl)-cyclopropanecarboxylic acid (Compound 1-148)

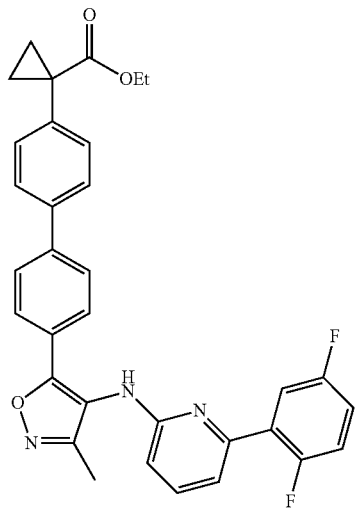 [SMILES: CCOC(=O)C1(c2ccc(-c3ccc(-c4onc(C)c4Nc4cccc(-c5cc(F)ccc5F)n4)cc3)cc2)CC1]

Step 1: 1-(4'-{4-[6-(2,5-Difluoro-phenyl)-pyridin-2-ylamino]-3-methyl-isoxazol-5-yl}-biphenyl-4-yl)-cyclopropanecarboxylic acid ethyl ester Prepared according to the procedure described in Example 1, Step 10, using 1-{4'-[4-(6-bromo-pyridin-2-ylamino)-3-methyl-isoxazol-5-yl]-biphenyl-4-yl}-cyclopropanecarboxylic acid ethyl ester and 2,5-difluoro-phenylboronic acid.

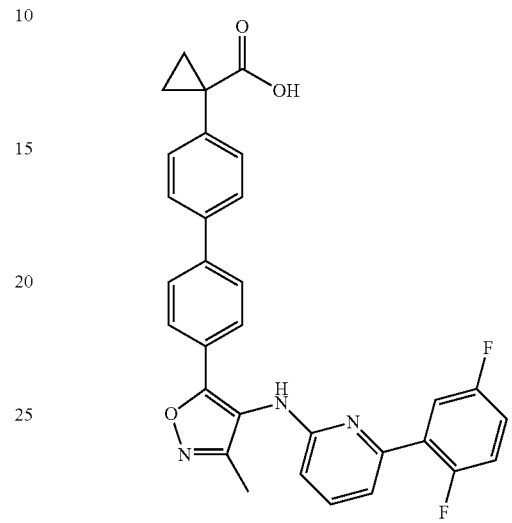

Step 2: 1-(4'-{4-[6-(2,5-Difluoro-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(2,5-difluoro-phenyl)-pyridin-2-ylamino]-3-methyl-isoxazol-5-yl}-biphenyl-4-yl)-cyclopropanecarboxylic acid ethyl ester.

Example 149

1-(4'-{3-Methyl-4-[6-(2H-tetrazol-5-yl)-pyridin-2-ylamino]-isoxazol-5-yl}-biphenyl-4-yl)-cyclopropanecarboxylic acid (Compound 1-149)

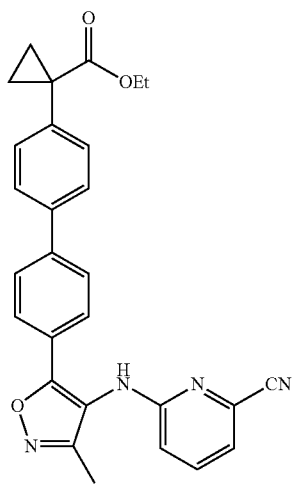 [SMILES: CCOC(=O)C1(c2ccc(-c3ccc(-c4onc(C)c4Nc4cccc(C#N)n4)cc3)cc2)CC1]

337

Step 1: 1-{4'-[4-(6-Cyano-pyridin-2-ylamino)-3-methyl-isoxazol-5-yl]-biphenyl-4-yl}-cyclopropanecarboxylic acid ethyl ester Prepared according to the procedure described in Example 134, Step 3, using 1-[4'-(4-amino-3-methyl-isoxazol-5-yl)-biphenyl-4-yl]-cyclopropanecarboxylic acid ethyl ester and 2-bromo-6-cyanopyridine.

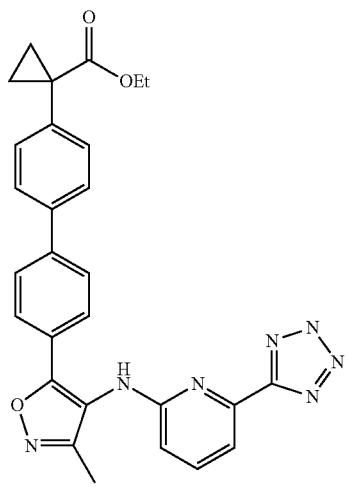

Step 2: 1-(4'-{3-Methyl-4-[6-(2H-tetrazol-5-yl)-pyridin-2-ylamino]-isoxazol-5-yl}-biphenyl-4-yl)-cyclopropanecarboxylic acid ethyl ester 1-{4'-[4-(6-Cyano-pyridin-2-ylamino)-3-methyl-isoxazol-5-yl]-biphenyl-4-yl}-cyclopropanecarboxylic acid ethyl ester (0.046 g, 0.1 mmol) and azidotributyltin(IV) (0.0996 g, 0.3 mmol) were dissolved in dichlorobenzene (1 mL) and heated to 110° C. for 14 hours. After cooling the reaction mixture was directly purified by silica gel chromatography to afford the title compound.

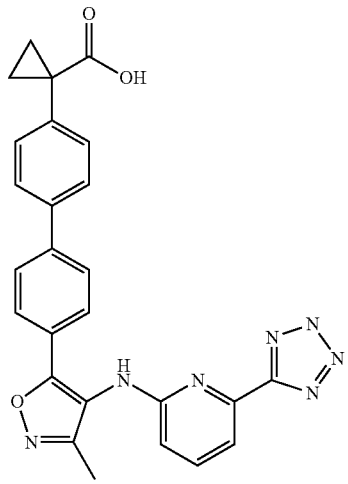 [SMILES: CCOC(=O)C1(c2ccc(-c3ccc(-c4onc(C)c4Nc4cccc(-c5nn[nH]n5)n4)cc3)cc2)CC1]

338

Step 3: 1-(4'-{3-Methyl-4-[6-(2H-tetrazol-5-yl)-pyridin-2-ylamino]-isoxazol-5-yl}-biphenyl-4-yl)-cyclopropanecarboxylic acid Prepared according to the procedure described in Example 1, Step 13, using 1-(4'-{3-Methyl-4-[6-(2H-tetrazol-5-yl)-pyridin-2-ylamino]-isoxazol-5-yl}-biphenyl-4-yl)-cyclopropanecarboxylic acid ethyl ester.

Example 150

1-(4'-{4-[6-(2,6-Dichloro-phenyl)-pyridin-2-ylamino]-3-methyl-isoxazol-5-yl}-biphenyl-4-yl)-cyclopropanecarboxylic acid (Compound 1-150)

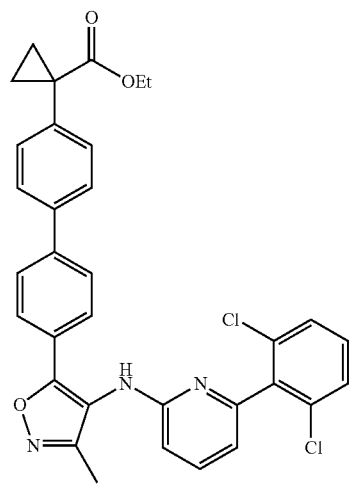 [SMILES: Cc1noc(-c2ccc(-c3ccc(C4(C(=O)O)CC4)cc3)cc2)c1Nc1cccc(-c2c(Cl)cccc2Cl)n1]

Step 1: 1-(4'-{4-[6-(2,6-Dichloro-phenyl)-pyridin-2-ylamino]-3-methyl-isoxazol-5-yl}-biphenyl-4-yl)-cyclopropanecarboxylic acid ethyl ester Prepared according to the procedure described in Example 42, Step 2, using 1-{4'-[4-(6-bromo-pyridin-2-ylamino)-3-methyl-isoxazol-5-yl]-biphenyl-4-yl}-cyclopropanecarboxylic acid ethyl ester and 2,6-dichloro-phenylboronic acid.

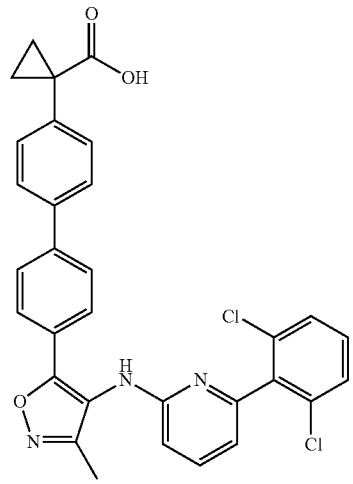

Step 2: 1-(4'-{4-[6-(2,6-Dichloro-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(2,6-dichloro-phenyl)-pyridin-2-ylamino]-3-methyl-isoxazol-5-yl}-biphenyl-4-yl)-cyclopropanecarboxylic acid ethyl ester.

Example 151

1-(4'-{4-[6-(2-Chloro-5-fluoro-phenyl)-pyridin-2-ylamino]-3-methyl-isoxazol-5-yl}-biphenyl-4-yl)-cyclopropanecarboxylic acid (Compound 1-151)

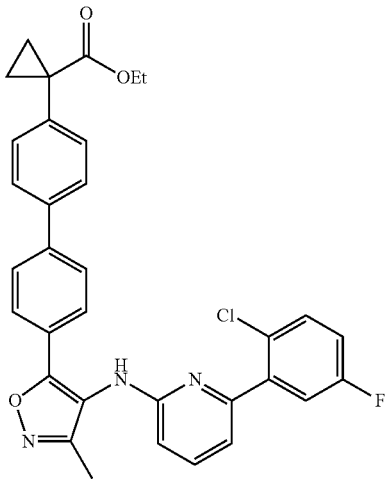

Step 1: 1-(4'-{4-[6-(2-Chloro-5-fluoro-phenyl)-pyridin-2-ylamino]-3-methyl-isoxazol-5-yl}-biphenyl-4-yl)-cyclopropanecarboxylic acid ethyl ester Prepared according to the procedure described in Example 42, Step 2, using 1-{4'-[4-(6-bromo-pyridin-2-ylamino)-3-methyl-isoxazol-5-yl]-biphenyl-4-yl}-cyclopropanecarboxylic acid ethyl ester and 2-chloro-5-fluoro-phenylboronic acid.

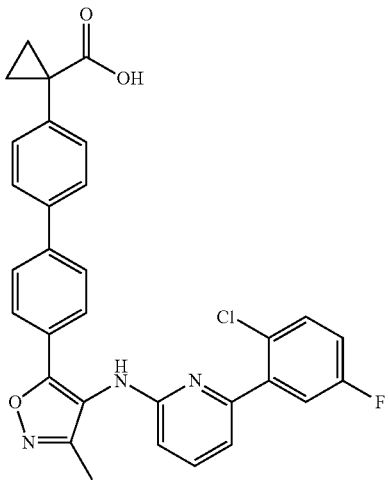 [SMILES: Cc1noc(-c2ccc(-c3ccc(C4(C(=O)O)CC4)cc3)cc2)c1Nc1cccc(-c2cc(F)ccc2Cl)n1]

Step 2: 1-(4'-{4-[6-(2-Chloro-5-fluoro-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(2-chloro-5-fluoro-phenyl)-pyridin-2-ylamino]-3-methyl-isoxazol-5-yl}-biphenyl-4-yl)-cyclopropanecarboxylic acid ethyl ester.

Example 152

1-(4'-{4-[6-(2,3-Difluoro-phenyl)-pyridin-2-ylamino]-3-methyl-isoxazol-5-yl}-biphenyl-4-yl)-cyclopropanecarboxylic acid (Compound 1-152)

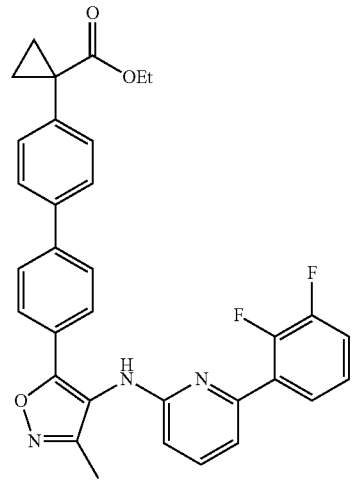

Step 1: 1-(4'-{4-[6-(2,3-Difluoro-phenyl)-pyridin-2-ylamino]-3-methyl-isoxazol-5-yl}-biphenyl-4-yl)-cyclopropanecarboxylic acid ethyl ester Prepared according to the procedure described in Example 42, Step 2, using 1-{4'-[4-(6-bromo-pyridin-2-ylamino)-3-methyl-isoxazol-5-yl]-biphenyl-4-yl}-cyclopropanecarboxylic acid ethyl ester and 2,3-difluoro-phenylboronic acid.

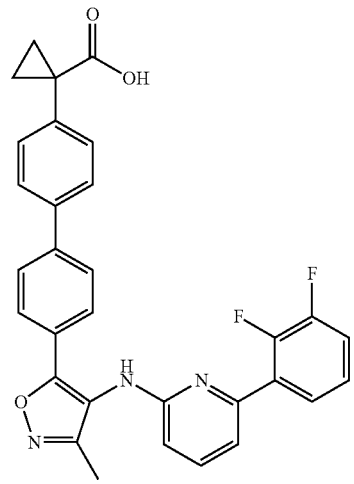 [SMILES: CCOC(=O)C1(c2ccc(-c3ccc(-c4onc(C)c4Nc4cccc(-c5cccc(F)c5F)n4)cc3)cc2)CC1]

Step 2: 1-(4'-{4-[6-(2,3-Difluoro-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(2,3-difluoro-phenyl)-pyridin-2-ylamino]-3-methyl-isoxazol-5-yl}-biphenyl-4-yl)-cyclopropanecarboxylic acid ethyl ester.

Example 153

1-(4'-{4-[6-(2-Chloro-3-fluoro-phenyl)-pyridin-2-ylamino]-3-methyl-isoxazol-5-yl}-biphenyl-4-yl)-cyclopropanecarboxylic acid (Compound 1-153)

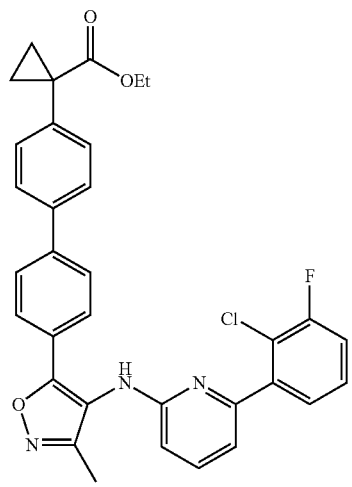 [SMILES: CCOC(=O)C1(c2ccc(-c3ccc(-c4onc(C)c4Nc4cccc(-c5cccc(F)c5Cl)n4)cc3)cc2)CC1]

Step 1: 1-(4'-{4-[6-(2-Chloro-3-fluoro-phenyl)-pyridin-2-ylamino]-3-methyl-isoxazol-5-yl}-biphenyl-4-yl)-cyclopropanecarboxylic acid ethyl ester Prepared according to the procedure described in Example 42, Step 2, using 1-{4'-[4-(6-bromo-pyridin-2-ylamino)-3-methyl-isoxazol-5-yl]-biphenyl-4-yl}-cyclopropanecarboxylic acid ethyl ester and 2-chloro-3-fluoro-phenylboronic acid.

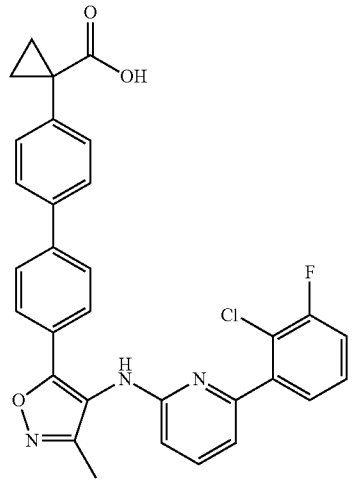 [SMILES: Cc1noc(-c2ccc(-c3ccc(C4(C(=O)O)CC4)cc3)cc2)c1Nc1cccc(-c2cccc(F)c2Cl)n1]

Step 2: 1-(4'-{4-[6-(2-Chloro-3-fluoro-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(2-chloro-3-fluoro-phenyl)-pyridin-2-ylamino]-3-methyl-isoxazol-5-yl}-biphenyl-4-yl)-cyclopropanecarboxylic acid ethyl ester.

Example 154

1-{4'-[4-(6-Cyclopropylmethoxy-pyridin-2-ylamino)-3-methyl-isoxazol-5-yl]-biphenyl-4-yl}-cyclopropanecarboxylic acid (Compound 1-154)

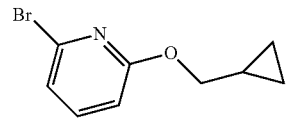 [SMILES: Brc1cccc(OCC2CC2)n1]

Step 1: 2-Bromo-6-cyclopropylmethoxy-pyridine

Prepared according to the procedure described in Example 139, Step 1, using 2,6-dibromo-pyridine and cyclopropyl-methanol.

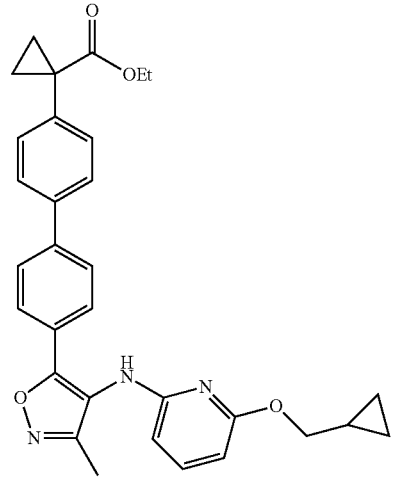

Step 2: 1-{4'-[4-(6-Cyclopropylmethoxy-pyridin-2-ylamino)-3-methyl-isoxazol-5-yl]-biphenyl-4-yl}-cyclopropanecarboxylic acid ethyl ester Prepared according to the procedure described in Example 134, Step 3, using 1-[4'-(4-amino-3-methyl-isoxazol-5-yl)-biphenyl-4-yl]-cyclopropanecarboxylic acid ethyl ester and 2-bromo-6-cyclopropylmethoxy-pyridine.

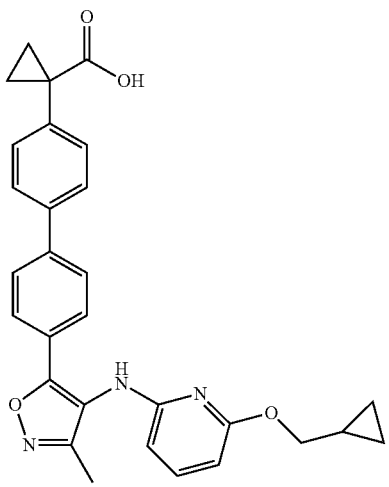 [SMILES: CCOC(=O)C1(c2ccc(-c3ccc(-c4onc(C)c4Nc4cccc(OCC5CC5)n4)cc3)cc2)CC1]

Step 3: 1-{4'-[4-(6-Cyclopropylmethoxy-pyridin-2-ylamino)-3-methyl-isoxazol-5-yl]-biphenyl-4-yl}-cyclopropanecarboxylic acid Prepared according to the procedure described in Example 1, Step 13, using 1-{4'-[4-(6-cyclopropylmethoxy-pyridin-2-ylamino)-3-methyl-isoxazol-5-yl]-biphenyl-4-yl}-cyclopropanecarboxylic acid ethyl ester.

Example 155

1-(4'-{4-[5-(2-Chloro-3-fluoro-phenyl)-pyridin-3-ylamino]-3-methyl-isoxazol-5-yl}-biphenyl-4-yl)-cyclopropanecarboxylic acid (Compound 1-155)

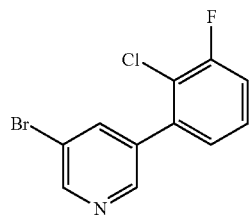 [SMILES: Fc1cccc(-c2cncc(Br)c2)c1Cl]

Step 1:
3-Bromo-5-(2-chloro-3-fluoro-phenyl)-pyridine

Prepared according to the procedure described in Example 42, Step 2, using 3,5-dibromo-pyridine and 2-chloro-3-fluoro-phenylboronic acid.

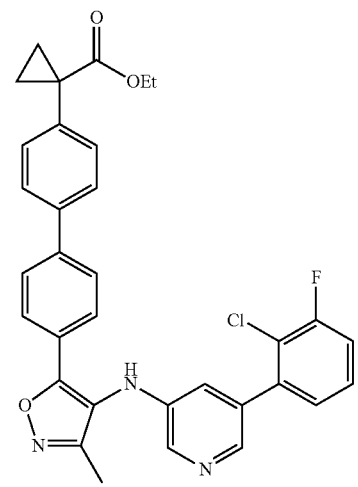 [SMILES: Cc1noc(-c2ccc(-c3ccc(C4(C(=O)O)CC4)cc3)cc2)c1Nc1cncc(-c2cccc(F)c2Cl)c1]

Step 2: 1-(4'-{4-[5-(2-Chloro-3-fluoro-phenyl)-pyridin-3-ylamino]-3-methyl-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 3-bromo-5-(2-chloro-3-fluoro-phenyl)-pyridine.

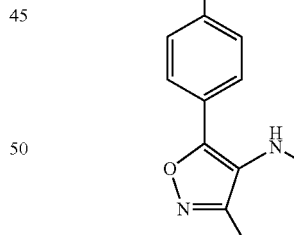

Step 3: 1-(4'-{4-[5-(2-Chloro-3-fluoro-phenyl)-pyridin-3-ylamino]-3-methyl-isoxazol-5-yl}-biphenyl-4-yl)-cyclopropanecarboxylic acid Prepared according to the procedure described in Example 1, Step 13, using 1-(4'-{4-[5-(2-chloro-3-fluoro-phenyl)-pyridin-3-ylamino]-3-methyl-isoxazol-5-yl}-biphenyl-4-yl)-cyclopropanecarboxylic acid ethyl ester.

Example 156

1-(4'-{4-[6-(3-Fluoro-2-methyl-phenyl)-pyridin-2-ylamino]-3-methyl-isoxazol-5-yl}-biphenyl-4-yl)-cyclopropanecarboxylic acid (Compound 1-156)

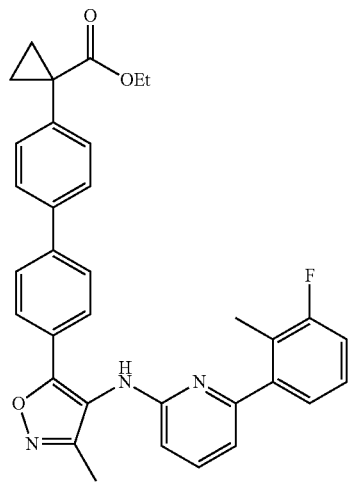 [SMILES: CCOC(=O)C1(c2ccc(-c3ccc(-c4onc(C)c4Nc4cccc(-c5cccc(F)c5C)n4)cc3)cc2)CC1]

Step 1: 1-(4'-{4-[6-(3-Fluoro-2-methyl-phenyl)-pyridin-2-ylamino]-3-methyl-isoxazol-5-yl}-biphenyl-4-yl)-cyclopropanecarboxylic acid ethyl ester Prepared according to the procedure described in Example 42, Step 2, using 1-{4'-[4-(6-bromo-pyridin-2-ylamino)-3-methyl-isoxazol-5-yl]-biphenyl-4-yl}-cyclopropanecarboxylic acid ethyl ester and 3-fluoro-2-metheyl-phenylboronic acid.

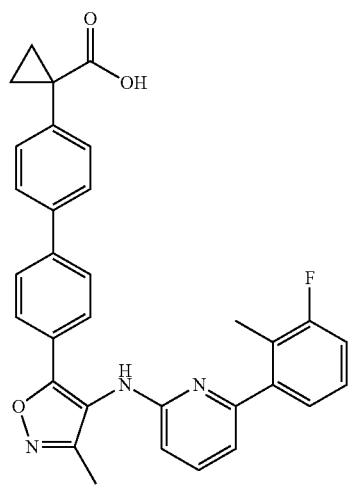 [SMILES: Cc1noc(-c2ccc(-c3ccc(C4(C(=O)O)CC4)cc3)cc2)c1Nc1cccc(-c2cccc(F)c2C)n1]

Step 2: 1-(4'-{4-[6-(3-Fluoro-2-methyl-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(3-fluoro-2-methyl-phenyl)-pyridin-2-ylamino]-3-methyl-isoxazol-5-yl}-biphenyl-4-yl)-cyclopropanecarboxylic acid ethyl ester.

Example 157

1-(4'-{4-[6-(2-Chloro-3-trifluoromethyl-phenyl)-pyridin-2-ylamino]-3-methyl-isoxazol-5-yl}-biphenyl-4-yl)-cyclopropanecarboxylic acid (Compound 1-157)

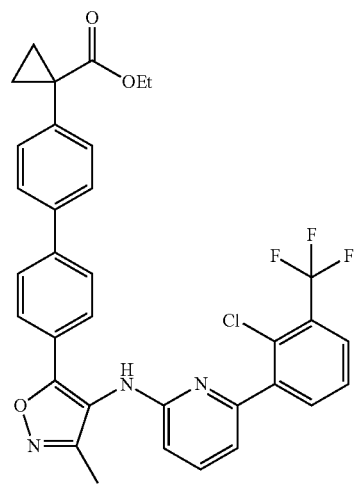 [SMILES: CCOC(=O)C1(c2ccc(-c3ccc(-c4onc(C)c4Nc4cccc(-c5cccc(C(F)(F)F)c5Cl)n4)cc3)cc2)CC1]

Step 1: 1-(4'-{4-[6-(2-Chloro-3-trifluoromethyl-phenyl)-pyridin-2-ylamino]-3-methyl-isoxazol-5-yl}-biphenyl-4-yl)-cyclopropanecarboxylic acid ethyl ester Prepared according to the procedure described in Example 42, Step 2, using 1-{4'-[4-(6-bromo-pyridin-2-ylamino)-3-methyl-isoxazol-5-yl]-biphenyl-4-yl}-cyclopropanecarboxylic acid ethyl ester and 2-chloro-3-(trifluoromethyel)phenylboronic acid.

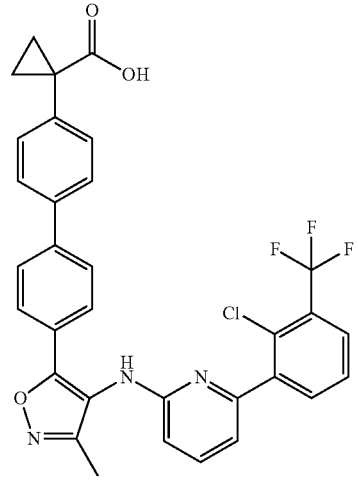 [SMILES: Cc1noc(-c2ccc(-c3ccc(C4(C(=O)O)CC4)cc3)cc2)c1Nc1cccc(-c2cccc(C(F)(F)F)c2Cl)n1]

Step 2: 1-(4'-{4-[6-(2-Chloro-3-trifluoromethyl-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(2-chloro-3-trifluoromethyl-phenyl)-pyridin-2-ylamino]-3-methyl-isoxazol-5-yl}-biphenyl-4-yl)-cyclopropanecarboxylic acid ethyl ester.

Example 158

Synthesis of 1-(4'-{4-[6-(2,3-Dichloro-phenyl)-pyridin-2-ylamino]-3-methyl-isoxazol-5-yl}-biphenyl-4-yl)-cyclopropanecarboxylic acid (Compound 1-158)

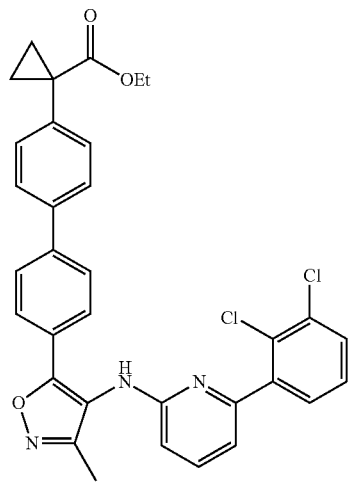

Step 1: 1-(4'-{4-[6-(2,3-Dichloro-phenyl)-pyridin-2-ylamino]-3-methyl-isoxazol-5-yl}-biphenyl-4-yl)-cyclopropanecarboxylic acid ethyl ester Prepared according to the procedure described in Example 42, Step 2, using 1-{4'-[4-(6-bromo-pyridin-2-ylamino)-3-methyl-isoxazol-5-yl]-biphenyl-4-yl}-cyclopropanecarboxylic acid ethyl ester and 2,3-dichlorophenylboronic acid.

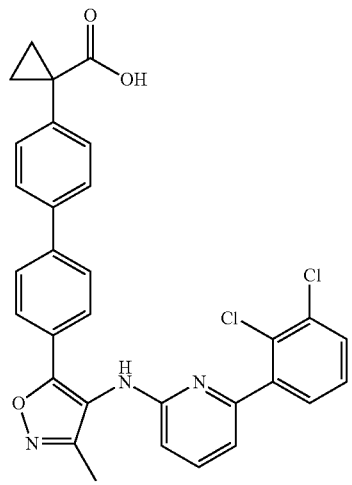 [SMILES: Cc1noc(-c2ccc(-c3ccc(C4(C(=O)O)CC4)cc3)cc2)c1Nc1cccc(-c2cccc(Cl)c2Cl)n1]

Step 2: 1-(4'-{4-[6-(2,3-Dichloro-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(2,3-dichloro-phenyl)-pyridin-2-ylamino]-3-methyl-isoxazol-5-yl}-biphenyl-4-yl)-cyclopropanecarboxylic acid ethyl ester.

Example 159

Synthesis of 1-(4'-{4-[6-(3-Fluoro-2-methoxy-phenyl)-pyridin-2-ylamino]-3-methyl-isoxazol-5-yl}-biphenyl-4-yl)-cyclopropanecarboxylic acid (Compound 1-159)

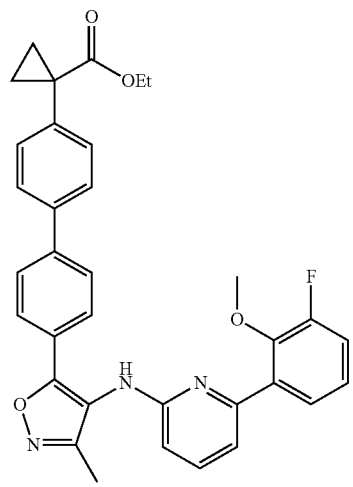 [SMILES: CCOC(=O)C1(c2ccc(-c3ccc(-c4onc(C)c4Nc4cccc(-c5cccc(F)c5OC)n4)cc3)cc2)CC1]

Step 1: 1-(4'-{4-[6-(3-Fluoro-2-methoxy-phenyl)-pyridin-2-ylamino]-3-methyl-isoxazol-5-yl}-biphenyl-4-yl)-cyclopropanecarboxylic acid ethyl ester Prepared according to the procedure described in Example 42, Step 2, using 1-{4'-[4-(6-bromo-pyridin-2-ylamino)-3-methyl-isoxazol-5-yl]-biphenyl-4-yl}-cyclopropanecarboxylic acid ethyl ester and 3-fluoro-2-methoxyphenylboronic acid.

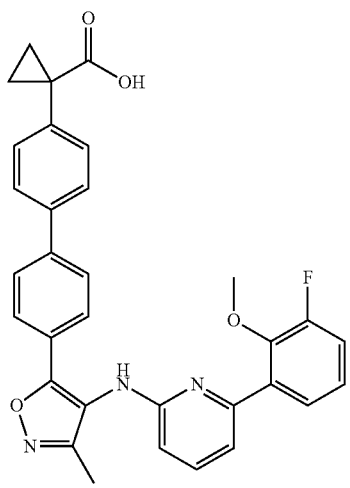 [SMILES: COc1c(F)cccc1-c1cccc(Nc2c(C)noc2-c2ccc(-c3ccc(C4(C(=O)O)CC4)cc3)cc2)n1]

Step 2: 1-(4'-{4-[6-(3-Fluoro-2-methoxy-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(3-fluoro-2-methoxy-phenyl)-pyridin-2-ylamino]-3-methyl-isoxazol-5-yl}-biphenyl-4-yl)-cyclopropanecarboxylic acid ethyl ester.

Example 160

Synthesis of 1-(4'-{4-[5-(3-Chloro-phenyl)-pyridin-3-ylamino]-3-methyl-isoxazol-5-yl}-biphenyl-4-yl)-cyclopropanecarboxylic acid (Compound 1-160)

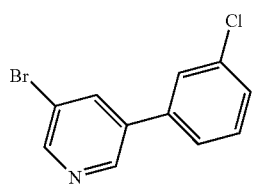 [SMILES: Clc1cccc(-c2cncc(Br)c2)c1]

Step 1: 3-Bromo-5-(3-chloro-phenyl)-pyridine

Prepared according to the procedure described in Example 1, Step 10, using 3,5-dibromo-pyridine and 3-chlorophenyl-boronic acid.

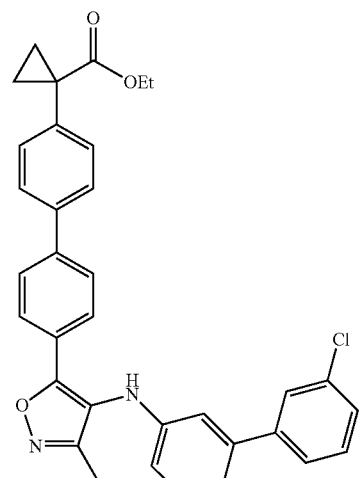

Step 2: 1-(4'-{4-[5-(3-Chloro-phenyl)-pyridin-3-ylamino]-3-methyl-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 3-bromo-5-(3-chloro-phenyl)-pyridine.

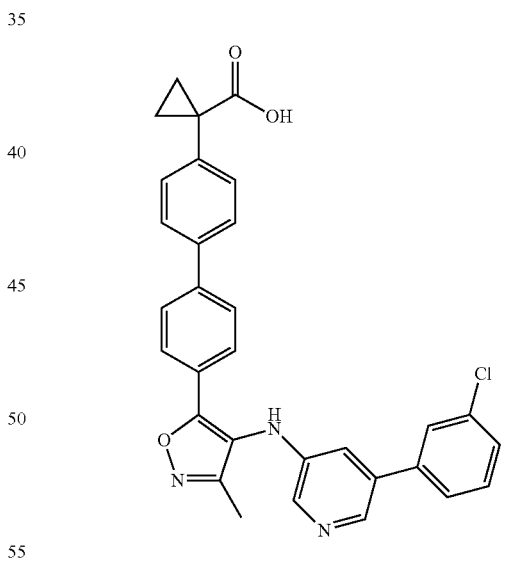

Step 3: 1-(4'-{4-[5-(3-Chloro-phenyl)-pyridin-3-ylamino]-3-methyl-isoxazol-5-yl}-biphenyl-4-yl)-cyclopropanecarboxylic acid Prepared according to the procedure described in Example 1, Step 13, using 1-(4'-{4-[5-(3-chloro-phenyl)-pyridin-3- ylamino]-3-methyl-isoxazol-5-yl}-biphenyl-4-yl)-cyclopropanecarboxylic acid ethyl ester.

Example 161

Synthesis of 1-(4'-{4-[5-(2,5-Difluoro-phenyl)-pyridin-3-ylamino]-3-methyl-isoxazol-5-yl}-biphenyl-4-yl)-cyclopropanecarboxylic acid (Compound 1-161)

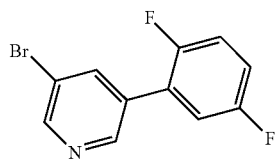 [SMILES: Fc1ccc(F)c(-c2cncc(Br)c2)c1]

Step 1: 3-Bromo-5-(2,5-difluoro-phenyl)-pyridine

Prepared according to the procedure described in Example 48, Step 2, using 3,5-dibromo-pyridine and 2,5-difluorophenylboronic acid.

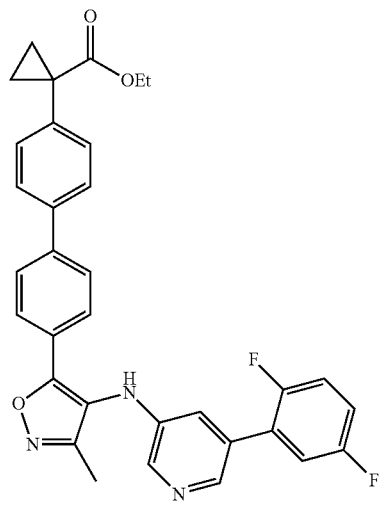

Step 2: 1-(4'-{4-[5-(2,5-Difluoro-phenyl)-pyridin-3-ylamino]-3-methyl-isoxazol-5-yl}-biphenyl-4-yl)-cyclopropanecarboxylic acid ethyl ester Prepared according to the procedure described in Example 68, Step 2, using 1-[4'-(4-amino-3-methyl-isoxazol-5-yl)-biphenyl-4-yl]-cyclopropanecarboxylic acid ethyl ester and 3-bromo-5-(2,5-difluoro-phenyl)-pyridine.

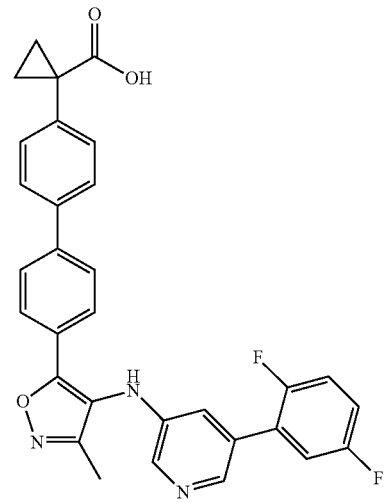 [SMILES: Cc1noc(-c2ccc(-c3ccc(C4(C(=O)O)CC4)cc3)cc2)c1Nc1cncc(-c2cc(F)ccc2F)c1]

Step 3: 1-(4'-{4-[5-(2,5-Difluoro-phenyl)-pyridin-3-ylamino]-3-methyl-isoxazol-5-yl}-biphenyl-4-yl)-cyclopropanecarboxylic acid Prepared according to the procedure described in Example 1, Step 13, using 1-(4'-{4-[5-(2,5-difluoro-phenyl)-pyridin-3-ylamino]-3-methyl-isoxazol-5-yl}-biphenyl-4-yl)-cyclopropanecarboxylic acid ethyl ester.

Example 162

Synthesis of 1-(4'-{4-[6-(3-Chloro-phenyl)-pyridin-2-ylamino]-3-methyl-isoxazol-5-yl}-biphenyl-4-yl)-cyclopropanecarboxylic acid (Compound 1-162)

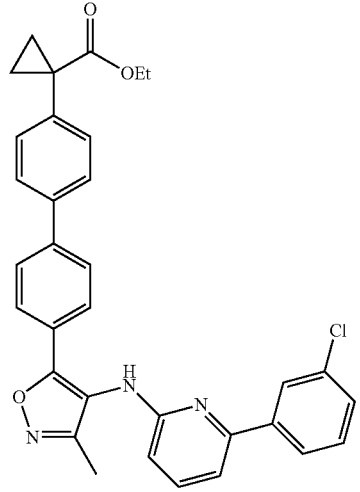 [SMILES: Cc1noc(-c2ccc(-c3ccc(C4(C(=O)O)CC4)cc3)cc2)c1Nc1cccc(-c2cccc(Cl)c2)n1]

Step 1: 1-(4'-{4-[6-(3-Chloro-phenyl)-pyridin-2-ylamino]-3-methyl-isoxazol-5-yl}-biphenyl-4-yl)-cyclopropanecarboxylic acid ethyl ester Prepared according to the procedure described in Example 42, Step 2, using 1-{4'-[4-(6-bromo-pyridin-2-ylamino)-3-methyl-isoxazol-5-yl]-biphenyl-4-yl}-cyclopropanecarboxylic acid ethyl ester and 3-chlorophenylboronic acid.

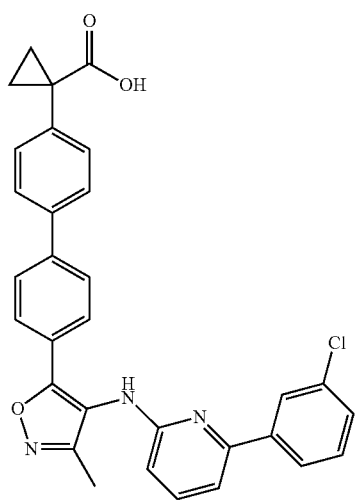

Step 2: 1-(4'-{4-[6-(3-Chloro-phenyl)-pyridin-2-ylamino]-3-methyl-isoxazol-5-yl}-biphenyl-4-yl)-cyclopropanecarboxylic acid Prepared according to the procedure described in Example 1, Step 13, using 1-(4'-{4-[6-(3-chloro-phenyl)-pyridin-2-ylamino]-3-methyl-isoxazol-5-yl}-biphenyl-4-yl)-cyclopropanecarboxylic acid ethyl ester.

Example 163

Synthesis of 1-{4'-[3-Ethyl-4-(6-phenyl-pyridin-2-ylamino)-isoxazol-5-yl]-biphenyl-4-yl}-cyclopropanecarboxylic acid (Compound 2-1)

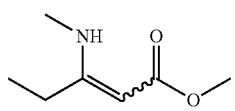

Step 1: 3-Methylamino-pent-2-enoic acid methyl ester

Prepared according to the procedure described in Example 1, Step 1, using 3-oxo-pentanoic acid methyl ester and methylamine.

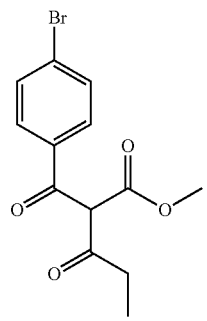 [SMILES: CCC(=O)C(C(=O)OC)C(=O)c1ccc(Br)cc1]

Step 2: 2-(4-Bromo-benzoyl)-3-oxo-pentanoic acid methyl ester

Prepared according to the procedure described in Example 1, Step 2, using 3-methylamino-pent-2-enoic acid methyl ester and 4-bromobenzoyl chloride.

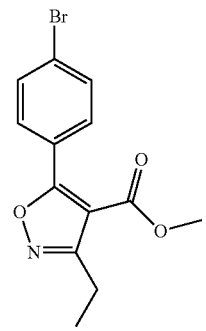 [SMILES: CCc1noc(-c2ccc(Br)cc2)c1C(=O)OC]

Step 3: 5-(4-Bromo-phenyl)-3-ethyl-isoxazole-4-carboxylic acid methyl ester

Prepared according to the procedure described in Example 1, Step 3, using 2-(4-bromo-benzoyl)-3-oxo-pentanoic acid methyl ester.

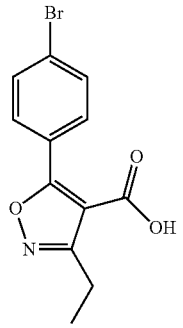 [SMILES: CCc1noc(-c2ccc(Br)cc2)c1C(=O)O]

Step 4: 5-(4-Bromo-phenyl)-3-ethyl-isoxazole-4-carboxylic acid

Prepared according to the procedure described in Example 1, Step 4, using 5-(4-bromo-phenyl)-3-ethyl-isoxazole-4-carboxylic acid methyl ester.

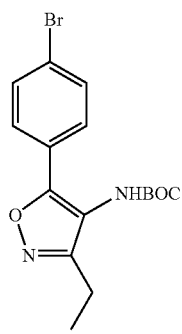

Step 5: [5-(4-Bromo-phenyl)-3-ethyl-isoxazol-4-yl]-carbamic acid tert-butyl ester Prepared according to the procedure described in Example 1, Step 5, using 5-(4-bromo-phenyl)-3-ethyl-isoxazole-4-carboxylic acid.

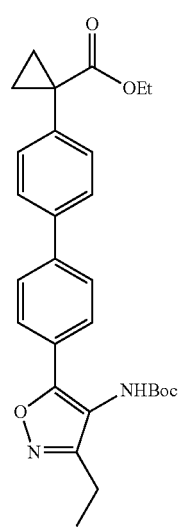 [SMILES: CCOC(=O)C1(c2ccc(-c3ccc(-c4onc(CC)c4NC(=O)OC(C)(C)C)cc3)cc2)CC1]

Step 6: 1-[4'-(4-tert-Butoxycarbonylamino-3-ethyl-isoxazol-5-yl)-biphenyl-4-yl]-cyclopropanecarboxylic acid ethyl ester Prepared according to the procedure described in Example 42, Step 2, using [5-(4-bromo-phenyl)-3-ethyl-isoxazol-4-yl]-carbamic acid tert-butyl ester and 1-[4-(4,4,5,5-tetramethyl-[1,3,2]dioxaborolan-2-yl)-phenyl]-cyclopropanecarboxylic acid ethyl ester.

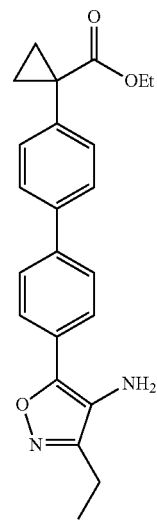 [SMILES: CCOC(=O)C1(c2ccc(-c3ccc(-c4onc(CC)c4N)cc3)cc2)CC1]

Step 7: 1-[4'-(4-Amino-3-ethyl-isoxazol-5-yl)-biphenyl-4-yl]-cyclopropanecarboxylic acid ethyl ester Prepared according to the procedure described in Example 1, Step 11, using 1-[4'-(4-tert-butoxycarbonylamino-3-ethyl-isoxazol-5-yl)-biphenyl-4-yl]-cyclopropanecarboxylic acid ethyl ester.

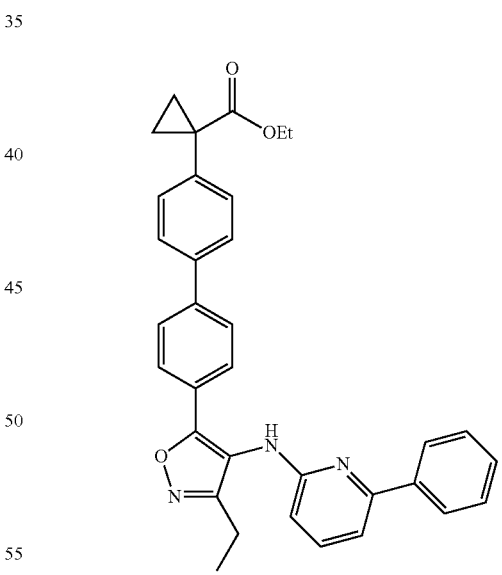

Step 8: 1-{4'-[3-Ethyl-4-(6-phenyl-pyridin-2-ylamino)-isoxazol-5-yl]-biphenyl-4-yl}-cyclopropanecarboxylic acid ethyl ester Prepared according to the procedure described in Example 68, Step 2, using 1-[4'-(4-amino-3-ethyl-isoxazol-5-yl)-biphenyl-4-yl]-cyclopropanecarboxylic acid ethyl ester and 2-bromo-6-phenyl-pyridine.

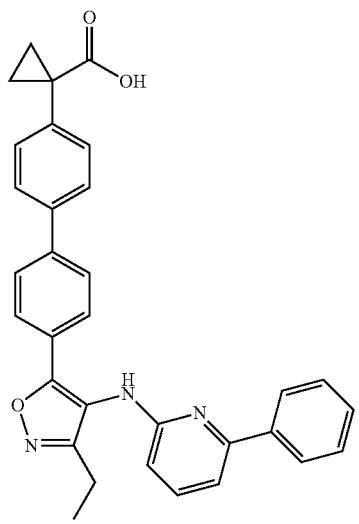 [SMILES: CCc1noc(-c2ccc(-c3ccc(C4(C(=O)O)CC4)cc3)cc2)c1Nc1cccc(-c2ccccc2)n1]

Step 9: 1-{4'-[3-Ethyl-4-(6-phenyl-pyridin-2-ylamino)-isoxazol-5-yl]-biphenyl-4-yl}-cyclopropanecarboxylic acid Prepared according to the procedure described in Example 1, Step 13, using 1-{4'-[3-ethyl-4-(6-phenyl-pyridin-2-ylamino)-isoxazol-5-yl]-biphenyl-4-yl}-cyclopropanecarboxylic acid ethyl ester.

Example 164

Synthesis of 1-{4'-[3-Ethyl-4-(5-phenyl-[1,3,4]oxadiazol-2-ylamino)-isoxazol-5-yl]-biphenyl-4-yl}-cyclopropanecarboxylic acid (Compound 2-2)

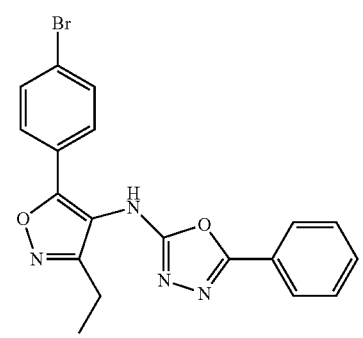 [SMILES: CCc1noc(-c2ccc(Br)cc2)c1Nc1nnc(-c2ccccc2)o1]

Step 1: [5-(4-Bromo-phenyl)-3-ethyl-isoxazol-4-yl]-(5-phenyl-[1,3,4]oxadiazol-2-yl)-amine Prepared according to the procedure described in Example 80, Step 1, using 5-(4-bromo-phenyl)-3-ethyl-isoxazole-4-carboxylic acid and benzoic acid hydrazide.

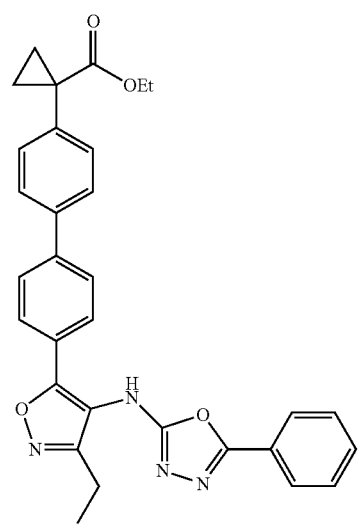 [SMILES: CCOC(=O)C1(c2ccc(-c3ccc(-c4onc(CC)c4Nc4nnc(-c5ccccc5)o4)cc3)cc2)CC1]

Step 2: 1-{4'-[3-Ethyl-4-(5-phenyl-[1,3,4]oxadiazol-2-ylamino)-isoxazol-5-yl]-biphenyl-4-yl}-cyclopropanecarboxylic acid ethyl ester Prepared according to the procedure described in Example 42, Step 2, using [5-(4-bromo-phenyl)-3-ethyl-isoxazol-4-yl]-(5-phenyl-[1,3,4]oxadiazol-2-yl)-amine and 1-[4-(4,4,5,5-tetramethyl-[1,3,2]dioxaborolan-2-yl)-phenyl]-cyclopropanecarboxylic acid ethyl ester.

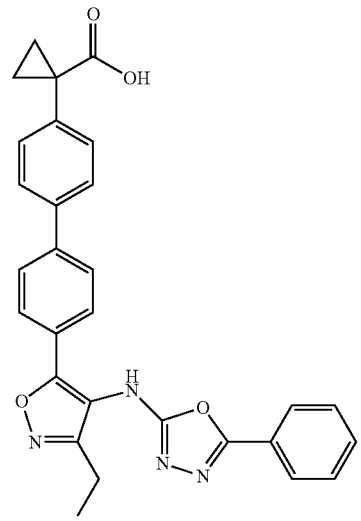 [SMILES: CCc1noc(-c2ccc(-c3ccc(C4(C(=O)O)CC4)cc3)cc2)c1Nc1nnc(-c2ccccc2)o1]

Step 3: 1-{4'-[3-Ethyl-4-(5-phenyl-[1,3,4]oxadiazol-2-ylamino)-isoxazol-5-yl]-biphenyl-4-yl}-cyclopropanecarboxylic acid Prepared according to the procedure described in Example 1, Step 13, using 1-{4'-[3-ethyl-4-(5-phenyl-[1,3,4]oxadiazol-2-ylamino)-isoxazol-5-yl]-biphenyl-4-yl}-cyclopropanecarboxylic acid ethyl ester.

Example 165

Synthesis of N-[1-(4'-{4-[(1-Benzyl-1H-[1,2,3]triazol-4-yl)-hydroxy-methyl]-3-methyl-isoxazol-5-yl}-biphenyl-4-yl)-cyclopropanecarbonyl]-methanesulfonamide (Enantiomer B) (Compound 3-1)

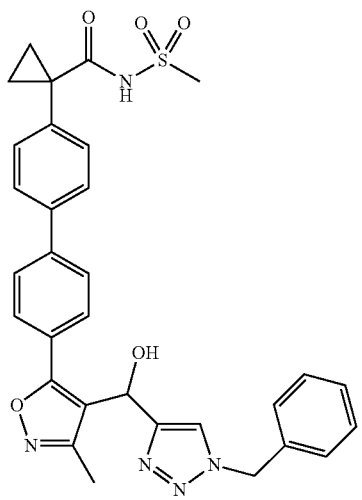 [SMILES: Cc1noc(-c2ccc(-c3ccc(C4(C(=O)NS(C)(=O)=O)CC4)cc3)cc2)c1C(O)c1cn(Cc2ccccc2)nn1]

A solution of 1-(4'-{4-[(1-benzyl-1H-[1,2,3]triazol-4-yl)-hydroxy-methyl]-3-methyl-isoxazol-5-yl}-biphenyl-4-yl)-cyclopropanecarboxylic acid (Enantiomer B) (0.100 g, 0.197 mmol), carbonyldiimidazole (0.080 g, 0.5 mmol), N,N-dimethylamino pyridine (0.002 g, 0.02 mmol) in THF (2 mL) was stirred at room temperature overnight. Added MeSO$_2$NH$_2$ (0.050 g, 0.5 mmol) and DBU (0.100 mL, 0.65 mmol) and the mixture heated to 100° C. in a capped vial for 4.5 hours. The solution was poured into sat. aqueous NH$_4$Cl, then water and EtOAc was added. The organic layer was separated, dried (Na$_2$SO$_4$), concentrated and the resulting reside purified by preparative HPLC to yield the title compound.

Example 166

Synthesis of N-[1-(4'-{4-[(5-Benzyl-[1,3,4]oxadiazol-2-yl)-hydroxy-methyl]-3-methyl-isoxazol-5-yl}-biphenyl-4-yl)-cyclopropanecarbonyl]-methanesulfonamide (Enantiomer A) (Compound 3-2)

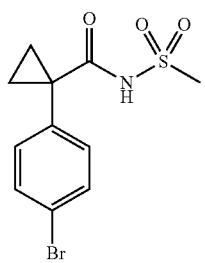 [SMILES: CS(=O)(=O)NC(=O)C1(c2ccc(Br)cc2)CC1]

Step 1: N-[1-(4-Bromo-phenyl)-cyclopropanecarbonyl]-methanesulfonamide 1-(4-Bromo-phenyl)-cyclopropanecarboxylic acid (22 g, 91.3 mmol) and SOCl$_2$ (13.6 mL, 183 mmol) in CH$_2$Cl$_2$ were heated together for 1.5 hours then evaporated to afford a dark oil. This oil was added via syringe over 30 minutes to a mixture of MeSO$_2$NH$_2$ (19 g, 200 mmol) in THF (250 mL) that was pre-treated at room temperature with NaH (60% in oil; 8.0 g, 200 mmol) for 1.5 hours. After a further 20 minutes, the mixture was poured into water, acidified and extracted with CH$_2$Cl$_2$, washed with water (2×) and evaporated to ~100 mL. Hexane (300 mL) was added and the product collected by filtration to yield the title compound (25 g).

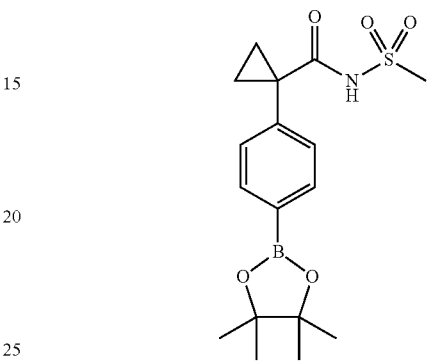

Step 2: N-{1-[4-(4,4,5,5-Tetramethyl-[1,3,2]dioxaborolan-2-yl)-phenyl]-cyclopropanecarbonyl}-methanesulfonamide N-[1-(4-Bromo-phenyl)-cyclopropanecarbonyl]-methanesulfonamide (22 g, 69 mmol), bis(pinacolato)diborane (21.1 g, 83 mmol), KOAc (21.6 g, 220 mmol) in dioxane (300 mL) were degassed with N$_2$ for 30 minutes and then (1,1'-bis (diphenylphosphino)ferrocene)-dichloropalladium(II) (1.0 g, 1.4 mmol) was added. The mixture was heated at reflux for 2 hours then at 70° C. for 16 hours. Then solution was poured into EtOAc/H$_2$O, acidified and the organic layer concentrated to give the boronate which was used in the next step without further purification.

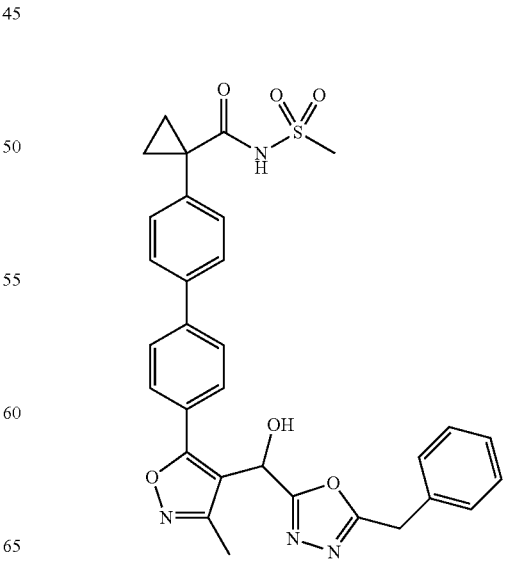

Step 3: N-[1-(4'-{4-[(5-Benzyl-[1,3,4]oxadiazol-2-yl)-hydroxy-methyl]-3-methyl-isoxazol-5-yl}-biphenyl-4-yl)-cyclopropanecarbonyl]-methanesulfonamide (Enantiomer A)

A solution of N-{1-[4-(4,4,5,5-tetramethyl-[1,3,2]dioxaborolan-2-yl)-phenyl]-cyclopropanecarbonyl}-methanesulfonamide (0.045 g, 0.124 mmol), 5-benzyl-[1,3,4]oxadiazol-2-yl)-[5-(4-bromo-phenyl)-3-methyl-isoxazol-4-yl]-methanol (Enantiomer A) (0.053 g, 0.124 mmol), NaHCO$_3$ (0.031 g, 0.372 mmol), DME (1.5 mL) and H$_2$O (1 mL) was degassed by bubbling with N$_2$ for 10 minutes. Tetrakis(triphenylphosphine)palladium(0) (0.007 g, 0.006 mmol) was added and the sealed reaction vial was stirred at 80° C. for 16 hours. The mixture was poured into EtOAc/H$_2$O, washed with 1N HCl then aqueous Na$_2$SO$_4$ and concentrated. The resulting reside purified by preparative HPLC to yield the title compound.

Example 167

Synthesis of N-{1-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-cyclopropanecarbonyl}-methanesulfonamide (Compound 3-3)

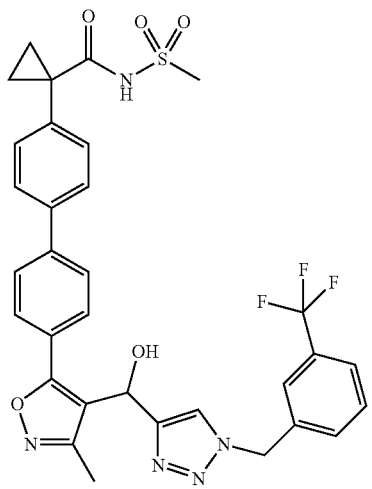 [SMILES: Cc1noc(-c2ccc(-c3ccc(C4(C(=O)NS(C)(=O)=O)CC4)cc3)cc2)c1C(O)c1cn(Cc2cccc(C(F)(F)F)c2)nn1]

Step 1: N-{1-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-cyclopropanecarbonyl}-methanesulfonamide Prepared according to the procedure described in Example 166, Step 3, using [5-(4-bromo-phenyl)-3-methyl-isoxazol-4-yl]-[1-(3-trifluoromethyl-benzyl)-1H-[1,2,3]triazol-4-yl]-methanol and N-{1-[4-(4,4,5,5-tetramethyl-[1,3,2]dioxaborolan-2-yl)-phenyl]-cyclopropanecarbonyl}-methanesulfonamide.

Example 168

Synthesis of N-(1-{4'-[3-Methyl-4-(5-phenyl-[1,3,4]oxadiazol-2-ylamino)-isoxazol-5-yl]-biphenyl-4-yl}-cyclopropanecarbonyl)-methanesulfonamide (Compound 3-4)

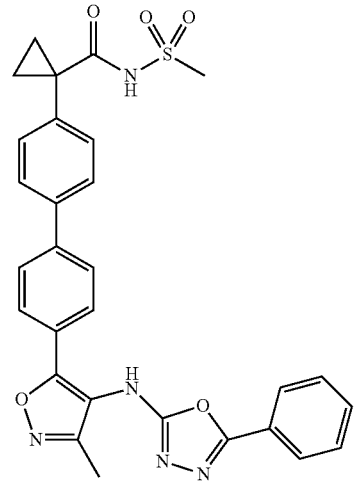 [SMILES: Cc1noc(-c2ccc(-c3ccc(C4(C(=O)NS(C)(=O)=O)CC4)cc3)cc2)c1Nc1nnc(-c2ccccc2)o1]

Step 1: N-(1-{4'-[3-Methyl-4-(5-phenyl-[1,3,4]oxadiazol-2-ylamino)-isoxazol-5-yl]-biphenyl-4-yl}-cyclopropanecarbonyl)-methanesulfonamide Prepared according to the procedure described in Example 166, Step 3, using [5-(4-bromo-phenyl)-3-methyl-isoxazol-4-yl]-(5-phenyl-[1,3,4]oxadiazol-2-yl)-amine and N-{1-[4-(4,4,5,5-tetramethyl-[1,3,2]dioxaborolan-2-yl)-phenyl]-cyclopropanecarbonyl}-methanesulfonamide.

Example 169

Synthesis of N-(1-{4'-[4-(6-Benzyl-pyridin-2-ylamino)-3-methyl-isoxazol-5-yl]-biphenyl-4-yl}-cyclopropanecarbonyl)-methanesulfonamide (Compound 3-5)

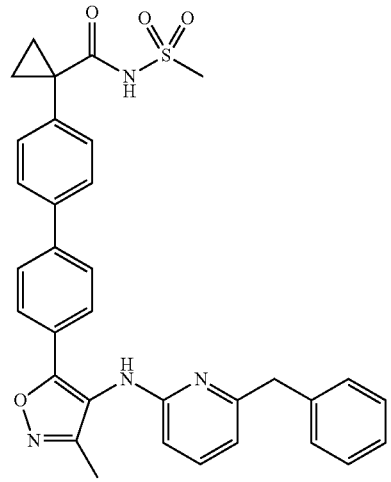 [SMILES: Cc1noc(-c2ccc(-c3ccc(C4(C(=O)NS(C)(=O)=O)CC4)cc3)cc2)c1Nc1cccc(Cc2ccccc2)n1]

Step 1: N-(1-{4'-[4-(6-Benzyl-pyridin-2-ylamino)-3-methyl-isoxazol-5-yl]-biphenyl-4-yl}-cyclopropanecarbonyl)-methanesulfonamide 1-{4'-[4-(6-benzyl-pyridin-2-ylamino)-3-methyl-isoxazol-5-yl]-biphenyl-4-yl}-cyclopropanecarboxylic acid (sodium salt; 0.050 g, 0.083 mmol), carbonyldiimidazole (0.0676 g, 0.417 mmol), MeSO$_2$NH$_2$ (0.0789 g, 0.83 mmol) and DBU (0.0248 mL, 0.166 mmol) were combined in THF (1 mL) and the mixture was heated to 70° C. in a capped vial for 25 hours. The mixture was purified by preparative HPLC to yield the title compound.

Example 170

Synthesis of N-(1-{4'-[3-Methyl-4-(6-phenyl-pyridin-2-ylamino)-isoxazol-5-yl]-biphenyl-4-yl}-cyclopropanecarbonyl)-methanesulfonamide (Compound 3-6)

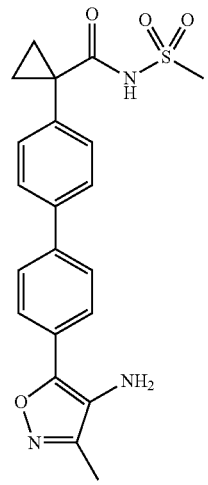

Step 2: N-{1-[4'-(4-Amino-3-methyl-isoxazol-5-yl)-biphenyl-4-yl]-cyclopropanecarbonyl}-methanesulfonamide {5-[4'-(1-M ethanesulfonylamino carbonyl-cyclopropyl)-biphenyl-4-yl]-3-methyl-isoxazol-4-yl}-carbamic acid tert-butyl ester (0.25 g, 0.49 mmol)) in CH$_2$Cl$_2$ (2 mL) and TFA (2 mL) was stirred overnight then poured into EtOAc/NaHCO$_3$ (aq). The organic layer was concentrated to yield the title compound that was used directly in the next step.

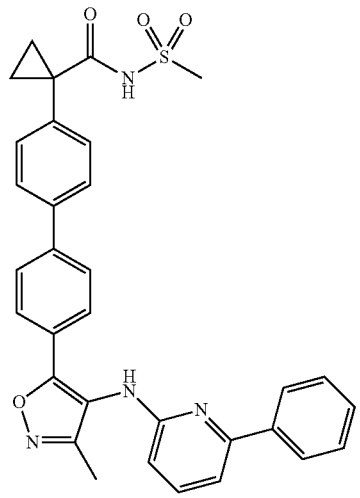

Step 3: N-(1-{4'-[3-Methyl-4-(6-phenyl-pyridin-2-ylamino)-isoxazol-5-yl]-biphenyl-4-yl}-cyclopropanecarbonyl)-methanesulfonamide N-{1-[4'-(4-Amino-3-methyl-isoxazol-5-yl)-biphenyl-4-yl]-cyclopropanecarbonyl}-methanesulfonamide (0.103 g, 0.25 mmol), 2-bromo-6-phenylpyridine (0.059 g, 0.25 mmol), potassium carbonate (0.243 g, 0.75 mmol), and BINAP (15 mg, 0.025 mmol) were combined in THF (10 mL) and the solution was degassed with N$_2$ for 10 minutes. Palladium(II)acetate (0.003 g, 0.0125 mmol) was added and degassing was continued for 10 minutes. The reaction mix-

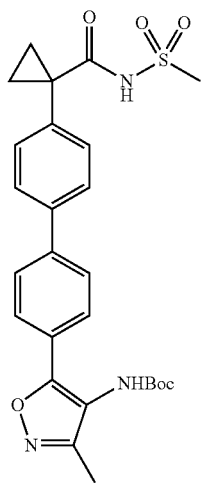 [SMILES: Cc1noc(-c2ccc(-c3ccc(C4(C(=O)NS(C)(=O)=O)CC4)cc3)cc2)c1NC(=O)OC(C)(C)C]

Step 1: {5-[4'-(1-Methanesulfonylaminocarbonyl-cyclopropyl)-biphenyl-4-yl]-3-methyl-isoxazol-4-yl}-carbamic acid tert-butyl ester Prepared according to the procedure described in Example 166, Step 3, using [5-(4-Bromo-phenyl)-3-methyl-isoxazol-4-yl]-carbamic acid tert-butyl ester and N-{1-[4-(4,4,5,5-tetramethyl-[1,3,2]dioxaborolan-2-yl)-phenyl]-cyclopropanecarbonyl}-methanesulfonamide.

ture was sealed and heated at 65° C. overnight then poured into EtOAc/water. The organic layer was concentrated and purified by silica gel chromatography to give the title compound.

In some embodiments, mass spectrometric data (mass spec. data) is obtained with a Shimadzu LCMS 2010A.

Example 171

Establishment of a CHO Cell Line Stably Expressing Human $LPA_1$

A 1.1 kb cDNA encoding the human $LPA_1$ receptor was cloned from human lung.

Human lung RNA (Clontech Laboratories, Inc. USA) was reverse transcribed using the RETROscript kit (Ambion, Inc.) and the full-length cDNA for human $LPA_1$ was obtained by PCR of the reverse transcription reaction. The nucleotide sequence of the cloned human $LPA_1$ was determined by sequencing and confirmed to be identical to the published human $LPA_1$ sequence (An et al. *Biochem. Biophys. Res. Commun.* 231:619 (1997). The cDNA was cloned into the pcDNA5/FRT expression plasmid and transfected in CHO cells using lipofectamine 2000 (Invitrogen Corp., USA). Clones stably expressing human $LPA_1$ were selected using hygromycin and identified as cells that show Ca-influx in response to LPA.

Example 172

Generation of Cells Transiently Expressing Human $LPA_2$

A vector containing the human $LPA_2$ receptor cDNA was obtained from the Missouri S&T cDNA Resource Center (www.cdna.org). The full-length cDNA fragment for human $LPA_2$ was obtained by PCR from the vector. The nucleotide sequence of the cloned human $LPA_2$ was determined by sequencing and confirmed to be identical to the published human $LPA_2$ sequence (NCBI accession number NM_004720). The cDNA was cloned into the pcDNA3.1 expression plasmid and transfected into B103 cells (Invitrogen Corp., USA) by seeding cells in a 96-well poly-D-lysine coated plate at 30,000-35,000 cells per well together with 0.2 µA lipofectamine 2000 and 0.2 µg of the $LPA_2$ expression vector. Cells were cultured overnight in complete media before being assayed for LPA-induced Ca-influx.

Example 173

Establishment of a CHO Cell Line Stably Expressing Human $LPA_3$

A vector containing the human $LPA_3$ receptor cDNA was obtained from the Missouri S&T cDNA Resource Center (www.cdna.org). The full-length cDNA fragment for human $LPA_3$ was obtained by PCR from the vector. The nucleotide sequence of the cloned human $LPA_3$ was determined by sequencing and confirmed to be identical to the published human $LPA_3$ sequence (NCBI accession number NM_012152). The cDNA was cloned into the pcDNA5/FRT expression plasmid and transfected in CHO cells using lipofectamine 2000 (Invitrogen Corp., USA). Clones stably expressing human $LPA_3$ were selected using hygromycin and identified as cells that show Ca-influx in response to LPA.

Example 174

LPA1 and LPA3 Calcium Flux Assays

Human $LPA_1$ or $LPA_3$ expressing CHO cells are seeded at 20,000-45,000 cells per well in a 96-well poly-D-lysine coated plate one or two days before the assay. Prior to the assay, the cells are washed once with PBS and then cultured in serum-free media overnight. On the day of the assay, a calcium indicator dye (Calcium 4, Molecular Devices) in assay buffer (HBSS with $Ca^{2+}$ and $Mg^{2+}$ and containing 20 mM Hepes and 0.3% fatty-acid free human serum albumin) is added to each well and incubation continued for 1 hour at 37° C. 10 µl of test compounds in 2.5% DMSO are added to the cells and incubation continued at room temperature for 30 minutes. Cells are the stimulated by the addition of 10 nM LPA and intracellular $Ca^{2+}$ measured using the Flexstation 3 (Molecular Devices). $IC_{50}$s are determined using Graphpad prism analysis of drug titration curves.

Example 175

LPA2 Calcium Flux Assay

Following an overnight culture with lipofectamine 2000 and the $LPA_2$ expression vector, the B103 cells are washed once with PBS then serum starved for 4 hours. A calcium indicator dye (Calcium 4, Molecular Devices) in assay buffer (HBSS with $Ca^{2+}$ and $Mg^{2+}$ and containing 20 mM Hepes and 0.3% fatty-acid free human serum albumin) is added to each well and incubation continued for 1 hour at 37° C. 10 µl of test compounds in 2.5% DMSO are added to the cells and incubation continued at room temperature for 30 minutes. Cells are the stimulated by the addition of 10 nM LPA and intracellular $Ca^{2+}$ measured using the Flexstation 3 (Molecular Devices). $IC_{50}$s are determined using Graphpad prism analysis of drug titration curves.

Example 176

GTPγS Binding Assay

The ability of a compound to inhibit binding of GTP to $LPA_1$ is assessed via a membrane GTPγS assay. CHO cells stably expressing the recombinant human $LPA_1$ receptor are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol. Membranes (~25 µg per well) are incubated in 96-well plates with 0.1 nM [$^{35}$S]-GTPγS, 900 nM LPA, 5 µM GDP, and test compound in Assay Buffer (50 mM Hepes, pH 7.4, 100 mM NaCl, 10 mM $MgCl_2$, 50 µg/ml saponin and 0.2% fatty-acid free human serum albumin) for 30 minutes at 30° C. The reactions are terminated by rapid filtration through Whatman GF/B glass fibre filter plates. The filter plates are washed 3 times with 1 ml cold Wash Buffer (50 mM Hepes, 7.5, 100 mM NaCl and 10 mM $MgCl_2$) and dried. Scintillant is then added to the plates and the radioactivity retained on the filters is determined on a Packard TopCount (Perkin Elmer). Specific binding is determined as total radioactive binding minus non-specific binding in the absence of the ligand (900 nM LPA). $IC_{50}$s were determined using Graphpad prism analysis of drug titration curves.

Illustrative in vitro biological data for representative compounds of Formula (I), (Ia), (II), (IIa), (III), (IIIa), (IV) and (V) is presented in the Table below.

TABLE 4

| Cmpd # | HLPA1 Ca Flux IC$_{50}$ |
|---|---|
| 1-1 | A |
| 1-2 | C |
| 1-3 | C |
| 1-4 | A |
| 1-5 | A |
| 1-6 | A |
| 1-7 | A |
| 1-8 | A |
| 1-9 | A |
| 1-10 | D |
| 1-11 | A |
| 1-12 | D |
| 1-13 | C |
| 1-14 | C |
| 1-15 | B |
| 1-16 | A |
| 1-17 | A |
| 1-18 | A |
| 1-19 | A |
| 1-20 | B |
| 1-21 | A |
| 1-22 | A |
| 1-23 | A |
| 1-24 | C |
| 1-25 | A |
| 1-26 | B |
| 1-27 | B |
| 1-28 | A |
| 1-29 | A |
| 1-30 | A |
| 1-31 | A |
| 1-32 | C |
| 1-33 | C |
| 1-34 | A |
| 1-35 | A |
| 1-36 | C |
| 1-37 | C |
| 1-38 | A |
| 1-39 | A |
| 1-40 | A |
| 1-41 | A |
| 1-42 | A |
| 1-43 | A |
| 1-44 | A |
| 1-45 | B |
| 1-46 | B |
| 1-47 | D |
| 1-48 | A |
| 1-49 | A |
| 1-50 | C |
| 1-51 | D |
| 1-52 | C |
| 1-53 | A |
| 1-54 | C |
| 1-55 | A |
| 1-56 | C |
| 1-57 | A |
| 1-58 | A |
| 1-59 | A |
| 1-60 | A |
| 1-61 | A |
| 1-62 | A |
| 1-63 | A |
| 1-64 | A |
| 1-65 | C |
| 1-66 | A |
| 1-67 | A |
| 1-68 | A |
| 1-69 | A |
| 1-70 | A |
| 1-71 | A |
| 1-72 | B |
| 1-73 | A |
| 1-74 | A |
| 1-75 | B |
| 1-76 | A |
| 1-77 | A |
| 1-78 | A |
| 1-79 | A |
| 1-80 | A |
| 1-81 | A |
| 1-82 | A |
| 1-83 | A |
| 1-84 | A |
| 1-85 | A |
| 1-86 | A |
| 1-87 | B |
| 1-88 | A |
| 1-89 | A |
| 1-90 | A |
| 1-91 | A |
| 1-92 | A |
| 1-93 | A |
| 1-94 | A |
| 1-95 | A |
| 1-96 | A |
| 1-97 | A |
| 1-98 | A |
| 1-99 | A |
| 1-100 | A |
| 1-101 | A |
| 1-102 | A |
| 1-103 | A |
| 1-104 | A |
| 1-105 | B |
| 1-106 | A |
| 1-107 | A |
| 1-108 | A |
| 1-109 | A |
| 1-110 | A |
| 1-111 | B |
| 1-112 | C |
| 1-113 | A |
| 1-114 | A |
| 1-115 | A |
| 1-116 | A |
| 1-117 | A |
| 1-118 | A |
| 1-119 | A |
| 1-120 | C |
| 1-121 | D |
| 1-122 | A |
| 1-123 | A |
| 1-124 | A |
| 1-125 | A |
| 1-126 | A |
| 1-127 | A |
| 1-128 | A |
| 1-129 | A |
| 1-130 | A |
| 1-131 | A |
| 1-132 | A |
| 1-133 | A |
| 1-134 | A |
| 1-135 | B |
| 1-136 | A |
| 1-137 | A |
| 1-138 | A |
| 1-139 | A |
| 1-140 | A |
| 1-141 | A |
| 1-142 | C |
| 1-143 | A |
| 1-144 | A |
| 1-145 | A |
| 1-146 | A |
| 1-147 | A |
| 1-148 | A |
| 1-149 | C |
| 1-150 | A |
| 1-151 | A |
| 1-152 | A |
| 1-153 | A |
| 1-154 | A |
| 1-155 | A |
| 1-156 | A |

TABLE 4-continued

| Cmpd # | HLPA1 Ca Flux IC$_{50}$ |
|---|---|
| 1-157 | A |
| 1-158 | A |
| 1-159 | A |
| 1-160 | A |
| 1-161 | A |
| 1-162 | A |
| 2-1 | A |
| 2-2 | A |
| 3-1 | A |
| 3-2 | A |
| 3-3 | C |
| 3-4 | A |
| 3-5 | A |
| 3-6 | A |

A = less than 0.3 µM;
B = greater than 0.3 µM and less than 1 µM;
C = greater than 1 µM and less than 50 µM;
D = greater than 50 µM.

Example 177

LPA1 Chemotaxis Assay

Chemotaxis of the A2058 human melanoma cells was measured using the Neuroprobe ChemoTx® System plates (8 µm pore size, 5.7 mm diameter sites). The filter sites were coated with 0.001% fibronectin (Sigma) in 20 mM Hepes, pH 7.4 and allowed to dry. A2058 cells were serum-starved for 24 hours, then harvested with Cell Stripper and resuspended in DMEM containing 0.1% fatty-acid-free bovine serum albumin (BSA) to a concentration of 1×10$^6$/ml. Cells were mixed with an equal volume of test compound (2×) in DMEM containing 0.1% fatty-acid-free BSA and incubated at 37° C. for 15 minutes. LPA (100 nM in DMEM containing 0.1% fatty-acid-free BSA) or vehicle was added to each well of the lower chamber and 50 µl of the cell suspension/test compound mix was applied to the upper portion of the ChemoTx plate. Plates were incubated at 37° C. for three hours and then the cells removed from the upper portion by rinsing with PBS and scraping. The filter was dried then stained with HEMA 3 Staining System (Fisher Scientific). The absorbance of the filter was read at 590 nM and IC$_{50}$s were determined using Symyx Assay Explorer.
In this experiment, compounds 1-25, 1-30, 1-41, 1-55, 1-58, 1-59, 1-67, 1-68, 1-73, 1-74, 1-77, 1-83, 1-84, 1-85, 1-86, 1-90, 1-93, 1-107, 1-108, 1-109, 1-113, 1-115, 1-116, 1-118, 1-146, 1-151, 1-153, 1-155, 1-156, 3-1, 3-2, 3-5 inhibited LPA-driven chemotaxis (IC$_{50}$ less than 100 nM) of human A2058 melanoma cells Example 178

Bleomycin-induced Lung Fibrosis Model in Mice

Female CD-1 mice (Harlan, 25-30 g) are housed 4 per cage, given free access to food and water and allowed to acclimate for at least 7 days prior to test initiation. After the habituation phase, mice are lightly anesthetized with isoflurane (5% in 100% O$_2$) and administered with bleomycin sulfate (0.01-5 U/kg, Henry Schein) via intratracheal instillation (Cuzzocrea S et al. *Am J Physiol Lung Cell Mol Physiol.* 2007 May; 292(5):L1095-104. Epub 2007 Jan. 12.). Mice are returned to their cages and monitored daily for the duration of the experiment. Test compound or vehicle is delivered po, ip or sc daily. The route and frequency of dosing is based on previously determined pharmacokinetic properties. All animals are sacrificed using inhaled isoflurane 3, 7, 14, 21 or 28 days after bleomycin instillation. Following sacrifice, mice are intubated with a 20 gauge angiocatheter attached to a 1 ml syringe. Lungs are lavaged with saline to obtain bronchoalveolar lavage fluid (BALF) and then removed and fixed in 10% neutral buffered formalin for subsequent histopathological analysis. BALF is centrifuged for 10 min at 800×g to pellet the cells and the cell supernatant removed and frozen at −80° C. for subsequent protein analysis using the DC protein assay kit (Biorad, Hercules, Calif.) and soluble collagen analysis using Sircol (Biocolor Ltd, UK). BALF is analyzed for concentrations of inflammatory, pro-fibrotic and tissue injury biomarkers including transforming growth factor β1, hyaluronic acid, tissue inhibitor of metalloproteinase-1, matrix matelloproteinase-7, connective tissue growth factor and lactate dehydrogenase activity, using commercially available ELISA. The cell pellet is re-suspended in PBS. Total cell counts are then obtained using a Hemavet hematology system (Drew Scientific, Wayne, Pa.) and differential cells counts are determined using Shandon cytospin (Thermo Scientific, Waltham, Mass.). Lung tissue is stained using hematoxylin and eosin (H&E) and trichrome and lung fibrosis is determined by semiquantitative histopathological scoring (Ashcroft T. et al. *J. Clin. Path.* 1988; 41; 4, 467-470.) using light microscopy (10× magnification) and quantitative, computer-assisted densitometry of collagen in lung tissue sections using light microscopy. The data are plotted using Graphpad prism and statistical differences between groups determined.
In the acute setting (3 day), Compound 1-41 significantly reduced total protein and collagen concentrations in broncheoalveolar lavage fluid (BALF).

Example 179

Mouse Carbon Tetrachloride (CCl$_4$)-induced Liver Fibrosis Model

Female C57BL/6 mice (Harlan, 20-25 g) housed 4/cage are given free access to food and water and allowed to acclimate for at least 7 days prior to test initiation. After the habituation phase, mice receive CCl$_4$ (0.5-1.0 ml/kg body weight) diluted in corn oil vehicle (100 µL volume) via i.p. injection twice a week for 4-6 weeks. (Higazi, A. A. et al., *Clin Exp Immunol.* 2008 April; 152(1):163-73. Epub 2008 Feb. 14). Control mice receive an equivalent volume of corn oil vehicle only. Test compound or vehicle is delivered po, ip or sc daily. At the end of the study (4-6 weeks after first i.p. injection of CCl$_4$), mice are sacrificed using inhaled isoflurane and blood is drawn via cardiac puncture for subsequent analysis of ALT/AST levels. The liver is harvested, and one half of the liver is frozen at −80° C. and the other half is fixed in 10% neutral buffered formalin for histological assessment of liver fibrosis using light microscopy (10× magnification). Liver tissue homogenates are analyzed for collagen levels using Sircol (Biocolor Ltd, UK). Fixed Liver tissue is stained using hematoxylin and eosin (H&E) and trichrome and liver fibrosis is determined by quantitative, computer-assisted densitometry of collagen in liver tissue sections using light microscopy. Plasma and liver tissue lysates are also analyzed for concentrations of inflammatory, pro-fibrotic and tissue injury biomarkers including transforming growth factor β1, hyaluronic acid, tissue inhibitor of metalloproteinase-1, matrix matelloproteinase-7, connective tissue growth factor and lactate dehydrogenase activity, using commercially available ELISA. The resulting data are plotted using Graphpad prism and statistical differences between groups determined.

Example 180

Mouse Intravenous LPA-induced Histamine Release

A mouse intravenous LPA-induced histamine release model is utilized to determine the in vivo potency of LPA receptor antagonists. Female CD-1 mice (weighing 25-35 grams) are administered compound (i.p., s.c. or p.o.) in a volume of 10 ml/kg 30 minutes to 24 hours prior to intravenous LPA challenge (300 µg/mouse in 0.1% FAF BSA). Immediately following LPA challenge mice are placed into an enclosed Plexiglas chamber and exposed to an isoflurane for a period of 2 minutes. They are removed, decapitated and trunk blood collected into tubes containing EDTA. Blood is then centrifuged at 10,000×g for 10 minutes at 4° C. Histamine concentrations in the plasma are determined by EIA. Drug concentrations in plasma are determined by mass spectrometry. The dose to achieve 50% inhibition of blood histamine release is calculated by nonlinear regression (Graphpad Prism) and plotted as the ED50. The plasma concentration associated with this dose is plotted as the $EC_{50}$.

Example 181

Mouse Unilateral Ureteral Obstruction Kidney Fibrosis Model

Female C57BL/6 mice (Harlan, 20-25 g) housed 4/cage will be given free access to food and water and allowed to acclimate for at least 7 days prior to test initiation. After the habituation phase, mice undergo unilateral ureteral obstruction (UUO) surgery or sham to left kidney. Briefly, a longitudinal, upper left incision is performed to expose the left kidney. The renal artery is located and 6/0 silk thread is passed between the artery and the ureter. The thread is looped around the ureter and knotted 3 times insuring full ligation of ureter. The kidney is returned to abdomen, the abdominal muscle is sutured and the skin is stapled closed. Mice are returned to their cages and monitored daily for the duration of the experiment. Test compound or vehicle is delivered po, ip or sc daily. The route and frequency of dosing is based on previously determined pharmacokinetic properties. All animals are sacrificed using inhaled isoflurane 4, 8 or 14 days after UUO surgery. Following sacrifice blood is drawn via cardiac puncture, the kidneys are harvested and one half of the kidney is frozen at −80° C. and the other half is fixed in 10% neutral buffered formalin for histological assessment of kidney fibrosis using light microscopy (10× magnification). Kidney tissue homogenates are analyzed for collagen levels using Sircol (Biocolor Ltd, UK). Fixed kidney tissue is also stained using hematoxylin and eosin (H&E) and trichrome and kidney fibrosis is determined by quantitative, computer-assisted densitometry of collagen in liver tissue sections using light microscopy. Plasma and kidney tissue lysates are also analyzed for concentrations of inflammatory, pro-fibrotic and tissue injury biomarkers including transforming growth factor β1, hyaluronic acid, tissue inhibitor of metalloproteinase-1, matrix matelloproteinase-7, connective tissue growth factor and lactate dehydrogenase activity, using commercially available ELISA. The resulting data are plotted using Graphpad prism and statistical differences between groups determined.

Example 182

Clinical Trial in Humans with Idiopathic Pulmonary Fibrosis (IPF) Purpose

The purposes of this study is to assess the efficacy of treatment with a compound of Formula (I), (Ia), (II), (IIa), (III), (IIIa), (IV) or (V) compared with placebo in patients with idiopathic pulmonary fibrosis (IPF) and to assess the safety of treatment with a compound of Formula (I), (Ia), (II), (IIa), (III), (IIIa), (IV) or (V) compared with placebo in patients with IPF.

The primary outcome variable is the absolute change in percent predicted forced vital capacity (FVC) from baseline to Week 72.

Secondary outcome measures include: composite outcomes of important IPF-related events; progression-free survival; categorical assessment of absolute change in percent predicted FVC from baseline to Week 72; change in Shortness-of-Breath from baseline to Week 72; change in percent predicted hemoglobin (Hb)-corrected carbon monoxide diffusing capacity (DLco) of the lungs from baseline to Week 72; change in oxygen saturation during the 6 minute walk test (6MWT) from baseline to Week 72; change in high-resolution computed tomography (HRCT) assessment from baseline to Week 72; change in distance walked in the 6MWT from baseline to Week 72.

Criteria

Patients eligible for this study include those patients that satisfy the following inclusion criteria: diagnosis of IPF; 40 to 80 years of age; FVC ≥50% predicted value; DLco ≥35% predicted value; either FVC or DLco ≤90% predicted value; no improvement in past year; able to walk 150 meters in 6 minutes and maintain saturation ≥83% while on no more than 6 L/min supplemental oxygen.

Patients are excluded from this study if they satisfy any of the following criteria: unable to undergo pulmonary function testing; evidence of significant obstructive lung disease or airway hyper-responsiveness; in the clinical opinion of the investigator, the patient is expected to need and be eligible for a lung transplant within 72 weeks of randomization; active infection; liver disease; cancer or other medical condition likely to result in death within 2 years; diabetes; pregnancy or lactation; substance abuse; personal or family history of long QT syndrome; other IPF treatment; unable to take study medication; withdrawal from other IPF trials.

Patients are orally dosed with either placebo or an amount of compound of Formula (I), (Ia), (II), (IIa), (III), (IIIa), (IV) or (V) (1 mg/day-1000 mg/day). The primary outcome variable will be the absolute change in percent predicted FVC from Baseline to Week 72. Patients will receive blinded study treatment from the time of randomization until the last patient randomized has been treated for 72 weeks. A Data Monitoring Committee (DMC) will periodically review safety and efficacy data to ensure patient safety.

After week 72, patients who meet the Progression of Disease (POD) definition, which is a ≥10% absolute decrease in percent predicted FVC or a ≥15% absolute decrease in percent predicted DLco, will be eligible to receive permitted IPF therapies in addition to their blinded study drug. Permitted IPF therapies include corticosteroids, azathioprine, cyclophosphamide and N-acetyl-cysteine.

Pharmaceutical Compositions

Example 183

Parenteral Composition

To prepare a parenteral pharmaceutical composition suitable for administration by injection (subcutaneous, intravenous, and the like), 100 mg of a water-soluble salt of a compound of Formula (I), (Ia), (II), (IIa), (III), (IIIa), (IV) or (V) is dissolved in water and then mixed with 10 mL of 0.9% sterile saline. The mixture is incorporated into a dosage unit form suitable for administration by injection In another embodiment, the following ingredients are mixed to form an injectable formulation: 1.2 g of a compound of Formula (I), (Ia), (II), (IIa), (III), (IIIa), (IV) or (V), 2.0 mL of sodium acetate buffer solution (0.4 M), HCl (1 N) or NaOH (1 M) (q.s. to suitable pH), water (distilled, sterile) (q.s. to 20 mL). All of the above ingredients, except water, are combined and stirred and if necessary, with slight heating if necessary. A sufficient quantity of water is then added.

Example 184

Oral Composition

To prepare a pharmaceutical composition for oral delivery, 100 mg of a compound of Formula (I), (Ia), (II), (IIa), (III), (IIIa), (IV) or (V) is mixed with 750 mg of starch. The mixture is incorporated into an oral dosage unit for, such as a hard gelatin capsule, which is suitable for oral administration.

Example 185

Sublingual (Hard Lozenge) Composition

To prepare a pharmaceutical composition for buccal delivery, such as a hard lozenge, mix 100 mg of a compound of Formula (I), (Ia), (II), (IIa), (III), (IIIa), (IV) or (V) with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 186

Fast-Disintegrating Sublingual Tablet

A fast-disintegrating sublingual tablet is prepared by mixing 48.5% by weight of a compound of Formula (I), (Ia), (II), (IIa), (III), (IIIa), (IV) or (V), 44.5% by weight of microcrystalline cellulose (KG-802), 5% by weight of low-substituted hydroxypropyl cellulose (50 μm), and 2% by weight of magnesium stearate. Tablets are prepared by direct compression (*AAPS PharmSciTech.* 2006; 7(2):E41). The total weight of the compressed tablets is maintained at 150 mg. The formulation is prepared by mixing the amount of a compound of Formula (I), (Ia), (II), (IIa), (III), (IIIa), (IV) or (V) with the total quantity of microcrystalline cellulose (MCC) and two-thirds of the quantity of low-substituted hydroxypropyl cellulose (L-HPC) by using a three dimensional manual mixer (Lnversina®, Bioengineering AG, Switzerland) for 4.5 minutes. All of the magnesium stearate (MS) and the remaining one-third of the quantity of L-HPC are added 30 seconds before the end of mixing.

Example 187

Inhalation Composition

To prepare a pharmaceutical composition for inhalation delivery, 20 mg of a compound of Formula (I), (Ia), (II), (IIa), (III), (IIIa), (IV) or (V) is mixed with 50 mg of anhydrous citric acid and 100 mL of 0.9% sodium chloride solution. The mixture is incorporated into an inhalation delivery unit, such as a nebulizer, which is suitable for inhalation administration.

Example 186

Rectal Gel Composition

To prepare a pharmaceutical composition for rectal delivery, 100 mg of a compound of Formula (I), (Ia), (II), (IIa), (III), (IIIa), (IV) or (V) is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 188

Topical Gel Composition

To prepare a pharmaceutical topical gel composition, 100 mg of a compound of Formula (I), (Ia), (II), (IIa), (III), (IIIa), (IV) or (V) is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topicl administration.

Example 189

Ophthalmic Solution Composition

To prepare a pharmaceutical opthalmic solution composition, 100 mg of a compound of Formula (I), (Ia), (II), (IIa), (III), (IIIa), (IV) or (V) is mixed with 0.9 g of NaCl in 100 mL of purified water and filterd using a 0.2 micron filter. The resulting isotonic solution is then incorporated into ophthalmic delivery units, such as eye drop containers, which are suitable for ophthalmic administration.

Example 190

Nasal Spray Solution

To prepare a pharmaceutical nasal spray solution, 10 g of a compound of Formula (I), (Ia), (II), (IIa), (III), (IIIa), (IV) or (V) is mixed with 30 mL of a 0.05M phosphate buffer solution (pH 4.4). The solution is placed in a nasal administrator designed to deliver 100 μl of spray for each application.

The examples and embodiments described herein are for illustrative purposes only and various modifications or changes suggested to persons skilled in the art are to be included within the spirit and purview of this application and scope of the appended claims.

What is claimed is:
1. A compound, or pharmaceutically acceptable salt thereof, selected from the group consisting of:
  1-{4'-[4-(2-Benzyl-cyclohexylamino)-3-methyl-isoxazol-5-yl]-biphenyl-4-yl}-cyclopropanecarboxylic acid;
  1-{4'-[3-Methyl-4-(4-o-tolyl-piperazine-1-carbonyl)-isoxazol-5-yl]-biphenyl-4-yl}-cyclopropanecarboxylic acid;
  1-(4'-{4-[4-(3,4-Dichloro-benzenesulfonyl)-piperazine-1-carbonyl]-3-methyl-isoxazol-5-yl}-biphenyl-4-yl)-cyclopropanecarboxylic acid;
  1-{4'-[3-Methyl-4-(3-phenethyl-oxiranyl)-isoxazol-5-yl]-biphenyl-4-yl}-cyclopropanecarboxylic acid;

1-{4'[3-Methyl-4-(2-oxo-4-phenyl-pyrrolidin-1-ylmethyl)-isoxazol-5-yl]-biphenyl-4-yl}-cyclopropanecarboxylic acid;

1-{4'-[3-Methyl-4-(4-phenyl-piperidin-1-ylmethyl)-isoxazol-5-yl]-biphenyl-4-yl}-cyclopropanecarboxylic acid;

1-{4'-[4-(2-Imino-5-phenyl-[1,3,4]oxadiazol-3-ylmethyl)-3-methyl-isoxazol-5-yl]-biphenyl-4-yl}-cyclopropanecarboxylic acid;

1-{4'-[4((S)-4-Benzyl-2-oxo-oxazolidin-3-ylmethyl)-3-methyl-isoxazol-5-yl]-biphenyl-4-yl}-cyclopropanecarboxylic acid;

1-{4'-[3-Methyl-4((S)-2-oxo-4-phenyl-oxazolidin-3-ylmethyl)-isoxazol-5-yl]-biphenyl-4-yl}-cyclopropanecarboxylic acid;

1-{4'-[3-Methyl-4R,5S)-4-methyl-2-oxo-5-phenyl-oxazolidin-3-ylmethyl)-isoxazol-5-yl]-biphenyl-4-yl}-cyclopropanecarboxylic acid;

1-{4'-[3-Methyl-4-((4S,5R)-4-methyl-2-oxo-5-phenyl-oxazolidin-3-ylmethyl)-isoxazol-5-yl]-biphenyl-4-yl}-cyclopropanecarboxylic acid;

1-{4'-[3-Methyl-4-(3-phenyl-pyrrolidin-1-ylmethyl)-isoxazol-5-yl]-biphenyl-4-yl}-cyclopropanecarboxylic acid;

1-{4'-[3-Methyl-4-(3-phenyl-piperidin-1-ylmethyl)-isoxazol-5-yl]-biphenyl-4-yl}-cyclopropanecarboxylic acid;

1-{4'-[3-Methyl-4-(2-oxo-5-phenyl-oxazolidin-3-ylmethyl)-isoxazol-5-yl]-biphenyl-4-yl}-cyclopropanecarboxylic acid;

1-[4'-(3-Methyl-4-{2-[methyl-((R)-1-phenyl-ethyl)-carbamoyl]-cyclopropyl}-isoxazol-5-yl)-biphenyl-4-yl]-cyclopropanecarboxylic acid;

1-[4'-(3-Methyl-4-{2-[methyl-((R)-1-phenyl-ethyl)-carbamoyl]-cyclopropyl}-isoxazol-5-yl)-biphenyl-4-yl]-cyclopropanecarboxylic acid;

1-{4'-[4-(3-Benzyl-2-oxo-oxazolidin-5-yl)-3-methyl-isoxazol-5-yl]-biphenyl-4-yl}-cyclopropanecarboxylic acid;

[1-(4'-{4-[4-(4-Benzyl-phenyl)-1-hydroxy-butyl]-3-methyl-isoxazol-5-yl}-biphenyl-4-yl)-cyclopropyl]-acetic acid;

[1-(4'-{4-[1-Hydroxy-4-(4-phenoxy-phenyl)-butyl]-3-methyl-isoxazol-5-yl}-biphenyl-4-yl)-cyclopropyl]-acetic acid;

1-{4'-[4-(1-Benzyl-piperidin-4-ylamino)-3-methyl-isoxazol-5-yl]-biphenyl-4-yl}-cyclopropanecarboxylic acid;

(1-{4'-[4-(1-Benzyl-piperidin-4-ylamino)-3-methyl-isoxazol-5-yl]-biphenyl-4-yl}-cyclopropyl)-acetic acid;

[1-(4'-{4-[Hydroxy-(5-phenyl-[1,3,4]oxadiazol-2-yl)-methyl]-3-methyl-isoxazol-5-yl}-biphenyl-4-yl)-cyclopropyl]-acetic acid;

[1-(4'-{3-Methyl-4-[1-(3-phenyl-isoxazol-5-yl)-ethylamino]-isoxazol-5-yl}-biphenyl-4-yl)-cyclopropyl]-acetic acid;

[1-(4'-{3-Methyl-4-[1-(3-phenyl-isoxazol-5-yl)-ethylamino]-isoxazol-5-yl}-biphenyl-4-yl)-cyclopropyl]-acetic acid (Enantiomer A);

[1-(4'-{3-Methyl-4-[1-(3-phenyl-isoxazol-5-yl)-ethylamino]-isoxazol-5-yl}-biphenyl-4-yl)-cyclopropyl]-acetic acid (Enantiomer B);

{1-[4'-(3-Methyl-4-{1-methyl-2-[4(4-trifluoromethyl-benzyloxy)-phenyl]-ethylamino}-isoxazol-5-yl)-biphenyl-4-yl]-cyclopropyl}-acetic acid;

1-(4'-{4-[(1-Benzyl-1H-[1,2,3]triazol-4-yl)-methanesulfonylamino-methyl]-3-methyl-isoxazol-5-yl}-biphenyl-4-yl)-cyclopropanecarboxylic acid;

(4'-{4-[(1-Benzyl-1H-[1,2,3]triazol-4-yl)-hydroxy-methyl]-3-methyl-isoxazol-5-yl}-biphenyl-4-yl)-acetic acid;

3-(4'-{4-[(1-Benzyl-1H-[1,2,3]triazol-4-yl)-hydroxy-methyl]-3-methyl-isoxazol-5-yl}-biphenyl-4-yl)-propionic acid;

[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-acetic acid;

3-[4'-(4-{Hydroxy-[1-(3-trifluoromethyl-benzyl)-1H-[1,2,3]triazol-4-yl]-methyl}-3-methyl-isoxazol-5-yl)-biphenyl-4-yl]-propionic acid;

[1-(4'-{4-[(5-Benzyl-[1,3,4]oxadiazol-2-yl)-hydroxy-methyl]-3-methyl-isoxazol-5-yl}-biphenyl-4-yl)-cyclopropyl]-acetic acid;

[4'-(4-{[1-(3,4-Dichloro-benzyl)-1H-[1,2,3]triazol-4-yl]-hydroxy-methyl}-3-methyl-isoxazol-5-yl)-biphenyl-4-yl]-acetic acid;

1-(4'-{3-Methyl-4-[trans-1-(2-phenyl-cyclopropyl)-ethylamino]-isoxazol-5-yl}-biphenyl-4-yl)-cyclopropanecarboxylic acid;

{4'[3-Methyl-4-(6-phenyl-pyridin-2-ylamino)-isoxazol-5-yl]-biphenyl-4-yl}-acetic acid;

1-{4'-[3-Methyl-4-(6-phenoxy-pyridin-2-ylamino)-isoxazol-5-yl]-biphenyl-4-yl}-cyclopropanecarboxylic acid;

3-{4'-[3-Methyl-4-(5-phenyl[1,3,4]oxadiazol-2-ylamino)-isoxazol-5-yl]-biphenyl-4-yl}-propionic acid;

1-{4'-[3-Methyl-4-(3-phenoxy-phenylamino)-isoxazol-5-yl]-biphenyl-4-yl}-cyclopropanecarboxylic acid;

1-{4'-[4-(6'-Ethoxy-[2,3']bipyridinyl-6-ylamino)-3-methyl-isoxazol-5-yl]-biphenyl-4-yl}-cyclopropanecarboxylic acid;

1-(4'-{4-[3-(2-Methoxy-pyridin-3-yl)-phenylamino]-3-methyl-isoxazol-5-yl}-biphenyl-4-yl)-cyclopropanecarboxylic acid;

1-{4'-[4-(2'-Methoxy-[2,3']bipyridinyl-6-ylamino)-3-methyl-isoxazol-5-yl]-biphenyl-4-yl}-cyclopropanecarboxylic acid;

1-{4'-[4-(6'-Methoxy-[2,3']bipyridinyl-6-ylamino)-3-methyl-isoxazol-5-yl]-biphenyl-4-yl}-cyclopropanecarboxylic acid;

1-{4'-[4-([2,4']Bipyridinyl-6-ylamino)-3-methyl-isoxazol-5-yl]-biphenyl-4-yl}-cyclopropanecarboxylic acid;

1-(4'-{4-[3-(6-Methoxy-pyridin-3-yl)-phenylamino]-3-methyl-isoxazol-5-yl}-biphenyl-4-yl)-cyclopropanecarboxylic acid;

1-{4'-[3-Methyl-4-(3-pyridin-3-yl-phenylamino)-isoxazol-5-yl]-biphenyl-4-yl}-cyclopropanecarboxylic acid;

1-(4'-{4-[3-(5-Methoxy-pyridin-3-yl)-phenylamino]-3-methyl-isoxazol-5-yl}-biphenyl-4-yl)-cyclopropanecarboxylic acid;

1-{4'-{3-Methyl-4-[6-(methyl-phenyl-amino)-pyridin-2-ylamino]-isoxazol-5-yl}-biphenyl-4yl)-cyclopropanecarboxylic acid;

1-(4'-{3-Methyl-4-[3-(methyl-phenyl-amino)-phenylamino]-isoxazol-5-yl}-biphenyl-4-yl)-cyclopropanecarboxylic acid;

1-(4'-{4- [Bis-(6-benzyl-pyridin-2-yl)-amino]-3-methyl-isoxazol-5-yl}-biphenyl-4-yl)-cyclopropanecarboxylic acid;

1-(4'-{4-[(2'-Dimethylaminomethyl-biphenyl-3-carbonyl)-amino]-3-methyl-isoxazol-5-yl}-biphenyl-4-yl)-cyclopropanecarboxylic acid;
1-{4'-[3-Methyl-4-(6-pyrazol-1-yl-pyridin-2-ylamino)-isoxazol-5-yl]-biphenyl-4-yl}-cyclopropanecarboxylic acid;
1-{4'-[3-Methyl-4-(6-morpholin-4-yl-pyridin-2-ylamino)-isoxazol-5-yl]-biphenyl-4-yl}-cyclopropanecarboxylic acid;
1-{4'-[4-(6-Benzyloxy-pyridin-2-ylamino)-3-methyl-isoxazol-5-yl]-biphenyl-4-yl}-cyclopropanecarboxylic acid;
1-{4'-[3-Methyl-4-(6-phenylsulfanyl-pyridin-2-ylamino)-isoxazol-5-yl]-biphenyl-4-yl}-cyclopropanecarboxylic acid;
1-{4'-[4-(6-Benzenesulfinyl-pyridin-2-ylamino)-3-methyl-isoxazol-5-yl]-biphenyl-4-yl}-cyclopropanecarboxylic acid;
1-{4'-[4-(6-Benzenesulfonyl-pyridin-2-ylamino)-3-methyl-isoxazol-5-yl]-biphenyl-4-yl}-cyclopropanecarboxylic acid;
3-{4'-[3-Methyl-4-(6-phenyl-pyridin-2-ylamino)-isoxazol-5-yl]-biphenyl-4-yl}-propionic acid;
2-Methyl-2-{4'-[3-methyl-4-(6-phenyl-pyridin-2-ylamino)-isoxazol-5-yl]-biphenyl-4-yl}-propionic acid;
(1-{4'-[3-Methyl-4-(6-phenyl-pyridin-2-ylamino)-isoxazol-5-yl]-biphenyl-4-yl}-cyclopropyl)-acetic acid;
1-{4'-[4-(6-Cyclopentylethynyl-pyridin-2-ylamino)-3-methyl-isoxazol-5-yl]-biphenyl-4-yl}-cyclopropanecarboxylic acid;
1-(4'-{3-Methyl-4-[6-(pyrrolidine-1-carbonyl)-pyridin-2-ylamino]-isoxazol-5-yl}-biphenyl-4-yl)-cyclopropanecarboxylic acid;
1-{4'-[4-(6-Cyclopropylcarbamoyl-pyridin-2-ylamino)-3-methyl-isoxazol-5-yl]-biphenyl-4-yl}-cyclopropanecarboxylic acid;
1-{4'-[4-(6-Cyclohexyloxy-pyridin-2-ylamino)-3-methyl-isoxazol-5-yl]-biphenyl-4-yl}-cyclopropanecarboxylic acid;
1-{4'-[4-(6-Cyclobutoxy-pyridin-2-ylamino)-3-methyl-isoxazol-5-yl]-biphenyl-4-yl}-cyclopropanecarboxylic acid;
1-(4'-{4-[6-(1-Cyclohexyl-ethoxy)-pyridin-2-ylamino]-3-methyl-isoxazol-5-yl}-biphenyl-4-yl)-cyclopropanecarboxylic acid;
1-{4'-[3-Methyl-4-(6-phenethyloxy-pyridin-2-ylamino)-isoxazol-5-yl]-biphenyl-4-yl}-cyclopropanecarboxylic acid;
4'-[3-Methyl-4-(5-phenyl-[1,3,4]oxadiazol-2-ylamino)-isoxazol-5-yl]-biphenyl-4-carboxylic acid;
1-(4'-{3-Methyl-4-[6-(2-oxo-oxazolidin-3-yl)-pyridin-2-ylamino]-isoxazol-5-yl}-biphenyl-4-yl)-cyclopropanecarboxylic acid;
1-(4'-{4-[6-(3-Carbamoyl-phenyl)-pyridin-2-ylamino]-3-methyl-isoxazol-5-yl}-biphenyl-4-yl)-cyclopropanecarboxylic acid;
1-(4'-{3-Methyl-4-[6-(2H-tetrazol-5-yl)-pyridin-2-ylamino]-isoxazol-5-yl}-biphenyl-4-yl)-cyclopropanecarboxylic acid; and
1-{4'-[4-(6-Cyclopropylmethoxy-pyridin-2-ylamino)-3-methyl-isoxazol-5-yl]-biphenyl-4-yl}-cyclopropanecarboxylic acid.

2. A pharmaceutical composition comprising a compound according to claim 1, or a pharmaceutically acceptable salt thereof.

3. A method for treating fibrosis in a mammal comprising administering a therapeutically effective amount of a compound of claim 1, or a pharmaceutically acceptable salt thereof

4. The method of claim 3 wherein said fibrosis comprises lung fibrosis, renal fibrosis, hepatic fibrosis or cutaneous fibrosis.

\* \* \* \* \*